US009492534B2

(12) United States Patent
Szalay et al.

(10) Patent No.: US 9,492,534 B2
(45) **Date of Patent: *Nov. 15, 2016**

(54) MICROORGANISMS FOR THERAPY

(71) Applicant: GENELUX CORPORATION, San Diego, CA (US)

(72) Inventors: Aladar A. Szalay, Highland, CA (US); Tatyana Timiryasova, Scotrun, PA (US); Yong A. Yu, San Diego, CA (US); Qian Zhang, San Diego, CA (US)

(73) Assignee: Genelux Corporation, San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/301,813

(22) Filed: Jun. 11, 2014

(65) Prior Publication Data

US 2014/0294891 A1 Oct. 2, 2014

Related U.S. Application Data

(60) Continuation of application No. 13/507,572, filed on Jul. 10, 2012, now Pat. No. 8,784,836, which is a continuation of application No. 12/589,694, filed on Oct. 26, 2009, now Pat. No. 8,221,769, which is a continuation of application No. 11/796,028, filed on Apr. 25, 2007, now abandoned, which is a division of application No. 10/872,156, filed on Jun. 18, 2004, now Pat. No. 7,588,767.

(30) Foreign Application Priority Data

| | | |
|---|---|---|
| Jun. 18, 2003 | (EP) | 03013826 |
| Aug. 14, 2003 | (EP) | 03018478 |
| Oct. 22, 2003 | (EP) | 03024283 |

(51) Int. Cl.

| | |
|---|---|
| ***A61K 39/285*** | (2006.01) |
| ***A61K 35/768*** | (2015.01) |
| ***C12P 19/34*** | (2006.01) |
| ***A61K 35/744*** | (2015.01) |
| ***C12P 21/02*** | (2006.01) |
| ***C12N 7/00*** | (2006.01) |
| ***C07K 16/40*** | (2006.01) |
| ***A61K 35/74*** | (2015.01) |
| ***C07K 16/30*** | (2006.01) |
| ***C12N 15/86*** | (2006.01) |
| ***A61K 39/00*** | (2006.01) |
| ***A61K 48/00*** | (2006.01) |

(52) U.S. Cl.

CPC ............ *A61K 39/285* (2013.01); *A61K 35/74* (2013.01); *A61K 35/744* (2013.01); *A61K 35/768* (2013.01); *C07K 16/30* (2013.01); *C07K 16/40* (2013.01); *C12N 7/00* (2013.01); *C12N 15/86* (2013.01); *C12P 19/34* (2013.01); *C12P 21/02* (2013.01); *A61K 39/00* (2013.01); *A61K 48/00* (2013.01); *A61K 2039/5254* (2013.01); *A61K 2039/5256* (2013.01); *C12N 2710/24132* (2013.01); *C12N 2710/24143* (2013.01); *C12N 2710/24161* (2013.01)

(58) Field of Classification Search

None

See application file for complete search history.

(56) References Cited

U.S. PATENT DOCUMENTS

| | | | | |
|---|---|---|---|---|
| 4,216,226 | A | 8/1980 | Fukuyasu et al. | 424/311 |
| 4,315,914 | A | 2/1982 | Arakawa et al. | 424/89 |
| 4,442,203 | A | 4/1984 | Varshavsky | 435/6 |
| 4,603,112 | A | 7/1986 | Paoletti et al. | 435/235.1 |
| 4,722,848 | A | 2/1988 | Paoletti et al. | 424/199.1 |
| 4,769,330 | A | 9/1988 | Paoletti et al. | 435/436 |
| 4,778,759 | A | 10/1988 | Szalay et al. | 435/477 |
| 5,110,587 | A | 5/1992 | Paoletti et al. | 435/235.1 |
| 5,155,020 | A | 10/1992 | Paoletti | 435/69.1 |
| 5,221,623 | A | 6/1993 | Legocki et al. | 435/252.3 |
| 5,283,187 | A | 2/1994 | Aebischer et al. | 435/182 |
| 5,300,436 | A | 4/1994 | Goldstein et al. | 435/190 |
| 5,364,773 | A | 11/1994 | Paoletti et al. | 435/69.1 |
| 5,368,855 | A | 11/1994 | Boyle et al. | 435/320.1 |
| 5,378,457 | A | 1/1995 | Paoletti et al. | 424/205.1 |
| 5,494,807 | A | 2/1996 | Paoletti | 435/69.3 |
| 5,550,050 | A | 8/1996 | Holland et al. | 435/382 |

(Continued)

FOREIGN PATENT DOCUMENTS

| | | |
|---|---|---|
| AU | 709336 | 4/1995 |
| CA | 2105277 | 12/2006 |

(Continued)

OTHER PUBLICATIONS

Letter/Written Disclosure of the Supplemental Information Disclosure Statement for the above-referenced application, mailed herewith on Sep. 25, 2015, 2 pages.

(Continued)

*Primary Examiner* — Benjamin P Blumel

(74) *Attorney, Agent, or Firm* — Dentons US LLP; Stephanie Seidman

(57) ABSTRACT

Therapeutic methods and vaccinia virus therefor are provided. The viruses are designed so that they accumulate in immunoprivileged tissues and cells, such as in tumors and other proliferating tissue and in inflamed tissues, compared to other tissues, cells and organs, so that they exhibit relatively low toxicity to host organisms. Combinations of the viruses and anti-cancer agents and uses thereof for treating cancer also are provided.

14 Claims, 2 Drawing Sheets

(56) References Cited

U.S. PATENT DOCUMENTS 5,639,275 A 6/1997 Baetge et al. ............ 604/891.1
5,646,298 A 7/1997 Powell .......................... 548/181
5,650,135 A 7/1997 Contag et al. ................ 424/9.1
5,650,148 A 7/1997 Gage et al. .................. 424/93.2
5,653,975 A 8/1997 Baetge et al. .............. 424/93.1
5,656,481 A 8/1997 Baetge et al. ............... 435/325
5,676,943 A 10/1997 Baetge et al. ............ 424/93.21
5,693,533 A 12/1997 Raney et al. ................ 435/366
5,704,910 A 1/1998 Humes .......................... 604/502
5,710,137 A 1/1998 Fisher ............................ 514/44
5,718,902 A 2/1998 Yilma et al. ............... 424/211.1
5,750,103 A 5/1998 Cherksey .................. 424/93.21
5,756,455 A 5/1998 Kinzler et al. ................. 514/12
5,762,938 A 6/1998 Paoletti et al. ........... 424/199.1
5,762,959 A 6/1998 Soon-Shiong et al. ....... 424/451
5,795,790 A 8/1998 Schinstine et al. ........... 435/382
5,798,113 A 8/1998 Dionne et al. ............... 424/422
5,800,828 A 9/1998 Dionne et al. ............... 424/422
5,800,829 A 9/1998 Dionne et al. ............... 424/422
5,830,702 A 11/1998 Portnoy et al. ........... 424/184.1
5,833,975 A 11/1998 Paoletti et al. ............. 424/93.2
5,833,979 A 11/1998 Schinstine et al. ........ 424/93.21
5,834,001 A 11/1998 Dionne et al. ............... 424/422
5,837,234 A 11/1998 Gentile et al. .............. 424/93.7
5,840,576 A 11/1998 Schinstine et al. ........... 435/325
5,842,431 A 12/1998 Wu .............................. 112/232
5,853,385 A 12/1998 Emerich et al. ............. 604/500
5,853,717 A 12/1998 Schinstine et al. ........ 424/93.21
5,861,290 A 1/1999 Goldsmith et al. ........... 435/456
5,866,131 A 2/1999 Ramshaw et al. ......... 424/186.1
5,976,796 A 11/1999 Szalay et al. ..................... 435/6
6,007,806 A 12/1999 Lathe et al. ................. 424/93.2
6,025,155 A 2/2000 Hadlaczky et al. ......... 435/69.1
6,045,802 A 4/2000 Schlom et al. ............ 424/199.1
6,077,697 A 6/2000 Hadlaczky et al. ....... 435/172.3
6,080,849 A 6/2000 Bermudes et al. .......... 536/23.7
6,093,700 A 7/2000 Mastrangelo et al. .......... 514/44
6,099,848 A 8/2000 Frankel et al. ............ 424/246.1
6,106,826 A 8/2000 Brandt et al. ................ 424/93.2
6,190,657 B1 2/2001 Pawelek et al. ............. 424/93.1
6,217,847 B1 4/2001 Contag et al. ................ 424/9.1
6,232,523 B1 5/2001 Tan et al. ........................ 800/10
6,235,967 B1 5/2001 Tan et al. ........................ 800/10
6,235,968 B1 5/2001 Tan et al. ........................ 800/10
6,251,384 B1 6/2001 Tan et al. .................. 424/93.21
6,265,189 B1 7/2001 Paoletti et al. ............. 435/70.1
6,265,557 B1 7/2001 Diamond et al. ............ 536/23.1
6,416,754 B1 7/2002 Brown et al. .............. 424/93.21
6,428,968 B1 8/2002 Molnar-Kimber et al. ........................... 435/7.23
6,448,073 B1 9/2002 Jager et al. ................ 435/320.1
6,455,673 B1 9/2002 Collier .......................... 530/350
6,491,905 B1 12/2002 Sorscher et al. ............. 435/325
6,503,703 B1 1/2003 Palese et al. ..................... 435/5
6,511,967 B1 1/2003 Weissleder et al. ............ 514/44
6,537,594 B1 3/2003 Paoletti et al. .............. 424/93.2
6,548,068 B1 4/2003 Schlom et al. ............ 424/199.1
6,589,531 B1 7/2003 Andino-Pavlovsky et al. ......................... 424/199.1
6,596,279 B1 7/2003 Paoletti et al. ............ 424/199.1
6,627,190 B2 9/2003 Wold et al. .................. 424/93.2
6,649,143 B1 11/2003 Contag et al. ................ 424/9.1
6,649,159 B2 11/2003 Yang et al. ................ 424/93.21
6,652,849 B2 11/2003 Brown et al. ................ 424/93.2
6,685,935 B1 2/2004 Pawelek et al. ............. 424/93.2
6,713,293 B1 3/2004 Grummt et al. .............. 435/182
6,743,967 B2 6/2004 Hadlaczky et al. ............ 800/25
6,759,038 B2 7/2004 Tan et al. .................. 424/93.21
6,884,414 B1 4/2005 Palese et al. ................ 424/93.2
6,984,374 B2 1/2006 Szalay et al. .................. 424/9.1
7,045,313 B1 5/2006 Moss et al. .................. 435/69.1
7,118,740 B1 10/2006 Russell et al. ............... 424/93.6
7,470,426 B1 12/2008 Roberts et al. .............. 424/93.2
7,588,767 B2 9/2009 Szalay et al. ............. 424/199.1
7,588,771 B2 9/2009 Szalay et al. ............. 424/232.1
7,662,398 B2 2/2010 Szalay et al. ............. 424/232.1
7,754,221 B2 7/2010 Szalay et al. ............. 424/199.1
7,763,420 B2 7/2010 Stritzker et al. .................. 435/4
7,820,184 B2 10/2010 Stritzker et al. ........... 424/241.1
8,021,662 B2 9/2011 Szalay et al. ............. 424/138.1
8,043,612 B2 10/2011 Roberts et al. .............. 424/93.6
8,052,968 B2 11/2011 Chen et al. ................ 424/199.1
8,066,984 B2 11/2011 Szalay et al. ............. 424/93.21
8,105,578 B2 1/2012 Roberts et al. .............. 424/93.6
8,137,904 B2 3/2012 Szalay et al. ..................... 435/4
8,221,769 B2 7/2012 Szalay et al. ............. 424/232.1
8,323,959 B2 12/2012 Szalay et al. ............. 435/320.1
8,357,486 B2 1/2013 Stritzker et al. .................. 435/4
8,568,707 B2 10/2013 Szalay et al. .................. 424/9.3
8,586,022 B2 11/2013 Szalay et al. ................ 424/93.2
8,642,257 B2 2/2014 Szalay et al. ..................... 435/5
8,784,836 B2 7/2014 Szalay et al. ............. 424/199.1
8,852,927 B2 10/2014 Szalay et al. ............. 435/320.1
8,859,256 B2 10/2014 Szalay et al. ................. 435/210
8,865,153 B2 10/2014 Szalay et al. ................ 424/93.2
9,005,602 B2 * 4/2015 Szalay ........................ 424/93.3
2001/0008025 A1 7/2001 Hadlaczky et al. .............. 800/8
2001/0029023 A1 10/2001 Szalay et al. .................. 435/7.1
2002/0054865 A1 5/2002 Fujimori et al. ........... 424/93.21
2002/0160410 A1 10/2002 Hadlaczky et al. ............. 435/6
2002/0160970 A1 10/2002 Hadlaczky et al. ............ 514/44
2002/0168344 A1 11/2002 Coffey et al. ................ 424/93.2
2003/0009015 A1 1/2003 Ulrich et al. ................ 536/23.1
2003/0031628 A1 2/2003 Zhao et al. .................... 424/9.6
2003/0031681 A1 2/2003 McCart et al. ............ 424/186.1
2003/0033617 A1 2/2003 Hadlaczky et al. .............. 800/6
2003/0044384 A1 3/2003 Roberts et al. .............. 424/93.2
2003/0059400 A1 3/2003 Szalay ........................ 424/93.2
2003/0083293 A1 5/2003 Hadlaczky et al. ............ 514/44
2003/0086906 A1 5/2003 Mastrangelo et al. ....... 424/93.2
2003/0101480 A1 5/2003 Hadlaczky et al. .......... 800/278
2003/0133949 A1 7/2003 Szalay et al. ............. 424/200.1
2003/0161788 A1 8/2003 Zhao et al. .................... 424/9.6
2003/0165465 A1 9/2003 Roberts et al. .............. 424/93.2
2003/0165477 A1 9/2003 Balloul et al. ............. 424/93.21
2003/0198627 A1 10/2003 Arts et al. ................. 424/93.21
2003/0213007 A1 11/2003 Slattery et al. ................. 800/15
2003/0228261 A1 12/2003 Szalay et al. ................ 424/9.34
2003/0228330 A1 12/2003 Falkner et al. ............ 424/232.1
2004/0076622 A1 4/2004 Studeny et al. ........... 424/93.21
2004/0091995 A1 5/2004 Schlom et al. ............ 435/235.1
2004/0115703 A1 6/2004 Schwartz et al. .............. 424/9.2
2004/0143861 A1 7/2004 Hadlaczky et al. ............ 800/14
2004/0213741 A1 10/2004 Szalay et al. .................. 424/9.6
2004/0234455 A1 11/2004 Szalay et al. .................. 424/9.6
2005/0025745 A1 2/2005 Fujimori ...................... 424/93.2
2005/0025747 A1 2/2005 Laidlaw et al. ............. 424/93.2
2005/0031643 A1 2/2005 Szalay et al. ............. 424/199.1
2005/0063993 A1 3/2005 Schlom et al. ............ 424/199.1
2005/0069491 A1 3/2005 Szalay et al. ................ 424/1.11
2005/0249670 A1 11/2005 Szalay et al. ................ 424/9.32
2006/0004191 A1 1/2006 Jhiang et al. ............... 536/23.5
2006/0051370 A1 3/2006 Szalay et al. ............. 424/199.1
2006/0099224 A1 5/2006 Kirn .......................... 424/199.1
2006/0134801 A1 6/2006 Chada et al. ................. 436/177
2006/0193832 A1 8/2006 Domann et al. ................ 514/44
2007/0025981 A1 2/2007 Szalay et al. ............. 424/130.1
2007/0086984 A1 4/2007 Coffey et al. ................ 424/93.2
2007/0202572 A1 8/2007 Szalay et al. ............... 435/69.1
2007/0212727 A1 9/2007 Szalay et al. ..................... 435/6
2008/0193373 A1 8/2008 Stritzker et al. ............. 424/1.17
2008/0226674 A1 9/2008 Kotani et al. .............. 424/207.1
2009/0053244 A1 2/2009 Chen et al. ................ 424/174.1
2009/0081639 A1 3/2009 Hill et al. ........................ 435/5
2009/0098529 A1 4/2009 Chen et al. ....................... 435/5
2009/0117034 A1 5/2009 Chen et al. .................. 424/1.17
2009/0117047 A1 5/2009 Szalay et al. .................. 424/9.3
2009/0117048 A1 5/2009 Szalay et al. .................. 424/9.3
2009/0117049 A1 5/2009 Szalay et al. .................. 424/9.3
2009/0117082 A1 5/2009 Lee et al. ..................... 424/93.6
2009/0123382 A1 5/2009 Szalay et al. .................. 424/9.6
2009/0136917 A1 5/2009 Szalay et al. ..................... 435/5
2009/0155287 A1 6/2009 Chen et al. ................ 424/158.1
2009/0162288 A1 6/2009 Chen et al. .................... 424/9.3

(56) References Cited

U.S. PATENT DOCUMENTS

| | | | | |
|---|---|---|---|---|
| 2010/0008946 | A1 | 1/2010 | Szalay et al. | 424/199.1 |
| 2010/0062016 | A1 | 3/2010 | Szalay et al. | 424/199.1 |
| 2010/0196325 | A1 | 8/2010 | Szalay et al. | 424/93.6 |
| 2010/0233078 | A1 | 9/2010 | Szalay et al. | 424/1.17 |
| 2011/0064650 | A1 | 3/2011 | Szalay | 424/1.11 |
| 2011/0293527 | A1 | 12/2011 | Chen et al. | 424/9.3 |
| 2011/0300176 | A1 | 12/2011 | Szalay | 424/199.1 |
| 2012/0020883 | A1 | 1/2012 | Stritzker et al. | |
| 2012/0052003 | A9 | 3/2012 | Szalay | 424/1.11 |
| 2012/0244068 | A1 | 9/2012 | Chen et al. | 424/1.11 |
| 2012/0276010 | A1 | 11/2012 | Szalay et al. | 424/9.1 |
| 2012/0308484 | A1 | 12/2012 | Szalay et al. | 424/9.3 |
| 2013/0129614 | A9 | 5/2013 | Szalay et al. | 424/1.11 |
| 2013/0130292 | A1 | 5/2013 | Szalay et al. | 435/18 |
| 2013/0273007 | A1 | 10/2013 | Szalay et al. | 424/93.2 |
| 2013/0280170 | A1 | 10/2013 | Szalay | 424/9.2 |
| 2014/0086976 | A1 | 3/2014 | Szalay et al. | 424/445 |
| 2014/0087362 | A1 | 3/2014 | Szalay et al. | 435/5 |
| 2014/0140959 | A1 | 5/2014 | Szalay et al. | 424/93.2 |
| 2014/0271549 | A1 | 9/2014 | Szalay | 424/93.2 |
| 2015/0024403 | A1 | 1/2015 | Szalay et al. | 435/7.4 |
| 2015/0175976 | A1 | 6/2015 | Szalay et al. | C12N 7/00 |

FOREIGN PATENT DOCUMENTS

| | | |
|---|---|---|
| EP | 0 037 441 | 10/1981 |
| EP | 0 761 687 | 3/1997 |
| EP | 0 861 093 | 9/1998 |
| EP | 1 146 125 | 10/2001 |
| EP | 1 281 767 | 2/2003 |
| EP | 1 281 772 | 2/2003 |
| EP | 1 281 777 | 2/2003 |
| EP | 03 013 826.7 | 6/2003 |
| EP | 03 018 478.2 | 8/2003 |
| EP | 03 024 283.8 | 10/2003 |
| EP | 1 369 491 | 12/2003 |
| EP | 1 489 164 | 12/2004 |
| EP | 1 254 250 | 3/2005 |
| EP | 1 512 746 | 3/2005 |
| EP | 1 526 185 | 4/2005 |
| JP | 55-35004 | 3/1980 |
| JP | 9-502993 | 3/1997 |
| JP | 2002-97144 | 4/2002 |
| WO | WO 88/00617 | 1/1988 |
| WO | WO 90/13658 | 11/1990 |
| WO | WO 91/07989 | 6/1991 |
| WO | WO 91/19810 | 12/1991 |
| WO | WO 92/22327 | 12/1992 |
| WO | WO 93/01296 | 1/1993 |
| WO | WO 94/10302 | 5/1994 |
| WO | WO 95/31105 | 11/1995 |
| WO | WO 96/11279 | 4/1996 |
| WO | WO 96/40238 | 12/1996 |
| WO | WO 97/18841 | 5/1997 |
| WO | WO 97/40183 | 10/1997 |
| WO | WO 98/14605 | 4/1998 |
| WO | WO 99/18799 | 4/1999 |
| WO | WO 99/32646 | 7/1999 |
| WO | WO 00/47237 | 8/2000 |
| WO | WO 00/62735 | 10/2000 |
| WO | WO 00/73479 | 12/2000 |
| WO | WO 01/05229 | 1/2001 |
| WO | WO 01/12234 | 2/2001 |
| WO | WO 01/14579 | 3/2001 |
| WO | WO 01/18195 | 3/2001 |
| WO | WO 01/20989 | 3/2001 |
| WO | WO 01/24637 | 4/2001 |
| WO | WO 01/25397 | 4/2001 |
| WO | WO 01/25399 | 4/2001 |
| WO | WO 01/48246 | 7/2001 |
| WO | WO 01/53467 | 7/2001 |
| WO | WO 01/55444 | 8/2001 |
| WO | WO 03/006069 | 1/2003 |
| WO | WO 03/014380 | 2/2003 |
| WO | WO 03/045153 | 6/2003 |
| WO | WO 03/049117 | 6/2003 |
| WO | WO 03/057007 | 7/2003 |
| WO | WO 03/063593 | 8/2003 |
| WO | WO 03/092600 | 11/2003 |
| WO | WO 03/102168 | 12/2003 |
| WO | WO 03/102169 | 12/2003 |
| WO | WO 03/104485 | 12/2003 |
| WO | WO 04/000236 | 12/2003 |
| WO | WO 2004/014314 | 2/2004 |
| WO | WO 2004/030631 | 4/2004 |
| WO | WO 2004/044175 | 5/2004 |
| WO | WO 2004/098534 | 11/2004 |
| WO | WO 2005/047458 | 5/2005 |
| WO | WO 2005/057488 | 6/2005 |
| WO | WO 2005/072622 | 8/2005 |
| WO | WO 2006/050274 | 5/2006 |
| WO | WO 2007/075879 | 7/2007 |
| WO | WO 2008/100292 | 8/2008 |

OTHER PUBLICATIONS

Advani et al., "Oncolytic vaccinia virus encoding an anti-VEGF antibody improves the therapeutic efficacy of fractionated radiotherapy in lung tumor xenografts," Abstract, ASTRO 53rd Annual Meeting, Miami Beach, FL, Oct. 2-6, 2011, 2 pages.

Mell et al., "Phase I trial of intravenous attenuated vaccinia virus (GL-ONC1) with concurrent chemoradiotherapy (CRT) for locoregionally advanced head and neck carcinoma," J. Clinical Oncology 33(15):6026 (2015).

Stritzker et al., "Inducible gene-expression in tumors colonized by modified oncolytic vaccinia virus strains" J Virol. 8(19):11556-11567 (2014).

Final Office Action, issued Nov. 6, 2014, in connection with U.S. Appl. No. 11/976,028, 6 pages.

U.S. Appl. No. 13/999,616, filed Mar. 11, 2014.

U.S. Appl. No. 14/205,174, filed Mar. 31, 2014.

Letter/Written Disclosure of the Information Disclosure Statement for the above-referenced application, mailed on Aug. 1, 2014, 13 pages.

AACR Press Release Sep. 15, 2011, Virus shows promise for imaging and treating pancreatic cancer, Published on Sep. 15, 2011 [online][retrieved on Jan. 28, 2013] Retrieved from:<URL:aacr.org/home/public--media/aacr-press-releases.aspx?d=2438 [2 pages].

Aboody et al., "Neural stem cells display extensive tropism for pathology in adult brain: evidence from intracranial gliomas," Proc. Natl. Acad. Sci. U.S.A.. 97(23):12846-12851 (2000).

Adonai et al., "Ex vivo cell labeling with $^{64}$Cu-pyruvaldehyde-bis($N^4$-methylthiosemicarbazone) for imaging cell trafficking in mice with positron-emission tomography," Proc. Natl. Acad. Sci. U.S.A. 99:3030-3035 (2002).

Advani et al., "Oncolytic vaccinia virus encoding an anti-VEGF antibody improves the efficacy of fractionated radiotherapy in tumor xenografts," Poster, ASTRO 53rd Annual Meeting, Miami Beach, FL, Oct. 2-6, 2011, 1 page.

Advani et al., "Radiotargeting systemically administered oncolytic vaccinia virus to preferentially replicate in radiated gliomas," Abstract, ASTRO 53rd Annual Meeting, Miami Beach, FL, Oct. 2-6, 2011, 2 pages.

Advani et al., "Preferential replication of systemically delivered oncolytic vaccinia virus to focally irradiated glioma xenografts," Clin Cancer Res. 18(9):2579-2590 (2012).

Advani et al., "Radiotargeting systemically administered oncolytic vaccinia virus to preferentially replicate in radiated gliomas," Abstract, ASTRO 53rd Annual Meeting, Miami Beach, FL, Oct. 2-6, 2011, 1 page.

Advani et al., "Replication-competent, non-neuroinvasive genetically engineered herpes virus is highly effective in the treatment of therapy-resistant experimental human tumors," Cancer Res. 59: 2055-2058 (1999).

Advisory Committee on Immunization Practices (ACIP), "Smallpox vaccination and adverse reactions: guidance for clinicians," MMWR 52(RR-4):1-29 (2003).

(56) References Cited

OTHER PUBLICATIONS

Advisory Committee on Immunization Practices (ACIP), "Vaccinia (smallpox) vaccine: recommendations of the Advisory Committee on Immunization Practices (ACIP)," MMWR 50(RR-10):1-26 (2001).
Ady et al., "Oncolytic immunotherapy using recombinant vaccinia virus GLV-1h68 kills sorafenib-resistant hepatocellular carcinoma efficiently," Surgery, doi: 10.1016/j.surg.2014.03.031. [Epub ahead of print] 156(2):263-269 (2014).
Afanasieva et al., "Single-chain antibody and its derivatives directed against vascular endothelial growth factor: application for antiangiogenic gene therapy," Gene Ther. 10:1850-1859 (2003).
Aguilar et al., "The *nifEN* genes participating in FeMo cofactor biosynthesis and genes encoding dinitrogenase are part of the same operon in *Bradyrhizobium* species," Mol. Gen. Genet. 224(3):413-420 (1990).
Aksac, "Antibody formation against Agrobacterium tumefaciens in patients with various cancers," Turk. Hij. Tecr. Biyol. Derg. 34(1-2):48-51 (1974) [Article in Turkish].
Alcamí et al., "Vaccinia virus strains Lister, USSR and Evans express soluble and cell-surface tumour necrosis factor receptors," J. Gen. Virol. 80:949-959 (1999).
Altenbrunn et al., "Scintographic tumor localization in mice with radioiodinated anti-clostridium antibodies," Int. J. Nucl. Med. Biol. 8(1):90-93 (1981).
Altschul et al., "Basic local alignment search tool," J. Mol. Biol. 215:403-410 (1990).
Al'tshtein et al., "Isolation of a recombinant vaccinia virus based on the LIVP strain inducing the surface antigen of the hepatitis B virus," Dokl. Akad. Nauk. SSSR 285(3):696-699 (1985) [Article in Russian].
Amato et al., "Luminous with promise," Chem. Eng. News. 84(49):69-73 (2006).
Anaissie et al., "Pseudomonas putida. Newly recognized pathogen in patients with cancer," Am. J. Med. 82(6):1191-1194 (1987).
Anand et al., "Clostridium difficile infection associated with antineoplastic chemotherapy: a review," Clin. Infect. Dis. 17(1):109-113 (1993).
Ando et al., "Unmasking of growth of dermovaccinia strain dairen I in L cells by acid treatment of cells after virus adsorption," Japan. J. Microbiol. 14(3):181-186 (1979).
Antoine et al., "Characterization of the vaccinia MVA hemagglutinin gene locus and its evaluation as an insertion site for foreign genes," Gene 177:43-46 (1996).
Antoine et al., "The complete genomic sequence of the modified vaccinia Ankara strain: comparison with other orthopoxviruses," Virology 244:365-396 (1998).
Arab et al., "Verotoxin induces apoptosis and the complete, rapid, long-term elimination of human astrocytoma xenografts in nude mice," Oncol. Res. 11(1):33-39 (1999).
Arakawa et al., "Clinical trial of attenuated vaccinia virus AS strain in the treatment of advanced adenocarcinoma. Report on two cases," J. Cancer Res. Clin. Oncol. 113(1):95-98 (1987).
Ascierto et al., "Permissivity of the NCI-60 cancer cell lines to oncolytic Vaccinia Virus GLV-1H68," BMC Cancer 11(1):451, 30 pages (2011).
ATCC Accession No. 37253 (accessed Jun. 30, 2005) (2 pages).
ATCC Accession No. VR-1549, Retrieved from the Internet:<URL: atcc.org/ATCCAdvancedCatalogSearch/ProductDetails/tabid/452/Default.aspx?ATCCNum=VR-1549&Template=animalVirology, [retrieved on Apr. 28, 2010] [3 pages].
Ausubel et al., "Generation of recombinant vaccinia viruses," Unit 16.17 in *Short Protocols in Molecular Biology 2nd edition: a compendium of Methods from Current Protocols in Molecular Biology*, Green Publishing and John Wiley and Sons: New York, 15:16.71-16.82 (1992).
Azmi et al., "In situ localization of endogenous cytokinins during shooty tumor development on Eucalyptus globulus Labill," Planta 213(1):29-36 (2001).
Baeksgaard et al., "Acute tumor lyssi syndrome in solid tumors—a case report and review of the literature," Cancer Chemother. Pharmacol., 51:187-192 (2003).
Baker et al., "Potential antiviral therapeutics for smallpox, monkeypox, and other orthopoxvirus infections," Antivir. Res. 57:13-23 (2003).
Baker et al., "Transducers of life and death: TNF receptor superfamily and associated proteins," Oncogene 12(1):1-9 (1996).
Balkwill, F., "Chemokine biology in cancer," Seminars in Immunol. 15:49-55 (2003).
Banerjee et al., "Bacillus infections in patients with cancer," Arch. Intern . . . Med. 148(8):1769-1774 (1988).
Barrett, A., "Yellow fever vaccines," Biologicals 25:17-25 (1997).
Barzon et al., "Endocrine aspects of cancer gene therapy," Endocrine Reviews 25(1):1-44 (2004).
Bauerschmitz et al., "Treatment of ovarian cancer with a tropism modified oncolytic adenovirus," Cancer Res. 62: 1266-1270 (2002).
Baxby, D., "Poxviruses," Chapter 15 in *Principles and Practice of Clinical Virology*, Zuckerman et al.(eds.), John Wiley & Sons Ltd., pp. 451-465 (2000).
Beebe et al., "Recovery of uncommon bacteria from blood: association with neoplastic disease," Clin. Microbiol. Rev. 8(3):336-356 (1995).
Beemtsen et al., "Genetics of mosquito vector competenc," Microbiol. Mol. Biol. Rev. 64(1):115-137 (2000).
Belas et al., "Bacterial bioluminescence: isolation and expression of the luciferase genes from Vibrio harveyi," Science 218:791-793 (1982).
Belin et al., "An oncolytic vaccinia virus expressing the human sodium iodine symporter prolongs survival and facilitates SPECT/CT imaging in an orthotopic model of malignant pleural mesothelioma," Surgery 154(3):486-495 (2013).
Bell et al., "Getting oncolytic virus therapies off the ground," Cancer Cell 4:7-11 (2003).
Bendig, M., "The production of foreign proteins in mammalian cells," Genet. Eng. 7:91-127 (1988).
Benes et al., "M13 and pUC vectors with new unique restriction sites for cloning," Gene 130:151-152 (1993).
Bennett et al., "Positron emission tomography imaging for herpes virus infection: implications for oncolytic viral treatments of cancer," Nature Med. 7(7):859-863 (2001).
Benning, N. and D. Hasset, "Vaccinia virus infection during murine pregnancy: a new pathogenesis model for vaccinia fetalis," J. Viro . 78(6):3133-3139 (2004).
Bentires-Alj et al., "Cytosine deaminase suicide gene therapy for peritoneal carcinomatosis," Cancer Gene Ther. 7(1):20-26 (2000).
Berger et al., "Recent advances in imaging endogenous or transferred gene expression utilizing radionuclide technologies in living subjects," Breast Cancer Res. 3:28-35 (2001).
Bergsland et al., "Shedding old paradigms: developing viruses to treat cancer," J. Clin. Oncol. 20(9):2220-2222 (2002).
Bermudes et al., "Live bacteria as anticancer agents and tumor-selective protein delivery vectors," Curr. Opin. Drug Disc. 5(2):194-199 (2002).
Bermudes et al., "Tumor-targeted *Salmonella*: highly selective delivery vectors," Adv. Exp. Med. Biol. 465:57-63 (2000).
Bernards et al., "Effective tumor immunotherapy directed against an oncogene-encoded product using a vaccinia virus vector," Proc. Natl. Acad. Sci. U.S.A. 84:6854-6858 (1987).
Beshara et al., "Kinetic analysis of $^{52}$Fe-labelled iron(III) hydroxide-sucrose complex following bolus administration using positron emission tomography," Br. J. Haematol. 104:288-295 (1999).
Beshara et al., "Pharmacokinetics and red cell utilization of iron(III) hydroxide-sucrose complex in anaemic patients: a study using positron emission tomography," Br. J. Haematol. 104:296-302 (1999).
Beyer et al., "Oncoretrovirus and lentivirus vectors pseudotyped with lymphocytic choriomeningitis virus glycoprotein: generation, concentration, and broad host range," J. Virol. 76(3):1488-1495 (2002).
Bickels et al., "Coley's toxin: historical perspective," Isr. Med. Assoc. J. 4(6):471-472 (2002).

(56) References Cited

OTHER PUBLICATIONS

Biffi et al., "Antiproliferative effect of fermented milk on the growth of a human breast cancer cell line," Nutr. Cancer. 28(1):93-99 (1997).
Bisno et al., "Streptococcal infections of skin and soft tissues," N. Engl. J. Med. 334(4):240-245 (1996).
Blanchard et al., "Modified vaccinia virus Ankara undergoes limited replication in human cells and lacks several immunomodulatory proteins: implications for use as a human vaccine," J. Gen. Virol. 79:1159-1167 (1998).
Blasberg et al., "Herpes simplex virus thymidine kinase as a marker/reporter gene for PET imaging of gene therapy," J. Nucl. Med. 43(2):163-169 (1999).
Blasco et al., "Selection of recombinant vaccinia viruses on the basis of plaque formation," Gene 158:157-162 (1995).
Blechacz et al., "Engineered measles virus as a novel oncolytic viral therapy system for hepatocellular carcinoma," Hepatology 44(6):1465-1477 (2006).
Block et al., "Gene therapy of metastatic colon carcinoma: regression of multiple hepatic metastases by adenoviral expression of bacterial cytosine deaminase," Cancer Gene Ther. 7(3):438-445 (2000).
Bodey et al., "Clostridial bacteremia in cancer patients. A 12-year experience," Cancer 67(7):1928-1942 (1991).
Bogdahn et al., "Autocrine tumor cell growth-inhibiting activities from human malignant melanoma," Cancer Res. 49:5358-5363 (1989).
Bogdanov et al., "Antitumor action of glycopeptides from the cell wall of Lactobacillus bulgaricus," Bull. Exp. Biol. Med. 84(12):1750-1753 (1977) [translated from the original Russian article: Byulleten' Eksperimental'noi Biologii I Meditsiny 84(12):709-712 (1977)].
Bogdanov et al., "Antitumour glycopeptides from Lactobacillus bulgaricus cell wall," FEBS Lett. 57(3):259-261 (1975).
Boland et al., "Adenovirus-mediated transfer of the thyroid sodium/iodide symporter gene into tumors for a targeted radiotherapy," Cancer Res. 60:3484-3492 (2000).
Bonnekoh et al., "Adenoviral-mediated herpes simplex virus-thymidine kinase gene transfer in vivo for treatment of experimental human melanoma," J. Invest. Dermatol. 106(6):1163-1168 (1996).
Borellini et al., "The transfer of technology from the laboratory to the clinic: in process controls and final product testing," Chapter 18 in *Gene Therapy Technologies, Applications and Regulations*, Meager, A. (Ed.), John Wiley & Sons Ltd., pp. 359-373 (1999).
Boulanger et al., "Morphogenesis and release of fowlpox virusm," J. Gen. Virol. 81:675-687 (2000).
Bouvier et al., "Functional characterization of the human dopamine D-4.2 receptor using vaccinia virus as an expression system," Eur. J. Pharmacol. 290(1):11-17 (1995).
Boyd, J., "Facilities for large-scale production of vectors under GMP conditions," Chapter 20 in Gene Therapy Technologies, Applications and Regulations, A. Meager (Ed.), pp. 383-400 (1999).
Brader et al., "Imaging genetically engineered oncolytic vaccinia virus (GLV-1h99) using a human norepinephrine transporter reporter gene," Clin. Cancer Res. 15(11):3791-3801 (2009).
Brain et al., "Pulmonary intravascular macrophages: their contribution to the mononuclear phagocyte system in 13 species," Am. J. Physiol. 276(1 pt 1):L146-L154 (1999).
Breman et al., "Diagnosis and management of smallpox," N. Engl. J. Med. 346(17):1300-1308 (2002).
Brockstedt et al., "Development of anti-tumor immunity against a non-immunogenic mammary carcinoma through in vivo somatic GM-CSF, IL-2, and HSVtk combination gene therapy," Mol. Ther. 6(5):627-636 (2002).
Broder et al., "Expression of foreign genes in cultured human primary macrophages using recombinant vaccinia virus vectors," Gene 142:167-174 (1994).
Broder et al., "Recombinant vaccinia viruses," Mol. Biotechnol. 13:223-245 (1999).
Brown, "Killer into cure-oncolytic viruses," Microbiol. Today 56:128-131 (2005).
Browne et al., "Cancer screening by systemic administration of a gene delivery vector encoding tumor-selective secretable biomarker expression," PLoS One 6:(5):e19530, 9 pages (2011).
Broyles, S., "Vaccinia virus transcription," J. Gen. Virol. 84:2293-2303 (2003).
Brunke et al., "Luciferase assembly after transport into mammalian microsomes involves molecular chaperones and peptidyl-prolyl cis/trans-isomerases," J. Biol. Chem. 271(38):23487-23494 (1996).
Buckel et al., "Combination of fractionated irradiation with anti-VEGF expressing vaccinia virus therapy enhances tumor control by simultaneous radiosensitization of tumor associated endothelium," Int. J. Cancer 133(12):2989-2999 (2013).
Buller et al., "Decreased virulence of recombinant vaccinia virus expression vectors is associated with a thymidine kinase-negative phenotype," Nature 317:813-815 (1985).
Buller et al., Found in *Vaccinia Viruses as Vectors for Vaccine Antigens*, New York: Elsevier, Quinnan, G., ed., pp. 37-46 (1985).
Calonder et al., "Kinetic modeling of $^{52}$Fe/$^{52m}$Mn-citrate at the blood-brain barrier by positron emission tomography," J. Neurochem. 73:2047-2055 (1999).
Carrillo et al., "The multiple sequence alignment problem in biology," SIAM J. Applied Math 48:1073-1082 (1988).
Carroll et al., "Active site of Pseudomonas aeruginosa exotoxin A," J. Biol. Chem. 262:8707-8711 (1987).
Carter et al., "Vaccinia virus cores are transported on microtubules," J. Gen. Virol. 84:2443-2458 (2003).
Casado et al, "Strategies to accomplish targeted expression of transgenes in ovarian cancer for molecular therapeutic applications," Clin. Cancer Res. 7(8):2496-2504 (2001).
Cavanagh et al., "Travellers in many guises: the origins and destinations of dendritic cells," Immunol. Cell Biol. 80:448-462 (2002).
Certified English translation of abstract for Aksac, "Antibody formation against Agrobacterium tumefaciens in patients with various cancers," Turk. Hij. Tecr. Biyol. Derg. 34(1-2):48-51 (1974) [Article in Turkish].
Certified English translation of Al'tshtein [Altshteyn] et al., "Isolation of a recombinant vaccinia virus based on the LIVP strain inducing the surface antigen of the hepatitis B virus," Dokl. Akad. Nauk. SSSR. 285(3):696-699 (1985) [Article in Russian].
Certified English Translation of Chernos et al., "Verifying the safety, inoculability, reactogenicity and antigenic properties of a live recombinant smallpox-hepatitis B vaccine in an experiment on volunteers," Vopr. Virusol. (Moscow) 35:132-135 (1990) [Article in Russian].
Certified English translation of Timiryasova et al., "Analysis of reporter gene expression in various regions of the genome of the vaccinia virus," Mol. Biol. 27(2):392-401 (1993) [Article in Russian].
Chakrabarti et al., "Compact, synthetic, vaccinia virus early/late promoter for protein expression," BioTechniques 23(6):1094-1097 (1997).
Chakrabarti et al., "Vaccinia virus expression vector: coexpression of β-galactosidase provides visual screening of recombinant virus plaques," Mol. Cell Biol. 5:3403-3409 (1985).
Chalfie et al., "Green fluorescent protein as a marker for gene expression," Science 263:802-805 (1994).
Chaloupka et al., "Comparative analysis of six european influenza vaccines," Eur. J. Microbiol. Infect. Dis. 15(2):121-127 (1996).
Chamberlain et al., "Costimulation enhances the active immunotherapy effect of recombinant anticancer vaccines," Cancer Res. 56:2832-2836 (1996).
Chambers et al., "Dissemination and growth of cancer cells in metastatic sites," Nat. Rev. Cancer 2:563-572 (2002).
Chambers et al., "Molecular biology of breast cancer metastasis. Clinical implications of experimental studies on metastatic inefficiency," Breast Cancer Res. 2:400-407 (2000).
Chang et al., "Differential apoptotic susceptibility to anti-Fas IgM and anticancer drugs in a human endometrial adenocarcinoma cell line HHUA on laminin and type I collagen," Osaka City Med. J. 44(2):173-180 (1998).

(56) References Cited

OTHER PUBLICATIONS

Chaudhuri et al., "Light-based imaging of green fluorescent protein-positive ovarian cancer xenografts during therapy," Gynecol. Oncol. 82(3):581-589 (2001).
Cheadle et al., "Bugs as drugs for cancer," Immunol. 107:10-19 (2002).
Chen et al. "Cancer gene therapy by direct tumor injections of a nonviral T7 vector encoding a thymidine kinase gene," Hum. Gene Ther. 9(5):729-736 (1998).
Chen et al., "A novel recombinant vaccinia virus expressing the human norepinephrine transporter retains oncolytic potential and facilitates deep tissue imaging," Mol. Med. 15(5-6):144-151 (2009).
Chen et al., "Oncolytic vaccinia virus: a theranostic agent for cancer," Future Virology, 5(6):763-784 (2010).
Chen et al., "Oncolytic viruses," Advances in Virology, vol. 2012:Article ID 320206, 2 pages (2012).
Chen et al., "Real-time monitoring of vaccinia virus infection in cultured cells and in living mice using light-emitting proteins," Proceedings of the 14th International Symposium on Bioluminescence & Chemiluminescence: Chemistry, Biology and Applications, World Scientific: Singapore: 181-184 (2007).
Chen et al., "Replication efficiency of oncolytic vaccinia virus in cell cultures prognosticates the virulence and antitumor efficacy in mice," J. Translational Med. 9(1):164, 11 pages, epub date Sep. 27, 2011.
Chen et al., "Targeting hematologic malignancies with oncolytic vaccinia virus constructs," J Immunother Cancer. 1(Suppl 1):P226 (2013).
Chen et al., "Tropism of oncolytic vaccinia virus constructs for human mononuclear cell subsets," 27th Annual Meeting Final Program, Society for Immunotherapy of Cancer (SITC), Oct. 26-28, 2012, North Bethesda MD. [oral presentation abstract] 1 page.
Chen et al., "Tropism of oncolytic vaccinia virus constructs for human mononuclear cell subsets," 27th Annual Meeting Final Program, Society for Immunotherapy of Cancer (SITC), Oct. 26-28, 2012, North Bethesda MD. [Presentation slides] [online]Retrieved from:URL:sitcancer.org/meetings/am12/presentations/index.php?filename=AM-FRI-3.15 pm Boris Minev SITC_2012.pdf, 9 pages.
Chen et al., "Evaluation of combined vaccinia virus-mediated antitumor gene therapy with p53, IL-2, and IL-12 in a glioma model," Cancer Gene Ther. 7(11):1437-1447 (2000).
Chen et al., "Evaluation of cytokine toxicity induced by vaccinia virus-mediated IL-2 and IL-2 antitumor immunotherapy," Cytokine 15(61):305-314 (2001).
Chen et al., "Low-dose vaccinia virus-mediated cytokine gene therapy of glioma," J. Immunother. 24(1):46-57 (2001).
Chernajovsky et al., "Fighting cancer with oncolytic viruses," BMJ 332(7534):170-172 (2006).
Chernichenko et al., "Oncolytic vaccinia therapy of salivary gland carcinoma," JAMA Otolaryngol Head Neck Surg 139(2):173-182 (2013).
Chernos et al., "Verifying the safety, inoculability, reactogenicity and antigenic properties of a live recombinant smallpox-hepatitis B vaccine in an experiment on volunteers," Vopr. Virusol. (Moscow) 35:132-135 (1990) [article in the Russian language].
Chiang et al., "Anti-proliferative effect of apigenin and its apoptotic induction in human Hep G2 cells," Cancer Lett 237:207-214 (2006).
Child et al., "Insertional inactivation of the large subunit of ribonucleotide reductase encoded by vaccinia virus is associated with reduced virulence in vivo," Virol. 174:625-629 (1990).
Chiocca, E., "Oncolytic viruses," Nat. Rev. Cancer 2(12):938-950 (2002).
Chkheidze et al., "Identification of DNA binding proteins in vaccinia virus by DNA-protein crosslinking," FEBS 336(2):340-342 (1993).
Cichutek, K., "Development and regulation of gene therapy drugs in Germany," Chapter 17 in *Gene Therapy Technologies, Applications and Regulations*, Meager, A. (Ed.), John Wiley & Sons Ltd. pp. 347-358 (1999).
Clairmont et al., "Enhanced antitumor activity from tumor-targeting Salmonella expressing endostatin," American Association for Cancer Research: 91st Annual Meeting of the AACR, 41:732 Abstract #4653 (Apr. 1-5, 2000).
Clairmont et al., "Biodistribution and genetic stability of the novel antitumor agent VNP20009, a genetically modified strain of *Salmonella typhimurium*," J. Infect. Dis. 181(6):1996-2002 (2000).
ClinicalTrials.gov, "A Study of GL-ONC1, an oncolytic vaccinia virus, in patients with advanced peritoneal carcinomatosis," [online][retrieved on Oct. 7, 2013] Retrieved from: <URL:clinicaltrials.gov/ct2/show?term=genelux&rank=1>, 4 pages.
ClinicalTrials.gov, "Intra-pleural administration of GL-ONC1, a genetically modified vaccinia virus, in patients with malignant pleural effusion: primary, metastases and mesothelioma," [online][retrieved on Oct. 7, 2013] Retrieved from:<URL:clinicaltrials.gov/ct2/show?term=genelux&rank=4>, 4 pages.
ClinicalTrials.gov, "Safety study of attenuated vaccinia virus (GL-ONC1)with combination therapy in head & neck cancer," [online][retrieved on Oct. 7, 2013] Retrieved from:<URL:clinicaltrials.gov/ct2/show?term=genelux&rank=2>, 4 pages.
ClinicalTrials.gov, "Safety study of GL-ONC1, an oncolytic virus, in patients with advanced solid tumors," [online][retrieved on Dec. 2, 2008] Retrieved from: <URL: clinicaltrials.gov/ct2/show/NCT00794131?term—genelux&rank=1, 4 pages.
Cole, A. and T. Ganz, "Human antimicrobial peptides: analysis and application," Biotechniques 29(4):822-831 (2000).
Colinas et al., "A DNA ligase gene in the copenhagen strain of vaccinia virus is nonessential for viral replication and recombination," Virology 179:267-275 (1990).
Collins et al., "Suppression of SV40 tumors after immunization with group A *Streptococcus pyogenes* and *Bordetella pertussis*," Cancer Res. 34(5):932-937 (1974).
Compton et al., "Insertion of nonhomologous DNA into the yeast genome mediated by homologous recombination with a cotransforming plasmid," Mol. Gen. Genet. 188(1):44-50 (1982).
Condeelis et al., "Intravital imaging of cell movement in tumours," Nat. Rev. Cancer 3:921-930 (2003).
Conry et al., "Phase I trial of a recombinant vaccinia virus encoding carcinoembryonic antigen in metastatic adenocarcinoma: comparison of intradermal versus subcutaneous administration," Clin. Cancer Res. 5:2330-2337 (1999).
Contag et al., "Visualizing gene expression in living mammals using a bioluminescent reporter," Photochem. Photobiol. 66(4):523-531 (1997).
Contag et al., "Photonic detection of bacterial pathogens in living hosts," Mol. Microbiol. 18:593-603 (1995).
Corral et al., "Phase I clinical trial of genetically modified and oncolytic vaccinia virus GL-ONC1 with green fluorescent protein imaging," [poster] 7th NCRI Cancer Conference, Liverpool, UK. Nov. 6-9, 2011, 1 page.
Corral et al., "Phase I clinical trial of genetically modified and oncolytic vaccinia virus GL-ONC1 with green fluorescent protein imaging," [abstract] 7th NCRI Cancer Conference, Liverpool, UK. Nov. 6-9, 2011, 2 pages.
Coupar et al., "A general method for the construction of recombinant vaccinia viruses expressing multiple foreign genes," Gene 68:1-10 (1988).
Coupar et al., "Insertion sites for recombinant vaccinia virus construction: effects on expression of a foreign protein," J. Gen. Virol. 81:431-439 (2000).
Coussens et al., "Inflammation and cancer," Nature 420:860-867 (2002).
Craperi et al. "Increased bax expression is associated with cell death induced by ganciclovir in a herpes thymidine kinase gene-expressing glioma cell line," Hum. Gene Ther. 10(4):679-688 (1999).
Crystal, "Transfer of genes to humans: early lessons and obstacles to success," Science 270:404-410 (1995).
Culver et al., "In vivo gene transfer with retroviral vector-producer cells for treatment of experimental brain tumors," Science 256(5063):1550-1552 (1992).

(56) References Cited

OTHER PUBLICATIONS

Dai et al., "Oncolytic vaccinia virus in combination with radiation shows synergistic antitumor efficacy in pancreatic cancer," Cancer Lett. 344(2):282-290 (2014).
Dang et al., "Combination bacteriolytic therapy for the treatment of experimental tumors," Proc. Natl. Acad. Sci. U.S.A. 98(26):15155-15160 (2001).
Davis et al., "Oncolytic virotherapy for cancer treatment: challenges and solutions," J. Gene Med. 7(11):1380-1389 (2005).
Davis et al., "The role of inflammation in vascular injury and repair," J. Thromb. Haemost. 1:1699-1709 (2003).
Davis, C., "The many faces of epidermal growth factor repeats," New Biol. 2(5):410-419 (1990).
Davison et al., "New vaccinia virus recombination plasmids incorporating a synthetic late promoter for high level expression of foreign proteins," Nucleic Acids Res. 18:4285-4286 (1990).
Davison, A. and B. Moss., "Structure of vaccinia virus early promoters," J. Mol. Biol. 210:749-769 (1989).
De Clercq E., "Acyclic nucleoside phosphonates: a new dimension to the chemotherapy of DNA virus and retrovirus infections," J. Med. Microbiol. 47(1):1-3 (1998).
De Clercq E., "Historical perspectives in the development of antiviral agents against poxviruses," Viruses 2:1322-1339 (2010).
De Clercq E., "Cidofovir in the therapy and short-term prophylaxis of poxvirus infections," Trends Pharmacol. Sci. 23(10):456-458 (2002).
de Lorenzo, V., "Isolation and characterization of microcin E492 from Klebsiella pneumoniae," Arch. Microbiol. 139(1):72-75 (1984).
de Wet et al., "Firefly luciferase gene: structure and expression in mammalian cells," Mol. Cell. Biol. 7: 725-737 (1987).
Demers et al., "Pharmacologic indicators of antitumor efficacy for oncolytic virotherapy," Cancer Res. 63:4003-4008 (2003).
Demkowicz et al., "Human cytotoxic T-cell memory: long-lived responses to vaccinia virus," J. Virol. 70(4):2627-2631 (1996).
Derwent English abstract for Japanese Patent Publication JP 55035004, published Feb. 3, 1987, entitled, "Cellular immunopotentiator—contg. Vaccinia attenuated virus showing no infectivity to man or rabbit and has lost humoral immunity," Derwent Accession No. 2512008, 1 page.
Derwent English abstract for WO 1994/10302, published May 11, 1994 entitled: "Vectors inhibiting HIV replication in potential host cells—contg. DNA encoding Pol, Gag, Env, Rev, and/or Tat in antisense direction and further DNA causing spontaneous amplification," Derwent Accession No. 1994-152544 [19], 2 pages.
Devereux et al., "A comprehensive set of sequence analysis programs for the VAX," Nucleic Acids Res. 12(1):387-395 (1984).
Dietrich et al., "Delivery of antigen-encoding plasmid DNA into the cytosol of macrophages by attenuated suicide Listeria monocytogenes," Nat. Biotechnol. 16(2):181-185 (1998).
Ding et al., "Zinc-dependent dimers observed in crystals of human endostatin," Proc. Natl. Acad. Sci. U.S.A. 95:10443-10448 (1998).
DiStefano et al., "Viral-induced remission in chronic lymphocytic leukemia?" Arch. Intern. Med. 139(8):946 (1979).
Djeha et al., "Combined adenovirus-mediated nitroreductase gene delivery and CB1954 treatment: a well-tolerated therapy for established solid tumors," Mol. Ther. 3(2):233-240 (2001).
Djeha et al., "Expression of *Escherichia coli* B nitroreductase in established human tumor xenografts in mice results in potent antitumoral and bystander effects upon systemic administration of the prodrug CB1954," Cancer Gene Ther. 7(5):721-731 (2000).
Dobbelstein, M., "Viruses in therapy—royal road or dead end?" Virus Res. 92:219-221 (2003).
Domi et al., "Cloning the vaccinia virus genome as a bacterial artificial chromosome in *Escherichia coli* and recovery of infectious virus in mammalian cells," Proc. Natl. Acad. Sci. U.S.A. 99(19):12415-12420 (2002).
Donat et al., "Preferential colonization of metastases by oncolytic vaccinia virus strain GLV-1h68 in a human PC-3 prostate cancer model in nude mice," PLOS ONE 7(9):e45942, 13 pages. (2012).
Drexler et al., "Modified vaccinia virus Ankara as antigen delivery system: how can we best use its potential," Curr. Opin. Biotechnol. 15(6):506-512 (2004).
Duggal et al., "Vaccinia virus expressing bone morphogenetic protein-4 in novel glioblastoma orthotopic models facilitates enchanced tumor regression and long-term survival," J. of Translational Medicine 11:155 [article in press doi:10.1186/1479-5876-11-155], 14 pages. (2013).
Duncan et al., "Intracellular metabolism of indium-111-DTPA-labeled receptor targeted proteins," J. Nucl. Med. 34(10):1728-1738 (1993).
Dunn et al., "Cancer inununoediting: from immunosurveillance to tumor escape," Nat. Immunol. 3(11):991-998 (2002).
Earl et al., "T-lymphocyte priming and protection against friend leukemia by vaccinia-retrovirus env gene recombinant," Science 234:728-731 (1986).
Eastham et al. "Prostate cancer gene therapy: herpes simplex virus thymidine kinase gene transduction followed by ganciclovir in mouse and human prostate cancer models," Hum. Gene Ther. 7(4):515-523 (1996).
Ebert et al., "Oncolytic vesicular stomatitis virus for treatment of orthotopic hepatocellular carcinoma in immune-competent rats," Cancer Res. 63:3605-3611 (2003).
Ebert et al., "Syncytia induction enhances the oncolytic potential of vesicular stomatitis virus in virotherapy for cancer," Cancer Res. 64:3265-3270 (2004).
Eck et al., "Gene-Based Therapy," in *Goodman & Gilman's The Pharmacological Basis of Therapeutics*, McGraw-Hill, New York, p. 77-101 (1996).
Ehrengruber, M., "Alphaviral gene transfer in neurobiology," Brain Res. Bull. 59(1):13-22 (2002).
Ehrig et al, "Growth inhibition of different human colorectal cancer xenografts after a single intravenous injection of oncolytic vaccinia virus GLV-1h68," Journal of Translation Medicine 11:79, 32 pages (2013).
Eliopoulos et al., "CD40 induces apoptosis in carcinoma cells through activation of cytotoxic ligands of the tumor necrosis factor superfamily," Mol. Cell Biol. 20(15):5503-5515 (2000).
Emens, L., "Cancer vaccines:on the threshold of success," Expert Opin. Emerg. Drugs 13(2):295-308 (2008).
Engebrecht et al., "Measuring gene expression with light," Science 227:1345-1347 (1985).
Enserink, M., "Public health. Treating vaccine reactions: two lifelines, but no guarantees," Science 298(5602):2313 (2002).
Escher et al., "Bacterial luciferase αβ fusion protein is fully active as a monomer and highly sensitive in vivo to elevated temperature," Proc. Natl. Acad. Sci. U.S.A. 86(17):6528-6532 (1989).
Escher et al., "GroE-mediated folding of bacterial luciferases in vivo," Mol. Gen. Genet. 238(1-2):65-73 (1993).
Escher et al., "The β subunit polypeptide of Vibrio harveyi luciferase determines light emission at 42° C," Mol. Gen. Genet. 230(3):385-393 (1991).
Esposito et al., "Poxviruses," Chapter 85 in *Field's Virology*, 4th Edn., vol. 2, Edited by Knipe, M. and P. Howley (Eds.), Philadelphia: Lippincott Williams & Wilkins, 2885-2921 (2001).
Essbauer et al., "Viruses of lower vertebrates," J. Vet. Med. B. Infect. Dis. Vet. Public Health 48(6):403-475 (2001).
Estin et al, "Recombinant vaccinia virus vaccine against the human melanoma antigen p97 for use in immunotherapy," Proc. Natl. Acad. Sci. U.S.A. 85:1052-1056 (1988).
Everts et al., "Replication-selective oncolytic viruses in the treatment of cancer," Cancer Gene Ther. 12:141-161 (2005).
Fabricius et al., "Quantitative investigations into the elimination of in vitro-obtained spores of the non-pathogenic Clostridium butyricum strain CNRZ 528, and their persistence in organs of different species following intravenous spore administration," Res. Microbiol. 144:741-753 (1993).
Farkas-Himsley et al., "The bacterial colicin active against tumor cells in vitro and in vivo is verotoxin 1," Proc. Natl. Acad. Sci. U.S.A. 92(15):6996-7000 (1995).
FASEB Public Release Jan. 30, 2014, "Engineered virus is effective against triple negative breast cancer cells" [online] [retrieved Mar.

(56) References Cited

OTHER PUBLICATIONS 24, 2014] [Retrieved from:<URL:eurekalert.org/pub_releases/2014-01/foas-evi013014.php#, 1 page.
Fatyol et al., "The p14$^{ARF}$ tumor suppressor protein facilitates nucleolar sequestration of hypoxia-inducible factor-1I (HIF-1I ) and inhibits HIF-1-mediated transcription," J. Biol. Chem. 276(30):28421-28429 (2001).
Feng et al, "The antitumor activity of a mixed bacterial vaccine against mouse hepatoma," Chinese Pharm. J. 30(7):405-407 (1995) [Article in Chinese; English abstract on last page of article].
Fernández-Piñas et al., "Expresssion of luxCD-E in *Anabaena* sp. can replace the use of exogenous aldehyde for in vivo localization of transcription by luxAB," Gene 150:169-174 (1994).
Ferretti et al., "Complete genome sequence of an M1 strain of *Streptococcus pyogenes*," Proc. Natl. Acad. Sci. U.S.A. 98(8):4658-4663 (2001).
Fidler, "The pathogenesis of cancer metastasis: the 'seed and soil' hypothesis revisited," Nat. Cancer Res. 3:1-6 (2003).
Fikes, B. "New tool finds, fights cancer," San Diego Union-Tribune, Published Feb. 11, 2013, 1 page (2013).
Flexner et al., "Characterization of human immunodeficiency virus gag/pol gene products expressed by recombinant vaccinia viruses," Virol. 166:339-349 (1988).
Flexner et al., "Successful vaccination with a polyvalent live vector despite existing immunity to an expressed antigen," Nature 355:259-262 (1988).
Fodor et al., "Vaccinia virus mediated p53 gene therapy for bladder cancer in an orthotopic murine model," J. Urol. 173(2):604-9 (2005).
Foran et al., "Nucleotide sequence of the LuxA and LuxB genes of the bioluminescent marine bacterium Vibrio fischeri," Nucleic Acids Res. 16: 777 (1988).
Forbes et al., "Sparse initial entrapment of systematically injected *Salmonella typhimurium* leads to heterogenous accumulation within tumors," Cancer Res. 63: 5188-5193 (2003).
Fox, A., "Emergency and compassionate-use INDs and accelerated NDS or ANDA Approvals—procedures, benefits and pitfalls," Chapter 26 in *Principles and Practice of Pharmaceutical Medicine*, Fletcher et al.(Eds.), John Wiley & Sons, pp. 299-305 (2002).
Francis et al., "Monitoring bioluminescent *Staphyloccus aureus* infections in living mice using a novel luxABCDE construct," Infect. Immun. 68(6): 3594-3600 (2000).
Freitag et al., "Examination of Listeria monocytogenes intracellular gene expression by using green fluorescent protein of Aequorea victoria," Infect. Immun. 67:1844-1852 (1999).
Frentzen et al., "Anti-VEGF single chain antibody GLAF-1 encoded by oncolytic vaccinia virus significantly enhances antitumor therapy," Proc. Natl. Acad. Sci. U.S.A. 106(31):12915-12920 (2009).
Friberg et al., "On the growth rates of human malignant tumors: implications for medical decision making," J. Surg. Oncol. 65:284-297 (1997).
Friedlos et al., "Three new prodrugs for suicide gene therapy using carboxypeptidase G2 elicit bystander efficacy in two xenograft models," Cancer Res. 62(6):1724-1729 (2002).
Gallagher, R., "Vaccination undermined," The Scientist 17(22):1-3 (2003).
Galmiche et al., "Expression of a functional single chain antibody on the surface of extracellular enveloped vaccinia virus as a step towards selective tumour cell targeting," J. Gen. Virol. 78:3019-3027 (1997).
Gambhir et al., "Imaging transgene expression with radionuclide imaging technologies," Neoplasia 2(1-2):118-138 (2000).
Gautam et al., "Delivery systems for pulmonary gene therapy," Am. J. Respir. Med. 1(1):35-46 (2002).
Genbank Accession No. AF177421, "*Arabidopsis halleri* subsp. *halleri* clone 122.5.1 ribosomal RNA intergenic region and external transcribed spacer region, completesequence," Published on Oct. 11, 2005 [online][retrieved on Sep. 22, 2011] Retrieved from:<URL:ncbi.nlm.nih.gov/nuccore/AF177421 [2 pages].
Genelux Press Release, "Virus engineered to express melanin offers new possibilities to diagnose and treat solid tumor cancers," Published on Feb. 11, 2013 [online] [retrieved on Jul. 3, 2013] Retrieved from:<URL:genelux.com/february-11-2013//, 2 pages.
Genelux Press Release, "First patient treated in Genelux Phase I trial with GL-ONC1 at Memorial Sloan Kettering Cancer Center," Published on Feb. 5, 2013 [online][retrieved on Jul. 3, 2013] Retrieved from:<URL:genelux.com/february-05-2013/, 3 pages.
Genelux Press Release Jun. 14, 2012, "Genelux corporation announces first patient dosed in phase I combination clinical trial of GL-ONC1," [online] Published on Jun. 14, 2012 [online][retrieved on Jan. 28, 2013] Retrieved from:<URL:genelux.com/genelux2012/?page_id=2701, 2 pages.
Genelux Press Release, "Genelux presents abstracts at the 7th international meeting on replicating oncolytic virus therapeutics in Quebec," Published on Jun. 15, 2013 [online][retrieved on Jul. 3, 2013] Retrieved from:<URL:genelux.com/june-15-2013/, 2 pages.
Genelux Press Release, "Industry veteran with more than 25 years experience will lead development and european commercialization and growth," Published on Jun. 27, 2013 [online][retrieved on Oct. 7, 2013] Retrieved from:<URL:genelux.com/june-27-2013/, 2 pages.
Genelux Press Release Jun. 28, 2012, "Genelux corporation announces ground-breaking clinical study evaluating oncolytic vaccinia virus in canine cancer patients," [online] Published on Jun. 28, 2012 [online][retrieved on Jan. 28, 2013] Retrieved from:<URL:genelux.com/genelux2012/?page_id=3824, 2 pages.
Genelux Press Release Jun. 6, 2011, "ASCO poster presentation unveils preliminary results of phase I clinical trial involving intraveneous administration of GL-ONC1 to patients with advanced solid tumor cancers," [online] Published on Jun. 6, 2011 [retrieved on Jan. 28, 2013] Retrieved from:<URL:genelux.com/genelux2012/?page_id=1357, 1 page.
Genelux Press Release May 30, 2012, "Genelux corporation announces phase I data presentation at 2012 ASCO Annual Meeting of GL-ONC1, its oncolytic virus lead product candidate," [online] Published on May 30, 2012 [online][retrieved on Jan. 28, 2013] Retrieved from:<URL:genelux.com/genelux2012/?page_id=2686 &preview=true, 2 pages.
Genelux Press Release, "Genelux corporation presents abstracts at 2013 ASCO annual meeting for clinical trials of GL-ONC1, its oncolytic virus lead product candidate," Published on May 30, 2013 [online][retrieved on Jul. 3, 2013] Retrieved from:<URL:genelux.com/may-30-2013/, 2 pages.
Genelux Press Release May 31, 2012, "Genelux corporation announces treatment of first patient in phase I/II clinical trial of GL-ONC1 in advanced peritoneal cavity cancers," [online] Published on May 31, 2012 [online][retrieved on Jan. 28, 2013] Retrieved from:<URL:genelux.com/genelux2012/?page_id=2691, 2 pages.
Genelux Press Release Nov. 1, 2012, "Genelux corporation announces early results of a phase I/II clinical trial of virotherapeutic GL-ONC1 in advanced peritoneal cavity cancers," [online] Published on Nov. 1, 2012 [online][retrieved on Jan. 28, 2013] Retrieved from:<URL:genelux.com/genelux2012/?page_id=4157, 3 pages.
Genelux Press Release Nov. 18, 2013, "Genelux Corporation's GL-ONC1 selected by Elsevier among its 'Top 10 Oncology Projects to Watch'" [online] [retrieved Mar. 21, 2014] [Retrieved from:<URL:genelux.com/november-18-2013/ , 2 pages.
Gentschev et al., "Characterization and evaluation of a new oncolytic Vaccinia Virus strain LIVP6.1.1 for canine cancer therapy," Bioengineered 4(2):1-6 (2013).
Gentschev et al., "Efficient colonization and therapy of human hepatocellular carcinoma (HCC) using the oncolytic vaccinia virus strain GLV-1h68," PLoS One. 6(7):1-9 (2011).
Gentschev et al., "Preclinical evaluation of oncolytic vaccinia virus for therapy of canine soft tissue sarcoma," PLoS One 7:(5) 37239, 12 pages (2012).
Gentschev et al., "Regression of human prostate tumors and metastases in nude mice following treatment with the recombinant oncolytic vaccinia virus GLV-1h68," J. Biomed. Biotechnol. 2010:1-11 (2010).

(56) References Cited

OTHER PUBLICATIONS

Gentschev et al., "Significant growth inhibition of canine mammary carcinoma xenografts following treatment with oncolytic vaccinia virus GLV-1h68," J. Oncol. 2010:1-10 (2010).
Gentschev et al., "Use of an oncolytic vaccinia virus for treatment of canine breast cancer in nude mice: preclinical development of a therapeutic agent," Cancer Gene Ther. 16(4):320-328 (2009).
Gherardi et al., "Recombinant poxviruses as mucosal vaccine vectors," J. Gen. Virol. 86:2925-2936 (2005).
Gholami et al., "Vaccinia virus GLV-1h153 in combination with 131I shows increased efficiency in treating triple-negative breast cancer," FASEB Journal, Published online before print Nov. 1, 2013 [article in press doi:10.1096/fj.13-237222], 7 pages (2013).
Gholami et al., "Vaccinia virus GLV-1h153 is a novel agent for detection and effective local control of positive surgical margins for breast cancer," Breast Cancer Res 15(2):R26, 11 pages (2013).
Gholami et al., "Vaccinia virus GLV-1h153 is effective in treating and preventing metastatic triple-negative breast cancer," Annals of Surgery 256(3):437-445 (2012).
Giacomin et al., "Expression of a PALI promoter luciferase gene function in Arabidopsis thaliana in response to infection by phytopathogenic bacteria," Plant Sci. 116: 59-72 (1996).
Giavedoni et al., "Vaccinia virus recombinants expressing chimeric proteins of human immunodeficiency virus and gamma-interferon are attenuated for nude mice," Proc. Natl. Acad. Sci. 89:3409-3413 (1992).
Giedlin et al., "Vesicular stomatitis virus: an exciting new therapeutic oncolytic virus candidate for cancer or just another chapter from *Field's Virology*?" Cancer Cell 4: 241-243 (2003).
Gnant et al, "Tumor-specific gene delivery using recombinant vaccinia virus in a rabbit model of liver metastases," J. Natl. Cancer Inst. 91(20):1744-1750 (1999).
Gnant et al., "Regional versus systemic delivery of recombinant vaccinia virus as suicide gene therapy for murine liver metastases," Ann. Surg. 230(3):352-361 (1999).
Gnant et al., "Sensitization of tumor necrosis factor α-resistant human melanoma by tumor-specific in vivo transfer of the gene encoding endothelial monocyte-activating polypeptide II using recombinant vaccinia virus," Cancer Res. 59:4668-4674 (1999).
Gnant et al., "Systemic administration of a recombinant vaccinia virus expressing the cytosine deaminase gene and subsequent treatment with 5-fluorocytosine leads to tumor-specific gene expression and prolongation of survival in mice," Cancer Res. 59(14):3396-3403 (1999).
Goebel et al., "Appendix to 'The complete DNA sequence of vaccinia virus,'" Virology 179:517-563 (1990).
Goebel et al., "The complete DNA sequence of vaccinia virus," Virology 179:247-266 (1990).
Golstein, "Cell death: TRAIL and its receptors," Curr. Biol. 7(12):R750-R753 (1997).
Gomella et al., "Phase I study of intravesical vaccinia virus as a vector for gene therapy of bladder cancer," J. Urol. 166:1291-1295 (2001).
Gómez et al., "Recombinant proteins produced by vaccinia virus vectors can be incorporated within the virion (IMV form) into different compartments," Arch. Virol. 146: 875-892 (2001).
Gorecki, D., "Prospects and problems of gene therapy: an update," Expert Opin. Emerg. Drugs 6(2):187-198 (2001).
Gray, J., "Evidence emerges for early metastasis and parallel evolution of primary and metastatic tumors," Cancer Cell 4(1):4-6 (2003).
Greco et al., "Development of a novel enzyme/prodrug combination for gene therapy of cancer: horseradish peroxidase/indole-3-acetic acid," Cancer Gene Ther. 7(11):1414-1420 (2000).
Green et al., "A matter of life and death," Cancer Cell 1:19-30 (2002).
Greer III, L. and A. Szalay, Imaging of light emission from the expression of luciferases in living cells and organisms: a review, Luminescence 17(1):43-74 (2002).
Greinwald et al., "Treatment of lymphangiomas in children: an update of Picibanil (Ok-432) sclerotherapy," Otolaryngol. Head Neck Surg. 121(4):381-387 (1999).
Gribskov et al., "Sigma factors from *E. coli, B. subtilis*, phage SP01, and phage T4 are homologous proteins," Nucl. Acids Res. 14:6745-6763 (1986).
Gridley et al., "Evaluation of radiation effects against C6 glioma in combination with vaccinia virus-p53 gene therapy," Int. J. Oncol. 13(5):1093-1098 (1998).
Gridley et al., "Proton radiation and TNF-α/Bax gene therapy for orthotopic C6 brain tumor in Wistar rats," Technol. Cancer Res. Treat. 3(2):217-227 (2004).
Griffin, D., "A review of alphavirus replication in neurons," Neurosci. Biobehay. Rev. 22(6):721-723 (1998).
Grote et al., "Live attenuated measles virus induces regression of human lymphoma xenografts in immunodeficient mice," Blood 97(12):3746-3754 (2001).
Grove et al. "Virus-directed enzyme prodrug therapy using CB1954," Anti-Cancer Drug Des. 14(6):461-472 (1999).
Guo et al., "The enhanced tumor selectivity of an oncolytic vaccinia lacking the host range and antiapoptosis genes SPI-1 and SPI-2," Cancer Res. 65(21):9991-9998 (2005).
Guo et al., "Vaccinia as a vector for gene delivery," Expert Opin. Biol. Ther. 4(6):901-917 (2004).
Gura, T., "Systems for identifying new drugs are often faulty," Science 278:1041-1042 (1997).
Guy et al., "Expression of the neu protooncogene in the mammary epithelium of transgenic mice induces metastatic disease," Proc. Natl. Acad. Sci.U.S.A. 89:10578-10582 (1992).
Hacein-Bey-Abina et al., "A serious adverse event after successful gene therapy for X-linked severe combined immunodeficiency," N. Engl. J. Med. 348(3):255-266 (2003).
Haddad et al., "A novel genetically modified oncolytic vaccinia virus is effective against a wide range of human cancers," Annals of Surgical Oncology, 3:S665-S674 (2012).
Haddad et al., "Imaging characteristics, tissue distribution, and spread of a novel oncolytic vaccinia virus carrying the human sodium iodide symporter," PLoS One. 7(8):e41647, 13 pages (2012).
Haddad et al., "A vaccinia virus encoding the human sodium iodide symporter facilitates long-term image monitoring of virotherapy and targeted radiotherapy of pancreatic cancer," J. Nucl. Med. 53:1933-1942 (2012).
Haghighat et al., "Antitumor effect of IL-2, p53, and bax gene transfer in C6 glioma cells," Anticancer Res. 20(3A):1337-1342 (2000).
Hall et al., "Adenovirus-mediated herpes simplex virus thymidine kinase gene and ganciclovir therapy leads to systemic activity against spontaneous and induced metastasis in an orthotopic mouse model of prostate cancer," Int. J. Cancer 70(2):183-187 (1997).
Hall et al., "In vitro efficacy of transferrin-toxin conjugates against glioblastoma multiforme," J. Neurosurg. 76(5):838-844 (1992).
Hall et al., "In vivo efficacy of intrathecal transferrin-Pseudomonas exotoxin A immunotoxin against LOX melanoma," Neurosurg. 34(4):649-655; discussion 655-656 (1994).
Halsell et al., "Myopericarditis following smallpox vaccination among vaccinia-naïve US military personnel," J. Am. Med. Assoc. 289(24): 3283-3289 (2003).
Hamblin et al., "Rapid control of wound infections by targeted photodynamic therapy monitored by in vivo bioluminescence imaging," Photochem. Photobiol. 75(1):51-57 (2002).
Hanahan et al., "The hallmarks of cancer," Cell 100:57-70 (2000).
Hansen et al., "Remission of chronic lymphocytic leukemia after smallpox vaccination," Arch. Intern. Med. 138:1137-1138 (1978).
Hansen et al., "Assessment of GFP fluorescence in cells of *Streptococcus gordonii* under conditions of low pH and low oxygen concentration," Microbiol. 147:1383-1391 (2001).
Harrington, Kevin, "GL-ONC1 Phase I Trial at Royal Marsden Hospital," Roche-Genelux Meeting, Penzberg, Germany, Sep. 19, 2011 [poster] 25 pages.
Harrison et al., "Gene-modified PA1-STK cells home to tumor sites in patients with malignant pleural mesothelioma," Ann. Thorac. Surg. 70(2):407-411 (2000).

(56) References Cited

OTHER PUBLICATIONS

Hasegawa et al., "Avoidance of bone marrow suppression using A-5021 as a nucleoside analog for retrovirus-mediated herpes simplex virus type I thymidine kinase gene therapy," Cancer Gene Ther. 7(4):557-562 (2000).
Hasegawa et al., "In vivo tumor delivery of the green fluorescent protein gene to report future occurrence of metastasis," Cancer Gene Ther. 7:1336-1340 (2000).
Hatta, M., "Antitumor mechanisms of Eubacterium lentum and its components," Asian Pac. J. Allergy Immunol. 13:129-137 (1995).
Hauser et al., "Poxvirus as a vector to transduce human dendritic cells for immunotherapy: abortive infection but reduced APC function," Gene Ther. 7(18):1575-1583 (2000).
Hawkins et al., "Oncolytic biotherapy: a novel therapeutic platform," Lancet Oncol. 3:17-26 (2002).
He et al., "Effective oncolytic vaccinia therapy for human sarcomas," J. Surg. Res. 175(2):e53-e60 (2012).
He et al., "In vivo quantitation of rare circulating tumor cells by multiphoton intravital flow cytometry," Proc. Natl. Acad. Sci. 104(28):11760-11765 (2007).
Heise et al., "Efficacy of a replication-competent adenovirus (ONYX-015) following intratumoral injection: intratumoral spread and distribution effects," Cancer Gene Ther. 6(6):499-504 (1999).
Hemarm et al., "High-copy expression vector based on amplification-promoting sequences," DNA Cell Biol. 13:437-445 (1994).
Hermiston et al., "Armed therapeutic viruses: strategies and challenges to arming oncolytic viruses with therapeutic genes," Cancer Gene Ther. 9:1022-1035 (2002).
Hermiston et al., "Genetically based therapeutics for cancer: similarities and contrasts with traditional drug discovery and development," Mol. Ther. 11(4):496-507 (2005).
Herrlinger et al., "Neural precursor cells for delivery of replication-conditional HSV-1 vectors to intracerebral gliomas," Mol Ther. 1(4):347-357 (2000).
Hersey et al., "Adjuvant immunotherapy of patients with high-risk melanoma using vaccinia viral lysates of melanoma: results of a randomized trial," J. Clin. Oncol. 20(20):4181-4190 (2002).
Hess et al., "Bacterial glucuronidase as general marker for oncolytic virotherapy or other biological therapies," J. Transl Med. 9:172, 12 pages (2011).
Hess et al., "Listeria monocytogenes p60 supports host cell invasion by and in vivo survival of attenuated *Salmonella typhimurium*," Infect. Immun. 63(5):2047-2053 (1995).
Hetz et al., "Microcin E492, a channel-forming bacteriocin from Klebsiella pneumoniae, induces apoptosis in some human cell lines," Proc. Natl. Acad. Sci. U.S.A. 99(5):2696-2701 (2002).
Hiller et al., "Characterization of intracellular and extracellular vaccinia virus variants: $N_1$-isonicotinoyl-$N_2$-3-methyl-4-chlorobenzoylhydrazine interferes with cytoplasmic virus dissemination and release," J. Virol. 39(3):903-913 (1981).
Hofmann et al., "Vaccinia virus GLV-1h237 carrying a Walker A motif mutation of mouse Cdc6 protein enhances human breast tumor therapy in mouse xenografts," Int. J. Oncol. 38(3):871-878 (2011).
Hollinshead et al., "Vaccinia virus utilizes microtubules for movement to the cell surface," J. Cell Biol. 154:389-402 (2001).
Hostanska et al., "Aqueous ethanolic extract of St. John's wort (*Hypericum perforation* L.) induces growth inhibition and apoptosis in human malignant cells in vitro," Pharmazie 57(5):323-31 (2002).
Hsueh et al., "Outbreak of Pseudomonas fluorescens bacteremia among oncology patients," J. Clin. Microbiol. 36(10):2914-2917 (1998).
Huang et al., "Bacterial penetration across the blood-brain barrier during the development of neonatal meningitis," Microbes Infect. 2(10):1237-1244 (2000).
Huang et al., "Impact of liver P450 reductase suppression on cyclophosphamide activation, pharmacokinetics and antitumoral activity in a cytochrome P450-based cancer gene therapy model," Cancer Gene Ther. 7(7):1034-1042 (2000).
Huang et al., "Oncolysis of hepatic metastasis of colorectal cancer by recombinant vesticular stomatitis virus in immune-competent mice," Mol. Ther. 8(3):434-440 (2003).
Huebner et al. "Production of type-specific antigen in virus-free hamster tumor cells induced by adenovirus type 12," Proc. Natl. Acad. Sci. 51:432-439 (1964).
Hughes et al., "Financial Aspects of Clinical Trials", Chapter 42 in *Principles and Practice of Pharmaceutical Medicine*, Fletcher et al.(eds.), pp. 501-512, John Wiley & Sons, Ltd. (2002).
Hughes et al., "Vaccinia virus encodes an active thymidylate kinase that complements a cdc8 mutant of *Saccharomyces cerevisiae*," J. Biol. Chem. 266(30):20103-20109 (1991).
Humlova et al., "Vaccinia virus induces apoptosis of infected macrophages," J. Gen. Virol. 83:2821-2832 (2002).
Hurst et al., "A novel model of a metastatic human breast tumour xenograft line," Br. J. Cancer 68:274-276 (1993).
Ianaro et al., "A nitric oxide synthase inhibitor reduces inflammation, down-regulates inflammatory cytokines and enhances interleukin-10 production in carrageenin-induced oedema in mice," Immunol. 82(3):370-375 (1994).
Iartaro et al., "Expression of TGF-β in attenuated *Salmonella typhimurium*: oral administration leads to the reduction of inflammation, Il-2 and IFN-γ, but enhancement of IL-10, in carrageein-induced oedema in mice," Immunol. 84:8-15 (1995).
Ikeda et al., "Oncolytic virus therapy of multiple tumors in the brain requires suppression of innate and elicited antiviral responses," Nat. Med. (8):881-887 (1999).
Isaacs et al., "Vaccinia virus complement-control protein prevents antibody-dependent complement-enhanced neutralization of infectivity and contributes to virulence," Proc. Natl. Acad. Sci. U.S.A. 89:628-632 (1992).
Jacobs et al., "Positron emission tomography-based imaging of transgene expression mediated by replication-conditional, oncolytic herpes simplex virus type I mutant vectors in vivo," Cancer Res. 61:2983-2995 (2001).
Jain et al., "Intratumoral lymphatic vessels: a case of mistaken identity or malfunction?" J. Natl. Cancer Inst. 94(6):417-421 (2002).
Jain et al., "Can engineered bacteria help control cancer?" Proc. Natl. Acad. Sci. U.S.A. 98(26): 14748-14750 (2001).
Jain, R., "Molecular regulation of vessel maturation," Nat. Med. 9(6):685-693 (2003).
Jemal et al., "Cancer statistics, 2003," CA Cancer J. Clin. 53(1):5-26 (2003).
Jeong, K. and S. Lee, "Secretory production of human leptin in *Escherichia coli*," Biotechnol.Bioeng. 67:398-407 (2000).
Jia et al., "Viral vectors for cancer gene therapy: viral dissemination and tumor targeting," Curr. Gene Ther. 5:133-142 (2005).
Jiang et al., "Apoptosis in human hepatoma cell lines by chemotherapeutic drugs via Fas-dependent and Fas-independent pathways," Hepatology 29(1):101-110 (1999).
Johnson et al., "An update on the vaccinia virus genome," Virology 196:381-401 (1993).
Johnson et al., "Improved tumor-specific immunotoxins in the treatment of CNS and leptomeningeal neoplasia," J. Neurosurg. 70(2):240-248 (1989).
Joklik, W., "The purification of four strains of poxviruses," Virology 18:9-18 (1962).
Jordan et al., "Melanocyte-directed enzyme prodrug therapy (MDEPT): development of second generation prodrugs for targeted treatment of malignant melanoma," Bioorg. Med. Chem. 9(6):1549-1958 (2001).
Kaklij et al., "Antitumor activity of *Streptococcus thermophilus* against fibrosarcoma: role of T-cells," Cancer Lett. 56(1):37-43 (1991).
Kaklij et al., "Tumor-specific transplantation resistance in mice after treatment of initial tumors with *Streptococcus thermophilus*," Microbiol Immunol. 40(1):55-58 (199).
Kammertoens et al., "Combined chemotherapy of murine mammary tumors by local activation of the prodrugs ifosfamide and 5-fluorocytosine," Cancer Gene Ther. 7(4):629-636 (2000).

(56) References Cited

OTHER PUBLICATIONS

Kan et al., "Direct retroviral delivery of human cytochrome P450 2B6 for gene-directed enzyme prodrug therapy of cancer," Cancer Gene Ther. 8(7):473-482 (2001).
Kanerva et al., "Chlorpromazine and apigenin reduce adenovirus replication and decrease replication associated toxicity," J. Gene Med. 9:3-9 (2007).
Kantor et al., "Antitumor activity and immune responses induced by a recombinant carcinoembryonic antigen-vaccinia virus vaccine," J. Natl. Cancer Inst. 84:1084-1091 (1992).
Kaplitt et al., "Mutant herpes simplex virus induced regression of tumors growing in immunocompetent rats," J. Neurooncol. 19(2):137-147 (1994).
Karupiah et al., "Vaccinia virus-mediated damage of murine ovaries and protection by viruses-expressed interleukin-2," Immunol. Cell Biol. 68: 325-333 (1990).
Kass et al, "Induction of protective host immunity to carcinoembryonic antigen (CEA), a self-antigen in CEA transgenic mice, by immunizing with a recombinant vaccinia-CEA virus," Cancer Res. 59:676-683 (1999).
Kato et al., "Antitumor activity of Lactobacillus casei in mice," Gann. 72(4):517-523 (1981).
Kato et al., "Correlation between increase in Ia-bearing macrophages and induction of T cell-dependent antitumor activity by Lactobacillus casei in mice," Cancer Immunol. Immunother. 26(3):215-221 (1988).
Katz et al., "Mutations in the vaccinia virus A33R and B5R envelope proteins that enhance release of extracellular virions and eliminate formation of actin-containing microvilli without preventing tyrosine phosphorylation of the A36R protein," J. Virol. 77:12266-12275 (2003).
Kaufman et al., "A recombinant vaccinia virus expressing human carcinoembryonic antigen CEA," Int. J. Cancer 48(6):900-907 (1991).
Kaufman et al., "Insertion of interleukin-2 (IL-2) and interleukin-12 (IL-12) genes into vaccinia virus results in effective anti-tumor responses without toxicity," Vaccine 20:1862-1869 (2002).
Kaufman et al., "Phase II randomized study of vaccine treatment of advanced prostate cancer (E7897): a trial of the Eastern Cooperative Oncology Group," J. Clin. Oncol. 22:2122-2132 (2004).
Kawa et al., "The effect of attenuated vaccinia virus AS strain on multiple myeloma; a case report," Japan. J. Exp. Med. 58(1):79-81 (1987).
Kawamura et al., "Expression of *Escherichia coli* uracil phosphoribosyltransferase gene in murine colon carcinoma cells augments the antitumoral effect of 5-fluorouracil and induces protective immunity," Cancer Gene Ther. 7(4):637-643 (2000).
Kaye et al., "A single amino acid substitution results in a retinoblastoma protein defective in phosphorylation and oncoprotein binding," Proc. Natl. Acad. Sci. U.S.A. 87:6922-6926 (1990).
Keith et al., "Evaluation of nucleoside phosphonates and their analogs and prodrugs for inhibition of orthopoxvirus replication," Antimicrob. Agents Chemother. 47(7):2193-2198 (2003).
Kelkar et al., "Antitumor activity of lactic acid bacteria on a solid fibrosarcoma, sarcoma-180 and Ehrlich ascites carcinoma," Cancer Lett. 42(1-2):73-77 (1988).
Kelland et al. "Of mice and men: values and liabilities of the athymic nude mouse model in anticancer drug development," Eur. J. Cancer 40:827-836 (2004).
Kelly et al., "Novel oncolytic agent GLV-1h68 is effective against malignant pleural mesothelioma," Hum. Gene Ther. 19(8):774-782 (2008).
Kelly et al., "Real-time intraoperative detection of melanoma lymph node metastases using recombinant vaccinia virus GLV-1h68 in an immunocompetent animal model," Int. J. Cancer 124(4):911-918 (2009).
Kerbel et al., "Human tumor xenografts as predictive preclinical models for anticancer drug activity in humans," Cancer Biol. Ther. 2:4(suppl. 1):S134-S139 (2003).
Keresó et al., "De novo chromosome formations by large-scale amplification of the centromeric region of mouse chromosomes," Chromosome Res. 4(3):226-239 (1996).
Kern, E., "In vitro activity of potential anti-poxvirus agents," Antiviral Res. 57:35-40 (2003).
Ketlinsky et al., "Mechanism of the anti-tumoral effect of the blastolysin fraction isolated from Lactobacillus bulgaricus," Vopr Onkol. 33(3):51-56 (1987) [Article in Russian; English abstract on last page of article].
Khuri et al., "A controlled trial of intratumoral ONYX-015, a selectively-replicating adenovirus, in combination with cisplatin and 5-fluorouracil in patients wih recurrent head and neck cancer," Nat. Med. 6(8):879-885 (2000).
Kihara et al., "Analysis of sequences required for the cytotoxic action of a chimeric toxin composed of Pseudomonas exotoxin and transforming growth factor $\alpha$," Bioconj.Chem. 5:532-538 (1994).
Kim et al. "A tale of two trials: selectively replicating herpesviruses for brain tumors," Gene Ther. 7(10):815-816 (2000).
Kim et al., "Overview analysis of adjuvant therapies for melanoma—a special reference to results from vaccinia melanoma oncolysate adjuvant therapy trials," Surg. Oncol. 10:53-59 (2001).
Kimura et al., "Selective localization and growth of Bifidobacterium bifidum in mouse tumors following intravenous administration," Cancer Res. 40(6):2061-2068 (1980).
Kim et al., "Replication-selective virotherapy for cancer: biological principles, risk management and future directions," Nat. Med. 7:781-787 (2001).
Kim et al., "Replicating viruses as selective cancer therapeutics," Mol. Med. Today 2(12):519-527 (1996).
Kleer et al., "Molecular biology of breast cancer metastasis Inflammatory breast cancer: clinical syndrome and molecular determinants," Breast Cancer Res. 2:423-429 (2000).
Kneissl et al., "Interaction and assembly of murine pre-replicative complex proteins in yeast and mouse cells," J. Mol. Biol. 327(1):111-128 (2003).
Kohler et al., "Continuous cultures of fused cells secreting antibody of predefined specificity," Nature 256:495-497 (1975).
Kohwi et al., "Antitumor effect of Bifidobacterium infantis in mice," Gann. 69(5):613-618 (1978).
Kokkinakis et al., "Effect of long-term depletion of plasma methionine on the growth and survival of human brain tumor xenografts in athymic mice," Nutr. Cancer 29(3):195-204 (1997).
Kolowsky et al., "Length of foreign DNA in chimeric plasmids determines the efficiency of its integration into the chromosome of the cyanobacterium Synechococcus R2," Gene 27(3):289-299 (1984).
Kondo et al., "Activity of immunotoxins constructed with modified Pseudomonas exotoxin A lacking the cell recognition domain," J.Biol.Chem. 263:9470-9475 (1988).
Kopylova-Sviridova et al., "Transient expression assay in a baculovirus system using firefly luciferase gene as a reporter," Virus Genes 6(4):379-386 (1992).
Kotwal et al., "Mapping and insertional mutagenesis of a vaccinia virus gene encoding a 13,800-Da secreted protein," Virology 171:579-587 (1989).
Koyama et al., "Combined suicide gene therapy for human colon cancer cells using adenovirus-mediated transfer of *Escherichia coli* cytosine deaminase gene and *Escherichia coli* uracil phosphoribosyltransferase gene with 5-fluorocytosine," Cancer Gene Ther. 7(7):1015-1022 (2000).
Kozak, "Structural features in eukaryotic mRNAs that modulate the initiation of translation," J. Biol. Chem. 266:19867-19870 (1991).
Krauss et al., "An investigation of incorporation of cellular antigens into vaccinia virus particles," J. Gen. Virol. 83:2347-2359 (2002).
Kruse et al., "Enzyme assembly after de novo synthesis in rabbit reticulocyte lysate involves molecular chaperones and immunophilins," J. Biol. Chem. 270(6):2588-2594 (1995).
Kunik et al., "Genetic transformation of HeLa cells by Agrobacterium," Proc. Natl. Acad. Sci. U.S.A. 98(4):1871-1876 (2001).

(56) References Cited

OTHER PUBLICATIONS

Kutinova et al., "Hepatitis B virus proteins expressed by recombinant vaccinia viruses: influence of preS2 sequence on expression surface and nucleocapsid proteins in human diploid cells," Arch. Virol. 134:1-15 (1994).
Kutinova et al., "Search for optimal parent for recombinant vaccinia virus vaccines. Study of three vaccinia virus vaccinal strains and several virus lines derived from them," Vaccine 13(5):487-493 (1995).
Kwak et al., "Poxviruses as vectors for cancer immunotherapy," Curr. Opin. Drug Disc. Develop. 6(2): 161-168 (2003).
Kyula et al., "Synergistic cytotoxicity of radiation and oncolytic Lister strain vaccinia in V600D/EBRAF mutant melanoma depends on JNK and TNF-alpha signaling," Oncogene doi:10.1038/onc.2013.112, 1-13 (2013).
Lachmann et al., "Gene transfer with herpes simplex vectors," Curr. Opin. Mol. Ther. 1(5):622-632 (1999).
Lamberton et al., "Construction and characterization of a bioluminescent *Streptococcus pyogene*," Proceedings of the 12th International Symposium on Bioluminescence and Chemiluminescence in *Progress & Current Appications*, Stanley, P. and L. Kricka et al. (Eds). World Scientific Publishing Co. Pte. Ltd., pp. 85-88 (2002).
Lamberton et al., "Generation and characterization of a bioluminescent *Streptococcus pyogenes*," Proceedings of the 12th International Symposium on Bioluminescence & Chemiluminescence: Apr. 5-9, 2002, Robinson College, University of Cambridge, UK, p. 3.22 (2002).
Lamensans et al., "Enhancement of immunity against murine syngeneic tumors by a fraction extracted from non-pathogenic mycobacteria," Proc. Natl. Acad. Sci. U.S.A. 72(9):3656-3660 (1975).
Lammertyn et al., "Evaluation of a novel subtilisin inhibitor gene and mutant derivatives for the expression and secretion of mouse tumor necrosis factor alpha by Streptomyces lividans," Appl. Environ. Microbiol. 63(5):1808-1813 (1997).
Lane et al., "Complications of smallpox vaccination, 1968: results of ten statewide surveys," J. Infect. Dis. 122:303-309 (1970).
Lane et al., "Complications of smallpox vaccinations, 1968: national surveillance in the United States," New Engl. J. Med. 281:1201-1208 (1969).
Langridge et al, "Detection of baculovirus gene expression in insect cells and larvae by low light video image analysis," J. Virol. Methods 61(1-2):151-156 (1996).
Langridge et al., "Bacterial and coelenterate luciferases as reporter genes in plant cells," Chapter 37 in Methods Mol Biol. 82:385-396 (1998).
Langridge et al., "Uptake of DNA and RNA into cells mediated by electroporation," Methods Enzymol. 153:336-350 (1987).
Larocca et al., "Gene transfer to mammalian cells using genetically targeted filamentous bacteriophage," FASEB J. 13:727-734 (1999).
Larson et al. "Triumph over mischance: a role for nuclear medicine in gene therapy," J. Nucl. Med. 38(8):1230-1233 (1997).
Lathe et al., "Tumour prevention and rejection with recombinant vaccinia," Nature 326:878-880 (1987).
Lattime et al., "In situ cytokine gene transfection using vaccinia virus vectors," Semin. Oncol. 23(1):88-100 (1996).
Lauer et al., "Phase I/II clinical trial of a genetically modified and oncolytic vaccinia virus GL-ONC1 in patients with unresactable, chemotherapy-resistant peritoneal carcinomatosis," Journal of Clinical Oncology, 2013 ASCO Annual Meeting Proceedings 31(15 Supple):3098 (2013).
Lawrence, J., "The bacteriology of burns," J. Hosp. Infect. 6: 3-17 (1985).
Lee et al. "Prodrug and antedrug: two diametrical approaches in designing safer drugs," Arch. Pharm. Res. 25(2): 111-136 (2002).
Lee et al., "Molecular attenuation of vaccinia virus: mutant generation and animal characterization," J. Virol. 66:2617-2630 (1992).
Lee et al., "The lux genes of the luminous bacterial symbiont Photobacterium leiognathi, of the ponyfish," Eur. J. Biochem. 201:161-167 (1991).
Legocki et al., "Bioluminescence in soybean root nodules: demonstration of a general approach to assay gene expression in vivo by using bacterial luciferase," Proc. Natl. Acad. Sci. 83:9080-9084 (1986).
Lemmon et al., "Anaerobic bacteria as a gene delivery system that is controlled by the tumor microenvironment," Gene Ther. 4:791-796 (1997).
Lemmon et al., "Anaerobic bacteria as a gene delivery system to tumors," Proceedings of the 85th Annual Meeting of the American Association for Cancer Research, San Francisco, CA Apr. 10-13, 1994, published in Proc. Am. Cancer Research Assn 35:374 (1994).
Ley, K., "The role of selectins in inflammation and disease," Trends Molec. Med. 9(6): 263-268 (2003).
Li et al., "Bifidobacterium adolescentis as a delivery system of endostatin for cancer gene therapy: Selective Inhibitor of angiogenesis and hypoxic tumor growth," Cancer Gene Ther. 10:105-111 (2003).
Li et al., "Oncolytic virotherapy as personalized cancer vaccine," Int. J. Cancer 123:493-499 (2008).
Li et al., "An engineered and assembled fusion protein of antitumor antibiotic lidamycin and scFV antibody directed against type IV collagenase," Yaoxue Xuebao 35(7):488-491 (2000) [English abstract on last page of article].
Li et al., "Enzyme/prodrug gene therapy approach for breast cancer using a recombinant adenovirus expressing *Escherichia coli* cytosine deaminase," Cancer Gene Ther. 4(2):113-117 (1997).
Liau et al., "Treatment of intracranial gliomas with bone marrow-derived dendritic cells pulsed with tumor antigens," J. Neurosurg. 90(6):1115-1124 (1999).
Lin et al., "Oncolytic vaccinia virotherapy of anaplastic thyroid cancer in vivo," J. Clin. Endocrinol. Metab. 93:4403-4407 (2008).
Lin et al., "Treatment of anaplastic thyroid carcinoma in vitro with a mutant vaccinia virus," Surgery 142(6):976-983 (2007). Presented at the 28th Annual Meeting of the American Association of Endocrine Surgeons, Tuscon, Arizona, Apr. 29 to May 1, 2007.
Lindsey, H., "Modified cold virus kills colon cancer," Lancet Oncol. 3(5):264 (2002).
Liu et al., "An E1B-19 kDa gene deletion mutant adenovirus demonstrates tumor necrosis factor-enhanced cancer selectivity and enhanced oncolytic potency," Molec. Ther. 9(6):786-803 (2004).
Liu et al., "Anticancer efficacy of systemically delivered anaerobic bacteria as gene therapy vectors targeting tumor hypoxia/necrosis," Gene Ther. 9(4):291-296 (2002).
Liu et al., "Clinical trial results with oncolytic virotherapy: a century of promise, a decade of progress," Nat. Clin. Pract. Oncol. 4:101-116 (2007).
Liu et al., "Detection of GDNF secretion in glial cell culture and from transformed cell implants in the brains of live animals," Mol. Genet. Genomics 266(4):614-623 (2001).
Liu et al., "Visualizing and quantifying protein secretion using a Renilla luciferase-GFP fusion protein," Luminescence 15(1):45-49 (2000).
Lopez et al., "Infections in children with malignant disease in Argentina," Cancer 47(5):1023-1030 (1981).
Lorenz et al., "Expression of the Renilla reniformis luciferase gene in mammalian cells," J Biolumin Chemilumin. 11(1):31-37 (1996).
Lorenz et al., "Isolation and expression of a cDNA encoding Renilla reniformis luciferase," Proc. Natl. Acad. Sci. U.S.A. 88:4438-4442 (1991).
Louie et al., "In vivo visualization of gene expression using magnetic resonance imaging," Nature Biotechnol. 18:321-325 (2000).
Lu et al., "Delivery of adenoviral vectors to the prostate for gene therapy," Cancer Gene Ther. 6(1):64-72 (1999).
Lusso, P., "Chemokines and viruses: the dearest enemies," Virol. 273:228-240 (2000).
Lyford, J., "Gene therapy 'cause T-cell leukemia': insertional mutagenesis pinpointed as cause of T-cell Leukemia in X-SCID gene therapy trial," The Scientist (Daily News, Oct. 20, 2003) pp. 1-4 (2003).
MacDonald et al., "Cancer spread and micrometastasis development: quantitative approaches for in vivo models," BioEssays 24: 885-893 (2002).

(56) References Cited

OTHER PUBLICATIONS

Mackenzie et al., "Human mesenchymal stem cells persist, demonstrate site-specific multipotential differentiation, and are present in sites of wound healing and tissue regeneration after transplantation into fetal sheep," Blood Cell. Mol. Dis. 27(3):601-604 (2001).
MacLaren et al., "Receptive non-invasive imaging of the dopamine D2 recepter gene in living animals," Gene Ther. 6:785-791 (1995).
MacLeod et al., "Expression of genes from the marine bacterium Alteromonas haloplanktis 214 in *Escherichia coli* K-12," Arch. Microbiol. 142(3):248-252 (1985).
Maeda et al., "Tumor vascular permeability and the EPR effect in macromolecular therapeutics: a review," J. Control. Release 65:271-284 (2000).
Mahy, B., "An overview on the use of a viral pathogen as a bioterrorism agent: why smallpox?" Antivir. Res. 57: 1-5 (2003).
Maim et al., "Molecular weight determination program," Nucleic Acids Res. 12(1 Pt 2):695-702 (1984).
Makower et al., "Phase II clinical trial of intralesional administration of the oncolytic adenovirus ONYX-015 in patients with hepatobiliary tumors with correlative p53 studies," Clin. Cancer Res . . . 9: 693-702 (2003).
Martino et al., "Bacteremia due to glucose non-fermenting gram-negative bacilli in patients with hematological neoplasias and solid tumors," Eur. J. Clin. Microbiol. Infect. Dis. 15(7):610-615 (1996).
Mastrangelo et al., "Virotherapy clinical trials for regional disease: In situ immune modulation using recombinant poxvirus vectors," Cancer Gene Ther. 9:1013-1021 (2002).
Mastrangelo et al., "Poxvirus vectors: orphaned and underappreciated," J. Clin. Invest., 105(8):1031-1034 (2000).
Matz et al., "Fluorescent proteins from nonbioluminescent *Anthozoa* species," Nat. Biotech. 17:969-973 (1999).
Mayerhofer et al., "Monitoring of spatial expression of firefly luciferase in transformed zebrafish," J. Biolumin. Chemilumin. 10(5):271-275 (1995).
Mayford et al., "CaMKII regulates the frequency-response function of hippocampal synapses for the production of both LTD and LTP," Cell 81:891-904 (1995).
Mayr et al., "The smallpox vaccination strain MVA: marker, genetic structure, experience gained with the parenteral vaccination and behavior in organisms with a debilitated defense mechanism," Zentbl. Bakteriol. Hyg. Abt 1 Orig. B 167: 375-390 (1978) [In German, English abstract on first page of article].
McAllister et al., "Recombinant yellow fever viruses are effective therapeutic vaccines for treatment of murine experimental solid tumors and pulmonary metastases," J. Virol. 74:9197-9205 (2000).
McAneny et al., "Results of a Phase I trial of a recombinant vaccinia virus that expresses carcinoembryonic antigen in patients with advanced colorectal cancer," Ann. Surg. Oncol. 3(5):495-500 (1996).
McCart et al., "Complex interaction between the replicating oncolytic effect and the enzyme/prodrug effect of vaccinia-mediated tumor regression," Gene Ther. 7:1217-1223 (2000).
McCart et al., "Oncolytic vaccinia virus expressing the human somatostatin receptor SSTR2: molecular imaging after systemic delivery using 111In-pentetreotide," Mol. Ther. 10(3):553-561 (2004).
McCart et al., "Systemic cancer therapy with a tumor-selective vaccinia virus mutant lacking thymidine kinase and vaccinia growth factor genes," Cancer Res. 61:8751-8757 (2001).
McCluskie et al., "Route and method of delivery of DNA vaccine influence immune responses in mice and non-human primates," Mol. Med. 5:287-300 (1999).
McDonald et al., "Imaging of angiogenesis: from microscope to clinic," Nature Med. 9(6):713-725 (2003).
McFadden, G., "Gleevec casts a pox on poxviruses," Nat. Med. 11(7):711-712 (2005).
McIntosh et al., "A probiotic strain of L. acidophilus reduces DMH-induced large intestinal tumors in male Sprague-Dawley rats," Nutr. Cancer 35(2):153-159 (1999).
Meadows et al., "Some biological properties and an in vivo evaluation of tyrosine phenol-lyase on growth of B-16 melanoma," Cancer Res. 36(1):167-171 (1976).
Meager et al., "The development of the regulatory process in europe for biological medicines: how it affects gene therapy products," Chapter 16 in *Gene Therapy Technologies, Applications and Regulations*, Meager, A., (Ed.), John Wiley & Sons Ltd., pp. 319-346 (1999).
Meck et al., "A virus-directed enzyme prodrug therapy approach to purging neuroblastoma cells from hematopoietic cells using adenovirus encoding rabbit carboxylesterase and CPT-11," Cancer Res. 61(13):5083-5089 (2001).
MedicineNet.com, "Tumor-cancer information on MedicineNet.com," [online][retrieved on May 30, 2007] Retrieved from:<URL:medterms.com/script/main/art.asp?articlekey=5863 [2 pages].
Meighen et al., "Multiple repetitive elements and organization of the lux operons of luminescent terrestrial bacteria," J. Bacteriol. 174(16):5371-5381 (1992).
Mengaud et al., "Expression in *Escherichia coli* and sequence analysis of the listeriolysin O determinant of Listeria monocytogenes," Infect. Immun. 56(4):766-772 (1988).
Metzger et al., "Human cytomegalovirus UL97 kinase confers ganciclovir susceptibility to recombinant vaccinia virus," J. Virol. 68(12):8423-8427 (1994).
Meyer et al., "Mapping of deletions in the genome of the highly attenuated vaccinia virus MVA and their influence on virulence," J. Gen. Virol. 72(Pt 5):1031-1038 (1991).
Micheau et al., "Sensitization of cancer cells treated with cytotoxic drugs to fas-mediated cytotoxicity," J. Natl. Cancer Inst. 89(11):783-789 (1997).
Michl et al., "Claudin-4: a new target for pancreatic cancer treatment using Clostridium perfringens enterotoxin," Gastroent. 121(3):678-684 (2001).
Middleton et al., "Leukocyte extravasation: chemokine transport and presentation by the endothelium," Blood 100(12):3853-3860 (2002).
Miki et al., "Methioninase gene therapy of human cancer cells is synergistic with recombinant methioninase treatment," Cancer Res. 60(10):2696-2702 (2000).
Mikryukov et al., "Structural-functional organization of segment of vaccinia virus genome," Soviet Biotechnology (Biotekhnologiya) 4: 19-25 (1988) [English edition, corresponds to pp. 442-449 in the Russian language edition].
Milbrandt, E., "A novel source of enterococcal endocarditis," Clin. Cardiol. 21(2):123-126 (1998).
Minton et al., "Chemotherapeutic tumour targeting using clostridial spores," FEMS Microbiol. Rev. 17(3):357-364 (1995).
Mirzadeh et al., "Radiometal labeling of immunoproteins: covalent linkage of 2-(4-isothiocyanatobenzyl)diethylenetriaminepentaacetic acid ligands to immunoglobulin," Bioconj. Chem. 1(1):59-65 (1990).
Mizutani et al., "Doxorubicin sensitizes human bladder carcinoma cells to Fas-mediated cytotoxicity," Cancer 79(6):1180-1189 (1997).
Mizutani et al., "Inhibitory effect of some intestinal bacteria on liver tumorigenesis in gnotobiotic C3H/He male mice," Cancer Lett. 11(2):89-95 (1980).
Mizutani et al., "Sensitization of human bladder cancer cells to Fas-mediated cytotoxicity by cisdiamminedichloroplatinum diamminedichloroplatinum (II)," J. Urol. 160(2):561-570 (1998).
Mohr et al., "Rabbit cytochrome P450 4B1: A novel prodrug activating gene for pharmacogene therapy of hepatocellular carcinoma," Cancer Gene Ther. 7(7):1008-1014 (2000).
Moolten, "Tumor chemosensitivity conferred by inserted herpes thymidine kinase genes: paradigm for a prospective cancer control strategy," Cancer Res. 46(10):5276-5281 (1986).
Moore et al., "Measuring transferrin receptor gene expression by NMR imaging," Biochim. Biophys. Acta 1402(3):239-249 (1998).
Moore et al., "Steroid hormone synthesis by a vaccinia enzyme: a new type of virus virulence factor," EMBO J. 11(5):1973-1980 (1992) [corrigendum in EMBO J. 11(9):3490 (1992)].

(56) References Cited

OTHER PUBLICATIONS

Moore, A., “Effects of viruses on tumors,” Annu. Rev. Microbiol. 8:393-402 (1954).
Morena, A., “Natural killer cells and dendritic cells: rendezvous in abused tissues,” Nat. Rev. Immunol. 2: 957-964 (2002).
Morinaga et al., “Antitumor activity and its properties of Eubacterium lentum,” Jpn. J. Cancer Res. (Gann) 79:117-124 (1988).
Moroz et al., “Imaging hNET reporter gene expression with 124I-MIBG,” J. Nucl. Med. 48:827-836 (2007).
Morris et al., “Plasmid vectors capable of transferring large DNA fragments to yeast,” DNA. 1(1):27-36 (1981).
Morscher et al., “Imaging virus-mediated melanin production using Multispectral Optoacoustic Tomography (MSOT),” British Society for Gene and Cell Therapy Conference Abstracts, P0015, Human Gene Therapy 24:A16 (2013).
Moss, B., “Poxviridae: the viruses and their replication,” Chapter 83 in *Fields Virology*, 3rd Edn, Fields et al., (Eds.), Philadelphia: Lippincott—Raven, 2637-2671 (1996).
Moss, B., “Poxviridae: the viruses and their replication,” Chapter 84 in *Field's Virology*, 4th Edn., vol. 2, Knipe, D., and P. Howley (Eds.), Philadelphia: Lippincott Williams & Wilkins, 2849-2883 (2001).
Moss, B., “Genetically engineered poxviruses for recombinant gene expression, vaccination, and safety,” Proc. Natl. Acad. Sci. U.S.A. 93:11341-11348 (1996).
Moss, B., “Poxvirus vectors: cytoplasmic expression of transferred genes,” Curr. Opin. Genet. Dev. 3:86-90 (1993).
Mountz et al., “Technetium-99m NeoTect imaging in vivo of T cells from hCAR transgenic mice,” FASEB J. 16(5):A1211 March Meeting abstract (2002).
Mukherjee et al., “Replication-restricted vaccinia as a cytokine gene therapy vector in cancer: persistent transgene expression despite antibody generation,” Cancer Gene Ther. 7(5):663-670 (2000).
Mullen et al., “Viral oncolysis,” The Oncologist 7:106-119 (2002).
Mulryan et al., “Attenuated recombinant vaccinia virus expressing oncofetal antigen (tumor-associated antigen) 5T4 induces active therapy of established tumors,” Mol. Cancer Ther. 1(12):1129-1137 (2002).
Muravlev et al., “Protective activity of vaccinia virus envelope proteins isolated with the use of nonionic detergents,” Voprosy Virusologii 40(4):154-158 (1995) [article in Russian, English summary on last page of article].
Murosaki et al., “Antitumor effect of heat-killed Lactobacillus plantarum L-137 through restoration of impaired interleukin-12 production in tumor-bearing mice,” Cancer Immunol. Immunother. 49(3):I57-164 (2000).
Mutschler et al., “10. Chemotherapy of Malignant Tumors” in: *Drug Actions: Basic Principles and Therapeutic Aspects* (medpharm (CRC Press), Suttgart, pp. 595-612 (1995).
Myklebust et al., “Eradication of small cell lung cancer cells from human bone marrow with immunotoxins,” Cancer Res. 53(16):3784-3788 (1993).
Nagahari et al., “Secretion into the culture medium of a foreign gene product from *Escherichia coli*: use of the ompF gene for secretion of human β-endorphin,” EMBO J. 4(13A):3589-3592 (1985).
Naik et al., “Intravenous and isolated limb perfusion delivery of wild type and a tumor-selective replicating mutant vaccinia virus in nonhuman primates,” Hum. Gene Ther. 17:30-45 (2006).
Nakamura et al., “Induction of apoptosis in HL60 leukemic cells by anticancer drugs in combination with anti-Fas monoclonal antibody,” Anticancer Res. 17(1A):173-179 (1997).
Nakao et al., “*Escherichia coli* Shiga toxin,” J. Nat. Toxins 9(3):299-313 (2000).
Nauciel et al., “Inhibition of tumor growth by the peptidoglycan from Bacillus megaterium,” J. Natl. Cancer Inst. 59(6):1723-1726 (1977).
Naumov et al., “Cellular expression of green fluorescent protein, coupled with high-resolution in vivo videomicroscopy, to monitor steps in tumor metastasis,” J Cell Sci. 112(Pt 12):1835-1842 (1999).
NCBI Nucleotide AF012825 (date of last modification Aug. 6, 2002) (96 pages).
NCBI Nucleotide AF095689 (date of last modification Feb. 14, 2000) (89 pages).
NCBI Nucleotide AF380138 (date of last modification Dec. 13, 2001) (99 pages).
NCBI Nucleotide AX003206 (date of last modification Aug. 24, 2000) (3 pages).
NCBI Nucleotide AY009089 (date of last modification Jul. 30, 2002) (114 pages).
NCBI Nucleotide AY243312 (date of last modification Apr. 10, 2003) (102 pages).
NCBI Nucleotide AY484669 (date of last modification Mar. 30, 2004) (92 pages).
NCBI Nucleotide AY603355 (date of last modification May 15, 2004) (92 pages).
NCBI Nucleotide M35027 (date of last modification Aug. 3, 1993) (92 pages).
NCBI Nucleotide M57977 (date of last modification Apr. 14, 2000) (9 pages).
NCBI Nucleotide U94848 (date of last modification Apr. 14, 2003) (85 pages).
NCBI Nucleotide X69198 (date of last modification Sep. 10, 2004) (93 pages).
NCBI Nucleotide X94355 (date of last modification May 09, 2003) (108 pages).
NCBI Protein AAA48282 (date of last modification Apr. 14, 2000) (1 page).
Needleman et al., “A general method applicable to the search for similarities in the amino acid sequences of two proteins,” J. Mol. Biol. 48:443-453 (1970).
Netesova et al., “Structural and functional studies of the HindIII-I-Genome Fragment of Vaccinia virus Strain L-IVP,” Mol Biol (Mosk.) Nov.-Dec.; 25(6): 1526-1532 (1991) [article in Russian, English summary on last page of article].
Nettleton et al., “Parapoxviruses are strongly inhibited in vitro by cidofovir,” Antivir. Res. 48:205-208 (2000).
Neubauer et al., “Specific detection of monekypox virus by polymerase chain reaction,” J. Virol. Meth. 74:201-207 (1998).
Newton et al., “Expression and characterization of recombinant human eosinophil-derived neurotoxin and eosinophil-derived neurotoxin-anti-transferrin receptor sFv,” J. Biol. Chem. 269(43):26739-26745 (1994).
Neyts et al., “Therapy and short-term prophylaxis of poxvirus infections: historical background and perspectives”, Antivir. Res. 57:25-33 (2003).
Nguyen, A. and P. Daugherty, “Evolutionary optimization of fluorescent proteins for intracellular Fret,” Nat Biotechnol. 23(3):355-360 (2005).
Nibbering et al., “Radiolabelled antimicrobial peptides for imaging of infections: a review,” Nucl. Med. Commun. 19(12):1117-11121 (1998).
Nichterlein et al., “Clinafloxacin (CI 960) is superior to standard therapeutics in the treatment of murine listeriosis and salmonellosis,” Zentralbl. Bakteriol. 286:401-412 (1997).
Nisato et al., “Lymphangiogenesis and tumor metastasis,” Thromb. Haemost. 90:591-597 (2003).
Nogrady, M., “*Medicinal Chemistry. A Biochemical Approach*,” New York: Oxford University Press, pp. 388-392 (1985).
Nolan et al., “Plasmid mapping computer program,” Nucleic Acids Res. 12(1 Pt 2):717-729 (1984).
Norton et al., “Expression of secreted platelet-derived growth factor-B by recombinant nonreplicating and noncytopathic vaccinia virus,” Ann. Surg. 224(4):555-562 (1996).
Nuyts et al., “Clostridium spores for tumor-specific drug delivery,” Anticancer Drugs 13(2):115-125 (2002).
Ober et al., “Immunogenicity and safety of defective vaccinia virus lister:comparison with modified vaccinia virus Ankara,” J. Virol. 76(15):7713-7723 (2002).
O'Brien et al., “Shiga toxin: biochemistry, genetics, mode of action, and role in pathogenesis,” Curr. Top. Microbiol. Immunol. 180:65-94 (1992).

(56) References Cited

OTHER PUBLICATIONS

Oertli et al., "Non-replicating recombinant vaccinia virus encoding murine B-7 molecules effective costimulation of naive CD4+ splenocytes in vitro," J. Gen. Virol. 77:3121-3125 (1996).
Okada et al., "Sensitization of human tumor cells to homologous complement by vaccinia virus treatment," Cancer Immunol Immunother 25(1):7-9 (1987).
Okamoto et al., "Severe impairment of anti-cancer effect of lipoteichoic acid-relatedmolecule isolated from a penicillin-killed *Streptococcus pyogenes* in toll-like receptor 4-deficient mice," Int. Immunopharmacol. 1(9-10):1789-1795 (2001).
O'Kane et al., "Visualization of bioluminescence as a marker of gene expression in rhizobium-infected soybean root nodules," J. Plant Mol. Biol. 10:387-399 (1988).
Okuse et al., "Enhancement of antiviral activity against hepatitis C virus in vitro by interferon combination therapy," Antiviral Res. 65:23-34 (2005).
Olsson et al., "Engineering of monomeric bacterial luciferases by fusion of luxA and luxB genes in Vibrio harveyi," Gene 81(2):335-347 (1989).
Olsson et al., "The use of the luxA gene of the bacterial luciferase operon as a reporter gene,"Mol. Gen. Genet. 215(1):1-9 (1988).
O'Mahony et al., "Probiotic impact on microbial flora, inflammation and tumour development in IL-10 knockout mice," Aliment. Pharmacol. Ther. 15(8):1219-1225 (2001).
Orkin, S. and A. Motulsky, "Report and recommendations of the panel to assess the NIH investment in research on gene therapy," Published Dec. 7, 1995, 41 pages.
Overholser et al., "Experimental bacterial endocarditis after dental extractions in rats with periodontitis," J. Infect. Dis. 155(1):107-112 (1987).
Overwijk et al., "Vaccination with a recombinant vaccinia virus enclding a 'self' antigen induces autoimmune vitiligo and tumor cell destruction in mice: Requirement for CD4+ T lymphocytes," Proc. Natl. Acad. Sci. USA 96:2982-2987 (1999).
Pace, B., "Strep Throat," JAMA 284(22):2964 (2000).
Padera et al., "Lymphatic metastasis in the absence of functional intratumor lymphatics," Science 296:1883-1886 (2002).
Pak et al., "Cloning of the growth factor gene from vaccinia virus LIVP strain in *Escherichia coli* cells," Mol. Gen. Mikrobiol. Virusol. 9-10:19-21 (1992) [article in Russian, English summary on last page of article].
Pan et al., "Regression of established B16F10 melanoma with a recombinant Listeria monocytogenes vaccine," Cancer Res. 59:5264-5269 (1999).
Paniacli et al., "Vaccinia virus vectors utilizing the /?-galactosidase assay for rapid selection of recombinant viruses and measurement of gene expression," Gene 47:193-199 (1986).
Paoletti et al., "Applications of pox virus vectors to vaccination: an update, "Proc. Natl. Acad. Sci. 93:11349-11353 (1996).
Parato et al., "Recent progress in the battle between oncolytic viruses and tumours," Nature Rev. 5:965-976 (2005).
Pardal et al., "Applying the principles of stem-cell biology to cancer," Nature Rev. Cancer 3:895-902 (2003).
Parish, C., "Cancer immunotherapy: the past, the present and the future," Immunol. Cell Biol. 81:106-113 (2003).
Patel et al., "A poxvirus-derived vector that directs high levels of expression of cloned genes in mammalian cells," Proc. Natl. Acad. Sci. U.S.A. 85: 9431-9435 (1988).
Patil et al., "Virotherapy of canine tumors with oncolytic vaccinia virus GLV-1h109 expressing an anti-Vegf single-chain antibody," PLoS One 7(10):e47472, 13 pages (2012).
Patyar et al., "Bacteria in cancer therapy: a novel experimental strategy," Journal of Biomedical Science 17:21, 9 pages (2010).
Paul et al., "Redirected cellular cytotoxicity by infection of effector cells with a recombinant vaccinia virus encoding a tumor-specific monoclonal antibody," Cancer Gene Ther. 7(4):615-23 (2000).
Pawelek et al., "Bacteria as tumour-targeting vectors," Lancet Oncol. 4:548-556 (2003).
Pawelek et al., "Tumor-targeted *Salmonella* as a novel anticancer vector," Cancer Res. 57(20):4537-4544 (1997).
Pearson et al., "Improved tools for biological sequence comparison," Proc. Natl. Acad. Sci. U.S.A. 85:2444-2448 (1988).
Pecora et al., "Phase I Trial of intravenous administration of PV701, an oncolytic virus, in patients with advanced solid cancers," J. Clin. Oncol. 20(9):2251-2266 (2002).
Pedersen et al., "A phase I clinical trial of genetically modified and imageable oncolytic vaccinia virus GL-ONC1 with clinical green fluorescent protein (GFP) imaging," J. Clin. Oncol 29:(abstr 2577) (2011) [Abstract] ASCO Annual Meeting, Jun. 3-7, 2011, 2 pages.
Pedersen et al., "A phase I clinical trial of genetically modified and imageable oncolytic vaccinia virus GL-ONC1 with clinical green fluorescent protein (GFP) imaging," J. Clin. Oncol 29:(abstr 2577) (2011) [Poster] ASCO Annual Meeting, Jun. 3-7, 2011, 1 page.
Pekhov et al., "Cytotoxic effect of methionine-gamma-lyase on neoplastic cells in culture," Biull. Eksp. Biol. Med. 95(5):87/88 (1983) [Article in Russian, English abstract on last page of article].
Pencavel et al., "Administration of oncolytic vaccinia virus GLV1h68 by isolated limb perfusion to an immunocompetent rat model of advanced extremity sarcoma," European Journal of Cancer 47:S663 (2011).
Penheitner et al., "Pinhole micro-SPECT/CT for noninvasive monitoring and quantitation of oncolytic virus dispersion and percent infection in solid tumors," Gene Ther. 19(3):279-287 (2012).
Peplinski et al., "Prevention of murine breast cancer by vaccination with tumor cells modified by cytokine-producing recombinant vaccinia viruses" Annals Surg. Oncol. 3(1):15-23 (1996).
Peplinski et al., "Vaccinia Virus for Human Gene Therapy", Surgical Oncology Clinics of North America, 7(3):575-588 (1998).
Peplinski et al., "In vivo gene therapy of a murine pancreas tumor with recombinant vaccinia virus encoding human interleukin-1beta," Surgery 118:185-191 (1995).
Perkus et al., "Deletion of 55 open reading frames from the termini of vaccinia virus," Virology 180:406-410 (1991).
Perkus et al., "Recombinant vaccinia virus: immunization against multiple pathogens," Science 229(4717):981-984 (1985).
Pfeifer et al., "Gene therapy: promises and problems," Ann. Rev. Genomics Hum. Genet. 2:77-211 (2001).
Pfleiderer et al., "A novel vaccinia virus expression system allowing construction of recombinants without the need for selection markers, plasmids and bacterial hosts," J. Gen. Virol. 76:2957-2962 (1995).
Pfleiderer et al., "Requirements for optimal expression of secreted and nonsecreted recombinant proteins in vaccinia virus systems," Protein Exp. Purif 6(5):559-569 (1995).
Phillips-Jones, M., "Bioluminescence (lux) expression in the anaerobe Clostridium perfringens," FEMS Microbiol. Lett. 106:265-270 (1993).
Phillips-Jones, M., "Use of lux reporter system for monitoring rapid changes in $\alpha$-toxin gene expression in Clostridium perfringens during growth," FEMS Microbiol. Lett. 188: 29-33 (2000).
Picot et al., "Pseudomonas fluorescens as a potential pathogen: adherence to nerve cells," Microbes Infect. 3(12):985-395 (2001).
Pilcher, H., "GM bug activates cancer drug: bacteria targets medicine to shrivel mouse tumours," Published on Apr. 22, 2004 [online][retrieved on Nov. 18, 2004] Retrieved from:<URL:nature.com/news/2004/040419/full/040419-9.html [3 pages].
Pinkert et al., "An albumin enhancer located 10 kb upstream functions along with its promoter to direct efficient, liver-specific expression in transgenic mice," Genes Dev. 1:268-276 (1987).
Plucienniczak et al., "Nucelotide sequence of a cluster and late genes in a conserved segment of the vaccinia virus genome," Nucleic Acids Research 13(3):993-998 (1985).
Pluen, A. et al., "Role of tumor-host interactions in interstitial diffusion of macromolecules: Cranial vs. subcutaneous tumors," Proc. Natl. Acad. Sci. U.S.A., 98(8):4628-4633 (2001).
Polverini et al., "Assay and purification of naturally occuring inhibitor of angiogenesis," Methods Enzymol. 198:440-450 (1991).
Pongor et al., "Microcomputer programs for prediction and comparative evaluation of protein secondary structure from nucleotide sequence data: application to ribulose-1,5-bisphosphate carboxylase sequences," DNA. 4(4):319-326 (1985).

(56) References Cited

OTHER PUBLICATIONS

Pongor et al., "Prediction of homology and divergence in the secondary structure of polypeptides," Proc. Natl. Acad. Sci. U.S.A. 82(2):366-370 (1985).
Poptani et al., "Monitoring thymidine kinase and ganciclovir-induced changes in rat malignant glioma in vivo by nuclear magnetic resonance imaging," Cancer Gene Ther. 5(2):101-109 (1998).
Prasher et al., "Primary structure of the Aequorea victoris green-fluorescent protein," Gene 111:229-233 (1992).
Prasher et al., "Sequence comparison of complementary DNAs encoding Aequorin isotypes," Biochem. 26:1326-1332 (1987).
Presta et al., "Humanization of an anti-vascular endothelial growth factor monoclonal antibody for the therapy of solid tumors and other disorders," Cancer Res. 57:4593-4599 (1997).
Prikhod'ko, G. and 1. Babkin, "5'-variable genome sequence of vaccinia virus LIVP. Possible role of short direct repeats in formation of DNA deletions," Genetika 27(1):13-26 (1991) [article in Russian, English summary on last page of article].
Prikhod'ko et al., "Cloning, sequencing and translation analysis of the vaccinia virus LIVP HindIII N fragment," Genetika 27(6):955-963 (1991) [article in Russian, English summary on last page of article].
Proudfoot et al., "Strategies for chemokine antagonists as therapeutics," Sem. Immunol. 15:57-65 (2003).
Puhlmann et al., "Thymidine kinase-deleted vaccinia virus expressing purine nucleoside phosphorylase as a vector for tumor-directed gene therapy," Hum Gene Ther. 10(4):649-657 (1999).
Puhlmann et al., "Vaccinia virus as a vector for tumor-directed gene therapy: biodistribution of a thymidine kinase-deleted mutant," Cancer Gene Therapy 7(1): 66-73 (2000).
Qazi et al, "Real-time monitoring of intracellular *Staphylococcus aureus* replication," J. Bacteriol. 186(4):1065-1077 (2004).
Qin et al., "Construction of recombinant vaccinia virus expressing GM-CSF and its use as a tumor vaccine," Gene Ther. 3(1):59-66 (1996).
Qin et al., "Cancer gene therapy using tumor cells infected with recombinant vaccinia virus expressing GM-CSF," Hum. Gene Ther. 7:1853-1860 (1996).
Quenelle et al., "Efficacy of multiple- or single-dose cidofovir against vaccinia and cowpox virus infections in mice," Antimicrob. Agents Chemother. 47(10):3275-3280 (2003).
Raab et al., "Four-color labeling of cell culture and tumors of live mice upon infection with: GFP-Ruc and RFP-CBG99 expressing vaccinia virus strains," Proceedings of the 14th International Symposium on Bioluminescence & Chemiluminescence: Chemistry, Biology and Applications, World Scientific: Singapore, 197-200 (2007).
Ramirez et al., "Biology of attenuated modified vaccinia virus Ankara recombinant vector in mice: Virus fate and activation of B- and T-Cell immune responses in comparsion with the Western Reserve Strain and advantages as a vaccine," J. Virol. 74(2):923-933 (2000).
Ramirez et al., "Tissue distribution of the Ankara strain of vaccinia virus (MVA) after mucosal or systemic administration," Arch. Virol. 148:827-839 (2003).
Rangarajan et al., "Comparative biology of mouse versus human cells: modeling human cancer in mice," Nature Rev. Cancer 3:952-959 (2003).
Ransohoff et al., "Three or more routes for leukocyte migration into the central nervous system," Nat. Rev. Immunol. 3:569-581 (2003).
Rao et al., "Il-12 is an effective adjuvant to recombinant vaccinia virus-based tumor vaccines," J. Immunol. 156: 3357-3365 (1996).
Reddy et al., "Folate-mediated targeting of therapeutic and imaging agents to cancers," Crit. Rev. Ther. Drug Carrier Syst. 15(6):587-627 (1998).
Reeves et al., "Disabling poxvirus pathogenesis by inhibition of Abl-family tyrosine kinases," Nat. Med. 11(7):731-739 (2005).
Rehemtulla et al., "Rapid and quantitative assessment of cancer treatment response using in vivo bioluminescence imaging," Neoplasia 2(6):491-495 (2000).
Reinboth et al., "Correlation between human and oncolytic vaccinia virus transcriptional profile," 27th Annual Meeting Final Program, Society for Immunotherapy of Cancer (SITC), Oct. 26-28, 2012, North Bethesda MD. [Poster 82 abstract], 3 pages.
Reinboth et al., "Correlates between host and viral transcriptional program associated with different oncolytic vaccinia virus isolates," Hum Gene Ther Methods, 23(5):285-296 (2012).
Reno, J., "Exclusive: Does San Diego biotech firm have a cure for cancer," Published on Jul. 17, 2013 [online][retrieved on Oct. 7, 2013] Retrieved from:<URL:therenodispatch.blogspot.com/2013/07/exclusive-does-san-diego-biotech-firm.html, 8 pages.
Reno, F., "Non-clinical toxicology," in *Principles and Practice of Pharmaceutical Medicine*, Fletcher et al.(eds.), Ch.6, John Wiley & Sons Ltd., pp. 55-64 (c2002).
Reimer et al., "Identification and localization of transformed cells in Agrobacterium tumefaciens-induced plant tumors," Planta. 209(4):399-405 (1999).
Ribas et al., "Current Developments in Cancer Vaccines and Cellular Immunotherapy", Journal of Clinical Oncology, 21(12):2415-2432 (2003).
Ring, C., "Cytolytic viruses as potential anti-cancer agents," J. Gen. Virol., 83:491-502 (2002).
Rocchetta et al., "Validation of a noninvasive, real-time imaging technology using bioluminescent *Escherichia coli* in the neutropenic mouse thigh model of infection," Antimicrob. Agents Chemother. 45(1):129-137 (2001).
Rodriguez et al., "Expression of the firefly luciferase gene in vaccinia virus: A highly sensitive gene marker to follow virus dissemination in tissues of infected animals," Proc. Natl. Acad. Sci. U.S.A. 85:1667-1671 (1988).
Rodriguez et al., "Highly attenuated vaccinia virus mutants for the generation of safe recombinant viruses," Proc. Natl. Acad. Sci. U.S.A. 86:1287-1291 (1989).
Roenigk et al., "Immunotherapy of malignant melanoma with vaccinia virus," Arch Dermatol 109:668-673 (1977).
Rolston et al., "In vitro activity of LY264826, a new glycopeptide antibiotic, against gram-positive bacteria isolated from patients in cancer," Antimicrob. Agents Chemother. 34(11):2137-2141 (1990).
Roseman et al., "The vaccinia virus HindIII fragment: nucleotide sequence of the left 6.2kb," Virology 178:410-418 (1990).
Roth et al., "p53 as a target for cancer vaccines: recombinant canarypox virus vectors expressing p53 protect mice against lethal tumor cell challenge," Proc. Natl. Acad. Sci. U.S.A. 93:4781-4786 (1996).
Rothenberg et al., "Improving the evaluation of new cancer treatments: challenges and opportunities," Nat. Rev. Cancer 3:303-309 (2003).
Rubanyi et al., "The future of human gene therapy," Mol. Aspects Med. 22:113-142 (2001).
Rudinger, J., "Characteristics of the amino acids as components of a peptide hormone sequence," Peptide Hormones, Parsons, University Park Press, Baltimore, p. 1-7 (1976).
Ruef et al., "Sternal wound infection after heart operations in pediatric patients associated with nasal carriage of *Staphylococcus aureus*," J. Thorac. Cardiovasc. Surg. 112(3):681-686 (1996).
Saito et al., "Effects of a bacteriocin from *Mycobacterium smegmatis* on BALB/3T3 and simian virus 40-transformed BALB/c mouse cells," Microbiol. Immunol. 25(1):13-22 (1981).
Sakamoto et al., "Antitumor effect of normal intestinal microflora on Ehrlich ascites tumor," Jpn. J. Cancer Res. (Gann) 79:109-116 (1988).
Santoro et al., "Rat model of experimental endocarditis," Infect. Immun. 19(3):915-918 (1978).
Schaefer et al., "Vaccinia virus-mediated intra-tumoral expression of matrix metalloproteinase 9 enhances oncolysis of PC-3 xenograft tumors," BMC Cancer 12(1):366, 20 pages (2012).
Schempp et al., "Inhibition of tumour cell growth by hyperforin, a novel anticancer drug from St. John's wort that acts by induction of apoptosis," Oncogene 21(8):1242-1250 (2002).
Schirrmacher et al., "Antitumor effects of Newcastle Disease Virus in vivo: local versus systemic effects," Int. J. Oncol. 18(5):945-952 (2001).

(56) References Cited

OTHER PUBLICATIONS

Schlör et al., "In vivo and in vitro studies on interactions between the components of the hemolysin (HlyA) secretion machinery of *Escherichia coli*," Mol.Gen.Genet. 256:306-319 (1997).
Schmidt et al., "Generation of effective cancer vaccines genetically engineered to secrete cytokines using adenovirus-enhanced transferrinfection (AVET)," Gene 190(1):211-216 (1997).
Schoen et al., "Bacterial delivery of functional messenger RNA to mammalian cells," Cell Microbiol. 7(5):709-724 (2005).
Scholl et al., "Recombinant vaccinia virus encoding human MUC1 and IL2 as immunotherapy in patients with breast cancer," J. Immunother. 23(5):570-580 (2000).
Schroder, J., "Epithelial antimicrobial peptides: innate local host response elements," Cell Mol. Life Sci. 56(1-2):32-46 (1999).
Schuller et al., "Investigation and management of Clostridium difficile colonisation in a paediatric oncology unit," Arch. Dis. Child. 72(3):219-222 (1995).
Schwartz, R., and M. Dayhoff, eds., "Matrices for detecting distant relationships," in *Atlas of Protein Sequence and Structure*, Chapter 23, National Biomedical Research Foundation, pp. 353-358 (1979).
Sekine et al., "A new morphologically characterized cell wall preparation (whole peptidoglycan) from Bifidobacterium infantis with a higher efficacy on the regression of an established tumor in mice," Cancer Res. 45(3):1300-1307 (1985).
Sekine et al., "Analysis of antitumor properties of effector cells stimulated with a cell wall preparation (WPG) of Bifidobacterium infantis," Biol. Pharm. Bull. 18(1):148-153 (1995).
Serganova et al., "Non-invasive molecular imaging and reporter genes," Cent. Eur. J. Biol. 1(1):88-123 (2006).
Seubert et al., "Enhanced tumor therapy using vaccinia virus strain GLV-1h68 in combination with a β-galactosidase-activatable prodrug seco-analog of duocarmycin SA," Cancer Gene Ther. 18:42-52 (2011).
Shapiro et al., "Biotechnology products and their development," in *Principles and Practice of Pharmaceutical Medicine*, Fletcher et al.(eds.), Ch.17, John Wiley & Sons, pp. 191-201 (2002).
Shariatmadari et al., "Improved technique for detection of enhanced green fluorescent protein in transgenic mice," Biotechniques 30:1282-1285 (2001).
Sharma et al., "Death the Fas way: regulation and pathophysiology of CD95 and its ligand," Pharmacol. Ther. 88(3):333-347 (2000).
Shata et al., "Optimization of recombinant vaccinia-based ELISPOT assay," J. Immunological Methods 283: 281-289 (2003).
Shchelkunov et al., "The gene encoding the late nonstructural 36K protein of vaccinia virus is essential for virus reproduction," Virus Research 28: 273-283 (1993).
Shen et al., "Fighting cancer with vaccinia virus: Teaching new tricks to an old dog," Mol. Therapy 11(2):180-195 (2005).
Shenk, T., "Delivery systems for gene therapy: the adenovirus," in *Stem Cell Biology and Gene Therapy*, Quesenberry et al. (Eds.), Ch.6, Wiley-Liss, Inc., pp. 161-178 (1998).
Shepherd, A., "Good laboratory practice in the research and development laboratory," in *Gene Therapy Technologies, Applications and Regulations*, Meager, A. (Ed.), Ch.19, John Wiley & Sons Ltd., 375-381 (1999).
Shida et al., "Effects and virulences of recombinant vaccinia viruses derived from attenuated strains that express the human T-cell leukemia virus type I envelope gene," J. Virol. 62(12):4474-4480 (1988).
Shilo et al., "DNA sequences homologous to vertebrate oncogenes are conserved in *Drosophila melanogaster*," Proc. Natl. Acad. Sci. U.S.A. 78:6789-6792 (1981).
Shimizu et al, "Significance of priming of hosts with virus in the tumor-specific immunotherapy model utilizing virus-reactive helper T cell activity," Nippon Gan Chiryo Gakkai Shi. 24(5):1007-14 (1989) [Article in Japanese; English abstract on second page of article].
Shimizu et al., "Antitumor activity of 2-keto-3-deoxyoctonate-free lipopolysaccharide of vibrio anguillarum in mice," Gann 74(2): 279-284 (1983).
Shimizu et al., "Antitumor activity of marine bacteria, vibrio anguillarum, in mice," Gann 70:429-433 (1979).
Shimizu et al., "Immunotherapy of tumor-bearing mice utilizing virus help," Cancer Immunol. Immunother. 27(3):223-227 (1988).
Shinozaki et al., "Oncolysis of multifocal hepatocellular carcinoma in the rat liver by hepatic artery infusion of vesicular stomatitis virus," Mol. Ther. 9(3):368-376 (2004).
Sidwell et al., "In vivo antiviral properties of biologically active compounds," Appl. Microbiol. 16(2):370-392 (1968).
Silva et al., "Cloning, overexpression, and purification of functional human purine nucleoside phosphorylase," Protein Expr. Purif. 27(1):158-164 (2003).
Simon et al., "Surveillance for nosocomial and central line-related infections among pediatric hematology-oncology patients," Infect. Control Hosp. Epidemiol. 21(9):592-596 (2000).
Simonds et al., "Deoxyribonucleic acid hybridization among strains of lactobacilli," J. Bacteriol. 107(1):382-384 (1971).
Sinkovics, J. and J. Horvath, "New developments in the virus therapy of cancer: a historical review," Intervirology 36:193-214 (1993).
Sinkovics et al., "Newcastle disease virus (NDV): brief history of its oncolytic strains," J. Clin. Virol. 16:1-15 (2000).
Sinkovics et al., "Virus therapy of human cancers," Melanoma Res. 13:431-432 (2003).
Sivanandham et al., "Therapeutic effect of a vaccinia colon oncolysate prepared with interleukin-2-gene encoded vaccinia virus studied in a syngeneic CC-36 murine colon hepatic metastasis model," Cancer Immunol. Immunother. 38:259-264 (1994).
Sivanandham et al., "Colon cancer cell vaccine prepared with replication-deficient vaccinia viruses encoding B7.1 and interleukin-2 induce antitumor response in syngeneic mice," Cancer Immunol. Immunother. 46(5):261-7 (1998).
Skolnick et al., "From genes to protein structure and function: novel applications of computational approaches in the genomic era," Trends Biotech. 18:34-39 (2000).
Smee et al., "A review of compounds exhibiting anti-orthopoxvirus activity in animal models," Antiviral Res. 57:41-52 (2003).
Smee et al., "Effects of cidofovir on the pathogenesis of a lethal vaccinia virus respiratory infection in mice," Antiviral Res. 52:55-62 (2001).
Smee et al., "Effects of cidofovir on the pathogenesis of a lethal vaccinia virus respiratory infection in mice," Antivir. Res., 52: 55-62 (2001).
Smith et al., "Infectious poxvirus vectors have capacity for at least 25000 base pairs of foreign DNA," Gene 25:21-28 (1983).
Smith et al., "Oncolytic viruses as novel anticancer agents: turning one scourge against another," Exp. Opin. Invest. Drugs 9(2):311-327 (2000).
Smith et al., "The formation and function of extracellular enveloped vaccinia virus," J. Gen. Virol. 83: 2915-2931 (2002).
Smith et al., "Comparison of biosequences," Adv. Appl. Math. 2:482-489 (1981).
Smyth et al., "Bovine enterovirus as an oncolytic virus: foetal calf serum facilitates its infection of human cells," Int. J. Mol. Med. 10(1):49-53 (2002).
Soby et al., "Catabolite-repressor-like protein regulates the expression of a gene under the control of the *Escherichia coli* lac promoter in the plant pathogen *Xanthomonas campestris* pv. Campestris," Appl. Microbiol. Biotechnol. 46(5-6):559-561 (1996).
Somia et al., "Gene therapy: trial and tribulations," Nat. Rev. Genet. 1(2):91-99 (2000).
Sorscher et al., "Tumor cell bystander killing in colonic carcinoma utilizing the *Escherichia coli* DeoD gene to generate toxic purines," Gene Ther. 1(4):233-238 (1994).
Spencer et al., "Unilateral transplantation of human fetal mesencephalic tissue into the caudate nucleus of patients with Parkinson's disease," New Eng. J. Med. 327:1541-1548 (1992).
Spooner et al., "In suicide gene therapy, the site of subcellular localization of the activating enzyme is more important than the rate at which it activates prodrug," Cancer Gene Ther. 7(10):1348-1356 (2000).

(56) References Cited

OTHER PUBLICATIONS

Sroller et al., "Effect of 3-beta-hydroxysteroid dehydrogenase gene deletion on virulence and immunogenicity of different vaccinia viruses and their recombinants," Arch. Virol. 143:1311-1320 (1998).
St. Louis University, "A new way to kill cancer: SLU research shows viruses can destroy lung, colon tumors," retrieved from the Internet:<URL: sciencedaily.com/releases/2004/05/040517071951.htm, [retrieved on Jun. 3, 2010] [2 pages].
Steele et al., "Recent developments in the virus therapy of cancer," P.S.E.B.M. 223:118-127 (2000).
Steff et al., "Detection of a decrease in green fluorescent protein fluorescence for the monitoring of cell death: an assay amenable to high-throughput screening technologies," Cytometry 45:237-243 (2001).
Steffens et al., "Enhanced green fluorescent protein fusion proteins of herpes simplex virus type 1 thymidine kinase and cytochrome P450 4B1: applications for prodrug-activating gene therapy," Cancer Gene Ther. 7(5):806-812 (2000).
Stehle et al., "Plasma protein (albumin) catabolism by the tumor itself—implications for tumor metabolism and the genesis of cachexia," Crit. Rev. Oncol. Hematol. 26:77-100 (1997).
Stevens, "Streptococcal toxic-shock syndrome: spectrum of disease, pathogenesis, and new concepts in treatment," Emerg. Infect. Dis. 1(3):69-78 (1995).
Stienlauf et al., "Kinetics of formation of neutralizing antibodies against vaccinia virus following re-vaccination," Vaccine 17:201-204 (1999).
Stocked et al., "A Survey of the humoral immune response of cancer patients to a panel of human tumor antigens," J. Exp. Med. 187(8): 1349-1354 (1998).
Stojdl et al., "VSV strains with defects in their ability to shutdown innate immunity are potent systemic anti-cancer agents," Cancer Cell 4:263-275 (2003).
Stritzker et al., "Vaccinia virus-mediated melanin production allows MR and optoacoustic deep tissue imaging and laser-induced thermotherapy of cancer," Proc. Natl. Acad. Sci. 110(9):3316-3320 (2013).
Stritzker, J. and A. Szalay, "Single-agent combinatorial cancer therapy," Proc. Natl. Acad. Sci. USA 110(21):8325-8326 (2013).
Stroncek et al., "Highlights of the society for immunotherapy of cancer (SITC) 27th annual meeting," Journal for ImmunoTherapy of Cancer 1:4, 11 pages (2013).
Studeny et al., "Bone marrow-derived mesenchymal stem cells as vehicles for interferon-β delivery into tumors," Cancer Res. 62:3603-3608 (2002).
Sudimack et al., "Targeted drug delivery via the folate receptor," Adv. Drug Deliv. Rev. 41(2):147-62 (2000).
Sugimoto et al., "Characteristics of an attenuated vaccinia virus strain, LC16m0, and its recombinant virus vaccines," Vaccine 12(8):675-681 (1994).
Sugimoto et al., "Gene structures of low-neurovirulent vaccinia virus LC16m0, LC16m8, and their Lister Original (LO) strains," Microb. Immuol. 29:421-428 (1985).
Sui et al., "Cell cycle-dependent antagonistic interactions between paclitaxel and gamma-radiation in combination therapy," Clin. Canc. Res. 10:4848-4857 (2004).
Sutter et al., "Vaccinia vectors as candidate vaccines: the development of modified vaccinia virus Ankara for antigen delivery," Curr. Drug Targets—Infectious Disorders 3(3):263-271 (2003).
Sutton et al., "In vivo adenovirus-mediated suicide gene therapy of orthotopic bladder cancer," Mol. Ther. 2(3):211-217 (2000).
Suvorov et al., "Physical and genetic chromosomal map of an M type 1 strain of *Streptococcus pyogenes*," J. Bacteriol. 178(18): 5546-5549 (1996).
Suzuki et al. "Coexpression of the partial androgen receptor enhances the efficacy of prostate-specific antigen promoter-driven suicide gene therapy for prostate cancer cells at low testosterone concentrations," Cancer Res. 61(4):1276-1279 (2001).
Suzuki et al., "Bacterial transformation using temperature-sensitive mutants deficient in peptidoglycan synthesis," Methods Enzymol. 68:331-342 (1979).
Suzuki et al., "Management of orbital lymphangioma using intralesional injection of OK-432," Br. J. Opthalmol. 84(6):614-617 (2000).
Symons et al., "A study of the vaccinia virus interferon-y receptor and its contribution to virus virulence", Journal of General Virology, 83: 1953-1964 (2002).
Szalay et al, "Genetic engineering of halotolerance in microorganisms: a summary," Basic Life Sci. 14:321-332 (1979).
Szalay et al., "Separation of the complementary strands of DNA fragments on polyacrylamide gels," Nucleic Acids Res. 4(5):1569-1578 (1977).
Sze et al., "Dr. Gary J. Becker Young Investigator Award: intraarterial adenovirus for metastatic gastrointestinal cancer: activity, radiographic response, and survival," J. Vasc. Interv. Radiol. 14(3):279-290 (2003).
Takahashi-Nishimaki et al., "Genetic analysis of vaccinia virus Lister strain and its attenuated mutant LC16m8: production of intermediate variants by homologous recombination," J. Gen. Virol. 68: 2705-2710 (1987).
Tanaka et al, "Preliminary evaluation of intratumoral injection of a *Streptococcus pyrogenes* preparation in patients with malignant brain tumors," Cancer 46(7):1688-1694 (1980).
Tartaglia et al., "NYVAC: a highly attenuated strain of vaccinia virus," Virology 188(1):217-232 (1992).
Taylor et al., "Comparison of the virulence of wild-type thymidine kinase (tk)-deficient and tk+ phenotypes of vaccinia virus recombinants after intranasal inoculation of mice," J. Gen. Virol. 72 (Pt 1):125-130 (1991).
Technology Evaluation Center, "Special report: vaccines for the treatment of malignant melanoma," TEC Assessment Program, 16(4):1-46 (2001).
t'Hart et al., "Gene thereapy in nonhuman primate models of human autoimmune disease," Gene Ther. 10:890-901 (2003).
Thatcher et al., "The potential of acetaminophen as a prodrug in gene-directed enzyme prodrug therapy," Cancer Gene Ther. 7(4):521-525 (2000).
Theuer et al., "A recombinant form of pseudomonas exotoxin directed at the epidermal growth factor receptor that is cytotoxic without requiring proteolytic processing," J.Biol.Chem. 267(24): 16872-16877 (1992).
Theys et al., "Specific targeting of cytosine deaminase to solid tumors by engineered Clostridium acetobutylicum," Cancer Gene Ther. 8(4):294-297 (2001).
Theys et al., "Stable *Escherichia coli*-Clostridium acetobutylicum shuttle vector for secretion of murine tumor necrosis factor alpha," Appl. Environ. Microbiol. 65(10):4295-4300 (1999).
Theys et al., "Tumor-specific gene delivery using genetically engineered bacteria," Curr. Gene Ther. 3(3): 207-221 (2003).
Thorne et al., "Vaccinia virus and oncolytic virotherapy of cancer," Curr. Opin. Mol. Ther. 7(4):359-365 (2005).
Tietze et al., "Highly selective glycosylated prodrugs of cytostatic CC-1065 analogues for antibody-directed enzyme tumor therapy," Chembiochem. 2(10):758-65 (2001).
Timiriasova et al., "Analysis of reporter gene expression at different segments of the vaccinia virus genome," Mol. Biol. (Mosk.) 27(2):392-401 (1993) [article in Russian, English abstract on last page of article].
Timiryasova et al., "Antitumor effect of vaccinia virus in glioma model," Oncol. Res. 11(3):133-144 (1999).
Timiryasova et al., "Replication-deficient vaccinia virus gene therapy vector: evalution of exogenous gene expression mediated by PUV-inactivated virus in glioma cells," J. Gene Med. 3:468-477 (2001).
Timiryasova et al., "Visualization of vaccinia virus infection using the renilla-luciferase-GFP fusion protein," Bioluminescence & Chemiluminescence: Proceedings of the 11th International Symposium on Bioluminescence Chemiluminescence: Asilomar Conference Grounds, Pacific Grove, Monterey, California: Sep. 6-10, 2000, (eds.): Case et al., World Scientific Publishing Co., pp. 457-460 (2001).

(56) References Cited

OTHER PUBLICATIONS

Timiryasova et al., "Construction of recombinant vaccinia viruses using PUV-inactivated virus as a helper," BioTechniques 31:534-540 (2001).
Timiryasova et al., "Radiation enhances the anti-tumor effects of vaccinia-p53 gene therapy in glioma," Technol. Cancer Res. Treat. 2(3):223-235 (2003).
Timiryasova et al., "Vaccinia virus-mediated expression of wild-type p53 suppresses glioma cell growth and induces apoptosis," Int. J. Oncol. 14(5):845-854 (1999).
Tjuvajev et al., "Salmonella-based tumor-targeted cancer therapy: tumor amplified protein expression therapy (TAPET™) for diagnostic imaging," J. Controlled Release 74:313-315 (2001).
Tjuvajev et al., "Imaging adenoviral-mediated herpes virus thymidine kinase gene transfer and expression in vivo," Cancer Res. 59: 5186-5193 (1999).
Tjuvajev et al., "Imaging herpes virus thymidine kinase gene transfer and expression by positron emission tomography,"Cancer Res. 58(19): 4333-4341 (1998).
Tjuvajev et al., "Imaging the expression of transfected genes in vivo," Cancer Res. 55(24):6126-6132 (1995).
Tjuvajev et al., "Noninvasive imaging of herpes virus thymidine kinase gene therapy and expression: a potential method for monitoring clinical gene therapy," Cancer Res. 56(18):4087-4095 (1996).
Toguchi et al., "Suicide gene therapy of C6 glioma cells mediated by replication-deficient and replication competent vaccinia viruses," Cancer Gene Ther. 10:S32 (2003) presented at the Eleventh International Conference on Gene Therapy of Cancer, Dec. 12-14, 2002, San Diego California.
Tokugawa et al., "A model system for the continuous production of a heterologous protein using a novel secretion promoting factor which operates in *Escherichia coli*," J. Biotechnol. 37:33-37 (1994).
Tokugawa et al., "A novel protein secretion factor from a *Vibrio* species which operates in *Escherichia coli*," J. Biotechnol. 35:69-76 (1994).
Tonetti et al., "Stable transfection of an estrogen receptor beta cDNA isoform into MDA-MB-231 breast cancer cells," J. Steroid Biochem. Mol. Biol. 87(1):47-55 (2003).
Topalis et al., "Substrate specificity of vaccinia virus thymidylate kinase," FEBS J. 272(24):6254-6265 (2005).
Torkin et al., "Induction of caspase-dependent, p53-mediated apoptosis by apigenin in human neuroblastoma," Molecular Cancer Therapeutics 4:1-11 (2005).
Toso et al., "Phase I study of the intravenous administration of attenuated *Salmonella typhimurium* to patients with metastatic melanoma," J. Clin. Oncol. 20(1):142-152 (2002).
Toth et al., "An oncolytic adenovirus vector combining enhanced cell-to-cell spreading, mediated by the ADP cytolytic protein, with selective replication in cancer cells with deregulated Wnt signaling," Cancer Res. 64:3638-3644 (2004).
Tresco et al., "Polymer-encapsulated PC12 Cells: Long-term survival and associated reduction in lesion-induced rotational behavior," Cell Transplant. 1:255-264 (1992).
Tscharke et al., "A model for vaccinia virus pathogenesis and immunity based on intradermal injection of mouse ear pinnae," J. Gen. Virol. 80:2751-2755 (1999).
Tscharke et al., "Dermal infection with vaccinia virus reveals roles for virus proteins not seen using other inoculation routes," J. Gen. Virol. 83:1977-1986 (2002).
Tseng et al., "In vivo antitumor activity of Sindbis viral vectors," J. Natl. Cancer Inst. 94(23):1790-1802 (2002).
Tseng et al., "Systemic tumor targeting and killing by Sindbis viral vectors," Nat. Biotechnol. 22(1):70-77 (2004).
Tsung et al., "Immune response against large tumors eradicated by treatment with cyclophosphamide and IL-12," J. Immunol. 160:1369-1377 (1998).
Tsung et al., "Gene expression and cytopathic effect of vaccinia virus inactivated by psoralen and long-wave UV light," J. Virol. 70:165-171 (1996).
Tysome et al., "Lister strain of vaccinia virus armed with endostatin-angiostatin fusion gene as a novel therapeutic agent for human pancreatic cancer," Gene Ther. 16(10):1223-1233 (2009).
Ullrich et al., "Vascularization is a general requirement for growth of plant and animal tumours," J. Exp. Bot. 51(353):1951-1960 (2000).
Umphress et al., "Vaccinia virus mediated expression of human APC induces apoptosis in colon cancer cells," Transgenics 4:19-33 (2003).
Upton et al., "Poxvirus orthologous clusters: toward defining the minimum essential poxvirus genome," J. Virol. 77(13):7590-7600 (2003).
Vanderplasschen et al., "Antibodies against vaccinia virus do not neutralize extracellular enveloped virus but prevent virus release from infected cells and comet formation," J. Gen. Virol. 78:2041-2048 (1997).
Vanderplasschen et al., "Intracellular and extracellular vaccinia virions enter cells by different mechanisms," J. Gen. Virol. 79:877-887 (1998).
Varghese et al., "Oncolytic herpes simplex virus vectors for cancer virotherapy," Cancer Gene Ther. 9:967-978 (2002).
Vector: Ministry of Public Health and Social Development of Russian Federation, State Research Center of Virology and Biotechnology, "WHO Collaborating Centre for Orthopoxvirus Diagnosis and Repository for Variola Virus Strains and DNA," retrieved from the Internet:<URL: vector.nsc.ru/DesktopDefault.aspx?lcid=9 &tabid=294&tabindex=1, [retrieved on Nov. 3, 2008] [1 page].
Veijola et al., "Cloning, baculovirus expression, and characterization of the a subunit of prolyl 4-hydroxylase from the nematode Caenorhabditis elegans," J. Biol. Chem. 269:26746-26753 (1994).
Vento et al., "Infections in patients with cancer undergoing chemotherapy: aetiology, prevention, and treatment," Lancet 4:595-604 (2003).
Verma et al., "Gene therapy—promises, problems and prospects," Nature 389:239-242 (1997).
Vestweber, "Regulation of endothelial cell contacts during leukocyte extravasation," Curr. Opin. Cell Biol. 14:587-593 (2002).
Vidal et al., "Tissue-specific control elements of the Thy-1 gene," EMBO J. 9(3):833-840 (1990).
Vile et al., "The oncolytic virotherapy treatment platform for cancer: unique biological and biosafety points to consider," Cancer Gene Ther. 9:1062-1067 (2002).
Vitfell-Pedersen et al., Preliminary results of a Phase 1 study of intravenous administration of GL-ONC1 Vaccinia virus in patients with advanced solid cancer with real time imaging. In 6th NCRI Cancer Conference; BT Convention Center, Liverpool, UK. 2010 [abstract] European J Cancer Supplements 8(7):23 (2010).
Vogel, J., "Outsourcing clinical drug development activities to contract reseach organizations (CROs): critical success factors," in *Principles and Practice of Pharmaceutical Medicine*, Fletcher et al.(eds.), Ch.40, John Wiley & Sons Ltd., 461-482 (2002).
Vogt et al., "Untersuchungen über die Möglichkeit der Tumorlokalisation in vivo auf ser Basis eines szintigrafischer Klostridienstäbchen-Nachweises mit $^{131}$J-markierten Antikörpern und F(ab')$_2$-Antikörperfragmenten," Zeitschrift für Experimentelle Chirurgie 12(4):209-215 (1979) [article in German, English summary on the last page of the article].
Voisey et al., "Elimination of internal restriction enzyme sites from a bacterial luminescence (luxCDABE) operon," Biotechniques 24(1):56-58 (1998).
Volm et al., "Enhancement of incorporation of $^{131}$Iododeoxyuridine into tumors after application of *Clostridium oncolyticum* s. *butyricum* (M 55)," Eur. J. Nucl. Med. 2(2):117-120 (1977).
Wahl et al., "Improved radioimaging and tumor localization with monoclonal F(ab')$_2$," J. Nucl. Med. 24:316-325 (1983).
Wallack et al., "A Phase III randomized, double-blind, multiinstitutional trial of vaccinia melanoma oncolysate-active specific immunotherapy for patients with Stage II melanoma," Cancer 75(1): 34-42 (1995).
Wallack et al., "Increased survival of patients treated with a vaccinia melanoma oncolysate vaccine," Ann. Surg. 226(2):198-206 (1997).
Wallack et al., "Surgical adjuvant active specific immunotherapy for patients with Stage III melanoma: the final analysis of data from a

(56) References Cited

OTHER PUBLICATIONS

Phase III, randomized, double-blind, multicenter vaccinia melanoma oncolysate trial," J. Am. Coll. Surg. 187(1):69-79 (1998).
Wang et al., "Oncolytic vaccinia virus GLV-1h68 strain shows enhanced replication in human breast cancer stem-like cells in comparison to breast cancer cells," J. Transl. Med. 10(1):167 (2012).
Wang et al., "Optical detection and virotherapy of live metastatic tumor cells in body fluids with vaccinia strains," PLoS One 3:8(9):e71105, 12 pages (2013).
Wang et al., "The Renilla luciferase-modified GFP fusion protein is functional in transformed cells," Bioluminescence & chemiluminescence: Proceedings of the 9th International Symposium on Bioluminescence Chemiluminescence: Woods Hole, Massachusetts, Oct. 1996 / (eds.) Hastings et al., John Wiley & Sons Ltd. (1997).
Wang et al., "A study of protein-protein interactions in living cells using luminescence resonance energy transfer (LRET) from Renilla luciferase to Aequorea GFP," Mol. Gen. Genet. 264(5):578-587 (2001).
Wang et al., "Renilla luciferase—Aequorea GFP (Ruc-GFP) fusion protein, a novel dual reporter for real-time imaging of gene expression in cell cultures and in live animals," Mol. Genet. Genomics. 268(2):160-168 (2002).
Warrington et al., "Developing VDEPT for DT-diaphorase (NQO1) using an AAV vector plasmid," Int. J. Radiat. Oncol. Biol. Phys. 42(4):909-912 (1998).
Watson et al., *Molecular Biology of the Gene*, 4th Edition, 1987, The Benjamin/Cummings Pub. co., p. 224.
Webley et al., "Measurement of the critical DNA lesions produced by antibody-directed enzyme prodrug therapy (ADEPT) in vitro, in vivo and in clinical material," Br. J. Cancer 84(12):1671-1676 (2001).
Weedon et al., "Sensitisation of human carcinoma cells to the prodrug CB1954 by adenovirus vector-mediated expression of *E. coli* nitroreductase," Int. J. Cancer 86(6):848-854 (2000).
Wegner et al., "Cis-acting suquences from mouse rDNA promote plasmid DNA amplification and persistence in mouse cells: implication of HMG-I in their function," Nucleic Acids Res. 17:9909-9932 (1989).
Wehl et al., "Trends in infection morbidity in a pediatric oncology ward, 1986-1995," Med. Pediatr. Oncol. 32(5):336-343 (1999).
Weibel et al., "Imaging of intratumoral inflammation during oncolytic virotherapy of tumors by 19F-Magnetic resonance imaging (MRI)," PLoS One 8(2):e56317, 12 pages (2013).
Weibel et al., "Treatment of malignant effusion by oncolytic virotherapy in an experimental subcutaneous xenograft model of lung cancer," J. Transl. Med. 11:106, 13 pages (2013).
Weintraub, A., "Pet dogs help biotech startups find new weapons to fight cancer," Xconomy, Jul. 25, 2012, [online] [retrieved on Jan. 28, 2013] [Retrieved from:<URL:xconomy.com/san-diego/2012/07/25/pet-dogs-help-biotech-startups-find-new-weapons-to-fight-cancer/?single_page=true], 7 pages.
Weissleder et al., "In vivo imaging of tumors with protease-activated near-infrared fluorescent probes," Nature Biotech. 17:375-378 (1999).
Weissleder et al., "In vivo magnetic resonance imaging of transgene expression," Nat. Med. 6(3): 351-354 (2000).
Weissleder et al., "Drug targeting in magnetic resonance imaging," Magnetic Resonance Quarterly 8(1):55-63 (1992).
Welling et al., "Radiochemical and biological characteristics of 99mTc-UBI 29-41 for imaging of bacterial infections," Nucl. Med. Biol. 29(4):413-422 (2002).
Welling et al., "Technetium-99m labelled antimicrobial peptides discriminate between bacterial infections and sterile inflammations," Eur. J. Nucl. Med. 27(3):292-301 (2000).
West et al., "Identification of a somatodendritic targeting signal in the cytoplasmic domain of the transferrin receptor," J. Neurosci. 17(16):6038-6047 (1997).
Westphal et al., "The nitroreductase/CB1954 combination in Epstein-Barr virus-positive B-cell lines: induction of bystander killing in vitro and in vivo," Cancer Gene Ther. 7(1):97-106 (2000).
Wharton et al., "Recommendations for using smallpox vaccine in a pre-event vaccination program," MMWR 52(RR-7):1-16 (2003).
Whitley, R., "Smallpox: a potential agent of bioterrorism," Antiviral Res. 57: 7-12 (2003).
Williams et al., "Stable integration of foreign DNA into the chromosome of the cyanobacterium Synechococcus R2," Gene 24(1):37-51 (1983).
Williams, "Southwestern Internal Medicine Conference: Prospects for Gene Therapy of Ischemic Heart Disease," The American Journal of the Medical Sciences 306(2):129-136 (1993).
Winn et al., "Behavioral recovery following intrastriatal implantation of microencapsulated PC12 cells," Exp. Neurol. 113:322-329 (1991).
Winn, et al., "Polymer-encapsulated cells genetically modified to secrete human nerve growth factor promote the survival of axotomized septal cholinergic neurons," Proc. Natl. Acad. Sci. U.S.A. 91:2324-2328 (1994).
Wisher, "Biosafety and product release testing issues relevant to replication-competent oncolytic viruses," Cancer Gene Ther. 9:1056-1061 (2002).
Wittrup, "Tumor targeting theory," IBC's 15$^{th}$ Annual International Antibody Engineering Conference entitled Antibody Engineering: Forging the Future of Antibody Therapeutics, Nov. 30-Dec. 3, 2003—The Paradise Point Resort—San Diego, CA, pp. 1-17.
Wlodaver et al., "Laboratory-acquired vaccinia infection," J. Clin. Virol. xxx: 1-5 (2003).
Wolffe et al., "Deletion of the vaccinia virus B5R gene encoding a 42-kilodalton membrane glycoprotein inhibits extracellular virus envelope formation and dissemination," J. Virol. 67(8): 4732-4741 (1993) [erratum in J. Virol. 67:5709-5711 (1993)].
Wollowski et al., "Protective role of probiotics and prebiotics in colon cancer," Am. J. Clin. Nutr. 73 (2 Suppl):451S-455S (2001).
Wong et al., "Chemokines: attractive mediators of the immune response," Semin. Immunol. 15: 5-14 (2003).
Woo et al., "Advances in oncolytic viral therapy," Curr. Opin. Investig. Drugs 7:549-559 (2006).
Worschech et al., "Systemic treatment of xenografts with vaccinia virus GLV-1h68 reveals the immunologic facet of oncolytic therapy," BMC Genomics 10:301, 22 pages (2009).
Worschech et al., "The immunologic aspects of poxvirus oncolytic therapy," Cancer Immunol. Immunother. 58(9):1355-1362 (2009).
Wu et al., "Biological purging of breast cancer cells using an attenuated replication-competent herpes simplex virus in human hematopoietic stem cell transplantation," Cancer Res. 61(7):3009-15 (2001).
Wu et al., "High resolution microPET imaging of carcino-embryonic antigen-positive xenografts by using a copper-64-labeled engineered antibody fragment," Proc. Natl. Acad. Sci. U.S.A. 97(15): 8495-8500 (2000).
Xie et al., "Adenovirus-mediated tissue-targeted expression of a caspase-9-based artificial death switch for the treatment of prostate cancer," Cancer Res. 61:6795-6804 (2001).
Xiong et al., "Cell cycle dependent antagonistic interactions between Paclitaxel and Carboplatin in combination therapy," Cancer Biol. Ther. 6(7):1067-1073 (2007).
Yadav et al., "Migration of leukocytes through the vessel wall and beyond," Thromb. Haemost. 90: 598-606 (2003).
Yamamoto et al., "Production of L-forms of *Streptococcus pyogenes* and their antitumor effects," Jpn. J. Exp. Med. 50(5):383-388 (1980).
Yang et al., "An orally bioavailable antipoxvirus compound (ST-246) inhibits extracellular virus formation and protects mice from lethal orthopoxvirus challenge," J. Virol. 79:13139-13149 (2005).
Yang et al., "Effects of growth medium composition, iron sources and atmospheric oxygen concentrations on production of luciferase-bacterial magnetic particle complex by a recombinant Magnetospirillum magneticum AMB-1," Enzyme Microb. Technol. 29:13-19 (2001).
Yang et al., "Visualizing gene expression by whole-body fluorescence imaging," Proc. Natl. Acad. Sci. 97(22):12278-12282 (2000).

(56) References Cited

OTHER PUBLICATIONS

Yang et al., "Whole-body optical imaging of green fluorescent protein-expressing tumors and metastases," Proc. Natl. Acad. Sci. U.S.A. 97(3):1206-1211 (2000).
Yazawa et al., "Bifidobacterium longum as a delivery system for cancer gene therapy: selective localization and growth in hypoxic tumors," Cancer Gene Ther. 7(2):269-274 (2000).
Yazawa et al., "Bifidobacterium longum as a delivery system for gene therapy of chemically induced rat mammary tumors," Breast Cancer Res. Treat. 66(2):165-170 (2001).
Yazawa et al., "Current progress in suicide gene therapy for cancer," World J. Surg. 26(7):783-789 (2002).
Yettra, M., "Remission of chronic lymphocytic leukemia after smallpox vaccination," Arch. Intern. Med. 139(5):603 (1979).
Yoon et al., "Markedly enhanced cytolysis by E1b-19kD-deleted oncolytic adenovirus in combination with cisplatin," Human Gene Therapy 17:379-390 (2006).
Yoshida et al., "Cell growth-inhibitory action of SAGP, an antitumor glycoprotein from *Streptococcus pyogenes* (Su strain)," Jpn. J. Pharmacol. 45(2):143-147 (1987).
Yoshida et al., "Characterization of a streptococcal antitumor glycoprotein (SAGP)," Life Sciences 62(12):1043-1053 (1998).
Yoshida et al., "Growth-inhibitory effect of streptococcal antitumor glycoprotein on human epidermoid carcinoma A43I cells: involvement of dephosphorylation of epidermal growth factor receptor," Cancer Res. 61(16):6151-6157 (2001).
Yu et al., "Real-time imaging of tumors using replication-competent light emitting microorganisms," Methods Mol. Biol. 872:159-175 (2012).
Yu et al. "Visualization of tumors and metastases in live animals with bacteria and vaccinia virus an encoding light-emitting proteins," Nat. Biotech. 22(3):313-320 (2004).
Yu et al., "Oncolytic vaccinia therapy of squamous cell carcinoma," Mol. Cancer 8:45, 9 pages (2009).
Yu et al., "A Renilla luciferase-Aequorea GFP (ruc-gfp) fusion gene construct permits real-time detection of promoter activation by exogenously administered mifepristone in vivo," Mol. Genet. Genomics. 268(2):169-178 (2002).
Yu et al., "Optical imaging: bacteria, viruses, and mammalian cells encoding light-emitting proteins reveal the locations of primary tumors and metastases in animals,"Anal. Bioanal. Chem. 377(6):964-972 (2003).
Yu et al., "Regression of human pancreatic tumor xenografts in mice after a single systemic injection of recombinant vaccinia virus GLV-1h68," Mol. Cancer Ther. 8:141-151 (2009).
Yu et al., "Visualization of molecular and cellular events with green fluorescent proteins in developing embryos: a review," Luminescence 18(1):1-18 (2003) [Erratum in: Luminescence 18(4):243 (2003)].
Yun et al. "Nitrogenase promoter-lacZ fusion studies of essential nitrogen fixation genes in Bradyrhizobium japonicum I110," J. Bacteriol. 167(3):784-791 (1986).
Zambryski et al., "Tumor induction by Agrobacterium tumefaciens: analysis of the boundaries of T-DNA," J. Mol. Appl. Genet. 1(4):361-370 (1982).
Zaucha et al., "The pathology of experimental aerosolized monkeypox virus infection in cynomolgus monkeys (*Macaca fascicularis*)," Lab. Invest. 81:1581-1600 (2001).
Zeh et al., "Development of a replication-selective, oncolytic poxvirus for the treatment of human cancers," Cancer Gene Ther. 9:1001-1012 (2002).
Zhang et al., "Eradication of solid human breast tumors in nude mice with an intravenously injected light emitting oncolytic vaccinia virus," Cancer Res. 67(20):10038-10046 (2007).
Zhang et al., "The highly attenuated oncolytic recombinant vaccinia virus GLV-1h68: comparative genomic features and the contribution of F14.5L inactivation," Mol. Genet. Genomics 282(4):417-435 (2009).
Zhang et al., "Urothelium-specific expression of an oncogene in transgenic mice induced the formation of carcinoma in situ and invasive transitional cell carcinoma," Cancer Res. 59:3512-3517 (1999).
Zhao et al., "Spatial-temporal imaging of bacterial infection and antibiotic response in intact animals," Proc. Natl. Acad. Sci. 98(17):9814-9818 (2001).
Zheng et al., "Tumor amplified protein expression therapy: *Salmonella* as a tumor-selective protein delivery vector," Oncol. Res. 12(3):127-135 (2000).
Zhu et al., "Smad3 mutant mice develop metastatic colorectal cancer," Cell 94: 703-714 (1998).
Zimmermann et al., "Independent regulatory elements in the nestin gene direct transgene expression to neural stem cells," Neuron 12:11-24 (1994).
Zinkernagel, R., "Uncertainties—discrepancies in immunology," Immunol. Rev. 185:103-125 (2002).
Zinn et al., "Noninvasive monitoring of gene transfer using a reporter receptor imaged with a high-affinity peptide radiolabeled with 99mTc or 188Re," J. Nucl. Med. 41(5):887-895 (2000).
Zinn et al., "Simultaneous evaluation of dual gene transfer to adherent cells by gamma-ray imaging," Nucl. Med. Biol. 28(2):135-144 (2001).
Zinoviev et al., "Identification of the gene encoding vaccinia virus immunodominant protein p35," Gene 147: 209-214 (1994).
Zolotukhin et al., "A "humanized" green fluorescent protein cDNA adapted for high-level expression in mammalian cells," J. Virol. 70:4646-4654 (1996).
zur Hausen, H., "Papillomaviruses and cancer: from basic studies to clinical application," Nature Rev. Cancer 2(5):342-350 (2002).
First complaint, filed in the Superior Court for the State of California, County of Los Angeles, dated Dec. 21, 2005 (Case No. BC344912) *Genelux Corporation, a Delaware corporation* (Plaintiff) vs. *Dr. Bernard Huber, an individual; Patentanwälte Huber & Schüssler, a partnership under the Code Gesellschaft des Burgerlichen Rechts; Dr. Gerd Stehle, an individual; and Does 1 through 10, inclusive* (Defendants).
Stipulation and Order of Dismissal. Case No. CV06-1462 Ag(FMOx).
Petition for Retroactive Grant of Foreign Filing License, filed on May 9, 2008, in connection with U.S. Appl. No. 10/872,156.
Joint Stipulation Regarding Defendants' Motion to Compel: (1) Deposition Testimony on Identified Subjects Pursuant to Rule 30 (B)(6), and (2) The Production of Documents [Local Rule 37-2.1]. Case No. CV06-1462 AG (FMOx).
Notice of Removal of Action Under 28 U.S.C. 1441 (Diversity) Case No. CV06-1462 AG (FMOx), *Genelux Corporation, a Delaware corporation* (Plaintiff) vs. *Dr. Bernard Huber, an individual; Patentanwälte Huber & Schüssler, a partnership under the Code Gesellschaft des Burgerlichen Rechts; Dr. Gerd Stehle, an individual*; and Does 1 through 10, inclusive (Defendants).
Answer and Counterclaims for Fraud, Negligent Misrepresentation, Breach of Fiduciary Duty; Breach of Contract; and Indemnity. Case No. CV06-1462 AG (FMOx), *Genelux Corporation, a Delaware corporation* (Plaintiff) vs. *Dr. Bernard Huber, an individual; Patentanwälte Huber & Schüssler, a partnership under the Code Gesellschaft des Burgerlichen Rechts; Dr. Gerd Stehle, an individual; and Does 1 through 10, inclusive* (Defendants); *Dr. Bernard Huber, an individual; Patentanwälte Huber & Schüssler, a partnership under the Code Gesellschaft des Burgerlichen Rechts; Dr. Gerd Stehle, an individual* (Counterclaimants) vs. *Genelux Corporation, a Delaware corporation, Ronald Simus, an individual, David Wood, an individual, and Aladar A. Szalay, an individual* (Counterdefendants).
Report of Parties' Planning Meeting for Scheduling Conference. Case No. CV06-1462 AG (FMOx).
Notice of Motion and Motion to Compel Further Responses by Defendant/Counterclaimant Dr. Bernard Huber to Interrogatories; Joint Stipulation of the Parties; Declaration of Howard M Loeb. Case No. CV06-1462 AG (FMOx).
Order Regarding Discovery Motions. Case No. CV06-1462 AG (FMOx).
Declaration of Paula K. Schoeneck.

(56) References Cited

OTHER PUBLICATIONS

Notice of Motion and Motion to Dismiss Counterclaimants Huber and Stehle's Fourth Cause of Action for Failure to State a Claim upon which Relief can be Granted; Memorandum of Points and Authorities; Declaration Pursuant to Local Rule 7-3. Case No. CV06-1462 GHK (FMOx).
Counterclaimants' Opposition to Counterdefendant Genelux's Motion to Dismiss. Case No. CV06-1462 GHK (FMOx).
Reply to Opposition to Motion to Dismiss Counterclaimants Huber and Stehle's Fourth Cause of Action for Failure to State a Claim upon which Relief can be Granted. Case No. CV06-1462 GHK (FMOx).
Court Order granting Genelux's motion to dismiss. Case No. CV06-1462 GHK (FMOx).
First Amended Counterclaims for Fraud; Negligent Misrepresentation, Breach of Fiduciary Duty; Breach of Contract; Breach of the Implied Covenant of Good Faith and Fair Dealing; and Indemnity. Case No. CV06-1462 GHK (FMOx).
Notice of Motion and Motion to Dismiss Counterclaimants Huber and Stehle's Seventh Cause of Action for Failure to State a Claim Upon Which Relief Can be Granted; Memorandum of Points and Authorities; Declaration Pursuant to Local Rule 7-3. Case No. CV06-1462 GHK (FMOx).
Counterclaimants' Opposition to Motion to Dismiss Seventh Cause of Action. Case No. CV06-1462 GHK (FMOx).
Reply to Opposition to Motion to Dismiss Counterclaimants Huber and Stehle's Seventh Cause of Action for Failure to State a Claim Upon Which Relief can be Granted Case No. CV06-1462 AG(FMOx).
(In Chambers) Order Denying Motion to Dismiss Counterclaimants' Seventh Cause of Action. Case No. CV06-1462 AG(FMOx).
Reply to First Amended Counterclaims. Case No. CV06-1462 AG(FMOx).
Office Action, issued Oct. 25, 2006, in connection with U.S. Appl. No. 10/872,156, 9 pages.
Office Action, issued Jul. 31, 2007, in connection with U.S. Appl. No. 10/872,156, 9 pages.
Office Action, issued May 12, 2008, in connection with U.S. Appl. No. 10/872,156, 9 pages.
Office Action, issued Dec. 18, 2006, in connection with U.S. Appl. No. 11/238,025, 15 pages.
Office Action, issued Dec. 6, 2007, in connection with U.S. Appl. No. 11/238,025, 12 pages.
Office Action, issued Sep. 2, 2008, in connection with U.S. Appl. No. 11/238,025, 13 pages.
Office Action, issued Nov. 28, 2007, in connection with U.S. Appl. No. 11/529,662, 13 pages.
Office Action, issued Apr. 1, 2008, in connection with U.S. Appl. No. 11/796,028, 18 pages.
Office Action, issued Jan. 30, 2009, in connection with U.S. Appl. No. 11/796,028, 17 pages.
Office Action, issued Apr. 3, 2008, in connection with U.S. Appl. No. 11/796,027, 18 pages.
Office Action, issued Feb. 2, 2009, in connection with U.S. Appl. No. 11/796,027, 12 pages.
Office Action, issued Nov. 4, 2009, in connection with U.S. Appl. No. 11/796,027, 7 pages.
Office Action, issued Sep. 25, 2006, in connection with Canadian Patent Application Serial No. 2,527,225, 5 pages.
Office Action, issued Dec. 21, 2007, in connection with Canadian Patent Application U.S. Appl. No. 2,527,225, 8 pages.
International Preliminary Report on Patentability, issued Feb. 9, 2006, in connection with International Patent Application No. WO/US2004/019866, 28 pages.
Office Action, issued Aug. 1, 2007, in connection with U.S. Appl. No. 10/866,606, 15 pages.
Office Action, issued Mar. 18, 2008, in connection with U.S. Appl. No. 10/866,606, 24 pages.
Office Action, issued Dec. 18, 2008, in connection with U.S. Appl. No. 10/866,606, 16 pages.
Office Action, issued Nov. 19, 2007, in connection with U.S. Appl. No. 10/485,179, 29 pages.
Office Action, issued Apr. 9, 2009, in connection with U.S. Appl. No. 10/485,179, 43 pages.
Examination Report, issued Dec. 13, 2006, in connection with European Patent Application Serial No. 03018478.2, 4 pages.
Examination Report, issued Oct. 31, 2006, in connection with European Patent Application Serial No. 03024283.8, 5 pages.
Office Action, issued Aug. 13, 2009, in connection with U.S. Appl. No. 11/975,090, 11 pages.
Search Report and Written Opinion, issued Aug. 2, 2010, in connection with corresponding Singapore Patent Application No. 200719015-0, 8 pages.
Response to Written Opinion, filed Jan. 3, 2011, in connection with corresponding Singapore Patent Application No. 200719015-0, 10 pages.
Notice of Allowance, issued May 13, 2011, in connection with related U.S. Appl. No. 11/796,027, 8 pages.
Written Opinion, issued May 20, 2011, in connection with corresponding Singapore Patent Application No. 200719015-0, 7 pages.
Office Action, issued Jul. 20, 2011, in connection with related U.S. Appl. No. 10/485,179, 26 pages.
Notice of Acceptance issued on Jul. 13, 2011, in connection with Australian Patent Application No. 2008264201, 3 pages.
Appeal Brief Instructions issued on Nov. 8, 2011, in connection with Japanese Patent Application No. 2006-0287210, 7 pages.
Response on Oct. 20, 2011, to Written Opinion issued on May 20, 2011, in connection with Singapore Patent Application No. 200719015-0, 7 pages.
Office Action, issued Dec. 20, 2011, in connection with corresponding Japanese Patent Application No. 2009-136914, with detailed report of Office Action in English, 9 pages.
Examination Report, issued Feb. 7, 2012, in connection with corresponding Indian Patent Application No. 275/MUMNP/2010, 4 pages.
Examination Report, issued Mar. 27, 2012, in connection with corresponding Singapore Application No. 200719015-0, 7 pages.
Office Action, issued Sep. 2, 2011, in connection with related U.S. Appl. No. 12/589,694, 9 pages.
Notice of Allowance, issued Mar. 23, 2011, in connection with related U.S. Appl. No. 12/589,694, 8 pages.
Response on May 23, 2012, to Office Action issued on Dec. 21, 2011, in connection with Japanese Patent Application No. 2006-0287210, 7 pages.
Examiner's Report, issued Aug. 20, 2010, in connection with corresponding Australian Patent Application No. 2008264201, 6 pages.
Office Action, issued Oct. 21, 2010, in connection with related U.S. Appl. No. 10/485,179, 28 pages.
Office Action, issued Dec. 9, 2010, in connection with corresponding U.S. Appl. No. 12/148,542, 18 pages.
Response to Australian Examiner's Report, filed Mar. 24, 2011, in connection with corresponding Australian Patent Application No. 2008264201, 37 pages.
Official Action, issued Dec. 11, 2012, in connection with corresponding Japanese Patent Application No. 2009-136914, 7 pages. [in Japanese with detailed report in English].
Response to Office Action, mailed Feb. 7, 2013, in connection with corresponding India Patent Application No. 275/MUMNP/2010, 38 pages.
Restriction Requirement, issued Jul. 11, 2006, in connection with corresponding U.S. Appl. No. 10/872,156, 12 pages.
Response to Restriction Requirement, submitted Aug. 2, 2006, in connection with corresponding U.S. Appl. No. 10/872,156, 6 pages.
Response to Office Action, submitted Apr. 25, 2007, in connection with corresponding U.S. Appl. No. 10/872,156, 24 pages.
Response to Office Action, submitted Jan. 31, 2008, in connection with corresponding U.S. Appl. No. 10/872,156, 20 pages.
Response to Office Action, submitted Sep. 12, 2008, in connection with corresponding U.S. Appl. No. 10/872,156, 17 pages.
Notice of Allowance, issued Dec. 30, 2008, in connection with corresponding U.S. Appl. No. 10/872,156, 7 pages.

(56) References Cited

OTHER PUBLICATIONS

Restriction Requirement, issued Sep. 15, 2006, in connection with corresponding U.S. Appl. No. 11/238,025, 9 pages.
Response to Restriction Requirement, submitted Sep. 26, 2006, in connection with corresponding U.S. Appl. No. 11/238,025, 8 pages.
Response to Office Action, submitted Jun. 18, 2007, in connection with corresponding U.S. Appl. No. 11/238,025, 35 pages.
Request for Continued Examination, issued Jun. 6, 2008, in connection with corresponding U.S. Appl. No. 11/238,025, 28 pages.
Response to Office Action, submitted Mar. 2, 2009, in connection with corresponding U.S. Appl. No. 11/238,025, 15 pages.
Notice of Allowance, issued May 11, 2009, in connection with corresponding U.S. Appl. No. 11/238,025, 22 pages.
Restriction Requirement, issued Jun. 19, 2007, in connection with corresponding U.S. Appl. No. 11/529,662, 12 pages.
Response to Restriction Requirement, submitted Aug. 20, 2007, in connection with corresponding U.S. Appl. No. 11/529,662, 7 pages.
Response to Office Action, submitted May 28, 2008, in connection with corresponding U.S. Appl. No. 11/529,662, 41 pages.
Supp. Response to Office Action, submitted Jun. 2, 2008, in connection with corresponding U.S. Appl. No. 11/529,662, 3 pages.
Office Action, issued Aug. 22, 2008, in connection with corresponding U.S. Appl. No. 11/529,662, 10 pages.
Response to Office Action, submitted Nov. 3, 2008, in connection with corresponding U.S. Appl. No. 11/529,662, 9 pages.
Office Action, issued Feb. 25, 2009, in connection with corresponding U.S. Appl. No. 11/529,662, 9 pages.
Response to Office Action, submitted May 1, 2009, in connection with corresponding U.S. Appl. No. 11/529,662, 6 pages.
Notice of Allowance, issued Jul. 30, 2009, in connection with corresponding U.S. Appl. No. 11/529,662, 8 pages.
Restriction Requirement, issued Oct. 31, 2007, in connection with corresponding U.S. Appl. No. 11/796,028, 10 pages.
Response to Restriction Requirement, submitted Dec. 28, 2007, in connection with corresponding U.S. Appl. No. 11/796,028, 6 pages.
Response to Office Action, submitted Oct. 1, 2008, in connection with corresponding U.S. Appl. No. 11/796,028, 25 pages.
Response to Office Action, submitted Jul. 30, 2009, in connection with corresponding U.S. Appl. No. 11/796,028, 20 pages.
Office Action, issued Nov. 13, 2009, in connection with corresponding U.S. Appl. No. 11/796,028, 7 pages.
Request for Continued Examination, issued Feb. 11, 2010, in connection with corresponding U.S. Appl. No. 11/796,028, 16 pages.
Supp. Response to Office Action, submitted Feb. 12, 2010, in connection with corresponding U.S. Appl. No. 11/796,028, 6 pages.
Restriction Requirement, issued Oct. 1, 2007, in connection with corresponding U.S. Appl. No. 11/796,027, 7 pages.
Response to Restriction Requirement, submitted Dec. 28, 2007, in connection with corresponding U.S. Appl. No. 11/796,027, 5 pages.
Response to Office Action, submitted Oct. 3, 2008, in connection with corresponding U.S. Appl. No. 11/796,027, 27 pages.
Request for Continued Examination, issued Aug. 3, 2009, in connection with corresponding U.S. Appl. No. 11/796,027, 19 pages.
Response to Office Action, submitted Apr. 9, 2010, in connection with corresponding U.S. Appl. No. 11/796,027, 19 pages.
Office Action, issued Jul. 15, 2010, in connection with corresponding U.S. Appl. No. 11/796,027, 11 pages.
Response to Office Action, submitted Dec. 3, 2010, in connection with corresponding U.S. Appl. No. 11/796,027, 21 pages.
Restriction Requirement, issued Jan. 30, 2009, in connection with corresponding U.S. Appl. No. 12/148,542, 10 pages.
Response to Restriction Requirement, submitted Feb. 13, 2009, in connection with corresponding U.S. Appl. No. 12/148,542, 7 pages.
Office Action, issued Jun. 10, 2009, in connection with corresponding U.S. Appl. No. 12/148,542, 8 pages.
Response to Office Action, submitted Dec. 10, 2009, in connection with corresponding U.S. Appl. No. 12/148,542, 17 pages.
Office Action, issued Apr. 8, 2010, in connection with corresponding U.S. Appl. No. 12/148,542, 10 pages.
Response to Office Action, submitted Oct. 8, 2010, in connection with corresponding U.S. Appl. No. 12/148,542, 21 pages.
Response to Office Action, submitted Jun. 9, 2011, in connection with corresponding U.S. Appl. No. 12/148,542, 27 pages.
Advisory Action, issued Jul. 13, 2011, in connection with corresponding U.S. Appl. No. 12/148,542, 3 pages.
Appeal Brief, issued Jan. 13, 2012, in connection with corresponding U.S. Appl. No. 12/148,542, 131 pages.
Examiner's Answer, issued Mar. 5, 2012, in connection with corresponding U.S. Appl. No. 12/148,542, 18 pages.
Notice of Allowance, issued Jun. 29, 2012, in connection with corresponding U.S. Appl. No. 12/148,542, 8 pages.
Notice of Allowance, issued Jan. 22, 2010, in connection with corresponding U.S. Appl. No. 12/462,074, 10 pages.
Restriction Requirement, issued Apr. 19, 2011, in connection with corresponding U.S. Appl. No. 12/589,694, 8 pages.
Response to Restriction Requirement, submitted Jun. 3, 2011, in connection with corresponding U.S. Appl. No. 12/589,694, 4 pages.
Response to Office Action, submitted Nov. 22, 2011, in connection with corresponding U.S. Appl. No. 12/589,694, 17 pages.
Examiner's Report, issued Mar. 12, 2008, in connection with corresponding Australian Patent Application No. 2004289953, 10 pages.
Response to Examiner's Report, submitted Sep. 4, 2008, in connection with corresponding Australian Patent Application No. 2004289953, 17 pages.
Notice of Acceptance, issued Sep. 16, 2008, in connection with corresponding Australian Patent Application No. 2004289953, 4 pages.
Official Action, issued Mar. 13, 2012, in connection with corresponding Brazilian Patent Application No. PI 0411526-0, 3 pages.
Response to Official Action, submitted Mar. 28, 2012, in connection with corresponding Brazilian Patent Application No. PI 0411526-0, 3 pages.
Response to Examiner's Report, submitted Sep. 27, 2007, in connection with corresponding Canadian Patent Application No. 2527225, 28 pages.
Response to Examiner's Report, submitted Oct. 16, 2008, in connection with corresponding Canadian Patent Application No. 2527225, 22 pages.
Examiner's Report, issued Nov. 13, 2008, in connection with corresponding Canadian Patent Application No. 2527225, 4 pages.
Response to Examiner's Report, submitted Feb. 9, 2009, in connection with corresponding Canadian Patent Application No. 2527225, 9 pages.
Examiner's Report, issued Mar. 20, 2009, in connection with corresponding Canadian Patent Application No. 2527225, 2 pages.
Response to Examiner's Report, submitted Jul. 10, 2009, in connection with corresponding Canadian Patent Application No. 2527225, 8 pages.
Notice of Allowance, issued Oct. 20, 2009, in connection with corresponding Canadian Patent Application No. 2527225, 2 pages.
Office Action, issued Sep. 7, 2007, in connection with corresponding Chinese Patent Application No. 200480023610.8, 13 pages.
Instructions for Response to Office Action, submitted Mar. 19, 2008, in connection with corresponding Chinese Patent Application No. 200480023610.8, 15 pages.
Office Action, issued Oct. 10, 2008, in connection with corresponding Chinese Patent Application No. 200480023610.8, 9 pages.
Instructions for Response to Office Action, submitted Feb. 23, 2009, in connection with corresponding Chinese Patent Application No. 200480023610.8, 10 pages.
Decision to Grant, issued Aug. 7, 2009, in connection with corresponding Chinese Patent Application No. 200480023610.8, 4 pages.
Partial European Search Report, issued Oct. 29, 2003, in connection with corresponding European Patent Application No. EP 03013826.7, 13 pages.
European Search Report, issued Dec. 18, 2003, in connection with corresponding European Patent Application No. EP 03013826.7, 5 pages.
International Preliminary Report on Patentability, issued Feb. 9, 2006, in connection with corresponding International Patent Application No. PCT/US2004/019866, 28 pages.

(56) References Cited

OTHER PUBLICATIONS

Communication Rules 109 and 110 EPC, issued Feb. 7, 2006, in connection with corresponding European Patent Application No. EP04816752.2, 2 pages.
Response to Rule 109 and 110 Communication, submitted Mar. 10, 2006, in connection with corresponding European Patent Application No. EP04816752.2, 13 pages.
Office Action, issued Jun. 4, 2007, in connection with corresponding European Patent Application No. EP04816752.2, 4 pages.
Response to Office Action, submitted Oct. 2, 2007, in connection with corresponding European Patent Application No. EP04816752.2, 15 pages.
Office Action, issued Nov. 8, 2007, in connection with corresponding European Patent Application No. EP04816752.2, 3 pages.
Response to Office Action, submitted Jan. 16, 2008, in connection with corresponding European Patent Application No. EP04816752.2, 5 pages.
Rule 71(3) Communication, issued Apr. 15, 2008, in connection with corresponding European Patent Application No. EP04816752.2, 7 pages.
Notice of Grant, issued Jan. 7, 2009, in connection with corresponding European Patent Application No. EP04816752.2, 1 page.
Partial European Search Report, issued Jan. 26, 2009, in connection with corresponding European Patent Application No. EP0819998.7, 4 pages.
European Search Report and Written Opinion, issued Apr. 21, 2009, in connection with corresponding European Patent Application No. EP0819998.7, 11 pages.
Examination Report, issued Oct. 1, 2010, in connection with corresponding European Patent Application No. EP0819998.7, 3 pages.
Response to Examination Report, submitted Jan. 27, 2011, in connection with corresponding European Patent Application No. EP0819998.7, 4 pages.
Rule 71(3) Communication, issued Jul. 25, 2011, in connection with corresponding European Patent Application No. EP0819998.7, 8 pages.
Notice of Grant, issued Jan. 19, 2012, in connection with corresponding European Patent Application No. EP0819998.7, 1 page.
Notice of Grant, issued May 8, 2009, in connection with corresponding Hong Kong Patent Application No. 6106250.6, 1 page.
Notice of Grant, issued Sep. 21, 2012, in connection with corresponding Hong Kong Patent Application No. 9106084.5, 7 pages.
Examination Report, issued Feb. 10, 2009, in connection with corresponding Indian Patent Application No. 00052/MUMNP/2006, 3 pages.
Response to Examination Report, submitted Feb. 10, 2010, in connection with corresponding Indian Patent Application No. 00052/MUMNP/2006, 28 pages.
Notification of Hearing, issued Sep. 3, 2010, in connection with corresponding Indian Patent Application No. 00052/MUMNP/2006, 5 pages.
Notification of Hearing, issued Sep. 19, 2013, in connection with corresponding Indian Patent Application No. 275/MUMNP/2010, 1 page.
Instructions for Response to Notification of Hearing, submitted Oct. 18, 2013, in connection with corresponding Indian Patent Application No. 275/MUMNP/2010, 17 pages.
Translation of Office Action, issued Nov. 18, 2008, in connection with corresponding Israeli Patent Application No. 171859, 1 page.
Response to Office Action, submitted Feb. 16, 2009, in connection with corresponding Israeli Patent Application No. 171859, 9 pages.
Notice of Allowance, issued Feb. 1, 2011, in connection with corresponding Israeli Patent Application No. 171859, 3 pp.pages.
Office Action, issued Jul. 25, 2006, in connection with corresponding Japanese Patent Application No. 2006-517504, 6 pages.
Instructions for Response to Office Action, submitted Oct. 17, 2006, in connection with corresponding Japanese Patent Application No. 2006-517504, 16 pages.
Office Action, issued Dec. 26, 2006, in connection with corresponding Japanese Patent Application No. 2006-517504, 4 pages.
Instructions for Response to Office Action, submitted Dec. 28, 2006, in connection with corresponding Japanese Patent Application No. 2006-517504, 8 pages.
Notice of Grant, issued Mar. 30, 2007, in connection with corresponding Japanese Patent Application No. 2006-517504, 2 pages.
Office Action, issued Aug. 7, 2007, in connection with corresponding Japanese Patent Application No. 2006-0287210, 6 pages.
Instructions for Response to Office Action, submitted Dec. 27, 2007, in connection with corresponding Japanese Patent Application No. 2006-0287210, 10 pages.
Office Action, issued Jun. 24, 2008, in connection with corresponding Japanese Patent Application No. 2006-0287210, 4 pages.
Response to Office Action, submitted Dec. 1, 2008, in connection with corresponding Japanese Patent Application No. 2006-0287210, 7 pages.
Office Action, issued Mar. 10, 2009, in connection with corresponding Japanese Patent Application No. 2006-0287210, 4 pages.
Instructions for Response to Office Action, submitted May 27, 2009, in connection with corresponding Japanese Patent Application No. 2006-0287210, 4 pages.
Office Action, issued May 17, 2011, in connection with corresponding Japanese Patent Application No. 2006-0287210, 6 pages.
Response to Office Action, submitted Feb. 6, 2012, in connection with corresponding Japanese Patent Application No. 2006-0287210, 6 pages.
Notice of Grant, issued Feb. 28, 2012, in connection with corresponding Japanese Patent Application No. 2006-0287210, 1 page.
Office Action, issued Jun. 24, 2008, in connection with corresponding Japanese Patent Application No. 2008-017869, 8 pages.
Instructions for Response to Office Action, submitted Dec. 1, 2008, in connection with corresponding Japanese Patent Application No. 2008-017869, 7 pages.
Notice of Grant, issued Mar. 10, 2009, in connection with corresponding Japanese Patent Application No. 2008-017869, 1 page.
Notice of Grant, issued Jul. 23, 2013, in connection with corresponding Japanese Patent Application No. 2009-136914, 7 pages.
Response to Office Action, submitted May 24, 2013, in connection with corresponding Japanese Patent Application No. 2009-136914, 27 pages.
Translation of Office Action, issued Sep. 12, 2008, in connection with corresponding Mexican Patent Application No. PA/A/2005/013879, 2 pages.
Instructions for Response to Office Action, submitted Nov. 7, 2008, in connection with corresponding Mexican Patent Application No. PA/A/2005/013879, 2 pages.
Notice of Allowance, issued May 11, 2009, in connection with corresponding Mexican Patent Application No. PA/A/2005/013879, 2 pages.
Translation of Office Action, issued Mar. 1, 2011, in connection with corresponding Mexican Patent Application No. MX/A/2009/007011, 2 pages.
Instructions for Response to Office Action, submitted Apr. 18, 2011, in connection with corresponding Mexican Patent Application No. MX/A/2009/007011, 2 pages.
Notice of Allowance, issued May 23, 2011, in connection with corresponding Mexican Patent Application No. MX/A/2009/007011, 2 pages.
Summary of Office Action, issued Apr. 28, 2008, in connection with corresponding Russian Patent Application No. 2006100679, 3 pages.
Instructions for Response to Office Action, submitted Aug. 14, 2008, in connection with corresponding Russian Patent Application No. 2006100679, 12 pages.
Summary of Office Action, issued Jan. 12, 2009, in connection with corresponding Russian Patent Application No. 2006100679, 3 pages.
Instructions for Response to Office Action, submitted Jan. 28, 2009, in connection with corresponding Russian Patent Application No. 2006100679, 9 pages.

(56) References Cited

OTHER PUBLICATIONS

Further Instructions for Response to Office Action, submitted Jan. 30, 2009, in connection with corresponding Russian Patent Application No. 2006100679, 2 pages.
Decision to Grant, issued May 14, 2009, in connection with corresponding Russian Patent Application No. 2006100679, 1 page.
Notice of Grant, issued Oct. 15, 2012, in connection with corresponding Singapore Patent Application No. 200719015-0, 1 page.
Office Action, issued Mar. 19, 2014, in connection with U.S. Appl. No. 11/796,028, 15 pages.
International Search Report, issued Jul. 7, 2005, in connection with corresponding International Patent Application No. PCT/US04/19866, 12 pages.
Response to Office Action, submitted Jun. 19, 2014, in connection with U.S. Appl. No. 11/796,028, 27 pages.
Restriction Requirement, issued Apr. 4, 2013, in connection with U.S. Appl. No. 13/507,572, 10 pages.
Response to Restriction Requirement, submitted May 3, 2013, in connection with U.S. Appl. No. 13/507,572, 6 pages.
Office Action, issued Aug. 27, 2013, in connection with U.S. Appl. No. 13/507,572, 17 pages.
Response to Office Action, issued Jan. 30, 2014, in connection with U.S. Appl. No. 13/507,572, 39 pages.
Notice of Allowance, issued Mar. 5, 2014, in connection with U.S. Appl. No. 13/507,572, 10 pages.
Further instructions for response to Notification of Hearing, sent Apr. 8, 2014, in connection with corresponding Indian Patent Application No. 275/MUMNP/2010, 12 pages.
Written submission after Hearing, submitted May 5, 2014, in connection with corresponding Indian Patent Application No. 275/MUMNP/2010, 21 pages.
Office Action, issued Jan. 31, 2012, and English summary, in connection with corresponding Japanese Patent Application No. 2006-0287210, 2 pages.
U.S. Appl. No. 14/501,692, filed Sep. 30, 2014.
U.S. Appl. No. 14/638,604, filed Mar. 4, 2015.

* cited by examiner

MICROORGANISMS FOR THERAPY

RELATED APPLICATIONS

This application is a continuation of allowed U.S. application Ser. No. 13/507,572, to Aladar A. Szalay; Tatyana Timiryasova; Yong A. Yu; Qian Zhang, filed Jul. 10, 2012, entitled "MICROORGANISMS FOR THERAPY," which is a continuation of U.S. application Ser. No. 12/589,694, to Aladar A. Szalay; Tatyana Timiryasova; Yong A. Yu; Qian Zhang, filed Oct. 26, 2009, entitled "MICROORGANISMS FOR THERAPY," which is a continuation of U.S. application Ser. No. 11/796,028, to Aladar A. Szalay; Tatyana Timiryasova; Yong A. Yu; Qian Zhang, filed on Apr. 25, 2007, entitled "MICROORGANISMS FOR THERAPY," which is a divisional of U.S. application Ser. No. 10/872,156, to Aladar A. Szalay, Tatyana Timiryasova, Yong A. Yu and Qian Zhang, filed on Jun. 18, 2004, entitled "MICROORGANISMS FOR THERAPY," which claims the benefit of priority under 35 U.S.C. §119(a) to each of EP 03 013 826.7, filed 18 Jun. 2003, entitled "RECOMBINANT VACCINIA VIRUSES USEFUL AS TUMOR-SPECIFIC DELIVERY VEHICLE FOR CANCER GENE THERAPY AND VACCINATION;" EP 03 018 478.2, filed 14 Aug. 2003, entitled "METHOD FOR THE PRODUCTION OF A POLYPEPTIDE, RNA OR OTHER COMPOUND IN TUMOR TISSUE;" and EP 03 024 283.8, filed 22 Oct. 2003, entitled "USE OF A MICROORGANISM OR CELL TO INDUCE AUTOIMMUNIZATION OF AN ORGANISM AGAINST A TUMOR." The subject matter of each of these applications is incorporated by reference in its entirety.

This application is also a continuation of allowed U.S. application Ser. No. 12/589,694, to Aladar A. Szalay; Tatyana Timiryasova; Yong A. Yu; Qian Zhang, filed Oct. 26, 2009, entitled "MICROORGANISMS FOR THERAPY," which is a continuation of U.S. application Ser. No. 11/796,028, to Aladar A. Szalay; Tatyana Timiryasova; Yong A. Yu; Qian Zhang, filed on Apr. 25, 2007, entitled "MICROORGANISMS FOR THERAPY," which is a divisional of U.S. application Ser. No. 10/872,156, to Aladar A. Szalay, Tatyana Timiryasova, Yong A. Yu and Qian Zhang, filed on Jun. 18, 2004, entitled "MICROORGANISMS FOR THERAPY," which claims the benefit of priority under 35 U.S.C. §119(a) to each of EP 03 013 826.7, filed 18 Jun. 2003, entitled "RECOMBINANT VACCINIA VIRUSES USEFUL AS TUMOR-SPECIFIC DELIVERY VEHICLE FOR CANCER GENE THERAPY AND VACCINATION;" EP 03 018 478.2, filed 14 Aug. 2003, entitled "METHOD FOR THE PRODUCTION OF A POLYPEPTIDE, RNA OR OTHER COMPOUND IN TUMOR TISSUE;" and EP 03 024 283.8, filed 22 Oct. 2003, entitled "USE OF A MICROORGANISM OR CELL TO INDUCE AUTOIMMUNIZATION OF AN ORGANISM AGAINST A TUMOR." The subject matter of each of these applications is incorporated by reference in its entirety.

This application is also a continuation of U.S. application Ser. No. 11/796,028, to Aladar A. Szalay; Tatyana Timiryasova; Yong A. Yu; Qian Zhang, filed on Apr. 25, 2007, entitled "MICROORGANISMS FOR THERAPY," which is a divisional of U.S. application Ser. No. 10/872,156, to Aladar A. Szalay, Tatyana Timiryasova, Yong A. Yu and Qian Zhang, filed on Jun. 18, 2004, entitled "MICROORGANISMS FOR THERAPY," which claims the benefit of priority under 35 U.S.C. §119(a) to each of EP 03 013 826.7, filed 18 Jun. 2003, entitled "RECOMBINANT VACCINIA VIRUSES USEFUL AS TUMOR-SPECIFIC DELIVERY VEHICLE FOR CANCER GENE THERAPY AND VACCINATION;" EP 03 018 478.2, filed 14 Aug. 2003, entitled "METHOD FOR THE PRODUCTION OF A POLYPEPTIDE, RNA OR OTHER COMPOUND IN TUMOR TISSUE;" and EP 03 024 283.8, filed 22 Oct. 2003, entitled "USE OF A MICROORGANISM OR CELL TO INDUCE AUTOIMMUNIZATION OF AN ORGANISM AGAINST A TUMOR." The subject matter of each of these applications is incorporated by reference in its entirety.

This application also is related to International Application Serial No. PCT/US04/19866, filed on Jun. 18, 2004. This application also is related to U.S. application Ser. No. 10/866,606, filed Jun. 10, 2004, entitled "LIGHT EMITTING MICROORGANISMS AND CELLS FOR DIAGNOSIS AND THERAPY OF TUMORS," which is a continuation of U.S. application Ser. No. 10/189,918, filed Jul. 3, 2002, entitled "LIGHT EMITTING MICROORGANISMS AND CELLS FOR DIAGNOSIS AND THERAPY OF TUMORS"; U.S. application Ser. No. 10/849,664, filed May 19, 2004, entitled, "LIGHT EMITTING MICROORGANISMS AND CELLS FOR DIAGNOSIS AND THERAPY OF DISEASES ASSOCIATED WITH WOUNDED OR INFLAMED TISSUE" which is a continuation of U.S. application Ser. No. 10/163,763, filed Jun. 5, 2002, entitled "LIGHT EMITTING MICROORGANISMS AND CELLS FOR DIAGNOSIS AND THERAPY OF DISEASES ASSOCIATED WITH WOUNDED OR INFLAMED TISSUE"; International PCT Application WO 03/014380, filed Jul. 31, 2002, entitled "MICROOROGANISMS AND CELLS FOR DIAGNOSIS AND THERAPY OF TUMORS;" PCT Application WO 03/104485, filed Jun. 5, 2003, entitled, "LIGHT EMITTING MICROORGANISMS AND CELLS FOR DIAGNOSIS AND THERAPY OF DISEASES ASSOCIATED WITH WOUNDED OR INFLAMED TISSUE;" EP Application No. 01 118 417.3, filed Jul. 31, 2001, entitled "LIGHT EMITTING MICROORGANISMS AND CELLS FOR TUMOUR DIAGNOSIS/THERAPY;" EP Application No. 01 125 911.6, filed Oct. 30, 2001, entitled "LIGHT EMITTING MICROORGANISMS AND CELLS FOR DIAGNOSIS AND THERAPY OF TUMORS;" EP Application No. 02 794 632.6, filed Jan. 28, 2004, entitled "VACCINIA VIRUS FOR DIAGNOSIS AND THERAPY OF TUMORS;" and EP Application No. 02 012 552.2, filed Jun. 5, 2002, entitled "LIGHT EMITTING MICROORGANISMS AND CELLS FOR DIAGNOSIS AND THERAPY OF DISEASES ASSOCIATED WITH WOUNDED OR INFLAMED TISSUE." The subject matter of each of these applications is incorporated by reference in its entirety.

INCORPORATION BY REFERENCE OF SEQUENCE LISTING PROVIDED ELECTRONICALLY

An electronic version of the Sequence Listing is filed herewith, the contents of which are incorporated by reference in their entirety. The electronic file was created on Jun. 6, 2014, is 264 kilobytes in size, and titled 4802Jseq001.txt.

FIELD OF THE INVENTION

Vaccines that contain attenuated or modified microorganisms, including microbes and cells, and methods for preparing the microorganisms and vaccines are provided. In particular, modified bacteria, eukaryotic cells and viruses are provided and methods of use thereof for treatment of proliferative and inflammatory disorders and for production of products in tumors are provided.

BACKGROUND

In the late 19th century, a variety of attempts were made to treat cancer patients with microorganisms. One surgeon, William Coley, administered live *Streptococcus pyogenes* to patients with tumors with limited success. In the early 20th century, scientists documented vaccinia viral oncolysis in mice, which led to administration of several live viruses to patients with tumors from the 1940s through the 1960s. These forays into this avenue of cancer treatment were not successful.

Since that time, a variety of genetically engineered viruses have been tested for treatment of cancers. In one study, for example, nude mice bearing nonmetastatic colon adenocarcinoma cells were systemically injected with a WR strain of vaccinia virus modified by having a vaccinia growth factor deletion and an enhanced green fluorescence protein inserted into the thymidine kinase locus. The virus was observed to have antitumor effect, including one complete response, despite a lack of exogenous therapeutic genes in the modified virus (McCart et al. (2001) *Cancer Res* 1:8751-8757). In another study, vaccinia melanoma oncolysate (VMO) was injected into sites near melanoma positive lymph nodes in a Phase III clinical trial of melanoma patients. As a control, New York City Board of Health strain vaccinia virus (VV) was administered to melanoma patients. The melanoma patients treated with VMO had a survival rate better than that for untreated patients, but similar to patients treated with the VV control (Kim et al. (2001) *Surgical Oncol* 10:53-59).

Other studies have demonstrated limited success with this approach. This therapy is not completely effective, particularly for systemically delivered viruses or bacteria. Limitations on the control of microbial vehicle function in vivo result in ineffective therapeutic results as well as raising safety concerns. It would be desirable to improve this type of therapy or to develop more effective approaches for treatments of neoplastic disease. Therefore, among the objects herein, it is an object to provide therapeutic methods and microorganisms for the treatment of neoplastic and other diseases.

SUMMARY

Provided herein are therapeutic methods and microorganisms, including viruses, bacteria and eukaryotic cells, for uses in the methods for the treatment of neoplastic diseases and other diseases. Diseases for treatment are those in which the targeted tissues and/or cells are immunoprivileged in that they, and often the local environment thereof, somehow escape or are inaccessible to the immune system. Such tissues include tumors and other tissues and cells involved in other proliferative disorders, wounds and other tissues involved in inflammatory responses. The microorganisms, which include bacterial cells, viruses and mammalian cells, are selected or are designed to be non-pathogenic and to preferentially accumulate in the immunoprivileged tissues. The microorganisms, once in the tissues or cells or vicinity thereof, affect the cell membranes of the cells in such tissues so that they become leaky or lyse, but sufficiently slowly so that the targeted cells and tumors leak enough antigen or other proteins for a time sufficient to elicit an immune response.

The microorganisms are administered by any route, including systemic administration, such as i.v. or using oral or nasal or other delivery systems that direct agents to the lymphatics. In exemplary methods, the microorganisms are used to treat tumors and to prevent recurrence and metastatic spread. Exemplary microorganisms include highly attenuated viruses and bacteria, as well as mammalian cells. The microorganisms are optionally modified to deliver other products, including other therapeutic products to the targeted tissues.

When the microorganisms are administered to a host that contains tumors, the tumors in the host essentially become antigen and protein factories. This can be exploited so that the tumors can be used to produce proteins or other cellular products encoded by or produced by the microorganisms. In addition, the host sera can be harvested to isolate antibodies to products produced by the microorganisms as well as the tumor cells. Hence also provided are methods for producing gene products by administering the microorganisms to an animal, generally a non-human animal, and harvesting the tumors to isolate the product. Also provided are methods for producing antibodies to selected proteins or cell products, such as metabolites or intermediates, by administering a microorganism that expresses or produces the protein or other product to a host, typically a non-human host; and harvesting serum from the host and isolating antibodies that specifically bind to the protein or other product.

Thus provided are methods and microorganisms for elimination of immunoprivileged cells or tissues, particularly tumors. The methods include administration, typically systemic administration, with a microorganism that preferentially accumulates in immunoprivileged cells, such as tumor cells, resulting in leakage proteins and other compounds, such as tumor antigens, resulting in vaccination of the host against non-host proteins and, such as the tumor antigens, providing for elimination of the immunoprivileged cells, such as tumor cells, by the host's immune system. The microorganisms are selected not for their ability to rapidly lyse cells, but rather for the ability to accumulate in immunoprivileged cells, such as tumors, resulting in a leakage of antigens in a sufficient amount and for a sufficient time to elicit an immune response.

Hence provided are uses of microorganisms or cells containing heterologous DNA, polypeptides or RNA to induce autoimmunization of an organism against a tumor. In particular, the microorganisms are selected or designed to accumulate in tumors and to accumulate very little, if at all (to be non-toxic to the host) in non-tumorous cells, tissues or organs, and to in some manner result in the tumor cell lyses or cell membrane disruption such that tumor antigens leak. Exemplary of such microorganisms are the LIVP-derived vaccinia virus and the bacteria described herein and also mammalian cells modified to target the tumors and to disrupt the cells membrane. The microorganisms can be modified to express heterologous products that mediate or increase the leakage of the tumor cell antigens and/or that are therapeutic, such as anti-tumor compounds.

Also provided are methods for production of antibodies against a tumor by (a) injecting a microorganism or cell containing a DNA sequence encoding a desired polypeptide or RNA into an organism bearing a tumor and (b) isolating antibodies against the tumor.

Provided are attenuated microorganisms that accumulate in immunoprivileged tissues and cells, such as tumor cells, but do not accumulate to toxic levels in non-targeted organs and tissues, and that upon administration to an animal bearing the immunoprivileged tissues and cells, result in autoimmunity, such as by production of anti-tumor (or anti-tumor antigen) antibodies against the immunoprivileged cells or products thereof. The microorganisms are selected or produced to render the immunoprivileged cells leaky, such as by a slow lysis or apoptotic process. The goal is to achieve such leakiness, but to not lyse the cells so rapidly that the host cannot mount an immune response.

Uses of and methods of use of the microorganisms for eliminating immunoprivileged tissues and cells are provided. The microorganisms optionally include reporter genes and/or other heterologous nucleic acids that disrupt genes in the microorganism and can also encode and provide therapeutic products or products, such as RNA, including RNAi, that alter gene and/or protein expression in the cells or tissues where the microorganism accumulates. Among the viruses provided are attenuated pox viruses that contain a modified TK and HA gene and a modified F3 gene or locus that corresponds to the F3 gene in vaccinia. In particular, provided are recombinant vaccinia viruses that contain a modified TK and HA gene and optionally a modified F3 gene or locus, wherein the resulting virus does not accumulate to toxic levels in non-targeted organs. Vaccinia viruses where the TK gene and F3 gene are modified and vaccinia viruses where the HA and F3 gene are modified, and viruses where all three genes are modified are provided. Modification includes inactivation by insertion, deletion or replacement of one or more nucleotide bases whereby an activity or product of the virus is altered. Included among the alterations is insertion of heterologous nucleic acid, such as therapeutic protein-encoding nucleic acids.

In exemplary embodiments, the vaccinia viruses are Lister strain viruses, particularly LIVP strain viruses (LIVP refers to the Lister virus from the Institute of Viral Preparations, Moscow, Russia, the original source for this now widely disseminated virus strain). Modifications include modification of the virus at the unique NotI site in the locus designed F3. In particular, the modification can be at position 35 of the F3 locus (gene) or at position 1475 inside of the HindIII-F fragment of vaccinia virus DNA strain LIVP.

The heterologous nucleic acid can include regulatory sequences operatively linked to the nucleic acid encoding the protein. Regulatory sequences include promoters, such as the vaccinia virus early/late promoter p7.5 and an early/late vaccinia pE/L promoter. The heterologous nucleic acid in the microorganism can encode a detectable protein or a product capable of inducing a detectable signal. Inclusion of detectable protein or a product that can generate a detectable signal permits monitoring of the distribution of the administered microorganism as well as monitoring therapeutic efficacy, since the microorganism will be eliminated when the immunoprivileged cells are eliminated.

Host cells containing the recombinant viruses, such as the triple mutant vaccinia virus exemplified herein are provided. Also contemplated are tumor cells that contain any of the microorganisms provided herein or used in the methods.

Pharmaceutical compositions containing the microorganisms in a pharmaceutically acceptable vehicle for use in the methods herein are provided. The pharmaceutical compositions can be formulated for any mode of administration, including, but not limited to systemic administration, such as for intravenous administration or is formulated. The compositions can contain a delivery vehicle, such as a lipid-based carrier, including liposomes and micelles associated with the microorganism.

Also provided are methods (and uses of the microorganisms) for eliminating immunoprivileged cells, such as tumor cells in an animal, by administering the pharmaceutical compositions to an animal, whereby the virus accumulates in the immunoprivileged cells, thereby mediating autoimmunization resulting in elimination of the cells or a reduction in their number.

Therapeutic methods for eliminating immunoprivileged cells or tissues, in an animal, by administering a microorganism to an animal, where the microorganism accumulates in the immunoprivileged cells; the microorganism does not accumulate in unaffected organs and tissues and has low toxicity in the animal; and the microorganism results in leakage of the cell membranes in the immunoprivileged cells, whereby the animal produces autoantibodies against the cells or products of the cells are provided. These methods include tumor treatment, treatment for inflammatory conditions, including wounds, and proliferative disorders, including psoriasis, cancers, diabetic retinopathies, restenosis and other such disorders. It is desirable for the microorganisms to not accumulate in unaffected organs, particularly the ovaries or testes.

The microorganisms attenuated include attenuated viruses, such as pox viruses and other cytoplasmic viruses, bacteria such as *vibrio, E. coli, salmonella, streptococcus* and *listeria* and mammalian cells, such as immune cells, including B cells and lymphocytes, such as T cells, and stem cells.

Also provided are methods for production of a polypeptide or RNA or compound, such as a cellular product, and uses of the microorganism therefore are provided. Such methods can include the steps of: (a) administering a microorganism containing nucleic acid encoding the polypeptide or RNA or producing the product compound to tumor-bearing animal, where the microorganism accumulates in the immunoprivileged cells; and the microorganism does not accumulate to toxic levels in organs and tissues that do not comprise immunoprivileged cells or tissues; (b) harvesting the tumor tissue from the animal; and (c) isolating the polypeptide or RNA or compound from the tumor.

As noted, the microorganisms include eukaryotic cells, prokaryotic cells and viruses, such as a cytoplasmic virus or an attenuated bacterium or a stem cell or an immune cell. The bacterium can be selected from among attenuated *vibrio, E. coli, listeria, salmonella* and *streptococcus* strains. The microorganism can express or produce detectable products, such as a fluorescent protein (i.e., green, red and blue fluorescent proteins and modified variants thereof), and/or luciferase which, when contacted with a luciferin produces light, and also can encode additional products, such as therapeutic products. In the methods and uses provided herein, the animals can be non-human animals or can include humans.

Also provided are methods for simultaneously producing a polypeptide, RNA molecule or cellular compound and an antibody that specifically reacts with the polypeptide, RNA molecule or compound, by: a) administering a microorganism to a tumor-bearing animal, wherein the microorganism expresses or produces the compound, polypeptide or RNA molecule; and b) isolating the antibody from serum in the animal. The method optionally includes, after step a) harvesting the tumor tissue from the animal; and isolating the polypeptide, RNA molecule or cellular compound from the tumor tissue.

Also provided are methods for eliminating immunoprivileged cells or tissues in an animal, such as tumor cells, and uses of the microorganisms therefore by administering at least two microorganisms, wherein the microorganisms are administered simultaneously, sequentially or intermittently, wherein the microorganisms accumulate in the immunoprivileged cells, whereby the animal is autoimmunized against the immunoprivileged cells or tissues.

Uses of at least two microorganisms for formulation of a medicament for elimination of immunoprivileged cells or tissues, wherein they accumulate in the immunoprivileged cells, whereby the animal is autoimmunized against the immunoprivileged cells or tissues are provided. Combinations containing at least two microorganisms formulated for administration to an animal for elimination of immunoprivileged cells or tissues are provided. Kits containing packaged combination optionally with instructions for administration and other reagents are provided.

Uses of a microorganism encoding heterologous nucleic acid for inducing autoimmunization against products produced in immunoprivileged cells, wherein, when administered, the microorganism accumulates in immunoprivileged tissues and does not accumulate or accumulates at a sufficiently low level in other tissues or organs to be non-toxic to an animal containing the immunoprivileged tissues are provided.

Methods for the production of antibodies against products produced in immunoprivileged tissues or cells by: (a) administering a microorganism containing nucleic acid encoding a selected protein or RNA into an animal containing the immunoprivileged tissues or cells; and (b) isolating antibodies against the protein or RNA from the blood or serum of the animal are provided.

Also provided are methods for inhibiting growth of immunoprivileged cells or tissue in a subject by: (a) administering to a subject a modified microorganism, wherein the modified microorganism encodes a detectable gene product; (b) monitoring the presence of the detectable gene product in the subject until the detectable gene product is substantially present only in immunoprivileged tissue or cells of a subject; and (c) administering to a subject a therapeutic compound that works in conjunction with the microorganism to inhibit growth of immunoprivileged cells or tissue or by: (a) administering to a subject a modified microorganism that encodes a detectable gene product; (b) administering to a subject a therapeutic substance that reduces the pathogenicity of the microorganism; (c) monitoring the presence of the detectable gene product in the subject until the detectable gene product is substantially present only in immunoprivileged tissue or cells of a subject; and (d) terminating or suspending administration of the therapeutic compound, whereby the microorganism increases in pathogenicity and the growth of the immunoprivileged cells or tissue is inhibited.

DETAILED DESCRIPTION

Figure 1:
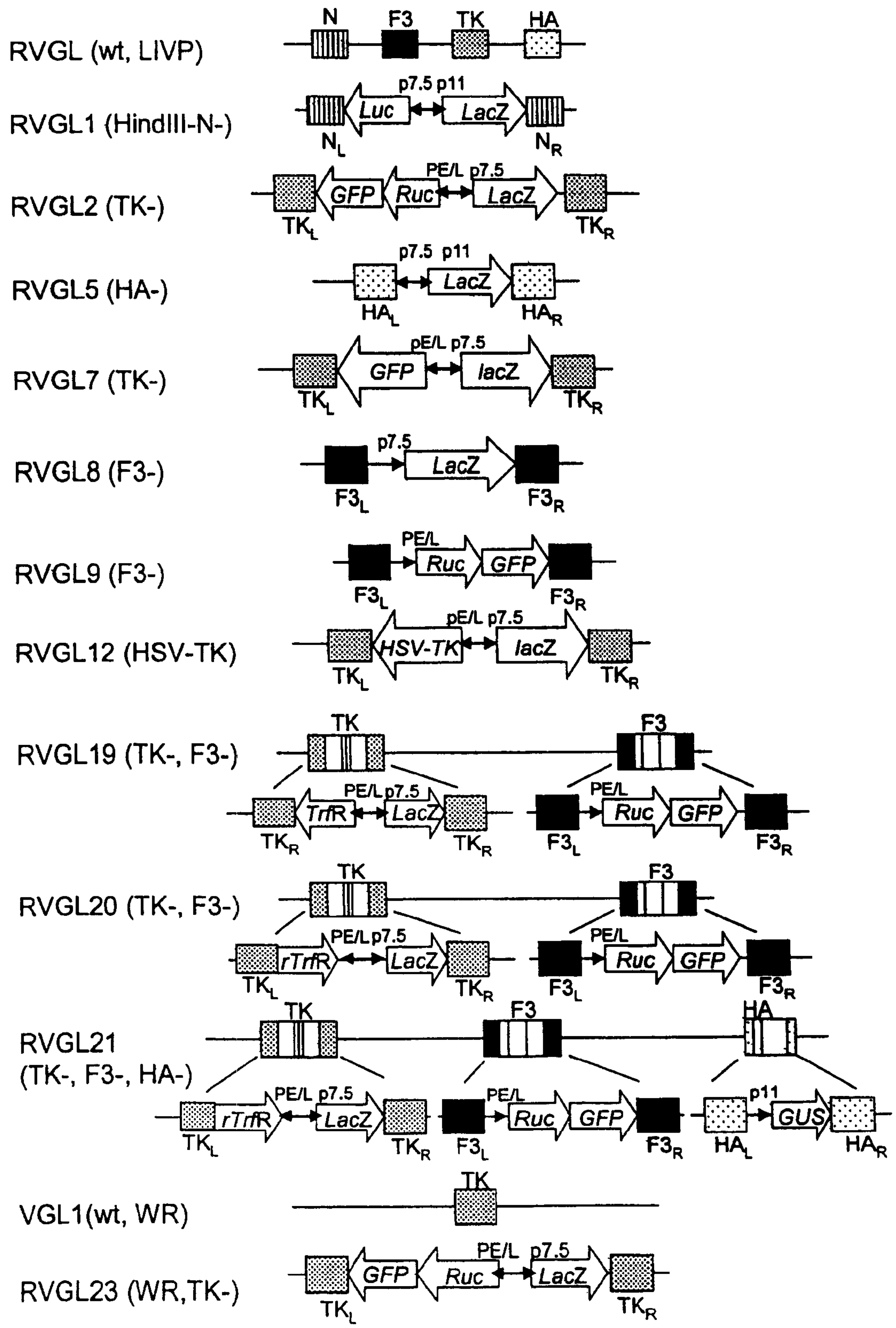
FIG. 1: Schematic of the various vaccinia strains described in the Examples. Results achieved with the viruses are described in the Examples.

A. Definitions
B. Microorganisms for Tumor-Specific Therapy
1. Characteristics
  a. Attenuated
    i. Reduced toxicity
    ii. Accumulate in immunoprivileged cells and tissues, such as tumor, not substantially in other organs
    iii. Ability to Elicit or Enhance Immune Response to Tumor Cell
    iv. Balance of Pathogenicity and Release of Tumor Antigens
  b. Immunogenicity
  c. Replication Competent
  d. Genetic Variants
    i. Modified Characteristics
    ii. Exogenous Gene Expression
    iii. Detectable gene product
    iv. Therapeutic gene product
    v. Expressing a superantigen
    vi. Expressing a gene product to be harvested
2. Viruses
  a. Cytoplasmic viruses
    i. Poxviruses
      a. Vaccinia Virus
      b. Modified Vaccinia Viruses
      c. The F3 Gene
      d. Multiple Modifications
      e. The Lister Strain
    ii. Other cytoplasmic viruses
  b. Adenovirus, Herpes, Retroviruses
3. Bacteria
  a. Aerobic bacteria
  b. Anaerobic bacteria
4. Eukaryotic cells
C. Methods for Making an Attenuated Microorganism
1. Genetic Modifications
2. Screening for above characteristics
D. Therapeutic Methods
1. Administration
  a. Steps prior to administering the microorganism
  b. Mode of administration
  c. Dosage
  d. Number of administrations
  e. Co-administrations
    i. Administering a plurality of microorganisms
    ii. Therapeutic compounds
  f. State of subject
2. Monitoring
  a. Monitoring microorganismal gene expression
  b. Monitoring tumor size
  c. Monitoring antibody titer
  d. Monitoring general health diagnostics
  e. Monitoring coordinated with treatment
E. Methods of Producing Gene Products and Antibodies
1. Production of Recombinant Proteins and RNA molecules
2. Production of Antibodies
F. Pharmaceutical Compositions, combinations and kits
1. Pharmaceutical Compositions
2. Host Cells
3. Combinations
4. Kits
G. Examples A. Definitions Unless defined otherwise, all technical and scientific terms used herein have the same meaning as is commonly understood by one of skill in the art to which the invention(s) belong. All patents, patent applications, published applications and publications, websites and other published materials referred to throughout the entire disclosure herein, unless noted otherwise, are incorporated by reference in their entirety. In the event that there are a plurality of definitions for terms herein, those in this section prevail. Where reference is made to a URL or other such identifier or address, it is understood that such identifiers can change and particular information on the internet can come and go, but equivalent information is known and can be readily accessed, such as by searching the internet and/or appropriate databases. Reference thereto evidences the availability and public dissemination of such information.

As used herein, microorganisms refers to isolated cells or viruses, including eukaryotic cells, such as mammalian cells, viruses and bacteria. The microorganisms are modified or selected for their ability to accumulate in tumors and other immunoprivileged cells and tissues, and to minimize accumulation in other tissues or organs. Accumulation occurs by virtue of selection or modification of the microorganisms for particular traits or by proper selection of cells. The microorganism can be further modified to alter a trait thereof and/or to deliver a gene product. The microorganisms provided herein are typically modified relative to wild type to exhibit one or more characteristics such as reduced pathogenicity, reduced toxicity, preferential accumulation in tumors relative to normal organs or tissues, increased immunogenicity, increased ability to elicit or enhance an immune response to tumor cells, increased lytic or tumor cell killing capacity, decreased lytic or tumor cell killing capacity.

As used herein, immunoprivileged cells and tissues refer to cells and tissues, such as solid tumors and wounded tissues, which are sequestered from the immune system. Generally administration of a microorganism elicits an immune response that clears the microorganism; immunoprivileged sites, however, are shielded or sequestered from the immune response, permitting the microorganisms to survive and generally to replicate. Immunoprivileged tissues include inflamed tissues, such as wounded tissues, and proliferating tissues, such as tumor tissues.

As used herein, "modified" with reference to a gene refers to a deleted gene, or a gene encoding a gene product having one or more truncations, mutations, insertions or deletions, typically accompanied by at least a change, generally a partial loss of function.

As used herein F3 gene refers to a gene or locus in a virus, such as a vaccinia virus, that corresponds to the F3 gene of vaccinia virus strain LIVP. This includes the F3 gene of any vaccinia virus strain or poxvirus encoding a gene product having substantially the same or at least a related biological function or locus in the genome. F3 genes encompassed herein typically have at least about 40%, at least about 50%, at least about 60%, at least about 70%, at least about 80%, at least about 85%, at least about 90%, at least about 93%, at least about 95%, at least about 96%, at least about 97%, at least about 98%, or at least about 99% identity along the full length of the sequence of nucleotides set forth in SEQ ID NO:1. The proteins encoded by F3 genes encompassed herein typically have at least about 50%, at least about 60%, at least about 65%, at least about 70%, at least about 75%, at least about 85%, at least about 90%, at least about 93%, at least about 95%, at least about 96%, at least about 97%, at least about 98%, or at least about 99% identity to the sequence of amino acids set forth SEQ ID NO:2 along the full-length sequence thereof. Also included are corresponding loci in other viruses that when modified or eliminated result in reduced toxicity and/or enhanced accumulation in tumors (compared to non-tumorous cells, tissues and organs). The corresponding loci in other viruses equivalent to the F3 gene in LIVP can be determined by the structural location of the gene in the viral genome: the LIVP F3 gene is located on the HindIII-F fragment of vaccinia virus between open reading frames F14L and F15L as defined by Goebel et al., Virology (1990) 179:247-266, and in the opposite orientation of ORFs F14L and F15L; thus corresponding loci in other viruses such as poxviruses including orthopoxviruses are included.

As used herein, attenuate toxicity of a microorganism means to reduce or eliminate deleterious or toxic effects to a host upon administration of the microorganism compared to the unattenuated microorganism.

As use herein, a microorganism with low toxicity means that upon administration a microorganism does not accumulate in organs and tissues in the host to an extent that results in damage or harm to organs or that impact on survival of the host to a greater extent than the disease being treated does.

As used herein, subject (or organism) refers to an animal, including a human being.

As used herein, animal includes any animal, such as, but are not limited to primates including humans, gorillas and monkeys; rodents, such as mice and rats; fowl, such as chickens; ruminants, such as goats, cows, deer, sheep; ovine, and other animals including pigs, horses, cats, dogs, and rabbits. Non-human animals exclude humans as the contemplated animal.

As used herein, accumulation of a microorganism in a targeted tissue refers to the distribution of the microorganism throughout the organism after a time period long enough for the microbes to infect the host's organs or tissues. As one skilled in the art will recognize, the time period for infection of a microbe will vary depending on the microbe, the targeted organ(s) or tissue(s), the immunocompetence of the host, and dosage. Generally, accumulation can be determined at time-points from about 1 day to about 1 week after infection with the microbes. For purposes herein, the microorganisms preferentially accumulate in the target tissue, such as a tumor, but are cleared from other tissues and organs in the host to the extent that toxicity of the microorganism is mild or tolerable and at most not fatal.

As used herein, preferential accumulation refers to accumulation of a microorganism at a first location at a higher level than accumulation at a second location. Thus, a microorganism that preferentially accumulates in immunoprivileged tissue such as tumor relative to normal tissues or organs refers to a microorganism that accumulates in immunoprivileged tissue such as tumor at a higher level than the microorganism accumulates in normal tissues or organs.

As used herein, a "compound" produced in a tumor or other immunoprivileged site refers to any compound that is produced in the tumor by virtue of the presence of an introduced microorganism, generally a recombinant microorganism, expressing one or more genes. For example, a compound produced in a tumor can be, for example, a metabolite, an encoded polypeptide or RNA, or compound that is generated by a recombinant polypeptide (e.g., enzyme) and the cellular machinery of the tumor or immunoprivileged tissue or cells.

As used herein, a delivery vehicle for administration refers to a lipid-based or other polymer-based composition, such as liposome, micelle or reverse micelle, that associates with an agent, such as a microorganism provided herein, for delivery into a host animal.

As used herein, the term "viral vector" is used according to its art-recognized meaning. It refers to a nucleic acid vector construct that includes at least one element of viral origin and can be packaged into a viral vector particle. The viral vector particles can be used for the purpose of transferring DNA, RNA or other nucleic acids into cells either in vitro or in vivo. Viral vectors include, but are not limited to, retroviral vectors, vaccinia vectors, lentiviral vectors, herpes virus vectors (e.g., HSV), baculoviral vectors, cytomegalovirus (CMV) vectors, papillomavirus vectors, simian virus (SV40) vectors, semliki forest virus vectors, phage vectors, adenoviral vectors, and adeno-associated viral (AAV) vectors.

As used herein, oncolytic viruses refer to viruses that replicate selectively in tumor cells.

As used herein, "disease or disorder" refers to a pathological condition in an organism resulting from, e.g., infection or genetic defect, and characterized by identifiable symptoms.

As used herein, neoplasm (neoplasia) refers to abnormal new growth, and thus means the same as tumor, which can be benign or malignant. Unlike hyperplasia, neoplastic proliferation persists even in the absence of the original stimulus.

As used herein, neoplastic disease refers to any disorder involving cancer, including tumor development, growth, metastasis and progression.

As used herein, cancer is a general term for diseases caused by or characterized by any type of malignant tumor.

As used herein, malignant, as applies to tumors, refers to primary tumors that have the capacity of metastasis with loss of growth control and positional control.

As used herein, metastasis refers to a growth of abnormal or neoplastic cells distant from the site primarily involved by the morbid process.

As used herein, an anti-cancer agent or compound (used interchangeably with "anti-tumor or anti-neoplastic agent") refers to any agents or compounds used in anti-cancer treatment. These include any agents, when used alone or in combination with other compounds, that can alleviate, reduce, ameliorate, prevent, or place or maintain in a state of remission of clinical symptoms or diagnostic markers associated with neoplastic disease, tumors and cancer, and can be used in methods, combinations and compositions provided herein. Exemplary anti-neoplastic agents include the microorganism provided herein used singly or in combination and/or in combination with other agents, such as alkylating agents, antimetabolite, certain natural products, platinum coordination complexes, anthracenediones, substituted ureas, methylhydrazine derivatives, adrenocortical suppressants, certain hormones, antagonists and anti-cancer polysaccharides.

In general, for practice of the methods herein and when using the microorganisms provided herein, the original tumor is not excised, but is employed to accumulate the administered microorganism and as the cells become leaky or lyse to become an antigen or other product factor. The antigens can serve to elicit an immune response in the host. The antigens and products can be isolated from the tumor.

As used herein, angiogenesis is intended to encompass the totality of processes directly or indirectly involved in the establishment and maintenance of new vasculature (neovascularization), including, but not limited to, neovascularization associated with tumors and neovascularization associated with wounds.

As used herein, by homologous means about greater than 25% nucleic acid sequence identity, such as 25%, 40%, 60%, 70%, 80%, 90% or 95%. If necessary the percentage homology will be specified. The terms "homology" and "identity" are often used interchangeably but homology for proteins can include conservative amino acid changes. In general, sequences (protein or nucleic acid) are aligned so that the highest order match is obtained (see, e.g.: Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part I, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991; Carillo et al. (1988) SIAM J Applied Math 48:1073). By sequence identity, the number of identical amino acids is determined by standard alignment algorithm programs, and used with default gap penalties established by each supplier. Substantially homologous nucleic acid molecules would hybridize typically at moderate stringency or at high stringency all along the length of the nucleic acid or along at least about 70%, 80% or 90% of the full length nucleic acid molecule of interest. Also provided are nucleic acid molecules that contain degenerate codons in place of codons in the hybridizing nucleic acid molecule. (For proteins, for determination of homology conservative amino acids can be aligned as well as identical amino acids; in this case percentage of identity and percentage homology vary). Whether any two nucleic acid molecules have nucleotide sequences that are at least 80%, 85%, 90%, 95%, 96%, 97%, 98% or 99% "identical" can be determined using known computer algorithms such as the "FASTA" program, using for example, the default parameters as in Pearson et al. (1988) Proc. Natl. Acad. Sci. USA 85:2444 (other programs include the GCG program package (Devereux, J., et al., Nucleic Acids Research 12(I):387 (1984)), BLASTP, BLASTN, FASTA Altschul, S. F., et al., J Molec Biol 215:403 (1990); Guide to Huge Computers, Mrtin J. Bishop, ed., Academic Press, San Diego, 1994, and Carillo et al. (1988) SIAM J Applied Math 48:1073). For example, the BLAST function of the National Center for Biotechnology Information database can be used to determine identity. Other commercially or publicly available programs include, DNAStar "MegAlign" program (Madison, Wis.) and the University of Wisconsin Genetics Computer Group (UWG) "Gap" program (Madison Wis.)). Percent homology or identity of proteins and/or nucleic acid molecules can be determined, for example, by comparing sequence information using a GAP computer program (e.g., Needleman et al. (1970) J. Mol. Biol. 48:443, as revised by Smith and Waterman ((1981) Adv. Appl. Math. 2:482).

Briefly, a GAP program defines similarity as the number of aligned symbols (i.e., nucleotides or amino acids) that are similar, divided by the total number of symbols in the shorter of the two sequences. Default parameters for the GAP program can include: (1) a unary comparison matrix (containing a value of 1 for identities and 0 for non-identities) and the weighted comparison matrix of Gribskov et al. (1986) Nucl. Acids Res. 14:6745, as described by Schwartz and Dayhoff, eds., ATLAS OF PROTEIN SEQUENCE AND STRUCTURE, National Biomedical Research Foundation, pp. 353-358 (1979); (2) a penalty of 3.0 for each gap and an additional 0.10 penalty for each symbol in each gap; and (3) no penalty for end gaps. Therefore, as used herein, the term "identity" represents a comparison between a test and a reference polypeptide or polynucleotide.

As used herein, recitation that amino acids of a polypeptide correspond to amino acids in a disclosed sequence, such as amino acids set forth in the Sequence listing, refers to amino acids identified upon alignment of the polypeptide with the disclosed sequence to maximize identity or homology (where conserved amino acids are aligned) using a standard alignment algorithm, such as the GAP algorithm.

As used herein, the term "at least 90% identical to" refers to percent identities from 90 to 100% relative to the reference polypeptides. Identity at a level of 90% or more is indicative of the fact that, assuming for exemplification purposes a test and reference polynucleotide length of 100 amino acids are compared, no more than 10% (i.e., 10 out of 100) of amino acids in the test polypeptide differs from that of the reference polypeptides. Similar comparisons can be made between a test and reference polynucleotides. Such differences can be represented as point mutations randomly distributed over the entire length of an amino acid sequence or they can be clustered in one or more locations of varying length up to the maximum allowable, e.g., 10/100 amino acid difference (approximately 90% identity). Differences are defined as nucleic acid or amino acid substitutions, insertions or deletions. At the level of homologies or identities above about 85-90%, the result should be independent of the program and gap parameters set; such high levels of identity can be assessed readily, often without relying on software.

As used herein, primer refers to an oligonucleotide containing two or more deoxyribonucleotides or ribonucleotides, typically more than three, from which synthesis of a primer extension product can be initiated. Experimental conditions conducive to synthesis include the presence of nucleoside triphosphates and an agent for polymerization and extension, such as DNA polymerase, and a suitable buffer, temperature and pH.

As used herein, chemiluminescence refers to a chemical reaction in which energy is specifically channeled to a molecule causing it to become electronically excited and subsequently to release a photon thereby emitting visible light. Temperature does not contribute to this channeled energy. Thus, chemiluminescence involves the direct conversion of chemical energy to light energy.

As used herein, luminescence refers to the detectable EM radiation, generally, UV, IR or visible EM radiation that is produced when the excited product of an exergic chemical process reverts to its ground state with the emission of light. Chemiluminescence is luminescence that results from a chemical reaction. Bioluminescence is chemiluminescence that results from a chemical reaction using biological molecules (or synthetic versions or analogs thereof) as substrates and/or enzymes.

As used herein, bioluminescence, which is a type of chemiluminescence, refers to the emission of light by biological molecules, particularly proteins. The essential condition for bioluminescence is molecular oxygen, either bound or free in the presence of an oxygenase, a luciferase, which acts on a substrate, a luciferin. Bioluminescence is generated by an enzyme or other protein (luciferase) that is an oxygenase that acts on a substrate luciferin (a bioluminescence substrate) in the presence of molecular oxygen, and transforms the substrate to an excited state, which, upon return to a lower energy level releases the energy in the form of light.

As used herein, the substrates and enzymes for producing bioluminescence are generically referred to as luciferin and luciferase, respectively. When reference is made to a particular species thereof, for clarity, each generic term is used with the name of the organism from which it derives, for example, bacterial luciferin or firefly luciferase.

As used herein, luciferase refers to oxygenases that catalyze a light emitting reaction. For instance, bacterial luciferases catalyze the oxidation of flavin mononucleotide (FMN) and aliphatic aldehydes, which reaction produces light. Another class of luciferases, found among marine arthropods, catalyzes the oxidation of *Cypridina* (*Vargula*) luciferin, and another class of luciferases catalyzes the oxidation of Coleoptera luciferin.

Thus, luciferase refers to an enzyme or photoprotein that catalyzes a bioluminescent reaction (a reaction that produces bioluminescence). The luciferases, such as firefly and *Gaussia* and *Renilla* luciferases, are enzymes which act catalytically and are unchanged during the bioluminescence generating reaction. The luciferase photoproteins, such as the aequorin photoprotein to which luciferin is noncovalently bound, are changed, such as by release of the luciferin, during bioluminescence generating reaction. The luciferase is a protein that occurs naturally in an organism or a variant or mutant thereof, such as a variant produced by mutagenesis that has one or more properties, such as thermal stability, that differ from the naturally-occurring protein. Luciferases and modified mutant or variant forms thereof are well known. For purposes herein, reference to luciferase refers to either the photoproteins or luciferases.

Thus, reference, for example, to "*Renilla* luciferase" means an enzyme isolated from member of the genus *Renilla* or an equivalent molecule obtained from any other source, such as from another related copepod, or that has been prepared synthetically. It is intended to encompass *Renilla* luciferases with conservative amino acid substitutions that do not substantially alter activity. Suitable conservative substitutions of amino acids are known to those of skill in the art and can be made generally without altering the biological activity of the resulting molecule. Those of skill in the art recognize that, in general, single amino acid substitutions in non-essential regions of a polypeptide do not substantially alter biological activity (see, e.g., Watson et al. Molecular Biology of the Gene, 4th Edition, 1987, The Benjamin/Cummings Pub. co., p. 224).

As used herein, "*Aequorea* GFP" refers to GFPs from the genus *Aequorea* and to mutants or variants thereof. Such variants and GFPs from other species are well known and are available and known to those of skill in the art. This nomenclature encompass GFPs with conservative amino acid substitutions that do not substantially alter activity and physical properties, such as the emission spectra and ability to shift the spectral output of bioluminescence generating systems. The luciferases and luciferin and activators thereof are referred to as bioluminescence generating reagents or components. Typically, a subset of these reagents will be provided or combined with an article of manufacture. Bioluminescence will be produced upon contacting the combination with the remaining reagents. Thus, as used herein, the component luciferases, luciferins, and other factors, such as $O_2$, $Mg^{2+}$, $Ca^{2+}$ also are referred to as bioluminescence generating reagents (or agents or components).

As used herein, bioluminescence substrate refers to the compound that is oxidized in the presence of a luciferase, and any necessary activators, and generates light. These substrates are referred to as luciferins herein, are substrates that undergo oxidation in a bioluminescence reaction. These bioluminescence substrates include any luciferin or analog thereof or any synthetic compound with which a luciferase interacts to generate light. Typical substrates include those that are oxidized in the presence of a luciferase or protein in a light-generating reaction. Bioluminescence substrates, thus, include those compounds that those of skill in the art recognize as luciferins. Luciferins, for example, include firefly luciferin, *Cypridina* (also known as *Vargula*) luciferin (coelenterazine), bacterial luciferin, as well as synthetic analogs of these substrates or other compounds that are oxidized in the presence of a luciferase in a reaction the produces bioluminescence.

As used herein, capable of conversion into a bioluminescence substrate means susceptible to chemical reaction, such as oxidation or reduction, that yields a bioluminescence substrate. For example, the luminescence producing reaction of bioluminescent bacteria involves the reduction of a flavin mononucleotide group (FMN) to reduced flavin mononucleotide (FMNH2) by a flavin reductase enzyme. The reduced flavin mononucleotide (substrate) then reacts with oxygen (an activator) and bacterial luciferase to form an intermediate peroxy flavin that undergoes further reaction, in the presence of a long-chain aldehyde, to generate light. With respect to this reaction, the reduced flavin and the long chain aldehyde are substrates.

As used herein, a bioluminescence generating system refers to the set of reagents required to conduct a bioluminescent reaction. Thus, the specific luciferase, luciferin and other substrates, solvents and other reagents that can be required to complete a bioluminescent reaction from a bioluminescence system. Thus a bioluminescence generating system refers to any set of reagents that, under appropriate reaction conditions, yield bioluminescence. Appropriate reaction conditions refers to the conditions necessary for a bioluminescence reaction to occur, such as pH, salt concentrations and temperature. In general, bioluminescence systems include a bioluminescence substrate, luciferin, a luciferase, which includes enzymes, luciferases and photoproteins, and one or more activators. A specific bioluminescence system may be identified by reference to the specific organism from which the luciferase derives; for example, the *Renilla* bioluminescence system includes a *Renilla* luciferase, such as a luciferase isolated from the *Renilla* or produced using recombinant means or modifications of these luciferases. This system also includes the particular activators necessary to complete the bioluminescence reaction, such as oxygen and a substrate with which the luciferase reacts in the presence of the oxygen to produce light.

As used herein, a fluorescent protein refers to a protein that possesses the ability to fluoresce (i.e., to absorb energy at one wavelength and emit it at another wavelength). For example, a green fluorescent protein refers to a polypeptide that has a peak in the emission spectrum at about 510 nm.

As used herein, genetic therapy or gene therapy involves the transfer of heterologous nucleic acid, such as DNA, into certain cells, target cells, of a mammal, particularly a human, with a disorder or conditions for which such therapy is sought. The nucleic acid, such as DNA, is introduced into the selected target cells, such as directly or in a vector or other delivery vehicle, in a manner such that the heterologous nucleic acid, such as DNA, is expressed and a therapeutic product encoded thereby is produced. Alternatively, the heterologous nucleic acid, such as DNA, can in some manner mediate expression of DNA that encodes the therapeutic product, or it can encode a product, such as a peptide or RNA that in some manner mediates, directly or indirectly, expression of a therapeutic product. Genetic therapy also can be used to deliver nucleic acid encoding a gene product that replaces a defective gene or supplements a gene product produced by the mammal or the cell in which it is introduced. The introduced nucleic acid can encode a therapeutic compound, such as a growth factor inhibitor thereof, or a tumor necrosis factor or inhibitor thereof, such as a receptor therefor, that is not normally produced in the mammalian host or that is not produced in therapeutically effective amounts or at a therapeutically useful time. The heterologous nucleic acid, such as DNA, encoding the therapeutic product can be modified prior to introduction into the cells of the afflicted host in order to enhance or otherwise alter the product or expression thereof. Genetic therapy also can involve delivery of an inhibitor or repressor or other modulator of gene expression.

As used herein, heterologous nucleic acid is nucleic acid that is not normally produced in vivo by the microorganism from which it is expressed or that is produced by a microorganism but is at a different locus or expressed differently or that mediates or encodes mediators that alter expression of endogenous nucleic acid, such as DNA, by affecting transcription, translation, or other regulatable biochemical processes. Heterologous nucleic acid is often not endogenous to the cell into which it is introduced, but has been obtained from another cell or prepared synthetically. Heterologous nucleic acid, however, can be endogenous, but is nucleic acid that is expressed from a different locus or altered in its expression or sequence. Generally, although not necessarily, such nucleic acid encodes RNA and proteins that are not normally produced by the cell or in the same way in the cell in which it is expressed. Heterologous nucleic acid, such as DNA, also can be referred to as foreign nucleic acid, such as DNA. Thus, heterologous nucleic acid or foreign nucleic acid includes a nucleic acid molecule not present in the exact orientation or position as the counterpart nucleic acid molecule, such as DNA, is found in a genome. It also can refer to a nucleic acid molecule from another organism or species (i.e., exogenous). Any nucleic acid, such as DNA, that one of skill in the art would recognize or consider as heterologous or foreign to the cell in which the nucleic acid is expressed is herein encompassed by heterologous nucleic acid; heterologous nucleic acid includes exogenously added nucleic acid that also is expressed endogenously. Examples of heterologous nucleic acid include, but are not limited to, nucleic acid that encodes traceable marker proteins, such as a protein that confers drug resistance, nucleic acid that encodes therapeutically effective substances, such as anti-cancer agents, enzymes and hormones, and nucleic acid, such as DNA, that encodes other types of proteins, such as antibodies. Antibodies that are encoded by heterologous nucleic acid can be secreted or expressed on the surface of the cell in which the heterologous nucleic acid has been introduced.

As used herein, a therapeutically effective product for gene therapy is a product that is encoded by heterologous nucleic acid, typically DNA, (or an RNA product such as dsRNA, RNAi, including siRNA, that, upon introduction of the nucleic acid into a host, a product is expressed that ameliorates or eliminates the symptoms, manifestations of an inherited or acquired disease or that cures the disease. Also included are biologically active nucleic acid molecules, such as RNAi and antisense.

As used herein, cancer or tumor treatment or agent refers to any therapeutic regimen and/or compound that, when used alone or in combination with other treatments or compounds, can alleviate, reduce, ameliorate, prevent, or place or maintain in a state of remission of clinical symptoms or diagnostic markers associated with deficient angiogenesis.

As used herein, nucleic acids include DNA, RNA and analogs thereof, including peptide nucleic acids (PNA) and mixtures thereof. Nucleic acids can be single or double-stranded. When referring to probes or primers, which are optionally labeled, such as with a detectable label, such as a fluorescent or radiolabel, single-stranded molecules are provided. Such molecules are typically of a length such that their target is statistically unique or of low copy number (typically less than 5, generally less than 3) for probing or priming a library. Generally a probe or primer contains at least 14, 16 or 30 contiguous nucleotides of sequence complementary to or identical to a gene of interest. Probes and primers can be 10, 20, 30, 50, 100 or more nucleic acids long.

As used herein, operative linkage of heterologous nucleic acids to regulatory and effector sequences of nucleotides, such as promoters, enhancers, transcriptional and translational stop sites, and other signal sequences refers to the relationship between such nucleic acid, such as DNA, and such sequences of nucleotides. For example, operative linkage of heterologous DNA to a promoter refers to the physical relationship between the DNA and the promoter such that the transcription of such DNA is initiated from the promoter by an RNA polymerase that specifically recognizes, binds to and transcribes the DNA. Thus, operatively linked or operationally associated refers to the functional relationship of nucleic acid, such as DNA, with regulatory and effector sequences of nucleotides, such as promoters, enhancers, transcriptional and translational stop sites, and other signal sequences. For example, operative linkage of DNA to a promoter refers to the physical and functional relationship between the DNA and the promoter such that the transcription of such DNA is initiated from the promoter by an RNA polymerase that specifically recognizes, binds to and transcribes the DNA. In order to optimize expression and/or in vitro transcription, it can be necessary to remove, add or alter 5' untranslated portions of the clones to eliminate extra, potentially inappropriate alternative translation initiation (i.e., start) codons or other sequences that can interfere with or reduce expression, either at the level of transcription or translation. Alternatively, consensus ribosome binding sites (see, e.g., Kozak J. Biol. Chem. 266:19867-19870 (1991)) can be inserted immediately 5' of the start codon and can enhance expression. The desirability of (or need for) such modification can be empirically determined.

As used herein, a sequence complementary to at least a portion of an RNA, with reference to antisense oligonucleotides, means a sequence of nucleotides having sufficient complementarity to be able to hybridize with the RNA, generally under moderate or high stringency conditions, forming a stable duplex; in the case of double-stranded antisense nucleic acids, a single strand of the duplex DNA (or dsRNA) can thus be tested, or triplex formation can be assayed. The ability to hybridize depends on the degree of complementarity and the length of the antisense nucleic acid. Generally, the longer the hybridizing nucleic acid, the more base mismatches with an encoding RNA it can contain and still form a stable duplex (or triplex, as the case can be). One skilled in the art can ascertain a tolerable degree of mismatch by use of standard procedures to determine the melting point of the hybridized complex.

As used herein, amelioration of the symptoms of a particular disorder such as by administration of a particular pharmaceutical composition, refers to any lessening, whether permanent or temporary, lasting or transient that can be attributed to or associated with administration of the composition.

As used herein, antisense polynucleotides refer to synthetic sequences of nucleotide bases complementary to mRNA or the sense strand of double-stranded DNA. A mixture of sense and antisense polynucleotides under appropriate conditions leads to the binding of the two molecules, or hybridization. When these polynucleotides bind to (hybridize with) mRNA, inhibition of protein synthesis (translation) occurs. When these polynucleotides bind to double-stranded DNA, inhibition of RNA synthesis (transcription) occurs. The resulting inhibition of translation and/or transcription leads to an inhibition of the synthesis of the protein encoded by the sense strand. Antisense nucleic acid molecules typically contain a sufficient number of nucleotides to specifically bind to a target nucleic acid, generally at least 5 contiguous nucleotides, often at least 14 or 16 or 30 contiguous nucleotides or modified nucleotides complementary to the coding portion of a nucleic acid molecule that encodes a gene of interest.

As used herein, antibody refers to an immunoglobulin, whether natural or partially or wholly synthetically produced, including any derivative thereof that retains the specific binding ability of the antibody. Hence antibody includes any protein having a binding domain that is homologous or substantially homologous to an immunoglobulin binding domain. Antibodies include members of any immunoglobulin class, including IgG, IgM, IgA, IgD and IgE.

As used herein, antibody fragment refers to any derivative of an antibody that is less then full length, retaining at least a portion of the full-length antibody's specific binding ability. Examples of antibody fragments include, but are not limited to, Fab, Fab', F(ab)2, single-chain Fvs (scFV), FV, dsFV diabody and Fd fragments. The fragment can include multiple chains linked together, such as by disulfide bridges. An antibody fragment generally contains at least about 50 amino acids and typically at least 200 amino acids.

As used herein, a Fv antibody fragment is composed of one variable heavy chain domain ($V_H$) and one variable light chain domain linked by noncovalent interactions.

As used herein, a dsFV refers to an Fv with an engineered intermolecular disulfide bond, which stabilizes the $V_H$-$V_L$ pair.

As used herein, a F(ab)2 fragment is an antibody fragment that results from digestion of an immunoglobulin with pepsin at pH 4.0-4.5; it can be recombinantly produced to produce the equivalent fragment.

As used herein, Fab fragments are antibody fragments that result from digestion of an immunoglobulin with papain; it can be recombinantly produced to produce the equivalent fragment.

As used herein, scFVs refer to antibody fragments that contain a variable light chain ($V_L$) and variable heavy chain ($V_H$) covalently connected by a polypeptide linker in any order. The linker is of a length such that the two variable domains are bridged without substantial interference. Included linkers are (Gly-Ser)n residues with some Glu or Lys residues dispersed throughout to increase solubility.

As used herein, humanized antibodies refer to antibodies that are modified to include human sequences of amino acids so that administration to a human does not provoke an immune response. Methods for preparation of such antibodies are known. For example, to produce such antibodies, the encoding nucleic acid in the hybridoma or other prokaryotic or eukaryotic cell, such as an *E. coli* or a CHO cell, that expresses the monoclonal antibody is altered by recombinant nucleic acid techniques to express an antibody in which the amino acid composition of the non-variable region is based on human antibodies. Computer programs have been designed to identify such non-variable regions.

As used herein, diabodies are dimeric scFV; diabodies typically have shorter peptide linkers than scFvs, and they generally dimerize.

As used herein, production by recombinant means by using recombinant DNA methods means the use of the well known methods of molecular biology for expressing proteins encoded by cloned DNA.

As used herein the term assessing or determining is intended to include quantitative and qualitative determination in the sense of obtaining an absolute value for the activity of a product, and also of obtaining an index, ratio, percentage, visual or other value indicative of the level of the activity. Assessment can be direct or indirect.

As used herein, biological activity refers to the in vivo activities of a compound or microorganisms or physiological responses that result upon in vivo administration thereof or of composition or other mixture. Biological activity, thus, encompasses therapeutic effects and pharmaceutical activity of such compounds, compositions and mixtures. Biological activities can be observed in in vitro systems designed to test or use such activities.

As used herein, an effective amount of a microorganism or compound for treating a particular disease is an amount that is sufficient to ameliorate, or in some manner reduce the symptoms associated with the disease. Such an amount can be administered as a single dosage or can be administered according to a regimen, whereby it is effective. The amount can cure the disease but, typically, is administered in order to ameliorate the symptoms of the disease. Repeated administration can be required to achieve the desired amelioration of symptoms.

As used herein equivalent, when referring to two sequences of nucleic acids, means that the two sequences in question encode the same sequence of amino acids or equivalent proteins. When equivalent is used in referring to two proteins or peptides or other molecules, it means that the two proteins or peptides have substantially the same amino acid sequence with only amino acid substitutions (such as, but not limited to, conservative changes) or structure and the any changes do not substantially alter the activity or function of the protein or peptide. When equivalent refers to a property, the property does not need to be present to the same extent (e.g., two peptides can exhibit different rates of the same type of enzymatic activity), but the activities are usually substantially the same. Complementary, when referring to two nucleotide sequences, means that the two sequences of nucleotides are capable of hybridizing, typically with less than 25%, 15% or 5% mismatches between opposed nucleotides. If necessary, the percentage of complementarity will be specified. Typically the two molecules are selected such that they will hybridize under conditions of high stringency.

As used herein, an agent or compound that modulates the activity of a protein or expression of a gene or nucleic acid either decreases or increases or otherwise alters the activity of the protein or, in some manner, up- or down-regulates or otherwise alters expression of the nucleic acid in a cell.

As used herein, a method for treating or preventing neoplastic disease means that any of the symptoms, such as the tumor, metastasis thereof, the vascularization of the tumors or other parameters by which the disease is characterized are reduced, ameliorated, prevented, placed in a state of remission, or maintained in a state of remission. It also means that the hallmarks of neoplastic disease and metastasis can be eliminated, reduced or prevented by the treatment. Non-limiting examples of the hallmarks include uncontrolled degradation of the basement membrane and proximal extracellular matrix, migration, division, and organization of the endothelial cells into new functioning capillaries, and the persistence of such functioning capillaries.

As used herein, a prodrug is a compound that, upon in vivo administration, is metabolized or otherwise converted to the biologically, pharmaceutically or therapeutically active form of the compound. To produce a prodrug, the pharmaceutically active compound is modified such that the active compound is regenerated by metabolic processes. The prodrug can be designed to alter the metabolic stability or the transport characteristics of a drug, to mask side effects or toxicity, to improve the flavor of a drug or to alter other characteristics or properties of a drug. By virtue of knowledge of pharmacodynamic processes and drug metabolism in vivo, those of skill in the art, once a pharmaceutically active compound is known, can design prodrugs of the compound (see, e.g., Nogrady (1985) Medicinal Chemistry A Biochemical Approach, Oxford University Press, New York, pages 388-392).

As used herein, a promoter region or promoter element or regulatory region refers to a segment of DNA or RNA that controls transcription of the DNA or RNA to which it is operatively linked. The promoter region includes specific sequences that are sufficient for RNA polymerase recognition, binding and transcription initiation. This portion of the promoter region is referred to as the promoter. In addition, the promoter region includes sequences that modulate this recognition, binding and transcription initiation activity of RNA polymerase. These sequences can be cis acting or can be responsive to trans acting factors. Promoters, depending upon the nature of the regulation, can be constitutive or regulated. Exemplary promoters contemplated for use in prokaryotes include the bacteriophage T7 and T3 promoters.

As used herein, a receptor refers to a molecule that has an affinity for a ligand. Receptors can be naturally-occurring or synthetic molecules. Receptors also can be referred to in the art as anti-ligands. As used herein, the receptor and anti-ligand are interchangeable. Receptors can be used in their unaltered state or bound to other polypeptides, including as homodimers. Receptors can be attached to, covalently or noncovalently, or in physical contact with, a binding member, either directly or indirectly via a specific binding substance or linker. Examples of receptors, include, but are not limited to: antibodies, cell membrane receptors surface receptors and internalizing receptors, monoclonal antibodies and antisera reactive with specific antigenic determinants (such as on viruses, cells, or other materials), drugs, polynucleotides, nucleic acids, peptides, cofactors, lectins, sugars, polysaccharides, cells, cellular membranes, and organelles.

As used herein, sample refers to anything that can contain an analyte for which an analyte assay is desired. The sample can be a biological sample, such as a biological fluid or a biological tissue. Examples of biological fluids include urine, blood, plasma, serum, saliva, semen, stool, sputum, cerebral spinal fluid, tears, mucus, amniotic fluid or the like. Biological tissues are aggregates of cells, usually of a particular kind together with their intercellular substance that form one of the structural materials of a human, animal, plant, bacterial, fungal or viral structure, including connective, epithelium, muscle and nerve tissues. Examples of biological tissues also include organs, tumors, lymph nodes, arteries and individual cell(s).

As used herein: stringency of hybridization in determining percentage mismatch is as follows:

1) high stringency: 0.1×SSPE, 0.1% SDS, 65° C.

2) medium stringency: 0.2×SSPE, 0.1% SDS, 50° C.

3) low stringency: 1.0×SSPE, 0.1% SDS, 50° C.

Those of skill in the art know that the washing step selects for stable hybrids and also know the ingredients of SSPE (see, e.g., Sambrook, E. F. Fritsch, T. Maniatis, in: Molecular Cloning, A Laboratory Manual, Cold Spring Harbor Laboratory Press (1989), vol. 3, p. B.13, see, also, numerous catalogs that describe commonly used laboratory solutions). SSPE is pH 7.4 phosphate-buffered 0.18 M NaCl. Further, those of skill in the art recognize that the stability of hybrids is determined by Tm, which is a function of the sodium ion concentration and temperature: (Tm=81.5° C.-16.6(log 10[$Na^+$])+0.41(% G+C)−600/l)), so that the only parameters in the wash conditions critical to hybrid stability are sodium ion concentration in the SSPE (or SSC) and temperature. Any nucleic acid molecules provided herein can also include those that hybridize under conditions of at least low stringency, generally moderate or high stringency, along at least 70, 80, 90% of the full length of the disclosed molecule. It is understood that equivalent stringencies can be achieved using alternative buffers, salts and temperatures. By way of example and not limitation, procedures using conditions of low stringency are as follows (see also Shilo and Weinberg, Proc. Natl. Acad. Sci. USA 78:6789-6792 (1981)):

Filters containing DNA are pretreated for 6 hours at 40° C. in a solution containing 35% formamide, 5×SSC, 50 mM Tris-HCl (pH 7.5), 5 mM EDTA, 0.1% PVP, 0.1% Ficoll, 1% BSA, and 500 μg/ml denatured salmon sperm DNA (10×SSC is 1.5 M sodium chloride, and 0.15 M sodium citrate, adjusted to a pH of 7). Hybridizations are carried out in the same solution with the following modifications: 0.02% PVP, 0.02% Ficoll, 0.2% BSA, 100 Tg/ml salmon sperm DNA, 10% (wt/vol) dextran sulfate, and 5-20×$10^6$ cpm $^{32}$P-labeled probe is used. Filters are incubated in hybridization mixture for 18-20 hours at 40° C., and then washed for 1.5 hours at 55° C. in a solution containing 2×SSC, 25 mM Tris-HCl (pH 7.4), 5 mM EDTA, and 0.1% SDS. The wash solution is replaced with fresh solution and incubated an additional 1.5 hours at 60° C. Filters are blotted dry and exposed for autoradiography. If necessary, filters are washed for a third time at 65-68° C. and reexposed to film. Other conditions of low stringency which can be used are well known in the art (e.g., as employed for cross-species hybridizations).

By way of example and not way of limitation, procedures using conditions of moderate stringency include, for example, but are not limited to, procedures using such conditions of moderate stringency are as follows: Filters containing DNA are pretreated for 6 hours at 55° C. in a solution containing 6×SSC, 5×Denhart's solution, 0.5% SDS and 100 μg/ml denatured salmon sperm DNA. Hybridizations are carried out in the same solution and 5-20×$10^6$ cpm $^{32}$P-labeled probe is used. Filters are incubated in hybridization mixture for 18-20 hours at 55° C., and then washed twice for 30 minutes at 60° C. in a solution containing 1×SSC and 0.1% SDS. Filters are blotted dry and exposed for autoradiography. Other conditions of moderate stringency which can be used are well-known in the art. Washing of filters is done at 37° C. for 1 hour in a solution containing 2×SSC, 0.1% SDS. By way of example and not way of limitation, procedures using conditions of high stringency are as follows: Prehybridization of filters containing DNA is carried out for 8 hours to overnight at 65° C. in buffer composed of 6×SSC, 50 mM Tris-HCl (pH 7.5), 1 mM EDTA, 0.02% PVP, 0.02% Ficoll, 0.02% BSA, and 500 Tg/ml denatured salmon sperm DNA. Filters are hybridized for 48 hours at 65° C. in prehybridization mixture containing 100 μg/ml denatured salmon sperm DNA and 5-20×$10^6$ cpm of $^{32}$P-labeled probe. Washing of filters is done at 37° C. for 1 hour in a solution containing 2×SSC, 0.01% PVP, 0.01% Ficoll, and 0.01% BSA. This is followed by a wash in 0.1×SSC at 50° C. for 45 minutes before autoradiography. Other conditions of high stringency which can be used are well known in the art.

The term substantially identical or homologous or similar varies with the context as understood by those skilled in the relevant art and generally means at least 60% or 70%, preferably means at least 80%, more preferably at least 90%, and most preferably at least 95% , 96%, 97%, 98%, 99% or greater identity.

As used herein, substantially identical to a product means sufficiently similar so that the property of interest is sufficiently unchanged so that the substantially identical product can be used in place of the product.

As used herein, substantially pure means sufficiently homogeneous to appear free of readily detectable impurities as determined by standard methods of analysis, such as thin layer chromatography (TLC), gel electrophoresis and high performance liquid chromatography (HPLC), used by those of skill in the art to assess such purity, or sufficiently pure such that further purification would not detectably alter the physical and chemical properties, such as enzymatic and biological activities, of the substance. Methods for purification of the compounds to produce substantially chemically pure compounds are known to those of skill in the art. A substantially chemically pure compound can, however, be a mixture of stereoisomers or isomers. In such instances, further purification might increase the specific activity of the compound.

As used herein, a molecule, such as an antibody, that specifically binds to a polypeptide typically has a binding affinity (Ka) of at least about $10^6$ l/mol, $10^7$ l/mol, $10^8$ l/mol, $10^9$ l/mol, $10^{10}$ l/mol or greater and binds to a protein of interest generally with at least 2-fold, 5-fold, generally 10-fold or even 100-fold or greater, affinity than to other proteins. For example, an antibody that specifically binds to the protease domain compared to the full-length molecule, such as the zymogen form, binds with at least about 2-fold, typically 5-fold or 10-fold higher affinity, to a polypeptide that contains only the protease domain than to the zymogen form of the full-length. Such specific binding also is referred to as selective binding. Thus, specific or selective binding refers to greater binding affinity (generally at least 2-fold, 5-fold, 10-fold or more) to a targeted site or locus compared to a non-targeted site or locus.

As used herein, the terms a therapeutic agent, therapeutic compound, therapeutic regimen, or chemotherapeutic include conventional drugs and drug therapies, including vaccines, which are known to those skilled in the art.

As used herein, treatment means any manner in which the symptoms of a condition, disorder or disease are ameliorated or otherwise beneficially altered. Treatment also encompasses any pharmaceutical use of the microorganisms described and provided herein.

As used herein, proliferative disorders include any disorders involving abnormal proliferation of cells. Such disorders include, but are not limited to, neoplastic diseases, psoriasis, restenosis, macular degeneration, diabetic retinopathies, inflammatory responses and disorders, including wound healing responses.

As used herein, vector (or plasmid) refers to discrete elements that are used to introduce heterologous nucleic acid into cells for either expression or replication thereof. The vectors typically remain episomal, but can be designed to effect integration of a gene or portion thereof into a chromosome of the genome. Also contemplated are vectors that are artificial chromosomes, such as yeast artificial chromosomes and mammalian artificial chromosomes. Selection and use of such vectors are well known to those of skill in the art. An expression vector includes vectors capable of expressing DNA that is operatively linked with regulatory sequences, such as promoter regions, that are capable of effecting expression of such DNA fragments. Thus, an expression vector refers to a recombinant DNA or RNA construct, such as a plasmid, a phage, recombinant virus or other vector that, upon introduction into an appropriate host cell, results in expression of the cloned DNA. Appropriate expression vectors are well known to those of skill in the art and include those that are replicable in eukaryotic cells and/or prokaryotic cells and those that remain episomal or those which integrate into the host cell genome.

As used herein, a combination refers to any association between two or among more items.

As used herein, a composition refers to any mixture. It can be a solution, a suspension, an emulsion, liquid, powder, a paste, aqueous, non-aqueous or any combination thereof.

As used herein, fluid refers to any composition that can flow. Fluids thus encompass compositions that are in the form of semi-solids, pastes, solutions, aqueous mixtures, gels, lotions, creams and other such compositions.

As used herein, a kit is a packaged combination optionally including instructions for use of the combination and/or other reactions and components for such use.

For clarity of disclosure, and not by way of limitation, the detailed description is divided into the subsections that follow.

B. Microorganisms for Tumor-Specific Therapy

Provided herein are microorganisms, and methods for making and using such microorganisms for therapy of neoplastic disease and other proliferative disorders and inflammatory disorders. The microbe (or microorganism)-mediated treatment methods provided herein involve administration of microorganisms to hosts, accumulation of the microorganism in the targeted cell or tissue, such as in a tumor, resulting in leaking or lysing of the cells, whereby an immune response against leaked or released antigens is mounted, thereby resulting in an inhibition of the tissues or cells in which the microorganism accumulates.

In addition to the gene therapeutic methods of cancer treatment, live attenuated microorganisms can be used for vaccination, such as in cancer vaccination or antitumor immunity. Immunization, for example, against a tumor can include a tumor-specific T-cell-mediated response through microbe-delivered antigens or cytokines. To do so, the microbes can be specifically targeted to the tumor tissues, with minimal infection to any other key organs and also can be modified or provided to produce the antigens and/or cytokines.

The microorganisms provided herein and the use of such microorganisms herein can accumulate in immunoprivileged cells or immunoprivileged tissues, including tumors and/or metastases, and also including wounded tissues and cells. While the microorganisms provided herein can typically be cleared from the subject to whom the microorganisms are administered by activity of the subject's immune system, microorganisms can nevertheless accumulate, survive and proliferate in immunoprivileged cells and tissues such as tumors because such immunoprivileged areas are sequestered from the host's immune system. Accordingly, the methods provided herein, as applied to tumors and/or metastases, and therapeutic methods relating thereto, can readily be applied to other immunoprivileged cells and tissues, including wounded cells and tissues.

1. Characteristics

The microorganisms provided herein and used in the methods herein are attenuated, immunogenic, and replication competent.

a. Attenuated

The microbes used in the methods provided herein are typically attenuated. Attenuated microbes have a decreased capacity to cause disease in a host. The decreased capacity can result from any of a variety of different modifications to the ability of a microbe to be pathogenic. For example, a microbe can have reduced toxicity, reduced ability to accumulate in non-tumorous organs or tissue, reduced ability to cause cell lysis or cell death, or reduced ability to replicate compared to the non-attenuated form thereof. The attenuated microbes provided herein, however, retain at least some capacity to replicate and to cause immunoprivileged cells and tissues, such as tumor cells to leak or lyse, undergo cell death, or otherwise cause or enhance an immune response to immunoprivileged cells and tissues, such as tumor cells.

i. Reduced Toxicity

Microbes can be toxic to their hosts by manufacturing one or more compounds that worsen the health condition of the host. Toxicity to the host can be manifested in any of a variety of manners, including septic shock, neurological effects, or muscular effects. The microbes provided herein can have a reduced toxicity to the host. The reduced toxicity of a microbe of the present methods and compositions can range from a toxicity in which the host experiences no toxic effects, to a toxicity in which the host does not typically die from the toxic effects of the microbes. In some embodiments, the microbes are of a reduced toxicity such that a host typically has no significant long-term effect from the presence of the microbes in the host, beyond any effect on tumorous, metastatic or necrotic organs or tissues. For example, the reduced toxicity can be a minor fever or minor infection, which lasts for less than about a month, and following the fever or infection, the host experiences no adverse effects resultant from the fever or infection. In another example, the reduced toxicity can be measured as an unintentional decline in body weight of about 5% or less for the host after administration of the microbes. In other examples, the microbe has no toxicity to the host.

Exemplary vaccinia viruses of the LIVP strain (a widely available attenuated Lister strain) that have reduced toxicity compared to other vaccinia viruses employed and are further modified. Modified LIVP were prepared. These modified LIVP include insertions in the TK and/or HA genes and in the locus designed F3. As an example of reduced toxicity, recombinant vaccinia viruses were tested for their toxicity to mice with impaired immune systems (nude mice) relative to the corresponding wild type vaccinia virus. Intravenous (i.v.) injection of wild type vaccinia virus VGL (strain LIVP) at $1\times10^7$ PFU/mouse causes toxicity in nude mice: three mice out of seven lost the weight and died (one mouse died in one week after virus injection, one mouse died ten days after virus injection. Similar modifications can be made to other pox viruses and other viruses to reduce toxicity thereof. Such modifications can be empirically identified, if necessary.

ii. Accumulate in Immunoprivileged Cells and Tissues, Such as Tumor, not Substantially in Other Organs Microbes can accumulate in any of a variety of tissues and organs of the host. Accumulation can be evenly distributed over the entire host organism, or can be concentrated in one or a few organs or tissues, The microbes provided herein can accumulate in targeted tissues, such as immunoprivileged cells and tissues, such as tumors and also metastases. In some embodiments, the microbes provided herein exhibit accumulation in immunoprivileged cells and tissues, such as tumor cells relative to normal organs or tissues that is equal to or greater than the accumulation that occurs with wild type microbes. In other embodiments the microbes provided herein exhibit accumulation in immunoprivileged cells and tissues, such as tumor cells that is equal to or greater than the accumulation in any other particular organ or tissue. For example, the microbes provided herein can demonstrate an accumulation in immunoprivileged cells and tissues, such as tumor cells that is at least about 2-fold greater, at least about 5-fold greater, at least about 10-fold greater, at least about 100-fold greater, at least about 1,000-fold greater, at least about 10,000-fold greater, at least about 100,000-fold greater, or at least about 1,000,000-fold greater, than the accumulation in any other particular organ or tissue.

In some embodiments, a microbe can accumulate in targeted tissues and cells, such as immunoprivileged cells and tissues, such as tumor cells, without accumulating in one or more selected tissues or organs. For example, a microbe can accumulate in tumor cells without accumulating in the brain. In another example, a microbe can accumulate in tumor cells without accumulating in neural cells. In another example, a microbe can accumulate in tumor cells without accumulating in ovaries. In another example, a microbe can accumulate in tumor cells without accumulating in the blood. In another example, a microbe can accumulate in tumor cells without accumulating in the heart. In another example, a microbe can accumulate in tumor cells without accumulating in the bladder. In another example, a microbe can accumulate in tumor cells without accumulating in testes. In another example, a microbe can accumulate in tumor cells without accumulating in the spleen. In another example, a microbe can accumulate in tumor cells without accumulating in the lungs.

One skilled in the art can determine the desired capability for the microbes to selectively accumulate in targeted tissue or cells, such as in an immunoprivileged cells and tissues, such as tumor rather than non-target organs or tissues, according to a variety of factors known in the art, including, but not limited to, toxicity of the microbes, dosage, tumor to be treated, immunocompetence of host, and disease state of the host.

Provided herein as an example of selective accumulation in immunoprivileged cells and tissues, such as tumors relative to normal organs or tissues, presence of various vaccinia viruses was assayed in tumor samples and different organs. Wild type VGL virus (LIVP) was recovered from tumor, testes, bladder, and liver and as well as from brain. Recombinant virus RVGL9 was found mostly in tumors, and no virus was recovered from brain tissue in six tested animals. Therefore, this finding demonstrates the tumor accumulation properties of a recombinant vaccinia virus of the LIVP strain with an insertion in the F3 gene for tumor therapy purposes.

iii. Ability to Elicit or Enhance Immune Response to Tumor Cells

The microorganisms herein cause or enhance an immune response to antigens in the targeted tissues or cells, such as immunoprivileged cells and tissues, such as tumor cells. The immune response can be triggered by any of a variety of mechanisms, including the presence of immunostimulatory cytokines and the release of antigenic compounds that can cause an immune response.

Cells, in response to an infection such as a microorganismal infection, can send out signals to stimulate an immune response against the cells. Exemplary signals sent from such cells include antigens, cytokines and chemokines such as interferon-gamma and interleukin-15. The microorganism provided herein can cause targeted cells to send out such signals in response to infection by the microbes, resulting in a stimulation of the host's immune system against the targeted cells or tissues, such as tumor cells.

In another embodiment, targeted cells or tissues, such as tumor cells, can contain one or more compounds that can be recognized by the host's immune system in mounting an immune response against a tumor. Such antigenic compounds can be compounds on the cell surface or the tumor cell, and can be protein, carbohydrate, lipid, nucleic acid, or combinations thereof. Microbe-mediated release of antigenic compounds can result in triggering the host's immune system to mount an immune response against the tumor. The amount of antigenic compound released by the tumor cells is any amount sufficient to trigger an immune response in a subject; for example, the antigenic compounds released from one or more tumor cells can trigger a host immune response in the organism that is known to be accessible to leukocytes.

The time duration of antigen release is an amount of time sufficient for the host to establish an immune response to one or more tumor antigens. In some embodiments, the duration is an amount of time sufficient for the host to establish a sustained immune response to one or more tumor antigens. One skilled in the art can determine such a time duration based on a variety of factors affecting the time duration for a subject to develop an immune response, including the level of the tumor antigen in the subject, the number of different tumor antigens, the antigenicity of the antigen, the immunocompetence of the host, and the access of the antigenic material to the vasculature of the host. Typically, the duration of antigen release can be at least about a week, at least about 10 days, at least about two weeks, or at least about a month.

The microorganism provided herein can have any of a variety of properties that can cause target cells and tissues, such as tumor cells, to release antigenic compounds. Exemplary properties are the ability to lyse cells and the ability to elicit apoptosis in tumor cells. Microbes that are unable to lyse tumor cells or cause tumor cell death can nevertheless be used in the methods provided herein when such microbes can cause some release or display of antigenic compounds from tumor cells. A variety of mechanisms for antigen release or display without lysis or cell death are known in the art, and any such mechanism can be used by the microbes provided herein, including, but not limited to, secretion of antigenic compounds, enhanced cell membrane permeability, or altered cell surface expression or altered MHC presentation in tumor cells when the tumor cells can be accessed by the host's immune system. Regardless of the mechanism by which the host's immune system is activated, the net result of the presence of the microbes in the tumor is a stimulation of the host's immune system, at least in part, against the tumor cells. In one example, the microbes can cause an immune response against tumor cells not infected by the microbes.

In one embodiment, the microbes provided herein can cause tumor cells to release an antigen that is not present on the tumor cell surface. Tumor cells can produce compounds such as proteins that can cause an immune response; however, in circumstances in which the antigenic compound is not on the tumor cell surface, the tumor can proliferate, and even metastasize, without the antigenic compound causing an immune response. Within the scope of the present methods, the microbes provided herein can cause antigenic compounds within the cell to release away from the cell and away from the tumor, which can result in triggering an immune response to such an antigen. Even if not all cells of a tumor are releasing antigens, the immune response can initially be targeted toward the "leaky" tumor cells, and the bystander effect of the immune response can result in further tumor cell death around the "leaky" tumor cells.

iv. Balance of Pathogenicity and Release of Tumor Antigens

Typical methods of involving treatment of targeted cells and tissues, such as immunoprivileged cells and tissues, such as tumors, are designed to cause rapid and complete removal thereof. For example, many viruses, bacterial or eukaryotic cells can cause lysis and/or apoptosis in a variety of cells, including tumor cells. Microorganisms that can vigorously lyse or cause cell death can be highly pathogenic, and can even kill the host. Furthermore, therapeutic methods based upon such rapid and complete lysis are typically therapeutically ineffective.

In contrast, the microorganisms provided herein are not aggressive in causing cell death or lysis. They can have only a limited or no ability to cause cell death as long as they accumulate in the target cells or tissues and result in alteration of cell membranes to cause leakage of antigens against which an immune response is mounted. It is desirable that their apoptotic or lytic effect is sufficiently slow or ineffective to permit sufficient antigenic leakage for a sufficient time for the host to mount an effective immune response against the target tissues. Such immune response alone or in combination with the lytic/apoptotic effect of the microorganism results in elimination of the target tissue and also elimination of future development, such as metastases and reoccurrence, of such tissues or cells. While the microbes provided herein can have a limited ability to cause cell death, the microbes provided herein can nevertheless stimulate the host's immune system to attack tumor cells. As a result, such microorganisms also are typically unlikely to have substantial toxicity to the host.

In one embodiment, the microbes have a limited, or no, ability to cause tumor cell death, while still causing or enhancing an immune response against tumor cells. In one example, the rate of microorganism-mediated tumor cell death is less than the rate of tumor cell growth or replication. In another example, the rate of microorganism-mediated tumor cell death is slow enough for the host to establish a sustained immune response to one or more tumor antigens. Typically, the time for of cell death is sufficient to establish an anti-tumor immune response and can be at least about a week, at least about 10 days, at least about two weeks, or at least about a month, depending upon the host and the targeted cells or tissues.

In another embodiment, the microbes provided herein can cause cell death in tumor cells, without causing substantial cell death in non-tumor tissues. In such an embodiment, the microbes can aggressively kill tumor cells, as long as no substantial cell death occurs in non-tumor cells, and optionally, so long as the host has sufficient capability to mount an immune response against the tumor cells.

In one embodiment, the ability of the microbes to cause cell death is slower than the host's immune response against the microbes. The ability for the host to control infection by the microbes can be determined by the immune response (e.g., antibody titer) against microorganismal antigens. Typically, after the host has mounted immune response against the microbes, the microbes can have reduced pathogenicity in the host. Thus, when the ability of the microbes to cause cell death is slower than the host's immune response against the microbes, microbe-mediated cell death can occur without risk of serious disease or death to the host. In one example, the ability of the microbes to cause tumor cell death is slower than the host's immune response against the microbes.

b. Immunogenicity

The microorganisms provided herein also can be immunogenic. An immunogenic microorganism can create a host immune response against the microorganism. In one embodiment, the microorganisms can be sufficiently immunogenic to result in a large anti-(microorganism) antibody titer. The microorganisms provided herein can have the ability to elicit an immune response. The immune response can be activated in response to viral antigens or can be activated as a result of microorganismal-infection induced cytokine or chemokine production. Immune response against the microorganism can decrease the likelihood of pathogenicity toward the host organism.

Immune response against the microorganism also can result in target tissue or cell, such as tumor cell, killing. In one embodiment, the immune response against microorganismal infection can result in an immune response against tumor cells, including developing antibodies against tumor antigens. In one example, an immune response mounted against the microorganism can result in tumor cell killing by the "bystander effect," where uninfected tumor cells nearby infected tumor cells are killed at the same time as infected cells, or alternatively, where uninfected tumor cells nearby extracellular microorganisms are killed at the same time as the microorganisms. As a result of bystander effect tumor cell death, tumor cell antigens can be released from cells, and the host organism's immune system can mount an immune response against tumor cell antigens, resulting in an immune response against the tumor itself.

In one embodiment, the microorganism can be selected or modified to express one or more antigenic compounds, including superantigenic compounds. The antigenic compounds such as superantigens can be endogenous gene products or can be exogenous gene products. Superantigens, including toxoids, are known in the art and described elsewhere herein.

c. Replication Competent

The microorganisms provided herein can be replication competent. In a variety of viral or bacterial systems, the administered microorganism is rendered replication incompetent to limit pathogenicity risk to the host. While replication incompetence can protect the host from the microorganism, that also limits the ability of the microorganism to infect and kill tumor cells, and typically results in only a short-lived effect. In contrast, the microorganisms provided herein can be attenuated but replication competent, resulting in low toxicity to the host and accumulation mainly or solely in tumors. Thus, the microorganisms provided herein can be replication competent without creating a pathogenicity risk to the host.

Attenuation of the microorganisms provided herein can include, but is not limited to, reducing the replication competence of the microorganism. For example, a microorganism can be modified to decrease or eliminate an activity related to replication, such as a transcriptional activator that regulates replication in the microorganism. In an example, a microorganism, such as a virus, can have the viral thymidine kinase gene modified.

d. Genetic Variants

The microorganisms provided herein can be modified from their wild type form. Modifications can include any of a variety of changes, and typically include changes to the genome or nucleic acid molecules of the microorganisms. Exemplary nucleic acid molecular modifications include truncations, insertions, deletions and mutations. In an exemplary modification, a microorganismal gene can be modified by truncation, insertion, deletion or mutation. In an exemplary insertion, an exogenous gene can be inserted into the genome of the microorganism.

i. Modified Characteristics

Modifications of the microorganisms provided herein can result in a modification of microorganismal characteristics, including those provided herein such as pathogenicity, toxicity, ability to preferentially accumulate in tumor, ability to lyse cells or cause cell death, ability to elicit an immune response against tumor cells, immunogenicity, replication competence. Variants can be obtained by general methods such as mutagenesis and passage in cell or tissue culture and selection of desired properties, as is known in the art, as exemplified for respiratory syncytial virus in Murphy et al., Virus Res. 1994, 32:13-26.

Variants also can be obtained by mutagenic methods in which nucleic acid residues of the microorganism are added, removed or modified relative to the wild type. Any of a variety of known mutagenic methods can be used, including recombination-based methods, restriction endonuclease-based methods, and PCR-based methods. Mutagenic methods can be directed against particular nucleotide sequences such as genes, or can be random, where selection methods based on desired characteristics can be used to select mutated microorganisms. Any of a variety of microorganismal modifications can be made, according to the selected microorganism and the particular known modifications of the selected microorganism.

ii. Exogenous Gene Expression

The microorganisms provided herein also can have the ability to express one or more exogenous genes. Gene expression can include expression of a protein encoded by a gene and/or expression of an RNA molecule encoded by a gene. In some embodiments, the microorganisms can express exogenous genes at levels high enough that permit harvesting products of the exogenous genes from the tumor. Expression of endogenous genes can be controlled by a constitutive promoter, or by an inducible promoter. Expression can also be influenced by one or more proteins or RNA molecules expressed by the microorganism. An exemplary inducible promoter system can include a chimeric transcription factor containing a progesterone receptor fused to the yeast GAL4 DNA-binding domain and to the activation domain of the herpes simplex virus protein VP16, and a synthetic promoter containing a series of GAL4 recognition sequences upstream of the adenovirus major late E1B TATA box, linked to one or more exogenous genes; in this exemplary system, administration of RU486 to a subject can result in induction of the exogenous genes. Exogenous genes expressed can include genes encoding a therapeutic gene product, genes encoding a detectable gene product such as a gene product that can be used for imaging, genes encoding a gene product to be harvested, genes encoding an antigen of an antibody to be harvested. The microorganisms provided herein can be used for expressing genes in vivo and in vitro. Exemplary proteins include reporter proteins (*E. coli* β-galactosidase, β-glucuronidase, xanthineguanine phosphoribosyltransferase), proteins facilitating detection, i.e., a detectable protein or a protein capable of inducing a detectable signal, (e.g., luciferase, green and red fluorescent proteins, transferrin receptor), proteins useful for tumor therapy (Pseudomonas exotoxin, diphtheria toxin, p53, Arf, Bax, tumor necrosis factor-alpha, HSV TK, *E. coli* purine nucleoside phosphorylase, angiostatin, endostatin, different cytokines) and many other proteins.

iii. Detectable Gene Product

The microorganisms provided herein can express one or more genes whose products are detectable or whose products can provide a detectable signal. A variety of detectable gene products, such as detectable proteins are known in the art, and can be used with the microorganisms provided herein. Detectable proteins include receptors or other proteins that can specifically bind a detectable compound, proteins that can emit a detectable signal such as a fluorescence signal, enzymes that can catalyze a detectable reaction or catalyze formation of a detectable product.

In some embodiments, the microorganism expresses a gene encoding a protein that can emit a detectable signal or that can catalyze a detectable reaction. A variety of DNA sequences encoding proteins that can emit a detectable signal or that can catalyze a detectable reaction, such as luminescent or fluorescent proteins, are known and can be used in the microorganisms and methods provided herein. Exemplary genes encoding light-emitting proteins include genes from bacterial luciferase from *Vibrio harveyi* (Belas et al., Science 218 (1982), 791-793), bacterial luciferase from *Vibrio fischeri* (Foran and Brown, Nucleic acids Res. 16 (1988), 177), firefly luciferase (de Wet et al., Mol. Cell. Biol. 7 (1987), 725-737), aequorin from *Aequorea victoria* (Prasher et al., Biochem. 26 (1987), 1326-1332), *Renilla* luciferase from *Renilla reniformis* (Lorenz et al., PNAS USA 88 (1991), 4438-4442) and green fluorescent protein from *Aequorea victoria* (Prasher et al., Gene 111 (1987), 229-233). Transformation and expression of these genes in microorganisms can permit detection of microorganismal colonies, for example, using a low light imaging camera. Fusion of the lux A and lux B genes can result in a fully functional luciferase protein (Escher et al., PNAS 86 (1989), 6528-6532). This fusion gene (Fab2) has introduced into a variety of microorganisms followed by microorganismal infection and imaging based on luciferase expression. In some embodiments, luciferases expressed in bacteria can require exogenously added substrates such as decanal or coelenterazine for light emission. In other embodiments, microorganisms can express a complete lux operon, which can include proteins that can provide luciferase substrates such as decanal. For example, bacteria containing the complete lux operon sequence, when injected intraperitoneally, intramuscularly, or intravenously, allowed the visualization and localization of bacteria in live mice indicating that the luciferase light emission can penetrate the tissues and can be detected externally (Contag et al., Mol. Microbiol. 18 (1995), 593-603).

In other embodiments, the microorganism can express a gene that can bind a detectable compound or that can form a product that can bind a detectable compound. A variety of gene products, such as proteins, that can specifically bind a detectable compound are known in the art, including receptors, metal binding proteins, ligand binding proteins, and antibodies. Any of a variety of detectable compounds can be used, and can be imaged by any of a variety of known imaging methods. Exemplary compounds include receptor ligands and antigens for antibodies. The ligand can be labeled according to the imaging method to be used. Exemplary imaging methods include any of a variety magnetic resonance methods such as magnetic resonance imaging (MRI) and magnetic resonance spectroscopy (MRS), and also include any of a variety of tomographic methods including computed tomography (CT), computed axial tomography (CAT), electron beam computed tomography (EBCT), high resolution computed tomography (HRCT), hypocycloidal tomography, positron emission tomography (PET), single-photon emission computed tomography (SPECT), spiral computed tomography and ultrasonic tomography.

Labels appropriate for magnetic resonance imaging are known in the art, and include, for example, gadolinium chelates and iron oxides. Use of chelates in contrast agents is known in the art. Labels appropriate for tomographic imaging methods are known in the art, and include, for example, β-emitters such as $^{11}$C, $^{13}$N, $^{15}$O or $^{64}$Cu or (b) γ-emitters such as $^{123}$I. Other exemplary radionuclides that can be used, for example, as tracers for PET include $^{55}$Co, $^{67}$Ga, $^{68}$Ga, $^{60}$Cu(II), $^{67}$Cu(II), $^{57}$Ni, $^{52}$Fe and $^{18}$F. Examples of useful radionuclide-labeled agents are $^{64}$Cu-labeled engineered antibody fragment (Wu et al., PNAS USA 97 (2002), 8495-8500), $^{64}$Cu-labeled somatostatin (Lewis et al., J. Med. Chem. 42 (1999), 1341-1347), $^{64}$Cu-pyruvaldehyde-bis (N4methylthiosemicarbazone)-($^{64}$Cu-PTSM) (Adonai et al., PNAS USA 99 (2002), 3030-3035), $^{52}$Fe-citrate (Leenders et al., J. Neural. Transm. Suppl. 43 (1994), 123-132), $^{52}$Fe/$^{52m}$Mn-citrate (Calonder et al., J. Neurochem. 73 (1999), 2047-2055) and $^{52}$Fe-labeled iron (III) hydroxide-sucrose complex (Beshara et al., Br. J. Haematol. 104 (1999), 288-295, 296-302).

iv. Therapeutic Gene Product

The microorganisms provided herein can express one or more genes whose products cause cell death or whose products cause an anti-tumor immune response, such genes can be considered therapeutic genes. A variety of therapeutic gene products, such as toxic or apoptotic proteins, or siRNA, are known in the art, and can be used with the microorganisms provided herein. The therapeutic genes can act by directly killing the host cell, for example, as a channel-forming or other lytic protein, or by triggering apoptosis, or by inhibiting essential cellular processes, or by triggering an immune response against the cell, or by interacting with a compound that has a similar effect, for example, by converting a less active compound to a cytotoxic compound.

In some embodiments, the microorganism can express a therapeutic protein. A large number of therapeutic proteins that can be expressed for tumor treatment are known in the art, including, but not limited to tumor suppressors, toxins, cytostatic proteins, and cytokines An exemplary, non-limiting list of such proteins includes WT1, p53, p16, Rb, BRCA1, cystic fibrosis transmembrane regulator (CFTR), Factor VIII, low density lipoprotein receptor, beta-galactosidase, alpha-galactosidase, beta-glucocerebrosidase, insulin, parathyroid hormone, alpha-1-antitrypsin, rsCD40L, Fas-ligand, TRAIL, TNF, antibodies, microcin E492, diphtheria toxin, *Pseudomonas* exotoxin, *Escherichia coli* Shig toxin, *Escherichia coli* Verotoxin 1, and hyperforin.

In other embodiments, the microorganism can express a protein that converts a less active compound into a compound that causes tumor cell death. Exemplary methods of conversion of such a prodrug compound include enzymatic conversion and photolytic conversion. A large variety of protein/compound pairs are known in the art, and include, but are not limited to Herpes simplex virus thymidine kinase/gancyclovir, varicella zoster thymidine kinase/gancyclovir, cytosine deaminase/5-fluorouracil, purine nucleoside phosphorylase/6-methylpurine deoxyriboside, beta lactamase/cephalosporin-doxorubicin, carboxypeptidase G2/4-[(2-chloroethyl)(2-mesuloxyethyl)amino]benzoyl-L-glutamic acid, cytochrome P450/acetominophen, horseradish peroxidase/indole-3-acetic acid, nitroreductase/CB1954, rabbit carboxylesterase/7-ethyl-10-[4-(1-piperidino)-1-piperidino]carbonyloxycamptothecin, mushroom tyrosinase/bis-(2-chloroethyl)amino-4-hydroxyphenylaminomethanone 28, beta galactosidase/1-chloromethyl-5-hydroxy-1,2-dihyro-3H-benz[e]indole, beta glucuronidase/epirubicin glucuronide, thymidine phosphorylase/5'-deoxy-5-fluorouridine, deoxycytidine kinase/cytosine arabinoside, and linamerase/linamarin.

In another embodiment, the therapeutic gene product can be an siRNA molecule. The siRNA molecule can be directed against expression of a tumor-promoting gene, such as, but not limited to, an oncogene, growth factor, angiogenesis promoting gene, or a receptor. The siRNA molecule also can be directed against expression of any gene essential for cell growth, cell replication or cell survival. The siRNA molecule also can be directed against expression of any gene that stabilizes the cell membrane or otherwise limits the number of tumor cell antigens released from the tumor cell. Design of an siRNA can be readily determined according to the selected target of the siRNA; methods of siRNA design and downregulation of genes are known in the art, as exemplified in U.S. Pat. Pub. No. 20030198627.

In one embodiment, the therapeutic compound can be controlled by a regulatory sequence. Suitable regulatory sequences which, for example, are functional in a mammalian host cell are well known in the art. In one example, the regulatory sequence can contain a natural or synthetic vaccinia virus promoter. In another embodiment, the regulatory sequence contains a poxvirus promoter. When viral microorganisms are used, strong late promoters can be used to achieve high levels of expression of the foreign genes. Early and intermediate-stage promoters, however, can also be used. In one embodiment, the promoters contain early and late promoter elements, for example, the vaccinia virus early/late promoter p7.5, vaccinia late promoter p11, a synthetic early/late vaccinia pE/L promoter (Patel et al., (1988), Proc. Natl. Acad. Sci. USA 85, 9431-9435; Davison and Moss, (1989), J Mol Biol 210, 749-769; Davison et al., (1990), Nucleic Acids Res. 18, 4285-4286; Chakrabarti et al., (1997), BioTechniques 23, 1094-1097).

v. Expressing a Superantigen

The microorganisms provided herein can be modified to express one or more superantigens. Superantigens are antigens that can activate a large immune response, often brought about by a large response of T cells. A variety of superantigens are known in the art including, but not limited to, diphtheria toxin, staphylococcal enterotoxins (SEA, SEB, SEC1, SEC2, SED, SEE and SEH), Toxic Shock Syndrome Toxin 1, Exfoliating Toxins (EXft), Streptococcal Pyrogenic Exotoxin A, B and C (SPE A, B and C), Mouse Mammary Tumor Virus proteins (MMTV), Streptococcal M proteins, Clostridial Perfringens Enterotoxin (CPET), mycoplasma arthritis superantigens.

Since many superantigens also are toxins, if expression of a microorganism of reduced toxicity is desired, the superantigen can be modified to retain at least some of its superantigenicity while reducing its toxicity, resulting in a compound such as a toxoid. A variety of recombinant superantigens and toxoids of superantigens are known in the art, and can readily be expressed in the microorganisms provided herein. Exemplary toxoids include toxoids of diphtheria toxin, as exemplified in U.S. Pat. No. 6,455,673 and toxoids of Staphylococcal enterotoxins, as exemplified in U.S. Pat. Pub. No. 20030009015.

vi. Expressing a Gene Product to be Harvested

Exemplary genes expressible by a microorganism for the purpose of harvesting include human genes. An exemplary list of genes includes the list of human genes and genetic disorders authored and edited by Dr. Victor A. McKusick and his colleagues at Johns Hopkins University and elsewhere, and developed for the World Wide Web by NCBI, the National Center for Biotechnology Information. Online Mendelian Inheritance in Man, OMIM™. Center for Medical Genetics, Johns Hopkins University (Baltimore, Md.) and National Center for Biotechnology Information, National Library of Medicine (Bethesda, Md.), 1999. and those available in public databases, such as PubMed and GenBank (see, e.g., (ncbi.nlm.nih.gov/entrez/query.fcgi?db=OMIM) These genes include, but are not limited to: 239f2h9, 3pk, 4ebp1, 4ebp2, al1, al2 m1, al2m2, al2m3, al2m4, a15, a1b, a1bg, alst, a2m, a2mr, a2mrap, aa, aaa, aaa, aabt, aac1, aac2, aact, aadac, aanat, aars, aas, aat, aaysl, abc1, abc2, abc3, abc7, abc8, abcr, abi1, abl1, abl2, abl1, abo, abp, abp1, abpa, abpx, abr, acaa, acac, acaca, acacb, acad1, acadm, acads, acadsb, acadv1, acat, acat1, acat2, acc, accb, accn1, accn2, accpn, ace1, ach, ache, achm1, achm2, achrb, achrd, achrg, ac1s, ac1y, aco1, aco2, acox, acox1, acox2, acox3, acp1, acp2, acp5, acpp, acr, acrv1, acs3, acs3, acs4, act2, act35, acta1, acta2, acta3, actb, actc, actg1, actg2, act11, actn1, actn2, actn3, actsa, acug, acvr1, acvr2b, acvrl1, acvrlk1, acvrlk2, acvrlk3, acy1, ad1, ad2, ad3, ad4, ad5, ada, adam10, adam11, adam12, adam3, adam3a, adam3b, adam8, adar, adarb1, adarb2, adcp1, adcp2, adcy1, adcy2, adcy3, adcy3, adcy4, adcy5, adcy6, adcy7, adcy8, adcy9, adcyap1, adcyap1r1, add1, add2, add3, add1, adfn, adh1, adh2, adh3, adh4, adh5, adh7, adhaps, adhc1, adhr, adhr, adk, ad1, adm, admlx, adora1, adora2a, adora2b, adora21, adora21, adora3, adprt, adra1a, adra1b, adra1c, adra1d, adra2a, adra2b, adra2c, adra211, adra212, adra2r, adrb1, adrb1r, adrb2, adrb2r11, adrb3, adrbk1, adrbk2, ads1, adss, adtb1, adx, adxr, ae1, ae2, ae3, aeg11, aemk, aes, af10, af17, af4, af6, af8t, af9, afd1, afdn, afg3, afg311, afm, afp, afx1, aga, agc1, ager, ag1, agmx1, agmx2, agp1, agp7, agps, agrn, agrp, agrt, ags, agt, agti1, agtr1, agtr1a, agtr2, agtrl1, agxt, ahc, ahcy, ahd, ahds, ahnak, aho2, ahr, ahsg, ahx, aib1, aic, aic1, aied, aih1, aih2, aih3, aim1, air, airc, aire, ak1, ak2, ak3, akap149, akt1, akt2, aku, alad, alas1, alas2, alb, alb2, alba, alcam, ald, aldh1, aldh10, aldh2, aldh3, aldh4, aldh5, aldh6, aldh9, ald11, aldoa, aldob, aldoc, aldr1, alds, alk, alk1, alk2, alk3, alk6, alms1, aloxl2, alox15, alox5, alp, alpi, alp1, alpp, alppl2, alr, alr, als1, als2, als4, als5, alss, ambn, ambp, amcd1, amcd2b, amcn, amcn1, amcx1, amd1, amdm, amelx, amely, amfr, amg, amg1, amgx, amh, amhr, amhr2, aml1, aml1t1, aml2, aml3, amog, ampd1, ampd2, ampd3, amph, amph1, ampk, amt, amy1a, amy1b, amy1c, amy2a, amy2b, an 2, anc, ancr, ang, ang1, anh1, ank1, ank2, ank3, anop1, anova, anp, anpep, anpra, anprb, anprc, ans, anti, ant2, ant3, ant3y, anx1, anx11, anx13, anx2, anx214, anx3, anx4, anx5, anx6, anx7, anx8, aoah, aoc2, aox1, ap2tf, apah1, apba1, apba2, apbb1, apbb2, apc, apcs, ape, apeced, apeh, apex, api1, api2, api3, apj, aplp, aplp1, aplp2, apnh, apo31, apoa1, apoa2, apoa4, apob, apobec1, apoc1, apoc2, apoc3, apoc4, apod, apoe, apoer2, apoh, apolmt, apolp1, apolp2, app, appbp1, appl1, aprf, aprt, aps, apt1, aptl1g1, apx1, apy, aqdq, aqp0, aqp1, aqp2, aqp21, aqp3, aqp4, aqp5, aqp6, aqp7, ar, ar1, ara, araf1, araf2, arcn1, ard1, ard1, areg, arf1, arf2, arf3, arf41, arf5, arg, arg1, args, arh12, arh6, arh9, arha, arhb, arhc, arhg, arhgap2, arhgap3, arhgap6, arhgdia, arhgdib, arhh, arix, ar12, armd1, arnt, arnt1, aro, arp, arp1, arpkd, arr3, arrb1, arrb2, arsa, arsacs, arsb, arsc1, arsc2, arsd, arse, arsf, art, art1, art3, art4, arts, arvd1, arvd2, arvd3, arvd4, as, asat, asb, ascl1, ascl2, asct1, asd1, asd2, asgr1, asgr2, ash1, asip, as1, asln, asm1, asma, asmd, asmt, asmtlx, asmty, asnrs, asns, aspa, ass, astm1, astn, asv, at, at1, at2r1, at3, ata, atbf1, atcay, atf1, ath1, aths, atm, atoh1, atox1, atp1a1, atp1a2, atp1a3, atp1a11, atp1b1, atp1b2, atp1b3, atp1b11, atp1g1, atp2a1, atp2a2, atp2a3, atp2b, atp2b1, atp2b2, atp2b2, atp2b3, atp2b4, atp4a, atp4b, atp5, atp5a, atp5b, atp5g1, atp5g2, atp5g3, atp5o, atp6a, atp6b1, atp6c, atp6e, atp6n1, atp7a, atp7b, atpm, atpsb, atpsk1, atpsk2, atq1, atr, atr, atr1, atr1, atr2, atrc1, atrc2, atrx, ats, atsv, atx1, atx2, au, auf1, auf1a, aut, avcd, aved, avp, avpr1a, avpr1b, avpr2, avpr3, avrp, aysd, awa1, ax1, axl1g, axsf, azf1, azf2, azgp1, azu1, b120, b144, blg1, b29, b2m, b2mr, b3galt4, b4galt1, ba2r, bab1, bag1, bai1, bai2, bai3, bak1, bam22, bap1, bap135, bapx1, bard1, bark2, bas, bat1, bat2, bat3, bat4, bat5, bax, bb1, bbbg1, bbbg2, bbs1, bbs2, bbs3, bbs4, bbs5, bcas1, bcat1, bcat2, bcate2, bcd1, bcei, bche, bckdha, bckdhb, bcl1, bcl10, bcl2, bcl2a1, bcl212, bcl3, bcl5, bcl6, bcl7, bcl7a, bcl8, bcl9, bclw, bcm, bcm1, bcma, bcns, bcns, bcp, bcpm, bcpr, bcr, bcrl2, bcrl3, bcrl4, bcsg1, bct1, bct2, bdb, bdb1, bdc, bde, bdkrb1, bdkrb2, bdmf, bdmr, bdnf, bed, bedp, bek, bene, bevi, bf, bf1, bf2, bfhd, bfic, bfls, bfnc2, bfp, bfsp1, bft, bglap, bgmr, bgn, bgp, bhd, bhpcdh, bhr1, bicd1, bid, bigh3, bin1, bir, bjs, bkma1, blast1, blau, blk, blm, blmh, bltr, blvra, blvrb, blym, bmal1, bmd, bmh, bmi1, bmp1, bmp2, bmp2a, bmp2b1, bmp3, bmp4, bmp5, bmp6, bmp7, bmp8, bmpr1a, bmpr1b, bmx, bmyb, bn51t, bnc, bnc1, bnp, bor, bpad, bpag1, bpag2, bpes, bpes1, bpes2, bpgm, bph1, bpi, br, br140, braf, brca1, brca2, brca3, brcacox, brcd1, brcd2, brdt, brf1, brhc, brie, brks, brn3a, brn3b, brn3c, brrn1, brw1c, bs, bsap, bsep, bsf2, bsg, bsnd, bss1, bst1, bst2, btak, btc, btd, bteb, bteb1, btg1, btg2, bths, btk, btk1, btn, bts, bub1b, bubr1, bwr1a, bwr1b, bws, bwscr1a, bwscr1b, bzrp, bzx, c11orf13, c1nh, c1qa, c1qb, c1qbp, c1qg, c1r, c1s, c2, c21orf1, c21orf2, c21orf3, c2ta, c3, c3br, c3dr, c3g, c4a, c4b, c4 bpa, c4 bpb, c4f, c4s, c5, c5ar, c5r1, c6, c7, c8a, c8b, c8g, c9, ca1, ca12, ca125, ca2, ca21h, ca3, ca4, ca5, ca6, ca1, ca8, ca9, caaf1, cabp9k, cac, cac, caca, cacd, cacna1a, cacna1b, cacna1c, cacna1d, cacna1e, cacna1f, cacna1s, cacna2, cacnb1, cacnb2, cacnb3, cacnb4, cacng, cacnl1a1, cacnl1a2, cacnl1a3, cacnl1a4, cacnl1a5, cacnl1a6, cacnl2a, cacnlb1, cacnlg, cacp, cact, cacy, cad, cad11, cadasi1, cae1, cae3, caf, caf1a, caga, cagb, cain, cak, cak1, cal11, calb1, calb2, calb3, calc1, calc2, calca, calcb, calcr, cald1, calla, calm1, calm2, calm3, calm11, calm13, calna, calna3, calnb, calnb1, calr, cals, calt, calu, cam, camk4, camkg, caml1, camlg, camp, can, canp3, canx, cap2, cae3, cap37, capb, capg, cap1, capn1, capn2, capn3, capn4, cappa2, cappb, capr, caps, capza2, capzb, car, carp, cars, cart1, cas, cas2, casi1, casp1, casp10, casp2, casp3, casp3, casp4, casp5, casp6, casp7, casp8, casq1, casq2, casr cast, cat, cat1, cat4, catf1, catm, cav1, cav2, cae3, cbbm, cbd, cbfa1, cbfa2, cbfa2t1, cbfa3, cbfb, cbg, cb1, cb12, cbln2, cbp, cbp, cbp2, cbp68, cbr1, cbs, cbt, cbt1, cc10, cca, cca1, ccal1, ccal2, ccbl1, ccckr5, ccg1, ccg2, cch11a1, cch11a2, cch11a3, cch1b1, cck, cckar, cckbr, cc1, ccm1, ccm2, ccm3, ccn1, ccna, ccnb1, ccnc, ccnd1, ccnd2, ccnd3, ccne, ccnf, ccng1, ccnh, cent, ccnt1, cco, ccr10, ccr2, ccr3, ccr9, ccsp, cct, ccv, cczs, cd, cd10, cd11a, cd11b, cd11c, cd13, cd137, cd14, cd15, cd151, cd156, cd16, cd164, cd18, cd19, cd1a, cd1b, cd1c, cd1d, cd1e, cd2, cd20, cd22, cd23, cd24, cd26, cd27, cd271, cd28, cd281g, cd281g2, cd30, cd32, cd33, cd34, cd36, cd3611, cd3612, cd37, cd38, cd39, cd3911, cd3d, cd3e, cd3g, cd3z, cd4, cd40, cd401g, cd41b, cd43, cd44, cd45, cd46, cd47, cd48, cd49b, cd49d, cd5, cd53, cd57, cd58, cd59, cd51, cd6, cd63, cd64, cd68, cd69, cd7, cd70, cd71, cd72, cd74, cd79a, cd79b, cd80, cd81, cd82, cd82, cd86, cd8a, cd8b, cd8b1, cd9, cd94, cd95, cd97, cd99, cda, cda1, cda3, cdan1, cdan2, cdan3, cdb2, cdc2, cdc20, cdc25a, cdc25b, cdc25c, cdc27, cdc211, cdc212, cdc214, cdc34, cdc42, cdc51, cdc7, cdc711, cdcd1, cdcd2, cdcd3, cdc11, cdcre1, cdg1, cdgd1, cdgg1, cdgs2, cdh1, cdh11, cdh12, cdh13, cdh14, cdh15, cdh16, cdh16, cdh17, cd2, cdh3, cdh3, cdh5, cdh7, cdh8, cdhb, cdhh, cdhp, cdhs, cdk2, cdk3, cdk4, cdk5, cdk7, cdk8, cdk9, cdkn1, cdkn1a, cdkn1b, cdkn1c, cdkn2a, cdkn2b, cdkn2d, cdkn3, cdkn4, cdl1, cdm, cdmp1, cdmt, cdpx1, cdpx2, cdpxr, cdr1, cdr2, cdr3, cdr62a, cdsn, cdsp, cdtb, cdw50, cdx1, cdx2, cdx3, cdx4, cea, cebp, cebpa, cebpb, cebpd, cebpe, cecr, ce1, cel1, cen1, cenpa, cenpb, cenpc, cenpc1, cenpe, cenpf, cerd4, ces, ces1, cetn1, cetp, cf, cf2r, cfag, cfag, cfc, cfd1, cfeom1, cfeom2, cfh, cfl1, cfl2, cfnd, cfns, cftr, cg1, cga, cgat, cgb, cgd, cgf1, cgh, cgrp, cgs23, cgt, cgthba, chac, chat, chc1, chd1, chd2, chd3, chd4, chd5, chdr, che1, che2, ched, chek1, chga, chgb, chgc, chh, chi311, chip28, chit, chk1, chlr1, chlr2, chm, chm1, chn, chn1, chn2, chop 10, chr, chr39a, chr39b, chr39c, chrm1, chrm2, chrm3, chrm4, chrm5, chrna1, chrna2, chrna3, chrna4, chrna5, chrna7, chrnb1, chrnb2, chrnb3, chrnb4, chrnd, chrne, chrng, chrs, chs1, chx10, ciipx, cip1, cirbp, cish, ck2a1, ckap1, ckb, ckbb, ckbe, ckm, ckmm, ckmt1, ckmt2, ckn1, ckn2, ckr3, ckrl1, ckrl3, c1, c1100, cla1, cla1, clac, clapb1, clapm1, claps3, clc, clc7, clck2, clcn1, clcn2, clcn3, clcn4, clcn5, clcn6, clcn7, clcnka, clcnkb, cld, cldn3, cldn5, clg, clg1, clg3, clg4a, clg4b, cli, clim1, clim2, clk2, clk3, cln1, cln2, cln3, cln5, cln6, cln80, clns1a, clns1b, clp, clpp, clps, clta, cltb, cltc, cltcl1, cltd, clth, clu, cma1, cmah, cmar, cmd1, cmd1a, cmd1b, cmd1c, cmd1d, cmd1e, cmd1f, cmd3a, cmdj, cmh1, cmh2, cmh3, cmh4, cmh6, cmkbr1, cmkbr2, cmkbr3, cmkbr5, cmkbr6, cmkbr7, cmkbr8, cmkbr9, cmkbr12, cmklr1, cmkr11, cmkr12, cm1, cmm, cmm2, cmoat, cmp, cmpd1, cmpd2, cmpd2, cmpd3, cmpx1, cmt1a, cmt1b, cmt2a, cmt2b, cmt2d, cmt2d, cmt4a, cmt4b, cmtnd, cmtx1, cmtx2, cna1, cna2, cnbp1, cnc, cncg1, cncg2, cncg31, cnd, cng3, cnga1, cnga3, cngb1, cnn1, cnn2, cnn3, cnp, cnr1, cnsn, cntf, cntfr, cntn1, co, coca1, coca2, coch, cod1, cod2, coh1, coi1, col10a1, col11a1, col11a2, col12a11, col13a1, col15a1, col16a1, col17a1, col18a1, col19a1, col1a1, col1a2, col1ar, col2a1, col3a1, col4a1, col4a2, col4a3, col4a4, col4a5, col4a6, col5a1, col5a2, col6a1, col6a2, col6a3, col7a1, col8a1, col8a2, col9a1, col9a1, col9a2, col9a3, colq, comp, comt, copeb, copt1, copt2, cord1, cord2, cord5, cord6, cort, cot, cox10, cox4, cox5b, cox6a1, cox6b, cox7a1, cox7a2, cox7a3, cox7am, cox8, cp, cp107, cp115, cp20, cp47, cp49, cpa1, cpa3, cpb2, cpb2, cpd, cpe, cpetr2, cpm, cpn, cpn1, cpn2, cpo, cpp, cpp32, cpp32, cppi, cps1, cpsb, cpsd, cpt1a, cpt1b, cpt2, cpu, cpx, cpx, cpxd, cr1, cr2, cr3a, crabp1, crabp2, crapb, crarf, crat, crbp1, crbp2, crd, crd1, creb1, creb2, crebbp, creb11, crem, crfb4, crfr2, crh, crhbp, crhr, crhr1, crhr2, crip, crk, crk1, crm1, crmp1, crmp2, crp, crp1, crs, crs1c, crs2, crs3, crsa, crt, crtl1, crtm, crx, cry1, cry2, crya1, crya2, cryaa, cryab, cryb1, cryb2, cryb3, cryba1, cryba2, cryba4, crybb1, crybb2, crybb3, crygl, cryg2, cryg3, cryg4, cryg8, cryg, cryga, crygb, crygc, crygd, crygs, crym, cryz, cs, csa, csb, csbp1, csci, csd, csd2, csda, cse, cse11, csf1, csf1r, csf2, csf2ra, csf2rb, csf2ry, csf3, csf3r, csh1, csh2, csk, csmf, csn1, csn10, csn2, csn3, csnb1, csnb2, csnb3, csnk1a1, csnk1d, csnk1e, csnklg2, csnk2a1, csnk2a2, csnk2b, csnu3, cso, cspb, cspg1, cspg2, cspg3, csr, csrb, csrp, csrp1, csrp2, cst1, cst1, cst2, cst3, cst4, cst4, cst5, cst6, csta, cstb, csx, ct2, ctaa1, ctaa2, ctag, ctb, ctbp1, ctbp2, ctgf, cth, cthm, ctk, ctla1, ctla3, ctla4, ctla8, ctm, ctnna1, ctnna2, ctnnb1, ctnnd, ctnnd1, ctnr, ctns, ctp, ctpct, ctps, ctr1, ctr2, ctrb1, ctr1, ctsa, ctsb, ctsc, ctsd, ctse, ctsg, ctsg12, ctsh, ctsk, cts1, ctss, ctsw, ctsz, ctx, cubn, cul3, cul4b, cul5, cutl1, cvap, cvd1, cv1, cx26, cx31, cx32, cx37, cx40, cx43, cx46, cx50, cxb3s, cxcr4, cxorf4, cyb5, cyb561, cyba, cybb, cyc1, cyk4, cyld1, cymp, cyp1, cyp11a, cyp11b1, cyp11b2, cyp17, cyp19, cyp1a1, cyp1a2, cyp1b1, cyp21, cyp24, cyp27, cyp27a1, cyp27b1, cyp2a, cyp2a3, cyp2a6, cyp2b, cyp2c, cyp2c19, cyp2c9, cyp2d, cyp2d, cyp2e, cyp2e1, cyp2f1, cyp2j2, cyp3a4, cyp4a11, cyp4b1, cyp51, cyp7, cyp7a1, cyr61, cyrn1, cyrn2, czp3, d10s105e, d10s170, d10s170, d11s302e, d11s636, d11s813e, d11s833e, d12s2489e, d12s53e, d13s1056e, d13s25, d14s46e, d15s12, d15s226e, d15s227e, d16s2531e, d16s469e, d17s136e, d17s811e, d18s892e, d19s204, d19s381e, d1s111, d1s155e, d1s166e, d1s1733e, d1s2223e, d1s61, d2h, d2s201e, d2s448, d2s488e, d2s69e, d3s1231e, d3s1319e, d3s48e, d4, d4s90, d5s1708, d5s346, d6, d6s1101, d6s207e, d6s2245e, d6s228e, d6s229e, d6s230e, d6s231e, d6s51e, d6s52e, d6s54e, d6s81e, d6s82e, d7s437, d8s2298e, d9s46e, da1, da2b, dab2, dac, dad1, daf, dag, dag1, dag2, dagk1, dagk4, dam10, dam6, damox, dan, dao, dap, dap3, dap5, dapk1, dar, dat1, dax1, daxx, daz, dazh, daz1, dba, dbccr1, dbcn, dbh, dbi, dbi, db1, dbm, dbn1, dbp, dbp, dbp1, dbp2, dbpa, dbt, dbx, dby, dcc, dce, dci, dck, dcn, dcoh, dcp1, dcr, dcr3, dct, dctn1, dcx, ddb1, ddb2, ddc, ddh1, ddh2, ddit1, ddit3, ddost, ddp, ddpac, ddr, ddx1, ddx10, ddx11, ddx12, ddx15, ddx16, ddx2a, ddx3, ddx5, ddx6, ddx9, dec, deer, def1, def4, defy, def6, defa1, defa4, defa5, defa6, defb1, defb2, dek, denn, dents, dep1, der12, des, dff1, dffa, dffrx, dffry, dfn1, dfn2, dfn3, dfn4, dfn6, dfna1, dfna10, dfna11, dfna12, dfna13, dfna2, dfna2, dfha4, dfha5, dfna6, dfna7, dfna8, dfna9, dfnb1, dfnb12, dfnb13, dfnb14, dfnb16, dfnb17, dfnb18, dfnb2, dfnb3, dfnb4, dfnb5, dfnb6, dfnb7, dfnb8, dfnb9, dgcr, dgcr2, dgcr2, dgcr6, dgi1, dgka, dgkq, dgpt, dgpt, dgs, dgs2, dgsi, dgu, dhc2, dhcr7, dhfr, dhlag, dhp, dhpr, dhps, dhrd, dhtr, di, di1, dia, dia1, dia2, dia4, diaph1, diaph2, dif2, diff6, dipi, dir, dkc, dkc1, dlc1, dld, dlg1, dlg2, dlg3, dlg4, dlst, dlx1, dlx2, dlx2, dl3, dlx4, dlx5, dlx6, dlx7, dlx8, dm, dm2, dmahp, dmbt1, dmd, dmda1, dmd1, dmh, dmk, dmp1, dmpk, dmsfh, dmt, dmt1, dmtn, dna21, dnah, dnah1, dnah11, dnah12, dnah2, dnahc1, dnahc11, dnahc2, dnahc3, dnase1, dnase111, dnase113, dnase2, dnch2, dnc1, dncm, dnec1, dne11, dn1, dn11, dn111, dnm1, dnmt1, dnmt2, dnpk1, dns, dntt, do, doc1, doc2, dock1, dock180, dod, dok1, dom, dp1, dp1, dp2, dp3, dpagt2, dpc4, dpd, dpde1, dpde2, dpde3, dpde4, dpep1, dph212, dpp, dpp4, dpp6, dpt, dpyd, dpys, dpys11, dpys12, dr1, dr3, dr31g, dr5, dra, drad, drada, dra1, drd1, drd1b, drd1b, drd112, drd2, drd3, drd4, drd5, dri11, drp1, drp1, drp2, drp2, drp3, drp1a, drt, dsc1, dsc2, dsc3, dsc3, dsc4, dscam, dscr, dsg1, dsg2, dsg3, dsp, dspg3, dspp, dss, dss1, dtd, dtdp2, dtdst, dtna, dtr, dts, dus, dusp1, dusp11, dusp2, dusp3, dusp4, dusp5, dusp6, dusp7, dusp8, dut, dv1, dv11, dv11, dv13, dxf68s1e, dxs1272e, dxs128, dxs1283e, dxs423e, dxs435e, dxs522e, dxs648, dxs707, dxs8237e, dxys155e, dylx2, dyrk, dys, dysf, dyt1, dyt3, dyt5, dyt6, dyt7, dyt8, dyt9, dyx1, dyx2, e11s, e14, e1b, e2a, e2f1, e2f2, e2f3, e2f4, e3, e4f, e4f1, e4tf1a, e4tf1b, ea1, eaac1, eaat1, eaat2, eac, ead, eag, eap, ear1, ear2, ear3, ebaf, ebf, ebi1, ebm, ebn1, ebn1, ebn2, ebr2a, ebs1, ebvm1, ebvs1, ec1, eca1, ecb2, ece1, ecgf1, ech1, echs1, eck, ecm1, ecp, ecs1, ect2, ed1, ed2, ed3, ed4, eda, eda3, eddr1, edg3, edg6, edh, edh17b2, edh17b2, edh17b3, edm1, edm2, edm3, edmd, edmd2, edn, edn1, edn2, edn3, ednra, ednrb, eec1, eec2, eef1a1, eef1a2, eef1b1, eef1b2, eef1b3, eef1b4, eef2, eeg1, eegv1, eek, een, ef1a, ef2, efe2, efemp1, efl6, efmr, etha1, efna3, efna4, efnb1, efnb2, efnb3, efp, eftu, egf, egfr, egi, egr1, egr2, egr3, egr4, ehhadh, ehoc1, ei, eif1a, eif2g A, eif2s3 A, eif3s10, eif3s6, eif4a1, eif4a2, eif4c, eif4e, eif4ebp1, eif4e2, eif4e11, eif4e12, eif4g, eif4g1, eif4g2, eif5a, ejm1, el1, ela1, ela2, elam1, elanh2, elav11, elav12, elav14, elc, ele1, elf3, elk1, elk2, elk3, elk4, el1, eln, em9, emap, emap1, emd, emd2, emk 1, emp1, emp55, emr1, ems1, emt, emtb, emx1, emx2, en1, en2, ena78, end, endog, enfl2, eng, en1, eno1, eno2, eno3, enpep, ent1, entk, enur1, enur2, enx2, eos, ep3, ep300, epa, epb3, epb311, epb41, epb4112, epb42, epb49, epb72, epha1, epha2, epha3, epha8, ephb1, ephb2, ephb3, ephb4, ephb6, epht1, epht2, epht3, ephx1, ephx2, epim, eplg1, eplg2, eplg3, eplg4, eplg5, eplg8, epm1, epm2, epm2a, epmr, epo, epor, eppk, eprs, eps15, eps8, ept, erba1, erba2, erba12, erba13, erbb2, erbb3, erbb4, erc55, ercc1, ercc2, ercc3, ercc4, ercc5, ercc6, ercm1, erda1, erf1, erg, erg3, ergic53, erh, erk, erk1, erk2, erk3, erm, erpl 1, erv1, erv1, erv3, ervr, ervtlervt2, ervt3, ervt4, ervt5, eryf1, es1, es130, esa, esa1, esa4, esat, esb3, esd, esg, esr, esr1, esr2, esr11, esr12, esrra, esrrb, esrrg, ess1, est, est, est2, est25263, esx, etfa, etfb, etfdh, etk1, etk2, etm1, etm2, eto, ets1, ets2, etv1, etv3, etv4, etv5, etv6, evc, evc1, evda, evdb, evi1, evi2, evi2a, evi2b, evp1, evr1, evx1, evx2, ews, ewsr1, exlm1, ext1, ext2, ext3, ext11, ext12, eya1, eya2, eya3, eycl1, eycl3, ezh1, ezh1, ezh2, f10, f11, f12, f13a, f13a1, f13b, f2, f2r, f2r12, f2r13, f3, f5, f5f8d, f7, f7e, f7r, f8a, f8b, f8c, f8vwf, f9, fa, fa1, faa, fabp1, fabp2fabp3, fabp4, fabp6, fac1, faca, face, facd, face, fac11, fac12, fac13, fac14, facv11, fad, fadd, fadk, fah, fak2, faldh, fal139, falz, fanca, fancc, fancd, fance, fancg, fap, fapa, farr, fas, fas1, fasn, fast1, fat, fau, fbln1, fbln2, fbn1, fbn2, fbn1, fbp1, fcar, fcc1, fcc, fce2, fcer1a, feer1b, feer1g, feer2, fcgr1a, fcgr1b, fegr1c, fegr2a, fegr3a, fcgrt, fcmd, fen1, fcn2, fcp, fcp1, fcpx, fct3a, fdc, fdft1, fdh, fdps11, fdps12, fdps13, fdps14, fdps15, fdx1, fdxr, fe65, fe6511, fea, feb1, feb2, fecb, fech, fen1, feo, feom, feom1, feom2, fer, fes, fet1, fevr, ffm, fga, fgarat, fgb, fgc, fgd1, fgdy, fgf1, fgf10, fgfl1, fgf12, fgf13, fgf14, fgf2, fgf2, fgf3, fgf4, fgf5, fgf6, fgf7, fgf8, faf9, fgfa, fgfb, fgfr1, fgfr2, fgfr3, fgfr4, fgg, fgr, fgs1, fh, fh, fh3, fhe, fnf1, fhf3, fhf4, fhh2, fhit, fh11, fh12, fhr2, fic1, figf, fih, fim, fim1, fim3, fimg, fkbpl2, fkbp1a, fkbp2, fkh2, fkh11, fkh110, fkh112, fkh115, fkh116, fkh117, fkh12, fkh15, fkh16, fkh17, fkh18, fkh19, fkhr, fkhr11, flg, fli1, flii, fln1, fln2, flna, flnb, flnms, flot2, flt1, flt2, flt3, flt4, fmf, fmn, fmo1, fmo2, fmo3, fmod, fmr1, fmr2, fms, fl1, fn12, fnra, fnrb, fhrb1, fnta, fntb, folh, folh1, folr1, folr2, folt, fos, fosb, fos11, fos12, fpah, fpc, fpd1, fpdmm, fpf, fpgs, fp1, fpp, fpr1, fprh1, fprh2, fpr11, fpr12, fprp, fps12, fps13, fps14, fps15, fr, frap1, fraxa, fraxe, fraxf, frda, freac2, freac6, freac9, frg1, frp1, frv1, frv2, frv3, fsg1, fsgs, fshb, fshd1a, fshmd1a, fshprh1, fshr, fssv, fth1, fth16, ft1, ftz1, ftzf1, fuca1, fuca2, fur, fus, fuse, fut1, fut2, fut3, fut4, fut5, fut6, fut7, fut8, fvt1, fxr1, fxy, fy, fyn, fzd1, fzd2, fzd3, fzd5, fzd6, fzd7, fzr, g0s8, g10p1, g10p2, g17, g10p1, g19p1, g1p1, g1p2, g1p3, g22p1, g6 pc, g6pd, g6pd1, g6pd1, g6pt, g6pt1, g6s, g7p1, ga2, gaa, gabatr, gabpa, gabpb1, gabra1, gabra2, gabra3, gabra4, gabra5, gabra6, gabrb1, gabrb2, gabrb3, gabrd, gabre, gabrg1, gabrg2, gabrg3, gabrr1, gabrr2, gad1, gad2, gad3, gadd153, gadd45, gak, ga1, galbp, galc, gale, galgt, galk1, galk2, galn, galnact, galnr, galnr1, gains, galnt1, galnt2, galnt3, galr1, galt, gan, gan1, ganab, ganc, gap, gaplm, gap43, gapd, gar22, garp, gars, gart, gas, gas1, gas2, gas41, gash, gas7, gasr, gast, gata1, gata2, gata3, gata4, gata6, gay1, gba, gbas, gbbb1, gbbb2, gbe1, gbp1, gbx2, gc, gcap, gcap2, gcdh, gef1, gcf2, gcfx, gcg, gcgr, gch1, gck, gckr, gcn511, gen512, gcnf, gent1, gcnt2, gcp, gcp2, gcs, ges1, gcsf, gcsfr, gcsp, gctg, gcy, gda, gde, gdf5, gdf8, gdh, gdi1, gdi2, gdid4, gdld, gdnf, gdnfr, gdnfra, gdnfrb, gdx, gdxy, ge, gem, geney, gey, gf1, gf1, gfap, gfer, gfer, gfi1, gfpt, gfra1, gfra2, ggcx, ggt1, ggt2, ggta1, ggtb1, ggtb2, gh1, gh2, ghc®, ghdx, ghn, ghr, ghrf, ghrh, ghrhr, ghs, ghv, gif, gifb, gip, gip, gipr, girk1, girk2, girk3, girk4, gja1, gja3, gja4, gja5, gja8, gjb1, gjb2, gjb3, gk, gk2, gla, glat, glb1, glb2, glc1a, glc1b, glc1c, glc1d, glc1f, glc3a, glc3b, glc1c, glc1r, glct2, glct3, gldc, glepp1, glg1, gli, gli2, gli3, gli4, glnn, gins, glo1, glo2, glp1r, glra1, glra2, glra3, glrb, glrx, gls, glud1, glud2, glu1, glur1, glur2, glur3, glur4, glur5, glur6, glur7, glut1, glut2, glut3, glut4, glut5, glvr1, glvr2, giy96, glya, glyb, glys1, glyt1, glyt1, glyt2, gm2a, gma, gmcsf, gmds, gm1, gmpr, gmps, gna11, gna15, gna16, gnai1, gnai2, gnai2a, gnai2b, gnai21, gnai3, gna1, gnao1, gnaq, gnas, gnas1, gnat1, gnat2, gnaz, gnb1, gnb2, gnb3, gng5, gn11, gnpta, gnrh1, gnrh2, gnrhr, gns, gnt1, golga4, got1, got2, gp130, gp1ba, gp1bb, gp2, gp2b, gp39, gp3a, gp75, gp78, gp9, gpa, gpam, gpat, gpb, gpc, gpc1, gpc3, gpc4, gpd, gpd1, gpd2, gpds1, gpe, gpi, gpi2, gpm6a, gpm6b, gpoa, gpr1, gpr10, gpr11, gpr12, gpr13, gpr15, gpr17, gpr18, gpr19, gpr2, gpr20, gpr21, gpr22, gpr23, gpr25, gpr29, gpr3, gpr30, gpr31, gpr32, gpr35, gpr37, gpr39, gpr4, gpr5, gpr6, gpr7, gpr8, gpr9, gprcy4, gprk21, gprk4, gprk5, gprk6, gprv28, gpsa, gpsc, gpt, gpx1, gpx2, gpx3, gpx4, gr2, grb1, grb10, grb2, grf2, gria1, gria2, gria3, gria4, grid2, grik1, grik2, grik3, grik4, grik5, grin1, grin2a, grin2b, grin2c, grin2d, grina, grk1, grk5, grk6, gr1, gr111, grm3, grm8, grmp, grn, gro1, gro2, gro3, grp, grp58, grp78, grpr, grx, gs, gs1, gsas, gsc, gsc1, gse, gshs, gs1, gsm1, gsn, gsp, gspt1, gsr, gss, gstl2, gstl1, gst2, gst2, gst3, gst4, gst5, gsta1, gsta2, gstm1, gstm11, gstm2, gstm3, gstm4, gstm5, gstp1, gstt2, gt1, gt335, gta, gtb, gtbp, gtd, gtf2e2, gtf2f1, gtf2h1, gtf2h2, gtf2h4, gtf21, gtf2s, gtf3a, gtg, guc1a2, guc1a3, guc1b3, guc2c, guc2d, guc2f, guca1a, guca1b, guca2, guca2, guca2a, guca2b, gucsa3, gucsb3, gucyla2, gucyla3, gucylb3, gucy2c, gucy2d, gucy2f, guk1, guk2, gulo, gulop, gusb, gusm, gust, gxp1, gypa, gypb, gypc, gype, gys, gys1, gys2, gzma, gzmb, gzmh, gzmm, h, h142t, h19, h1f0, h1f1, h1f2, h1f3, h1f4, h1f5, h1fv, h2a, h2ax, h2az, h2b, h2b, h3f2, h3f3b, h3 ft, h3t, h4, h4f2, h4f5, h4fa, h4fb, h4fe, h4fg, h4fh, h4f1, h4fj, h4fk, h4f1, h4fm, h4m, h6, ha2, habp1, hadha, hadhb, hadhsc, haf, hagh, hah1, haip1, ha1, hap, hap1, hap2, hars, has2, hat1, hausp, hb1, hb1, hb6, hba1, hba2, hbac, hbb, hbbc, hbd, hbe1, hbegf, hbf2, hbg1, hbg2, hbgr, hbhr, hbm, hbp, hbq1, hbz, hc2, hc3, hca, hcat2, hccs, hcdh, hcf2, hcfc1, hcg, hck, h11, hc12, hc13, hcls1, hcp, hcp1, hcs, hcvs, hd, hdac1, hdc, hdgf, hdhc7, hdlbp, hdld, hdldt1, hdr, hed, hed, hegf1, hek, hek3, heln1, hemi, hema, hemb, hemc, hempas, hen1, hen2, hep, hep10, her2, her4, herg, herv1, hes1, hesx1, het, hexa, hexb, hf1, hf10, hfc1, hfe, hfe2, hfh11, hfsp, hgd, hgf, hgf, hgf1, hg1, hh, hh72, hhc1, hhc2, hhd, hhh, hhmjg, hhr23a, hht1, hht2, hiap2, higm1, hilda, hint, hiomt, hip, hip1, hip116, hip2, hir, hira, his1, his2, hive1, hivep1, hivep2, hjcd, hk1, hk2, hk3, hk33, hke4, hke6, hkr1, hkr2, hkr3, hkr4, hl 11, hl19, hla-a, hla-b, hla-c, hla-cda12, hla-dma, hla-dmb, hla-dna, hla-dob, hla-dpa1hla-dpb1, hla-dqa1, hla-drlb, hla-dra, hla-e, hla-f, hla-g, hla-ha2, hladp, hlaf, hlals, hlcs, hlm2, hlp, hlp3, hlr1, hlr2, hlt, hlx1, hlxb9, hmaa, hmab, hmat1, hmbs, hmcs, hmg1, hmg14, hmg17, hmg2, hmgc1, hmgcr, hmgcs1, hmgcs2, hmgic, hmgiy, hmgx, hmmr, hmn2, hmox1, hmox2, hmr, hms1, hmsn1, hmx1, hmx2, hnd, hnf1a, hnf2, hnf3a, hnf3b, hnf4a, hnp36, hnpcc6, hnrpa1, hnrpa2b1, hnrpd, hnrpf, hnrpg, hnrph1, hnrph2, hnrph3, hnrpk, homg, hops, hox10, hox11, hox12, hox1, hox1a, hox1b, hox1c, hox1d, hox1e, hox1f, hox1g, hox1h, hox1i, hox1j, hox2, hox2a, hox2b, hox2c, hox2d, hox2e, hox2f, hox2g, hox2h, hox21, hox3, hox3a, hox3b, hox3c, hox3d, hox3e, hox3f, hox3g, hox4, hox4a, hox4b, hox4c, hox4d, hox4e, hox4f, hox4g, hox4h, hox41, hox7, hox8, hoxa1, hoxa10, hoxa11, hoxa13, hoxa3, hoxa4, hoxa5, hoxa6, hoxa7, hoxa9, hoxa, hoxb1, hoxb2, hoxb3, hoxb4, hoxb5, hoxb6, hoxb7, hoxb8, hoxb9, hoxb, hoxc12, hoxc13, hoxc4, hoxc5, hoxc6, hoxc8, hoxc9, hoxc, hoxd1, hoxd10, hoxd11, hoxd12, hoxd13, hoxd3, hoxd4, hoxd8, hoxd9, hoxd, hoxhb9, hp, hp4, hpafp, hpc1, hpc2, hpca, hpca11, hpcx, hpd, hpdr1, hpdr2, hpe1, hpe2, hpe3, hpe4, hpe5, hpect1, hpfh, hpfh2, hpgd, hplh1, hp1h2, hpn, hpr, hprt, hprt1, hps, hpt, hpt1, hptp, hptx, hpv18i1, hpv18i2, hpx, hr, hras, hrb, hrc, hrc1, hrca1, hrd, hres1, hrf, hrg, hrga, hrh1, hrh2, hrmt111, hrpt2, hrx, hrx, hry, hsa11, hsa12, hsan1, hsas1, hscr2, hsd1, hsd11b1, hsd11b2, hsd11k, hsd111, hsd17b1, hsd17b2, hsd17b3, hsd17b4, hsd3b1, hsd3b2, hsh, hsn1, hsorc1, hsp27, hsp73, hspa1a, hspa1b, hspa11, hspa2, hspa3, hspa4, hspa5, hspa6, hspa7, hspa8, hspa9, hspb1, hspb2, hspc2, hspca11, hspca12, hspca13, hspca14, hspcb, hspg1, hspg2, hsr1, hsst, hstd, hstf1, htc2, htf4, htk, htk1, ht1, htlf, htlvr, htn1, htn2, htn3, htnb, htor, htr1a, htr1b, htr1d, htr1e, htr1e1, htr1f, htr2a, htr2b, htr2c, htr3, htr4, htr5a, htr6, htr7, htrx1, hts1, htt, htx, htx1, hub, hud, hup2, hur, hus, hyls, hvbs1, hvbs6, hvbs7, hvem, hvh2, hvh3, hvh8, hxb, hxb1, hy, hya, hya11, hyd2, hygn1, hy1, hyp, hyplip1, hypp, hypx, hyr, hyrc1, hys, ia1, ia2, iap, iapp, iar, iars, ibd1, ibd2, ibm2, ibsp, ica1, icam1, icam2, icam3, icca, ich1, icr2, icr2b, ics1, id1, id2, id3, id4, ida, idd, iddm1, iddm10, iddm11, iddm12, iddm13, iddm15, iddm17, iddm2, iddm3, iddm4, iddm5, iddm6, iddm7, iddm8, iddmx, ide, idg2, idh1, idh2, idh3a, idh3g, ido, ids, idua, ier1, ier3, iex1, if, ifcr, ifgr2, ifi16, ifi27, ifi35, ifi4, ifi5111, ifi54, ifi56, ifi616, ifi78, ifna1, ifna10, ifna13, ifna14, ifna16, ifna17, ifna21, ifna6, ifna7, ifna8, ifna, ifnai1, ifnar1, ifnar2, ifnb1, ifnb2, ifnb3, ifng, ifngr1, ifngr2, ifngt1, ifhr, ifnw1, ifrd2, iga, igat, igb, igbp1, igd1, igda1, igdc1, igds2, iger, iges, igf1, igf1r, igf2, igf2r, igfbp1, igfbp10, igfbp2, igfbp3, igfbp4, igfbp6, igfbp7, igfr1, igfr2, igfr3, igh, igha1, igha2, ighd, ighdy2, ighe, ighg1, ighg2, ighg3, ighg4, ighj, ighm, ighmbp2, ighr, ighv, igi, ig, igk, igkc, igkde1, igkj, igkjrb1, igkv, iglc, iglc1, ig1j, iglp1, iglp2, iglv, igm, igo1, igsf1, ihh, ik1, ikba, il10, il10r, il11, il11ra, il12a, il12b, il12rb1, il12rb2, il13, il13ra1, il13ra2, il15, il15ra, il17, il1a, il1b, il1bc, il1r2, il1ra, il1rap, il1rb, il1rn, il2, il2r, il2ra, il2rb, il2rg, il3, il3ra, il3ray, il4, il4r, il4ra, il5, il5ra, il6, il6r, il6st, il7, il7r, il8, il8ra, il8rb, il9, il9r, ila, ilf1, illbp, imd1, imd2, imd4, imd5, imd6, impa1, impdh1, impdh2, impdh11, impg1, impt1, indx, infa2, infa4, infa5, ing1, inha, inhba, inhbb, inhbc, ini1, ink4b, inlu, inp10, inpp1, inpp5a, inpp5b, inpp5d, inpp11, ins, insig1, ins1, ins13, ins14, insr, insrr, int1, int111, int2, int3, int4, int6, iosca, ip2, ipf1, ip1, ipm150, ipox, ipp, ipp2, ipw, iqgap1, ir10, ir20, ireb1, ireb2, irf1, irf2, irf4, irf4, irr, irs1, isa, iscw, is11, islr, isot, issx, it15, itba1, itba2, itf, itf2, itga1, itga2, itga2b, itga4, itga5, itga6, itga7, itgad, itga1, itgam, itgav, itgax, itgb1, itgb2, itgb3, itgb4, itgb6, itgb7, iti, itih1, itih2, itih3, itih4, itih11, iti1, itk, itm1, itpa, itpka, itpkb, itpr1, itpr2, itpr3, itsn, ivd, iv1, jag1, jak1, jak2, jak3, jbs, jcap, jh8, jip, jk, jme, jmj, joag, jpd, jrk, jrk1, jtk14, jtv1, jun, junb, jund, jup, jv18, jws, k12t, kai1, kal1, kar, kars, katp1, kcna1, kcna10, kcna1b, kcna2b, kcna3, kcna4, kcna5, kcna6, kcna7, kcna8, kcna9, kcnab1, kcnab2, kcnb1, kcnc1, kcnc2, kcnc3, kcnc4, kcne1, kcnh1, kcnh2, kcnj1, kcnj10, kcnj11, kcnj12, kcnj15, kcnj3, kcnj4, kcnj5, kcnj6, kcnj6, kcnj7, kcnj8, kcnjn1, kcnk1, kcnk2, kcnk3, kcnma1, kcnq1, kcnq2, kcnq3, kcnq4, kcns2, kd, kdr, ke1, kera, kf1, kfs, kfsd, kfs1, khk, kiaa0122, kid, kid1, kif2, kif3c, kif5b, kip1, kip2, kiss1, kit, klc2, klk1, klk2, klk3, klk3, klkb1, klkr, klrb1, klrc1, klrc2, klrc3, klrc4, klrd1, klst, kms, kms, kng, kno, kns1, kns2, kns11, kns14, kox1, kox11, kox12, kox13, kox15, kox16, kox18, kox19, kox2, kox2, kox22, kox25, kox30, kox32, kox4, kox5, kox6, kox7, kox9, kpna3, kpps1, kpps2, krag, kraslp, kras2, krev1, krg2, krn1, krn11, krox20, krt1, krt10, krt12, krt13, krt14, krt15, krt16, krt17, krt18, krt19, krt2a, krt2e, krt3, krt4, krt5, krt6a, krt6b, krt7, krt8, krt9, krtha2, krtha5, krthb1, krthb6, ks, ktn1, ku70, kup, kvlqt1, kwe, 11.2, 11 cam, 123mrp, lab7, lab72, lac, laci, lacs, lad, lad, lad1, laf4, lag3, lag5, lair1, lak1, lalba, lal1, lam1, lama1, lama2, lama3, lama3, lama4, lama5, lamb1, lamb2, lamb2, lamb2t, lamb3, lambr, lamc1, lamc2, lamm, lamnb2, lamp, lamp1, lamp2, lamr1, lams, lap, lap18, laptm5, lar, lar1, lard, large, lars, lbp, lbr, lea, lca1, lcad, lcamb, lcat, lccs, lcfs2, lch, lck, lcn1, lcn2, lco, lcp1, lcp2, lct, ld, ld78, ldb1, ldb2, ldc, ldh1, ldh3, ldha, ldhb, ldhc, ldlr, le, lect2, lef1, lefty1, lefty2, lep, lepr, lerk5, lerk8, leu1, leu7, leut, lfa1a, lfa3, lfh11, lfp, lga1s1, lga1s3, lga1s3bp, lga1s7, lgcr, lgmd1, lgmd1a, lgmd1b, lgmd1c, lgmd1d, lgmd2b, lgmd2c, lgmd2d, lgmd2e, lgmd2f, lgmd2g, lgmd2h, lgs, lgtn, lhb, lhcgr, lhs, lhx1, lhx3, li, li2, lif, lifr, lig1, lig3, lig4, lim1, lim2, limab1, limk1, limpii, lip2, lipa, lipb, lipc, lipd, lipe, lipo, lis1, lis2, lisx, litaf, lkb1, lkn1, llg11, lman1, lmn1, lmn2, lmna, lmnb1, lmnb2, lmo1, lmo2, lmo3, lmo4, lmo5, lmp10, lmp2, lmp7, lmpx, lms, lmx1, lmx1a, lmx1b, lmyc, lnhr, lnrh, locr, loh11cr2a, lor, lot1, lox, lox1, lox11, lpa, 1paab, 1paata, 1pap lpc1, lpc2d, lpd1, lph, lp1, lp1, lpna3, lpp, lps, lpsa, lqt1, lqt2, lqt3, lqt4, lr3, lre1, lre2, lrp, lrp1, lrp2, lrp5, lrp7, lrp8, lrpap1, lrpr1, lrs1, lsamp, lsirf, ls1, lsn, lsp1, lss, lst1, lta, lta4h, ltb, ltb4r, ltbp1, ltbp2, ltbp2, ltbp3, ltbp3, ltbr, ltc4s, ltf, ltk, ltn, lu, 1 um, luxs, luzp, lw, ly64, ly6e, ly9, lyam1, lyb2, lyf1, ly11, lyn, lyp, lyst, lyt10, lyz, lztr1, m11s1, m130, m17s1, m17s2, m195, m1s1, m3s1, m4s1, m6a, m6b, m6p2, m6pr, m6s1, m7v1, m7vs1, mab211, mac1a, mac2, mac25, macam1, macs, mad, mad211, madd, madh1, madh2, madh3, madh4, madh5, madh6, madh6, madh7, madh9, madm, madr1, maf, mafd1, mafd2, mag, mage1, mageb3, mageb4, mage11, magoh, magp, magp1, magp2, mak, mal, mal1, man2a2, mana1, mana2, mana2x, manb, manb1, manba, maoa, maob, map1a, map1a1c3, map1b, map1b1c3, map2, map4, map80, map97, mapk1, mapkap3, mapkkk4, mapt, mar, mark3, mars, mas1, masp1, mat1a, mat2a, mata1, mata2, matk, matn1, matn3, max, maz, mb, mbd1, mb1, mb12, mbp, mbp1, mbs, mbs2, mc1r, mc2r, mc3r, mc4r, mc5r, mcad, mcc, mcdc1, mcdr1, mcf2, mcf3, mcfd1, mch2, mch3, mch4, mch5, mckd, mc1, mc11, mcm, mcm2, mcm2, mcm3, mcm6, mcm7, mcmt, mcop, mcor, mcp, mcp1, mcp3, mcph1, mcr, mcs, mcsf, mcsp, mct1, md1, mdb, mdc, mdcr, mddc, mdeg, mdf1, mdg, mdg1, mdh1, mdh2, mdk, mdk, mdm2, mdm4, mdr1, mdr3, mdrs1, mdrv, mds, mds1, mdu1, mdu2, mdu3, mdx, me1, me2, mea, meati, mec11, mecp2, med, mef, mef2a, mef2b, mef2c, mef2d, mefv, mehmo, meis1, meis2, mekk, mekk1, mekk4, me1, mel18, melf, memo1, men1, men2a, meox1, meox2, mep1a, mep1b, mer2, mer6, mest, met, metrs, mfap1, mfap2, mfap3, mfap4, mfd1, mfi2, mfs1, mfs2, mft, mfts, mg50, mga, mga1, mga3, mgat1, mgat2, mgat5, mgc1, mgcn, mgcr, mgct, mgdf, mgea, mgf, mgi, mgmt, mgp, mgsa, mgst1, mgst2, mhc, mhc2ta, mhp2, mhs, mhs2, mhs3, mhs4, mhs6, mia, mic10, mic11, mic12, mic17, mic18, mic2, mic2x, mic2y, mic3, mic4, mic7, mica, micb, midi, midas, mif, mif, mig, mip, mip2a, mip2b, mip3b, mipep, mitf, miwc, mjd, mk, mki67, mkks, mkp2, mkp3, mkpx, mks, mks, mks1, mks2, mla1, mlck, mlf1, mlf2, mlh1, mlk1, mlk3, ml1, ml12, ml1t1, ml1t2, ml1t3, ml1t4, ml1t6, ml1t7, mlm, mlm, mln, mlp, mlr, mlrg, mlrw, mls, mltn, mlvar, mlvi2, mlvt, mmac1, mme, mmp1, mmp10, mmp11, mmp12, mmp13, mmp14, mmp15, mmp16, mmp17, mmp19, mmp2, mmp21, mmp22, mmp3, mmp7, mmp8, mmp9, mn, mn, mnb, mnbh, mnda, mng1, mnk, mns, mnt, mocod, mocs1, mocs2, mody1, mody3, mog, mok2, mom1, mos, mot2, mov34, mox1, mox2, mox44, moz, mp19, mpb1, mpd1, mpdz, mpe, mpe16, mpg, mpi, mpif2, mp1, mp11g, mpo, mpp1, mpp2, mpp3, mppb, mpri, mprn, mps2, mps3a, mps3c, mps4a, mpsh, mpts, mpv17, mpz, mr1, mr77, mrbc, mrc1, mre11, mre11a, mrg1, mrgh, mros, mrp, mrp, mrp1, mrp123, mrs, mrsd, mrsr, mrst, mrx1, mrx14, mrx2, mrx20, mrx21, mrx23, mrx29, mrx41, mrx48, mrx49, mrx9, mrxa, mrxs1, mrxs2, mrxs3, mrxs4, mrxs5, mrxs6, mrxs8, ms3315, ms336, msg1, msh2, msh3, msh4, msh6, msi1, msk16, msk39, msk41, mslr1, msmb, msn, msr1, mss1, mss4, mss4, msse, mst, mst1, mst1r, mstd, mstn, msud1, msx1, msx2, mt1a, mt1b, mt1e, mt1f, mt1g, mt1h, mt1i, mt1j, mt1k, mt11, mtlx, mt2, mt2a, mt3, mtacr1, mtap, mtbt1, mtcp1, mterf, mtf1, mth1, mthfc, mthfd, mthfr, mtk1, mtm1, mtmr1, mtmx, mtnr1a, mtnr1b, mtp, mtpa, mtr, mtrns, mtrr, mts, mts, mts1, mts1, mts2, mttf1, mtx, mtxn, mu, muc1, muc2, muc3, muc4, muc5, muc5ac, muc5b, much, muc8, mu1, mum1, mupp1, musk, mut, mvk, mvlk, mvwf, mwfe, mx, mx1, mx2, mxi1, mxs1, myb, myb11, myb12, mybpc1, mybpc2, mybpc3, mybpcf, mybph, myc, myc11, myc12, myclk1, mycn, myd88, myf3, myf4, myf5, myf6, myh1, myh10, myh11, myh12, myh2, myh3, myh4, myh6, myh7, myh8, myh9, myk1, my1, my11, my12, my13, my14, my15, mylk, mymy, myo10, myo15, myo1a, myo1c, myo1d, myo1e, myo5a, myo6, myo7a, myo9b, myoc, myod1, myog, myp1, myp2, myp3, myr5, mzf1, n33, nab1, nab2, nabc1, nac1a, naca, nacae, nacp, nadmr, naga, nagc, naglu, nagr1, naip, namsd, nanta3, nap114, nap2, nap21, napb, naptb, nars, nat1, nat1, nat2, nb, nb4s, nbat, nbc3, nbccs, nbccs, nbia1, nbs, nbs, nbs1, nca, ncad, ncam1, ncan, ncbp, ncc1, ncc2, ncc3, ncc4, ncct, ncf1, ncf2, ncf4, nck, ncl, ncst2, ncx1, ncx2, nd, ndhii, ndn, ndp, ndst1, ndufa1, ndufa2, ndufa5, ndufa6, ndufa7, ndufb8, ndufb9, ndufs1, ndufs2, ndufs4, ndufs7, ndufs8, ndufv1, ndufv2, ndufv3, neb, nec1, nec2, nedd1, nedd2, nedd4, nefh, nef1, negf1, negf2, ne111, neb 112, nem1, neo1, nep, net, nett, neu, neu, neud4, neurod, neurod2, neurod3, nf1, nf1a, nf2, nfatc1, nfatc2, nfatp, nfe1, nfe2, nfe211, nfe212, nfe2u, nfia, nfib, nfic, nfix, nfkb1, nfkb2, nfkb3, nfkbia, nfkbi11, nfrkb, nfya, nfyb, nga1, ngbe, ngfb, ngfg, ngfic, ngfr, ng1, ngn, nhbp, nhcp1, nhcp2, nhe1, nhe3, nhe4, nhe5, nhlh1, nhlh2, nhp211, nhs, nid, niddm1, ninj1, nipp1, nipsnap1, nipsnap2, nis, nklr, nkcc1, nkcc2, nkg2, nkg2a, nkg2c, nkg2e, nkg2f, nkhc, nkna, nknar, nknb, nkrp1a, nks1, nksf2, nktr, nkx2a, nkx3.2, nkx3a, nkx6a, nli, nm, nm1, nm23, nmb, nmbr, nmdar1, nmdar2a, nmdar2b, nmdar2c, nmdar2d, nmdara1, nme1, nme2, nme4, nmor1, nmor2, nms1, nmyc, nnat, nmnt, nno1, nog, noll, nos1, nos2a, nos2b, nos2c, nos3, not, notch1, notch2, notch3, notch4, nov, nov, nov2, nova1, nova3, novp, np, np10, npat, npc, npc1, npd, nph1, nph2, nph12, nphn, nphp1, nphp2, nphs1, npm1, nppa, nppb, nppc, npps, npr1, npr2, npr3, nps1, npt1, npt2, nptx2, npy, npylr, npy2r, npy3r, npy5r, npy6r, nqo2, nramp, nramp1, nramp2, nrap, nras, nrb54, nrcam, nrd1, nrf1, nrf1, nrf2, nrgn, nrip1, nrk2, nr1, nrtn, nru, ns1, nsf, nsp, nsp11, nsrd9, nt4, nt5, nt5, ntcp1, ntcp2, ntf3, ntf4, ntf5, nth11, ntn, ntn, ntn21, ntrk1, ntrk2, ntrk3, ntrk4, ntrkr1, ntrkr3, nts, ntt, ntt, nuc1, nucb1, numa1, nup214, nup98, nurr1, nv1, nys1, nys2, nysa, oa1, oa2, oa3, oar, oasd, oat, oat11, oat22, oat23, oatp, oaz, ob, ob10, obf1, obp, obr, oca2, ocm, ocp2, ocr1, ocr11, oct, oct1, oct1, oct2, oct2, oct3, oct7, octn2, octs3, odc1, oddd, odf1, odg1, odod, ofc1, ofc2, ofc3, ofd1, ofe og22, ogdh, ogg1, ogr1, ogs1, ogs2, ohds, ohs, oias, oip1, ok, olf1, olfmf, olfr1, olfr2, omg, omgp, omp, on, op2, opa1, opa2, opa3, opca3, opcm1, opd1, opg1, ophn1, op 11, opn, oppg, oprd1, oprk1, oprm1, oprt, opta2, optb1, oqt1, orld2, orlf1, orc11, orc21, orc41, orc51, orfx, orm1, orm2, orw, osbp, osm, osp, ost, ost48, osx, otc, otf1, otf2, otf3, otm, otof, ots, otx1, otx2, ovc, ovcs, ovo11, ox40, oxa11, oxct, oxt, oxtr, ozf, p, p, p1, p15, p16, p167, p28, p2rx3, p2rx4, p2ry1, p2ry2, p2ry4, p2ry7, p2u, p2x3, p2x4, p2y1, p2y2, p2y2, p2y4, p3p40phox, p450c11, p450c17, p450c2a, p450c2d, p450c2e, p450scc, p4ha, p4ha1, p4ha1, p4hb, p5cdh, p79r, pa2g4, pab1, pab2, pabp2, pabpl 1, pact, pact, pacapr, pace, pace4, paep, paf1, paf2, pafah, pafah1b1, pafah1b2, pafah1b3, paga, pah, pahx, pai1, pai2, paics, pak1, pak3, palb, pals, pam, pang, pap, papa, papa2, pappa, par1, par1, par2, par3, par4, par4, par5, park1, park2, park3, pawr, pax1, pax2, pax3, pax4, pax5, pax6, pax7, pax8, pax9, pbca, pbcra, pbfe, pbg pbt, pbx1, pbx2, pbx3, pc, pc1, pc2, pc3, pc3, pca1, pcad, pcap, pcar1, pcbc, pcbd, pcbp1, pcbp2, pcca, pccb, pcdh7, pcdx, pchc, pchc1, pci, pck1, pc1, pclp, pcm1, pcm1, pcmt1, pcna, pent, pcolce, pcp, pcp4, pcs, pcsk1, pcsk2, pcsk3, pcsk4, pcsk5, pcsk6, pctk1, pctk3, pcyt1, pdb, pdb2, pdc, pdc, pdcd1, pdcd2, pddr, pde1a, pde1b, pde1b1, pde3b, pde4a, pde4b, pde4c, pde4d, pde5a, pde6a, pde6b, pde6c, pde6d, pde6g, pde6h, pde7a, pdea, pdea2, pdeb pdeb, pdeg, pdeslb, pdgb, pdgfa, pdgfb, pdgfr, pdgfra, pdgfrb, pdha1, pdha2, pdhb, pdj, pdk4, pdnp1, pdnp2, pdnp3, pdr, pds, pds1, pdx1, pdyn, pe1, pea15, pebp2a1, pebp2a3, pecam1, ped, ped, pedf, pee, peg1, peg3, pemp, penk, pent, peo, peo1, peo2, pepa, pepb, pepc, pepd, pepe, pepn, peps, per, per2, peta3, pets1, pex1, pex5, pex6, pex7, pf4, pf4v1, pfas, pfbi, pfc, pfd, pfhb1, pfic1, pfic2, pfkfb1, pfkfb2, pfk1, pfk-mn, pfkp, pfkx, pfl, pfm, pfn1, pfn2, pfrx, pga3, pga4, pga5, pgam1, pgam2, pgamm, pgc, pgd, pgf, pgft, pgk1, pgk2, pgka, pgf, pgl1, pgl2, pgm1, pgm2, pgm3, pgm5, pgn, pgp, pgp1, pgr, pgs, pgt, pgy1, pgy3, pha1, pha2, pha2a, pha2b, phap1, phb, phc, phe1a, phe3, phex, phf1, phhi, phhi, phk, phka1, phka2, phkb, phkd, phkg1, phkg2, ph1, phl11, phog, phox1, phox2a, php, php1b, phpx, phyh, pi, pi10, pi3, pi4, pi5, pi6, pi7, pi8, pi9, piga, pigc, pigf, pigh, pigr, pik3c2b, pik3ca, pik3r1, pik4cb, pi1, pim1, pin, pin1, pin11, pip, pip5k1b, pir1, pir51, pit, pit1, pitpn, pitx1, pitx2, pitx3, pjs, pk1, pk120, pk3, pk428, pkca, pkcb, pkcc, pkcg, pkcs1, pkd1, pkd2, pkd4, pkdts, pkhd1, pklr, pkm2, pkp1, pks1, pks1, pks2, pku1, pl, pla2, pla2a, pla2b, pla2g1b, pla2g2a, pla2g4, pla2g4a, pla2g5, pla21, pla21, plag1, plag11, planh1, planh2, planh3, plat, plau, plaur, plb, plc, plc1, plcb3, plcb4, plcd1, plce, plcg1, plcg2, plc1, pld1, plec1, plg, plgf, plg1, pli, pin, plod, plod2, plos1, plp, pls, pls1, plt1, pltn, pltp, plzf, pmca1, pmca2, pmca3, pmca4, pmch, pmch11, pmch12, pmd, pme117, pmi1, pm1, pmm1, pmm2, pmp2, pmp22, pmp35, pmp69, pmp70, pms1, pms2, pms11, pms12, pmx1, pn1, pnd, pnem, pnkd, pnlip, pnmt, pnoc, pod1, podx1, pof, pof1, pol2rb, pola, polb, pold1, pold2, pole, polg, polr2a, polr2c, polr2e, polr2g, polr21, polrmt, polz, pomc, pon, pon1, pon2, pon3, por, pore, potx, poulf1, pou2f1, pou3f1, pou3f2, pou3f3, pou3f4, pou4f1, pou4f3, pou5f1, pp, pp14, pp2, pp4, pp5, ppac, ppard, pparg, ppargl, pparg2, ppat, ppbp, ppcd, ppd, ppef1, ppef2, ppfia3, ppgb, pph, pphl, ppia, ppid, ppil1, ppkb, ppks1, ppks2, pp1, ppla2, ppmx, ppnd, ppnoc, ppo1, ppox, ppp1a, ppp1ca, ppp1cb, ppp1cc, ppp1r2, ppp1r5, ppp1r7, pppd1r8, ppp2b, ppp2ca, ppp2cb, ppp2r1b, ppp2r4, ppp2r5a, ppp2r5b, ppp2r5c, ppp2r5d, ppp2r5e, ppp3ca, ppp3cb, ppp3 cc, pp 3r1, ppp4c, ppp5c, ppt, ppt2, ppx, ppy, ppyr1, pr, prad1, prb1, prb2, prb3, prb4, prca1, prca2, prcc, prcp, pre1p, prep, prf1, prg, prg1, prg1, prgs, prh1, prh2, prim1, prim2a, prim2b, prip, prk1, prkaa1, prkaa2, prkab1, prkaca, prkacb, prkacg, prkag1, prkag2, prkar1a, prkar1b, prkar2b, prkca, prkcb1, prkcd, prkcg, prkci, prkcl1, prkcnh1, prkcq, prkcsh, prkdc, prkg1, prkg1b, prkg2, prkgr1b, prkgr2, prkm1, prkm3, prkm4, prkm9, prkn, prkr, prkx, prky, pr1, prlr, prm1, prm2, prmt2, prnp, proa, proc, prodh, prohb, prop1, pros1, pros30, prox1, prp8, prph, prps1, prps2, pipsap1, prr1, prr2, prs, prca1, prss1, prssl1, prss2, prss7, prss8, prss11, prtn3, prts, psa, psa, psach, psap, psbg1, psbg2, psc2, psc5, psca, psd, psen1, psen2, psf1, psf2, psg1, psg11, psg12, psg13, psg2, psg3, psg4, psg5, psg6, psg7, psg8, psg11, pskh1, psm, psma1, psma2, psma3, psma5, psmb1, psmb10, psmb2, psmb3, psmb4, psmb5, psmb8, psmb9, psmc1, psmc2, psmc3, psmc5, psmd7, psmd9, psme1, psme2, psors1, psors2, psors3, psp, psps1, psps2, pss1, psst, pst, pst, pst1, psti, ptafr, ptc, ptc, ptc, etch, ptd, pten, ptgds, ptger1, ptger2, ptger3, ptgfr, ptgfrn, ptgir, ptgs1, ptgs2, pth, pthlh, pthr, pthr1, pthr2, ptk1, ptk2, ptk2b, ptk3, ptk7, ptlah, ptma, ptms, ptn, ptos1, ptp18, ptp1b, ptp4a1, ptp4a2, ptpa, ptpa, ptpd, ptpg, ptpg1, ptpgmc1, ptpn1, ptpn10, ptpn11, ptpn12, ptpn13, ptpn14, ptpn2, ptpn5, ptpn6, ptpn7, ptpra, ptprb, ptprc, ptprcap, ptprd, ptpre, ptprf, ptprg, ptprh, ptprj, ptprk, ptprl1, ptpr12, ptprm, ptprn, ptpro, ptprs, ptprz1, ptpt, pts, ptslr, ptx1, ptx3, pujo, pum, pur1, pur1, pura, pvalb, pvr, pvrl1, pvr12, pvrr1, pvrr2, pvs, pvt1, pwcr, pwp2, pwp2h, pws, pxaaa1, pxe, pxe1, pxf, pxmp1, pxmp11, pxmp3, pxr1, pycr1, pycs, pygb, pyg1, pygm, pyk2, pyst1, pyst2, pzp, gars, qdpr, qin, qm, qpc, qprs, rab, rab1, rabl3, rab1a, rab21, rab3a, rab3b, rab4, rab5, rab5a, rab6, rab7, rabgdla, rabgdib, rabggta, rabggtb, rabif, rac2, rac3, rad1, rad17, rad23a, rad23b, rad51a, rad51c, rad51d, rad5311, rad52, rad54, rad6a, rad6b, raf1, rafa1, rag1, rag2, rage, rala, ralb, ralgds, ramp, ranbp211, ranbp3, rao, rap1a, rap1b, rap1ga1, rap1gds1, rap2a, rap74, rapsn, rara, rarb, rarg, rars, rasa1, rasa2, rasgfr3, rask2, rb1, rbbp2, rbbp5, rbbp6, rb11, rb12, rbm1, rbm2, rbm3, rbmy1a1, rbp1, rbp2, rbp3, rbp4, rbp5, rbp56, rbp6, rbq3, rbtn1, rbtn11, rbtn12, rca1, rcac, rcc1, rccp1, rccp2, rcd1, rcd2, rcdp1, rcn1, rcn2, rcp, rcv1, rd, rdbp, rdc7, rdp, rdpa, rdre, rds, rdt, rdx, reca, rcc1, recq1, red1, red2, reg, reg1a, reg1, re1, rela, reln, ren, renbp, rens1, rent1, rep8, req, ret, rev3, rev31, rfc1, rfc2, rfc3, rfc4, rfc5, rfp, rfx1, rfx2, rfx5, rfxank, rfxap, rgc1, rgr, rgs, rgs1, rgsl4, rgsl6, rgs2, rgs2, rgs3, rgs5, rh50a, rhag, rhbd1, rhc, rhce, rhd, rheb2, rho, rho7, rhogap2, rhogap3, rhohl2, rhoh6, rhoh9, rhok, rhom1, rhom2, rhom3, rieg1, rieg2, rige, rigui, ring1, ring10, ring11, ringl2, ring3, ring31, ring4, ring5, ring6, ring7, rip, rip140, riz, rk, r1, rlbp1, rlf, rln1, r1n2, rmch1, rmd1, rmrp, rmrpr, rn5s1, rnase1, rnase2, rnase3, rnase4, rnase5, rnase6, rnasel, rnaseli, rne1, rnf1, rnf3, rnf4, rnf5, rnh, rnpep, rnpulz, rnr1, rnr2, rnr3, rnr4, rnr5, rns1, rns2, rns3, rns4, rns4, rns4i, rntmi, rnu1, rnu15a, rnu17a, rnu17b, rnu1a, rnu2, rnu3, ro52, rom1, romk1, ron, ror1, rora, rorb, rorc, rorg, ros1, rosp1, rox, rp1, rp10, rp105, rp11, rpl2, rp13, rp14, rp15, rp17, rp18, rp19, rp2, rp22, rp24, rp25, rp3, rp4, rp6, rp7, rp9, rpa1, rpa2, rpa3, rpd311, rpe, rpe65, rpe119rp122, rp123a, rp1231, rp129, rp130, rp135a, rp136a, rpl7a, rpms12, rpn1, rpn2, rpol2, rps11, rps14, rps17, rps17a, rps17b, rpsl711, rpsl712, rpsl8, rps20a, rps20b, rps24, rps25, rps3, rps4x, rps4y, rps6, rps6ka1, rps6ka2, rps6ka3, rps8, rpsml2, rptpm, rpu1, rpx, rrad, rras, rrbp1, rreb1, rrm1, rrm2, rrp, rrp22, rs1, rs1, rscla1, rsk1, rsk2, rsk3, rsn, rss, rsts, rsu1, rt6, rtef1, rtkn, rtn1, rtn2, rts, rts, rtt, rws, rxra, rxrb, rxrg, ryr1, ryr2, ryr3, rzrb, rzrg, s100a1, s100a10, s100a11, s100a12, s100a13, s100a2, s100a3, s100a4, s100a5, s100a6, s100a7, s100a8, s100a9, s100b, s100d, s100e, s100, s100p, s152, s4, s7, saa1, saa2, saa4, sacs, safb, sag, sah, sahh, sai1, sakap84, sal11, sal12, sams1, sams2, sap, sap1, sap1, sap2, sap62, sar, sar1, sar2, sard, sas, sat, satb1, satt, sbma, sc, sc1, sc5d1, sca1, sca10, sca2, sca2, sca3, sca4, sca5, scab, sca7, sca8, sca8, scar, scca1, scca2, sccd, scd, sceh, scg1, scg2, scg3, schad, scida, scidx, scidx1, sc1, scic1, scl1, scn, scn1a, scn1b, scn2a, scn2a1, scn2a2, scn2b, scn3a, scn4a, scn5a, scn6a, scn8a, scnn1a, scnn1b, scnn1d, scnn1g, scot, scp, scp1, scp2, scpn, scra1, scra1, scs, sctr, scya1, scya11, scya13, scya14, scya15, scya16, scya19, scya2, scya21, scya22, scya24, scya25, scya3, scya311, scya4, scya5, scya7, scya8, scyb5, scyb6, scyd1, sczd1, sczd2, sczd3, sczd4, sczd5, sczd6, sczd7, sczd8, sdc1, sdc2, sdc4, sdf1, sdf2, sdh1, sdh2, sdha, sdhb, sdhc, sdhd, sdhf, sds22, sdty3, sdys, se, sea, secl311, secl3r, sec14l, sec7, sed1, sedt, sef2, sel11, sele, sel1, selp, selp1g, sema3f, sema4, sema5, semg, semg1, semg2, sen1, sep, sepp1, serca1, serca3, serk1, ses1, set, sex, sf, sf1, sfa1, sfd, sfmd, sfrs1, sfrs2, sfrs7, sftb3, sftp1, sftp2, sftp4, sftpa1, sftpa2, sftpb, sftpc, sftpd, sgb, sgca, sgcb, sgcd, sgcg, sgd, sgk, sglt1, sglt2, sgm1, sgne1, sgp2, sgpa, sgsh, sh2d1a, sh3bp2, sh3d1a, sh3gbr, sh3p17, shb, shbg, shc1, shcl1, shfd1, shfd2, shfm1, shfm2, shfm3, shh, ship, shmt1, shmt2, shoc2, shot, shox, shox2, shps1, shs, shsf1, si, siah1, siah2, siasd, siat1, siat4, siat4c, siat8, sids, si1, silv, sim1, sim2, sipa1, sis, siv, six1, six5, sja, sjs, ski, ski2, ski2w, skiv21, skp1a, skp1b, skp2, sla, slap, slbp, slc, slc10a1, slc10a2, slc12a1, slc12a2, slc12a3, slc14a1, slc14a2, slc15a1, slc16a1, slc16a2, slc17a1, slc17a2, slc18a1, slc18a2, slc18a3, slc19a1, slc1a1, slc1a2, slc1a3, slc1a4, slc1a5, slc20a1, slc20a2, slc20a3, slc21a2, slc21a3, slc22a1, s1c22a2, s1c22a5, slc2a1, slc2a2, slc2a3, slc2a4, slc2a5, slc2c, slc3a1, slc4a1, slc4a2, slc4a6, slc5a1, slc5a2, slc5a3, slc5a5, slc6a1, slc6a10, slc6a12, slc6a2, slc6a3, slc6a4, slc6a6, slc6a8, slc6a9, slc7a1, slc1a2, slc1a4, slc7a5, slc7a7, slc8a1, slc8a2, slc9a1, slc9a2, slc9a3, slc9a4, slc9a5, sld, sle1, sleb1, slim1, sln, slo, slos, s1p76, sls, slug, sm1, sm22, sma4, smad1, smad1, smad2, smad3, smad4, smad5, smad6, smad7, smad9, sma1, smam1, smarca1, smarca2, smarca3, smarca5, smarcb1, smax2, smc1, smcc, smcr, smcx, smcy, sml1, smn, smn1, smn2, smnr, smo, smoh, smpd1, sms, smt3, smt3h1, smtn, smubp2, sn, snap25, snat, snca, sncb, sncg, snf2h, snf211, snf212, snf213, snf5, sn1, snn, snrp70, snrpa, snipe, snrpn, snt1, snt2b1, snt2b2, sntb1, snt1, snx, soat, sod1, sod2, sod3, solh, son, sord, sorl1, sos1, sos2, sox1, sox10, sox11, sox2, sox20, sox22, sox3, sox4, sox9, sp1, sp1, sp3, sp3, sp4, spa1, spag1, spag4, spam1, sparc, spat, spbp, spch1, spd, spf30, spg3a, spg4, spg5a, spg6, spg7, spg8, spg9, spgp, spgy1a, sph2, spi1, spink1, spk, spmd, spn, spp1, spp2, sppm, spr, sprk, sprr1a, sprr1b, sprr2a, sprr2b, sprr2c, sprr3, sps1, spsma, spta1, sptan1, sptb, sptbn1, sra1, sra2, src, src1, src1, src2, srd5a1, srd5a2, srebf1, srebf2, sri, srk, srm, srn1, srp14, srp19, srp46, srpr, srpx, srs, srvx, sry, ss, ss, ssa, ssa1, ssa2, ssadh, ssav1, ssbp, ssdd, ssr2, ssrc, sst, sstr1, sstr2, sstr3, sstr4, sstr5, ssx1, ssxt, st2, st3, st4, st5, st6, st8, sta, stac, stam, star, stat, stat1, stat3, stat4, stat5, ssx1, stc1, stch, std, std, step, step, stf1, stfa, stfb, stgd1, stgd2, stgd3, stgd4, sthe, stk1, stk11, stk15, stk2, stk6, st1, stm, stm2, stm7, stmy1, stmy2, stmy3, stp, stp1, stp2, sts, sts1, stx, stxlb, stx7, stxbp1, stxbp2, sultlc1, supt6h, sur, sur1, surf1, surf2, surf3, surf4, surf5, surf6, svct2, svmt, sw, sxi2, syb1, syb2, syb11, sycp1, syk, sym1, syn1, syn2, syn3, syngap, syns1, syp, syt, syt1, syt2, syt3, syt4, syt5, t, t3d, taa16, tac1r, tac2, tac2r, tac3, tacr1, tacr2, taf2, taf2a, taf2a, taf2d, taf2h, taf2n, tafii100, tagln, tak1, tal1, tal2, taldo1, tam, tan1, tap1, tap2, tapa1, tapbp, tapvr1, tars, tas, task, tat, taut, tax, tax1, m/z, tbg, tbp, tbp1, tbs, tbx1, tbx2, tbx3, tbx5, tbxa2r, tbxas1, tc1, tc2, tcbp, tcd, tcea1, tceb11, tceb3, tcf1, tcf12, tcf13, tcf1311, tcf14, tcf15, tcf17, tcf19, tcf2, tcf20, tcf21, tcf3, tcf4, tcf5, tcf611, tcf612, tcf7, tcf8, tcf9, tcfeb, tcf11, tcf14, tc11, tc11a, tc12, tc13, tc14, tc15, tcn1, tcn2, tco, tcof1, tcp1, tcp10, tcp11, tcp228, tcpt, tcra, tcrb, tcrd, tcrg, tcrz, tcs1, tcta, tcte1, tcte3, tcte11, tdf, tdfa, tdfx, tdg, tdgf1, tdn, tdo, tdo2, tdt, tead4, tec, tec, teck, tecta, tef, tegt, tek, te1, tem, tep1, terc, tert1, tert, tes1, tesk1, tex28, tf, tf2s, tf6, tfa, tfam, tfap2a, tfap2b, tfap2c, tfap4, tfcoup1, tfcoup2, tfcp2, tfdp1, tfdp2, tfe3, tff1, tff2, tff3, tfliia, tlh, tfpi, tfpi2, tfr, tfrc, tfs1, tft, tg, tg737, tgb1, tgb2, tgd, tgfa, tgfb1, tgfb2, tgfb3, tgfb4, tgfbi, tgfbr1, tgfbr2, tgfbr3, tgfbre, tgfr, tgm1, tgm2, tgm3, tgm4, tgn38, tgn46, th, thas, thbd, thbp1, thbs1, thbs2, thbs3, thc, thh, th1, thop1, thpo, thr1, thra, thra1, thra1, thrb, thrm, thrsp, thy1, tial1, tiam1, tiar, tic, tie, tie1, tie2, tigr, ti1, ti13, ti14, tiro, timp, timp1, timp2, timp3, tinur, titf1, titf2, tjp1, tk1, tk2, tkc, tkcr, tkr, tkt, tkt2, tktl 1, tla519, ticn, tle1, tle2, tle3, tlh1, tln, tlr1, tlr2, tlr3, tlr4, tlr5, tm4sf1, tm4sf2, tm7sf2, tmc, trod, tmdci, tmem1, tmf1, tmip, tmod, tmp, tmpo, tmprss2, tms, tmsa, tmsb, tmvcf, tna, tndm, tnf, tnfa, tnfaip1, tnfaip2, tnfaip4, tnfaip6, tnfar, tnfb, tnfbr, tnfc, tnfcr, tnfr1, tnfr2, tnfrsf10b, tnfrsf12, tnfrsf14, tnfrsf16, tnfrsf17, tnfrsf1a, tnfrsf1b, tnfrsf4, tnfrsf5, tnfrsf6, tnfrsf6b, tnfrsf7, tnfrsf8, tnfrsf9, tnfsf11, tnfsf12, tnfsf5, tnfsf6, tnfsf7, tnnc1, tnnc2, tnni1, tnni2, tnni3, tnnt1, tnnt2, tnnt3, tnp1, tnp2, tnr, tns, tnx, tnxa, toc, top1, top2, top2a, top2b, top3, tp1, tp120, tp250, tp53, tp53bp2, tp63, tp73, tpa, tpbg, tpc, tpc, tph, tph2, tpi1, tp12, tpm1, tpm2, tpm3, tpm4, tpmt, tpo, tpo, tpp2, tpr, tpr1, tprd, tps1, tps2, tpsn, tpst1, tpst2, tpt, tpt1, tptps, tpx, tpx1, tr, tr2, tr4, tra1, traf1, traf5, trailr2, tran, trance, trap170, trc3, trc8, tre, treb36, trek, trf1, trg1, trh, trhr, tric5, trio, trip 1, trip 14, trip6, trk, trk1, trka, trkb, trkc, trke, trl1, trl2, trm1, trm1, trm2, trma, trmi1, trmi2, trn, trn1, tro, trp1, trp1, trp2, trp3, trpc1, trpm2, trpo, trps1, trps2, trq1, trr, trr3, trrap, trsp, trt1, trt2, trv1, trv2, trv3, trv4, trv5, try1, try2, ts, ts13, ts546, tsbn51, tsc tsc1, tsc2, tsd, tse1, tsg101, tsg7, tshb, tshr, tsix, tsp3, tspy, tssc3, tst1, tst1, tsta3, tsy, ttc1, ttc3, ttf, ttf1, ttf2, ttg2, ttim1, ttn, ttp, ttp1, ttpa, ttr, tuba3, tubal1, tubb, tufm, tuft1, tulp1, tuple1, tw, tweak, twik1, twist, txgpl1, txk, txn, txnr, txnrd1, tyh, tyk1, tyk2, tyk3, tyros, tyr, tyr1, tyro3, tyrp1, tyrp2, tys, u17hg, ulrnp, u22hg, u2afl, u2aflrs1, u2aflrs2, u2aflrs3, uba52, ubb, ubc, ubc4, ubc7, ubc8, ubch2, ubc1, ube1, ube2, ube2a, ube2b, ube2e2, ube2g, ube2g2, ube2h, ube21, ube211, ube2v1, ube3a, ubh1, ubid4, ub11, uch11, ucn, ucp1, ucp2, ucp3, udpgdh, uev1, ufd11, ufs, ugalt, ugb, ugcg, ugdh, ugn, ugp1, ugp2, ugpp2, ugt1, ugt1a1, ugt2b11, ugt2b15, ugt2b17, ugt2b4, ugt2b7, ugt2b8, ugt2b9, ugt1, uhg, uhx1, ukhc, umod, umph2, umpk, umps, unc18, unc18b, und, ung, unr, unr, uox, up, upk1b, ups, uqbp, uqcrb, uqcrc1, uqcrc2, uqcrfs1, uqor1, uqor13, uqor22, urk, urkr, uroc, urod, uros, usf1, usf2, ush1, ush1a, ush1b, ush1c, ush1d, ush1e, ush1f, ush2a, ush3, usp11, usp5, usp7, usp9x, usp9y, ut1, ut2, ute, utr, utrn, utx, uty, uv20, uv24, uvo, vacht, vacm1, vamp1, vamp2, vars1, vasp, vat1, vat2, vav, vav1, vav2, vbch, vbp1, vcam1, vcf, vc1, vcp, vdac1, vdac2, vdd1, vdi, vdr, vegf, vegfb, vegfd, vegfr3, vgf, vg1, vgr1, vh1, vhr, vil1, vil2, vim, vip, vipr1, vipr2, vis1, vla1, vla5a, vlacs, vlcad, vldlr, vmat1, vmcm, vmd1, vmd2, vnra, vnt, vp, vpp1, vpp3, vpreb1, vpreb2, vrf, vrk1, vrk2, vrnf, vrni, vsn11, vtn, vwf, vws, waf1, wars, was, wbs, wd1, wdr2, wee1, wfrs, wfs, wfs1, wgn1, whcr, wi, wisp1, wisp2, wisp3, wnd, wnt1, wnt10b, wnt13, wnt14, wnt15, wnt2, wnt3, wnt5a, wnt7a, wnt7b, wnt8b, wrb, wrn, ws1, ws2a, ws2b, ws4, wsn, wss, wss, wt1, wt2, wt3, wt4, wt5, wts, wts1, wws, x11, xbp1, xbp2, xce, xdh, xe169, xe7, xe7y, xg, xgr, xh2, xiap, xic, xist, xk, xla, xla2, xlp, xlpd, xlrs1, xm, xpa, xpb, xpc, xpcc, xpct, xpf, xpf, xpg, xpmc2h, xpnpep2, xpo1, xrcc1, xrcc2, xrcc3, xrcc4, xrcc5, xrcc9, xrs, xs, xwnt2, yb1, yes1, yk140, y11, yrrm1, yt, ywha1, ywhab, ywhah, ywhaz, yy1, zac, zag, zan, zap70, zf87, zfm1, zfp3, zfp36, zfp37, zfx, zfy, zic1, zic2, zic3, zipk, znf1, znf10, znf117, znf11a, znf11b, znf12, znf121, znf123, znf124, znf125, znf126, znf13, znf14, znf141, znf144, znf146, znf147, znf157, znf16, znf160, znf162, znf163, znf165, znf169, znf173, znf179, znf189, znf19, znf192, znf193, znf195, znf198, znf2, znf20, znf200, znf204, znf217, znf22, znf23, znf24, znf25, znf26, znf27, znf29, znf3, znf32, znf34, znf35, znf36, znf38, znf4, znf40, znf41, znf42, znf44, znf45, znf46, znf5, znf6, znf69, znf7, znf70, znf71, znf72, znf73, znf74, znf75, znf75a, znf75c, znf76, znf77, znf79, znf8, zn80, znf81, znf83, znf9, znfc150, znfc25, znfxy, znt3, znt4, zp3a, zp3b, zpk, zws1, and zyx.

Furthermore, genes from bacteria, plants, yeast, and mammals (e.g., mice) can be used with the microorganisms provided herein. Non-limiting examples of *E. coli* genes include: aarF, aas, aat, abpS, abs, accA, accB, accC, accD, acd, aceA, aceB, aceE, aceF, aceK, ackA, ackB, acnA, acnB, acpD, acpP, acpS, acpX, acrA, acrB, acrC, acrD, acrE, acrF, acrR, acs, ada, add, adhB, adhC, adhE, adhR, adiA, adiY, adk, aegA, aer, aes, agaA, agaB, agaC, agaD, agaI, agaR, agaS, agaV, agaW, agaZ, agp, ahpC, ahpF, aidB, ais, alaS, alaT, alaU, alaV, alaW, alaX, aldA, aldB, aldH, alkA, alkB, alpA, alr, alsA, alsB, alsC, alsE, alsK, alx, amiA, amiB, amn, ampC, ampD, ampE, ampG, ampH, amtB, amyA, ansA, ansB, apaG, apaH, aphA, appA, appB, appC, appY, apt, aqpZ, araA, araB, araC, araD, araE, araF, araG, araH, araJ, arcA, arcB, argA, argB, argC, argD, argE, argF, argG, argH, argI, argM, argP, argQ, argR, argS, argT, argU, argV, argW, argX, argY, argZ, aroA, aroB, aroC, aroD, aroE, aroF, aroG, aroH, aroI, aroK, aroL, aroM, aroP, aroT, arsB, arsC, arsR, artI, artJ, artM, artP, artQ, ascB, ascF, ascG, asd, aslA, aslB, asmA, asnA, asnB, asnC, asnS, asnT, asnU, asnV, asnW, aspA, aspC, aspS, aspT, aspU, aspV, asr, asu, atoA, atoB, atoC, atoD, atoS, atpA, atpB, atpC, atpD, atpE, atpF, atpG, atpH, atpI, avtA, azaA, azaB, azl, bacA, baeR, baeS, barA, basR, basS, bax, bcp, bcr, betA, betB, betI, betT, bfd, bfm, bfr, bglA, bglB, bglF, bglG, bglJ, bglT, bglX, bioA, bioB, bioC, bioD, bioF, bioH, bioP, bipA, birA, bisC, bisZ, blc, bolA, bRNQ, brnR, brnS brnT, btuB, btuc, btuD, btuE, btuR, bymA, cadA, cadB, cadC, cafA, caiA, caiB, caiC, caiD, caiE, caiF, caiT, calA, caiC, calD, can, carA, carB, cbl, cbpA, cbt, cca, ccmA, ccmB, ccmC, ccmD, ccmE, ccmF, ccmG, ccmH, cdd, cde, cdh, cdsA, cdsS, cedA, celA, celB, celC, celD, celF, cfa, cfcA, chaA, chaB, chaC, cheA, cheB, cheR, cheW, cheY, cheZ, chpA, chpB, chpR, chpS, cirA, citA, citB, cld, cipA, clpB, clpP, clpX, cls, cmk, cmlA, cmr, cmtA, cmtB, coaA, cobS, cobT, cobU, codA, codB, cof, cog?, corA, cpdA, cpdB, cpsA, cpsB, cpsC, cpsD, cpsE, cpsF, cpsG, cpxA, cpxB, cpxP, cpxR, crcA, crcB, creA, creB, creC, creD, crg, crl, crp, crr, csdA, csgA, csgB, csgD, csgE, csgF, csgG, csiA, csiB, csiC, csiD, csiE, csiF, cspA, cspB, cspC, cspD, cspE, cspG, csrA, csrB, cstA, cstC, cup, cutA, cutC, cutE, cutF, cvaA(ColV), cvaB(ColV), cvaC(ColV), cvi(ColV), cvpA, cxm, cyaA, cybB, cybC, cycA, cydA, cydB, cydC, cydD, cynR, cynS, cynT, cynX, cyoA, cyoB, cyoC, cyoD, cyoE, cysA, cysB, cysC, cysD, cysE, cysG, cysH, cysI, cysJ, cysK, cysM, cysN, cysP, cysQ, cysS, cysT, cysU, cysW, cysX?, cysZ?, cytR, dacA, dacB, dacC, dacD, dadA, dadB, dadQ, dadX, dam, dapA, dapB, dapD, dapE, dapF, dbpA, dcd, dcm, dcp, dcrB, dctA, dctB, dcuA, dcuB, dcuC, ddIA, ddlB, ddpA, ddpB, ddpC, ddpD, ddpF, ddpX, deaD, dedA, dedD, def, degP, degQ, degS, del, deoA, deoB, deoC, deoD, deoR, dfp, dgd, dgkA, dgkR, dgoA, dgoD, dgoK, dgoR, dgoT, dgsA, dgt, dicA, dicB, dicC, dicF, dinB, dinD, dinF, dinG, dinI, dinY, dipZ, djlA, dksA, dld, dmsA, dmsB, dmsC, dnaA, dnaB, dnaC, dnaE, dnaG, duaI, dnaJ, dnaK, dnaL, dnaN, dnaQ, dnaT, dnaX, dppA, dppB, dppC, dppD, dppF, dppG, dps, dsbA, dsbB, dsbC, dsbG, dsdA, dsdC, dsdX, dsrA, dsrB, dut, dvl, dxs, ebgA, ebgB, ebgC, ebgR, ecfa, eco, ecpD, eda, edd, efp, enirA, emrB, emrD, emrE, endA, eno, entA, entB, entC, entD, entE, entF, envN envP, envQ, envR, envT, envY, envZ, epd, EppA, minigene, EppB, minigene, EppC, minigene, EppD, minigene, EppE, minigene, EppG, minigene, EppH, minigene, era, esp, evgA, evgS, exbB, exbC, exbD, expA, exuR, exuT, fabA, fabB, fabD, fabF, fabG, fabH, fabI, fabZ, fadA, fadB, fadD, fadE, fadH, fadL, fadR, farR, fatA, fbaA, fbaB, fbp, fcl, fcsA, fdhD, fdhE, fdhF, fdnG, fdnH, fdnI, fdoG, fdoH, fdoI, fdrA, fdx, feaB, feaR, fecA, fecB, fecC, fecD, fecE, fecI, fecR, feoA, feoB, fepA, fepB, fepC, fepD, fepE, fepG, fes, fexB, ffh, ffs, fhlA, fhlB, fhuA, fhuB, fhuD, fhuE, fhuF, fic, fimA, fimB, fimC, fimD, fimE, fimF, fimG, fimH, fimI, fipB, fipC, fis, fiu, fixA, fixB, fixC, fixX, fklB, fkpA, fldA, flgA, flgB, flgC, flgD, flgE, flgF, flgG, flgH, flgI, flgJ, flgK, flgL, flgM, flgN, flhA, flhB, flhc, flhD, fliA, fliC, fliD, fliE, fliF, fliG, fliH, fliI, fliJ, fliK, fliL, fliM, fliN, fliO, flip, fliQ, fliR, fliS, fliT, fliY, fliZ, flk, flu, fmt, thr, focA, focB, folA, folC, folD, folE, folK, folP, folX, fpr, frdA, frdB, frdC, frdD, frr, fruA, fruB, fruK, fruR, fsr, ftn, ftsA, ftsE, ftsI, ftsJ, ftsK, ftsL, ftsN, ftsQ, ftsW, ftsX, ftsY, ftsZ, fucA, fucI, fucK, fucO, fucP, fucR, fumA, fumB, fumC, fur, fusA, fusB, gabC gabD, gabP, gabT, gadA, gadB, gadR, galE, galF, galK, galM, galP, gaiR, galS, galT, galU, gapA, gapC, garA, garB, gatA, gatB, gatC, gatD, gatR, gatY, gatZ, gcd, gcl, gcpE, gcvA, gcvH, gcvP, gcvR, gcvT, gdhA, gef, ggt, gidA, gidB, gip, gleB, gleC, gleD, glcE, gleG, gldA, glf, glgA, glgB, glgC, glgP, glgS, glgX, glk, glmM, glmS, glmU, glmX, glnA, glnB, glnD, glnE, glnG, glnH, glnK, glhL, glnP, glnQ, glnR, glnS, glnT, glnU, ginV, glnW, glnX, gloA, glpA, glpB, glpC, glpD, gipE, gipF, gipG, glpK, glpQ, gipR, glpT, glpX, gltA, gltB, gltD, gltE, gltF, gltH, gltJ, gltK, gltL, gltM, gltP, gltR, gltS, gltT, gltU, gltv, gltW, gltX, glyA, glyQ, glyS, glyT, glyU, glyv, glyW, glyX, glyY, gmd, gmk, gmm, gnd, gntK, gntP, gntR, gntS, gntT, gntU, gntV, goaG, gor, gph, gpmA, gpp, gprA, gprB, gpsA, gpt, greA, greB, groL, groS, grpE, grxA, grxB, grxC, gshA, gshB, gsk, gsp, gsp*, gst, guaA, guaB, guaC, gurB, gurC, gutM, gutQ, gyrA, gyrB, hcaB, hcaC, hcaD, hcaE, hcaF, hcaR, hcaT, hdeA, hdeB, hdeD, hdhA, helD, hemA, hemB, hemC, hemD, hemE, hemF, hemG, hemH, hemK, hemL, hemM, hemX, hemY, hepA, het, hflB, hflC, hflK, hflX, hfq, hha, hipA, hipB, hisA, hisB, hisC, hisD, hisF, hisG, hisH, hisI, hisJ, hisM, hisP, hisQ, hisR, hisS, hipA, hiyE, hmp, hns, holA, holB, holC, holD, holE, hopB, hopC, hopD, hpt, hrpA, hrpB, hrsA, hscA, hscB, hsdM, hsdR, hsdS, hslC, hslD, hslE-H, hslJ, hslK, hslL-N, hslO-R, hslU, hslV, hslW, htgA, htpG, htpX, htrB, htrC, htrE, htrL, hupA, hupB, hyaA, hyaB, hyaC, hyaD, hyaE, hyaF, hybA, hybB, hybC, hybD, hybE, hybF, hybG, hycA, hycB, hycC, hycD, hycE, hycF, hycG, hycH, hycI, hydA, hydG, hydH, hydN, hyfA, hyfB, hyfC, hyfD, hyfE, hyfF, hyfG, hyfH, hyfI, hyfJ, hyfR, hypA, hypB, hypC, hypD, hypE, hypF, iadA, iap, ibpA, ibpB, icd, iclR, ihfA, ihfB, ileR, ileS, ileT, ileU, ileV, ileX, ileY, ilvA, ilvB, ilvC, ilvD, ilvE, ilvF, ilvG, ilvH, ilvI, ilvJ ilvM, iivN, ilvR, ilvU, ilvY, imp, inaA, inaR, infA, infB, infC, inm, insA(IS1), intA, isb(IS1), isfA, ispA, ispB, KanR, katE, katG, kba, kbl, kch, kdgK, kdgR, kdgT, kdpA, kdpB, kdpC, kdpD, kdpE, kdpF, kdsA, kdsB, kdtA, kdtB, kefB, kefC, kgtp, ksgA, ksgB, ksgC, ksgD, lacA, lacI, lacY, lacZ, lamB, lar, ldcC, ldhA, lepA, lepB, leuA, leuB, leuC, leuD, leuJ, leuO, leuP, leuQ, leuR, leuS, leuT, leuU, leuV, leuW, leuX, leuY, leuZ, lev, lexA, lgt, lhr, ligA, ligT, linB, lipA, lipB, lit, livF, livG, livH, livJ, livK, livM, lldD, IldP, lldR, lolA, lon, lpcA, lpcB, lpd, lplA, lpp, lpxA, lpxB, lpxC, lpxD, lpxK, lrb, lrhA, hp, Irs lspA, lysA, lysC, lysP, lysQ, lysR, lysS, lysT, lysU, lysV, lysW, lysX, lysY, lysZ, lytA, lytB, lyx, maa, mac, mae, mafA, mafB, malE, malF, malG, malI, malK, malM, malP, malQ, malS, malT, malX, malY, malZ, manA, manC, manX, manY, manZ, map, marA, marB, marR, mbrB, mcrA, mcrB, mcrC, mcrD, mdaB, mdh, mdoB, mdoG, mdoH, meb, melA, melB, melR, menA, menB, menC, menD, menE, menF, mepA, mesJ, metA, metB, metC, metD, metE, metF, metG, metH, metJ, metK, metL, metR, metT, metU, metV, metW, metY, metZ, mfd, mglA, mglB, mglC, mglR, mgsA, mgtA, mhpA, mhpB, mhpC, mhpD, mhpE, mhpF, mhpR, miaA, miaD, micF, minC, minD, minE, mioC, mltA, mltB, mltC, mltD, mmrA(rhlB), mng, mntA, moaA, moaB, moaC, moaD, moaE, mobA, mobB, moc, modA, modB, modC, modE, modF, moeA, moeB, mog, molR, motA, motB, mpl, mppA, mprA, mraA, mraY, mrcA, mrcB, mrdA, mrdB, mreB, mreC, mreD, mrp, mrr, msbA, msbB, mscL, msrA, msyB, mtg, mtgA, mtlA, mtlD, mtlR, mtr, mttA, mttB, mttC, mukB, mukE, mukF, mul, murA, murB, murC, murD, murE, murF, murG, murH, murI, mutG(putative), mutH, mutL, mutM, mutS, mutT, mutY, nac, nadA, nadB, nadC, nadE, nagA, nagB, nagC, nagD, nagE, nalB, nalD, nanA, nanE, nanK, nanR, nanT, napA, napB, napC, napD, napF, napG, napH, narG, narH, narI, narJ, narK, narL, narP, narQ, narU, narV, narW, narX, narY, narZ, ndh, ndk, neaB, nei, nemA, nfi, nfnA, nfnB, nfo, nfrA, nfrB, nfrD, nfsA, nhaA, nhaB, nhaR, nikA, nikB, nikC, nikD, nikE, nirB, nirC, nirD, nlpA, nlpB, nlpC, nlpD, nmpC(qsr'), non, npr, nrdA, nrdB, nrdD, nrdE, nrdF, nrdG, nrfA, nrfB, nrfC, nrfD, nrfE, nrfF, nrfG, nth, ntpA, nuoA, nuoB, nuoC, nuoE, nuoF, nuoG, nuoH, nuoI, nuoJ, nuoK, nuoL, nuoM, nuoN, nupC, nupG, nusA, nusB, nusG, nuvA, nuvC, ogrK, ogt, ompA, ompC, ompF, ompG, ompR, ompT, ompX, oppA, oppB, oppC, oppD, oppE, oppF, opr, ops, oraA, ordL, orf-23(purB, reg)orf195 (nikA-reg), orn, osmB, osmC, osmE, osmY, otsA, otsB, oxyR, oxyS, pabA, pabB, pabC, pac, pal, panB, panC, panD, panF, parC, parE, pat, pbpG, pck, pcm, pcnB, pdhR, pdxA, pdxB, pdxH, pdxJ, pdxK, pdxL, pdxY, pepA, pepD, pepE, pepN, pepP, pepQ, pepT, pfkA, pfkB, pflA, pflB, pflC, pflD, pfs, pgi, pgk, pgl, pgm, pgpA, pgpB, pgsA, pheA, pheP, pheS, pheT, pheU, pheV, phnC, phnD, phnE, phnF, phnG, phnH, phnI, phnJ, phnK, phnL, phnM, phnN, phnO, phnP, phoA, phoB, phoE, phoH, phoP, phoQ, phoR, phoU, phrB, phxB, pin, pioO, pit, pldA, pldB, plsB, plsC, plsX, pmbA, pncA, pncB, pnp, pntA, pntB, pnuC, poaR, polA, polB, popD, potA, potB, potC, potD, potE, potF, potG, potH, potI, poxA, poxB, ppa, ppc, pphA, pphB, ppiA, ppiB, ppiC, ppk, pppA, pps, ppx, pqiA, pqiB, pqqL, pqqM, prc, prfA, prfB, prfC, priA, priB, priC, prlC, prlZ, prmA, prmB, proA, proB, proC, proK, proL, proM, prop, proQ, proS, proT, proV, proW, proX, prpA, prpC, prpR, prr, prs, psd, psiF, pspA, pspB, pspC, pspE, pspF, pssA, pssR, pstA, pstB, pstC, pstS, psu, pta, pth, ptrA, ptrB, ptsG, ptsH, ptsI, ptsN, ptsP, purA, purB, purC, purD, purE, purF, purH, purK, purL, purM, purN, purP, purR, purT, purU, pus, putA, putP, pykA, pykF, pyrB, pyrC, pyrD, pyrE, pyrF, pyrG, pyrH, pyrI, qmeC, qmeD, qmeE, qor, queA, racC, racR, radA, radC, ranA, rarD, ras, rbfA, rbn, rbsA, rbsB, rbsC, rbsD, rbsK, rbsR, rcsA, rcsB, rcsC, rcsF, rdgA, rdgB, recA, recB, recC, recD, recE, recF, recG, recJ, recN, recO, recQ, recR, recT, relA, relB, relE, relF, relX, rep, rer, rfaB, rfaC, rfaD, rfaF, rfaG, rfaH, rfaI, rfaJ, rfaK, rfaL, rfaP, rfaQ, rfaS, rfaY, rfaZ, rfbA, rfbB, rfbC, rfbD, rfbX, rfc, rfe, rffA, rffC, rffD, rffE, rffG, rffH, rffM, rffT, rhaA, rhaB, rhaD, rhaR, rhaS, rhaT, rhlB, rhlE, rho, ribA, ribB, ribC, ribD, ribE, ribF, ridA, ridB, rimB, rimC, rimD, rimE, rimG, rimH, rimI, rimJ, rimK, rimL, rimM, rit, rlpA, rlpB, rluA, rluC, rluD, rmf, rna, rnb, rnc, rnd, rne, rnhA, rnhB, rnk, rnpA, rnpB, rnr, rnt, rob, rorB, rpe, rph, rpiA, rpiB, rpiR, rplA, rplB, rplC, rplD, rplE, rplF, rplI, rplJ, rplK, rplL, rplM, rplN, rplO, rplP, rplQ, rplR, rplS, rplT, rplU, rplV, rplW, rplX, rplY, rpmA, rpmB, rpmC, rpmD, rpmE, rpmF, rpmG, rpmH, rpmI, rpmJ, rpoA, rpoB, rpoC, rpoD, rpoE, rpoH, rpoN, rpoS, rpoZ, rpsA, rpsB, rpsC, rpsD, rpsE, rpsF, rpsG, rpsH, rpsI, rpsJ, rpsK, rpsL, rpsM, rpsN, rpsO, rpsP, rpsQ, rpsR, rpsS, rpsT, rpsU, rrfA, rrfB, rrfC, rrfD, rrfE, rrfF, rrfG, rrfH, rrlA, rrlB, rrlC, rrlD, rrlE, rrlG, rrlH, rrmA, rrsA, rrsB, rrsC, rrsD, rrsE, rrsG, rrsH, rsd, rseA, rseB, rseC, rspA, rspB, rssA, rssB, rsuA, rtcA, rtcB, rtcR, rtn, rus(qsr'), ruvA, ruvB, ruvC, sad, sanA, sapA, sapB, sapC, sapD, sapF, sbaA, sbcB, sbcC, sbcD, sbmA, sbmC (gyrl), sbp, sdaA, sdaB, sdaC, sdhA, sdhB, sdhC, sdhD, sdiA, sds, secA, secB, secD, secE, secF, secG, secY, selA, selB, selC, selD, semA, seqA, serA, serB, serC, serR serS, serT, serU, serV, serW, serX, sfa, sfcA, sfiC, sfsA, sfsB, shiA, sipC, sipD, sir, sixA, sloB, slp, slr, slt, slyD, slyX, smp, smtA, sodA, sodB, sodC, sohA, sohB, solA, soxR, soxS, speA, speB, speC, speD, speE, speF, speG, spf, spoT, sppA, spr, srlA, srlB, srlD, srlE, srlR, srmB, srnA, ssaE, ssaG, ssaH, ssb, sseA, sseB, sspA, sspB, ssrA, ssrS, ssyA, ssyD stfZ, stkA, stkB, stkC, stkD, stpA, strC, strM, stsA, sucA, sucB, sucC, sucD, sufI, sugE, suhA, suhB, sulA, supQ, surA, surE, syd, tabC, tag, talA, talB, tanA, tanB, tap, tar, tas, tauA, tauB, tauC, tauD, tbpA, tdcA, tdcB, tdcC, tdcD, tdcE, tdcF, tdcG, tdcR, tdh, tdi tdk, tehA, tehB, tesA, tesB, tgt, thdA, thdC, thdD, thiB?, thiC, thiD, thiE, thiF, thiG, thiH, thiI, thiJ, thiK, thiL, thiM, thrA, thrB, thrC, thrS, thrT, thrU, thrV, thrW, thyA, tig, tktA, tktB, tldD, tlnA, tmk, tnaA, tnaB, tnaC, tnm, tol-orf1, tol-orf2, tolA, tolB, tolC, tolD, tolE, tolI, tolJ, tolM, tolQ, tolR, tonB, topA, topB, torA, torC, torD, torR, torS, torT, tpiA, tpr, tpx, treA, treB, treC, treF, treR, trg, trkA, trkD, trkG, trkH, trmA, trmB, trmC, trmD, trmE, trmF, trmH, trmU, trnA, trpA, trpB, trpC, trpD, trpE, trpR, trpS, trpT, truA, truB, trxA, trxB, trxC, tsaA, tsf, tsmA, tsr, tsx, ttdA, ttdB, ttk, tufA, tuffB, tus, tynA, tyrA, tyrB, tyrP, tyrR, tyrS, tyrT, tyrU, tyrV, ubiA, ubiB, ubiC, ubiD, ubiE, ubiF, ubiG, ubiH, ubiX, ucpA, udk, udp, ugpA, ugpB, ugpC, ugpE, ugpQ, uhpA, uhpB, uhpC, uhpT, uidA, uidB, uidR, umuC, umuD, ung, upp, uppS, ups, uraA, usg-1, usbA, uspA, uup, uvh, uvrA, uvrB, uvrC, uvrD, uvs, uxaA, uxaB, uxaC, uxuA, uxuB, uxuR, valS, valT, valU, valV, valW, valX, valY, valZ, vsr, wrbA, xapA, xapB, xapR, xasA, xerC, xerD, xni, xseA, xseB, xthA, xylA, xylB, xylE, xylF, xylG, xylH, xylR, yccA, yhhP, yihG, yjaB, f147, yjaD, yohF, yqiE, yrfE, zipA, zntA, znuA, znuB, znuC, zur, and zwf.

Non-limiting examples of mouse genes include: Ilr1, Ilr2, Gas10, Tnp1, Inhbb, Inha, Creb1, Mpmv34, Acrd, Acrg, Il110, Otf1, Rab11b-r, Abl1, ald, Amh-rs1, Bc12B, Cchlla3, Ccnb1-rs2, Gpcr16, Htr5b, Idd5, Igfbp2, Igfbp5, Il8rb, Kras2-rs1, Mov7, Mpmv6, Mpmv16, Mpmv22, Mpmv25, Mpmv29, Mpmv42, Mtv7, Mtv27, Mtv39, Oprk1, Otf3-rs1, Otf8, Otf11-rs1, Ptgs2, Ren1, Ren2, Ril3, Sxv, Taz-4-rs1, Tgfb2, Wnt6, Xmmv6, Xmmv9, Xmmv36, Xmmv61, Xmmv74, Xmv21, Xmv32, Xmv41, Il2ra, Ab1, Mpmv3, Rap1a-ps2, anx, Mpmv43, Ryr3, Ras12-4, Adra2b, Avp, Glvr1, Il1a, Il1b, Mpmv28, Oxt, Pcsk2, a, Xmv10, Tcf4, Acra, Acra4, Ak1, Bdnf, bs, Cyct, Cyp24, Dbh, Fshb, Gcg, Gdf5, Gnas, Gpcr8, Grin1, Hcs4, Hior2, Hsp84-2, Idd12, Ilrn, Jund2, Kras3, Mc3r, Mpmv14, Mtv40, Mxi1-rs1, Otf3-rs2, Ptgs1, Ptpra, Rapsn, Src, Svp1, Svp3, Tcf3b, Wt1, Xmmv71, Xmv48, Ccna, Fgf2, Fth-rs1, Csfm, Mov10, Egf, Acrb2, Cap1, Crh, Fim3, Fps11, Glut2, Gpcr2, Gria2, Hsd3b-1, Hsd3b-2, Hsd3b-3, Hsd3b-4, Hsp86-ps2, Idd3, Il2, Il7, Mpvmv9, Mpmv20, Mtv4.8, Ngfb, Npra, Nras, Nras, Ntrk, Otf3-rs3, Otf3-rs4, Rap1a, Tshb, Xmmv22, Xmmv65, Mos, Ras12-7, Lyr, Ifa, Ifb, Jun, azh, db, Ipp, Mp1, Do1, Ak2, Ccnb1-rs4, Cdc211, Cga, Fgr, Foc1, Fps12, Gabrr1, Gabrr2, Gdf6, Glut1, Gnb1, Gpcr14, Grb2-ps, Grik3, Grik5, Hsp86-lps4, Htr1da, Htr1db, Idd9, Ifa1, Ifa2, Ifa3, Ifa4, Ifa5, Ifa6, Ifa7, Ifa8, Ifa9, Ifa10, Lap18, Lmyc1, Mpmv19, Mpmv44, Mtv13, Mtv14, Mtv17, Nppb, Otf6, Otf7, Ri12, Ski, Tnfr2, Wnt4, Xmmv8, Xmmv23, Xmmv62, Xmv1, Xmv2, Xmv8, Xmv9, Xmv14, Xmv44, Xpa, Tec, Fgf5, Nos1, Tcf1, Epo, Gnb2, Flt1, Flt3, Ache, Adra2c, Adrbk2, Afp, Alb1, Ccnb1-rs1, Clock, Cyp3, Cyp3a11, Cyp3a13, Drd1b, Drd5, Fgfr3, Flk1, Gc, Gnrhr, Gpcr1, Hcs5, Hnf1, Htr5a, I15r, I16, Kit, Ltrm3, Mgsa, Mpmv7, Mpmv13, Mpmv23, Mtv32, Mtv41, Pdgfa, Pdgfra, Por, Txk, Xmmv3, Xmmv5, Xmmv52, Xmv17, Xmv28, Xmv34, Xmv38, Xmv45, Zp3, Trh, Raf1, Fth-rs2, Ntf3, Kras2, Pthlh, Mov1, Alox5, Braf2, Cftr, Egr4, Fpsl10, Fgf6, Gdf3, Ghrfr, Glut3, Grin2a, Hior3, Hoxa10, hop, Ica1, I15r, Int41, Itpr1, Krag, Mad, Met, Mi, Mtv8, Mtv23, Mtv29, Mtv33, Mtv34, Nkna, Npy, ob, Otf3-rs5, Tgfa, Tnfr1, Wnt2, Wnt5B, Wnt7A, Xmmv27, Xmv24, Xmv61, Fosb, Ryr1, Ngfa, Ufo, Xrcc1, Abpa, Abpga, Gabra4, Gas2, Acra1, Ccnb1-rs7, Egfbp3, Xmv30, Zp2, Fes, Pcsk3, Calc, Ccnb1-rs10, Pth, Ad, Bc13, Cea, Cea2, Cea3, Cea4, CeaS, Cea6, Cebp, Dm9, Dm15, Drd4, Egfbp1, Egfbp2, Ercc2, Fgf3, Fgfr2, Gabra5, Gabrb3, Gtx, Hcs1, Igflr, Igf2, I14r, Ins2, Int40, Lhb, Mpmv1, Mtv1, Mtv35, Ngfg, Ntf5, Otf2, 2, Pkcc, Ras14, Rras, Ryr, Svp2, Tcf3g, Tgfb1, tub, Xmmv31, Xmmv35, Xmmv73, Xmv33, Xmv53, Taz83, Adrb3, Junb, Jund1, MeI, Gpcr19-rs2, Agt, Cadp, Ccnb1-rs9, E, Fgfr1, Gas6, Gnb-rs1, Hcs2, Insr, Maf, Mov34, Mpmv21, Mpmv41, Mtv21, Mtnr1a, Plat, Ras15-2, Ras16, Sntb2, Xmmv29, Xmv12, Xmv26, Xmv62, Epor, Gpcr13, Otf11, Pthr, Acra3, Acra5, Acrb4, Camk1, Cdc25Mm, Crbp, Crbp2, Csk, Cyp11a, Cyp19, Drd2, Ets1, Fli1, Gnai2, Gnat1, Gpcr6, Gria4, Hgf1, Hior1, Hpx, Hsp86-lps3, Hst2, Idd2, I11bc, Lag-rs1, Lap18-rs1, M11, Mpmv27, Penk, Pgr, Ras12-2, Tp11, Trf, Xmmv2, Xmmv67, Xmv15, Xmv16, Xmv25, Xmv60, Mgf, Amh, Braf, Cdc2a, Dmd1, Estr, Fps13, Fps14, Fps15, Gli, Gpcr17, Grik2, Ifgr, Igf1, Mpmv5, Mpmv12, Mpmv40, Myb, Oprm, Pg, Pmch, Ros1, Xmv31, Xmv51, Xmv54, Camk2b, Egfr, Int6, Lif, Mtv44, Ews, Csfgm, Flt4, I13, I14, I15, Irf1, Gria1, Glut4, Crhr, Csfg, Mov9, Xmv20, Acrb, Mpmv4, Mpmv15, Ngfr, Nos2, Rara, Taz4, Tcf2, Xmv42, Mtv3, Adra1, Crko, df, Erbb2, Gabra1, Gabra6, Gabrg2, Gh, Glra1, Grb2, Hnf1b, Hsp86-ps1, Idd4, Igfbp1, Igfbp3, I113, Int4, Mpmv2, Mpmv8, Mpmv18, Mtv45, nu, Pkca, Rab1, Re1, Shbg, Tcf7, Thra, Tnz1, Trp53, Wnt3, Wnt3A, Xmv4, XmvS, Xmv47, Xmv49, Xmv63, Akt, Amh-rs4, Ccs1, Fps16, Fos, Gdf7, Hcs3, Hsp70-2, Hsp84-3, Hsp86-1, hyt, Ltrm1, Max, Mpmv11, Mpmv24, Mtv9, Mtv30, Pomc1, Tcf3a, Tda2, Tgfb3, Tpo, Tshr, Xmmv21, Xmmv25, Xmmv34, Xmmv50, Gli3, Xmv55, Ryr2, Inhba, Gas1, Pcsk1, Amh-rs2, Ccnb1-rs6, Ccnb1-rs13, Crhpb, Dat1, Drd1a, Fgfr4, Fps17, Fim1, Gpcr15, Gpcr18, Hbvi, Hilda, Htr1a, Idd11, I19, Ltrm4, Mak, mes, P11, P12, Pr1, Ra1, Rasa, Srd5a1, Tpbp, Xmv13, Xmv27, Rarb, Rbp3, Htr2, Rb1, Acra2, Camkg, Cch11a2, Ccnb1-rs5, Ccnb1-rs12, Gnrh, Mtv11, Nras-ps, Otf3-rs6, Plau, Ptprg, Trp53-ps, Wnt5A, Xmv19, Ghr, I17r, Lifr, Mlvi2, Prlr, Myc, Ril1, cog, Amh-rs7, I12rb, Pdgfb, Acr, CP2, Rarg, Sp1-1, Wnt1, Afr1, Atf4, Bzrp, Ccnb1-rs11, Cyp11b, I13rb1, I13rb2, Ins3, Itga, Mlvi1, Mlvi3, Mtv36, Pdgfec, Svp5, Tef, Trhr, Wnt7B, Xmmv55, Xmmv72, Xmv37, Tnp2, Ets2, Casr, Chuck-rs1, din, Drd3, Erg, G22p1, Gap43, Gas4, Grik1, Htr1f, Ifgt, Int53, Ltrm2, Mpmv17, Mtv6, Mtvr1, Pit1, Xmv3, Xmv35, Xmv50, Igf2r, Mas, Tcd3, Glp1r, Idd1, Tla, Aeg1, Ccnb1-rs3, Cdc2b, Csi, Cyp21, Cyp21-ps1, Fps18, Gna-rs1, Gpcr19-rs1, Grr1, Grr2, Hom1, Hsc70t, Hsp70, Hsp70-1, Hsp70-3, Hsp84-1, Hst1, Hst4, Hst5, Hst6, Hye, Int3, Itpr3, Lap18-rs2, Otf3, Ptprs, Rab11b, Ras12-1, Ras12-3, Ras13, Rrs, Rxrb, Tas, Tcd1, Tcd2, Tera1, Tla-rs, Tnfa, Tnfb, Tpx1, Tpx2, Xmmv15, Xmv36, Xmv57, Csfmr, Pdgfrb, Adrb2, Apc, Camk2a, Camk4, Dcc, Fgf1, Gna1, Gpcr7, Gr11, Grp, Hsp74, Mcc, Mtv2, Mtv38, Ptpn2, Tp12, Xmv22, Xmv23, Xmv29, Fth, Csfgmra, Mxi1, Adra2a, Adrb1, Adrbk1, Chuck, Cyp17, Gna14, Gnb-ps1, Hcs6, Htr7, Ide, Ins1, Lpc1, Pomc2, Seao, Tlx1, Xmmv42, Xmv18, Tcfe3, Araf, Avpr2, mdx, Ar, Zfx, Otf9, Ccg1, Ccnb1-rs8, Fps19, Gabra3, Glra2, Glra4, Gria3, Grpr, Hsp74-ps1, Hst3, Htr1c, I12rg, Mov14, Mov15, Mtv28, Otf3-rs8, Sts, Sxa, Sxr, Xta, Tdy, Hya, Zfy1, Zfy2, Mov15, Mov24, Mtv31, Mtv42, Sdma, Spy, Sts, Sxa, Sxr, XmmvY, Xmv7, Xmv11, and Xmv40.

Non-limiting examples of *Phaseolus vulgaris* genes include: Acc, ace, Adk, Am, Amv-1, Amv-2, Ane, aph, Arc, Are, arg, Ar1 (Arc), asp, B, bc-u, bc-1.sup.1, bc-1.sup.2, bc-2.sup.1, bc-2.sup.2, bc-3, Bcm, Beg, Bip, blu, Bpm, Bsm, By-1, By-2, C, C/c, c.sup.cr, C.sup.cir, C.sup.ma (M, R.sup.ma), C.sup.r, C.sup.res, C.sup.rho, C.sup.st, [C.sup.st R Acc] (Aeq), c.sup.u (inh, i.sub.e), [c.sup.u Prp.sup.i] (Prp, c.sup.ui, Nud), [c.sup.uprp.sup.st] (prp.sup.st), [C Prp] (Prp), c.sup.v, [C R] (R), [C r](r), Ca, Cam, Cav, cc, ch1, c1, cm1, Co-1 (A), Co-2 (Are), Co-3 (Mexique 1), Co-3.sup.2, Co-4 (Mexique 2), Co-5 (Mexique 3), Co-6, Co-7, cr-1 cr-2, cry, cs, Ct, ctv-1 ctv-2, cyv (by-3), D (Can, Ins), Da, Db, def, dgs (g1, le), dia, Diap-1, Diap-2, diff, dis, D1-1 D1-2 (DL.sub.1 DL.sub.2), do, ds (te), dt-1.sup.a dt-2.sup.a, dt-1.sup.b dt-2.sup.b, dw-1 dw-2, Ea Eb, ers (restr), ers-2, Est-1, Est-2, exp, F, Fa, fast, Fb Fc, fa fb fc, Fcr, Fcr-2, fd, Fe-1 Fe-2, Fin (in), Fop-1, Fop-2, Fr, Fr-2, G (Flay, Ca, Och), Ga, gas, glb, Gpi-c1, Gr, Hb1 (L.sub.HB-1), Hbnc (SC.sub.HB-1), Hbp (PD.sub.HB-1), hmb, Hss, Hsw, Ht-1 Ht-2 (L-1 L-2), I, Ia Ib, ian-1 ian-2 (ia), lbd, ico, Igr (Ih), ilo, ip, iter, iv, iw, J (Sh), Ke, L, la, Lan, Ld, Lds (Ds), Lec, Li (L), lo, Ir-1 lr-2, mar, Me, MeI (Me), Mel-2 (Me-2), mel-3 (me-3), Mf, mi, mia, Mic (Mip), miv, Mrf, Mrf.sup.2, mrf, ms-1, Mue, mu mutator, Nag, Nd-1 Nd-2 (D-1 D-2), nie, and (sym-1), nnd-2, No, nts (nod), Nudus, ol, P, p.sup.gri (Gri, v.sup.Pal), pa, pc, pg (pa.sub.1), Pha, Pmv, ppd (neu), Pr, prc (pc), Prx, punc, ram, Rbcs (rbcS), rf-1, rf-2, rf-3, rfi (i), Rfs (m), Rk, rk, rk.sup.d (lin), rn-1 rn-2 (r r), rnd, Ro, Sal, sb, sb.sup.ms, sb-2, sb-3, si1, Skdh, s1, Smv, St, Sur, sw-1 sw-2, T, t (z-1), Th-1 Th-2, Tm, To, Tor (T), Tr, tri, try, Ts, tw, uni, Uni-2, uni.sup.nde, uni.sup.nie, Ur-1, Ur-2, Ur-2.sup.2, Ur-3 (Ur-3, Ur-4), Ur-3.sup.2, Ur-4, (Up-2, Ur-C), Ur-5, (B-190), Ur-6 (Ur.sub.a, Ur-G), Ur-7 (R.sub.B11), Ur-8 (Up-1), Ur-9 (Ur.sub.p), us, V (B1), v.sup.lae (Cor), v, var, vi (vir.sub.f), wb, Wmv, X.sup.su, y, and Z.

Non-limiting examples of *Saccharomyces cerevisiae* genes include: PRE3, PUP1, PUP3, PRE2, PRE10, PRE1, PRE8, SCL1, PUP2, PRE5, PRE7, PRE4, RPT2, RPT3, RPN3, RPN11, RPN12, RPT6, RPN1, RPN2, RPT1, RPT5, RPT4, SKI6, RRP4, DIS3, TSC10, RAT1, GND1, EXO70, ERG10, ACC1, RPP0, ACT1, ARP100, ARP3, PAN1, ARP2, ARP4, ARP9, SPE2, CYR1, ALA1, TPS1, TUB1, ABF1, DED81, NIP1, YHC1, SNU71, ATM1, MAK5, ROK1, DED1, SPB4, AUR1, PSE1, ALG1, TUB2, BPL1, MSL5, ERG24, ERG26, ERG25, CMD1, HCA4, SHE9, SHE10, CAK1, PIS1, CHO1, CDS1, ESR1, NUD1, CDC47, CDC13, CDC37, CDC1, CDC4, CDC20, CDC6, CDC46, CDC3, KAR1, BBP1, HRP1, CCT2, CCT3, HSP10, SMC1, SMC2, CHC1, CFT2, CLP1, COP1, SEC26, SEC27, RET2, SEC21, COF1, CCT4, CCT1, CCT6, SEC24, SEC7, PCF11, RNA15, RNA14, FIP1, YSH1, TFB4, TSM1, APC2, APC5, SEC31, TAF47, TAP42, MPP10, CDC53, CKS1, CDC28, KIN28, CNS1, ERG11, DBP10, DBP8, PRO3, DYS1, ALR1, TID3, DNA2, SSL2, RAD3, RFA3, RFA2, RFA1, RFC4, RFC5, RFC3, RFC2, RFC1, TOP2, RAP1, RPC25, PRI2, PRI1, POL1, POL12, HUS2, CDC2, POL2, DPB2, RPB10, RPA135, RPA190, RPA43, RPB8, RP026, RPB5, RPC40, RPC19, SRB7, SRB4, RGR1, RPB11, SRB6, RPB2, RPB7, RPO21, RET1, RPO31, RPC31, RPC34, RPC53, RPC82, RPB12, RPB3, DPM1, DIP2, RNT1, CDC8, CDC14, DUT1, UBA2, UBA1, UBC9, CDC34, ENP1, ERD2, SSS1, SEC61, SEC63, SEC62, GNA1, GPI8, DAM1, DUO1, IRR1, PRP3, TIM9, HSH49, SUP35, EXM2, MEX67, ERG9, ERG20, FAS2, FAS1, NOP1, FAD1, AOS1, FBA1, NCB2, BRN1, TUB4, GDI1, GOG5, SRM1, CDC25, SPT16, YIF2, BET4, CDC43, MRS6, BET2, PRO1, GLN1, GLN4, GRS1, YIP1, FOL2, GPA1, CDC42, SAR1, YPT1, SEC4, GSP1, TEM1, RHO1, CDC24, RNA1, GUK1, VMA16, PMA1, HKR1, SIS1, MGE1, HSP60, HSF1, HAS1, MOT3, HTS1, ESA1, HSL7, HOME, RIB7, SLY1, CSL4, PUR5, CSE1, IPP1, MDM1, USO1, SOF1, MAK11, LAS1, TEL2, DPB11, SGD1, FAL1, MTR3, MTR4, SPP2, SIK1, RRP7, POP4, RRP1, POP3, BFR2, CDC5, NRD1, MET30, MCM6, RRP46, SAS10, SCC2, ECO1, PRP43, BET3, BET5, STN1, NFS1, IDI1, SRP1, KAP95, CBF2, SKP1, CEP3, CTF13, ERG7, KRS1, PSA1, PMI40, ALG2, SSF1, MED7, RSC4, CDC54, MCM2, AFG2, ERG12, MVD1, CDC48, MHP1, ERV1, SSC1, TIM44, TIM17, TIM23, TOM22, TOM40, MAS1, MCD1, MMC1, STU1, JAC1, ABD1, CEG1, PAB1, MTR2, SEC16, ROT1, INO1, MLC1, MYO2, GPI2, SPT14, NAT2, NMT1, TRM1, NCP1, NBP1, ACF2, SPP41, NUT2, LCP5, PRP19, NMD3, RFT1, NNF1, NDC1, CRM1, KAR2, NIP29, NAB2, NIC96, NUP145, NUP49, NUP57, NUP159, NSP1, NUP82, CDC39, NPL4, POP7, NTF2, MAK16, NPL3, NOP2, NOP4, NHP2, NOP10, GAR1, NBP35, WBP1, STT3, SWP1, OST2, OST1, ORC1, ORC6, ORC5, ORC4, ORC3, RRR1, SAT2, PWP2, PEX3, TOR2, PIK1, SEC14, STT4, MSS4, PCM1, GPM1, SEC53, ERG8, YPD1, PAP1, NAB3, RRN7, SEN1, CFT1, PRP11, PRP21, PRP39, PRP24, PRP9, SLU7, PRP28, PRP31, IFH1, PTA1, SUB2, FMI1, MAS2, ESS1, PFY1, POL30, POP1, PDI1, RAM2, CDC7, SMP3, CDC15, YTH1, QR12, YAE1, SFI1, SEC1, BET1, SEC6, SEC13, SEC2, SEC8, CBF5, CDC19, YRB1, RHC18, DBF4, SDS22, MCM3, CEF1, ALG11, GAA1, MOB1, NIP7, TIP20, SEC5, SEC10, GPI10, RRP3, CDC45, DIB1, MIF2, HOP2, PBN1, NOP5, RPP1, POP5, POP8, POP6, ERO1, MPT1, DNA43, ESP1, SMC3, LST8, STS1, RPM2, RNR1, RNR2, RNR4, RPS20, RPL25, RPL3, RPL30, RPL32, RPL37A, RPL43A, RPL5, RPL10, RPS3, CET1, YRA1, SNM1, GLE1, DBP5, DRS1, DBP6, BRR2, RRN3, RRN6, RRN11, MED6, PRP16, RPR2, DIM1, RRP43, RRP42, RRP45, SEC20, BOS1, CDC12, GLC7, PKC1, IPL1, SGV1, NRK1, RAD53, LCB2, LCB1, MPS1, SES1, SPC3, SEC11, RIO1, ARP7, NEO1, YJU2, POB3, ARH1, IQG1, HRT1, HYM1, MAK21, FUN20, FUN9, NBN1, STB5, YIF1, SMX4, YKT6, SFT1, SMD1, PRP6, LSM2, NUF1, SPC97, SPC42, SPC98, CDC31, SPC19, SPC25, SPC34, SPC24, NUF2, PRP40, MCD4, ERG1, SMC4, CSE4, KRR1, SME1, TRA1, RLP7, SCH9, SMD3, SNP2, SSF2, SPC72, CDC27, CDC23, CDC16, APC1, APC11, APC4, ARC19, RPN6, RPN5, RSC6, RSC8, STH1, SFH1, TIM12, TIM22, TIM10, SQT1, SLS1, JSN1, STU2, SCD5, SSU72, ASM4, SED5, UFE1, SYF1, SYF2, CCT5, THF1, TOA2, TOA1, SUA7, TAF90, TAF61, TAF25, TAF60, TAF17, TAF145, TAF19, TAF40, TAF67, TFA2, TFA1, FCP1, TFG1, TFG2, TFB1, CCL1, SSL1, TFB3, TFB2, PZF1, BRF1, TFC5, TFC4, TFC3, TFC7, TFC6, TFC1, SPT15, THI80, THS1, SPT6, SPT5, ROX3, REB1, MCM1, MED4, MOT1, MED8, EFB1, YEF3, SUI1, CDC95, TIF11, SUI3, GCD11, SUI2, GCD6, GCD7, GCD2, GCD1, RPG1, GCD10, PRT1, TIF34, CDC33, TIF5, SUP45, GCD14, TIM54, SEC17, TPT1, TRL1, CCA1, SEN54, SEN2, SEN15, SEN34, WRS1, SLN1, TYS1, SNU56, PRP42, CUS1, PRP4, PRP8, SNU114, USS1, UFD1, SMT3, RSP5, QRI1, ALG7, UGP1, VTI1, VAS1, SEC18, CTR86, and ZPR1.

2. Viruses

The microorganisms provided herein include viruses. Such viruses typically have one or more of the microorganism characteristics provided herein. For example, viruses provided herein can have attenuated pathogenicity, reduced toxicity, preferential accumulation in immunoprivileged cells and tissues, such as tumor, ability to activate an immune response against tumor cells, immunogenic, replication competent, and are able to express exogenous proteins, and combinations thereof. In some embodiments, the viruses have an ability to activate an immune response against tumor cells without aggressively killing the tumor cells.

The viruses provided herein can be cytoplasmic viruses, such as poxviruses, or can be nuclear viruses such as adenoviruses. The viruses provided herein can have as part of their life cycle lysis of the host cell's plasma membrane. Alternatively, the viruses provided herein can have as part of their life cycle exit of the host cell by non-lytic pathways such as budding or exocytosis. The viruses provided herein can cause a host organism to develop an immune response to virus-infected tumor cells as a result of lysis or apoptosis induced as part of the viral life cycle. The viruses provided herein also can be genetically engineered to cause a host organism to develop an immune response to virus-infected tumor cells as a result of lysis or apoptosis, regardless of whether or not lysis or apoptosis is induced as part of the viral life cycle. In some embodiments, the viruses provided herein can cause the host organism to mount an immune response against tumor cells without lysing or causing cell death of the tumor cells.

One skilled in the art can select from any of a variety of viruses, according to a variety of factors, including, but not limited to, the intended use of the virus (e.g., exogenous protein production, antibody production or tumor therapy), the host organism, and the type of tumor.

a. Cytoplasmic Viruses

The viruses provided herein can be cytoplasmic viruses, where the life cycle of the virus does not require entry of viral nucleic acid molecules in to the nucleus of the host cell. A variety of cytoplasmic viruses are known, including, but not limited to, pox viruses, African swine flu family viruses, and various RNA viruses such as picorna viruses, calici viruses, toga viruses, corona viruses and rhabdo viruses. In some embodiments, viral nucleic acid molecules do not enter the host cell nucleus throughout the viral life cycle. In other embodiments, the viral life cycle can be performed without use of host cell nuclear proteins. In other embodiments, the virulence or pathogenicity of the virus can be modulated by modulating the activity of one or more viral proteins involved in viral replication.

i. Poxviruses

In one embodiment, the virus provided herein is selected from the pox virus family. Pox viruses include Chordopoxyirinae such as orthopoxvirus, parapoxvirus, avipoxvirus, capripoxvirus, leporipoxvirus, suipoxvirus, molluscipoxvirus and yatapoxvirus, as well as Entomopoxyirinae such as entomopoxvirus A, entomopoxvirus B, and entomopoxvirus A. Chordopoxyirinae are vertebrate poxviruses and have similar antigenicities, morphologies and host ranges; thus, any of a variety of such poxviruses can be used herein. One skilled in the art can select a particular genera or individual chordopoxyirinae according to the known properties of the genera or individual virus, and according to the selected characteristics of the virus (e.g., pathogenicity, ability to elicit and immune response, preferential tumor localization), the intended use of the virus, the tumor type and the host organism. Exemplary chordopoxyirinae genera are orthopoxvirus and avipoxvirus.

Avipoxviruses are known to infect a variety of different birds and have been administered to humans. Exemplary avipoxviruses include canarypox, fowlpox, juncopox, mynahpox, pigeonpox, psittacinepox, quailpox, peacockpox, penguinpox, sparrowpox, starlingpox, and turkeypox viruses.

Orthopoxviruses are known to infect a variety of different mammals including rodents, domesticated animals, primates and humans. Several orthopoxviruses have a broad host range, while others have narrower host range. Exemplary orthopoxviruses include buffalopox, camelpox, cowpox, ectromelia, monkeypox, raccoon pox, skunk pox, tatera pox, uasin gishu, vaccinia, variola and volepox viruses. In some embodiments, the orthopoxvirus selected can be an orthopoxvirus known to infect humans, such as cowpox, monkeypox, vaccinia or variola virus. Optionally, the orthopoxvirus known to infect humans can be selected from the group of orthopoxviruses with a broad host range, such as cowpox, monkeypox, or vaccinia virus.

a. Vaccinia Virus

One exemplary orthopoxvirus is vaccinia virus. A variety of vaccinia virus strains are available, including Western Reserve (WR), Copenhagen, Tashkent, Tian Tan, Lister, Wyeth, IHD-J, and IHD-W, Brighton, Ankara, MVA, Dairen I, L-IPV, LC16M8, LC16MO, LIVP, WR 65-16, Connaught, New York City Board of Health. Exemplary vaccinia viruses are Lister or LIVP vaccinia viruses. Any known vaccinia virus, or modifications thereof that correspond to those provided herein or known to those of skill in the art to reduce toxicity of a vaccinia virus. Generally, however, the mutation will be a multiple mutant and the virus will be further selected to reduce toxicity.

The linear dsDNA viral genome of vaccinia virus is approximately 200 kb in size, encoding a total of approximately 200 potential genes. Viral gene expression can be divided into three stages. In the early stage, gene expression is mainly for viral replication, and for defense against the host's immune system. In the intermediate stage, genes not available for expression in the early stage can be expressed, including late stage transactivators. In the late stage, active transcription is mainly for viral structural components for building mature viruses.

Vaccinia virus possesses a variety of features for use in cancer gene therapy and vaccination. It has a broad host and cell type range. Vaccinia is a cytoplasmic virus, thus, it does not insert its genome into the host genome during its life cycle. Unlike many other viruses that require the host's transcription machinery, vaccinia virus can support its own gene expression in the host cell cytoplasm using enzymes encoded in the viral genome. The vaccinia virus genome has a large carrying capacity for foreign genes, where up to 25 kb of exogenous DNA fragments (approximately 12% of the vaccinia genome size) can be inserted. The genomes of several of the vaccinia strains have been completely sequenced, and many essential and nonessential genes identified. Due to high sequence homology among different strains, genomic information from one vaccinia strain can be used for designing and generating modified viruses in other strains. Finally, the techniques for production of modified vaccinia strains by genetic engineering are well established (Moss, Curr. Opin. Genet. Dev. 3 (1993), 86-90; Broder and Earl, Mol. Biotechnol. 13 (1999), 223-245; Timiryasova et al., Biotechniques 31 (2001), 534-540).

Historically, vaccinia virus was used to immunize against smallpox infection. More recently, modified vaccinia viruses are being developed as vaccines to combat a variety of diseases. Attenuated vaccinia virus can trigger a cell-mediated immune response. Strategies such as prime/boost vaccination, vaccination with nonreplicating vaccinia virus or a combination of these strategies, have shown promising results for the development of safe and effective vaccination protocols. Mutant vaccinia viruses from previous studies exhibit a variety of shortcomings, including a lack of efficient delivery of the viral vehicle to the desired tissue only (e.g., specific accumulation in a tumors), a lack of safety because of possible serious complications (e.g., in young children, eczema vaccinatum and encephalitis, and in adults disseminated or progressive vaccinia may result if the individual is severely immunodeficient).

b. Modified Vaccinia Viruses

Provided herein are vaccinia viruses with insertions, mutations or deletions, as described more generally elsewhere herein. The vaccinia viruses are modified or selected to have low toxicity and to accumulate in the target tissue. Exemplary of such viruses are those from the LIVP strain.

Exemplary insertions, mutations or deletions are those that result in an attenuated vaccinia virus relative to the wild type strain. For example, vaccinia virus insertions, mutations or deletions can decrease pathogenicity of the vaccinia virus, for example, by reducing the toxicity, reducing the infectivity, reducing the ability to replicate, or reducing the number of non-tumor organs or tissues to which the vaccinia virus can accumulate. Other exemplary insertions, mutations or deletions include, but are not limited to, those that increase antigenicity of the microorganism, those that permit detection or imaging, those that increase toxicity of the microorganism (optionally, controlled by an inducible promoter). For example, modifications can be made in genes that are involved in nucleotide metabolism, host interactions and virus formation. Any of a variety of insertions, mutations or deletions of the vaccinia virus known in the art can be used herein, including insertions, mutations or deletions of: the thymidine kinase (TK) gene, the hemagglutinin (HA) gene, the VGF gene (as taught in U.S. Pat. Pub. No. 20030031681); a hemorrhagic region or an A type inclusion body region (as taught in U.S. Pat. No. 6,596,279); Hind III F, F13L, or Hind III M (as taught in U.S. Pat. No. 6,548,068); A33R, A34R, A36R or B5R genes (see, e.g., Katz et al., J. Virology 77:12266-12275 (2003)); SalF7L (see, e.g., Moore et al., EMBO J. 1992 11:1973-1980); N1L (see, e.g., Kotwal et al., Virology 1989 171:579-587); M1 lambda (see, e.g., Child et al., Virology. 1990 174:625-629); HR, HindIII-MK, HindIII-MKF, HindIII-CNM, RR, or BamF (see, e.g., Lee et al., J. Virol. 1992 66:2617-2630); or C21L (see, e.g., Isaacs et al., Proc Natl Acad Sci USA. 1992 89:628-632).

c. The F3 Gene

In addition to the mutations known in the art, the vaccinia viruses provided herein can have an insertion, mutation or deletion of the F3 gene (SEQ ID No: 1; an exemplary F3 gene is provided in GenBank Accession No. M57977, which contains the nucleotide and predicted amino acid sequences for LIVP strain F3; see also Mikryukov et al., Biotekhnologiya 4:442-449 (1988)). For example, the F3 gene has been modified at the unique single NotI restriction site located within the F3 gene at position 35 or at position 1475 inside of the HindIII-F fragment of vaccinia virus DNA strain LIVP (Mikryukov et al., Biotekhnologiya 4 (1988), 442-449) by insertion of a foreign DNA sequence into the NotI digested virus DNA. As provided herein, an insertion of a nucleic acid molecule, such as one containing lacZ, into the NotI site of the F3 gene of the LIVP strain (nucleotides 1473-1480 in M57977, or nucleotides 33-40 of SEQ ID NO: 1) can result in decreased accumulation of vaccinia viruses in non-tumorous organs of nude mice, including brain and heart, relative to wild type vaccinia virus. Thus for use in the methods provided herein, vaccinia viruses can contain an insertion, mutation or deletion of the F3 gene or a mutation of a corresponding locus. For example, as provided herein, F3-interrupted modified LIVP vaccinia virus can selectively replicate in tumor cells in vivo. Therefore, modified vaccinia viruses (e.g., modified strain LIVP) with the interrupted F3 gene can be used in the methods provided herein, such as methods of tumor-directed gene therapy and for detection of tumors and metastases.

Thus, provided herein are vaccinia viruses having a modification of the F3 gene. For example, the vaccinia viruses provided herein can contain an insertion of foreign DNA into the F3 gene. An exemplary insertion of foreign DNA is an insertion at a site equivalent to the NotI site of the F3 gene in vaccinia strain LIVP, or at position 35 of SEQ ID NO:1. An F3-modified vaccinia virus provided herein can colonize in tumors specifically, and therefore, can be used for tumor-specific therapeutic gene delivery. A GenBank data analysis with BLAST (Basic Local Alignment Search Tool) on nucleotide sequences of different strains of vaccinia virus was performed. Based on this analysis, it was found that in vaccinia virus strain Copenhagen (Goebel et al., Virology 179 (1990), 247-266) the NotI restriction site is located between two open reading frames (ORF) encoding F14L and F15L genes. Therefore, insertion of foreign genes into NotI site of the VV genome strain Copenhagen will not interrupt any vital genes. In VV strain LIVP, the NotI restriction site is located in the ORF encoding the F3 gene with unknown function (Mikryukov et al., Biotekhnologiya 4 (1988), 442-449). Thus, the insertion of foreign genes into the NotI site of the F3 gene interrupted the F3 gene. The ability to modify the F3 gene suggests that it may have a nonessential role for virus replication. Although the F3 gene is likely nonessential for virus replication, the results of the animal experiments suggest that interruption of the F3 gene is correlated with decreased viral virulence, the inability to replicate in brain or ovary, and the ability to replicate preferentially in tumor tissue.

The F3 gene is conserved in a variety of different vaccinia virus strains, including WR (nucleotides 42238-42387 of GenBank Accession No. AY243312.1, Ankara (nucleotides 37155-37304 of GenBank Accession No. U94848.1), Tian Tan (nucleotides 41808-41954 of GenBank Accession No. AF095689), Acambis 3000 (nucleotides 31365-31514 of GenBank Accession No. AY603355.1) and Copenhagen (nucleotides 45368-45517 of GenBank Accession No. M35027.1) strains. The F3 gene also is conserved in the larger family of poxviruses, particularly among orthopoxviruses such as cowpox (nucleotides 58498-58647 of GenBank Accession No. X94355.2), rabbitpox (nucleotides 46969-47118 of GenBank Accession No. AY484669.1), camelpox (nucleotides 43331-43480 of GenBank Accession No. AY009089.1), ectromelia (nucleotides 51008-51157 of GenBank Accession No. AF012825.2), monkeypox (nucleotides 42515-42660 of GenBank Accession No. AF380138.1), and variola viruses (nucleotides 33100-33249 of GenBank Accession No. X69198.1). Accordingly, also provided are modifications of the equivalent of the F3 gene in poxviruses, such as orthopoxviruses including a variety of vaccinia virus strains. One skilled in the art can identify the location of the equivalent F3 gene in a variety of poxviruses, orthopoxviruses and vaccinia viruses. For example, an equivalent of the F3 gene in poxviruses, orthopoxviruses and vaccinia viruses can include a gene that contains at least 80%, at least 85%, at least 90%, at least 92%, at least 94%, at least 95%, at least 96%, at least 97%, at least 98%, or at least 99% identity with the nucleotide sequence of the F3 gene in SEQ ID NO:1. In another example, an equivalent of the F3 gene in poxviruses, orthopoxviruses and vaccinia viruses can include a gene that contains at least 80%, at least 85%, at least 90%, at least 92%, at least 94%, at least 95%, at least 96%, at least 97%, at least 98%, or at least 99% identity with the amino acid sequence of F3 in SEQ ID NO:2. In another example, the equivalent to the F3 gene in LIVP can be determined by its structural location in the viral genome: the F3 gene is located on the HindIII-F fragment of vaccinia virus between open reading frames F14L and F15L as defined by Goebel et al., Virology (1990) 179:247-266, and in the opposite orientation of ORFs F14L and F15L; one skilled in the art can readily identify the gene located in the structurally equivalent region in a large variety of related viruses, such as a large variety of pox viruses.

Comparative protein sequence analysis revealed some insight into protein function. The closest match with the protein encoded by the F3 gene (strain LIVP) is a prolyl 4-hydroxylase alpha subunit precursor (4-PH alpha) from the nematode *Caenorhabditis elegans* (Veijola et al., J. Biol. Chem. 269 (1994), 26746-26753). This alpha subunit forms an active alpha-beta dimer with the human protein disulfide isomerase beta subunit. Prolyl 4-hydroxylase (EC 1.14.11.2) catalyzes the formation of 4-hydroxyproline in collagen. The vertebrate enzyme is an alpha 2-beta 2 tetramer, the beta subunit of which is identical to the protein disulfide-isomerase (PDI). The importance of this protein for vaccinia viral replication is unknown, but a deficiency of this protein can result in retargeting vaccinia virus to tumor tissue.

d. Multiple Modifications

The vaccinia viruses provided herein also can contain two or more insertions, mutations or deletions. Thus, included are vaccinia viruses containing two or more insertions, mutations or deletions of the loci provided herein or other loci known in the art. In one embodiment, a vaccinia virus contains an insertion, mutation or deletion in the F3 gene, and one or more additional insertions, mutations or deletions. In one embodiment of the modified vaccinia virus, at least the F3 gene has been modified by insertion of a foreign nucleotide sequence. Modifications such as modification of the F3 gene will typically result in at least partial inactivation of the gene or gene product. In one example, the F3 gene and the TK gene have been modified by insertion of a foreign nucleotide sequence. In another example, the F3 gene and the HA gene have been modified by insertion of a foreign nucleotide sequence. In another example, the F3 gene and both the TK and HA genes have been modified by insertion of a foreign nucleotide sequence. In another example, the HA gene and the TK gene have been modified by insertion of a foreign nucleotide sequence. Accordingly, the present compositions and methods include a modified vaccinia virus wherein two or more of (a) the F3 gene, (b) the TK gene, and (c) the HA gene have been modified. In one embodiment, at least two of the F3 gene, TK gene and HA gene have been inactivated, for example by insertion, deletion and/or replacement of nucleotide(s) within the coding region, or regulatory sequences of two or more of these genes have been inactivated by insertion, deletion or mutation.

e. The Lister Strain

In another embodiment, the viruses and methods provided herein can be based on modifications to the Lister strain of vaccinia virus. Lister (also referred to as Elstree) vaccinia virus is available from any of a variety of sources. For example, the Elstree vaccinia virus is available at the ATCC under Accession Number VR-1549. The Lister vaccinia strain has high transduction efficiency in tumor cells with high levels of gene expression.

In one embodiment, the Lister strain can be an attenuated Lister strain, such as the LIVP (Lister virus from the Institute of Viral Preparations, Moscow, Russia) strain, which was produced by further attenuation of the Lister strain. The LIVP strain was used for vaccination throughout the world, particularly in India and Russia, and is widely available.

The LIVP strain has a reduced pathogenicity while maintaining a high transduction efficiency. For example, as provided herein, F3-interrupted modified LIVP vaccinia virus can selectively replicate in tumor cells in vivo. In one embodiment, provided herein are modified LIVP viruses, including viruses having a modified TK gene, viruses having a modified HA gene, viruses having a modified F3 gene, and viruses having two or more of: modified HA gene, modified TK gene, and modified F3 gene.

ii. Other Cytoplasmic Viruses

Also provided herein are cytoplasmic viruses that are not poxviruses. Cytoplasmic viruses can replicate without introducing viral nucleic acid molecules into the nucleus of the host cell. A variety of such cytoplasmic viruses are known in the art, and include African swine flu family viruses and various RNA viruses such as arenaviruses, picornaviruses, caliciviruses, togaviruses, coronaviruses, paramyxoviruses, flaviviruses, reoviruses, and rhaboviruses. Exemplary togaviruses include Sindbis viruses. Exemplary arenaviruses include lymphocytic choriomeningitis virus. Exemplary rhaboviruses include vesicular stomatitis viruses. Exemplary paramyxo viruses include Newcastle Disease viruses and measles viruses. Exemplary picornaviruses include polio viruses, bovine enteroviruses and rhinoviruses. Exemplary flaviviruses include Yellow fever virus; attenuated Yellow fever viruses are known in the art, as exemplified in Barrett et al., Biologicals 25:17-25 (1997), and McAllister et al., J. Virol. 74:9197-9205 (2000).

Also provided herein are modifications of the viruses provided above to enhance one or more characteristics relative to the wild type virus. Such characteristics can include, but are not limited to, attenuated pathogenicity, reduced toxicity, preferential accumulation in tumor, increased ability to activate an immune response against tumor cells, increased immunogenicity, increased or decreased replication competence, and are able to express exogenous proteins, and combinations thereof. In some embodiments, the modified viruses have an ability to activate an immune response against tumor cells without aggressively killing the tumor cells. In other embodiments, the viruses can be modified to express one or more detectable genes, including genes that can be used for imaging. In other embodiments, the viruses can be modified to express one or more genes for harvesting the gene products and/or for harvesting antibodies against the gene products.

b. Adenovirus, Herpes, Retroviruses

Further provided herein are viruses that include in their life cycle entry of a nucleic acid molecule into the nucleus of the host cell. A variety of such viruses are known in the art, and include herpesviruses, papovaviruses, retroviruses, adenoviruses, parvoviruses and orthomyxoviruses. Exemplary herpesviruses include herpes simplex type 1 viruses, cytomegaloviruses, and Epstein-Barr viruses. Exemplary papovaviruses include human papillomavirus and SV40 viruses. Exemplary retroviruses include lentiviruses. Exemplary orthomyxoviruses include influenza viruses. Exemplary parvoviruses include adeno associated viruses.

Also provided herein are modifications of the viruses provided above to enhance one or more characteristics relative to the wild type virus. Such characteristics can include, but are not limited to, attenuated pathogenicity, reduced toxicity, preferential accumulation in tumor, increased ability to activate an immune response against tumor cells, increased immunogenicity, increased or decreased replication competence, and are able to express exogenous proteins, and combinations thereof. In some embodiments, the modified viruses have an ability to activate an immune response against tumor cells without aggressively killing the tumor cells. In other embodiments, the viruses can be modified to express one or more detectable genes, including genes that can be used for imaging. In other embodiments, the viruses can be modified to express one or more genes for harvesting the gene products and/or for harvesting antibodies against the gene products.

3. Bacteria

Bacteria can also be used in the methods provided herein. Any of a variety of bacteria possessing the desired characteristics can be used. In one embodiment, aerobic bacteria can be used. In another embodiment, anaerobic bacteria can be used. In another embodiment, extracellular bacteria can be used. In another embodiment, intracellular bacteria can be used.

In some embodiments, the bacteria provided herein can be extracellular bacteria. A variety of extracellular bacteria are known in the art and include *vibrio, lactobacillus, streptococcus, escherichia*. Exemplary bacteria include *Vibrio cholerae, Streptococcus pyogenes*, and *Escherichia coli*. In other embodiments, the bacteria provided herein can be intracellular bacteria. A variety of intracellular bacteria are known in the art and include *listeria, salmonella, clostridium*, and *bifodobacterium*. Exemplary intracellular bacteria include *Listeria monocytogenes, Salmonella typhimurium, Clostridium histolyticus, Clostridium butyricum, Bifodobacterium longum*, and *Bifodobacterium adolescentis*. Additional bacteria include plant bacteria such as *Clavibacter michiganensis* subsp. *michiganensis, Agrobacterium tumefaciens, Erwinia herbicola, Azorhizobium caulinodans, Xanthomonas campestris* pv. *vesicatoria*, and *Xanthomonas campestris* pv. *campestris*.

A further example of a bacteria provided herein are magnetic bacteria. Such bacteria allow tumor detection through the accumulation of iron-based contrast agents. Magnetic bacteria can be isolated from fresh and marine sediments. Magnetic bacteria can produce magnetic particles (Fe304) (Blakemore, Annu Rev. Microbiol. 36 (1982), 217-238). To do so, the magnetic bacteria have efficient iron uptake systems, which allow them to utilize both insoluble and soluble forms of iron. Magnetospirillum magnetic AMB-1 is an example of such magnetic bacteria that has been isolated and cultured for magnetic particle production (Yang et al., Enzyme Microb. Technol. 29 (2001), 13-19). As provided herein, these magnetic bacteria (naturally occurring or genetically modified), when injected intravenously, can selectively accumulate in tumor. Accordingly, these bacteria can be used for accumulating iron-based contrast agents in the tumors, which in turn allows tumor detection by MRI. Similarly, other naturally isolated metal accumulating strains of bacteria can be used for tumor targeting, absorption of metals from contrast agents, and tumor imaging.

Also provided herein are modifications of bacteria to enhance one or more characteristics relative to the wild type bacteria. Such characteristics can include, but are not limited to, attenuated pathogenicity, reduced toxicity, preferential accumulation in tumor, increased ability to activate an immune response against tumor cells, increased immunogenicity, increased or decreased replication competence, and are able to express exogenous proteins, and combinations thereof. In some embodiments, the modified bacteria have an ability to activate an immune response against tumor cells without aggressively killing the tumor cells. In other embodiments, the bacteria can be modified to express one or more detectable genes, including genes that can be used for imaging. In other embodiments, the bacteria can be modified to express one or more genes for harvesting the gene products and/or for harvesting antibodies against the gene products.

a. Aerobic Bacteria

Previous studies have postulated that anaerobic bacteria are preferred for administration to tumors (Lemmon et al., 1997 Gene Therapy 4:791-796). As provided herein, it has been determined that aerobic bacteria can survive and grow in tumors. Accordingly, a bacteria used in the methods provided herein can include a bacteria that can survive and grow in an oxygenated environment. In some embodiments, the bacteria must be in an oxygenated environment in order to survive and grow. A variety of aerobic bacteria are known in the art, including lactobacilli, *salmonella*, streptococci, staphylococci, *vibrio, listeria*, and *escherichia*. Exemplary bacteria include *Vibrio cholerae, Listeria monocytogenes, Salmonella typhimurium, Streptococcus pyogenes, Escherichia coli, Lactobacillus bulgaricus, Lactobacillus casei, Lactobacillus acidophilus, Lactobacillus brevis, Lactobacillus paracasei, Lactobacillus plantarum, Lactobacillus rhamnosus, Lactobacillus salivarius, Lactobacillus sporogenes, Lactobacillus lactis, Lactobacillus fermentum, Streptococcus thermophilus, Bacillus subtilis, Bacillus megaterium, Bacillus polymyxa, Myobacterium smegmatis, Mycobacterium vaccae, Mycobacterium microti, Mycobacterium habana, Enterococcus faecalis, Pseudomonas fluorescens*, and *Pseudomonas putida*.

b. Anaerobic Bacteria

A bacteria used in the methods provided herein can include a bacteria that does not require oxygen to survive and grow. In some embodiments, the bacteria must be in an oxygen-free environment in order to survive and grow. A variety of aerobic bacteria are known in the art, including *clostridium, bifodobacterium*. Exemplary bacteria include *Clostridium histolyticus, Clostridium butyricum, Clostridium novyi, Clostridium sordellii, Clostridium absonum, Clostridium bifermentans, Clostridium difficile, Clostridium histolyticum, Clostridium perfringens, Clostridium beijerinckii, Clostridium sporogenes, Staphylococcus aureus, Staphylococcus epidermidis, Bifidobacte-*

*rium longum, Bifidobacterium adolescentis, Bifidobacterium bifidum, Bifidobacterium infantis, Bifidobacterium laterosporus, Bifidobacterium animalis, Actinomyces israelii, Eubacterium lentum, Peptostreptococcus anaerobis, Peptococcus prevotti*, and *Acidaminococcus fermentans.*

4. Eukaryotic Cells

Also encompassed within the microorganisms provided herein and the methods of making and using such microorganisms are eukaryotic cells, including cells from multicellular eukaryotes, including mammals such as primates, where exemplary cells are human cells. Typically the cells are isolated cells. For example, eukaryotic cells can be tumor cells, including mammalian tumor cells such as primate tumor cells, where exemplary primate tumor cells are human tumor cells such as human breast cancer cells. In another example, eukaryotic cells can include fibrosarcoma cells such as human fibrosarcoma cells. Exemplary human fibrosarcoma cells include HT1080 (ATCC Accession Nos. CCL-121, CRL-12011 or CRL-12012). In another example, eukaryotic cells can include stem cells, including mammalian stem cells such as primate stem cells, where exemplary primate stem cells are human stem cells.

Also provided herein are modifications of eukaryotic cells to enhance one or more characteristics relative to the wild type cells. Such characteristics can include, but are not limited to, attenuated pathogenicity, reduced toxicity, preferential accumulation in tumor, increased ability to activate an immune response against tumor cells, increased immunogenicity, increased or decreased replication competence, and are able to express exogenous proteins, and combinations thereof. In some embodiments, the modified eukaryotic cells have an ability to activate an immune response against tumor cells without aggressively killing the tumor cells. In other embodiments, the eukaryotic cells can be modified to express one or more detectable genes, including genes that can be used for imaging. In other embodiments, the eukaryotic cells can be modified to express one or more genes for harvesting the gene products and/or for harvesting antibodies against the gene products.

C. Methods for Making A Modified Microorganism

The microorganisms provided herein can be formed by standard methodologies well known in the art for modifying microorganisms such as viruses, bacteria and eukaryotic cells. Briefly, the methods include introducing into microorganisms one or more genetic modification, followed by screening the microorganisms for properties reflective of the modification or for other desired properties.

1. Genetic Modifications

Standard techniques in molecular biology can be used to generate the modified microorganisms provided herein. Such techniques include various nucleic acid manipulation techniques, nucleic acid transfer protocols, nucleic acid amplification protocols, and other molecular biology techniques known in the art. For example, point mutations can be introduced into a gene of interest through the use of oligonucleotide mediated site-directed mutagenesis. Alternatively, homologous recombination can be used to introduce a mutation or exogenous sequence into a target sequence of interest. Nucleic acid transfer protocols include calcium chloride transformation/transfection, electroporation, liposome mediated nucleic acid transfer, N-[1-(2,3-Dioloyloxy)propyl]-N,N,N-trimethylammonium methylsulfate meditated transformation, and others. In an alternative mutagenesis protocol, point mutations in a particular gene can also be selected for using a positive selection pressure. See, e.g., Current Techniques in Molecular Biology, (Ed. Ausubel, et al.). Nucleic acid amplification protocols include but are not limited to the polymerase chain reaction (PCR). Use of nucleic acid tools such as plasmids, vectors, promoters and other regulating sequences, are well known in the art for a large variety of viruses and cellular organisms. Further a large variety of nucleic acid tools are available from many different sources including ATCC, and various commercial sources. One skilled in the art will be readily able to select the appropriate tools and methods for genetic modifications of any particular virus or cellular organism according to the knowledge in the art and design choice.

Any of a variety of modifications can be readily accomplished using standard molecular biological methods known in the art. The modifications will typically be one or more truncations, deletions, mutations or insertions of the microorganismal genome. In one embodiment, the modification can be specifically directed to a particular sequence. The modifications can be directed to any of a variety of regions of the microorganismal genome, including, but not limited to, a regulatory sequence, to a gene-encoding sequence, or to a sequence without a known role. Any of a variety of regions of microorganismal genomes that are available for modification are readily known in the art for many microorganisms, including the microorganisms specifically listed herein. As a non-limiting example, the loci of a variety of vaccinia genes provided hereinelsewhere exemplify the number of different regions that can be targeted for modification in the microorganisms provided herein. In another embodiment, the modification can be fully or partially random, whereupon selection of any particular modified microorganism can be determined according to the desired properties of the modified the microorganism.

In some embodiments, the microorganism can be modified to express an exogenous gene. Exemplary exogenous gene products include proteins and RNA molecules. The modified microorganisms can express a detectable gene product, a therapeutic gene product, a gene product for manufacturing or harvesting, or an antigenic gene product for antibody harvesting. The characteristics of such gene products are described hereinelsewhere. In some embodiments of modifying an organism to express an exogenous gene, the modification can also contain one or more regulatory sequences to regulate expression of the exogenous gene. As is known in the art, regulatory sequences can permit constitutive expression of the exogenous gene or can permit inducible expression of the exogenous gene. Further, the regulatory sequence can permit control of the level of expression of the exogenous gene. In some examples, inducible expression can be under the control of cellular or other factors present in a tumor cell or present in a microorganism-infected tumor cell. In other examples, inducible expression can be under the control of an administerable substance, including IPTG, RU486 or other known induction compounds. Any of a variety of regulatory sequences are available to one skilled in the art according to known factors and design preferences. In some embodiments, such as gene product manufacture and harvesting, the regulatory sequence can result in constitutive, high levels of gene expression. In some embodiments, such as anti-(gene product) antibody harvesting, the regulatory sequence can result in constitutive, lower levels of gene expression. In tumor therapy embodiments, a therapeutic protein can be under the control of an internally inducible promoter or an externally inducible promoter.

In other embodiments, organ or tissue-specific expression can be controlled by regulatory sequences. In order to achieve expression only in the target organ, for example, a tumor to be treated, the foreign nucleotide sequence can be linked to a tissue specific promoter and used for gene therapy. Such promoters are well known to those skilled in the art (see e.g., Zimmermann et al., (1994) Neuron 12, 11-24; Vidal et al.; (1990) EMBO J. 9, 833-840; Mayford et al., (1995), Cell 81, 891-904; Pinkert et al., (1987) Genes & Dev. 1, 268-76).

In some embodiments, the microorganisms can be modified to express two or more proteins, where any combination of the two or more proteins can be one or more detectable gene products, therapeutic gene products, gene products for manufacturing or harvesting, or antigenic gene products for antibody harvesting. In one embodiment, a microorganism can be modified to express a detectable protein and a therapeutic protein. In another embodiment, a microorganism can be modified to express two or more gene products for detection or two or more therapeutic gene products. For example, one or more proteins involved in biosynthesis of a luciferase substrate can be expressed along with luciferase. When two or more exogenous genes are introduced, the genes can be regulated under the same or different regulatory sequences, and the genes can be inserted in the same or different regions of the microorganismal genome, in a single or a plurality of genetic manipulation steps. In some embodiments, one gene, such as a gene encoding a detectable gene product, can be under the control of a constitutive promoter, while a second gene, such as a gene encoding a therapeutic gene product, can be under the control of an inducible promoter. Methods for inserting two or more genes in to a microorganism are known in the art and can be readily performed for a wide variety of microorganisms using a wide variety of exogenous genes, regulatory sequences, and/or other nucleic acid sequences.

In an example of performing microorganismal modification methods, vaccinia virus strain LIVP was modified to contain insertions of exogenous DNA in three different locations of the viral genome. Using general methods known in the art, known molecular biology tools, and sequences known in the art or disclosed herein can be used to create modified vaccinia virus strains, including viruses containing insertions in the F3 gene, TK gene and/or HA gene. See, e.g., Mikryukov, et al., Biotekhnologya 4 (1998), 442-449; Goebel et al., Virology 179 (1990), 247-266; Antoine et al., Virology 244 (1998), 365-396; Mayr et al., Zentbl. Bakteriol. Hyg. Abt 1 Orig. B 167 (1978), 375-390; Ando and Matumoto, Jpn. J. Microbial. 14 (1979), 181-186; Sugimoto et al., Microbial. Immuol. 29 (1985), 421-428; Takahashi-Nishimaki et al., J. Gen. Virol. 68 (1987), 2705-2710). These methods include, for example, in vitro recombination techniques, synthetic methods and in vivo recombination methods as described, for example, in Sambrook et al., Molecular Cloning: A Laboratory Manual, 2nd edition, Cold Spring Harbor Laboratory Press, cold Spring Harbor N.Y. (1989), and in the Examples disclosed herein. The person skilled in the art can isolate the gene encoding the gene product of F3 (or a related gene product) from any vaccinia strain using, for example, the nucleotide sequence of the F3 gene of SEQ ID NO:1 or SEQ ID NOS: 10, 12, 14, 16, 18, 20, 22, 24, 26, 28, 30 or 32, or a fragment thereof as a probe for screening a library.

Methods of producing recombinant microorganisms are known in the art. Provided herein for exemplary purposes are methods of producing a recombinant vaccinia virus. A recombinant vaccinia virus with an insertion in the F3 gene (NotI site of LIVP) can be prepared by the following steps: (a) generating (i) a vaccinia shuttle plasmid containing the modified F3 gene inserted at restriction site X and (ii) a dephosphorylated wt VV (VGL) DNA digested at restriction site X; (b) transfecting host cells infected with PUV-inactivated helper VV (VGL) with a mixture of the constructs of (i) and (ii) of step a; and (c) isolating the recombinant vaccinia viruses from the transfectants. One skilled in the art knows how to perform such methods, for example by following the instructions given in Example 1 and the legend to FIG. 1; see also Timiryasova et al., Biotechniques 31 (2001), 534-540. In one embodiment, restriction site X is a unique restriction site. A variety of suitable host cells also are known to the person skilled in the art and include many mammalian, avian and insect cells and tissues which are susceptible for vaccinia virus infection, including chicken embryo, rabbit, hamster and monkey kidney cells, for example, HeLa cells, $RK_{13}$, CV-1, Vero, BSC40 and BSC-1 monkey kidney cells.

2. Screening for Above Characteristics

Modified microorganisms can be screened for any desired characteristics, including the characteristics described herein such as attenuated pathogenicity, reduced toxicity, preferential accumulation in tumor, increased ability to activate an immune response against tumor cells, increased immunogenicity, increased or decreased replication competence, and are able to express exogenous proteins, and combinations thereof. For example, the modified microorganisms can be screened for the ability to activate an immune response against tumor cells without aggressively killing the tumor cells. In another example, the microorganisms can be screened for expression of one or more detectable genes, including genes that can be used for imaging, or for expression of one or more genes for manufacture or harvest of the gene products and/or for harvest of antibodies against the gene products.

Any of a variety of known methods for screening for such characteristics can be performed, as demonstrated in the Examples provided herein. One Exemplary method for screening for desired characteristics includes, but is not limited to, monitoring growth, replication and/or gene expression (including expression of an exogenous gene) in cell culture or other in vitro medium. The cell culture can be from any organism, and from any tissue source, and can include tumorous tissues. Other exemplary methods for screening for desired characteristics include, but are not limited to, administering a microorganism to animal, including non-human animals such as a mouse, monkey or ape, and optionally also including humans, and monitoring the microorganism, the tumor, and or the animal; monitoring can be performed by in vivo imaging of the microorganism and/or the tumor (e.g., low light imaging of microorganismal gene expression or ultrasonic tumor imaging), external monitoring of the tumor (e.g., external measurement of tumor size), monitoring the animal (e.g., monitoring animal weight, blood panel, antibody titer, spleen size, or liver size). Other exemplary methods for screening for desired characteristics include, but are not limited to, harvesting a non-human animal for the effects and location of the microorganism and expression by the microorganism, including methods such as harvesting a variety of organs including a tumor to determine presence of the microorganism and/or gene expression by the microorganism in the organs or tumor, harvesting of organs associated with an immune response or microorganismal clearance such as the spleen or liver, harvesting the tumor to determine tumor size and viability of tumor cells, harvesting antibodies or antibody producing cells. Such screening and monitoring methods can be used in any of a variety of combinations, as is known in art. In one embodiment, a microorganism can be screened by administering the microorganism to an animal such as a non-human animal or a human, followed by monitoring by in vivo imaging. In another embodiment, a microorganism can be screened by administering the microorganism to an animal such as a non-human animal, monitoring by in vivo imaging, and then harvesting the animal. Thus, provided herein are methods for screening a microorganism for desired characteristics by administering the microorganism to an animal such as an animal with a tumor, and monitoring the animal, tumor (if present), and/or microorganism in the animal for one or more characteristics. Also provided herein are methods for screening a microorganism for desired characteristics by administering the microorganism to a non-human animal such as a non-human animal with a tumor, harvesting the animal, and assaying the animal's organs, antibody titer, and/or tumor (if present) for one or more characteristics.

Provided herein are methods for screening a microorganism for attenuated pathogenicity or reduced toxicity, where the pathogenicity or toxicity can be determined by a variety of techniques, including, but not limited to, assessing the health state of the subject, measuring the body weight of a subject, blood or urine analysis of a subject, and monitoring tissue distribution of the microorganism within the subject; such techniques can be performed on a living subject in vivo, or can be performed post mortem. Methods also can include the ability of the microorganisms to lyse cells or cause cell death, which can be determined in vivo or in vitro.

When a subject drops below a threshold body weight, the microorganism can be considered pathogenic to the subject. Exemplary thresholds can be a drop of about 5% or more, a drop of about 10% or more, or a drop of about 15% or more in body weight relative to a reference. A body weight reference can be selected from any of a variety of references used in the art; for example, a body weight reference can be the weight of the subject prior to administration of the microorganism, the body weight reference can be a control subject having the same condition as the test subject (e.g., normal or tumor-injected), where the change in weight of the control is compared to the change in weight of the test subject for the time period after administration of the microorganism.

Blood or urine analysis of the subject can indicate level of immune response, level of toxins in the subject, or other levels of stress to cells, tissues or organs of the subject such as kidneys, pancreas, liver and spleen. Levels increased above established threshold levels can indicate pathogenicity of the microorganism to the subject. Threshold levels of components of blood or urine for indicating microorganismal pathogenicity are well known in the art, and any such thresholds can be selected herein according to the desired tolerance of pathogenicity or toxicity of the microorganism.

Tissue distribution of a microorganism in a subject can indicate pathogenicity or toxicity of the microorganism. In one embodiment, tissue distribution of a microorganism that is not pathogenic or toxic can be mostly in tumor relative to other tissues or organs. Microorganisms located mostly in tumor can accumulate, for example, at least about 2-fold greater, at least about 5-fold greater, at least about 10-fold greater, at least about 100-fold greater, at least about 1,000-fold greater, at least about 10,000-fold greater, at least about 100,000-fold greater, or at least about 1,000,000-fold greater, than the microorganisms that accumulate in any other particular organ or tissue.

Provided herein are methods for screening a microorganism for tissue distribution or accumulation, where the tissue distribution can be determined by a variety of techniques, including, but not limited to, harvesting a non-human subject, in vivo imaging a detectable gene product in subject. Harvesting can be accomplished by euthanizing the non-human subject, and determining the accumulation of microorganisms in tumor and, optionally, the accumulation in one or more additional tissues or organs. The accumulation can be determined by any of a variety of methods, including, but not limited to, detecting gene products such as detectable gene products (e.g., gfp or beta galactosidase), histological or microscopic evaluation of tissue, organ or tumor samples, or measuring the number of plaque or colony forming units present in a tissue, organ or tumor sample. In one embodiment, the desired amount of tissue distribution of a microorganism can be mostly in tumor relative to other tissues or organs. Microorganisms located mostly in tumor can accumulate, for example, at least about 2-fold greater, at least about 5-fold greater, at least about 10-fold greater, at least about 100-fold greater, at least about 1,000-fold greater, at least about 10,000-fold greater, at least about 100,000-fold greater, or at least about 1,000,000-fold greater, than the microorganisms that accumulate in any other particular organ or tissue.

Also provided herein are methods of screening for microorganisms that can elicit an immune response, where the immune response can be against the tumor cells or against the microorganisms. A variety of methods for measuring the ability to elicit an immune response are known in the art, and include measuring an overall increase in immune activity in a subject, measuring an increase in anti-microorganism or anti-tumor antibodies in a subject, testing the ability of a microorganism-treated (typically a non-human) subject to prevent later infection/tumor formation or to rapidly eliminate microorganisms or tumor cells. Methods also can include the ability of the microorganisms to lyse cells or cause cell death, which can be determined in vivo or in vitro.

Also provided herein are methods for determining increased or decreased replication competence, by monitoring the speed of replication of the microorganisms. Such measurements can be performed in vivo or in vitro. For example, the speed of replication in a cell culture can be used to determine replication competence of a microorganism. In another example, the speed of replication in a tissue, organ or tumor in a subject can be used to measure replication competence. In some embodiments, decreased replication competence in non-tumor tissues and organs can be the characteristic to be selected in a screen. In other embodiments, increased replication competence in tumors can be the characteristic to be selected in a screen.

Also provided herein are methods for determining the ability of a microorganism to express genes, such as exogenous genes. Such methods can be performed in vivo or in vitro. For example, the microorganisms can be screened on selective plates for the ability to express a gene that permits survival of the microorganism or permits the microorganism to provide a detectable signal, such as turning X-gal blue. Such methods also can be performed in vivo, where expression can be determined, for example, by harvesting tissues, organs or tumors a non-human subject or by in vivo imaging of a subject.

Also provided herein are methods for determining the ability of a microorganism to express genes toward which the subject can develop antibodies, including exogenous genes toward which the subject can develop antibodies. Such methods can be performed in vivo using any of a variety of non-human subjects. For example, gene expression can be determined, for example, by bleeding a non-human subject to which a microorganism has been administered, and assaying the blood (or serum) for the presence of antibodies against the microorganism-expressed gene, or by any other method generally used for polyclonal antibody harvesting, such as production bleeds and terminal bleeds.

Also provided herein are methods for screening a microorganism that has two or more characteristics provided herein, including screening for attenuated pathogenicity, reduced toxicity, preferential accumulation in tumor, increased ability to activate an immune response against tumor cells, increased immunogenicity, increased or decreased replication competence, ability to express exogenous proteins, and ability to elicit antibody production against a microorganismally expressed gene product. A single monitoring technique, such as in vivo imaging, can be used to verify two or more characteristics, or a variety of different monitoring techniques can be used, as can be determined by one skilled in the art according to the selected characteristics and according to the monitoring techniques used.

D. Therapeutic Methods

Provided herein are therapeutic methods, including methods of treating or preventing immunoprivileged cells or tissue, including cancerous cells, tumor and metastasis. The methods provided herein include administering a microorganism to a subject containing a tumor and/or metastases. The methods provided herein do not require the microorganism to kill tumor cells or decrease the tumor size. Instead, the methods provided herein include administering to a subject a microorganism that can cause or enhance an anti-tumor immune response in the subject. In some embodiments, the microorganisms provided herein can be administered to a subject without causing microorganism-induced disease in the subject. In some embodiments, the microorganisms can accumulate in tumors or metastases. In some embodiments, the microorganisms can elicit an anti-tumor immune response in the subject, where typically the microorganism-mediated anti-tumor immune response can develop over several days, such as a week or more, 10 days or more, two weeks or more, or a month or more, as a result of little or no microorganism-cause tumor cell death. In some exemplary methods, the microorganism can be present in the tumor, and can cause an anti-tumor immune response without the microorganism itself causing enough tumor cell death to prevent tumor growth.

In some embodiments, provided herein are methods for eliciting or enhancing antibody production against a selected antigen or a selected antigen type in a subject, where the methods include administering to a subject a microorganism that can accumulate in a tumor and/or metastasis, and can cause release of a selected antigen or selected antigen type from the tumor, resulting in antibody production against the selected antigen or selected antigen type. The administered microorganisms can posses one or more characteristics including attenuated pathogenicity, low toxicity, preferential accumulation in tumor, ability to activate an immune response against tumor cells, immunogenicity, replication competence, ability to express exogenous genes, and ability to elicit antibody production against a microorganismally expressed gene product.

Any of a variety of antigens can be targeted in the methods provided herein, including a selected antigen such as an exogenous gene product expressed by the microorganism, or a selected antigen type such as one or more tumor antigens release from the tumor as a result of microorganism infection of the tumor (e.g., by lysis, apoptosis, secretion or other mechanism of causing antigen release from the tumor). In at least some embodiments, it can be desirable to maintain release of the selected antigen or selected antigen type over a series of days, for example, at least a week, at least ten days, at least two weeks or at least a month.

Also provided herein are methods for providing a sustained antigen release within a subject, where the methods include administering to a subject a microorganism that can accumulate in a tumor and/or metastasis, and can cause sustained release of an antigen, resulting in antibody production against the antigen. The sustained release of antigen can last for several days, for example, at least a week, at least ten days, at least two weeks or at least a month. The administered microorganisms can posses one or more characteristics including attenuated pathogenicity, low toxicity, preferential accumulation in tumor, ability to activate an immune response against tumor cells, immunogenicity, replication competence, ability to express exogenous genes, and ability to elicit antibody production against a microorganismally expressed gene product. The sustained release of antigen can result in an immune response by the microorganism-infected host, in which the host can develop antibodies against the antigen, and/or the host can mount an immune response against cells expressing the antigen, including an immune response against tumor cells. Thus, the sustained release of antigen can result in immunization against tumor cells. In some embodiments, the microorganism-mediated sustained antigen release-induced immune response against tumor cells can result in complete removal or killing of all tumor cells.

Also provided herein are methods for inhibiting tumor growth in a subject, where the methods include administering to a subject a microorganism that can accumulate in a tumor and/or metastasis, and can cause or enhance an anti-tumor immune response. The anti-tumor immune response induced as a result of tumor or metastases-accumulated microorganisms can result in inhibition of tumor growth. The administered microorganisms can posses one or more characteristics including attenuated pathogenicity, low toxicity, preferential accumulation in tumor, ability to activate an immune response against tumor cells, immunogenicity, replication competence, ability to express exogenous genes, and ability to elicit antibody production against a microorganismally expressed gene product.

Also provided herein are methods for inhibiting growth or formation of a metastasis in a subject, where the methods include administering to a subject a microorganism that can accumulate in a tumor and/or metastasis, and can cause or enhance an anti-tumor immune response. The anti-tumor immune response induced as a result of tumor or metastasis-accumulated microorganisms can result in inhibition of metastasis growth or formation. The administered microorganisms can posses one or more characteristics including attenuated pathogenicity, low toxicity, preferential accumulation in tumor, ability to activate an immune response against tumor cells, immunogenicity, replication competence, ability to express exogenous genes, and ability to elicit antibody production against a microorganismally expressed gene product.

Also provided herein are methods for decreasing the size of a tumor and/or metastasis in a subject, where the methods include administering to a subject a microorganism that can accumulate in a tumor and/or metastasis, and can cause or enhance an anti-tumor immune response. The anti-tumor immune response induced as a result of tumor or metastasis-accumulated microorganisms can result in a decrease in the size of the tumor and/or metastasis. The administered microorganisms can posses one or more characteristics including attenuated pathogenicity, low toxicity, preferential accumulation in tumor, ability to activate an immune response against tumor cells, immunogenicity, replication competence, ability to express exogenous genes, and ability to elicit antibody production against a microorganismally expressed gene product.

Also provided herein are methods for eliminating a tumor and/or metastasis from a subject, where the methods include administering to a subject a microorganism that can accumulate in a tumor and/or metastasis, and can cause or enhance an anti-tumor immune response. The anti-tumor immune response induced as a result of tumor or metastasis-accumulated microorganisms can result in elimination of the tumor and/or metastasis from the subject. The administered microorganisms can posses one or more characteristics including attenuated pathogenicity, low toxicity, preferential accumulation in tumor, ability to activate an immune response against tumor cells, immunogenicity, replication competence, ability to express exogenous genes, and ability to elicit antibody production against a microorganismally expressed gene product.

Methods of reducing inhibiting tumor growth, inhibiting metastasis growth and/or formation, decreasing the size of a tumor or metastasis, eliminating a tumor or metastasis, or other tumor therapeutic methods provided herein include causing or enhancing an anti-tumor immune response in the host. The immune response of the host, being anti-tumor in nature, can be mounted against tumors and/or metastases in which microorganisms have accumulated, and can also be mounted against tumors and/or metastases in which microorganisms have not accumulated, including tumors and/or metastases that form after administration of the microorganisms to the subject. Accordingly, a tumor and/or metastasis whose growth or formation is inhibited, or whose size is decreased, or that is eliminated, can be a tumor and/or metastasis in which the microorganisms have accumulated, or also can be a tumor and/or metastasis in which the microorganisms have not accumulated. Accordingly, provided herein are methods of reducing inhibiting tumor growth, inhibiting metastasis growth and/or formation, decreasing the size of a tumor or metastasis, eliminating a tumor or metastasis, or other tumor therapeutic methods, where the method includes administering to a subject a microorganism, where the microorganism accumulates in at least one tumor or metastasis and causes or enhances an anti-tumor immune response in the subject, and the immune response also is mounted against a tumor and/or metastasis in which the microorganism cell did not accumulate. In another embodiment, methods are provided for inhibiting or preventing recurrence of a neoplastic disease or inhibiting or preventing new tumor growth, where the methods include administering to a subject a microorganism that can accumulate in a tumor and/or metastasis, and can cause or enhance an anti-tumor immune response, and the anti-tumor immune response can inhibit or prevent recurrence of a neoplastic disease or inhibit or prevent new tumor growth.

The tumor or neoplastic disease therapeutic methods provided herein, such as methods of reducing inhibiting tumor growth, inhibiting metastasis growth and/or formation, decreasing the size of a tumor or metastasis, eliminating a tumor or metastasis, or other tumor therapeutic methods, also can include administering to a subject a microorganism that can cause tumor cell lysis or tumor cell death. Such a microorganism can be the same microorganism as the microorganism that can cause or enhance an anti-tumor immune response in the subject. Microorganisms, such as the microorganisms provided herein, can cause cell lysis or tumor cell death as a result of expression of an endogenous gene or as a result of an exogenous gene. Endogenous or exogenous genes can cause tumor cell lysis or inhibit cell growth as a result of direct or indirect actions, as is known in the art, including lytic channel formation or activation of an apoptotic pathway. Gene products, such as exogenous gene products can function to activate a prodrug to an active, cytotoxic form, resulting in cell death where such genes are expressed.

Such methods of antigen production or tumor and/or metastasis treatment can include administration of a modified microorganism described herein or a microorganism having modifications with a functional equivalence to the vaccinia virus provided herein containing a modification of the F3 gene and the TK gene and/or the HA gene, for therapy, such as for gene therapy, for cancer gene therapy, or for vaccine therapy. Such a microorganism can be used to stimulate humoral and/or cellular immune response, induce strong cytotoxic T lymphocytes responses in subjects who may benefit from such responses. For example, the microorganism can provide prophylactic and therapeutic effects against a tumor infected by the microorganism or other infectious diseases, by rejection of cells from tumors or lesions using microorganisms that express immunoreactive antigens (Earl et al. (1986), Science 234, 728-831; Lathe et al. (1987), Nature (London) 326, 878-880), cellular tumor-associated antigens (Bernards et al., (1987), Proc. Natl. Acad. Sci. USA 84, 6854-6858; Estin et al. (1988), Proc. Natl. Acad. Sci. USA 85, 1052-1056; Kantor et al. (1992), J. Natl. Cancer Inst. 84, 1084-1091; Roth et al. (1996), Proc. Natl. Acad. Sci. USA 93, 4781-4786) and/or cytokines (e.g., IL-2, IL-12), costimulatory molecules (B7-1, B7-2) (Rao et al. (1996), J. Immunol. 156, 3357-3365; Chamberlain et al. (1996), Cancer Res. 56, 2832-2836; Oertli et al. (1996), J. Gen. Virol. 77, 3121-3125; Qin and Chatterjee (1996), Human Gene Ther. 7, 1853-1860; McAneny et al. (1996), Ann. Surg. Oncol. 3, 495-500), or other therapeutic proteins.

Provided herein, solid tumors can be treated with microorganisms, such as vaccinia viruses, resulting in an enormous tumor-specific microorganism replication, which can lead to tumor protein antigen and viral protein production in the tumors. As provided herein, vaccinia virus administration to mice resulted in lysis of the infected tumor cells and a resultant release of tumor-cell-specific antigens. Continuous leakage of these antigens into the body led to a very high level of antibody titer (in approximately 7-14 days) against tumor proteins, viral proteins, and the virus encoded engineered proteins in the mice. The newly synthesized antitumor antibodies and the enhanced macrophage, neutrophils count were continuously delivered via the vasculature to the tumor and thereby provided for the recruitment of an activated immune system against the tumor. The activated immune system then eliminated the foreign compounds of the tumor including the viral particles. This interconnected release of foreign antigens boosted antibody production and continuous response of the antibodies against the tumor proteins to function like an autoimmunizing vaccination system initiated by vaccinia viral infection and replication, followed by cell lysis, protein leakage and enhanced antibody production. Thus, the present methods can provide a complete process that can be applied to all tumor systems with immunoprivileged tumor sites as site of privileged viral, bacterial, and mammalian cell growth, which can lead to tumor elimination by the host's own immune system.

In other embodiments, methods are provided for immunizing a subject, where the methods include administering to the subject a microorganism that expresses one or more antigens against which antigens the subject will develop an immune response. The immunizing antigens can be endogenous to the microorganism, such as vaccinia antigens on a vaccinia virus used to immunize against smallpox, or the immunizing antigens can be exogenous antigens expressed by the microorganism, such as influenza or HIV antigens expressed on a viral capsid or bacterial cell surface. Thus, the microorganisms provided herein, including the modified vaccinia viruses can be used as vaccines.

1. Administration

In performing the methods provided herein, a microorganism can be administered to a subject, including a subject having a tumor or having neoplastic cells, or a subject to be immunized. An administered microorganism can be a microorganism provided herein or any other microorganism known for administration to a subject, for example, any known microorganism known for therapeutic administration to a subject, including antigenic microorganisms such as any microorganism known to be used for vaccination. In some embodiments, the microorganism administered is a microorganism containing a characteristic such as attenuated pathogenicity, low toxicity, preferential accumulation in tumor, ability to activate an immune response against tumor cells, high immunogenicity, replication competence, and ability to express exogenous proteins, and combinations thereof.

a. Steps Prior to Administering the Microorganism

In some embodiments, one or more steps can be performed prior to administration of the microorganism to the subject. Any of a variety of preceding steps can be performed, including, but not limited to diagnosing the subject with a condition appropriate for microorganismal administration, determining the immunocompetence of the subject, immunizing the subject, treating the subject with a chemotherapeutic agent, treating the subject with radiation, or surgically treating the subject.

For embodiments that include administering a microorganism to a tumor-bearing subject for therapeutic purposes, the subject has typically been previously diagnosed with a neoplastic condition. Diagnostic methods also can include determining the type of neoplastic condition, determining the stage of the neoplastic conditions, determining the size of one or more tumors in the subject, determining the presence or absence of metastatic or neoplastic cells in the lymph nodes of the subject, or determining the presence of metastases of the subject. Some embodiments of therapeutic methods for administering a microorganism to a subject can include a step of determination of the size of the primary tumor or the stage of the neoplastic disease, and if the size of the primary tumor is equal to or above a threshold volume, or if the stage of the neoplastic disease is at or above a threshold stage, a microorganism is administered to the subject. In a similar embodiment, if the size of the primary tumor is below a threshold volume, or if the stage of the neoplastic disease is at or below a threshold stage, the microorganism is not yet administered to the subject; such methods can include monitoring the subject until the tumor size or neoplastic disease stage reaches a threshold amount, and then administering the microorganism to the subject. Threshold sizes can vary according to several factors, including rate of growth of the tumor, ability of the microorganism to infect a tumor, and immunocompetence of the subject. Generally the threshold size will be a size sufficient for a microorganism to accumulate and replicate in or near the tumor without being completely removed by the host's immune system, and will typically also be a size sufficient to sustain a microorganismal infection for a time long enough for the host to mount an immune response against the tumor cells, typically about one week or more, about ten days or more, or about two weeks or more. Exemplary threshold tumor sizes for viruses such as vaccinia viruses are at least about 100 $mm^3$, at least about 200 $mm^3$, at least about 300 $mm^3$, at least about 400 $mm^3$, at least about 500 $mm^3$, at least about 750 $mm^3$, at least about 1000 $mm^3$, or at least about 1500 $mm^3$. Threshold neoplastic disease stages also can vary according to several factors, including specific requirement for staging a particular neoplastic disease, aggressiveness of growth of the neoplastic disease, ability of the microorganism to infect a tumor or metastasis, and immunocompetence of the subject. Generally the threshold stage will be a stage sufficient for a microorganism to accumulate and replicate in a tumor or metastasis without being completely removed by the host's immune system, and will typically also be a size sufficient to sustain a microorganismal infection for a time long enough for the host to mount an immune response against the neoplastic cells, typically about one week or more, about ten days or more, or about two weeks or more. Exemplary threshold stages are any stage beyond the lowest stage (e.g., Stage I or equivalent), or any stage where the primary tumor is larger than a threshold size, or any stage where metastatic cells are detected.

In other embodiments, prior to administering to the subject a microorganism, the immunocompetence of the subject can be determined. The methods of administering a microorganism to a subject provided herein can include causing or enhancing an immune response in a subject. Accordingly, prior to administering a microorganism to a subject, the ability of a subject to mount an immune response can be determined. Any of a variety of tests of immunocompetence known in the art can be performed in the methods provided herein. Exemplary immunocompetence tests can examine ABO hemagglutination titers (IgM), leukocyte adhesion deficiency (LAD), granulocyte function (NBT), T and B cell quantitation, tetanus antibody titers, salivary IgA, skin test, tonsil test, complement C3 levels, and factor B levels, and lymphocyte count. One skilled in the art can determine the desirability to administer a microorganism to a subject according to the level of immunocompetence of the subject, according to the immunogenicity of the microorganism, and, optionally, according to the immunogenicity of the neoplastic disease to be treated. Typically, a subject can be considered immunocompetent if the skilled artisan can determine that the subject is sufficiently competent to mount an immune response against the microorganism.

In some embodiments, the subject can be immunized prior to administering to the subject a microorganism according to the methods provided herein. Immunization can serve to increase the ability of a subject to mount an immune response against the microorganism, or increase the speed at which the subject can mount an immune response against a microorganism. Immunization also can serve to decrease the risk to the subject of pathogenicity of the microorganism. In some embodiments, the immunization can be performed with an immunization microorganism that is similar to the therapeutic microorganism to be administered. For example, the immunization microorganism can be a replication-incompetent variant of the therapeutic microorganism. In other embodiments, the immunization material can be digests of the therapeutic microorganism to be administered. Any of a variety of methods for immunizing a subject against a known microorganism are known in the art and can be used herein. In one example, vaccinia viruses treated with, for example, 1 microgram of psoralen and ultraviolet light at 365 nm for 4 minutes, can be rendered replication incompetent. In another embodiment, the microorganism can be selected as the same or similar to a microorganism against which the subject has been previously immunized, e.g., in a childhood vaccination.

In another embodiment, the subject can have administered thereto a microorganism without any previous steps of cancer treatment such as chemotherapy, radiation therapy or surgical removal of a tumor and/or metastases. The methods provided herein take advantage of the ability of the microorganisms to enter or localize near a tumor, where the tumor cells can be protected from the subject's immune system; the microorganisms can then proliferate in such an immunoprotected region and can also cause the release, typically a sustained release, of tumor antigens from the tumor to a location in which the subject's immune system can recognize the tumor antigens and mount an immune response. In such methods, existence of a tumor of sufficient size or sufficiently developed immunoprotected state can be advantageous for successful administration of the microorganism to the tumor, and for sufficient tumor antigen production. If a tumor is surgically removed, the microorganisms may not be able to localize to other neoplastic cells (e.g., small metastases) because such cells may not yet have matured sufficiently to create an immunoprotective environment in which the microorganisms can survive and proliferate, or even if the microorganisms can localize to neoplastic cells, the number of cells or size of the mass may be too small for the microorganisms to cause a sustained release of tumor antigens in order for the host to mount an anti-tumor immune response. Thus, for example, provided herein are methods of treating a tumor or neoplastic disease in which microorganisms are administered to a subject with a tumor or neoplastic disease without removing the primary tumor, or to a subject with a tumor or neoplastic disease in which at least some tumors or neoplastic cells are intentionally permitted to remain in the subject. In other typical cancer treatment methods such as chemotherapy or radiation therapy, such methods typically have a side effect of weakening the subject's immune system. This treatment of a subject by chemotherapy or radiation therapy can reduce the subject's ability to mount an anti-tumor immune response. Thus, for example, provided herein are methods of treating a tumor or neoplastic disease in which microorganisms are administered to a subject with a tumor or neoplastic disease without treating the subject with an immune system-weakening therapy, such as chemotherapy or radiation therapy.

In an alternative embodiment, prior to administration of a microorganism to the subject, the subject can be treated in one or more cancer treatment steps that do not remove the primary tumor or that do not weaken the immune system of the subject. A variety of more sophisticated cancer treatment methods are being developed in which the tumor can be treated without surgical removal or immune-system weakening therapy. Exemplary methods include administering a compound that decreases the rate of proliferation of the tumor or neoplastic cells without weakening the immune system (e.g., by administering tumor suppressor compounds or by administering tumor cell-specific compounds) or administering an angiogenesis-inhibiting compound. Thus, combined methods that include administering a microorganism to a subject can further improve cancer therapy. Thus, provided herein are methods of administering a microorganism to a subject, along with prior to or subsequent to, for example, administering a compound that slows tumor growth without weakening the subject's immune system or a compound that inhibits vascularization of the tumor.

b. Mode of Administration

Any mode of administration of a microorganism to a subject can be used, provided the mode of administration permits the microorganism to enter a tumor or metastasis. Modes of administration can include, but are not limited to, intravenous, intraperitoneal, subcutaneous, intramuscular, topical, intratumor, multipuncture (e.g., as used with smallpox vaccines), inhalation, intranasal, oral, intracavity (e.g., administering to the bladder via a catheter, administering to the gut by suppository or enema), aural, or ocular administration. One skilled in the art can select any mode of administration compatible with the subject and the microorganism, and that also is likely to result in the microorganism reaching tumors and/or metastases. The route of administration can be selected by one skilled in the art according to any of a variety of factors, including the nature of the disease, the kind of tumor, and the particular microorganism contained in the pharmaceutical composition. Administration to the target site can be performed, for example, by ballistic delivery, as a colloidal dispersion system, or systemic administration can be performed by injection into an artery.

c. Dosage

The dosage regimen can be any of a variety of methods and amounts, and can be determined by one skilled in the art according to known clinical factors. As is known in the medical arts, dosages for any one patient can depend on many factors, including the subject's species, size, body surface area, age, sex, immunocompetence, and general health, the particular microorganism to be administered, duration and route of administration, the kind and stage of the disease, for example, tumor size, and other compounds such as drugs being administered concurrently. In addition to the above factors, such levels can be affected by the infectivity of the microorganism, and the nature of the microorganism, as can be determined by one skilled in the art. At least some of the viruses used the in the methods provided herein can be more infectious than the bacteria used herein. Thus, in some embodiments of the present methods, virus can be administered at lower levels than bacteria. In the present methods, appropriate minimum dosage levels of microorganisms can be levels sufficient for the microorganism to survive, grow and replicate in a tumor or metastasis. Exemplary minimum levels for administering a virus to a 65 kg human can include at least about $5\times10^5$ plaque forming units (pfu), at least about $1\times10^6$ pfu, at least about $5\times10^6$ pfu, at least about $1\times10^7$ pfu, or at least about $1\times10^8$ pfu. Exemplary minimum levels for administering a bacterium to a 65 kg human can include at least about $5\times10^6$ colony forming units (cfu), at least about $1\times10^7$ cfu, at least about $5\times10^7$ cfu, at least about $1\times10^8$ cfu, or at least about $1\times10^9$ cfu. In the present methods, appropriate maximum dosage levels of microorganisms can be levels that are not toxic to the host, levels that do not cause splenomegaly of 3× or more, levels that do not result in colonies or plaques in normal tissues or organs after about 1 day or after about 3 days or after about 7 days. Exemplary maximum levels for administering a virus to a 65 kg human can include no more than about $5\times10^{10}$ pfu, no more than about $1\times10^{10}$ pfu, no more than about $5\times10^9$ pfu, no more than about $1\times10^9$ pfu, or no more than about $1\times10^8$ pfu. Exemplary maximum levels for administering a bacterium to a 65 kg human can include no more than about $5\times10^{11}$ pfu, no more than about $1\times10^{11}$ pfu, no more than about $5\times10^{10}$ pfu, no more than about $1\times10^{10}$ pfu, or no more than about $1\times10^9$ pfu.

d. Number of Administrations

The methods provided herein can include a single administration of a microorganism to a subject or multiple administrations of a microorganism to a subject. In some embodiments, a single administration is sufficient to establish a microorganism in a tumor, where the microorganism can proliferate and can cause or enhance an anti-tumor response in the subject; such methods do not require additional administrations of a microorganism in order to cause or enhance an anti-tumor response in a subject, which can result, for example in inhibition of tumor growth, inhibition of metastasis growth or formation, reduction in tumor or metastasis size, elimination of a tumor or metastasis, inhibition or prevention of recurrence of a neoplastic disease or new tumor formation, or other cancer therapeutic effects. In other embodiments, a microorganism can be administered on different occasions, separated in time typically by at least one day. Separate administrations can increase the likelihood of delivering a microorganism to a tumor or metastasis, where a previous administration may have been ineffective in delivering a microorganism to a tumor or metastasis. Separate administrations can increase the locations on a tumor or metastasis where microorganism proliferation can occur or can otherwise increase the titer of microorganism accumulated in the tumor, which can increase the scale of release of antigens or other compounds from the tumor in eliciting or enhancing a host's anti-tumor immune response, and also can, optionally, increase the level of microorganism-based tumor lysis or tumor cell death. Separate administrations of a microorganism can further extend a subject's immune response against microorganismal antigens, which can extend the host's immune response to tumors or metastases in which microorganisms have accumulated, and can increase the likelihood of a host mounting an anti-tumor immune response.

When separate administrations are performed, each administration can be a dosage amount that is the same or different relative to other administration dosage amounts. In one embodiment, all administration dosage amounts are the same. In other embodiments, a first dosage amount can be a larger dosage amount than one or more subsequent dosage amounts, for example, at least 10× larger, at least 100× larger, or at least 1000× larger than subsequent dosage amounts. In one example of a method of separate administrations in which the first dosage amount is greater than one or more subsequent dosage amounts, all subsequent dosage amounts can be the same, smaller amount relative to the first administration.

Separate administrations can include any number of two or more administrations, including two, three, four, five or six administrations. One skilled in the art can readily determine the number of administrations to perform or the desirability of performing one or more additional administrations according to methods known in the art for monitoring therapeutic methods and other monitoring methods provided herein. Accordingly, the methods provided herein include methods of providing to the subject one or more administrations of a microorganism, where the number of administrations can be determined by monitoring the subject, and, based on the results of the monitoring, determining whether or not to provide one or more additional administrations. Deciding on whether or not to provide one or more additional administrations can be based on a variety of monitoring results, including, but not limited to, indication of tumor growth or inhibition of tumor growth, appearance of new metastases or inhibition of metastasis, the subject's anti-microorganism antibody titer, the subject's anti-tumor antibody titer, the overall health of the subject, the weight of the subject, the presence of microorganism solely in tumor and/or metastases, the presence of microorganism in normal tissues or organs.

The time period between administrations can be any of a variety of time periods. The time period between administrations can be a function of any of a variety of factors, including monitoring steps, as described in relation to the number of administrations, the time period for a subject to mount an immune response, the time period for a subject to clear microorganism from normal tissue, or the time period for microorganismal proliferation in the tumor or metastasis. In one example, the time period can be a function of the time period for a subject to mount an immune response; for example, the time period can be more than the time period for a subject to mount an immune response, such as more than about one week, more than about ten days, more than about two weeks, or more than about a month; in another example, the time period can be less than the time period for a subject to mount an immune response, such as less than about one week, less than about ten days, less than about two weeks, or less than about a month. In another example, the time period can be a function of the time period for a subject to clear microorganism from normal tissue; for example, the time period can be more than the time period for a subject to clear microorganism from normal tissue, such as more than about a day, more than about two days, more than about three days, more than about five days, or more than about a week. In another example, the time period can be a function of the time period for microorganismal proliferation in the tumor or metastasis; for example, the time period can be more than the amount of time for a detectable signal to arise in a tumor or metastasis after administration of a microorganism expressing a detectable marker, such as about 3 days, about 5 days, about a week, about ten days, about two weeks, or about a month.

e. Co-administrations

Also provided are methods in which an additional therapeutic substance, such as a different therapeutic microorganism or a therapeutic compound is administered. These can be administered simultaneously, sequentially or intermittently with the first microorganism. The additional therapeutic substance can interact with the microorganism or a gene product thereof, or the additional therapeutic substance can act independently of the microorganism.

i. Administration of a Plurality of Microorganisms

Methods are provided for administering to a subject two or more microorganisms. Administration can be effected simultaneously, sequentially or intermittently. The plurality of microorganisms can be administered as a single composition or as two or more compositions. The two or more microorganisms can include at least two bacteria, at least two viruses, at least two eukaryotic cells, or two or more selected from among bacteria, viruses and eukaryotic cells. The plurality of microorganisms can be provided as combinations of compositions containing and/or as kits that include the microorganisms packaged for administration and optionally including instructions therefore. The compositions can contain the microorganisms formulated for single dosage administration (i.e., for direct administration) and can require dilution or other additions.

In one embodiment, at least one of the microorganisms is a modified microorganism such as those provided herein, having a characteristic such as low pathogenicity, low toxicity, preferential accumulation in tumor, ability to activate an immune response against tumor cells, immunogenic, replication competent, ability to express exogenous proteins, and combinations thereof. The microorganisms can be administered at approximately the same time, or can be administered at different times. The microorganisms can be administered in the same composition or in the same administration method, or can be administered in separate composition or by different administration methods.

In one example, a bacteria and a virus can be administered to a subject. The bacteria and virus can be administered at the same time, or at different times. For example, the virus can be administered prior to administering the bacteria, or the bacteria can be administered prior to administering the virus; typically the virus is administered prior to administering the bacteria. As provided herein, administering to a subject a virus prior to administering to the subject a bacterium can increase the amount of bacteria that can accumulate and/or proliferate in a tumor, relative to methods in which bacteria alone are administered.

Accordingly, the methods provided herein that include administration of virus prior to administration of bacteria permit the administration of a lower dosage amount of bacteria than would otherwise be administered in a method in which bacteria alone are administered or a method in which bacteria are administered at the same time as or prior to administration of a virus. For example, in some embodiments, a bacterium to be administered can have one or more properties that limit the ability of the bacterium to be used, such properties can include, but are not limited to toxicity, low tumor specificity of accumulation, and limited proliferation capacity. A bacterium to be administered that has one or more limiting properties can require administration in lower dosage amounts, or can require assistance in tumor-specific accumulation and/or proliferation. Provided herein are methods of administering such a bacterium with limiting properties, where prior to administering the bacterium, a virus is administered such that the limited bacterium can be administered in smaller quantities, can accumulate in tumor with increased specificity, and/or can have an increased ability to proliferate in a tumor.

The time period between administrations can be any time period that achieves the desired effects, as can be determined by one skilled in the art. Selection of a time period between administrations of different microorganisms can be determined according to parameters similar to those for selecting the time period between administrations of the same microorganism, including results from monitoring steps, the time period for a subject to mount an immune response, the time period for a subject to clear microorganism from normal tissue, or the time period for microorganismal proliferation in the tumor or metastasis. In one example, the time period can be a function of the time period for a subject to mount an immune response; for example, the time period can be more than the time period for a subject to mount an immune response, such as more than about one week, more than about ten days, more than about two weeks, or more than about a month; in another example, the time period can be less than the time period for a subject to mount an immune response, such as less than about one week, less than about ten days, less than about two weeks, or less than about a month. In another example, the time period can be a function of the time period for a subject to clear microorganism from normal tissue; for example, the time period can be more than the time period for a subject to clear microorganism from normal tissue, such as more than about a day, more than about two days, more than about three days, more than about five days, or more than about a week. In another example, the time period can be a function of the time period for microorganismal proliferation in the tumor or metastasis; for example, the time period can be more than the amount of time for a detectable signal to arise in a tumor or metastasis after administration of a microorganism expressing a detectable marker, such as about 3 days, about 5 days, about a week, about ten days, about two weeks, or about a month. In one example a virus can first be administered, and a bacteria can be administered about 5 days after administration of the virus. In another example, a virus can be first administered, and a bacterium can be administered upon detection of a virally-encoded detectable gene product in the tumor of the subject, optionally when the virally-encoded detectable gene product is detected only in the tumor of the subject.

ii. Therapeutic Compounds

The methods can include administering one or more therapeutic compounds to the subject in addition to administering a microorganism or plurality thereof to a subject. Therapeutic compounds can act independently, or in conjunction with the microorganism, for tumor therapeutic effects. Therapeutic compounds that can act independently include any of a variety of known chemotherapeutic compounds that can inhibit tumor growth, inhibit metastasis growth and/or formation, decrease the size of a tumor or metastasis, eliminate a tumor or metastasis, without reducing the ability of a microorganism to accumulate in a tumor, replicate in the tumor, and cause or enhance an anti-tumor immune response in the subject.

Therapeutic compounds that act in conjunction with the microorganisms include, for example, compounds that alter the expression of the microorganism or compounds that can interact with a microorganism-expressed gene, or compounds that can inhibit microorganismal proliferation, including compounds toxic to the microorganism. Therapeutic compounds that can act in conjunction with the microorganism include, for example, therapeutic compounds that increase the proliferation, toxicity, tumor cell killing, or immune response eliciting properties of a microorganism, and also can include, for example, therapeutic compounds that decrease the proliferation, toxicity, or cell killing properties of a microorganism. Thus, provided herein are methods of administering to a subject one or more therapeutic compounds that can act in conjunction with the microorganism to increase the proliferation, toxicity, tumor cell killing, or immune response eliciting properties of a microorganism. Also provided herein are methods of administering to a subject one or more therapeutic compounds that can act in conjunction with the microorganism to decrease the proliferation, toxicity, or cell killing properties of a microorganism.

In one embodiment, therapeutic compounds that can act in conjunction with the microorganism to increase the proliferation, toxicity, tumor cell killing, or immune response eliciting properties of a microorganism are compounds that can alter gene expression, where the altered gene expression can result in an increased killing of tumor cells or an increased anti-tumor immune response in the subject. A gene expression-altering compound can, for example, cause an increase or decrease in expression of one or more microorganismal genes, including endogenous microorganismal genes and/or exogenous microorganismal genes. For example, a gene expression-altering compound can induce or increase transcription of a gene in a microorganism such as an exogenous gene that can cause cell lysis or cell death, that can provoke an immune response, that can catalyze conversion of a prodrug-like compound, or that can inhibit expression of a tumor cell gene. Any of a wide variety of compounds that can alter gene expression are known in the art, including IPTG and RU486. Exemplary genes whose expression can be up-regulated include proteins and RNA molecules, including toxins, enzymes that can convert a prodrug to an anti-tumor drug, cytokines, transcription regulating proteins, siRNA, and ribozymes. In another example, a gene expression-altering compound can inhibit or decrease transcription of a gene in a microorganism such as an exogenous gene that can reduce microorganismal toxicity or reduces microorganismal proliferation. Any of a variety of compounds that can reduce or inhibit gene expression can be used in the methods provided herein, including siRNA compounds, transcriptional inhibitors or inhibitors of transcriptional activators. Exemplary genes whose expression can be down-regulated include proteins and RNA molecules, including microorganismal proteins or RNA that suppress lysis, nucleotide synthesis or proliferation, and cellular proteins or RNA molecules that suppress cell death, immunoreactivity, lysis, or microorganismal replication.

In another embodiment, therapeutic compounds that can act in conjunction with the microorganism to increase the proliferation, toxicity, tumor cell killing, or immune response eliciting properties of a microorganism are compounds that can interact with a microorganism-expressed gene product, and such interaction can result in an increased killing of tumor cells or an increased anti-tumor immune response in the subject. A therapeutic compound that can interact with a microorganism-expressed gene product can include, for example a prodrug or other compound that has little or no toxicity or other biological activity in its subject-administered form, but after interaction with a microorganism-expressed gene product, the compound can develop a property that results in tumor cell death, including but not limited to, cytotoxicity, ability to induce apoptosis, or ability to trigger an immune response. A variety of prodrug-like substances are known in the art and an exemplary set of such compounds are disclosed elsewhere herein, where such compounds can include gancyclovir, 5-fluorouracil, 6-methylpurine deoxyriboside, cephalosporin-doxorubicin, 4-[(2-chloroethyl)(2-mesuloxyethyl)amino]benzoyl-L-glutamic acid, acetominophen, indole-3-acetic acid, CB1954, 7-ethyl-10-[4-(1-piperidino)-1-piperidino]carbonyloxycamptothecin, bis-(2-chloroethyl)amino-4-hydroxyphenylaminomethanone 28, 1-chloromethyl-5-hydroxy-1,2-dihyro-3H-benz[e]indole, epirubicin-glucuronide, 5'-deoxy-5-fluorouridine, cytosine arabinoside, and linamarin.

In another embodiment, therapeutic compounds that can act in conjunction with the microorganism to decrease the proliferation, toxicity, or cell killing properties of a microorganism are compounds that can inhibit microorganismal replication, inhibit microorganismal toxins, or cause microorganismal death. A therapeutic compound that can inhibit microorganismal replication, inhibit microorganismal toxins, or cause microorganismal death can generally include a compound that can block one or more steps in the microorganismal life cycle, including, but not limited to, compounds that can inhibit microorganismal DNA replication, microorganismal RNA transcription, viral coat protein assembly, outer membrane or polysaccharide assembly. Any of a variety of compounds that can block one or more steps in a microorganismal life cycle are known in the art, including any known antibiotic, microorganismal DNA polymerase inhibitors, microorganismal RNA polymerase inhibitors, inhibitors of proteins that regulate microorganismal DNA replication or RNA transcription. In one example, when a microorganism is a bacteria, a compound can be an antibiotic. In another example, a microorganism can contain a gene encoding a microorganismal life cycle protein, such as DNA polymerase or RNA polymerase that can be inhibited by a compound that is, optionally, non-toxic to the host organism.

f. State of Subject

In another embodiment, the methods provided herein for administering a microorganism to a subject can be performed on a subject in any of a variety of states, including an anesthetized subject, an alert subject, a subject with elevated body temperature, a subject with reduced body temperature, or other state of the subject that is known to affect the accumulation of microorganism in the tumor. As provided herein, it has been determined that a subject that is anesthetized can have a decreased rate of accumulation of a microorganism in a tumor relative to a subject that is not anesthetized. Further provided herein, it has been determined that a subject with decreased body temperature can have a decreased rate of accumulation of a microorganism in a tumor relative to a subject with a normal body temperature. Accordingly, provided herein are methods of administering a microorganism to a subject, where the methods can include administering a microorganism to a subject where the subject is not under anesthesia, such as general anesthesia; for example, the subject can be under local anesthesia, or can be unanesthetized. Also provided herein are methods of administering a microorganism to a subject, where the methods can include administering a microorganism to a subject with altered body temperature, where the alteration of the body temperature can influence the ability of the microorganism to accumulate in a tumor; typically, a decrease in body temperature can decrease the ability of a microorganism to accumulate in a tumor. Thus, in one exemplary embodiment, a method is provided for administering a microorganism to a subject, where the method includes elevating the body temperature of the subject to a temperature above normal, and administering a microorganism to the subject, where the microorganism can accumulate in the tumor more readily in the subject with higher body temperature relative to the ability of the microorganism to accumulate in a tumor of a subject with a normal body temperature.

2. Monitoring

The methods provided herein can further include one or more steps of monitoring the subject, monitoring the tumor, and/or monitoring the microorganism administered to the subject. Any of a variety of monitoring steps can be included in the methods provided herein, including, but not limited to, monitoring tumor size, monitoring anti-(tumor antigen) antibody titer, monitoring the presence and/or size of metastases, monitoring the subject's lymph nodes, monitoring the subject's weight or other health indicators including blood or urine markers, monitoring anti-(microorganismal antigen) antibody titer, monitoring microorganismal expression of a detectable gene product, and directly monitoring microorganismal titer in a tumor, tissue or organ of a subject.

The purpose of the monitoring can be simply for assessing the health state of the subject or the progress of therapeutic treatment of the subject, or can be for determining whether or not further administration of the same or a different microorganism is warranted, or for determining when or whether or not to administer a compound to the subject where the compound can act to increase the efficacy of the therapeutic method, or the compound can act to decrease the pathogenicity of the microorganism administered to the subject.

a. Monitoring Microorganismal Gene Expression

In some embodiments, the methods provided herein can include monitoring one or more microorganismally expressed genes. Microorganisms, such as those provided herein or otherwise known in the art, can express one or more detectable gene products, including but not limited to, detectable proteins.

As provided herein, measurement of a detectable gene product expressed in a microorganism can provide an accurate determination of the level of microorganism present in the subject. As further provided herein, measurement of the location of the detectable gene product, for example, by imaging methods including tomographic methods, can determine the localization of the microorganism in the subject. Accordingly, the methods provided herein that include monitoring a detectable microorganismal gene product can be used to determine the presence or absence of the microorganism in one or more organs or tissues of a subject, and/or the presence or absence of the microorganism in a tumor or metastases of a subject. Further, the methods provided herein that include monitoring a detectable microorganismal gene product can be used to determine the titer of microorganism present in one or more organs, tissues, tumors or metastases. Methods that include monitoring the localization and/or titer of microorganisms in a subject can be used for determining the pathogenicity of a microorganism; since microorganismal infection, and particularly the level of infection, of normal tissues and organs can indicate the pathogenicity of the probe, methods of monitoring the localization and/or amount of microorganisms in a subject can be used to determine the pathogenicity of a microorganism. Since methods provided herein can be used to monitor the amount of microorganisms at any particular location in a subject, the methods that include monitoring the localization and/or titer of microorganisms in a subject can be performed at multiple time points, and, accordingly can determine the rate of microorganismal replication in a subject, including the rate of microorganismal replication in one or more organs or tissues of a subject; accordingly, the methods of monitoring a microorganismal gene product can be used for determining the replication competence of a microorganism. The methods provided herein also can be used to quantitate the amount of microorganism present in a variety of organs or tissues, and tumors or metastases, and can thereby indicate the degree of preferential accumulation of the microorganism in a subject; accordingly, the microorganismal gene product monitoring methods provided herein can be used in methods of determining the ability of a microorganism to accumulate in tumor or metastases in preference to normal tissues or organs. Since the microorganisms used in the methods provided herein can accumulate in an entire tumor or can accumulate at multiple sites in a tumor, and can also accumulate in metastases, the methods provided herein for monitoring a microorganismal gene product can be used to determine the size of a tumor or the number of metastases are present in a subject. Monitoring such presence of microorganismal gene product in tumor or metastasis over a range of time can be used to assess changes in the tumor or metastasis, including growth or shrinking of a tumor, or development of new metastases or disappearance of metastases, and also can be used to determine the rate of growth or shrinking of a tumor, or development of new metastases or disappearance of metastases, or the change in the rate of growth or shrinking of a tumor, or development of new metastases or disappearance of metastases. Accordingly, the methods of monitoring a microorganismal gene product can be used for monitoring a neoplastic disease in a subject, or for determining the efficacy of treatment of a neoplastic disease, by determining rate of growth or shrinking of a tumor, or development of new metastases or disappearance of metastases, or the change in the rate of growth or shrinking of a tumor, or development of new metastases or disappearance of metastases.

Any of a variety of detectable proteins can be detected in the monitoring methods provided herein; an exemplary, non-limiting list of such detectable proteins includes any of a variety of fluorescence proteins (e.g., green fluorescence proteins), any of a variety of luciferases, transferrin or other iron binding proteins; or receptors, binding proteins, and antibodies, where a compound that specifically binds the receptor, binding protein or antibody can be a detectable agent or can be labeled with a detectable substance (e.g., a radionuclide or imaging agent).

b. Monitoring Tumor Size

Also provided herein are methods of monitoring tumor and/or metastasis size and location. Tumor and/or metastasis size can be monitored by any of a variety of methods known in the art, including external assessment methods or tomographic or magnetic imaging methods. In addition to the methods known in the art, methods provided herein, for example, monitoring microorganismal gene expression, can be used for monitoring tumor and/or metastasis size.

Monitoring size over several time points can provide information regarding the increase or decrease in size of a tumor or metastasis, and can also provide information regarding the presence of additional tumors and/or metastases in the subject. Monitoring tumor size over several time points can provide information regarding the development of a neoplastic disease in a subject, including the efficacy of treatment of a neoplastic disease in a subject.

c. Monitoring Antibody Titer

The methods provided herein also can include monitoring the antibody titer in a subject, including antibodies produced in response to administration of a microorganism to a subject. The microorganisms administered in the methods provided herein can elicit an immune response to endogenous microorganismal antigens. The microorganisms administered in the methods provided herein also can elicit an immune response to exogenous genes expressed by a microorganism. The microorganisms administered in the methods provided herein also can elicit an immune response to tumor antigens. Monitoring antibody titer against microorganismal antigens, microorganismally expressed exogenous gene products, or tumor antigens can be used in methods of monitoring the toxicity of a microorganism, monitoring the efficacy of treatment methods, or monitoring the level of gene product or antibodies for production and/or harvesting.

In one embodiment, monitoring antibody titer can be used to monitor the toxicity of a microorganism. Antibody titer against a microorganism can vary over the time period after administration of the microorganism to the subject, where at some particular time points, a low anti-(microorganismal antigen) antibody titer can indicate a higher toxicity, while at other time points a high anti-(microorganismal antigen) antibody titer can indicate a higher toxicity. The microorganisms used in the methods provided herein can be immunogenic, and can, therefore, elicit an immune response soon after administering the microorganism to the subject. Generally, a microorganism against which a subject's immune system can quickly mount a strong immune response can be a microorganism that has low toxicity when the subject's immune system can remove the microorganism from all normal organs or tissues. Thus, in some embodiments, a high antibody titer against microorganismal antigens soon after administering the microorganism to a subject can indicate low toxicity of a microorganism. In contrast, a microorganism that is not highly immunogenic may infect a host organism without eliciting a strong immune response, which can result in a higher toxicity of the microorganism to the host. Accordingly, in some embodiments, a high antibody titer against microorganismal antigens soon after administering the microorganism to a subject can indicate low toxicity of a microorganism.

In other embodiments, monitoring antibody titer can be used to monitor the efficacy of treatment methods. In the methods provided herein, antibody titer, such as anti-(tumor antigen) antibody titer, can indicate the efficacy of a therapeutic method such as a therapeutic method to treat neoplastic disease. Therapeutic methods provided herein can include causing or enhancing an immune response against a tumor and/or metastasis. Thus, by monitoring the anti-(tumor antigen) antibody titer, it is possible to monitor the efficacy of a therapeutic method in causing or enhancing an immune response against a tumor and/or metastasis. The therapeutic methods provided herein also can include administering to a subject a microorganism that can accumulate in a tumor and can cause or enhance an anti-tumor immune response. Accordingly, it is possible to monitor the ability of a host to mount an immune response against microorganisms accumulated in a tumor or metastasis, which can indicate that a subject has also mounted an anti-tumor immune response, or can indicate that a subject is likely to mount an anti-tumor immune response, or can indicate that a subject is capable of mounting an anti-tumor immune response.

In other embodiments, monitoring antibody titer can be used for monitoring the level of gene product or antibodies for production and/or harvesting. As provided herein, methods can be used for producing proteins, RNA molecules or other compounds by expressing an exogenous gene in a microorganism that has accumulated in a tumor. Further provided herein are methods for producing antibodies against a protein, RNA molecule or other compound produced by exogenous gene expression of a microorganism that has accumulated in a tumor. Monitoring antibody titer against the protein, RNA molecule or other compound can indicate the level of production of the protein, RNA molecule or other compound by the tumor-accumulated microorganism, and also can directly indicate the level of antibodies specific for such a protein, RNA molecule or other compound.

d. Monitoring General Health Diagnostics

The methods provided herein also can include methods of monitoring the health of a subject. Some of the methods provided herein are therapeutic methods, including neoplastic disease therapeutic methods. Monitoring the health of a subject can be used to determine the efficacy of the therapeutic method, as is known in the art. The methods provided herein also can include a step of administering to a subject a microorganism. Monitoring the health of a subject can be used to determine the pathogenicity of a microorganism administered to a subject. Any of a variety of health diagnostic methods for monitoring disease such as neoplastic disease, infectious disease, or immune-related disease can be monitored, as is known in the art. For example, the weight, blood pressure, pulse, breathing, color, temperature or other observable state of a subject can indicate the health of a subject. In addition, the presence or absence or level of one or more components in a sample from a subject can indicate the health of a subject. Typical samples can include blood and urine samples, where the presence or absence or level of one or more components can be determined by performing, for example, a blood panel or a urine panel diagnostic test. Exemplary components indicative of a subject's health include, but are not limited to, white blood cell count, hematocrit, c-reactive protein concentration.

e. Monitoring Coordinated with Treatment

Also provided herein are methods of monitoring a therapy, where therapeutic decisions can be based on the results of the monitoring. Therapeutic methods provided herein can include administering to a subject a microorganism, where the microorganism can preferentially accumulate in a tumor and/or metastasis, and where the microorganism can cause or enhance an anti-tumor immune response. Such therapeutic methods can include a variety of steps including multiple administrations of a particular microorganism, administration of a second microorganism, or administration of a therapeutic compound. Determination of the amount, timing or type of microorganism or compound to administer to the subject can be based on one or more results from monitoring the subject. For example, the antibody titer in a subject can be used to determine whether or not it is desirable to administer a microorganism or compound, the quantity of microorganism or compound to administer, and the type of microorganism or compound to administer, where, for example, a low antibody titer can indicate the desirability of administering additional microorganism, a different microorganism, or a therapeutic compound such as a compound that induces microorganismal gene expression. In another example, the overall health state of a subject can be used to determine whether or not it is desirable to administer a microorganism or compound, the quantity of microorganism or compound to administer, and the type of microorganism or compound to administer, where, for example, determining that the subject is healthy can indicate the desirability of administering additional microorganism, a different microorganism, or a therapeutic compound such as a compound that induces microorganismal gene expression. In another example, monitoring a detectable microorganismally expressed gene product can be used to determine whether or not it is desirable to administer a microorganism or compound, the quantity of microorganism or compound to administer, and the type of microorganism or compound to administer. Such monitoring methods can be used to determine whether or not the therapeutic method is effective, whether or not the therapeutic method is pathogenic to the subject, whether or not the microorganism has accumulated in a tumor or metastasis, and whether or not the microorganism has accumulated in normal tissues or organs. Based on such determinations, the desirability and form of further therapeutic methods can be derived.

In one embodiment, determination of whether or not a therapeutic method is effective can be used to derive further therapeutic methods. Any of a variety of methods of monitoring can be used to determine whether or not a therapeutic method is effective, as provided herein or otherwise known in the art. If monitoring methods indicate that the therapeutic method is effective, a decision can be made to maintain the current course of therapy, which can include further administrations of a microorganism or compound, or a decision can be made that no further administrations are required. If monitoring methods indicate that the therapeutic method is ineffective, the monitoring results can indicate whether or not a course of treatment should be discontinued (e.g., when a microorganism is pathogenic to the subject), or changed (e.g., when a microorganism accumulates in a tumor without harming the host organism, but without eliciting an anti-tumor immune response), or increased in frequency or amount (e.g., when little or no microorganism accumulates in tumor).

In one example, monitoring can indicate that a microorganism is pathogenic to a subject. In such instances, a decision can be made to terminate administration of the microorganism to the subject, to administer lower levels of the microorganism to the subject, to administer a different microorganism to a subject, or to administer to a subject a compound that reduces the pathogenicity of the microorganism. In one example, administration of a microorganism that is determined to be pathogenic can be terminated. In another example, the dosage amount of a microorganism that is determined to be pathogenic can be decreased for subsequent administration; in one version of such an example, the subject can be pre-treated with another microorganism that can increase the ability of the pathogenic microorganism to accumulate in tumor, prior to re-administering the pathogenic microorganism to the subject. In another example, a subject can have administered thereto a bacteria or virus that is pathogenic to the subject; administration of such a pathogenic microorganism can be accompanied by administration of, for example an antibiotic, anti-microorganismal compound, pathogenicity attenuating compound (e.g., a compound that down-regulates the expression of a lytic or apoptotic gene product), or other compound that can decrease the proliferation, toxicity, or cell killing properties of a microorganism, as described herein elsewhere. In one variation of such an example, the localization of the microorganism can be monitored, and, upon determination that the microorganism is accumulated in tumor and/or metastases but not in normal tissues or organs, administration of the antibiotic, anti-microorganismal compound or pathogenicity attenuating compound can be terminated, and the pathogenic activity of the microorganism can be activated or increased, but limited to the tumor and/or metastasis. In another variation of such an example, after terminating administration of an antibiotic, anti-microorganismal compound or pathogenicity attenuating compound, the presence of the microorganism and/or pathogenicity of the microorganism can be further monitored, and administration of such a compound can be reinitiated if the microorganism is determined to pose a threat to the host by, for example, spreading to normal organs or tissues, releasing a toxin into the vasculature, or otherwise having pathogenic effects reaching beyond the tumor or metastasis.

In another example, monitoring can determine whether or not a microorganism has accumulated in a tumor or metastasis of a subject. Upon such a determination, a decision can be made to further administer additional microorganism, a different microorganism or a compound to the subject. In one example, monitoring the presence of a virus in a tumor or metastasis can be used in deciding to administer to the subject a bacterium, where, for example, the quantity of bacteria administered can be reduced according to the presence and/or quantity of virus in a tumor or metastasis. In a similar example, monitoring the presence of a virus in a tumor or metastasis can be used in deciding when to administer to the subject a bacterium, where, for example, the bacteria can be administered upon detecting to the presence and/or a selected quantity of virus in a tumor or metastasis. In another example, monitoring the presence of a microorganism in a tumor can be used in deciding to administer to the subject a compound, where the compound can increase the pathogenicity, proliferation, or immunogenicity of a microorganism or the compound can otherwise act in conjunction with the microorganism to increase the proliferation, toxicity, tumor cell killing, or immune response eliciting properties of a microorganism; in one variation of such an example, the microorganism can, for example have little or no lytic or cell killing capability in the absence of such a compound; in a further variation of such an example, monitoring of the presence of the microorganism in a tumor or metastasis can be coupled with monitoring the absence of the microorganism in normal tissues or organs, where the compound is administered if the microorganism is present in tumor or metastasis and not at all present or substantially not present in normal organs or tissues; in a further variation of such an example, the amount of microorganism in a tumor or metastasis can be monitored, where the compound is administered if the microorganism is present in tumor or metastasis at sufficient levels.

E. Methods Of Producing Gene Products And Antibodies

Provided herein are microorganisms, and methods for making and using such microorganisms for production products of exogenous genes and/or for production of antibodies specific for exogenous gene products. The methods provided herein result in efficient recombinant production of biologically active proteins. In EP A1 1 281 772, it is disclosed that when vaccinia virus (LIVP strain) carrying the light emitting fusion gene construct rVV-ruc-gfp (RVGL9) was injected intravenously into nude mice, the virus particles were found to be cleared from all internal organs within 4 days, as determined by extinction of light emission. In contrast, when the fate of the injected vaccinia virus was similarly followed in nude mice bearing tumors grown from subcutaneously implanted C6 rat glioma cells, virus particles were found to be retained over time in the tumor tissues, resulting in lasting light emission. The presence and amplification of the virus-encoded fusion proteins in the same tumor were monitored in live animals by observing GFP fluorescence under a stereomicroscope and by detecting luciferase-catalyzed light emission under a low-light video-imaging camera. Tumor-specific light emission was detected 4 days after viral injection in nude mice carrying subcutaneous C6 glioma implants. Tumor accumulation of rVV-ruc-gfp (RVGL9) virus particles was also seen in nude mice carrying subcutaneous tumors developed from implanted PC-3 human prostate cells, and in mice with orthotopically implanted MCF-7 human breast tumors. Further, intracranial C6 rat glioma cell implants in immunocompetent rats and MB-49 human bladder tumor cell implants in C57 mice were also targeted by the vaccinia virus. In addition to primary breast tumors, small metastatic tumors were also detected externally in the contralateral breast region, as well as in nodules on the exposed lung surface, suggesting metastasis to the contralateral breast and lung. In summary it was shown that light-emitting cells or microorganisms, for example, vaccinia virus can be used to detect and treat metastatic tumors.

Similar results were obtained with light-emitting bacteria (*Salmonella, Vibrio, Listeria, E. coli*) which were injected intravenously into mice and which could be visualized in whole animals under a low light imager immediately. No light emission was detected twenty four hours after bacterial injection in both athymic (nu/nu) mice and immunocompetent C57 mice as a result of clearing by the immune system. In nude mice bearing tumors developed from implanted C6 glioma cells, light emission was abolished from the animal entirely twenty four hours after delivery of bacteria, similar to mice without tumors. However, forty eight hours post-injection, a strong, rapidly increasing light emission originated only from the tumor regions was observed. This observation indicated a continuous bacterial replication in the tumor tissue. The extent of light emission was dependent on the bacterial strain used. The homing-in process together with the sustained light emission was also demonstrated in nude mice carrying prostate, bladder, and breast tumors. In addition to primary tumors, metastatic tumors could also be visualized as exemplified in the breast tumor model. Tumor-specific light emission was also observed in immunocompetent C57 mice, with bladder tumors as well as in Lewis rats with brain glioma implants. Once in the tumor, the light-emitting bacteria were not observed to be released into the circulation and to re-colonize subsequently implanted tumors in the same animal. Further, mammalian cells expressing the Ruc-GFP fusion protein, upon injection into the bloodstream, were also found to home in to, and propagate in, glioma tumors. These findings opened the way for designing multifunctional viral vectors useful for the detection of tumors based on signals such as light emission, for suppression of tumor development and angiogenesis signaled by, for example, light extinction and the development of bacterial and mammalian cell-based tumor targeting systems in combination with therapeutic gene constructs for the treatment of cancer. These systems have the following advantages: (a) They target the tumor specifically without affecting normal tissue; (b) the expression and secretion of the therapeutic gene constructs can be, optionally, under the control of an inducible promoter enabling secretion to be switched on or off; and (c) the location of the delivery system inside the tumor can be verified by direct visualization before activating gene expression and protein delivery.

As provided herein, the system described above based on the accumulation of bacteria, viruses and eukaryotic cells in tumors can be used for simple, quick, and inexpensive production of proteins and other biological compounds originating from cloned nucleotide sequences. This system also is useful for the concomitant overproduction of polypeptides, RNA or other biological compounds (in tumor tissue) and antibodies against those compounds (in the serum) in the same animal. As provided herein, after intravenous injection, a microorganism such as vaccinia virus can enter the tumor of an animal and, due to the immunoprivileged state of the tumor, can replicate preferentially in the tumor tissues and thereby can overproduce the inserted gene encoded protein in the tumors. After harvesting the tumor tissues, the localized and overexpressed protein can be isolated by a simple procedure from tumor homogenates. In addition, based on the findings that only 0.2 to 0.3% of the desired proteins produced in the tumor were found in the blood stream of the same animal, a simultaneous vaccination of the mouse and efficient antibody production against the overproduced protein was achieved. Thus, serum from the same mouse (or any other animal) can be harvested and used as mouse-derived antibodies against the proteins or other products overproduced in the tumor.

Thus, provided herein are methods of producing gene products and or antibodies in a non-human subject, by administering to a subject containing a tumor, a microorganism, where the microorganism expresses a selected protein or RNA to be produced, a protein or RNA whose expression can result in the formation of a compound to be produced, or a selected protein or RNA against which an antibody is to be produced. The methods provided herein can further include administering to a subject containing a tumor, a microorganism expressing an exogenous gene encoding a selected protein or RNA to be produced, a protein or RNA whose expression can result in the formation of a compound to be produced, or a selected protein or RNA against which an antibody is to be produced. The methods provided herein can further include administering to a subject containing a tumor, a microorganism expressing a gene encoding a selected protein or RNA to be produced, a protein or RNA whose expression can result in the formation of a compound to be produced, or a selected protein or RNA against which an antibody is to be produced, where such gene expression can be regulated, for example, by a transcriptional activator or inducer, or a transcriptional suppressor. The methods provided herein for producing a protein, RNA, compound or antibody can further include monitoring the localization and/or level of the microorganism in the subject by detecting a detectable protein, where the detectable protein can indicate the expression of the selected gene, or can indicate the readiness of the microorganism to be induced to express the selected gene or for suppression of expression to be terminated or suspended. Also provided herein are methods of producing gene products and or antibodies in a non-human subject, by administering to a subject containing a tumor, a microorganism, where the microorganism expresses a selected protein or RNA to be produced, a protein or RNA whose expression can result in the formation of a compound to be produced, or a selected protein or RNA against which an antibody is to be produced, where the subject to which the microorganism is administered is not a transgenic animal. Also provided herein are methods of producing gene products and or antibodies in a non-human subject, by administering to a subject containing a tumor, a microorganism, where the microorganism expresses a selected protein to be produced, where the tumor within the subject is selected according to its ability to post-translationally process the selected protein.

The advantages of the system, include:

(a) No production of a transgenic animal carrying the novel polypeptide-encoding cassette is required;
(b) the tumor system is more efficient than tissue culture;
(c) proteins interfering with animal development and other toxic proteins can be overproduced in tumors without negative effects to the host animal;
(d) the system is fast: within 4 to 6 weeks from cDNA cloning to protein and antisera purification;
(e) the system is relatively inexpensive and can be scaled up easily;
(f) correct protein folding and modifications can be achieved;
(g) high antigenicity can be achieved, which is beneficial for better antibody production; and
(h) species-specific-cell-based production of proteins in animals such as mice, with tumors as fermentors can be achieved.

Figure 2:
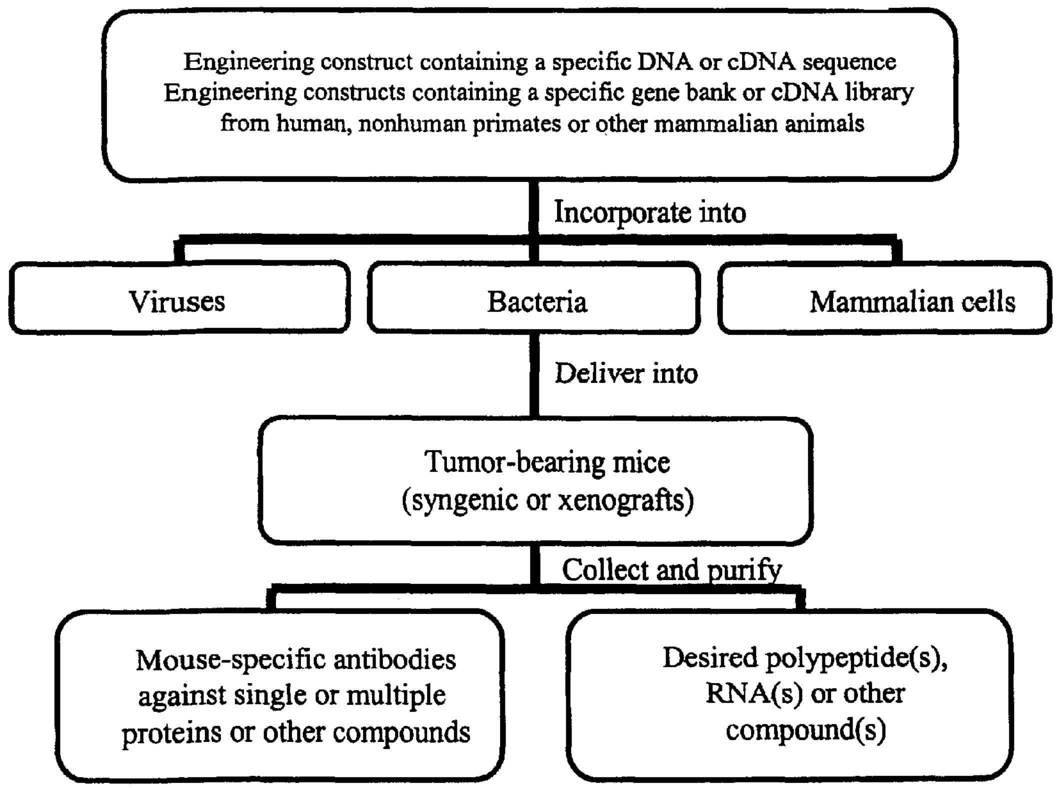
FIG. 2 sets forth a flow chart for a method for producing products, such as nucleic acid molecules, proteins and metabolic compounds or other cellular products in tumors.

Depiction of an exemplary method for production of gene products and/or antibodies against gene products is provided in FIG. 2.

In one embodiment, methods are provided for producing a desired polypeptide, RNA or compound, the method including the following steps: (a) injecting a microorganism containing a nucleotide sequence encoding the desired polypeptide or RNA into an animal bearing a tumor; (b) harvesting the tumor tissue from the animal; and (c) isolating the desired polypeptide, RNA or compound from the tumor tissue.

Steps of an exemplary method can be summarized as follows (shown for a particular embodiment, i.e. vaccinia virus additionally containing a gene encoding a light-emitting protein):

(1) Insertion of the desired DNA or cDNA into the vaccinia virus genome;
(2) modification of the vaccinia virus genome with light-emitting protein construct as expression marker;
(3) recombination and virus assembly in cell culture;

(4) screening of individual viral particles carrying inserts followed by large scale virus production and concentration;

(5) administration of the viral particles into mice or other animals bearing tumors of human, non-human primate or other mammalian origins;

(6) verification of viral replication and protein overproduction in animals based on light emission;

(7) harvest of tumor tissues and, optionally, the blood (separately); and (8) purification of overexpressed proteins from tumors and, optionally, antisera from blood using conventional methods.

Any microorganism can be used in the methods provided herein, provided that they replicate in the animal, are not pathogenic for the animal, for example, are attenuated, and are recognized by the immune system of the animal. In some embodiments, such microorganisms also can express exogenous genes. Suitable microorganisms and cells are, for example, disclosed in EP A1 1 281 772 and EP A1 1 281 767. The person skilled in the art also knows how to generate animals carrying the desired tumor (see, e.g., EP A1 1 281 767 or EP A1 1 281 777).

Also provided is a method for simultaneously producing a desired polypeptide, RNA or compound and an antibody directed to the polypeptide, RNA or compound, the method having the following steps: (a) administering a microorganism containing a nucleotide sequence encoding the desired polypeptide or RNA into an animal bearing a tumor; (b) harvesting the tumor tissue from the animal; (c) isolating the desired polypeptide, RNA or compound from the tumor tissue; and (d) isolating the antibody directed to the polypeptide, RNA or compound from the serum obtained from the animal. This approach can be used for generating polypeptides and/or antibodies against the polypeptides which are toxic or unstable, or which require species specific cellular environment for correct folding or modifications.

In another embodiment, the microorganism can further contain a nucleotide sequence encoding a detectable protein, such as a luminescent or fluorescent protein, or a protein capable of inducing a detectable signal.

Typically in methods for transfecting the microorganisms or cells with nucleotide sequences encoding the desired polypeptide or RNA and, optionally, a nucleotide sequence encoding a detectable protein such as a luminescent or fluorescent protein, or a protein capable of inducing a detectable signal, the nucleotide sequences are present in a vector or an expression vector. A person skilled in the art is familiar with a variety of expression vectors, which can be selected according to the microorganism used to infect the tumor, the cell type of the tumor, the organism to be infected, and other factors known in the art. In some embodiments, the microorganism can be a virus, including the viruses disclosed herein. Thus, the nucleotide sequences can be contained in a recombinant virus containing appropriate expression cassettes. Suitable viruses for use herein, include, but are not limited to, baculovirus, vaccinia, Sindbis virus, Sendai virus, adenovirus, an AAV virus or a parvovirus, such as MVM or H-1. The vector can also be a retrovirus, such as MoMULV, MoMuLV, HaMuSV, MuMTV, RSV or GaLV. For expression in mammalian cells, a suitable promoter is, for example, human cytomegalovirus immediate early promoter (pCMV). Furthermore, tissue and/or organ specific promoters can be used. For example, the nucleotide sequences can be operatively linked with a promoter allowing high expression. Such promoters can include, for example, inducible promoters; a variety of such promoters are known to persons skilled in the art.

For generating protein or RNA-encoding nucleotide sequences and for constructing expression vectors or viruses that contain the nucleotide sequences, it is possible to use general methods known in the art. These methods include, for example, in vitro recombination techniques, synthetic methods and in vivo recombination methods as known in the art, and exemplified in Sambrook et al., Molecular Cloning, A Laboratory Manual, 2nd edition (1989) Cold Spring Harbor Laboratory Press, Cold Spring Harbor, N.Y. Methods of transfecting cells, of phenotypically selecting transfectants cells, of phenotypically selecting transfectants and of expressing the nucleotide sequences by using vectors containing protein or RNA-encoding DNA are known in the art.

In some embodiments, the protein or RNA to be produced in the tumor can be linked to an inducible promoter, such as a promoter that can be induced by a substance endogenous to the subject, or by a substance that can be administered to a subject. Accordingly, provided herein are methods of producing a protein or RNA in a tumor, where the production can be induced by administration of a substance to a subject, and, optionally, harvesting the tumor and isolating the protein or RNA from the tumor. Such induction methods can be coupled with methods of monitoring a microorganism in a subject. For example, a microorganism can be monitored by detecting a detectable protein. In methods that include monitoring, detection of a desired localization and/or level of microorganism in the subject can be coordinated with induction of microorganismal gene expression. For example, when a microorganismally expressed detectable protein is detected in tumor, but not appreciably in normal organs or tissues, an inducer can be administered to the subject. In another example, when a microorganismally expressed detectable protein is detected in tumor, and also in normal organs or tissues, administration of an inducer can be suspended or postponed until the detectable protein is no longer detected in normal organs or tissues. In another example, when a microorganismally expressed detectable protein is detected at sufficient levels in tumor, an inducer can be administered to the subject. In another example, when a microorganismally expressed detectable protein is not detected at sufficient levels in tumor administration of an inducer can be suspended or postponed until the detectable protein is detected at sufficient levels in the tumor.

Also provided herein are methods of producing a protein or RNA in a tumor, by administering a microorganism encoding the protein or RNA, and a suppressor of gene expression. The suppressor of gene expression can be administered for a pre-defined period of time, or until the microorganism accumulated in tumor but not in normal organs or tissues, or until sufficient levels of the microorganism have accumulated in the tumor, at which point administration of the suppressor can be terminated or suspended, which can result in expression of the protein or RNA. As will be recognized by one skilled in the art, methods similar to those provided herein in regard to monitoring a detectable protein and administering an inducer, can also apply for terminating or suspending administration of a suppressor.

In one embodiment, the microorganism is a bacterium, for example, an attenuated bacterium, such as those provided herein. Exemplary bacteria include attenuated *Salmonella typhimurium*, attenuated *Vibrio cholerae*, attenuated *Listeria monocytogenes* or *E. coli*. Alternatively, viruses such as vaccinia virus, AAV, a retrovirus can be used in the methods provided herein. In exemplary methods, the virus is vaccinia virus. Other cells that can be used in the present methods include mammalian cells, such as fibroma cells, including human cells such as human fibroma cells.

Any of a variety of animals, including laboratory or livestock animals can be used, including for example, mice, rats and other rodents, rabbits, guinea pigs, pigs, sheep, goats, cows and horses. Exemplary animals are mice. The tumor can be generated by implanting tumor cells into the animal. Generally, for the production of a desired polypeptide, RNA, or compound, any solid tumor type can be used, such as a fast growing tumor type. Exemplary fast growing tumor types include C6 rat glioma and HCT116 human colon carcinoma. Generally, for the production of a desired antibody, a relatively slow growing tumor type can be used. Exemplary slow growing tumor types include HT1080 human fibrosarcoma and GI-101A human breast carcinoma. For T-independent antibody production, nu−/nu− mice bearing allogenic tumor or xenografts can be used; while for T-dependent antibody production, immunocompetent mice with syngenic tumors can be used. In some embodiments, such as where the compound to be produced is a protein, the microorganism selected can be a microorganism that uses the translational components (e.g., proteins, vesicles, substrates) of the tumor cells, such as, for example, a virus that uses the translational components of a tumor cell. In such instances, the tumor cell type can be selected according to the desired post-translational processing to be performed on the protein, including proteolysis, glycosylation, lipidylation, disulfide formation, and any refolding or multimer assembly that can require cellular components for completing. In some examples, the tumor cell type selected can be the same species as the protein to be expressed, thus resulting in species-specific post-translational processing of the protein; an exemplary tumor cell type-expressed protein species is human.

1. Production of Recombinant Proteins and RNA Molecules

The tumor tissue can be surgically removed from the animal. After homogenization of the tumor tissue, the desired polypeptide, RNA or other biological compound can be purified according to established methods. For example, in the case of a recombinant polypeptide, the polypeptide might contain a bindable tag such as a his-tag, and can be purified, for example, via column chromatography. The time necessary for accumulation of sufficient amounts of the polypeptide or RNA in the tumor of the animal depends on many factors, for example, the kind of animal or the kind of tumor, and can be determined by the skilled person by routine experimentation. In general, expression of the desired polypeptide can be detected two days after virus injection. The expression peaks approximately two weeks after injection, and lasts up to two months. In some embodiments, the amount of desired polypeptide or RNA in the tumor can be determined by monitoring a microorganismally expressed detectable substance, where the concentration of the detectable substance can reflect the amount of desired polypeptide or RNA in the tumor.

In another embodiment, the desired polypeptide, RNA or other compound can be manufactured in the subject, and provide a beneficial effect to the subject. In one example, a microorganism can encode a protein or RNA, or a protein that manufactures a compound that is not manufactured by the subject. In one example, a microorganism can encode a peptide hormone or cytokine, such as insulin, which can be released into the vasculature of a subject lacking the ability to produce insulin or requiring increased insulin concentrations in the vasculature. In another example, blood clotting factors can be manufactured in a subject with blood clotting deficiency, such as a hemophiliac. In some embodiments, the protein or RNA to be produced in the tumor can be linked to an inducible promoter, such as a promoter that can be induced by increased glucose concentrations. In such instances, the manufacture of the protein or RNA can be controlled in response to one or more substances in the subject or by one or more substances that can be administered to a subject, such as a compound that can induce transcription, for example, RU486. Thus, in some embodiments, the methods provided herein can include administering to a subject having a tumor, a microorganism that can express one or more genes encoding a beneficial gene product or a gene product that can manufacture a beneficial compound.

2. Production of Antibodies

Also provided are methods for producing a desired antibody, the method comprising the following steps: (a) administering a microorganism containing a nucleotide sequence encoding an antigen into an animal bearing a tumor; and (b) isolating the antibody directed to the antigen from the serum obtained from the animal. The antibodies directed to the antigen can be isolated and purified according to well known methods. Antibodies that are directed against specific contaminating antigens (e.g., bacteria antigens) can be removed by adsorption, and the antibodies directed against the target antigen can be separated from contaminating antibodies by affinity purification, for example, by immuno affinity chromatography using the recombinant antigen as the ligand of the column, by methods known in the art. Antibodies can be collected from the animal in a single harvest, or can be collected over time by collection bleeds, as is known in the art.

F. Pharmaceutical Compositions, Combinations And Kits

Provided herein are pharmaceutical compositions, combinations and kits containing a microorganism provided herein and one or more components. Pharmaceutical compositions can include a microorganism and a pharmaceutical carrier. Combinations can include two or more microorganisms, a microorganism and a detectable compound, a microorganism and a microorganism expression modulating compound, a microorganism and a therapeutic compound. Kits can include the pharmaceutical compositions and/or combinations provided herein, and one or more components such as instructions for use, a device for detecting a microorganism in a subject, a device for administering a compound to a subject, and a device for administering a compound to a subject.

1. Pharmaceutical Compositions

Also provided herein are pharmaceutical compositions containing a modified microorganism and a suitable pharmaceutical carrier. Examples of suitable pharmaceutical carriers are known in the art and include phosphate buffered saline solutions, water, emulsions, such as oil/water emulsions, various types of wetting agents, sterile solutions, etc. Such carriers can be formulated by conventional methods and can be administered to the subject at a suitable dose. Colloidal dispersion systems that can be used for delivery of microorganisms include macromolecule complexes, nanocapsules, microspheres, beads and lipid-based systems including oil-in-water emulsions (mixed), micelles, liposomes and lipoplexes. An exemplary colloidal system is a liposome. Organ-specific or cell-specific liposomes can be used in order to achieve delivery only to the desired tissue. The targeting of liposomes can be carried out by the person skilled in the art by applying commonly known methods. This targeting includes passive targeting (utilizing the natural tendency of the liposomes to distribute to cells of the RES in organs which contain sinusoidal capillaries) or active targeting (for example by coupling the liposome to a specific ligand, for example, an antibody, a receptor, sugar, glycolipid, protein etc., by well known methods). In the present methods, monoclonal antibodies can be used to target liposomes to specific tissues, for example, tumor tissue, via specific cell-surface ligands.

2. Host Cells

Also provided herein are host cells that contain a microorganism provided herein such as a modified vaccinia virus. These host cells can include any of a variety of mammalian, avian and insect cells and tissues that are susceptible to microorganisms, such as vaccinia virus infection, including chicken embryo, rabbit, hamster and monkey kidney cells, for example, CV-1, BSC40, Vero, BSC40 and BSC-1, and human HeLa cells. Methods of transforming these host cells, of phenotypically selecting transformants etc., are known in the art.

3. Combinations

Combinations can include a microorganism and one or more components. Any combination herein also can, in place of a microorganism, contain a pharmaceutical composition and/or a host cell containing a microorganism and one or more components.

Exemplary combinations can contain two or more microorganisms, a microorganism and a detectable compound, a microorganism and a microorganism expression modulating compound, or a microorganism and a therapeutic compound. Combinations that contain two or more microorganisms can contain, for example, two or more microorganisms that can both be administered to a subject in performing the methods provided herein, including sequentially administering the tow microorganisms. In one example, a combination can contain a virus and a bacterium, where, for example, the virus can first be administered to the subject, and the bacterium can be subsequently administered to the subject.

Combinations provided herein can contain a microorganism and a detectable compound. A detectable compound can include a ligand or substrate or other compound that can interact with and/or bind specifically to a microorganismally expressed protein or RNA molecule, and can provide a detectable signal, such as a signal detectable by tomographic, spectroscopic or magnetic resonance techniques. Exemplary detectable compounds can be, or can contain, an imaging agent such as a magnetic resonance, ultrasound or tomographic imaging agent, including a radionuclide. The detectable compound can include any of a variety of compounds as provided elsewhere herein or are otherwise known in the art. Typically, the detectable compound included with a microorganism in the combinations provided herein will be a compound that is a substrate, a ligand, or can otherwise specifically interact with, a protein or RNA encoded by the microorganism; in some examples, the protein or RNA is an exogenous protein or RNA. Exemplary microorganisms/detectable compounds include a microorganism encoding luciferase/luciferin, β-galactosidase/(4,7,10-tri(acetic acid)-1-(2-β-galactopyranosylethoxy)-1,4,7,10-tetraazacyclododecane) gadolinium (Egad), and other combinations known in the art.

Combinations provided herein can contain a microorganism and a microorganism gene expression modulating compound. Compounds that modulate gene expression are known in the art, and include, but are not limited to, transcriptional activators, inducers, transcriptional suppressors, RNA polymerase inhibitors, and RNA binding compounds such as siRNA or ribozymes. Any of a variety of gene expression modulating compounds known in the art can be included in the combinations provided herein. Typically, the gene expression modulating compound included with a microorganism in the combinations provided herein will be a compound that can bind, inhibit, or react with one or more compounds active in gene expression such as a transcription factor or RNA, of the microorganism of the combination. An exemplary microorganism/expression modulator can be a microorganism encoding a chimeric transcription factor complex having a mutant human progesterone receptor fused to a yeast GAL4 DNA-binding domain an activation domain of the herpes simplex virus protein VP16 and also containing a synthetic promoter containing a series of GAL4 recognition sequences upstream of the adenovirus major late E1B TATA box, where the compound can be RU486 (see, e.g., Yu et al., Mol Genet Genomics 2002 268:169-178). A variety of other microorganism/expression modulator combinations known in the art also can be included in the combinations provided herein.

Combinations provided herein can contain a microorganism and a therapeutic compound. Therapeutic compounds can include compounds that are substrates for microorganismally expressed enzymes, compound that can kill or inhibit microorganism growth or toxicity, or other therapeutic compounds provided herein or known in the art to act in concert with a microorganism. Typically, the therapeutic compound included with a microorganism in the combinations provided herein will be a compound that can act in concert with a microorganism, such as a substrate of an enzyme encoded by the microorganism, or an antimicroorganismal agent known to be effective against the microorganism of the combination. Exemplary microorganism/therapeutic compound combinations can include a microorganism encoding Herpes simplex virus thymidine kinase/gancyclovir, and *streptococcus pyogenes*/penicillin. Any of a variety of known combinations provided herein or otherwise known in the art can be included in the combinations provided herein.

4. Kits

Kits are packaged in combinations that optionally include other reagents or devices, or instructions for use. Any kit provided herein also can, in place of a microorganism, contain a pharmaceutical composition, a host cell containing a microorganism, and/or a combination, and one or more components.

Exemplary kits can include the microorganisms provided herein, and can optionally include one or more components such as instructions for use, a device for detecting a microorganism in a subject, a device for administering a compound to a subject, and a device for administering a compound to a subject.

In one example, a kit can contain instructions. Instructions typically include a tangible expression describing the microorganism and, optionally, other components included in the kit, and methods for administration, including methods for determining the proper state of the subject, the proper dosage amount, and the proper administration method, for administering the microorganism. Instructions can also include guidance for monitoring the subject over the duration of the treatment time.

In another example, a kit can contain a device for detecting a microorganism in a subject. Devices for detecting a microorganism in a subject can include a low light imaging device for detecting light, for example emitted from luciferase, or fluoresced from green fluorescence protein, a magnetic resonance measuring device such as an MRI or NMR device, a tomographic scanner, such as a PET, CT, CAT, SPECT or other related scanner, an ultrasound device, or other device that can be used to detect a protein expressed by the microorganism within the subject. Typically, the device of the kit will be able to detect one or more proteins expressed by the microorganism of the kit. Any of a variety of kits containing microorganisms and detection devices can be included in the kits provided herein, for example, a microorganism expressing luciferase and a low light imager, or a microorganism expressing green fluorescence protein and a low light imager.

Kits provided herein also can include a device for administering a microorganism to a subject. Any of a variety of devices known in the art for administering medications or vaccines can be included in the kits provided herein. Exemplary devices include a hypodermic needle, an intravenous needle, a catheter, a needle-less injection device, an inhaler, and a liquid dispenser such as an eyedropper. Typically, the device for administering a microorganism of the kit will be compatible with the microorganism of the kit; for example, a needle-less injection device such as a high pressure injection device can be included in kits with microorganisms not damaged by high pressure injection, but is typically not included in kits with microorganisms damaged by high pressure injection.

Kits provided herein also can include a device for administering a compound to a subject. Any of a variety of devices known in the art for administering medications to a subject can be included in the kits provided herein. Exemplary devices include a hypodermic needle, an intravenous needle, a catheter, a needle-less injection an inhaler, and a liquid dispenser. Typically the device for administering the compound of the kit will be compatible with the desired method of administration of the compound. For example, a compound to be delivered subcutaneously can be included in a kit with a hypodermic needle and syringe.

G. Examples

The following examples are included for illustrative purposes only and are not intended to limit the scope of the invention.

Example 1

Generation of Recombinant Viruses

A Wild type vaccinia virus (VV) strain LIVP (the well known viral strain, originally derived by attenuation of the strain Lister from the ATCC under Accession Number VR-1549, from the Institute of Viral Preparations, Moscow, Russia; see, Al'tshtein et al., (1983) Dokl. Akad. Nauk USSR 285:696-699) designed as VGL was used as a parental virus for the construction of recombinant viruses designated RVGLX herein. All vaccinia viruses were purified using sucrose gradient (Yoklik). VVs were propagated and titers were determined by plaque assays using CV-1 cells (ATCC No. CCL-70). Methods for constructing recombinant vaccinia viruses are known to those of skill in the art (see, e.g., Chakrabarti et al., (1985 Mol. Cell. Biol. 5:3403 and U.S. Pat. No. 4,722,848)). Table 1 summarizes the recombinant VV strains described in this Example.

Inactivation of VV by PUV Treatment

LIVP VV ($3\times10^8$ pfu/ml) was incubated with 1 μg/mlpsoralen (Calbiochem, La Jolla, Calif.), suspended in Hank's buffer at room temperature for 10 min, and then irradiated for 5 min in Stratalinker 1800 UV crosslinking unit (Stratagene, La Jolla Calif.) equipped with five 365 nm long wave UV bulb to produce PUV-VV.

RVGL8: LacZ Insertion into F3 of LIVP

Construction of recombinant vaccinia virus RVGL8 containing a lacZ gene inserted the NotI site was prepared as described in Timiryasova et al. (2001), BioTechniques 31, 534-540. Briefly it was prepared as follows. The BamHI/SmaI fragment (3293 bp) of pSC65 (see, Chakrabarti et al. (1997), BioTechniques 23, 1094-1097; see, also Current Protocols in Molecular Biology, Green Publishing and Wiley-Interscience Supplement 15:16.17.2 (1992); see also SEQ ID NO: 5 herein and SEQ ID NO: 57 in PCT International application No. WO 99/32646) containing the lacZ gene under the control of the vaccinia p7.5 promoter and strong synthetic vaccinia pE/L promoter was isolated by digestion with restriction enzymes, blunted with Klenow enzyme, and cloned into SmaI site of pNT8 plasmid (Timiryasova et al. (2001), BioTechniques 31: 534-540) to produce pNZ2 a shuttle plasmid.

To construct pNT8, the NotI region of the wild type VV strain LIVP was amplified using the following primers:

Forward: 5'-GGGAATTCTTATACATCCTGTTCTATC-3' (SEQ ID NO: 3);

Reverse: 5'-CCAAGCTTATGAGGAGTATTGCGGGGC-TAC-3' (SED ID NO: 4) with the VV as a template. The resulting 972 bp fragment contained flanking EcoRI and HindIII sites at the 5' and 3' ends, respectively. The PCR product was cleaved with EcoRI and HindIII and inserted in pUC28 (Benes et al., (1993) Gene 130: 151. Plasmid pUC28 is prepared from pUC18 (available from the ATCC under Accession Number 37253 by introducing a synthetic oligo adaptor using primers:

pUC28 I: 5'AATTCAGATCTCCATGGATCGATGAGCT 3' (SEQ ID NO: 6);

pUC28 II: 3'GTCTAGAGGTACCTAGCTAC 5' (SEQ ID NO: 7) into the EcoRI and SstI sites of pUC18. This introduces BglII, ClaI, and NcoI sites into the polylinker of pUC18.

Plasmid pNZ2 contains cDNA encoding the *E. coli* lacZ gene under the control of the vaccinia virus early/late promoter p7.5 and a synthetic early/late vaccinia pE/L promoter derived from the plasmid pSC65 (see, Chakrabarti et al. (1997), BioTechniques 23, 1094 1097; see, also Current Protocols in Molecular Biology, Green Publishing and Wiley-Interscience Supplement 15:16.17.2 (1992); see also SEQ ID NO: 5 herein and SEQ ID NO: 57 in PCT International application No. WO 99/32646). Plasmid pNZ2 provides for homologous recombination of lacZ into the NotI site of the VGL virus (ATCC VR-1549), to produce the recombinant vaccinia virus designated RVGL8. The complex of wild type vaccinia virus DNA digested with NotI and not digested plasmid DNA pNZ2 was transfected for in vivo recombination into PUV VV infected cells to produce RVGL8 (see FIG. 1). RVGL8 and the other recombinant vaccinia viruses described herein are listed in Table 1, below.

Mutant Virus Formation/Transfection

CV-1 African green monkey kidney fibroblasts (ATCC No. CCL-70) grown on 60 mm dishes (Corning, Corning, N.Y., USA) were infected with PUV-VV (strain LIVP treated with psoralen and UV; see, e.g., Tsung et al. (1996), J. Virol. 70, 165-171; Timiryasova et al. (2001), BioTechniques 31, 534-540; Timiryasova et al. (2001), J. Gene 3 Med. 3, 468-477) at multiplicity of infection (MOI) of 1.

Two hours post-infection, the cells were transfected with a mixture of NotI-digested viral DNA (4 μg) and intact plasmid DNA (4 μg). Lipid-mediated transfection of cells was carried out using 5 μl of GenePORTER reagent (Gene Therapy Systems, San Diego, Calif., USA) per tg of the DNA according to manufacturers' instructions. Cells were incubated in transfection mixture for 4 h and then supplemented with a medium containing 20% of fetal bovine serum. Cytopathic effects were monitored daily by light microscopy. Cells were incubated for 5-7 days until formation of the virus plaques and complete cytopathic effect. Then, infected cells were harvested, resuspended in 0.5 ml of medium, and frozen and thawed three times to release the virus. Single virus plaques were selected for the preparation of small and large recombinant virus stocks and analyzed for the insertion and expression of the genes.

Confirm Mutant

Viral DNA was analyzed by Southern blots. Briefly, to isolate viral DNA, confluent monolayers of CV-1 cells, grown on 10 cm plates, were infected with the wild type VV (strain LIVP) or VV of the virus stock obtained from a single recombinant plaque. When the cytopathic effect was complete, cells were harvested and the pellet was resuspended in 3 ml of 10 mM Tris-HCl, pH 9.0. Viral particles were lysed, treated with proteinase K, and the virus DNA was isolated by phenol/chloroform extraction, followed by ethanol precipitation. The DNA was resuspended in 100 μl of sterile water. The viral DNA samples were digested by NotI overnight at 37° C., followed by phenol-chloroform treatment, precipitated and 10 Tg of DNA samples were separated through a 0.8% agarose gel. The DNA was transferred to a positively charged nylon membrane (Roche Diagnostics Corporation, Indianapolis, Ind., USA) and fixed to the membrane using a GS Gene Linker (Bio-Rad Laboratories, Hercules, Calif., USA). The DIG-labeling of DNA was performed using a nonradioactive DNA labeling and detection kit (Roche Diagnostics Corporation) and incubating for 60 min at 37° C. The membrane was hybridized with a denatured DIG-labeled 3357 bp NotI-NotI DNA fragment of the plasmid pNZ2 encoding the lacZ gene. Hybridization conditions and blot development were performed as suggested by the manufacturer.

The predicted size of the band is 3357 bp. The hybridization of NotI digested viral DNAs with a 3357 bp DNA probe confirmed the integration of the lacZ gene into NotI site of virus genome.

Construction of RVGL2 and RVGL23 Viruses with a Single TK Gene Mutation

Vaccinia virus LIVP was used for the construction of recombinant virus RVGL2. Vaccinia virus Western Reserve (WR) was used for the construction of recombinant virus RVGL23. The cDNA of *Renilla* luciferase and *Aequorea* GFP fusion (ruc-gfp; 1788 bp; see, Wang et al., (1996) Bioluminescence Chemiluminescence 9:419-422; Wang et al., (2002) Mol. Genet. Genomics 268:160-168; Wang et al. (1997) pp 419-422 in Bioluminescence and Chemiluminescence: molecular reporting with photons, Hastings et al., eds., Wiley, Chicheser UK; see, also U.S. Pat. No. 5,976,796; see also SEQ ID NO: 8 herein, which sets forth a sequence for a ruc-gfp construct) was excised from plasmid pcDNA-ruc-gfp (RG), which is described in Wang et al., (1996) Bioluminescence Chemiluminescence 9:419-422 and Wang et al., (2002) Mol. Genet. Genomics 268:160-168 and briefly below, by restriction endonuclease PmeI and inserted into the SmaI site of pSC65 plasmid (see SEQ ID NO: 5; see, also herein and SEQ ID NO: 57 in PCT International application No. WO 99/32646), resulting in pSC65-RG-1 plasmid DNA.

Briefly to prepare pcDNA-ruc-gfp, the EcoRI-NotI fragment encoding the modified *Renilla* luciferase-ending DNA (see, Wang et al. (1997) pp 419-422 in Bioluminescence and Chemiluminescence: molecular reporting with photons, Hastings et al., eds., Wiley, Chicheser UK) was cloned into the pcDNA3.1 vector (Invitrogen, Carlsbad, Calif.), placing expression of the *Renilla* luciferase under control of the CMV promoter. The stop codon at the end of the *Renilla* luciferase ORF was removed, and the resulting plasmid digested with NotI. The NotI fragment containing the ORF encoding humanized *Aequorea* GFP (Zolotukhin et al., (1996) J. Virol. 70:4646-4654) was excised from the pTR-β-actin plasmid and inserted into the NotI site of the plasmid encoding the *Renilla* luciferase. The resulting plasmid was designated pcDNA-ruc- the ruc-gfp.

New plasmid pSC65-RG-1 containing ruc-gfp fusion under the control of the vaccinia PE/L promoter and *E. coli* β-galactosidase under control of p7.5 promoter of VV was used for the construction of a single TK gene interrupted virus RVGL2 of strain LIVP and RVGL23 of strain WR. CV-1 cells were infected with wt LIVP or wt WR virus at MOI of 0.1, and two hours later, pSC65-RG-1 plasmid DNA was transfected using FuGene6 transfection reagent (Roche). After 24 h of incubation, cells were three times frozen and thawed to release the virus. Recombinant viruses were screened on CV-cells in the presence of substrate 5-bromo-4-chloro-3-indolyl-β-D-galactopyranoside (X-gal, Stratagene, Cedar Creek, Tex., USA). After four cycles of virus purification, all virus plaques were positive for β-galactosidase expression. The expression of the ruc-gfp fusion protein was confirmed by luminescence assay and fluorescence microscopy, respectively. Schematic maps of the viruses are set forth in FIG. 1.

Construction of RVGL5 and RVGL9 Viruses with Single Gene Mutations

Recombinant vaccinia virus RVGL5 contains the lacZ gene under the control of the vaccinia late p11 promoter inserted into the HA gene of vaccinia genome (Timiryasova et al. (1993) Mol Biol 27:392-402; see, also, Timiryasova et al., (1992) Oncol. Res 11:133-144.). Recombinant vaccinia virus RVGL9 contains a fusion of the *Renilla* luciferase gene (ruc) and cDNA of green fluorescence protein (GFP) under the control of a synthetic early/late vaccinia promoter (PE/L) inserted into the F3 gene of the VV genome (Timiryasova et al., (2000)) pp. 457-459 in Proceedings of the 11th International Symposium on Bioluminescence and Chemiluminescence, Case et al., eds). RVGP5 and RVGLP9 were constructed as described for RVGLP2 and RVGLP23.

Construction of RVGL20 Virus with Double TK and F3 Gene Mutations

The cDNA of human transferrin receptor (hTR) (2800 bp) with polyA sequence was isolated from pCDTR1 plasmid (ATCC Accession No. 59324 and 59325) by BamHI, treated with Klenow and inserted into SalI site of pSC65 plasmid (SEQ ID NO: 5 herein and SEQ ID NO: 57 in PCT International application No. WO 99/32646), resulting in pSC-TfR and pSC-rTfR. Plasmid pSC-rTfR contains cDNA hTR in an orientation opposite to the vaccinia PE/L promoter and *E. coli* f3-galactosidase under control of the early/late vaccinia p7.5 promoter flanked by vaccinia sequences for insertion into vaccinia TK gene. pSC-rTfR was used for the construction of RVGL20 virus. RVGL9, a recombinant virus with single deletion carrying ruc-gfp fusion in the F3 gene locus, which contains a unique NotI site in the LIVP strain (see above, see, also, Timiryasova et al., (2000) pp. 457-459 in *Proceedings of the 11th International Symposium on Bioluminescence and Chemiluminescence*, Case et al., eds), was used as a parental virus for the creation of RVGL20 virus by homologous recombination as described above. A schematic of RVGL20 virus is set forth in FIG. 1.

Construction of RVGL21 Virus with Triple TK, F3 and HA Gene Mutations

The cDNA of the β-glucuronidase (gus) of *E. coli* (1879 bp) was released from pLacGus plasmid (Invitrogen; see SEQ ID NO: 9 herein) with XbaI (blunt ended with Klenow fragment) and HindIII, and cloned into pSCl1 plasmid pSC65 (Chakrabarti et al. (1985) Mol. Cell. Biol. 5:3403-3409; SEQ ID NO: 5 herein and SEQ ID NO: 57 in PCT International application No. WO 99/32646) digested with XhoI (treated with Klenow) and HindIII under the control of a vaccinia p11 late promoter, resulting in a plasmid pSC-GUS. The SmaI-HindIII fragment from pSC-GUS plasmid was inserted into pVY6 plasmid, a vector for inserting antigen genes into the hemagglutinin gene of vaccinia (see, e.g., Flexner et al., (1988) Nature 355:259-262; Flexner et al., (1988) Virology 166: 339-349; see also U.S. Pat. No. 5,718,902) digested with SmaI and BamHI, resulting in pVY-GUS plasmid. The resulting plasmid, designated pVY-GUS plasmid, contains the cDNA encoding gus under the control of the vaccinia late promoter p11 flanked by vaccinia sequences for insertion into the hemagglutinin (HA) gene. Recombinant virus RVGL20 with double deletions was used as the parental virus for the construction of RVGL21 virus. CV-1 cells were infected with RVGL20 virus at MOI of 0.1. Two hours after infection, cells were transected with pVY-GUS plasmid DNA using FuGene6 transfection reagent (Roche). Recombinant virus plagues were selected in CV-1 cells by color screening upon addition of O-glucuronidase substrate 5-bromo-4-chloro-3-indolyl-β-D-glucuronicacid (X-GlcA) (Research Products Int. Co., Mt. Prospect, Ill., USA) into agar medium. After eight cycles of purification in agar medium in the presence of X-GlcA pure recombinant virus RVGL21 was selected. RVGL21 virus has interruptions of TK, F3 and HA genes and is presented schematically in FIG. 1.

In Vitro Virus Growth

CV-1, C6 (ATCC No. CCL-107), B16-F10 (ATCC No. CRL-6475), and GI-101A (Rumbaugh-Goodwin Institute for Cancer Research Inc. Plantation, Fla.; U.S. Pat. No. 5,693,533) cells were seeded in 24-well plates at the density of $1\times10^5$, $2\times10^5$, $4\times10^5$, and $2\times10^5$ cells/well, respectively. The next day, the cells were simultaneously infected with 0.001 or 0.01 PFU/cell of a wild type LIVP and its mutants. The virus suspension was added to cell monolayer (0.15 ml/well) and incubated at 37° C. for 1 h with brief agitation every 10 min. Then, the virus was removed, appropriate complete growth medium was added (1 ml/well), and the cells were then incubated at 37° C. for 24, 48, 72 and 96 h after virus infection. To establish resting cell culture, a confluent monolayer of CV-1 cells was incubated for 6 days in DMEM with 5 FBS at 37° C. These resting cells were infected and harvested at the same time points after infection as described above. Virus from the infected cells was released by one cycle of freezing and thawing. Viral titers were determined in duplicates by plaque assay on CV-1 cells and expressed as PFU/ml.

TABLE 1

List of recombinant vaccinia viruses (VV)

| Designation | Prior Designation | Description | InsertionLocus/ loci | Reference |
|---|---|---|---|---|
| VGL | wt VV | strain LIVP VV | No Insertions | Publicly available |
| RVGL1 | recVV2 | (p7.5) Luc-(p11) LacZ of LIVP VV | HindIII-N-Interrupted | Timiryasova T M, Kopylova-Sviridova T N, Fodor I. Mol. Biol. (Russian) 27: 392-401 (1993); Timiryasova T M, Li J, Chen B. Chong D. Langridge W H R, Grid-ley D S, Fodor I. Oncol. Res. 11: 133-144 (1999) |
| RVGL5 | recVV8 | (p11) LacZ of LIVP VV | HA-Interrupted | Timiryasova T M, Kopylova-Sviridova T N, Fodor I. Mol. Biol. (Russian) 27: 392-401 (1993) |
| RVGL7 | rVV-EGFP or rVV-GFP | (PE/L) EGFP-(p7.5) LacZ of LIVP VV | TK-Interrupted | Umphress S, Timiryasova T., Arakawa T, Hilliker S, Fodor I, Langridge W. Transgenics 4: 19-33 (2003) |
| RVGL8 | rVV-Not-LacZ or rVV-Not-LZ | (p7.5) LacZ of LIVP VV | NotI (F3)-Interrupted | Timiryasova T M, Chen B, Fodor N, Fodor I. BioTechniques 31: 534-540 (2001) |
| RVGL9 | rVV-RG or rVV-ruc-gfp | (PE/L) Ruc-GFP of LIVP VV | NotI (F3)-Interrupted | Timiryasova T M, Yu Ya, Shabahang S, Fodor I, Szalay A A. Proceedings of the 11th International Symposium on Bioluminescence & Chemiluminescence pp. 457-460 (2000) |

TABLE 1-continued

List of recombinant vaccinia viruses (VV)

| Designation | Prior Designation | Description | InsertionLocus/ loci | Reference |
|---|---|---|---|---|
| RVGL12 | | Same as RVGL7, except that HSV TK is inserted in place of gfp | | |
| RVGL19 | | (PE/L) Trf-(p7.5) LacZ in Tk locus (PE/L) Ruc-GFP in F3 locus of LIVP VV | TK- and NotI (F3)- Interrupted | Herein |
| RVGL20 | | (PE/L) rTrf-(p7.5) LacZ in TK locus (PE/L) Ruc-GFP in F3 locus of LIVP V | Tk- and NotI (F3)- Interrupted | Herein |
| RVGL21 | | (PE/L) rTrf-(p7.5) LacZ in TK locus, (p11) LacZ in HA locus, (PE/L) Ruc-GFP in F3 locus of LIVP VV | Tk-, HA- interrupted and NotI (F3)- Interrupted | Herein |
| RVGL23 | | (PE/L) rTrf-(p7.5) LacZ in TK locus of WR VV | Tk- Interrupted | Herein |

Example 2

In Vitro Analysis of Virus Levels

LacZ

Analysis of lacZ expression induced by recombinant vaccinia virus was performed as described previously (Timiryasova et al. (2001), BioTechniques 31, 534-540). Briefly, CV-1 cells grown 6-well plates (Corning, Corning, N.Y., USA) were infected with ten-fold dilutions of the virus stock. The virus was allowed to absorb for 1 h at 37° C. with occasional rocking. Then, the virus inoculum was replaced with a complete medium containing 1% of agar, and the incubation was carried out for 48 h. To visualize the virus plaques, 300 Tg of X-Gal (Molecular Probes, Eugene, Oreg., USA) per ml and 0.1% of neutral red (Sigma, St. Louis, Mo., USA) were added to the second agar overlay, and plaques were counted and isolated after 12 h incubation at 37° C. Levels of vaccinia virus in cells in vitro could also be determined by measuring the plaque forming units (PFU) in the cells.

In Vitro Infectivity of VV's Measured by Plaque Forming Units

The ability of wt LIVP virus and its mutants to infect and replicate was analyzed in dividing and resting CV-1 cells as well as in three tumor cell lines (C6, GI-101A, B16-F10). The results demonstrate that vaccinia mutants can efficiently infect and replicate in dividing CV-1 cells at an MOI of 0.001. A significant yield of vaccinia virus was obtained from dividing CV-1 cells. The yield of wt VV and its mutants in dividing CV-1 cells was about 10 times higher than in resting CV-1 cells. There was no significant difference in viral recovery between vaccinia mutants and wt virus in vitro studies. The interruption of TK, F3 and HA genes made no difference to VV mutants replication in the dividing CV-1 cells. Three tumor cells were tested. The relative sensitivities to cytopathic effects at MOI of 0.001 were follows: CV-1 (dividing, highest), CV-1 (resting), C6, GI-101A, B16-F10 (lowest). Mouse B16-F10 melanoma cells were not sensitive to virus infection at MOI of 0.001. Very low viral titer was recovered from melanoma cells infected at MOI of 0.01. Also observed was that wt WR strain was able to infect melanoma cells in vitro more efficiently compared to LIVP strain and virus recovery was higher compared to LIVP strain.

Example 3

Animal Models and Assays

Animal Models

Athymic nude mice (nu/nu) and C57BL/6 mice (Harlan Animal Res., Inc., Wilmington, Mass.) at 6-8 weeks of age were used for animal studies. Mice in groups of five or four were infected i.v. with $10^7$ PFU of VV in a volume of 0.1 ml i.v. Mice were imaged by low-light imager and fluorescence imager for ruc and for gfp expression, respectively. The study was approved prior to initiation by the Animal Research Committee of LAB Research International Inc. (San Diego, Calif., USA). All animal care was performed under the direction of a licensed veterinarian of LAB Research International Inc. (San Diego, Calif., USA).

Glioma Model

To establish subcutaneous glioma tumor, rat glioma C6 cells (ATCC No. CCL-107) were collected by trypsinization, and $5\times10^5$ cells/0.1 ml/mouse were injected subcutaneously (s.c.) into right hind leg of 6-8 week old male athymic mice. On day 7 after C6 cell implantation when median tumor size was about 150 $mm^3$, viruses at the dose of $10^7$ PFU/0.1 ml/mouse were injected intravenously (i.v.). Mice were sacrificed 14 days after virus injection. In the kinetic studies using of RVGL9 virus, mice were sacrificed at 20 min, 1 h, 4 h, 18 h, 36 h, 3 d, 5 d, 7 d and 14 days after virus injection.

Breast Tumor Model

To develop sub cutaneous (s.c). breast tumor, human breast cancer GI-101 A cells (Rumbaugh-Goodwin Institute for Cancer Research Inc. Plantation, Fla.; U.S. Pat. No. 5,693,533) at the dose of $5\times10^6$ cells/0.1 ml/mouse were injected s.c. into the right hind leg of 6-8 week old female athymic mice. On day 30 after GI-101A cell implantation, when median tumor size was about 500 $mm^3$, viruses at the dose of $10^7$ PFU/mouse were injected i.v. Mice were sacrificed on day 14 after virus injection. Mice for survival experiments and breast tumor therapy studies were kept for long time periods (more than 100 days after virus injection). Mice that developed tumor with the size about 4000 $mm^3$, and/or lost 50% of body weight were sacrificed.

Melanomal Model

For a melanoma model, mouse melanoma B16-F10 cells (ATCC No. CRL-6475) at the dose of $2\times10^5$ cells/0.04 ml/mouse were injected into the foot pad of 6-8 week old male C57BL/6 mice. When the tumor was established (median size of tumor about 100 $mm^3$), on day 18 after cell implantation, viruses at the dose of $10^7$/mouse were injected i.v. Mice were sacrificed 10 days after virus injection.

Vaccinia Virus in Animal Models

Vaccinia Virus Recovery from Tumor and Organs of Nude Mice

From sacrificed animals blood was collected, and organs (lung, liver, spleen, kidneys, testes, ovaries, bladder, brain, heart) and tumors were harvested and homogenized in PBS containing a mixture of protease inhibitors. Scissors and forceps were changed after each organ dissection or incision to avoid cross-contamination of the tissues. Samples were frozen and thawed, centrifuged at 1,000 g for 5 min. Viral titer was determined in the supernatant diluted in serum-free medium on CV-1 cells by plaque assay and staining them with 1% (wt/vol) crystal violet solution after 48 h incubation. Each sample was assayed in duplicate and viral titer was expressed as mean PFU/g of tissue.

Assay Measurements

Survival studies were performed on 6-week old nude mice bearing s.c. human breast tumor. Mice were injected i.v. with $10^7$ of vaccinia viruses and followed for survival. Individual body weight was measured twice a week. Gain/loss of body weight after virus infection was calculated as the percentage: body weight (g)−tumor weight (g) on day of virus injection/body weight (g)−tumor weight (g) on day of monitoring× 100%. Spleens were excised from euthanized animals and weighed. The RSW was calculated as follows: RSW=weight of spleen (g)$\times10^4$/animal body weight (g)−tumor weight (g). Mice were euthanized when the mean tumor volume reached 3000 $mm^3$ or developed the signs of disease. Rapid $CO_2$ euthanasia was humanely performed in compliance with the *NIH Guide for the Care and Use of Laboratory Animals.*

Reporter Genes Assays

LacZ

*E. coli* β-galactosidase activity in tissue samples and in the serum of the mice was determined using chemiluminescent Galacto-Light Plus™ Assay system (Applied Biosystems, Bedford, Mass., USA) according to the instructions of the kit manufacturer. Briefly, 1-20 μl of the sample was transferred into the tube with 200 μl of 1:100 diluted Reaction Buffer Diluent and incubated at RT for 30 min. A 300 μl aliquot of accelerator (−II) was added into the tube with the sample, mixed quickly and the signal was read using luminometer. β-galactosidase activity was expressed as relative light units (RLU) per g of tissue. Purified *E. coli* β-galactosidase (Sigma) was used as a positive control and to generate a standard curve.

Luciferase

*Renilla* luciferase activity was measured in the supernatant of the tissue samples after they had been homogenized using a Turner TD 20e luminometer (Turner Designs, Sunnyvale, Calif., USA) as described previously (Yu and Szalay, 2002) with some modifications. In brief, 20 μl of the samples was added into 500 μl of luciferase assay buffer (0.5 M NaCl, 1 mM EDTA, 0.1 M potassium phosphate pH 7.4) containing a substrate coelenterazine. Luciferase activity was measured during 10-s interval and expressed as RLU per g of tissue.

Assay Results

Presence of RVGL9 Over Time

A vaccinia virus RVGL9 with a single F3 gene mutation and carrying ruc-gfp was used to assess the pattern of vector tissue distribution following i.v. administration into immunocompromised athymic mice bearing s.c. glioma tumors. The tissue distribution data using this recombinant virus showed virus distribution and tumor targeting by this VV strain. Kinetics studies were performed by noninvasive imaging of virus replication in the mice based on ruc and gfp expression. Four to five animals per group bearing s.c. rat glioma C6 tumor were injected with $10^7$ of RVGL9 virus via the tail vein. The animals were sacrificed at 20 min, 1, 4, 18 and 36 hours, 3, 5, and 14 days after virus injection. No viable viral particles were recovered from brain, bladder or testes at any time point after i.v. injection of virus. Some viral particles were recovered from spleen, heart and lung at early time points after virus injection. After 18 h post-infection, the titer of RVGL9 virus in these organs decreased. No virus was recovered in the heart tissue after 18 h; around 156.5 and 44 PFU/g tissue was recovered from spleen and lung, respectively, on day 14 as compared to 3221.0 and 3521.9 PFU/g tissue at 20 min after virus injection, respectively. The pattern of virus recovery from liver and kidneys was different from the pattern in the spleen, heart, or lung. No virus in the kidneys and 174.9 PFU/g tissue of virus was recovered from liver at an early time after virus injection. On day 5 after virus injection, the titer of virus in these organs increased and went down on day 14 post virus injection. In tumor tissue virus was detected starting 18 h after virus administration ($1.6\times10^3$ PFU/g tissue), and dramatically increased over the time of observation ($1.8\times10^8$ PFU/g tissue on day 7). Virus in the tumor tissue was detectable for more then 60 days after a single i.v. virus injection. The results demonstrate tumor-specific replication of these vaccinia mutants. A correlation was observed between the virus recovery and the transgene expression in tumors and in organs. Based on the data of RVGL9 virus kinetics, day 10 or day 14 was used for tissue distribution studies of different vaccinia mutants in melanoma and glioma and breast tumor models, respectively.

Presence of Various VV in Mice Bearing a Glioma Tumor

To examine tissue distribution of vaccinia virus in immunodeficient mice bearing an s.c. glioma tumor, viruses were injected i.v. at a dose of $1\times10^7$ PFU/0.1 ml/mouse on day 7 after C6 rat glioma cell implantation. Fourteen days after virus injection, mice were sacrificed and virus titer was determined in different tissues. Mice injected with wt WR virus were sick and dying due to viral pathogenicity. Hence, WR-injected mice were sacrificed on day 7 after virus injection. Wild type LIVP virus was recovered from all analyzed tissues as well as from brain. The amount of recovered virus particles from the mice injected with wt LIVP was much lower than wt WR strain of VV. The results are presented in Table 1A.

TABLE 1A

Viral recovery from nude mice tissues in glioma model.[a]

| | LIVP Wt | RVGL2 TK- | RVGL5 HA- | RVGL9 F3- | RVGL20 TK-, F3- | RVGL21 TK-, F3-, HA- | WR[b] Wt | RVGL23 TK-, WR |
|---|---|---|---|---|---|---|---|---|
| Brain | $1.2 \times 10^3$ | $1.4 \times 10^3$ | 0 | 0 | 0 | 0 | $1.4 \times 10^7$ | $1.9 \times 10^6$ |
| Kidneys | $6.1 \times 10^2$ | $6.7 \times 10^2$ | $1.6 \times 10^2$ | 34.6 | 33.3 | 36.6 | $5.4 \times 10^6$ | $7.9 \times 10^2$ |
| Lung | $2.9 \times 10^3$ | 0 | $1.6 \times 10^2$ | $1.4 \times 10^4$ | $6.7 \times 10^3$ | $2.4 \times 10^3$ | $1.9 \times 10^6$ | $2.1 \times 10^3$ |
| Spleen | $1.9 \times 10^2$ | 0 | $1.8 \times 10^2$ | $1.0 \times 10^3$ | $1.0 \times 10^2$ | $1.7 \times 10^2$ | $1.6 \times 10^6$ | $1.8 \times 10^3$ |
| Testes | $5.8 \times 10^4$ | 64.3 | $6.4 \times 10^2$ | $7.5 \times 10^2$ | 0 | 0 | $9.8 \times 10^4$ | $1.7 \times 10^3$ |
| Bladder | $6.4 \times 10^3$ | 0 | 0 | $2.9 \times 10^3$ | 0 | 0 | $2.8 \times 10^5$ | $1.2 \times 10^3$ |
| Liver | $3.4 \times 10^4$ | 63.6 | $4.2 \times 10^2$ | 33.6 | 96.6 | 30.8 | $7.1 \times 10^3$ | $5.6 \times 10^3$ |
| Heart | $6.0 \times 10^3$ | 0 | 0 | 0 | 0 | 0 | $1.4 \times 10^5$ | 0 |
| Serum[c] | 0 | 0 | 0 | 0 | 0 | 0 | $6.0 \times 10^2$ | 0 |
| Tumor | $5.4 \times 10^7$ | $1.5 \times 10^7$ | $3.8 \times 10^7$ | $2.9 \times 10^7$ | $3.9 \times 10^7$ | $1.9 \times 10^7$ | $1.9 \times 10^8$ | $3.7 \times 10^7$ |

The results demonstrate that 10000-fold more virus was recovered in the brain of mice injected with WR strain versus wt LIVP strain. Wild type WR strain virus was recovered from the serum (600 PFU/20 μl) of mice on day 7 after virus injection. No virus was recovered in the serum of the mice injected with LIVP mutants on day 14. The level of wt LIVP in serum was not tested on day 7. About $1.9\times10^6$ PFU/g tissue of TK-mutant of WR strain (RVGL23) was found in the brain tissue compared to $1.4\times10^3$ PFU/g tissue for mice injected with the TK-mutant of LIVP strain (RVGL2).

All other mutants of VV strain LIVP were found mostly in tumor only and no virus was recovered from brain tissue of mice injected with a double or triple mutant (Table 1A). Three times as many virus particles were recovered from the tumors of mice injected with WR compared to wt LIVP. The mean of viral recovery in tumor tissue of the mutants of LIVP strain was similar to the wt LIVP and equivalent to TK-mutant of WR strain.

Presence of Various VV in Mice Bearing a Breast Tumor

Data for tissue distribution in immunocompromised mice bearing s.c. GI-101A human breast are presented in Table 1B:

TABLE 1B

Viral recovery from nude mice tissues in breast cancer model.

| | LIVP Wt | RVGL2 TK- | RVGL5 HA- | RVGL9 F3- | RVGL20 TK-, F3- | RVGL21 TK-, F3-, HA- | WR[b] Wt | RVGL23 TK-, WR |
|---|---|---|---|---|---|---|---|---|
| Brain | 0 | 0 | 0 | 0 | 0 | 0 | $7.2 \times 10^6$ | $1.6 \times 10^4$ |
| Kidneys | $3.6 \times 10^3$ | 38.3 | 27 | $3.3 \times 10^2$ | 25.8 | 0 | $3.2 \times 10^7$ | $2.8 \times 10^5$ |
| Lung | $8.6 \times 10^3$ | $5.5 \times 10^2$ | 29.1 | $1.6 \times 10^3$ | $1.6 \times 10^3$ | $1.0 \times 10^3$ | $2.1 \times 10^6$ | $3.7 \times 10^3$ |
| Spleen | $5.5 \times 10^3$ | 99.5 | 0 | $1.8 \times 10^2$ | 0 | 0 | $1.6 \times 10^6$ | $1.8 \times 10^3$ |
| Ovaries | $1.6 \times 10^3$ | 0 | 0 | 0 | 0 | 0 | $8.0 \times 10^7$ | $2.7 \times 10^7$ |
| Bladder | $3.9 \times 10^3$ | 0 | 0 | 0 | 0 | 0 | $2.8 \times 10^4$ | $1.2 \times 10^3$ |
| Liver | $1.2 \times 10^4$ | 0 | $1.7 \times 10^2$ | $5.2 \times 10^2$ | $1.7 \times 10^2$ | $1.0 \times 10^2$ | $4.0 \times 10^5$ | $4.8 \times 10^5$ |
| Heart | $1.4 \times 10^2$ | 0 | 0 | 58.2 | $4.6 \times 10^2$ | 0 | $6.3 \times 10^4$ | $2.2 \times 10^3$ |
| Serum[c] | 0 | 0 | 0 | 0 | 0 | 0 | $2.4 \times 10^3$ | 0 |
| Tumor | $8.6 \times 10^8$ | $1.0 \times 10^9$ | $2.5 \times 10^8$ | $1.1 \times 10^9$ | $5.6 \times 10^8$ | $1.0 \times 10^9$ | $2.9 \times 10^9$ | $6.6 \times 10^8$ |

About 10-fold more viral particles were recovered from breast tumor tissue compared to glioma tumor tissue. No virus particles were recovered from the brain tissue of mice injected with either wt LIVP or its mutants. $7.2\times10^6$ and $1.6\times10^4$ PFU/g was recovered from brain tissue of mice injected with wt WR and TK-virus of WR strain VV, respectively (Table 1B). During the dissection of organs from euthanized mice, it was found that the ovaries from the mice being injected with wt WR and TK- of WR virus were drastically enlarged as compared to all other groups of mice. The analysis of viral recovery from ovaries demonstrated high titer of wt WR and TK-WR strain in ovaries, for example, $8.0\times10^7$ and $2.7\times10^7$ PFU/g, respectively. About $1.6\times10^3$ PFU/g was recovered from the ovaries of the mice injected with wt LIVP virus, however no virus particles at all were recovered from either ovaries or from brain of mice injected with the mutants derived from LIVP strain (Table 1B).

Presence of Various VV in Mice Bearing a Melanoma Tumor

The tissue distribution of VV in the immunocompetent mice bearing melanoma tumors on foot pads also were studied. BL/6 mice on day 17 after B16F10 melanoma cell implantation were i.v. injected with the viruses at the dose of $10^7$ PFU/mouse via the tail vein. All groups of mice were sacrificed on day 10 after virus injection due to huge tumor size in the PBS-injected control group. The results are set forth in Table 1C:

TABLE 1C

Viral recovery from C57BL/6 mice tissues in melanoma model.

| | LIVP Wt | RVGL2 TK- | RVGL5 HA- | RVGL9 F3- | RVGL20 TK-, F3- | RVGL21 TK-, F3-, HA- | WR[b] Wt | RVGL23 TK-, WR |
|---|---|---|---|---|---|---|---|---|
| Tumor | $5.4 \times 10^6$ | $3.9 \times 10^6$ | $3.7 \times 10^5$ | $9.5 \times 10^5$ | $2.5 \times 10^5$ | $2.4 \times 10^5$ | $9.9 \times 10^6$ | $2.2 \times 10^6$ |
| Tissues[e] | 0 | 0 | 0 | 0 | 0 | 0 | 0 | 0 |

[a]Mean of viral recovery PFU/g of tissue for 3-5 mice/group.

[b]Mice were sacrificed on day 7 after virus injection.

[c]PFU/20 μl of serum

[d]Mice were sacrificed on day 9 after virus injection.

[e]No virus was recovered in all tested tissue.

No virus was recovered from kidneys, lung, spleen, brain, testes, bladder, liver, heart, and serum of the immunocompetent mice injected with the viruses. Virus was only recovered from the tumor tissue. About 10-fold virus particles were recovered from the tumors of mice injected with wt LIVP, TK-LIVP, wt WR, and TK-WR compared to other groups.

Example 4

Reduction of Human Breast Tumor Implanted in Nude Mice by Recombinant Vaccinia Viruses RVGL7, RVGL9 and RVGL21

RVGL7 and RVGL9

FIG. 1 shows a schematic representation of the recombinant vaccinia viruses used for these experiments. RVGL7 was prepared as described for the preparation of RVGL9. RVGL7 contains nucleic acid encoding EGFP and lacZ, and includes pE/L and p7.5 regulator regions inserted into the TK gene.

Luminescence and Fluorescence Images of Tumors in a Nude Mouse

Human breast GI-101A cancer cells ($5\times10^6$ cells/mouse) were subcutaneously implanted into the right thigh of the mice. Thirty days after cell implantation RVGL9, the NotI (F3)-interrupted virus expressing a fusion of *Renilla* luciferase and green fluorescence protein (RVGL9=rVV-RG=rVVruc-gfp) was injected intravenously via tail vein at a dose of $1\times10^7$ PFU/mouse. A fluorescence image of GFP and low-light image of luciferase expression were taken nine days after virus injection, i.e. 39 days post cell implantation showing dissemination of the virus.

Reduction of Human Breast Tumor Implanted into Nude Mice by Vaccinia Viruses RVGL7 or RVGL9

Human breast GI-101A cancer cells ($5\times10^6$ cells/mouse) were subcutaneously implanted into the right thigh of the mice. Mice were injected i.v. with RVGL7=rVV-GFT=TK- or RVGL9-rVV-ruc-gfp=NotI (3)-interrupted viruses ($1\times10^7$ PFU/mouse in 0.1 ml) and PBS control on day 30 after cell implantation. Images were taken on day 65 after GI-101A cell implantation and 35 days after virus or PBS injection. The results demonstrate drastic reduction of tumor volume in the mice injected with TK- or NotI (F3)-interrupted vaccinia viruses compared with the tumor in the mice injected with PBS.

GFP in Human Breast Tumor after Viral Administration

Human breast GI-101A cancer cells ($5\times10^6$ cells/mouse) were subcutaneously implanted into the right thigh of the mice. Mice were injected i.v. with RVGL7=rVV-GFP=TK- or RVGL9=rVV-RG-rVV-ruc-gfp-NotI (F3)-interrupted viruses ($1\times10^7$ PFU/mouse in 0.1 ml) on day 30 after cell implantation. The data demonstrate GFP expression in tumor area in the mice injected with $TK^-$ or NotI (F3)-interrupted vaccinia viruses. No GFP signals were observed in other parts of the mice bodies. The results also showed that expression of GFP can be visualized as early as 48 h after virus injection through the tail vein. On day 16 after virus injection very strong signals of GFP which correspond to a tumor volume of about 1300-1620 $mm^3$ for TK- or NotI (F3)-interrupted virus, respectively were observed. Reduced GFP signals were observed on day 25 (1218-1277 $mm^3$ for TK- or NotI (F3)-interrupted virus, respectively) and 32 (514-887 $mm^3$ for TK- or NotI (F3)-interrupted virus, respectively) due to reduction of tumor volume.

Time Course of Breast Tumor Volume Over Time

GI-101A breast cancer cells were implanted subcutaneously into the right thigh of 4-5-week old female athymic (nu/nu) mice in the dose of $5\times10^6$ cells/mouse. Thirty days after tumor implantation, when the tumor reached about 500 $mm^3$ in volume, a single dose ($1\times10^7$ PFU/mouse in 0.1 ml) of RVGL7=rVV-GFP=TK- or RVGL9=rVV-RG=rVV-ruc-gfp=NotI (F3)-interrupted vaccinia viruses or PBS control was injected intravenously (via tail vein). Tumor dimensions were measured with vernier caliper twice a week and volumes were calculated as (L×H×W)/2, where L, H and W represent the length, width, and height of the tumor, respectively and expressed in $mm^3$. The data demonstrate significant (60-80% on day 65) tumor reduction in the mice injected with TK-, NotI (F3)-interrupted vaccinia viruses. In contrast, tumors grew very rapidly in the mice injected with PBS.

Monitoring of Tumor Regression by Light Extinction.

Subcutaneous GI-101A breast tumor reduction occurred in 100% of immunocompromised mice treated with a single i.v. injection of wt LIVP, single F3-, single TK-, and double F3-, TK-, mutants of LIVP strain. Some degree of toxicity was seen in the mice treated with the above viruses. RVGL21 virus with the triple deletions TK, F3 and HA genes which showed no toxicity in nude mice; hence this virus was used for long-term studies. The difference in antitumor activity and survival between high and low doses of treatment using the triple mutant RVGL21 virus was not significant. GFP expression in tumor area in the mice injected with RVGL21 was monitored. No GFP signals were observed in other parts of the mice bodies. Expression of GFP can be visualized as early as 48 h after virus injection through the tail vein. On day 16 after virus injection we observed very strong signals of GFP, which corresponded to tumor volume of about 1300-1620 $mm^3$ and reduced GFP signals on days 25 (1218-1277 $mm^3$) and 32 (514-887 $mm^3$) due to reduction of tumor volume. Tumor volume reduction also was apparent by visual inspection of the mice.

Example 5

Reduction of Vaccinia Virus Toxicity and Virulence

Reduction of Vaccinia Virus Pathogenicity by Monitoring Mouse Body Weight and Survival The percentage of body weight change in athymic and immunocompetent mice bearing different s.c. tumors after i.v. administration of the viruses was examined. Injection of wt LIVP and wt WR and some mutants at the dose of $10^7$ pfu/mouse via the tail vein led to a progressive vaccinia virus infection within a two week observation period. At one week after challenge, the mice showed typical blister formation on the tail and footpad. Later, weight loss, sometimes accompanied by swelling of the mouth region, in several cases led to death of the mice. In the case of wt WR strain of VV, mice started to die on day 7 after i.v. injection of virus. While mice receiving the recombinant LIVP viruses gained weight or remained the same weight over the same time period.

Body Weight in Glioma Model Nude Mice

Rat glioma C6 cells at the dose of $5\times10^5$/0.1 ml/mouse were implanted s.c. into the right thigh of nude mice (5-6 old male mice) on day 0. Vaccinia viruses were injected i.v. (via tail vein) at the dose of $1\times10^7$ PFU/0.1 ml/mouse on day 7. Animals were weighed twice a week. Gain/loss of body weight on day 14 post infection was calculated as the percentage: body weight–tumor weight on day of virus injection (g)/body weight-tumor weight on day 14 (g)× 100%. Injection of VGL (wild type vaccinia virus, strain LIVP) and RVGL5 (HindIII-N-interrupted) causes toxicity in nude mice: mice continue to lose the weight. Recombinant vaccinia viruses RVGL5 (HA-interrupted), RVGL7 (TK-interrupted), RVGL8 (NotI(F3)-interrupted), RVGL19 (double, TK- and NotI (F3)-interrupted) were less toxic in nude mice: after losing some body weight, 10 days post-infection, mice started to gain the body weight.

Nude mice with glioma that were injected with wild type WR strain of VV lost 31.9% of body weight on day 7 after virus injection. Mice injected with TK-virus of WR strain lost 22.4% of body weight on day 14 after virus injection compared to 1.5% in the group of mice injected with TK-virus of LIVP strain of VV. All mice injected with wild type LIVP strain survived for at least 14 days (the duration of the experiment). Mice without tumor injected with VGL (wt VV, strain LIVP) lost 11.23% of body weight. Mice bearing tumor injected with VGL (wt VV) or with RVGL1 (HindIII-N-interrupted) lost 15.79% and 10.18% of body weight, respectively. Mice in the wt LIVP group lost 15.8% of body weight versus 9.4% in the PBS injected group. Tumor-bearing mice injected with RVGL2 here(TK-), RVGL5 (HA-), RVGL7 (TK-), RVGL8 (F3-), RVGL9 (F3-), RVGL20 (TK-, F3-), RVGL21 (TK-, F3-, HA-) on day 14 after virus injection lost only 1.5%, 0.4%, 2.1%, 5.0%, 7.3%, 2.4%, and 3.2% of body weight, respectively. Tumor-bearing mice injected with virus carrying double gene interruption, RVGL19 (TK- and F3-) demonstrated 0.73% gain of body weight compared to the body weight on day 0. Based on the results of body weight, a single interruption of HA, TK, F3 (NotI site) and double interruption of TK, F3 (NotI site) genes in vaccinia virus genome reduces virulence and toxicity of the vaccinia virus strain LIVP.

Injection of wt VV strain WR, however, was extremely toxic to nude mice, which died on day 7 after virus injection. Wild type and mutant VVs of strain LIVP were less toxic in nude mice. Although nude mice injected with various LIVP strains lost some body weight, after day 10-post infection mice started to gain the body weight.

Body Weight in Breast Tumor Model Athymic Mice

The body weight change of athymic mice with s.c. GI-101A human breast tumor after i.v. injection of vaccinia viruses was monitored. Mice injected with wt WR strain lost 25.6% of body weight and died due to virus toxicity. Although mice injected with wt LIVP virus survived for longer time, mice lost 26.4% of body weight. Mice injected with TK-WR strain lost 17.8% of body weight, while mice injected with TK-LIVP virus gained 1.9% of body weight. All mice injected with other mutants of LIVP strain were stable; no virus related toxicity was observed in these mice.

Body Weight in Melanoma Model Immunocompetent Mice

The toxicity of the vaccinia viruses in immunocompetent C57BL/6 mice bearing mouse B16-F10 melanoma on their foot pad was studied. Although mice in all groups survived during the experiment, wt WR strain was more toxic in immunocompetent mice compared to wt LIVP and recombinant strains. Mice injected with wt WR strain lost about 11.4% of body weight on day 10 after i.v. injection of virus, while mice injected with wt LIVP strain and its double (RVGL20) and triple (RVGL21) mutants lost only 2.2%, 1.3%, and 0.6% of body weight, respectively, versus to 7.1% of body weight lost in PBS injected mice. Mice administered i.v. with RVGL2 (TK-), RVGL5 (HA-), RVGL9 (F3-), and RVGL23 (TK-WR strain) continued to gain weight over this same period.

Long-Term Survival after Viral Infection for Breast Tumor-Bearing Mice

To examine the effect of different mutations on long-term survival, mice bearing s.c. GI-101A human breast tumor received doses of $10^7$ virus i.v., and were observed for survival after viral infection. The results showed that there are differences in survival depending upon the virus injected. Injection of the nude mice bearing s.c. breast tumor with wt WR strain (i.v., $1\times10^7$/mouse) resulted in 100% mortality: four mice of five died on day 9 and one mouse died on day 11 after virus injection. Mice injected with strain LIVP survived for 35 days. Mice injected with a single mutated virus RVGL9 (F3-) developed the toxicity and 25% of mice died on day 34 after virus injection, however the deletion of F3 gene in LIVP strain prolonged the survival of mice up to 57 days. Mice injected with double mutant virus RVGL20 (F3-, TK-) began to die on day 34 after virus injection, but survived longer than F3-injected mice. The RVGL20 virus injected mice reached 50% survival point on day 65 and showed significantly longer survival time up to 116 days. The single mutant TK-virus of LIVP virus was less pathogenic than the single mutant F3- or double mutant F3-, TK-viruses; all mice were alive on day 80 after injection with TK-virus and 14.3% of the mice survived 130 days. All mice injected with the triple mutant TK-, F3-, and HA-virus (RVGL21) survived 130 days (duration of the experiment) and continued to live without any signs of virus toxicity compared to other groups of mice.

Splenomegaly in Various Mice

Immunocompetent C57BL/6 Mice

Several groups of the animals demonstrated enlargement of the spleen; therefore the relative spleen weight (RSW) was calculated. The results are shown in Table 2 as follows:

TABLE 2

Relative spleen weight (RSW) in mice with or without tumors.

| Groups | Glioma model nu/nu mice | Breast cancer model nu/nu mice | Melanoma model C57BL/6 mice |
|---|---|---|---|
| No tumor, PBS | 43.6 ± 4.1[a] | 50.5 ± 11.2[d] | 30.1 ± 2.8[g] |
| No tumor, LIVP | 67.2 ± 11.9 | 48.0 ± 13.1 | 68.1 ± 9.4 |
| Tumor, PBS | 92.4 ± 7.4[b] | 84.1 ± 14.6[e] | 106.0 ± 46.1[h] |
| LIVP | 98.2 ± 28.2[c] | 108.4 ± 39.4[f] | 148.4 ± 44.8[i] |
| RVGL2 | 96.0 ± 34.9 | 112.7 ± 15.6 | 51.9 ± 6.6 |
| RVGL5 | 143.8 ± 20.5 | 169.6 ± 31.7 | 61.6 ± 2.9 |
| RVGL9 | 73.9 ± 10.5 | 151.8 ± 27.9 | 63.3 ± 34.9 |
| RVGL20 | 84.9 ± 6.6 | 159.9 ± 22.7 | 106.7 ± 36.0 |
| RVGL21 | 114.4 ± 12.5 | 117.7 ± 15.3 | 63.0 ± 24.6 |
| WR | 37.3 ± 3.5 | 57.9 ± 10.9 | 70.5 ± 1.8 |
| RVGL23 | 46.9 ± 15.7 | 73.1 ± 19.3 | 97.0 ± 43.9 |

Mean ± SD for n = 4-8 mice/group.

RSW = weight of spleen (g) × $10^4$/(animal body weight (g) − tumor weight (g)).

[a]p ≤ 02.02 vs. all groups, except no tumor LIVP, WR, RVGL23

[b]p ≤ 0.039 vs. no tumor PBS, no tumor LIVP, RVGL5, WR, RVGL23

[c]p ≤ 0.046 vs. all groups, except PBS, RVGL2, RVGL20, RVGL21

[d]p ≤ 0.006 vs. all groups except no tumor LIVP, PBS, WR, RVGL23

[e]p ≤ 0.048 vs. all groups, except no tumor PBS, LIVP, RVGL2, WR, RVGL23

[f]p ≤ 0.045 vs. all groups, except PBS, RVGL2, RVGL21

[g]p ≤ 0.035 vs. PBS, LIVP, RVGL20, WR, RVGL23

[h]p ≤ 0.049 vs. all other groups, except no tumor LIVP, RVGL20, WR, RVGL23

[i]p ≤ 0.049 vs. all other groups.

As shown in the Table 2 above, some degree of splenomegaly was observed in mice. For immunocompetent C57BL/6 mice, a statistically significant difference ($p<0.035$) was found in tumorous mice injected with PBS, LIVP, RVGL20, WR and RVG123 compared to non-tumorous mice. In mice injected with wt VV strain LIVP spleen was enlarged greatly ($p<0.049$) versus all other groups. In contrast, the smallest spleens were found in the mice without tumor.

Nude Mice with a Glioma Tumor

In nude mice with or without s.c. glioma tumor, mice injected with wt WR or TK- of WR virus had the lowest RSW 37.3 or 46.9, respectively, which was similar to the RSW from the mice without tumor and injected with PBS (43.6). The largest RSW 143.8 and 114.4 was observed in RVGL5 (HA-) and RVGL21 (TK-, F3-, HA-) groups, respectively. No statistically significant difference was found among the groups of mice injected with wt LIVP, RVGL2, RVGL9, RVGL20 versus the PBS injected group.

Nude Mice with Breast Tumor

The results of RSW in the immunocompromised mice bearing s.c human breast tumor indicate that all mice injected with wt LIVP and its mutants have an enlarged spleen compared to the mice injected with wt WR or TK-WR viruses ($p<0.045$). The largest spleen was found in the mice injected with single HA-, single F3-, double F3-, TK-mutants of LIVP strain.

Other Results Using RVGL21 for Injection

Two mice, #437 and #458, survived more then 190 days after RVGL21 injection ($10^7$ and $4\times10^5$, respectively, i.v.) without any signs of diseases or virus related toxicities.

On day 30 after GI-101A cell implantation (tumor volume=594.9 mm$^3$), $10^7$ of RVGL21 was injected i.v. into mouse #437. On day 101 after virus injection (s.c. tumor size=220.4 mm$^3$), metastasis (hard tissue) in chest area under the skin was observed. The size of the tumor was 1223.6 mm$^3$, which disappeared by day 148. The s.c. tumor did not disappear, it started to grow back, but the mouse remained metastasis-free.

Mouse #458 had a first s.c. tumor (GI-101A) on the right hind quarter. When the first tumor started to shrink (day 29 after RVGL21 virus injection, tumor size=1924.3 mm$^3$), a second syngeneic tumor was implanted s.c. on the left hind quarter. The second tumor grew slowly, reached the size of 1205.7 mm$^3$ and started to shrink. The mouse was free of the first tumor on day 127 post virus injection; the size of the second tumor was 439.6 mm$^3$. The tumor continued to shrink and the cells died. The body gradually absorbed remaining tumor tissues that were contributed by the host (such as the tumor vascular skeleton that was coming from the host). Since these remains are not considered foreign, the immune system doesn't destroy them. The tumor cells, on the other hand, were long gone and cleared by the immune system and the virus. Reduction of the second syngeneic tumor demonstrates that this mouse developed antibodies against the tumor cells. The antibodies resulted in the reduction of the second syngeneic tumor.

Example 6

Use of a Microorganism or Cell to Induce Autoimmunization of an Organism Against a Tumor This example shows that the method provided herein and in priority application EP 03 018 478.2 relating to "The production of a polypeptide, RNA or other compound in a tumor tissue" also can be used for the production of antibodies against the tumor tissue. These antibodies provide for autoimmunization of the organism bearing the tumor. Furthermore, these antibodies can be isolated and used for the treatment of tumors in other organisms.

Methods and uses of microorganisms, including cells, which can contain DNA encoding a desired polypeptide or RNA, to induce autoimmunization of an organism against a tumor are provided. Also provided are methods for the production of antibodies against a tumor by: (a) injecting a microorganism, such as a virus or cell, optionally containing a DNA sequence encoding a desired polypeptide or RNA, into an organism bearing a tumor and (b) isolating antibodies against the tumor.

This Example further demonstrates that administration of microorganisms, such as the triple mutant vaccinia virus strain provided herein, which accumulate in tumors, causing them to release tumor antigens for a sufficient time to permit production of antibodies by the host. This is exemplified by showing a reduction and elimination of xenogeneic GI-101A solid breast carcinoma tumors and their metastases in nu−/nu− mice (T cell deficient mice).

Step#1: Female nu−/nu− mice of 5 weeks age were chosen, and the GI-101A cells grown in RPMI1640 medium, supplemented with estrogen and progesterone. The confluence was reached, cells were harvested, washed with phosphate buffered saline. Cells ($5\times10^6$ cells per mouse) were then injected subcutaneously into mice. The tumor growth was carefully monitored every two days.

Step#2: At two stages of tumor growth (at tumor size of 400-600 mm$^3$, and at tumor size of ~1700 mm$^3$), purified vaccinia viral particles (RVGL12) were delivered to each tumorous mice by intravenous injection through tail vein. The colony purified virus was amplified in CV-1 cell line and the intracellular viral particles were purified by centrifugation in sucrose gradient. Two concentrations of virus ($10^6$ pfu/100 µl and $10^7$ pfu/100 µl resuspended in PBS solution) were injected. The viral replication was monitored externally by visualization of virus-mediated green fluorescence protein expression. The tumor development was monitored by tumor volume determination with a digital caliper.

Vaccinia viruses RVGL12+GCV(gancyclovir), and RVGL12 (RVGL12 is the same as RVGL7, except that the nucleic acid encoding gfp is replaced by herpes simplex virus thymidine kinase (HSV TK; see, SEQ ID NOS: 35 and 36) were injected 67 days after GI-101A cellular implantation. A second administration referred to as RVGL12a, was injected 30 days after cellular implantation.

Step#3: After viral administration, it was determined that first the tumors continued to grow to a size of ~900 $mm^3$ (from 400-600 $mm^3$ at the time of viral injection), and to a size of ~2400 mm3 (from 1700 $mm^3$). Then the growth rate leveled off for approximately 6-8 days.

Step#4: Approximately 14 days after viral injection, the tumor volume started to decline rapidly. Forty days after viral application, all the treated animals showed more than 60% tumor regression. Sixty-five days after viral treatment and many of the animals had complete regression of tumors.

Step#5: Some of the animals were completely tumor-free for several weeks and their body weight returned to normal. RVGL-12+GCV treatment resulted in 86.3% reduction of tumor size (Day 52 after viral injection) from their peak volumes on Day 13, RVGL-12 treatment resulted in 84.5% reduction of tumor size (Day 52) from their peak volumes (Day 13). RVGL-12a treatment resulted in 98.3% reduction of tumor size (Day 89) from their peak volumes (Day 12). After PBS+GCV control treatment, the average volume of tumors were increased by 91.8% in 38 days Step#6: The level of immune activation was determined. Sera were obtained from the animals with regressing tumors and the immune titer determined against a foreign protein (e.g. green fluorescent protein), vaccinia viral proteins, and GI-101A cancer cell proteins were determined. The following antisera obtained from the following sources were used to analyze the following listed samples.

Samples:
1). Mouse cell lysate (control);
2). Purified and denatured vaccinia viral particles;
3). GI-101A tumor cell lysate;
4). Purified green fluorescent protein;
5). Purified luciferase protein;
6). Purified beta-galactosidase protein.

Antisera:
a). Antiserum from nontumorous mouse;
b). Antiserum from GI-101A tumorous mouse;
c). Antiserum from GI-101A tumorous mouse 14 days after vaccinia i.v. injection;
d). Antiserum from GI-101A tumorous mouse 65 days after vaccinia i.v. injection;
e). Antiserum from tumor-free mouse (after elimination of GI-101A tumor) 80 days after vaccinia i.v. injection.

The results showed that there was enormous tumor-specific vaccinia virus replication in the tumors, which led to tumor protein antigen and viral protein production in the tumors. In addition, the vaccinia virus did lyse the infected tumor cells thereby releasing tumor-cell-specific antigens. The continuous leakage of these antigens into the body led to a very high level of antibody titer (in approximately 7-14 days) against foreign cell proteins (tumor proteins), viral proteins, and the virus encoded engineered proteins in the mouse body. The newly synthesized antitumor antibodies and the enhanced macrophages, neutrophils counts were continuously delivered via the vasculature into the tumor and thereby providing for the recruitment of an activated immune system in the inside of the tumor. The active immune system then eliminated the tumor including the viral particles. This interconnected release of foreign antigens boosted antibody production and continuous return of the antibodies against the tumor-contained proteins function as an autoimmunization vaccination system, initiated by vaccinia viral replication, followed by cell lyses, protein leakage and enhanced antibody production.

Example 7

Production of β-Galactosidase and Anti β-Galactosidase Via Vaccinia Virus Delivered lacZ in Tumor Bearing Mice Thirty five athymic nu/nu mice (5 weeks old, 25 g, male) were used to demonstrate the biodistribution and tumor targeting of vaccinia virus (strain LIVP) with different deletions in the genome. Mice were divided into 7 groups with 5 in each group as presented in Table 1

| Group | No. mice | Tumor implanted | Virus Injected | Insertion locus |
|---|---|---|---|---|
| 1 | 5 | None | VGL | wtLIVP |
| 2 | 5 | C6, s.c. 5 × $10^5$ cells | VGL | wtLIVP |
| 3 | 5 | C6, s.c. 5 × $10^5$ cells | RVGL1 | N-luc, lacZ |
| 4 | 5 | C6, s.c. 5 × $10^5$ cells | RVGL5 | HA-lacZ |
| 5 | 5 | C6, s.c. 5 × $10^5$ cells | RVGL7 | TK-egfp, lacZ |
| 6 | 5 | C6, s.c. 5 × $10^5$ cells | RVGL8 | NotI-lacZ |
| 7 | 5 | C6, s.c. 5 × $10^5$ cells | RVGL19 | TK-rTrf, lacZ, NotI-RG |

C6 gliomas were subcutaneously developed in Groups 2 to 7. Five days after tumor cell implantation (5×$10^5$ cells/mouse), each animal was treated with 0.1 ml of virus at a multiplicity of infection (MOI) of 1×$10^7$ via tail vein injection. Two weeks after virus injection, all mice were sacrificed and blood samples were collected. Various organs and tumors also were taken from animals for virus titer and β-galactosidase analysis.

The β-galactosidase analysis was performed using the Galacto-Light Plus system (Applied Biosystems), a chemiluminescent reporter gene assay system for the detection of β-galactosidase, according to the manufacturer's instructions.

β-galactosidase Expression Measurements

In non-tumorous mice as well as in tumorous mice injected with wild type vaccinia virus (without reporter genes and without β-galactosidase gene) no β-galactosidase expression was detected in organs, blood and tumor samples. By contrast, in the tumors of mice infected with β-galactosidase expressing virus, high levels of β-galactosidase was expressed. β-galactosidase also was detected in blood samples as shown in Table 3, but no virus was recovered from blood samples.

TABLE 3

Production of β galactosidase by *vaccinia virus* in tumor and blood from tumor bearing mice (day 14 after virus injection)

| Group | Virus Injected | β-gal in tumor Tg/mg of total protein | β-gal in serum Tg/ml of total protein | Est. total β-gal/tumor (Tg) | Est. total β-gal/5 ml blood (Tg) |
|---|---|---|---|---|---|
| 3 | RVGL1 | 1.59 ± 0.41 | $1.38 \times 10^{-2} \pm 1.09 \times 10^{-2}$ | 489.84 | 4.00 |
| 4 | RVGL5 | 1.51 ± 0.37 | $1.16 \times 10^{-2} \pm 1.08 \times 10^{-2}$ | 330.21 | 3.62 |
| 5 | RVGL7 | 1.35 ± 0.59 | $0.95 \times 10^{-2} \pm 1.47 \times 10^{-2}$ | 616.60 | 1.83 |
| 6 | RVGL8 | 1.81 ± 0.42 | $0.86 \times 10^{-2} \pm 0.33 \times 10^{-2}$ | 962.36 | 2.38 |
| 7 | RVGL19 | 1.30 ± 0.44 | $0.26 \times 10^{-2} \pm 0.16 \times 10^{-2}$ | 463.75 | 0.60 |

Anti-β-galactosidase Antibody Production

To determine whether the amount of β-galactosidase presented in mouse blood was sufficient to elicit antibody production, sera taken from two mice (mouse #116 from Group 5, and #119 from Group 6) were collected and tested for primary antibodies against β-galactosidase in Western analysis. β-galactosidase from *E. coli* (Roche, 567 779) was used as the antigen standard, and the mouse monoclonal anti f3-galactosidase from *E. coli* (Sigma, G6282) was used as the antibody positive control. As additional sources of β-galactosidase, total protein was obtained from CV-1 cells 24 hours after infection with RVGL7 at MOI of 1 pfu/cell, and the tumor protein sample from mouse designated #143 (treated with RVGL7) was obtained.

The protein samples were prepared in triplicate, each set including a β-galactosidase antigen control, a cell lysate from RVGL7 infected CV-1 cells, and tumor lysate from mouse #143. All protein samples were separated by electrophoresis using a 10% polyacrylamide gel, and transferred to NitroBind nitrocellulose membrane (MSI) using a BioRad semidry blotting system. Immunoblotting was performed with either 1:3000 mouse monoclonal anti β-galactosidase, or 1:3000 mouse serum taken from either mouse #116 or #119, and 1:3000 Goat AntiMouse IgG-HRP (BioRad). An Amplified Opti-4CN Detection Kit (BioRad) was used for detection.

The results showed that sera taken from mouse #116 and #119 exhibited similar levels of antibody when compared to a commercial mouse anti-β-galactosidase standard, and demonstrated that the tumor bearing mice #116 and #119 produced antibodies against β-galactosidase.

Example 8

Mammalian Cells for Tumor Therapy

As shown herein, certain bacteria, viruses, and mammalian cells (BVMC), when administered systemically, again enter and selectively replicate in tumors Hence, systemically injected mammalian cells and certain bacterial (anaerobic bacteria, such as *Salmonella, Clostridium* sp., *Vibrio, E. coli*) cells gain entry into solid tumors and replicate in tumor-bearing organisms. Genetically-labeled cells can be used for tumor detection and therapy. In addition to gene expression in tumors through BVMC targeting, tumor-specific gene expression can be achieved by linking transgenes to tissue/tumor-specific promoters. To obtain tumor specific gene expression, a variety of systemic targeting schemes can be employed. These strategies include the use of tissue/tumor-specific promoters that allow the activation of gene expression only in specific organs, such as prostate-specific promoter-directed viral gene expression; the use of extracellular matrix (i.e. collagen)-targeted viral vectors; and the use of antibody-directed viral vectors. Conditionally-replicating viruses have also been explored as tumor-specific delivery vehicles for marker genes or therapeutic genes, such as oncolytic adenovirus vector particles, replication-selective HSV, vaccinia viruses and other such viruses.

When light-emitting protein encoded BVMC are injected systemically into rodents, tumor-specific marker gene expression is achieved and is detected in real time based on light emission. Consequently, the locations of primary tumors and previously unknown metastases in animals are revealed in vivo. Hence diagnosis can be coupled to therapy and to monitoring of therapy. The impaired lymphatic system in tumors may be responsible for the lack of clearance of bacteria from tumors by the host immunosurveillance after escaping the vascular system.

Example 9

Tumor Development is Inhibited Following *S. pyogenes* Administration

This example and following examples demonstrate the use of bacterial cells to colonize tumors, use of reporter in the cells to quantitate colonization; use of the colonized attenuated bacterial cells for tumor inhibition. Co-administration or sequential administration of bacteria and viruses. Administration of virus before bacteria increase tumor colonization by the bacteria. Administer bacteria that expresses an enzyme that will activate a prodrug, thereby targeting colonized cells.

Bacterial Strains

*Streptococcus pyogenes* M-type 1 T-type 1 (ATCC catalog no. 700294) was transformed with pDC123-luxF plasmid) that contains the bacterial luciferase expression cassette (Lamberton G R, Pereau M J, Illes K, Kelly I L, Chrisler J, Childers B J, Oberg K C, Szalay A A. 2002. *Construction and characterization of a bioluminescent Streptococcus pyogenes*. Proceedings of the 12th International Symposium on Bioluminescence and Chemiluminescence, Case J F, Herring P J, Robison B H, Haddock S H D, Kricka L J, Stanley P E (eds). Chichester: Wiley, pp 85-88. Luciferase can be detected in the presence of exogenous decanal.

Transformed *S. pyogenes* were grown overnight in BH1 media in the presence of 20 μg/ml of chloramphenicol at 37° C. After overnight growth, the bacteria were counted at $OD_{600}$ and bacteria were resuspended in BH1 media at the indicated density for injection.

Tumor Development and Bacterial Injection

Twenty 5-week old mice were injected subcutaneously in the right lateral thigh. Each mouse was injected with $5\times10^5$ C6 glioma cells transformed with pLEIN-derived retrovirus (Clontech; see also WO 03/14380). The subcutaneous tumors were developed for 7 days after implantation before bacterial injection.

For bacterial injection, the tumor-bearing mice were anesthetized with isofluorane. The suspensions were injected intravenously with a 1-cc insulin syringe equipped with a 29½-gauge needle through a surgically exposed femoral vein. After the injections, the incisions were sutured.

Tumor growth was monitored twice a week following bacterial injection using a digital caliper. In addition, fluorescence imaging and photographic images of the animals were taken at the end time points. The presence of luminescent bacteria was analyzed by intravenously injecting the animals with 30 μl of decanal. Analysis of whole animals for bacterial luciferase activity, followed methods similar to Yu et al. (2004) *Nature Biotechnology* 22(3): 313-20. Briefly, anesthetized animals were placed inside the dark box for photon counting (ARGUS 100 low light Imager, Hamamatsu). Photon collection was for 1 minute from ventral and dorsal sides of the animal and the images were recorded with Image Pro Plus 3.1 software (Media Cybernetics) and/or Lighttools® macroimaging system. A light image also was recorded. The luminescent images were superimposed on the light image to localize the luminescent activity on the animal. Total intensity of photon emission in localized regions, e.g. in the tumor region, also was recorded. *S. pyogenes* was isolated from removed tumors and ground tissue was plated on LB-chloramphenicol (20 μg/ml) plates. Luminescent bacteria were counted in the presence of decanal vapor.

Results

Four groups of mice were tested. Each group contained five mice.

| Group | *S. Pyogenes* |
|---|---|
| 1 | None |
| 2 | $1 \times 10^6$ |
| 3 | $1 \times 10^7$ |
| 4 | $5 \times 10^7$ |

Tumor volume was measured after 7 days of tumor development and the injection of *S. pyogenes*, through 21 days post-tumor development.

The control group of mice with no *S. pyogenes* had continuous and accelerating tumor growth over the 2-week period. The mice injected with *S. pyogenes* had slower tumor growth. Groups 3 and 4 had the slowest tumor growth rates. Both groups maintained a slower linear rate throughout the monitoring period, whereas the control group, not injected with bacteria, exhibited tumor growth that accelerated at later time periods.

At all time points following bacterial injection, tumor volumes were smaller in Groups 3 and 4 mice than in the control mice (Group 1). At day 21, the average tumor volume of the control group was approximately 2.5-3 fold greater than the average tumor volumes in Groups 3 and 4. Group 2, injected with the lowest titer of bacteria, also had a reduced tumor volume from the control group at the later time points, although the tumor volume was larger than Groups 3 and 4.

Bacterial colonization and tumor inhibition also is assayed in a fibrosarcoma model. HT1080 fibrosarcoma cells transformed with the pLEIN retrovirus are injected subcutaneously into the right lateral thigh of five week old nude male mice $5 \times 10^5$ cells/mouse). *S. pyogenes* transformed with pDC123-luxF is injected into the femoral vein of the animals after 8 or 14 days of tumor growth (5 animals on each day). A group of 5 animals are not injected as serve as a control group. Tumor growth and luciferase activity is monitored at subsequent time points. *S. pyogenes* is isolated from tumors and cultured on BH1+chloramphenicol (20 μg/ml) plates. Luminescent bacterial colonies are counted in the presence of decanal vapor.

Example 10

*Vibrio Cholera* Localization to Tumors

Plasmids and Bacterial Strains

Attenuated *Vibrio Cholerae*, strain Bengal 2 serotype 0139, M010 DattRS1, was transformed with pLITE201 which contains the luxCDABE cassette (Voisey et al. (1998) *Biotechniques* 24:56-58). The transformed strain is a light emitting strain due to the expression of the luciferase genes.

Tumor Development and Bacterial Injection

Groups of nude mice (n>20) were implanted with C6 glioma tumors (500 mm$^3$) as described in the Examples herein. $1 \times 10^8$ transformed bacteria (*V. Cholerae*) were suspended in 100 μl of phosphate buffered saline (PBS). The bacterial suspension was injected into the right hind leg of each mouse. The animals were then monitored after injection under a low light imager as described in Example 3.

In a separate experiment, for comparison, groups of nude mice (n>20) were implanted with C6 glioma tumors (500 mm$^3$) as described in the Examples herein. These mice were injected with $1 \times 10^8$ pfu/mouse of rVV-RUC-GFP (RVGL9) virus (see Example 1).

Results

Titer and Luciferase Activity

Mice from each of the two injected groups were sacrificed at time points after injection. Tumors were excised and homogenized. Bacterial and viral titers and luciferase activities were measured as described in the Examples herein.

Both bacterial and viral titer increased following injection. The increase in bacterial growth over time was proportional to luciferase levels in the tumors. A log-log plot of bacterial titer versus luciferase activity in tumors in the mice injected with *V. cholera* demonstrated a linear relationship between bacterial titer and luciferase activity. The groups of mice injected with rVV-RUC-GFP virus, also demonstrated a linear relationship between virus titer and luciferase activity.

| | Time after *V. Cholera*/pLITE injection | | | |
|---|---|---|---|---|
| | 4 hrs | 8 hrs | 16 hrs | 32 hrs |
| Bacterial Titer (cfu/tumor) | $3.79 \times 10^4 \pm 2.93$ | $3.14 \times 10^6 \pm 2.45$ | $1.08 \times 10^8 \pm 0$ 1.3 | $5.97 \times 10^8 \pm 4.26$ |

| | Time after rVV-ruc-gfp virus injection | | | |
|---|---|---|---|---|
| | 36 hrs | Day 3 | Day 5 | Day 7 |
| ViralTiter (pfu/tumor) | $3.26 \times 10^6 \pm 3.86$ | $7.22 \times 10^7 \pm 3.67$ | $1.17 \times 10^8 \pm 0.76$ | $3.77 \times 10^8 \pm 1.95$ |

The experiments demonstrated a linear relationship between titer and luciferase activity. Thus, luciferase activity of the injected bacteria and/or virus can be used a correlative measurement of titer.

Localization

Localization of *V. cholera* was performed as detailed in the Examples herein for virus. Briefly, organs and blood samples were isolated from animals euthanized with $CO_2$ gas. The organs were ground and plated on agar plates with chloramphenicol drug selection for analysis of bacterial titer.

Bacterial titer was assayed in tumor, liver, testes, spleen, kidney, lung, heart, bladder and brain of the injected mice. Samples were taken from mice sacrificed at zero, and subsequent times up to 150 hours following *V. cholera* injection.

At the time point immediately following injection (t=0), *V. cholera* was present in all samples, with the highest levels in the liver and spleen. By 50 hours post-injection, titer of *V. cholera* in all tissues had reduced with the exception of tumor tissue. In contrast, *V. cholera* titer had increased about 4 orders of magnitude as compared to time zero. This level increased slightly and then stayed constant throughout the remainder of the experiment. By 150 hours post-infection, titer in all samples except tumor had decreased. For example, the titer in liver had decreased by approximately 5 orders of magnitude from the time zero point. At the 150 hour point, the *V. cholera* titer in the tumor tissue was about 6 orders of magnitude greater than any other tissue sample.

Example 11

Co-administration and Sequential Administration of Bacteria and Virus

*V. Cholera*/pLITE (see Example 10) and vaccinia virus RVGL2 (see Example 1) were administered together or sequentially. Groups of nude mice with C6 glioma tumors were injected with bacteria and/or virus as shown in the Table below. Three male mice were injected per group. Bacteria and/or virus were injected on day 11 and day 16 following tumor implantation. Tumor growth, luciferase and GFP activity were monitored as described in the Examples herein.

| Group | Day 11 injection | Day 16 injection |
|---|---|---|
| 1 | $1 \times 10^7$ VV-TK$^-$-gfp-lacZ | $1 \times 10^7$ *V. Cholera*/pLITE |
| 2 | None | $1 \times 10^7$ *V. Cholera*/pLITE |
| 3 | $1 \times 10^7$ *V. Cholera*/pLITE | $1 \times 10^7$ VV-TK$^-$-gfp-lacZ |
| 4 | None | $1 \times 10^7$ VV-TK$^-$-gfp-lacZ |
| 5 | None | $1 \times 10^7$ VV-TK$^-$-gfp-lacZ and $1 \times 10^7$ *V. Cholera*/pLITE |

Results

On day 21 (21 days post tumor implantation) animals were sacrificed. Tumors were excised from each animal and ground. Viral titer was assayed on Groups 3, 4 and 5. Bacterial titer was assayed on Groups 1, 2 and 5. Titers (colony forming units and plaque forming units) were performed as previously described in the Examples.

A comparison of the bacterial titer in tumors Groups 1, 2 and 5 demonstrated that bacterial titer was highest in Group 1 that had been injected first with vaccinia virus at day 11, and followed by *V. cholera* injection on day 16. Co-injection of bacteria and virus at day 16 (Group 5) gave an intermediate bacterial titer. Group 2, injected only with *V. cholera* at day 16, had a lower bacterial titer in the tumor tissue than either of groups 1 or 5. Thus, tumors were more susceptible to bacterial colonization when first colonized by VV-TK$^-$-gfp-lacZ virus.

A comparison of the viral titer in Groups 3, 4 and 5 demonstrated that Group 4, with only virus injection at day 16, had the highest viral titer followed by Groups 5 and 3. The viral titer of Group 5 was slightly higher than Group 3, but not apparently significantly different. One mouse in Group 4 had a viral titer that was an extreme outlier in comparison to the viral titer of the other 2 mice in Group 4. When the numbers were reassessed without this mouse, the general trend remained the same. The average viral titer in Group 4 was much closer to the viral titers of Groups 3 and 5. The data from the three groups in this analysis was not significantly different. Thus, pre-administration of bacteria followed by administration of virus did not significantly change the viral colonization of the tumor as compared with viral administration alone.

Example 12

Tumor Inhibition by Administering PNP-Expressing Bacteria and Prodrug Plasmids SOD-DeoD contains the bacterial purine nucleoside phosphorylase gene (PNP) (Sorcher et al. (1994) GeneTher. 1(4):223-238), under the control of the constitutive SOD (superoxide dismutase) promoter. Plasmid pSOD-DeoD-lux, contains the luxCDABE expression cassette (Voisey et al. (1998) *Biotechniques* 24:56-58) inserted into pSOD-DeoD.

PNP converts the non-toxic prodrug 6-methylpurine deoxyribose (6-MPDR) to 6-methyl purine which inhibits DNA replication, transcription and translation (Sorcher et al. (1994) *GeneTher.* 1(4):223-238).

Tumor Growth Inhibition

Nude mice were injected with pLEIN retrovirus transformed C6 glioma cells. The pLEIN retrovirus expresses EGFP under the control of the viral promoter LTR (Clontech; see also WO 03/14380). *E. coli* DH5α expressing the bacterial purine nucleoside phosphorylase gene was injected at day 8 following tumor implantation with or without prodrug (6-methylpurine deoxyribose (6-MPDR)). Tumor volume was monitored at subsequent time points (as performed in previous examples).

| Group | Administered |
|---|---|
| 1 | *E. coli*/PNP + prodrug |
| 2 | *E. coli*/PNP |
| 3 | *E. coli* control + prodrug |

Groups 2 and 3 exhibited equal tumor growth over time points from 8 to 21 days post tumor implantation. Group 1, which received both the *E. coli* expressing PNP and the prodrug exhibited ~20% reduction in tumor size as compared to the control Groups 2 and 3 at the end time points.

To further test bacterial colonization and prodrug effects on tumor growth, a human breast cancer model, GI-101A adenocarcinoma in nude mice, was chosen. GI-101A was derived from GI-101. GI-101 originated from a local first recurrence of an infiltrating duct adenocarcinoma (stage IIIa, T3N2MX) in a 57 year old female patient by researchers at Rumbaugh-Goodwin Institute for Cancer Research. In the subcutaneous xenograft nude mice model, the tumor consistently metastasizes to the lungs. The GI-101A is a slower growing tumor model as compared to the C6 glioma tumor model.

Fifteen 4 week old female nude mice are each injected subcutaneously in the right lateral thigh with GI-101A cells. Thirty days after tumor development, bacteria are injected. *Escherichia coli* DH5α is transformed with pSOD-DeoD or pSOD-DeoD-lux. The bacteria are grown overnight in LB media in the presence of 20 μg/ml of chloramphenicol at 37° C. After overnight growth, the bacteria are counted at $OD_{600}$ and bacteria resuspended in BH1 media at the indicated density. The suspensions are injected intravenously with a 1-cc insulin syringe equipped with a 29½-gauge needle into the animal through a surgically exposed vein or as otherwise indicated. After the injections, the incisions are sutured.

Prodrug is administered to groups of mice every four days following injection of bacteria. Tumor growth is monitored twice per week using a digital caliper. Luciferase imaging is performed as described in the Examples herein. At the end point, the animal are sacrificed and organs are assayed as described in Example 9. Histological analyses are performed to determine the degree of tumor necrosis due to bacterial colonization and/or drug treatment.

Since modifications will be apparent to those of skill in the art, it is intended that this invention be limited only by the scope of the appended claims.

The invention claimed is:

1. An isolated cell, comprising a recombinant vaccinia virus that comprises a modified thymidine kinase (TK) gene and a modified hemagglutinin (HA) gene, and an insertion, deletion or mutation in the gene or locus designated F3, wherein:

each of the TK, HA and F3 gene or locus is inactivated; and the F3 locus occurs on the HindIII-F fragment of the vaccinia virus between open reading frames F14L and F15L.

2. The cell of claim 1, wherein heterologous nucleic acid is inserted into the TK and HA genes to inactivate them, and heterologous nucleic acid is inserted into the F3 locus.

3. The cell of claim 1, wherein the vaccinia virus is a strain selected from among Western Reserve (WR), Copenhagen, Tashkent, Tian Tan, Lister, Wyeth, IHD-J, and IHD-W, Ankara, MVA, Dairen I, L-IPV, LC16M8, LC16MO, LIVP, WR 65-16, Connaught and New York City Board of Health strains.

4. The cell of claim 1, wherein the insertion in the F3 locus is at a site corresponding to the unique NotI restriction site or position 1475 of the LIVP strain inside of the HindIII-F fragment of the LIVP strain of vaccinia virus.

5. The cell of claim 1, wherein at least one of the TK gene, HA gene and F3 locus comprises an insertion of heterologous nucleic acid that encodes a protein.

6. The cell of claim 5, wherein the encoded protein is an antibody or antigen-binding fragment thereof.

7. The cell of claim 5, wherein the encoded protein is a solute carrier protein (slc), a superoxide dismutase (sod), a colony stimulating factor (csf), monocyte chemotactic protein-1 (mcp-1), a nonmetastatic protein (nm), a neurogenin protein (ngn), erythropoietin (epo), bmp2, bmp2a, bmp4, tyrp1, tyrp2 or aim1 or an anti-tumor protein.

8. The cell of claim 7, wherein the encoded protein is an slc selected from among solute carrier 5 (slc5) and solute carrier 6 (slc6) transporter protein families.

9. The cell of claim 8, wherein the transporter protein is a norepinephrine transporter (net) or is a sodium-iodide symporter (nis).

10. The cell of claim 5, wherein the heterologous nucleic acid is operatively linked to a regulatory sequence.

11. The cell of claim 10, wherein the regulatory sequence comprises a promoter.

12. The cell of claim 10, wherein the regulatory sequence comprises the vaccinia virus early/late promoter p7.5.

13. The cell of claim 10, wherein the regulatory sequence comprises an early/late vaccinia pE/L promoter.

14. The cell of claim 5, wherein heterologous nucleic acid encodes a detectable protein or a protein capable of inducing a detectable signal.

* * * * *

UNITED STATES PATENT AND TRADEMARK OFFICE

CERTIFICATE OF CORRECTION

PATENT NO. : 9,492,534 B2
APPLICATION NO. : 14/301813
DATED : November 15, 2016
INVENTOR(S) : Szalay et al.

It is certified that error appears in the above-identified patent and that said Letters Patent is hereby corrected as shown below:

On the Title Page

In Item (56) References Cited, in OTHER PUBLICATIONS, on page 7, 2nd Column, Line 12, please replace "inununoediting" with —immunoediting—.

In Item (56) References Cited, in OTHER PUBLICATIONS, on page 10, 2nd Column, Line 68, please replace "(199)" with —(1996)—.

In Item (56) References Cited, in OTHER PUBLICATIONS, on page 14, 1st Column, Line 7, please replace "Morena" with the author's last name —Moretta—.

In Item (56) References Cited, in OTHER PUBLICATIONS, on page 16, 2nd Column, Line 15, please replace "Reimer" with the author's last name —Rezmer—.

In Item (56) References Cited, in OTHER PUBLICATIONS, on page 18, 1st Column, Line 32, please replace "Stocked" with the author's last name —Stockert—.

In the Specification

At Column 33, Line 27, please replace "aays1" with —aavs1—;

At Column 33, Line 62, please replace "anti" with —ant1—;

At Column 34, Line 21, please replace "aysd" with —avsd—;

At Column 34, Line 39, please replace "brie" with —bric—;

At Column 34, Line 46, please replace "ca1" with —ca7—;

Signed and Sealed this
Fifteenth Day of August, 2017

Joseph Matal

Joseph Matal
*Performing the Functions and Duties of the*
*Under Secretary of Commerce for Intellectual Property and*
*Director of the United States Patent and Trademark Office*

At Column 34, Line 56, please replace "cae3" with —cap3—;

At Column 34, Line 61, please replace "cae3" with —cav3—;

At Column 34, Line 66, please replace "cent" with —ccnt—;

At Column 36, Line 35, please replace "deer" with —decr—;

At Column 36, Line 35, please replace "defy" with —def5—;

At Column 36, Lines 38-39, please replace "dfha4, dfha5" with —dfna4, dfna5—;

At Column 37, Line 6, please replace "etha1" with —efna1—;

At Column 37, Line 34, please replace "face" with —facc—;

At Column 37, Line 38, please replace "fcc" with —fce—;

At Column 37, Line 38, please replace "feer1b, feer1g, feer2" with —fcer1b, fcer1g, fcer2—;

At Column 37, Line 39, please replace "fegr1c, fegr2a, fegr3a" with —fcgr1c, fcgr2a, fcgr3a—;

At Column 37, Line 39, please replace "fen1" with —fcn1—;

At Column 37, Line 43, please replace "fgfl1" with —fgf11—;

At Column 37, Line 45, please replace "fhe" with —fhc—;

At Column 37, Line 47, please replace "fkbpl2" with —fkbp12—;

At Column 37, Line 51, please replace "fhrb1" with —fnrb1—;

At Column 37, Line 60, please replace "g10p1" with —g17p1—;

At Column 37, Line 66, please replace "gains" with —galns—;

At Column 37, Line 67, please replace "gaplm" with —gap1m—;

At Column 38, Line 2, please replace "gash" with —gas6—;

At Column 38, Line 4, please replace "gef1" with —gcf1—;

At Column 38, Line 5, please replace "gen512" with —gcn512—;
At Column 38, Line 5, please replace "gent1" with —gcnt1—;

At Column 38, Line 5, please replace “ges1” with —gcs1—;

At Column 38, Line 14, please replace “gins” with —glns—;

At Column 38, Line 17, please replace “giy96” with —gly96—;

At Column 38, Line 38, please replace “gtf21” with —gtf2i—;

At Column 38, Line 46, please replace “h4f1” with —h4fi—;

At Column 38, Line 54, please replace “hemi” with —hem1—;

At Column 39, Line 6, please replace “hox21” with —hox2i—;

At Column 39, Line 8, please replace “hox41” with —hox4i—;

At Column 39, Line 20, please replace “hsd1” with —hsd11—;

At Column 39, Line 29, please replace “hyls” with —hvls—;

At Column 39, Line 40, please replace “ifhr” with —ifnr—;

At Column 39, Line 45, please replace “ig” with —igj—;

At Column 40, Line 20, please replace “lea” with —lca—;

At Column 40, Line 33, please replace “lp1” with —lpi—;

At Column 40, Lines 36-37, please replace “1 um” with —lum—;

At Column 40, Line 57, please replace “meati” with —mea6—;

At Column 40, Line 67, please replace “midi” with —mid1—;

At Column 41, Line 27, please replace “much” with —muc6—;

At Column 41, Line 46, please replace “nett” with —net1—;

At Column 41, Line 60, please replace “nph12” with —nphl2—;

At Column 41, Line 62, please replace “npylr” with —npy1r—;
At Column 42, Line 17, please replace “pabpl 1, pact, pact” with —pabpl1, pac1, pac1—;

At Column 42, Line 25, please replace “pent” with —pcnt—;

At Column 42, Line 39, please replace “pgf” with —pg1—;

At Column 42, Line 54, please replace “pin” with —pln—;

At Column 42, Line 61, please replace “pore” with —porc—;

At Column 43, Line 13, please replace “prca1” with —prsc1—;

At Column 43, Line 21, please replace “etch” with —ptch—;

At Column 43, Line 33, please replace “gars” with —qars—;

At Column 43, Line 44, please replace “rdre” with —rdrc—;

At Column 43, Line 44, please replace “rcc1” with —recc1—;

At Column 44, Line 8, please replace “scab” with —sca6—;

At Column 44, Line 10, please replace “scic1” with —sclc1—;

At Column 44, Line 38, please replace “slc1a2, slc1a4” with —slc7a2, slc7a4—;

At Column 44, Line 47, please replace “snipe” with —snrpe—;

At Column 44, Line 60, please replace “step” with —ste—;

At Column 45, Line 3, please replace “m/z” with —taz—;

At Column 45, Line 11, please replace “tert1” with —terf1—;

At Column 45, Line 22, please replace “trod” with —tmd—;

At Column 45, Line 44, please replace “tyros” with —tyms—;

At Column 46, Line 42, please replace “betl” with —betI—;

At Column 47, Line 5, please replace “duaI” with —dnaI—;

At Column 47, Line 26, please replace “thr” with —fnr—;
At Column 47, Lines 34-35, please replace “gleB, gleC, gleD, gIcE, gleG” with —glcB, glcC, glcD, gIcE, glcG—;

At Column 50, Line 28, please replace “Acral” with —Acra7—;

At Column 50, Line 30, please replace “CeaS” with —Cea5—;

At Column 52, Line 26, please replace “HOME” with —HOM6—;

At Column 53, Line 3, please replace “THF1” with —TBF1—;

At Column 54, Lines 3-4, please replace “Chordopoxyirinae” with —Chordopoxvirinae—;

At Column 54, Line 6, please replace “Entomopoxyirinae” with —Entomopoxvirinae—;

At Column 54, Line 8, please replace “Chordopoxyirinae” with —Chordopoxvirinae—;

At Column 54, Line 12, please replace “chordopoxyirinae” with —chordopoxvirinae—;

At Column 54, Line 17, please replace “chordopoxyirinae” with —chordopoxvirinae—.

SEQUENCE LISTING

```
<160> NUMBER OF SEQ ID NOS: 36

<210> SEQ ID NO 1
<211> LENGTH: 148
<212> TYPE: DNA
<213> ORGANISM: Artificial Sequence
<220> FEATURE:
<223> OTHER INFORMATION: LIVP F3

<400> SEQUENCE: 1

aatatagcaa cagtagttct tgctcctcct tgattctagc atcctcttca ttattttctt     60

ctacgtacat aaacatgtcc aatacgttag acaacacacc gacgatggcg gccgctacag    120

acacgaatat gactaaaccg atgaccat                                       148


<210> SEQ ID NO 2
<211> LENGTH: 49
<212> TYPE: PRT
<213> ORGANISM: Artificial Sequence
<220> FEATURE:
<223> OTHER INFORMATION: Translation LIVP F3

<400> SEQUENCE: 2

Met Val Ile Gly Leu Val Ile Phe Val Ser Val Ala Ala Ala Ile Val
 1               5                  10                  15

Gly Val Leu Ser Asn Val Leu Asp Met Phe Met Tyr Val Glu Glu Asn
            20                  25                  30

Asn Glu Glu Asp Ala Arg Ile Lys Glu Glu Gln Glu Leu Leu Leu Leu
        35                  40                  45

Tyr


<210> SEQ ID NO 3
<211> LENGTH: 27
<212> TYPE: DNA
<213> ORGANISM: Artificial Sequence
<220> FEATURE:
<223> OTHER INFORMATION: Forward primer

<400> SEQUENCE: 3

gggaattctt atacatcctg ttctatc                                         27


<210> SEQ ID NO 4
```

```
<211> LENGTH: 30
<212> TYPE: DNA
<213> ORGANISM: Artificial Sequence
<220> FEATURE:
<223> OTHER INFORMATION: Reverse primer

<400> SEQUENCE: 4

ccaagcttat gaggagtatt gcggggctac                                30


<210> SEQ ID NO 5
<211> LENGTH: 7252
<212> TYPE: DNA
<213> ORGANISM: Artificial Sequence
<220> FEATURE:
<223> OTHER INFORMATION: psc65
<300> PUBLICATION INFORMATION:
<308> DATABASE ACCESSION NUMBER: GenBank No. AX003206
<309> DATABASE ENTRY DATE: 2000-08-24

<400> SEQUENCE: 5

agcttttgcg atcaataaat ggatcacaac cagtatctct taacgatgtt cttcgcagat      60

gatgattcat tttttaagta tttggctagt caagatgatg aaatcttcat tatctgatat     120

attgcaaatc actcaatatc tagactttct gttattatta ttgatccaat caaaaaataa     180

attagaagcc gtgggtcatt gttatgaatc tctttcagag gaatacagac aattgacaaa     240

attcacagac tttcaagatt ttaaaaaact gtttaacaag gtccctattg ttacagatgg     300

aagggtcaaa cttaataaag gatatttgtt cgactttgtg attagtttga tgcgattcaa     360

aaaagaatcc tctctagcta ccaccgcaat agatcctgtt agatacatag atcctcgtcg     420

caatatcgca ttttctaacg tgatggatat attaaagtcg aataaagtga acaataatta     480

attctttatt gtcatcatga acggcggaca tattcagttg ataatcggcc ccatgttttc     540

aggtaaaagt acagaattaa ttagacgagt tagacgttat caaatagctc aatataaatg     600

cgtgactata aaatattcta acgataatag atacggaacg ggactatgga cgcatgataa     660

gaataatttt gaagcattgg aagcaactaa actatgtgat ctcttggaat caattacaga     720

tttctccgtg ataggtatcg atgaaggaca gttctttcca gacattgttg aattagatcg     780

ataaaaatta attaattacc cgggtaccag gcctagatct gtcgacttcg agcttattta     840

tattccaaaa aaaaaaaata aaatttcaat tttaagcttt tcactaattc caaacccacc     900

cgctttttat agtaagtttt tcacccataa ataataaata caataattaa tttctcgtaa     960

aagtagaaaa tatattctaa tttattgcac ggtaaggaag tagatcataa ctcgagcatg    1020

ggagatcccg tcgttttaca acgtcgtgac tgggaaaacc ctggcgttac ccaacttaat    1080

cgccttgcag cacatccccc tttcgccagc tggcgtaata gcgaagaggc ccgcaccgat    1140

cgcccttccc aacagttgcg cagcctgaat ggcgaatggc gctttgcctg gtttccggca    1200

ccagaagcgg tgccggaaag ctggctggag tgcgatcttc ctgaggccga tactgtcgtc    1260

gtcccctcaa actggcagat gcacggttac gatgcgccca tctacaccaa cgtaacctat    1320

cccattacgg tcaatccgcc gtttgttccc acggagaatc cgacgggttg ttactcgctc    1380

acatttaatg ttgatgaaag ctggctacag gaaggccaga cgcgaattat ttttgatggc    1440

gttaactcgg cgtttcatct gtggtgcaac gggcgctggg tcggttacgg ccaggacagt    1500

cgtttgccgt ctgaatttga cctgagcgca tttttacgcg ccggagaaaa ccgcctcgcg    1560

gtgatggtgc tgcgttggag tgacggcagt tatctggaag atcaggatat gtggcggatg    1620

agcggcattt tccgtgacgt ctcgttgctg cataaaccga ctacacaaat cagcgatttc    1680
```

-continued

```
catgttgcca ctcgctttaa tgatgatttc agccgcgctg tactggaggc tgaagttcag   1740
atgtgcggcg agttgcgtga ctacctacgg gtaacagttt ctttatggca gggtgaaacg   1800
caggtcgcca gcggcaccgc gcctttcggc ggtgaaatta tcgatgagcg tggtggttat   1860
gccgatcgcg tcacactacg tctcaacgtc gaaaacccga aactgtggag cgccgaaatc   1920
ccgaatctct atcgtgcggt ggttgaactg cacaccgccg acggcacgct gattgaagca   1980
gaagcctgcg atgtcggttt ccgcgaggtg cggattgaaa atggtctgct gctgctgaac   2040
ggcaagccgt tgctgattcg aggcgttaac cgtcacgagc atcatcctct gcatggtcag   2100
gtcatggatg agcagacgat ggtgcaggat atcctgctga tgaagcagaa caactttaac   2160
gccgtgcgct gttcgcatta tccgaaccat ccgctgtggt acacgctgtg cgaccgctac   2220
ggcctgtatg tggtggatga agccaatatt gaaacccacg gcatggtgcc aatgaatcgt   2280
ctgaccgatg atccgcgctg gctaccggcg atgagcgaac gcgtaacgcg aatggtgcag   2340
cgcgatcgta atcacccgag tgtgatcatc tggtcgctgg ggaatgaatc aggccacggc   2400
gctaatcacg acgcgctgta tcgctggatc aaatctgtcg atccttcccg cccggtgcag   2460
tatgaaggcg gcggagccga caccacggcc accgatatta tttgcccgat gtacgcgcgc   2520
gtggatgaag accagccctt cccggctgtg ccgaaatggt ccatcaaaaa atggctttcg   2580
ctacctggag agacgcgccc gctgatcctt tgcgaatacg cccacgcgat gggtaacagt   2640
cttggcggtt tcgctaaata ctggcaggcg tttcgtcagt atccccgttt acagggcggc   2700
ttcgtctggg actgggtgga tcagtcgctg attaaatatg atgaaaacgg caacccgtgg   2760
tcggcttacg gcggtgattt tggcgatacg ccgaacgatc gccagttctg tatgaacggt   2820
ctggtctttg ccgaccgcac gccgcatcca gcgctgacgg aagcaaaaca ccagcagcag   2880
tttttccagt tccgtttatc cgggcaaacc atcgaagtga ccagcgaata cctgttccgt   2940
catagcgata acgagctcct gcactggatg gtggcgctgg atggtaagcc gctggcaagc   3000
ggtgaagtgc ctctggatgt cgctccacaa ggtaaacagt tgattgaact gcctgaacta   3060
ccgcagccgg agagcgccgg gcaactctgg ctcacagtac gcgtagtgca accgaacgcg   3120
accgcatggt cagaagccgg gcacatcagc gcctggcagc agtggcgtct ggcggaaaac   3180
ctcagtgtga cgctccccgc cgcgtcccac gccatcccgc atctgaccac cagcgaaatg   3240
gatttttgca tcgagctggg taataagcgt tggcaattta accgccagtc aggctttctt   3300
tcacagatgt ggattggcga taaaaaacaa ctgctgacgc cgctgcgcga tcagttcacc   3360
cgtgcaccgc tggataacga cattggcgta agtgaagcga cccgcattga ccctaacgcc   3420
tgggtcgaac gctggaaggc ggcgggccat taccaggccg aagcagcgtt gttgcagtgc   3480
acggcagata cacttgctga tgcggtgctg attacgaccg ctcacgcgtg gcagcatcag   3540
gggaaaacct tatttatcag ccggaaaacc taccggattg atggtagtgg tcaaatggcg   3600
attaccgttg atgttgaagt ggcgagcgat acaccgcatc cggcgcggat tggcctgaac   3660
tgccagctgg cgcaggtagc agagcgggta aactggctcg gattagggcc gcaagaaaac   3720
tatcccgacc gccttactgc cgcctgtttt gaccgctggg atctgccatt gtcagacatg   3780
tataccccgt acgtcttccc gagcgaaaac ggtctgcgct gcgggacgcg cgaattgaat   3840
tatggcccac accagtggcg cggcgacttc cagttcaaca tcagccgcta cagtcaacag   3900
caactgatgg aaaccagcca tcgccatctg ctgcacgcgg aagaaggcac atggctgaat   3960
atcgacggtt tccatatggg gattggtggc gacgactcct ggagcccgtc agtatcggcg   4020
gaattcagct gagcgccggt cgctaccatt accagttggt ctggtgtcaa aaataataat   4080
```

```
aaccgggcag gggggatcct tctgtgagcg tatggcaaac gaaggaaaaa tagttatagt   4140
agccgcactc gatgggacat ttcaacgtaa accgtttaat aatattttga atcttattcc   4200
attatctgaa atggtggtaa aactaactgc tgtgtgtatg aaatgcttta aggaggcttc   4260
cttttctaaa cgattgggtg aggaaaccga gatagaaata ataggaggta atgatatgta   4320
tcaatcggtg tgtagaaagt gttacatcga ctcataatat tatatttttt atctaaaaaa   4380
ctaaaaataa acattgatta aattttaata taatacttaa aaatggatgt tgtgtcgtta   4440
gataaaccgt ttatgtattt tgaggaaatt gataatgagt tagattacga accagaaagt   4500
gcaaatgagg tcgcaaaaaa actgccgtat caaggacagt taaaactatt actaggagaa   4560
ttattttttc ttagtaagtt acagcgacac ggtatattag atggtgccac cgtagtgtat   4620
ataggatctg ctcccggtac acatatacgt tatttgagag atcatttcta taatttagga   4680
gtgatcatca aatggatgct aattgacggc cgccatcatg atcctatttt aaatggattg   4740
cgtgatgtga ctctagtgac tcggttcgtt gatgaggaat atctacgatc catcaaaaaa   4800
caactgcatc cttctaagat tattttaatt tctgatgtga gatccaaacg aggaggaaat   4860
gaacctagta cggcggattt actaagtaat tacgctctac aaaatgtcat gattagtatt   4920
ttaaaccccg tggcgtctag tcttaaatgg agatgcccgt ttccagatca atggatcaag   4980
gacttttata tcccacacgg taataaaatg ttacaacctt ttgctccttc atattcagct   5040
gaaatgagat tattaagtat ttataccggt gagaacatga gactgactcg ggccgcgttg   5100
ctggcgtttt tccataggct ccgcccccct gacgagcatc acaaaaatcg acgctcaagt   5160
cagaggtggc gaaacccgac aggactataa agataccagg cgtttccccc tggaagctcc   5220
ctcgtgcgct ctcctgttcc gaccctgccg cttaccggat acctgtccgc ctttctccct   5280
tcgggaagcg tggcgctttc tcaatgctca cgctgtaggt atctcagttc ggtgtaggtc   5340
gttcgctcca agctgggctg tgtgcacgaa ccccccgttc agcccgaccg ctgcgcctta   5400
tccggtaact atcgtcttga gtccaacccg gtaagacacg acttatcgcc actggcagca   5460
gccactggta acaggattag cagagcgagg tatgtaggcg gtgctacaga gttcttgaag   5520
tggtggccta actacggcta cactagaagg acagtatttg gtatctgcgc tctgctgaag   5580
ccagttacct tcggaaaaag agttggtagc tcttgatccg gcaaacaaac caccgctggt   5640
agcggtggtt tttttgtttg caagcagcag attacgcgca gaaaaaaagg atctcaagaa   5700
gatcctttga tcttttctac ggggtctgac gctcagtgga acgaaaactc acgttaaggg   5760
attttggtca tgagattatc aaaaaggatc ttcacctaga tccttttaaa ttaaaaatga   5820
agttttaaat caatctaaag tatatatgag taaacttggt ctgacagtta ccaatgctta   5880
atcagtgagg cacctatctc agcgatctgt ctatttcgtt catccatagt tgcctgactc   5940
cccgtcgtgt agataactac gatacgggag ggcttaccat ctggccccag tgctgcaatg   6000
ataccgcgag acccacgctc accggctcca gatttatcag caataaacca gccagccgga   6060
agggccgagc gcagaagtgg tcctgcaact ttatccgcct ccatccagtc tattaattgt   6120
tgccgggaag ctagagtaag tagttcgcca gttaatagtt tgcgcaacgt tgttgccatt   6180
gctgcaggca tcgtggtgtc acgctcgtcg tttggtatgg cttcattcag ctccggttcc   6240
caacgatcaa ggcgagttac atgatccccc atgttgtgca aaaaagcggt tagctccttc   6300
ggtcctccga tcgttgtcag aagtaagttg gccgcagtgt tatcactcat ggttatggca   6360
gcactgcata attctcttac tgtcatgcca tccgtaagat gcttttctgt gactggtgag   6420
```

```
tactcaacca agtcattctg agaatagtgt atgcggcgac cgagttgctc ttgcccggcg   6480

tcaacacggg ataataccgc gccacatagc agaactttaa aagtgctcat cattggaaaa   6540

cgttcttcgg ggcgaaaact ctcaaggatc ttaccgctgt tgagatccag ttcgatgtaa   6600

cccactcgtg cacccaactg atcttcagca tcttttactt tcaccagcgt ttctgggtga   6660

gcaaaaacag gaaggcaaaa tgccgcaaaa aagggaataa gggcgacacg gaaatgttga   6720

atactcatac tcttcctttt tcaatattat tgaagcattt atcagggtta ttgtctcatg   6780

agcggataca tatttgaatg tatttagaaa aataaacaaa taggggttcc gcgcacattt   6840

ccccgaaaag tgccacctga cgtctaagaa accattatta tcatgacatt aacctataaa   6900

aataggcgta tcacgaggcc ctttcgtctt cgaataaata cctgtgacgg aagatcactt   6960

cgcagaataa ataaatcctg gtgtccctgt tgataccggg aagccctggg ccaacttttg   7020

gcgaaaatga gacgttgatc ggcacgtaag aggttccaac tttcaccata atgaaataag   7080

atcactaccg ggcgtatttt ttgagttatc gagattttca ggagctaagg aagctaaaat   7140

ggagaaaaaa atcactggat ataccaccgt tgatatatcc caatggcatc gtaaagaaca   7200

ttttgaggca tttcagtcag ttgctcaatg tacctataac cagaccgttc ag           7252
```

```
<210> SEQ ID NO 6
<211> LENGTH: 28
<212> TYPE: DNA
<213> ORGANISM: Artificial Sequence
<220> FEATURE:
<223> OTHER INFORMATION: Primer pUC28 I

<400> SEQUENCE: 6

aattcagatc tccatggatc gatgagct                                        28


<210> SEQ ID NO 7
<211> LENGTH: 20
<212> TYPE: DNA
<213> ORGANISM: Artificial Sequence
<220> FEATURE:
<223> OTHER INFORMATION: Primer pUC28 II

<400> SEQUENCE: 7

catcgatcca tggagatctg                                                 20


<210> SEQ ID NO 8
<211> LENGTH: 1665
<212> TYPE: DNA
<213> ORGANISM: Artificial Sequence
<220> FEATURE:
<223> OTHER INFORMATION: Renilla luciferase-Aequeora GFP fusion gene

<400> SEQUENCE: 8

atgacttcga aagtttatga tccagaacaa aggaaacgga tgataactgg tccgcagtgg     60

tgggccagat gtaaacaaat gaatgttctt gattcattta ttaattatta tgattcagaa    120

aaacatgcag aaaatgctgt tatttttta catggtaacg cggcctcttc ttatttatgg     180

cgacatgttg tgccacatat tgagccagta gcgcggtgta ttataccaga tcttattggt    240

atgggcaaat caggcaaatc tggtaatggt tcttataggt tacttgatca ttacaaatat    300

cttactgcat ggtttgaact tcttaattta ccaaagaaga tcatttttgt cggccatgat    360

tggggtgctt gtttggcatt tcattatagc tatgagcatc aagataagat caaagcaata    420

gttcacgctg aaagtgtagt agatgtgatt gaatcatggg atgaatggcc tgatattgaa    480

gaagatattg cgttgatcaa atctgaagaa ggagaaaaaa tggttttgga gaataacttc    540
```

```
ttcgtggaaa ccatgttgcc atcaaaaatc atgagaaagt tagaaccaga agaatttgca    600

gcatatcttg aaccattcaa agacaaaggt gaagttcgtc gtccaacatt atcatggcct    660

cgtgaaatcc cgttagtaaa aggtggtaaa cctgacgttg tacaaattgt taggaattat    720

aatgcttatc tacgtgcaag tgatgattta ccaaaaatgt ttattgaatc ggatccagga    780

ttcttttcca atgctattgt tgaaggcgcc aagaagtttc ctaatactga atttgtcaaa    840

gtaaaaggtc ttcatttttc gcaagaagat gcacctgatg aaatgggaaa atatatcaaa    900

tcgttcgttg agcgagttct caaaaatgaa caagcggccg caccgcatat gagtaaagga    960

gaagaacttt tcactggagt tgtcccaatt cttgttgaat tagatggtga tgttaatggg   1020

cacaaatttt ctgtcagtgg agagggtgaa ggtgatgcaa catacggaaa acttaccctt   1080

aaatttattt gcactactgg aaaactacct gttccatggc caacacttgt cactactttc   1140

tcttatggtg ttcaatgctt ttcaagatac ccagatcata tgaaacagca tgactttttc   1200

aagagtgcca tgcccgaagg ttatgtacag gaaagaacta tatttttcaa agatgacggg   1260

aactacaaga cacgtgctga agtcaagttt gaaggtgata cccttgttaa tagaatcgag   1320

ttaaaaggta ttgattttaa agaagatgga aacattcttg gacacaaatt ggaatacaac   1380

tataactcac acaatgtata catcatggca gacaaacaaa agaatggaat caaagttaac   1440

ttcaaaatta gacacaacat tgaagatgga agcgttcaac tagcagacca ttatcaacaa   1500

aatactccaa ttggcgatgg ccctgtcctt ttaccagaca accattacct gtccacacaa   1560

tctgcccttt cgaaagatcc caacgaaaag agagaccaca tggtccttct tgagtttgta   1620

acagctgctg ggattacaca tggcatggat gaactataca aataa                   1665
```

<210> SEQ ID NO 9
<211> LENGTH: 11096
<212> TYPE: DNA
<213> ORGANISM: Artificial Sequence
<220> FEATURE:
<223> OTHER INFORMATION: pLacGus Plasmid

<400> SEQUENCE: 9

```
aagcttgcat gcctgcagca attcccgagg ctgtagccga cgatggtgcg ccaggagagt     60

tgttgattca ttgtttgcct ccctgctgcg gtttttcacc gaagttcatg ccagtccagc    120

gtttttgcag cagaaaagcc gccgacttcg gtttgcggtc gcgagtgaag atccctttct    180

tgttaccgcc aacgcgcaat atgccttgcg aggtcgcaaa atcggcgaaa ttccatacct    240

gttcaccgac gacggcgctg acgcgatcaa agacgcggtg atacatatcc agccatgcac    300

actgatactc ttcactccac atgtcggtgt acattgagtg cagcccggct aacgtatcca    360

cgccgtattc ggtgatgata atcggctgat gcagtttctc ctgccaggcc agaagttctt    420

tttccagtac cttctctgcc gtttccaaat cgccgctttg gacataccat ccgtaataac    480

ggttcaggca cagcacatca aagagatcgc tgatggtatc ggtgtgagcg tcgcagaaca    540

ttacattgac gcaggtgatc ggacgcgtcg ggtcgagttt acgcgttgct tccgccagtg    600

gcgcgaaata ttcccgtgca ccttgcggac gggtatccgg ttcgttggca atactccaca    660

tcaccacgct tgggtggttt ttgtcacgcg ctatcagctc tttaatcgcc tgtaagtgcg    720

cttgctgagt ttccccgttg actgcctctt cgctgtacag ttctttcggc ttgttgcccg    780

cttcgaaacc aatgcctaaa gagaggttaa agccgacagc agcagtttca tcaatcacca    840

cgatgccatg ttcatctgcc cagtcgagca tctcttcagc gtaagggtaa tgcgaggtac    900
```

```
ggtaggagtt ggccccaatc cagtccatta atgcgtggtc gtgcaccatc agcacgttat    960
cgaatccttt gccacgcaag tccgcatctt catgacgacc aaagccagta aagtagaacg   1020
gtttgtggtt aatcaggaac tgttcgccct tcactgccac tgaccggatg ccgacgcgaa   1080
gcgggtagat atcacactct gtctggcttt tggctgtgac gcacagttca tagagataac   1140
cttcacccgg ttgccagagg tgcggattca ccacttgcaa agtcccgcta gtgccttgtc   1200
cagttgcaac cacctgttga tccgcatcac gcagttcaac gctgacatca ccattggcca   1260
ccacctgcca gtcaacagac gcgtggttac agtcttgcgc gacatgcgtc accacggtga   1320
tatcgtccac ccaggtgttc ggcgtggtgt agagcattac gctgcgatgg attccggcat   1380
agttaaagaa atcatggaag taagactgct tttcttgcc gttttcgtcg gtaatcacca   1440
ttcccggcgg gatagtctgc cagttcagtt cgttgttcac acaaacggtg atacgtacac   1500
ttttcccggc aataacatac ggcgtgacat cggcttcaaa tggcgtatag ccgccctgat   1560
gctccatcac ttcctgatta ttgacccaca ctttgccgta atgagtgacc gcatcgaaac   1620
gcagcacgat acgctggcct gcccaacctt tcggtataaa gacttcgcgc tgataccaga   1680
cgttgcccgc ataattacga atatctgcat cggcgaactg atcgttaaaa ctgcctggca   1740
cagcaattgc ccggctttct tgtaacgcgc tttcccacca acgctgatca attccacagt   1800
tttcgcgatc cagactgaat gcccacaggc cgtcgagttt tttgatttca cgggttgggg   1860
tttctacagg acgtaacatt ctagacatta tagtttttc tccttgacgt taaagtatag   1920
aggtatatta acaatttttt gttgatactt ttattacatt tgaataagaa gtaatacaaa   1980
ccgaaaatgt tgaaagtatt agttaaagtg gttatgcagt ttttgcattt atatatctgt   2040
taatagatca aaaatcatcg gttcgctgat taattacccc agaaataagg ctaaaaaact   2100
aatcgcatta tcatccctcg agctatcacc gcaagggata aatatctaac accgtgcgtg   2160
ttgactattt tacctctggc ggtgataatg ctcgaggtaa gattagatat ggatatgtat   2220
atggatatgt atatggtggt aatgccatgt aatatgatta ttaaacttct ttgcgtccat   2280
ccaaaaaaaa agtaagaatt tttgaaaatt caatataaat gacagctcag ttacaaagtg   2340
aaagtacttc taaaattgtt ttggttacag gtggtgctgg atacattggt tcacacactg   2400
tggtagagct aattgagaat ggatatgact gtgttgttgc tgataacctg tcgaatagat   2460
cgacctgaag tctaggtccc tatttatttt tttatagtta tgttagtatt aagaacgtta   2520
tttatatttc aaatttttct ttttttctg tacagacgcg tgtacgaatt tcgacctcga   2580
ccggccggtt ttacaaatca gtaagcaggt cagtgcgtac gccatggccg gagtggctca   2640
cagtcggtgg tccggcagta caatggattt ccttacgcga aatacgggca gacatggcct   2700
gcccggttat tattattttt gacaccagac caactggtaa tggtagcgac cggcgctcag   2760
ctggaattcc gccgatactg acgggctcca ggagtcgtcg ccaccaatcc ccatatggaa   2820
accgtcgata ttcagccatg tgccttcttc cgcgtgcagc agatggcgat ggctggtttc   2880
catcagttgc tgttgactgt agcggctgat gttgaactgg aagtcgccgc gccactggtg   2940
tgggccataa ttcaattcgc gcgtcccgca gcgcagaccg ttttcgctcg ggaagacgta   3000
cggggtatac atgtctgaca atggcagatc ccagcggtca aaacaggcgg cagtaaggcg   3060
gtcgggatag ttttcttgcg gccctaatcc gagccagttt acccgctctg ctacctgcgc   3120
cagctggcag ttcaggccaa tccgcgccgg atgcggtgta tcgctcgcca cttcaacatc   3180
aacggtaatc gccatttgac cactaccatc aatccggtag gttttccggc tgataaataa   3240
ggttttcccc tgatgctgcc acgcgtgagc ggtcgtaatc agcaccgcat cagcaagtgt   3300
```

atctgccgtg cactgcaaca acgctgcttc ggcctggtaa tggcccgccg ccttccagcg 3360
ttcgacccag gcgttagggt caatgcgggt cgcttcactt acgccaatgt cgttatccag 3420
cggtgcacgg gtgaactgat cgcgcagcgg cgtcagcagt tgttttttat cgccaatcca 3480
catctgtgaa agaaagcctg actggcggtt aaattgccaa cgcttattac ccagctcgat 3540
gcaaaaatcc atttcgctgg tggtcagatg cgggatggcg tgggacgcgg cggggagcgt 3600
cacactgagg ttttccgcca gacgccactg ctgccaggcg ctgatgtgcc cggcttctga 3660
ccatgcggtc gcgttcggtt gcactacgcg tactgtgagc cagagttgcc cggcgctctc 3720
cggctgcggt agttcaggca gttcaatcaa ctgtttacct tgtggagcga catccagagg 3780
cacttcaccg cttgccagcg gcttaccatc cagcgccacc atccagtgca ggagctcgtt 3840
atcgctatga cggaacaggt attcgctggt cacttcgatg gtttgcccgg ataaacggaa 3900
ctggaaaaac tgctgctggt gttttgcttc cgtcagcgct ggatgcggcg tgcggtcggc 3960
aaagaccaga ccgttcatac agaactggcg atcgttcggc gtatcgccaa aatcaccgcc 4020
gtaagccgac cacgggttgc cgttttcatc atatttaatc agcgactgat ccacccagtc 4080
ccagacgaag ccgccctgta aacggggata ctgacgaaac gcctgccagt atttagcgaa 4140
accgccaaga ctgttaccca tcgcgtgggc gtattcgcaa aggatcagcg ggcgcgtctc 4200
tccaggtagc gaaagccatt ttttgatgga ccatttcggc acagccggga agggctggtc 4260
ttcatccacg cgcgcgtaca tcgggcaaat aatatcggtg gccgtggtgt cggctccgcc 4320
gccttcatac tgcaccgggc gggaaggatc gacagatttg atccagcgat acagcgcgtc 4380
gtgattagcg ccgtggcctg attcattccc cagcgaccag atgatcacac tcgggtgatt 4440
acgatcgcgc tgcaccattc gcgttacgcg ttcgctcatc gccggtagcc agcgcggatc 4500
atcggtcaga cgattcattg gcaccatgcc gtgggtttca atattggctt catccaccac 4560
atacaggccg tagcggtcgc acagcgtgta ccacagcgga tggttcggat aatgcgaaca 4620
gcgcacggcg ttaaagttgt tctgcttcat cagcaggata tcctgcacca tcgtctgctc 4680
atccatgacc tgaccatgca gaggatgatg ctcgtgacgg ttaacgcctc gaatcagcaa 4740
cggcttgccg ttcagcagca gcagaccatt ttcaatccgc acctcgcgga aaccgacatc 4800
gcaggcttct gcttcaatca gcgtgccgtc ggcggtgtgc agttcaacca ccgcacgata 4860
gagattcggg atttcggcgc tccacagttt cgggttttcg acgttcagac gtagtgtgac 4920
gcgatcggca taaccaccac gctcatcgat aatttcaccg ccgaaaggcg cggtgccgct 4980
ggcgacctgc gtttcaccct gccataaaga aactgttacc cgtaggtagt cacgcaactc 5040
gccgcacatc tgaacttcag cctccagtac agcgcggctg aaatcatcat taaagcgagt 5100
ggcaacatgg aaatcgctga tttgtgtagt cggtttatgc agcaacgaga cgtcacggaa 5160
aatgccgctc atccgccaca tatcctgatc ttccagataa ctgccgtcac tccagcgcag 5220
caccatcacc gcgaggcggt tttctccggc gcgtaaaaat gcgctcaggt caaattcaga 5280
cggcaaacga ctgtcctggc cgtaaccgac ccagcgcccg ttgcaccaca gatgaaacgc 5340
cgagttaacg ccatcaaaaa taattcgcgt ctggccttcc tgtagccagc tttcatcaac 5400
attaaatgtg agcgagtaac aacccgtcgg attctccgtg ggaacaaacg gcggattgac 5460
cgtaatggga taggtcacgt tggtgtagat gggcgcatcg taaccgtgca tctgccagtt 5520
tgaggggacg acgacagtat cggcctcagg aagatcgcac tccagccagc tttccggcac 5580
cgcttctggt gccggaaacc aggcaaagcg ccattcgcca ttcaggctgc gcaactgttg 5640

```
ggaagggcga tcggtgcggg cctcttcgct attacgccag ctggcgaaag ggggatgtgc   5700

tgcaaggcga ttaagtcggg aaacctgtcg tgccagctgc attaatgaat cggccaacgc   5760

gcggggagag gcggtttgcg tattgggcgc cagggtggtt tttcttttca ccagtgagac   5820

gggcaacagc caagctccgg atccgggctt ggccaagctt ggaattccgc acttttcggc   5880

caatggtctt ggtaattcct ttgcgctaga attgaactca ggtacaatca cttcttctga   5940

atgagattta gtcattatag ttttttctcc ttgacgttaa agtatagagg tatattaaca   6000

atttttttgtt gatactttta ttacatttga ataagaagta atacaaaccg aaaatgttga   6060

aagtattagt taaagtggtt atgcagtttt tgcatttata tatctgttaa tagatcaaaa   6120

atcatcgctt cgctgattaa ttaccccaga aataaggcta aaaaactaat cgcattatca   6180

tcccctcgac gtactgtaca tataaccact ggttttatat acagcagtac tgtacatata   6240

accactggtt ttatatacag cagtcgacgt actgtacata taaccactgg ttttatatac   6300

agcagtactg gacatataac cactggtttt atatacagca gtcgaggtaa gattagatat   6360

ggatatgtat atggatatgt atatggtggt aatgccatgt aatatgatta ttaaacttct   6420

ttgcgtccat ccaaaaaaaa agtaagaatt tttgaaaatt caatataaat gacagctcag   6480

ttacaaagtg aaagtacttc taaaattgtt ttggttacag gtggtgctgg atacattggt   6540

tcacacactg tggtagagct aattgagaat ggatatgact gtgttgttgc tgataacctg   6600

tcgaattcca agctcggatc cccgagctcg gatcccccta agaaaccatt attatcatga   6660

cattaaccta taaaaatagg cgtatcacga ggccctttcg tctcgcgcgt ttcggtgatg   6720

acggtgaaaa cctctgacac atgcagctcc cggagacggt cacagcttgt ctgtaagcgg   6780

atgccgggag cagacaagcc cgtcagggcg cgtcagcggg tgttggcggg tgtcggggct   6840

ggcttaacta tgcggcatca gagcagattg tactgagagt gcaccataac gcatttaagc   6900

ataaacacgc actatgccgt tcttctcatg tatatatata tacaggcaac acgcagatat   6960

aggtgcgacg tgaacagtga gctgtatgtg cgcagctcgc gttgcatttt cggaagcgct   7020

cgttttcgga aacgctttga agttcctatt ccgaagttcc tattctctag ctagaaagta   7080

taggaacttc agagcgcttt tgaaaaccaa aagcgctctg aagacgcact ttcaaaaaac   7140

caaaaacgca ccggactgta acgagctact aaaatattgc gaataccgct tccacaaaca   7200

ttgctcaaaa gtatctcttt gctatatatc tctgtgctat atccctatat aacctaccca   7260

tccacctttc gctccttgaa cttgcatcta aactcgacct ctacattttt tatgtttatc   7320

tctagtatta ctctttagac aaaaaaattg tagtaagaac tattcataga gtgaatcgaa   7380

aacaatacga aaatgtaaac atttcctata cgtagtatat agagacaaaa tagaagaaac   7440

cgttcataat tttctgacca atgaagaatc atcaacgcta tcactttctg ttcacaaagt   7500

atgcgcaatc cacatcggta tagaatataa tcggggatgc ctttatcttg aaaaaatgca   7560

cccgcagctt cgctagtaat cagtaaacgc gggaagtgga gtcaggcttt ttttatggaa   7620

gagaaaatag acaccaaagt agccttcttc taaccttaac ggacctacag tgcaaaaagt   7680

tatcaagaga ctgcattata gagcgcacaa aggagaaaaa aagtaatcta agatgctttg   7740

ttagaaaaat agcgctctcg ggatgcattt ttgtagaaca aaaaagaagt atagattctt   7800

tgttggtaaa atagcgctct cgcgttgcat ttctgttctg taaaaatgca gctcagattc   7860

tttgtttgaa aaattagcgc tctcgcgttg catttttgtt ttacaaaaat gaagcacaga   7920

ttcttcgttg gtaaaatagc gctttcgcgt tgcatttctg ttctgtaaaa atgcagctca   7980

gattctttgt ttgaaaaatt agcgctctcg cgttgcattt ttgttctaca aaatgaagca   8040
```

```
cagatgcttc gttgcttccg tgtggaagaa cgattacaac aggtgttgtc ctctgaggac   8100

ataaaataca caccgagatt catcaactca ttgctggagt tagcatatct acaattcaga   8160

agaactcgtc aagaaggcga tagaaggcga tgcgctgcga atcgggagcg gcgataccgt   8220

aaagcacgag gaagcggtca gcccattcgc cgccaagctc ttcagcaata tcacgggtag   8280

ccaacgctat gtcctgatag cggtccgcca cacccagccg gccacagtcg atgaatccag   8340

aaaagcggcc attttccacc atgatattcg gcaagcaggc atcgccatgg gtcacgacga   8400

gatcctcgcc gtcgggcatg ctcgccttga gcctggcgaa cagttcggct ggcgcgagcc   8460

cctgatgctc ttcgtccaga tcatcctgat cgacaagacc ggcttccatc cgagtacgtg   8520

ctcgctcgat gcgatgtttc gcttggtggt cgaatgggca ggtagccgga tcaagcgtat   8580

gcagccgccg cattgcatca gccatgatgg atactttctc ggcaggagca aggtgagatg   8640

acaggagatc ctgccccggc acttcgccca atagcagcca gtcccttccc gcttcagtga   8700

caacgtcgag cacagctgcg caaggaacgc ccgtcgtggc cagccacgat agccgcgctg   8760

cctcgtcttg cagttcattc agggcaccgg acaggtcggt cttgacaaaa agaaccgggc   8820

gcccctgcgc tgacagccgg aacacggcgg catcagagca gccgattgtc tgttgtgccc   8880

agtcatagcc gaatagcctc tccacccaag cggccggaga acctgcgtgc aatccatctt   8940

gttcaatcat gcgaaacgat cctcatcctg tctcttgatc agagcttgat cccctgcgcc   9000

atcagatcct tggcggcaag aaagccatcc agtttacttt gcagggcttc ccaaccttac   9060

cagagggcgc cccagctggc aattccggtt cgcttgctgt ccataaaacc gcccagtcta   9120

gctatcgcca tgtaagccca ctgcaagcta cctgctttct ctttgcgctt gcgttttccc   9180

ttgtccagat agcccagtag ctgacattca tccggggtca gcaccgtttc tgcggactgg   9240

ctttctacgt gaaaaggatc taggtgaaga tcctttttga taatctcatg accaaaatcc   9300

cttaacgtga gttttcgttc cactgagcgt cagaccccgt agaaaagatc aaaggatctt   9360

cttgagatcc tttttttctg cgcgtaatct gctgcttgca aacaaaaaaa ccaccgctac   9420

cagcggtggt ttgtttgccg gatcaagagc taccaactct ttttccgaag gtaactggct   9480

tcagcagagc gcagatacca aatactgttc ttctagtgta gccgtagtta ggccaccact   9540

tcaagaactc tgtagcaccg cctacatacc tcgctctgct aatcctgtta ccagtggctg   9600

ctgccagtgg cgataagtcg tgtcttaccg ggttggactc aagacgatag ttaccggata   9660

aggcgcagcg gtcgggctga acggggggtt cgtgcacaca gcccagcttg gagcgaacga   9720

cctacaccga actgagatac ctacagcgtg agctatgaga aagcgccacg cttcccgaag   9780

ggagaaaggc ggacaggtat ccggtaagcg gcagggtcgg aacaggagag cgcacgaggg   9840

agcttccagg gggaaacgcc tggtatcttt atagtcctgt cgggtttcgc cacctctgac   9900

ttgagcgtcg atttttgtga tgctcgtcag gggggcggag cctatggaaa aacgccagca   9960

acgcggcctt tttacggttc ctggcctttt gctggccttt tgctcacatg atataattca  10020

attgaagctc taatttgtga gtttagtata catgcattta cttataatac agttttttag  10080

ttttgctggc cgcatcttct caaatatgct tcccagcctg cttttctgta acgttcaccc  10140

tctaccttag catcccttcc ctttgcaaat agtcctcttc caacaataat aatgtcagat  10200

cctgtagaga ccacatcatc cacggttcta tactgttgac ccaatgcgtc tcccttgtca  10260

tctaaaccca caccgggtgt cataatcaac caatcgtaac cttcatctct tccacccatg  10320

tctctttgag caataaagcc gataacaaaa tctttgtcgc tcttcgcaat gtcaacagta  10380
```

```
cccttagtat attctccagt agatagggag cccttgcatg acaattctgc taacatcaaa  10440

aggcctctag gttcctttgt tacttcttct gccgcctgct tcaaaccgct aacaatacct  10500

gggcccacca caccgtgtgc attcgtaatg tctgcccatt ctgctattct gtatacaccc  10560

gcagagtact gcaatttgac tgtattacca atgtcagcaa attttctgtc ttcgaagagt  10620

aaaaaattgt acttggcgga taatgccttt agcggcttaa ctgtgccctc catggaaaaa  10680

tcagtcaaga tatccacatg tgtttttagt aaacaaattt tgggacctaa tgcttcaact  10740

aactccagta attccttggt ggtacgaaca tccaatgaag cacacaagtt tgtttgcttt  10800

tcgtgcatga tattaaatag cttggcagca acaggactag gatgagtagc agcacgttcc  10860

ttatatgtag ctttcgacat gatttatctt cgtttcctgc aggtttttgt tctgtgcagt  10920

tgggttaaga atactgggca atttcatgtt tcttcaacac tacatatgcg tatatatacc  10980

aatctaagtc tgtgctcctt ccttcgttct tccttctgtt cggagattac cgaatcaaaa  11040

aaatttcaag gaaaccgaaa tcaaaaaaaa gaataaaaaa aaaatgatga attgaa      11096


<210> SEQ ID NO 10
<211> LENGTH: 150
<212> TYPE: DNA
<213> ORGANISM: Vaccinia Virus/LIVP
<300> PUBLICATION INFORMATION:
<308> DATABASE ACCESSION NUMBER: GenBank No. M57977
<309> DATABASE ENTRY DATE: 2000-04-14

<400> SEQUENCE: 10

atggtcatcg gtttagtcat attcgtgtct gtggcggccg ccatcgtcgg tgtgttgtct     60

aacgtattgg acatgcttat gtacgtagaa gaaaataatg aagaggatgc tagaatcaag    120

gaggagcaag aactactgtt gctatattga                                     150


<210> SEQ ID NO 11
<211> LENGTH: 49
<212> TYPE: PRT
<213> ORGANISM: Vaccinia Virus/LIVP
<300> PUBLICATION INFORMATION:
<308> DATABASE ACCESSION NUMBER: GenBank No. AAA48282
<309> DATABASE ENTRY DATE: 2000-04-14

<400> SEQUENCE: 11

Met Val Ile Gly Leu Val Ile Phe Val Ser Val Ala Ala Ala Ile Val
 1               5                  10                  15

Gly Val Leu Ser Asn Val Leu Asp Met Leu Met Tyr Val Glu Glu Asn
            20                  25                  30

Asn Glu Glu Asp Ala Arg Ile Lys Glu Glu Gln Glu Leu Leu Leu Leu
        35                  40                  45

Tyr


<210> SEQ ID NO 12
<211> LENGTH: 150
<212> TYPE: DNA
<213> ORGANISM: Vaccinia Virus/WR
<300> PUBLICATION INFORMATION:
<308> DATABASE ACCESSION NUMBER: GenBank No. AY243312
<309> DATABASE ENTRY DATE: 2003-04-10

<400> SEQUENCE: 12

tcaatatagc aacagtagtt cttgctcctc cttgattcta gcatcctctt cattattttc     60

ttctacgtac ataagcatgt ccaatacgtt agacaacaca ccgacgatgg cggccgccac    120

agacacgaat atgactagac cgatgaccat                                     150
```

<210> SEQ ID NO 13
<211> LENGTH: 49
<212> TYPE: PRT
<213> ORGANISM: Vaccinia Virus/WR

<400> SEQUENCE: 13

```
Met Val Ile Gly Leu Val Ile Phe Val Ser Val Ala Ala Ala Ile Val
 1               5                  10                  15

Gly Val Leu Ser Asn Val Leu Asp Met Leu Met Tyr Val Glu Glu Asn
            20                  25                  30

Asn Glu Glu Asp Ala Arg Ile Lys Glu Glu Gln Glu Leu Leu Leu Leu
        35                  40                  45

Tyr
```

<210> SEQ ID NO 14
<211> LENGTH: 150
<212> TYPE: DNA
<213> ORGANISM: Vaccinia Virus/Ankara
<300> PUBLICATION INFORMATION:
<308> DATABASE ACCESSION NUMBER: GenBank No. U94848.1
<309> DATABASE ENTRY DATE: 2003-04-14

<400> SEQUENCE: 14

```
tcaatatagc aacagtagtt cttgctcctc cttgattcta gcatcctctt cattattttc     60

ttctacgtac ataaacatgt ccaatacgtt agacaacaca ccgacgatgg cggccgccac    120

agacacgaat atgactaaac cgatgaccat                                     150
```

<210> SEQ ID NO 15
<211> LENGTH: 49
<212> TYPE: PRT
<213> ORGANISM: Vaccinia Virus/Ankara

<400> SEQUENCE: 15

```
Met Val Ile Gly Leu Val Ile Phe Val Ser Val Ala Ala Ala Ile Val
 1               5                  10                  15

Gly Val Leu Ser Asn Val Leu Asp Met Phe Met Tyr Val Glu Glu Asn
            20                  25                  30

Asn Glu Glu Asp Ala Arg Ile Lys Glu Glu Gln Glu Leu Leu Leu Leu
        35                  40                  45

Tyr
```

<210> SEQ ID NO 16
<211> LENGTH: 146
<212> TYPE: DNA
<213> ORGANISM: Vaccinia Virus/Tian Tan
<300> PUBLICATION INFORMATION:
<308> DATABASE ACCESSION NUMBER: GenBank No. AF095689
<309> DATABASE ENTRY DATE: 2000-02-14

<400> SEQUENCE: 16

```
caatatagca acagtagttc ttgctcctcc ttgattctag catcctcttc attattttct     60

tctacgtaca taaacatgtc caatacgtta gacaacacac cgacgatggc cgccacagac    120

acgaatatga ctagaccgat gaccat                                         146
```

<210> SEQ ID NO 17
<211> LENGTH: 48
<212> TYPE: PRT
<213> ORGANISM: Vaccinia Virus/Tian Tan

<400> SEQUENCE: 17

```
Met Val Ile Gly Leu Val Ile Phe Val Ser Val Ala Ala Ile Val Gly
 1               5                  10                  15

Val Leu Ser Asn Val Leu Asp Met Phe Met Tyr Val Glu Glu Asn Asn
            20                  25                  30

Glu Glu Asp Ala Arg Ile Lys Glu Glu Gln Glu Leu Leu Leu Leu Tyr
        35                  40                  45
```

<210> SEQ ID NO 18
<211> LENGTH: 150
<212> TYPE: DNA
<213> ORGANISM: Vaccinia Virus/Acambis 3000 MVA
<300> PUBLICATION INFORMATION:
<308> DATABASE ACCESSION NUMBER: GenBank No. AY603355
<309> DATABASE ENTRY DATE: 2004-05-15

<400> SEQUENCE: 18

```
tcaatatagc aacagtagtt cttgctcctc cttgattcta gcatcctctt cattattttc     60

ttctacgtac ataaacatgt ccaatacgtt agacaacaca ccgacgatgg cggccgccac    120

agacacgaat atgactaaac cgatgaccat                                     150
```

<210> SEQ ID NO 19
<211> LENGTH: 49
<212> TYPE: PRT
<213> ORGANISM: Vaccinia Virus/Acambis 3000 MVA

<400> SEQUENCE: 19

```
Met Val Ile Gly Leu Val Ile Phe Val Ser Val Ala Ala Ala Ile Val
 1               5                  10                  15

Gly Val Leu Ser Asn Val Leu Asp Met Phe Met Tyr Val Glu Glu Asn
            20                  25                  30

Asn Glu Glu Asp Ala Arg Ile Lys Glu Glu Gln Glu Leu Leu Leu Leu
        35                  40                  45

Tyr
```

<210> SEQ ID NO 20
<211> LENGTH: 150
<212> TYPE: DNA
<213> ORGANISM: Vaccinia Virus/Copenhagen
<300> PUBLICATION INFORMATION:
<308> DATABASE ACCESSION NUMBER: GenBank No. M35027.1
<309> DATABASE ENTRY DATE: 1993-08-03

<400> SEQUENCE: 20

```
tcaatatagc aacagtagtt cttgctcctc cttgattcta gcatcctctt cattattttc     60

ttctacgtac ataaacatgt ccaatacgtt agacaacaca ccgacgatgg cggccgccac    120

agacacgaat atgactagac cgatgaccat                                     150
```

<210> SEQ ID NO 21
<211> LENGTH: 49
<212> TYPE: PRT
<213> ORGANISM: Vaccinia Virus/Copenhagen

<400> SEQUENCE: 21

```
Met Val Ile Gly Leu Val Ile Phe Val Ser Val Ala Ala Ala Ile Val
 1               5                  10                  15

Gly Val Leu Ser Asn Val Leu Asp Met Phe Met Tyr Val Glu Glu Asn
            20                  25                  30

Asn Glu Glu Asp Ala Arg Ile Lys Glu Glu Gln Glu Leu Leu Leu Leu
```

```
        35                  40                  45

Tyr


<210> SEQ ID NO 22
<211> LENGTH: 150
<212> TYPE: DNA
<213> ORGANISM: Cowpox Virus
<300> PUBLICATION INFORMATION:
<308> DATABASE ACCESSION NUMBER: GenBank No. X94355.2
<309> DATABASE ENTRY DATE: 2003-05-09

<400> SEQUENCE: 22

tcaatatagc aacagtagtt cttgctcctc cttgattcta gcatcctctt cattattttc     60

ttctacgtac ataagcatgt ccaatacgtt agacaacaca ccgacgatgg cggccgccac    120

agacacgaat atgactagac cgatgaccat                                     150


<210> SEQ ID NO 23
<211> LENGTH: 49
<212> TYPE: PRT
<213> ORGANISM: Cowpox Virus

<400> SEQUENCE: 23

Met Val Ile Gly Leu Val Ile Phe Val Ser Val Ala Ala Ala Ile Val
 1               5                  10                  15

Gly Val Leu Ser Asn Val Leu Asp Met Leu Met Tyr Val Glu Glu Asn
            20                  25                  30

Asn Glu Glu Asp Ala Arg Ile Lys Glu Glu Gln Glu Leu Leu Leu Leu
        35                  40                  45

Tyr


<210> SEQ ID NO 24
<211> LENGTH: 150
<212> TYPE: DNA
<213> ORGANISM: Rabbitpox Virus
<300> PUBLICATION INFORMATION:
<308> DATABASE ACCESSION NUMBER: GenBank No. AY484669
<309> DATABASE ENTRY DATE: 2004-03-30

<400> SEQUENCE: 24

tcaatatagc aacagtagtt cttgctcctc cttgattcta gcatcctctt cattattttc     60

ttctacgtac ataagcatgt ccaatacgtt agacaacaca ccgacgatgg cggccgccac    120

agacacgaat atgactagac cgatgaccat                                     150


<210> SEQ ID NO 25
<211> LENGTH: 49
<212> TYPE: PRT
<213> ORGANISM: Rabbitpox Virus

<400> SEQUENCE: 25

Met Val Ile Gly Leu Val Ile Phe Val Ser Val Ala Ala Ala Ile Val
 1               5                  10                  15

Gly Val Leu Ser Asn Val Leu Asp Met Leu Met Tyr Val Glu Glu Asn
            20                  25                  30

Asn Glu Glu Asp Ala Arg Ile Lys Glu Glu Gln Glu Leu Leu Leu Leu
        35                  40                  45

Tyr


<210> SEQ ID NO 26
<211> LENGTH: 150
```

```
<212> TYPE: DNA
<213> ORGANISM: Camelpox Virus/CMS
<300> PUBLICATION INFORMATION:
<308> DATABASE ACCESSION NUMBER: GenBank No. AY009089
<309> DATABASE ENTRY DATE: 2002-07-30

<400> SEQUENCE: 26

tcaatatagc aacagtagtt cttgctcctc cttaattcta gcatcttctt cattattttc     60

ttctacatac ataagcatgt ccaatacgtt agacaacaca ccgacgatgg cggccgccac    120

agacacgaat atgactagac cgatgaccat                                      150


<210> SEQ ID NO 27
<211> LENGTH: 49
<212> TYPE: PRT
<213> ORGANISM: Camelpox Virus/CMS

<400> SEQUENCE: 27

Met Val Ile Gly Leu Val Ile Phe Val Ser Val Ala Ala Ala Ile Val
 1               5                   10                  15

Gly Val Leu Ser Asn Val Leu Asp Met Leu Met Tyr Val Glu Glu Asn
            20                  25                  30

Asn Glu Glu Asp Ala Arg Ile Lys Glu Glu Gln Glu Leu Leu Leu Leu
        35                  40                  45

Tyr


<210> SEQ ID NO 28
<211> LENGTH: 150
<212> TYPE: DNA
<213> ORGANISM: Ectromelia Virus/Moscow
<300> PUBLICATION INFORMATION:
<308> DATABASE ACCESSION NUMBER: GenBank No. AF012825
<309> DATABASE ENTRY DATE: 2002-08-06

<400> SEQUENCE: 28

tcaatatagc aacaacagtt cttgctcctc cttgattcta gcatcctctt cattattttc     60

ttctacgtac ataagcatgt ccaatacgtt agacaacaca ccgacaatgg cggccgccac    120

agacacgaat atgactagac cgaggaccat                                      150


<210> SEQ ID NO 29
<211> LENGTH: 49
<212> TYPE: PRT
<213> ORGANISM: Ectromelia Virus/Moscow

<400> SEQUENCE: 29

Met Val Leu Gly Leu Val Ile Phe Val Ser Val Ala Ala Ala Ile Val
 1               5                   10                  15

Gly Val Leu Ser Asn Val Leu Asp Met Leu Met Tyr Val Glu Glu Asn
            20                  25                  30

Asn Glu Glu Asp Ala Arg Ile Lys Glu Glu Gln Glu Leu Leu Leu Leu
        35                  40                  45

Tyr


<210> SEQ ID NO 30
<211> LENGTH: 146
<212> TYPE: DNA
<213> ORGANISM: Monkeypox Virus/Zaire
<300> PUBLICATION INFORMATION:
<308> DATABASE ACCESSION NUMBER: GenBank No. AF380138
<309> DATABASE ENTRY DATE: 2001-12-13

<400> SEQUENCE: 30
```

```
tatagcaaca gtaattcttg ctcctccttg attttagcat cctcttcatt attttcttct     60

acgtacataa gcatgtccaa tacgttagac aacacaccga cgatggtggc cgccacagac    120

acgaatatga ctagaccgat gaccat                                         146


<210> SEQ ID NO 31
<211> LENGTH: 48
<212> TYPE: PRT
<213> ORGANISM: Monkeypox Virus/Zaire

<400> SEQUENCE: 31

Met Val Ile Gly Leu Val Ile Phe Val Ser Val Ala Ala Thr Ile Val
 1               5                  10                  15

Gly Val Leu Ser Asn Val Leu Asp Met Leu Met Tyr Val Glu Glu Asn
            20                  25                  30

Asn Glu Glu Asp Ala Lys Ile Lys Glu Glu Gln Glu Leu Leu Leu Leu
        35                  40                  45


<210> SEQ ID NO 32
<211> LENGTH: 150
<212> TYPE: DNA
<213> ORGANISM: Variola Virus
<300> PUBLICATION INFORMATION:
<308> DATABASE ACCESSION NUMBER: GenBank No. X69198.1
<309> DATABASE ENTRY DATE: 1996-12-13

<400> SEQUENCE: 32

tcaatatagc aacagtagtt cttgctcctc cttaattcta gcatcttctt cattattttc     60

ttctacatac ataagcatct ccaatacgtt agacagcaca ccgatgatgg cggccgccac    120

agacacgaat atgactagac tgatgaccat                                     150


<210> SEQ ID NO 33
<211> LENGTH: 49
<212> TYPE: PRT
<213> ORGANISM: Variola Virus

<400> SEQUENCE: 33

Met Val Ile Ser Leu Val Ile Phe Val Ser Val Ala Ala Ala Ile Ile
 1               5                  10                  15

Gly Val Leu Ser Asn Val Leu Glu Met Leu Met Tyr Val Glu Glu Asn
            20                  25                  30

Asn Glu Glu Asp Ala Arg Ile Lys Glu Glu Gln Glu Leu Leu Leu Leu
        35                  40                  45

Tyr


<210> SEQ ID NO 34
<211> LENGTH: 186854
<212> TYPE: DNA
<213> ORGANISM: Artificial Sequence
<220> FEATURE:
<223> OTHER INFORMATION: LIVP Complete Genome

<400> SEQUENCE: 34

ttccactatc tgtggtacga acggtttcat cttctttgat gccatcaccc agatgttcta     60

taaacttggt atcctcgtcc gatttcatat cctttgccaa ccaatacata tagctaaact    120

caggcatatg ttccacacat cctgaacaat gaaattctcc agaagatgtt acaatgtcta    180

gatttggaca tttggtttca accgcgttaa catatgagtg aacacaccca tacatgaaag    240

cgatgagaaa taggattctc atcttgccaa aatatcacta gaaaaaattt atttatcaat    300
```

```
tttaaaggta taaaaaatac ttattgttgc tcgaatattt tgtatttgat ggtatacgga    360
agattagaaa tgtaggtatt atcatcaact gattctatgg ttttatgtat tctatcatgt    420
ttcactattg cgttggaaat aatatcatat gcttccacat atattttatt ttgttttaac    480
tcataatact cacgtaattc tggattattg gcatatctat gaataatttt agctccatga    540
tcagtaaata ttaatgagaa catagtatta ccacctacca ttattttttt catctcattc    600
aattcttaat tgcaaagatc tatataatca ttatagcgtt gacttatgga ctctggaatc    660
ttagacgatg tacagtcatc tataatcatg gcatatttaa tacattgttt tatagcatag    720
tcgttatcta cgatgttaga tatttctctc aatgaatcaa tcacacaatc taatgtaggt    780
ttatgacata atagcatttt cagcagttca atgtttttag attcgttgat ggcaatggct    840
atacatgtat atccgttatt tgatctaatg ttgacatctg aaccggattc tagcagtaaa    900
gatactagag attgtttatt atatctaaca gccttgtgaa gaagtgtttc tcctcgtttg    960
tcaatcatgt taatgtcttt aagataaggt aggcaaatgt ttatagtact aagaattggg   1020
caagcataag acatgtcaca aagacccttt tttgtatgta taagtgtaaa aattataaca   1080
tccatagttg gatttacata ggtgtccaat cgggatctct ccatcatcga gataattgat   1140
ggcatctccc ttcctttttt agtagatatt tcatcgtgta agaatcaata ttaatatttc   1200
taaagtatcc gtgtatagcc tctttattta ccacagctcc atattccact agagggatat   1260
cgccgaatgt catatactca attagtatat gttggaggac atccgagttc attgttttca   1320
atatcaaaga gatggtttcc ttatcatttc tccatagtgg tacaatacta cacattattc   1380
cgtgcggctt tccattttcc aaaaacaatt tgaccaaatc taaatctaca tctttattgt   1440
atctataatc actatttaga taatcagcca taattcctcg agtgcaacat gttagatcgt   1500
ctatatatga ataagcagtg ttatctattc ctttcattaa caatttaacg atgtctatat   1560
ctatatgaga tgacttaata taatattgaa gagctgtaca atagttttta tctataaaag   1620
acggcttgat tccgtgatta attagacatt taacaacttc cggacgcaca tatgctctcg   1680
tatccgactc tgaatacaga tgagagatga tatacagatg caatacggta ccgcaatttc   1740
gtagttgata atcatcatac gcgtatcagt actcgtcctc ataaagaaca ctgcagccat   1800
tttctatgaa caaatcaata attttagaaa caggatcatt gtcattacat aattttctat   1860
aactgaacga tggttttcac atttaacact caagtcaaat ccatgttcta ccaacacctt   1920
tatcaagtca acgtctacat ttttggattt catatagctg aatatattaa agttatttat   1980
gttgctaaat ccagtggctt ctagtagagc catcgctata tccttattaa ctttaacatg   2040
tctactattt gtgtattctt ctaatggggt aagctgtctc caatttttgc gtaatggatt   2100
agtgccactg tctagtagta gtttgacgac ctcgacatta ttacaatgct cattaaaaag   2160
gtatgcgtgt aaagcattat tcttgaattg gttcctggta tcattaggat ctctgtcttt   2220
caacatctgt ttaagttcat caagagccac ctcctcattt tccaaatagt caaacatttt   2280
gactgaatga gctactgtga actctataca cccacacaac taatgtcatt aaatatcatg   2340
tcaaaaactt gtacaattat taataaaaat aatttagtgt ttaaatttta ccagttccag   2400
attttacacc tccgttaata cctccattaa ccccactgga cgatcctcct ccccacattc   2460
caccgccacc agatgtataa gttttagatc ctttattact accatcatgt ccatggataa   2520
agacactcca catgccgcca ctaccccctt tagaagacat attaataaga cttaaggaca   2580
agtttaacaa taaaattaat cacgagtacc ctactaccaa cctacactat tatatgatta   2640
```

-continued

```
tagtttctat ttttacagta ccttgactaa agtttctagt cacaagagca atactaccaa   2700

cctacactat tatatgatta tagtttctat ttttatagga acgcgtacga gaaaatcaaa   2760

tgtctaattt ctaacggtag tgttgataaa cgattgttat ccgcggatac ctcctctatc   2820

atgtcgtcta ttttcttact ttgttctatt aacttattag cattatatat tatttgatta   2880

taaaacttat attgcttatt agcccaatct gtaaatatcg gattattaac atatcgtttc   2940

tttgtaggtt tatttaacat gtacatcact gtaagcatgt ccttaccatt tattttaatt   3000

tgacgcatat ccgcaatttc tttttcgcag tcggttataa attctatata tgatggatac   3060

atgctacatg tgtacttata atcgactaat atgaagtact tgatacatat tttcagtaac   3120

gatttattat taccacctat gaataagtac ctgtgatcgt ctaggtaatc aactgttttc   3180

ttaatacatt cgatggttgg taatttactc agaataattt ccaatatctt aatatataat   3240

tctgctattt ctgggatata tttatctgcc agtataacac aaatagtaat acatgtaaac   3300

ccatattttg ttattatatt aatgtctgcg ccattatcta ttaaccattc tactaggctg   3360

acactatgcg actcaataca atgataaagt atactacatc catgtttatc tattttgttt   3420

atatcatcaa tatacggctt acaaagtttt agtatcgata acacatccaa ctcacgcata   3480

gagaaggtag ggaataatgg cataatattt attaggttat catcattgtc attatctaca   3540

actaagtttc catttttttaa aatatactcg acaactttag gatctctatt gccaaatttt   3600

tgaaaatatt tatttatatg cttaaatcta tataatgtag ctccttcatc aatcatacat   3660

ttaataacat tgatgtatac tgtatgataa gatacatatt ctaacaatag atcttgtata   3720

gaatctgtat atcttttaag aattgtggat attaggatat tattacataa actattacac   3780

aattctaaaa tataaaacgt atcacggtcg aataatagtt gatcaactat ataattatcg   3840

attttgtgat ttttcttcct aaactgttta cgtaaatagt tagatagaat attcattagt   3900

tcatgaccac tatagttact atcgaataac gcgtcaaata tttcccgttt aatatcgcat   3960

ttgtcaagat aataatagag tgtggtatgt tcacgataag tataataacg catctctttt   4020

tcgtgtgaaa ttaaatagtt tattacgtcc aaagatgtag cataaccatc ttgtgaccta   4080

gtaataatat aataatagag aactgtttta cccattctat catcataatc agtggtgtag   4140

tcgtaatcgt aatcgtctaa ttcatcatcc caattataat attcaccagc acgtctaatc   4200

tgttctattt tgatcttgta tccatactgt atgttgctac atgtaggtat tcctttatcc   4260

aataatagtt taaacacatc tacattggga tttgatgttg tagcgtattt ttctacaata   4320

ttaataccat ttttgatact atttatttct atacctttcg aaattagtaa tttcaataag   4380

tctatattga tgttatcaga acatagatat tcgaatatat caaaatcatt gatattttta   4440

tagtcgactg acgacaataa caaaatcaca acatcgtttt tgatattatt atttttcttg   4500

gtaacgtatg cctttaatgg agtttcacca tcatactcat ataatggatt tgcaccactt   4560

tctatcaatg attgtgcact gctggcatcg atgttaaatg ttttacaact atcatagagt   4620

atcttatcgt taaccatgat tggttgttga tgctatcgca ttttttggtt tctttcattt   4680

cagttatgta tggatttagc acgtttggga agcatgagct catatgattt cagtactgta   4740

gtgtcagtac tattagtttc aataagatca atctctagat ctatagaatc aaaacacgat   4800

aggtcagaag ataatgaata tctgtaggct tcttgttgta ctgtaacttc tggttttgtt   4860

agatggttgc atcgtgcttt aacgtcaatg gtacaaattt tatcctcgct ttgtgtatca   4920

tattcgtccc tactataaaa ttgtatattc agattatcat gcgatgtgta tacgctaacg   4980

gtatcaataa acggagcaca ccatttagtc ataaccgtaa tccaaaaatt tttaaagtat   5040
```

```
atcttaacga aagaagttgt gtcattgtct acggtgtatg gtactagatc ctcataagtg   5100

tatatatcta gagtaatgtt taatttatta aatggttgat aatatggatc ctcgtgacaa   5160

tttccgaaga tggaaataag acataaacac gcaataaatc taattgcgga catggttact   5220

ccttaaaaaa atacgaataa tcaccttggc tatttagtaa gtgtcattta acactatact   5280

catattaatc catggactca taatctctat acgggattaa cggatgttct atatacgggg   5340

atgagtagtt ctcttcttta actttatact ttttactaat catatttaga ctgatgtatg   5400

ggtaatagtg tttgaagagc tcgttctcat catcagaata aatcaatatc tctgtttttt   5460

tgttatacag atgtattaca gcctcatata ttacgtaata gaacgtgtca tctaccttat   5520

taactttcac cgcatagttg tttgcaaata cggttaatcc tttgacctcg tcgatttccg   5580

accaatctgg gcgtataatg aatctaaact ttaattgctt gtaatcattc gaaataattt   5640

ttagtttgca tccgtagtta tcccctttat gtaactgtaa atttctcaac gcgatatctc   5700

cattaataat gatgtcgaat tcgtgctgta tacccatact gaatggatga acgaataccg   5760

acggcgttaa tagtaattta ctttttcatc tttacatatt gggtactagt tttactatca   5820

taagtttata aattccacaa gctactatgg aataagccaa ccatcttagt ataccacaca   5880

tgtcttaaag tttattaatt aattacatgt tgttttatat atatcgctac gaatttaaag   5940

agaaattagt ttaggaagaa aaattatcta tctacatcat cacgtctctg tattctacga   6000

tagagtgcta ctttaagatg cgacagatcc gtgtcatcaa atatatactc cattaaaatg   6060

attattccgg cagcgaactt gatattggat atatcacaac ctttgttaat atctacgaca   6120

atagacagca gtcccatggt tccataaaca gtgagtttat ctttctttga agagatattt   6180

tgtagagatc ttataaaact gtcgaatgac atcgcattta tatctttagc taaatcgtat   6240

atgttaccat cgtaatatct aaccgcgtct atcttaaacg tttccatcgc tttaaagacg   6300

tttccgatag atggtctcat ttcatcagtc atactgagcc aacaaatata atcgtgtata   6360

acatctttga tagaatcaga ctctaaagaa aacgaatcgg ctttattata cgcattcatg   6420

ataaacttaa tgaaaaatgt ttttcgttgt ttaagttgga tgaatagtat gtcttaataa   6480

ttgttattat ttcattaatt aatatttagt aacgagtaca ctctataaaa acgagaatga   6540

cataactaat cataactagt tatcaaagtg tctaggacgc gtaattttca tatggtatag   6600

atcctgtaag cattgtctgt attctggagc tattttctct atcgcattag tgagttcaga   6660

atatgttata aatttaaatc gaataacgaa cataacttta gtaaagtcgt ctatattaac   6720

tcttttattt tctagccatc gtaataccat gtttaagata gtatattctc tagttactac   6780

gatctcatcg ttgtctagaa tatcacatac tgaatctaca tccaatttta gaaattggtc   6840

tgtgttacat atctcttcta tattattgtt gatgtattgt cgtagaaaac tattacgtag   6900

accattttct ttataaaacg aatatatagt actccaatta tctttaccga tatatttgca   6960

cacataatcc attctctcaa tcactacatc tttaagattt tcgttgttaa gatatttggc   7020

taaactatat aattctatta gatcatcaac agaatcagta tatatttttc tagatccaaa   7080

gacgaactct ttggcgtcct ctataatatt cccagaaaag atattttcgt gttttagttt   7140

atcgagatct gatctgttca tatacgccat gattgtacgg tacgttatga taaccgcata   7200

aaataaaaat ccattttcat ttttaaccaa tactattcat aattgagatt gatgtaatac   7260

tttgttactt tgaacgtaaa gacagtacac ggatccgtat ctccaacaag cacgtagtaa   7320

tcaaatttgg tgttgttaaa cttcgcaata ttcatcaatt tagatagaaa cttatactca   7380
```

-continued

```
tcatctgttt taggaatcca tgtattatta ccactttcca acttatcatt atcccaggct   7440
atgtttcgtc catcatcgtt gcgcagagtg aataattctt ttgtattcgg tagttcaaat   7500
atatgatcca tgcatagatc ggcaaagcta ttgtagatgt gatttttcct aaatctaata   7560
taaaactcgt ttactagcaa acactttcct gatttatcga ccaagacaca tatggtttct   7620
aaatctatca agtggtgggg atccatagtt atgacgcagt aacatatatt attacattct   7680
tgactgtcgc taatatctaa atatttattg ttatcgtatt ggattctgca tatagatggc   7740
ttgtatgtca aagatataga acacataacc aatttatagt cgcgctttac attctcgaat   7800
ctaaagttaa gagatttaga aaacattata tcctcggatg atgttatcac tgtttctgga   7860
gtaggatata ttaaagtctt tacagatttc gtccgattca aataaatcac taaataatat   7920
cccacattat catctgttag agtagtatca ttaaatctat tatattttat gaaagatata   7980
tcactgctca cctctatatt tcgtacattt ttaaactgtt tgtataatat ctctctgata   8040
caatcagata tatctattgt gtcggtagac gataccgtta catttgaatt aatggtgttc   8100
cattttacaa cttttaacaa gttgaccaat tcatttctaa tagtatcaaa ctctccatga   8160
ttaaatattt taatagtatc cattttatat cactacggac acaaagtagc tgacataaac   8220
cattgtataa tttttatgtt ttatgtttat tagcgtacac attttggaag ttccggcttc   8280
catgtatttc ctggagagca agtagatgat gaggaaccag atagtttata tccgtacttg   8340
cacttaaagt ctacattgtc gttgtatgag tatgatcttt taaacccgct agacaagtat   8400
ccgtttgata ttgtaggatg tggacattta acaatctgac acgtgggtgg atcggaccat   8460
tctcctcctg aacacaggac actagagtta ccaatcaacg aatatccact attgcaacta   8520
taagttacaa cgctcccatc ggtataaaaa tcctcgtatc cgttatgtct tccgttggat   8580
atagatggag ggattggca tttaacagat tcacaaatag gtgcctcggg attccatacc   8640
atagatccag tagatcctaa ttcacaatac gatttagatt caccgatcaa ctgatatccg   8700
ctattacaag agtacgttat actagagcca aagtctactc caccaatatc aagttggcca   8760
ttatcgatat ctcgaggcga tgggcatctc cgtttaatac attgattaaa gagtgtccat   8820
ccagtacctg tacatttagc atatataggt cccatttttt gctttctgta tccaggtaga   8880
catagatatt ctatagtgtc tcctatgttg taattagcat tagcatcagt ctccacacta   8940
ttcttaaatt tcatattaat gggtcgtgac ggaatagtac agcatgatag aacgcatcct   9000
attcccaaca atgtcaggaa cgtcacgctc tccaccttca tatttattta tccgtaaaaa   9060
tgttatcctg gacatcgtac aaataataaa aagcccatat atgttcgcta ttgtagaaat   9120
tgtttttcac agttgctcaa aaacgatggc agtgacttat gagttacgtt acactttgga   9180
gtctcatctt tagtaaacat atcataatat tcgatattac gagttgacat atcgaacaaa   9240
ttccaagtat ttgattttgg ataatattcg tattttgcat ctgctataat taagatataa   9300
tcaccgcaag aacacacgaa catctttcct acatggttaa agtacatgta caattctatc   9360
catttgtctt ccttaactat atatttgtat agataattac gagtctcgtg agtaattcca   9420
gtaattacat agatgtcgcc gtcgtactct acagcataaa ctatactatg atgtctaggc   9480
atgggagact tttttatcca acgattttta gtgaaacatt ccacatcgtt taatactaca   9540
tatttctcat acgtggtata aactccaccc attacatata tatcatcgtt tacgaatacc   9600
gacgcgcctg aatatctagg agtaattaag tttggaagtc ttatccattt cgaagtgccg   9660
tgtttcaaat attctgccac acccgttgaa atagaaaatt ctaatcctcc tattacatat   9720
aactttccat cgttaacaca agtactaact tctgatttta acgacgacat attagtaacc   9780
```

```
gttttccatt ttttcgtttt aagatctacc cgcgatacgg aataaacatg tctattgtta    9840
atcatgccgc caataatgta tagacaatta tgtaaaacat ttgcattata gaattgtcta    9900
tctgtattac cgactatcgt ccaatattct gttctaggag agtaatgggt tattgtggat    9960
atataatcag agtttttaat gactactata ttatgtttta taccatttcg tgtcactggc   10020
tttgtagatt tggatatagt taatcccaac aatgatatag cattgcgcat agtattagtc   10080
ataaacttgg gatgtaaaat gttgatgata tctacatcgt ttggattttt atgtatccac   10140
tttaataata tcatagctgt aacatcctca tgatttacgt taacgtcttc gtgggataag   10200
atagttgtca gttcatcctt tgataatttt ccaaattctg gatcggatgt caccgcagta   10260
atattgttga ttatttctga catcgacgca ttatatagtt ttttaattcc atatctttta   10320
gaaaagttaa acatccttat acaatttgtg aaattaatat tatgaatcat agtttttaca   10380
catagatcta ctacaggcgg aacatcaatt attatggcag caactagtat catttctaca   10440
ttgtttatgg tgatgtttat cttcttccag cgcatatagt ctaatagcga ttcaaacgcg   10500
tgatagttta taccattcaa tataatcgct tcatccttta gatggtgatc ctgaatgcgt   10560
ttaaaaaaat tatacggaga cgccgtaata atttccttat tcacttgtat aatttcccca   10620
ttgatagaaa atattacgct ttccattctt aaagtactat aagtaattat agtataatgt   10680
aaacgtttat atattcaata tttttataaa aatcattttg acattaattc ctttttaaat   10740
ttccgtctat catctataga aacgtattct atgaatttat aaaatgcttt tacgtgtcct   10800
atcgtaggcg atagaaccgc taaaaagcct atcgaatttc tacaaaagaa tctgttatat   10860
ggtataggga gagtataaaa cattaaatgt ccgtacttat taaagtattc agtagccaat   10920
cctaactctt tcgaatactt attaatggct cttgttctgt acgaatctat tttttttgaac  10980
aacggaccta gtggtatatc ttgttctatg tatctaaaat aatgtctgac tagatccgtt   11040
agtttaatat ccgcagtcat cttgtctaga atggcaaatc taactgcggg tttaggcttt   11100
agtttagttt ctatatctac atctatgtct ttatctaaca ccaaaaatat aatagctaat   11160
attttattac aatcatccgg atattcttct acgatctcac taactaatgt ttctttggtt   11220
atactagtat agtcactatc ggacaaataa agaaaatcag atgatcgatg aataatacat   11280
ttaaattcat catctgtaag atttttgaga tgtctcatta gaatattatt agggttagta   11340
ctcattatca ttcggcagct attacttatt ttattatttt tcaccatata gatcaatcat   11400
tagatcatca aaatatgttt caatcatcct aaagagtatg gtaaatgact cttcccatct   11460
aatttctgaa cgttcaccaa tgtctctagc cactttggca ctaatagcga tcattcgctt   11520
agcgtcttct atattattaa ctggttgatt caatctatct agcaatggac cgtcggacag   11580
cgtcattctc atgttcttaa tcaatgtaca tacatcgccg tcatctacca attcatccaa   11640
caacataagc tttttaaaat catcattata ataggtttga tcgttgtcat ttctccaaag   11700
aatatatcta ataagtagag tcctcatgct tagttaacaa ctattttttta tgttaaatca  11760
attagtacac cgctatgttt aatacttatt catattttag tttttaggat tgagaatcaa   11820
tacaaaaatt aatgcatcat taattttaga aatacttagt ttccacgtag tcaatgaaac   11880
atttgaactc atcgtacagg acgttctcgt acaggacgta actataaacc ggtttatatt   11940
tgttcaagat agatacaaat ccgataactt tttttacgaa ttctacggga tccactttaa  12000
aagtgtcata ccgggttctt tttatttttt taaacagatc aatggtgtga tgttgattag   12060
gtcttttacg aatttgatat agaatagcgt ttacatatcc tccataatgg tcaatcgcca   12120
```

```
tttgttcgta tgtcataaat tctttaatta tatgacactg tgtattattt agttcatcct  12180
tgttcattgt taggaatcta tccaaaatgg caattatact agaactatag gtgcgttgta  12240
tacacatatt gatgtgtctg tttatacaat caatgctact accttcgggt aaaattgtag  12300
catcatatac catttctagt actttaggtt cattattatc cattgcagag gacgtcatga  12360
tcgaatcata aaaaaatata ttatttttat gttattttgt taaaaataat catcgaatac  12420
ttcgtaagat actccttcat gaacataatc agttacaaaa cgtttatatg aagtaaagta  12480
tctacgattt ttacaaaagt ccggatgcat aagtacaaag tacgcgataa acggaataat  12540
aatagattta tctagtctat ctttttctat agctttcata gttagataca tggtctcaga  12600
agtaggatta tgtaacatca gcttcgataa aatgactggg ttatttagtc ttacacattc  12660
gctcatacat gtatgaccgt taactacaga gtctacacta aaatgattga acaatagata  12720
gtctaccatt gtttcgtatt cagatagtac agcgtagtac atggcatctt cacaaattat  12780
atcattgtct aatagatatt tgacgcatct tatggatccc acttcaacag ccatcttaaa  12840
atcggtagaa tcatattgct ttcctttatc attaataatt tctagaacat catctctatc  12900
ataaaagata caaatattaa ctgtttgatc cgtaataaca ttgctagtcg atagcaattt  12960
gttaataaga tgcgctgggc tcaatgtctt aataagaagt gtaagaggac tatctccgaa  13020
tttgttttgt ttattaacat ccgttgatgg aagtaaaaga tctataatgt ctacattctt  13080
gactgtttta gagcatacaa tatggagagg tgtatttcca tcatgatctg gttttgaggg  13140
actaattcct agtttcatca tccatgagat tgtagaagct tttggattgt ctgacataag  13200
atgtctatga atatgatttt tgccaaattt atccactatc ctggcttcga atccgatgga  13260
cattattttt ttaaacactc tttctgaagg atctgtacac gccaacaacg gaccacatcc  13320
ttcttcatca accgagttgt taatcttggc tccatactgt accaataaat ttattctctc  13380
tatgacttca tcatctgttc ccgagagata atatagaggc gttttatgct gtttatcaca  13440
cgcgtttgga tctgcgccgt gcgtcagcag catcgcgact attctattat tattaatttt  13500
agaagctata tgcaatggat aatttccatc atcatccgtc tcatttggag agtatcctct  13560
atgaagaagt tcttcgacaa atcgttcatc tagtccttta attccacaat acgcatgtag  13620
aatgtgataa ttatttccag aaggttcgat agcttgtagc atattcctaa atacatctaa  13680
atttttacta ttatatttgg cataaagaga tagataatac tcggccgaca taatgttgtc  13740
cattgtagta taaaaattaa tatttctatt tctgtatatt tgcaacaatt tactctctat  13800
aacaaatatc ataacttagt tcttttatgt caagaaggca ctggtttagt tcatctataa  13860
atgtcacgcc ataactacca cgcatgccat actcagaatt atgataaaga tatttatcct  13920
tggggtgtag gtaatgggga ttaatctttg ttggatcagt ctctaagtta acacatgtca  13980
cacatgatcc atttatagtt atatcacacg atgatgattt atgaattgat tccggaagat  14040
cgctatcgta ttttgtggtt ccacaattca tttccataca tgttattgtc acactaatat  14100
tatgatgaac tttatctagc cgctgagtgg taaacaacag aacagatagt ttattatctt  14160
taccaacacc ctcagccgct gccacaaatc tctgatccgt atccatgatg gtcatgttta  14220
tttctagtcc gtatccagtc aacactatgt tagcatttct gtcgatatag ctttcactca  14280
tatgacactc accaataata gtagaattaa tgtcgtaatt tacaccaata gtgagttcgg  14340
cggcaaagta ccaataccgg taatcttgtc gaggaggaca tatagtattc ttgtattcta  14400
ccgaataccc gagagatgcg atacaaaaga gcaagactaa tttgtaaacc atcttactca  14460
aaatatgtaa caatagtacg atgcaatgag taagacaata ggaaatctat cttatataca  14520
```

```
cataattatt ctatcaattt taccaattag ttagtgtaat gttaacaaaa atgtgggaga  14580
atctaattag tttttcttta cacaattgac gtacatgagt ctgagttcct tgtttttgct  14640
aattatttca tccaatttat tattcttgac gatatcgaga tcttttgtat aggagtcaaa  14700
cttgtattca acatgctttt ctataatcat tttagctatt tcggcatcat ccaatagtac  14760
attttccaga ttagcagaat agatattaat gtcgtatttg aacagagcct gtaacatctc  14820
aatgtcttta ttatctatag ccaatttaat gtccggaatg aagagaaggg aattattggt  14880
gtttgtcgac gtcatatagt cgagcaagag aatcatcata tccacgtgtc catttttat  14940
agtgatgtga atacaactaa ggagaatagc cagatcaaaa gtagatggta tctctgaaag  15000
aaagtaggaa acaatactta catcattaag catgacggca tgataaaatg aagttttcca  15060
tccagttttc ccatagaaca tcagtctcca atttttctta acaaacagtt ttaccgtttg  15120
catgttacca ctatcaaccg cataatacaa tgcggtgttt cccttgtcat caaattgtga  15180
atcatccagt ccactgaata gcaaaatctt tactattttg gtatcttcca atgtggctgc  15240
ctgatgtaat ggaaattcat tctctagaag atttttcaat gctccagcgt tcaacaacgt  15300
acatactaga cgcacgttat tatcagctat tgcataatac aaggcactat gtccatggac  15360
atccgcctta aatgtatctt tactagagag aaagcttttc agctgcttag acttccaagt  15420
attaattcgt gacagatcca tgtctgaaac gagacgctaa ttagtgtata tttttcatt  15480
ttttataatt ttgtcatatt gcaccagaat taataatatc tttaatagat ctgattagta  15540
gatacatggc tatcgcaaaa caacatatac acatttaata aaaataatat ttattaagaa  15600
aattcagatt tcacgtaccc atcaatataa ataaaataat gattccttac accgtaccca  15660
tattaaggag attccacctt acccataaac aatataaatc cagtaatatc atgtctgatg  15720
atgaacacaa atggtgtatt aaattccagt ttttcaggag atgatctcgc cgtagctacc  15780
ataatagtag atgcctctgc tacagttcct tgttcgtcga catctatctt tgcattctga  15840
aacattttat aaatatataa tgggtcccta gtcatatgtt taaacgacgc attatctgga  15900
ttaaacatac taggagccat catttcggct atcgacttaa tatccctctt attttcgata  15960
gaaaatttag ggagtttaag attgtacact ttattcccta attgagacga ccaatagtct  16020
aattttgcag ccgtgataga atctgtgaaa tgggtcatat tatcacctat tgccaggtac  16080
atactaatat tagcatcctt atacggaagg cgtaccatgt catattcttt gtcatcgatt  16140
gtgattgtat ttccttgcaa tttagtaact acgttcatca tgggaaccgt tttcgtaccg  16200
tacttattag taaaactagc attgcgtgtt ttagtgatat caaacggata ttgccatata  16260
cctttaaaat atatagtatt aatgattgcc catagagtat tattgtcgag catattagaa  16320
tctactacat tagacatacc ggatctacgt tctactatag aattaatttt attaaccgca  16380
tctcgtctaa agtttaatct atataggccg aatctatgat attgttgata atacgacggt  16440
ttaatgcaca cagtattatc tacgaaactt tgataagtta gatcagtgta cgtatattta  16500
gatgttttca gcttagctaa tcctgatatt aattctgtaa atgctggacc cagatctctt  16560
tttctcaaat ccatagtctt caataattct attctagtat tacctgatgc aggcaatagc  16620
gacataaaca tagaaaacga ataaccaaac ggtgagaaga caatattatc atcttgaata  16680
tttttatacg ctactatacc ggcattggta aatccttgta gacgataggc ggacgctgaa  16740
cacgctaacg atagtatcaa taacgcaatc atgattttat ggtattaata attaacctta  16800
tttttatgtt cggtataaaa aaattattga tgtctacaca tccttttgta attgacatct  16860
```

```
atatatcctt ttgtataatc aactctaatc actttaactt ttacagtttt ccctaccagt  16920

ttatccctat attcaacata tctatccata tgcatcttaa cactctctgc caagatagct  16980

tcagagtgag gatagtcaaa aagataaata tatagagcat aatcattctc gtatactctg  17040

ccctttatta catcacccgc attgggcaac gaataacaaa atgcaagcat cttgttaacg  17100

ggctcgtaaa ttgggataaa aattatgttt ttattgtctt atatctattt tattcaagag  17160

aatattcagg aatttctttt tccggttgta tctcgtcgca gtatatatca tttgtacatt  17220

gtttcatatt ttttaatagt ttacaccttt tagtaggact agtatcgtac aattcatagc  17280

tgtattttga attccaatca cgcataaaaa tatcttccaa ttgttgacga agacctaatc  17340

catcatccgg tgtaatatta atagatgctc cacatgtatc cgtaaagtaa tttcctgtcc  17400

aatttgaggt acctatatag gccgttttat cggttaccat atatttggca tggtttaccc  17460

tagaatacgg aatgggagga tcagcatctg gtacaataaa tagctttact tctatattta  17520

tgtttttaga ttttagcata gcgatagatc ttaaaaagtt tctcatgata aacgaagatc  17580

gttgccagca actaatcaat agcttaacgg atacttgtct gtctatagcg gatcttctta  17640

attcatcttc tatataaggc caaaacaaaa ttttacccgc cttcgaataa ataataggga  17700

taaagttcat aacagataca taaacgaatt tactcgcatt tctaatacat gacaataaag  17760

cggttaaatc attggttctt tccatagtac atagttgttg cggtgcagaa gcaataaata  17820

cagagtgtgg aacgccgctt acgttaatac taagaggatg atctgtatta taatacgacg  17880

gataaaagtt tttccaatta tatggtagat tgttaactcc aagataccag tatacctcaa  17940

aaatttgagt gagatccgct gccaagttcc tattattgaa gatcgcaata cccaattcct  18000

tgacctgagt tagtgatctc caatccatgt tagcgcttcc taaataaata tgtgtattat  18060

cagatatcca aaattttgta tgaagaactc ctcctaggat atttgtaata tctatgtatc  18120

gtacttcaac tccggccatt tgtagtcttt caacatcctt taatggtttg ttagatttat  18180

taacggctac tctaactcgt actcctcttt tgggtaattg tacaatctcg tttaatatta  18240

tcgtgccgaa attcgtaccc acttcatccg ataaactcca ataaaaagat gatatatcta  18300

gtgtttttgt ggtattggat agaatttccc tccacatgtt aaatgtagac aaatatactt  18360

tatcaaattg catacctata ggaatagttt ctgtaatcac tgcgattgta ttatccggat  18420

tcattttatt tgttaaaaga ataatcctat atcacttcac tctattaaaa atccaagttt  18480

ctatttcttt catgactgat tttttaactt catccgtttc cttatgaaga tgatgtttgg  18540

caccttcata aatttttatt tctctattac aatttgcatg ttgcatgaaa taatatgcac  18600

ctaaaacatc gctaatctta ttgtttgttc cctggagtat gagagtcggg ggggtgttaa  18660

tcttggaaat tatttttcta accttgttgg tagccttcaa gacctgacta gcaaatccag  18720

ccttaatttt ttcatgattg actaatgggt cgtattggta tttataaact ttatccatat  18780

ctctagatac tgattctgga catagctttc cgactggcgc atttggtgtg atggttccca  18840

taagtttggc agctagcaga ttcagtcttg aaacagcatc tgcattaact agaggagaca  18900

ttagaatcat tgctgtaaac aagtttggat tatcgtaaga ggctagctcc catggaatga  18960

cccaataagt agatttaata gttaccacgt gctgtaccaa agtcatcaat catcattttt  19020

tcaccattac ttcttccatg tccaatatga tcatgtgaga atactaaaat tcctaacgat  19080

gatatgtttt cagctagttc gtcataacgt ccagaatgtt taccagctcc atgacttatg  19140

aatactaatg ccttaggata tgtaataggt ttccaatatt tacaatatat gtaatcattg  19200

tccagattga acatacagtt tgcactcatg attcacgtta tataactatc aatattaaca  19260
```

```
gttcgtttga tgatcatatt atttttatgt tttattgata attgtaaaaa catacaatta  19320
aatcaatata gaggaaggag acggctactg tcttttgtaa gatagtcatg gcgactaaat  19380
tagattatga ggatgctgtt ttttactttg tggatgatga taaaatatgt agtcgcgact  19440
ccatcatcga tctaatagat gaatatatta cgtggagaaa tcatgttata gtgtttaaca  19500
aagatattac cagttgtgga agactgtaca aggaattgat gaagttcgat gatgtcgcta  19560
tacggtacta tggtattgat aaaattaatg agattgtcga agctatgagc gaaggagacc  19620
actacatcaa ttttacaaaa gtccatgatc aggaaagttt attcgctacc ataggaatat  19680
gtgctaaaat cactgaacat tggggataca aaaagatttc agaatctaga ttccaatcat  19740
tgggaaacat tacagatttg atgaccgacg ataatataaa catcttgata ctttttctag  19800
aaaaaaaatt gaattgatga tataggggtc ttcataacgc ataattatta cgttagcatt  19860
ctatatccgt gttaaaaaaa attatcctat catgtatttg agagttttat atgtagcaaa  19920
catgatagct gtgatgccaa taagctttag atattcacgc gtgctagtgt tagggatggt  19980
attatctggt ggtgaaatgt ccgttatata atctacaaaa caatcatcgc atatagtatg  20040
cgatagtaga gtaaacattt ttatagtttt tactggattc atacatcgtc tacccaattc  20100
ggttataaat gaaattgtcg ccaatcttac acccaacccc ttgttatcca ttagcatagt  20160
attaacttcg ttatttatgt cataaactgt aaatgatttt gtagatgcca tatcatacat  20220
gatattcatg tccctattat aatcattact aactttatca caatatatgt tgataatatc  20280
tatatatgat ctagtctttg tgggcaactg tctatacaag tcgtctaaac gttgtttact  20340
catatagtat cgaacagcca tcattacatg gtcccgttcc gttgatagat aatcgagtat  20400
gttagtggac ttgtcaaatc tatataccat attttctgga agtggatata catagtcgtg  20460
atcaacatta ttgctagcct catcttctat atcctgtact ataccattat ctatatcatc  20520
tacataatct atgatattat tacacataaa catcgacaac atactattgt ttattatcta  20580
agtcctgttg atccaaaccc ttgatctcct ctatttgtac tatctagaga ttgtacttct  20640
tccagttctg gataatatat acgttgatag attagctgag ctattctatc tccagtattt  20700
acattaaacg tacattttcc attattaata agaatgactc ctatgtttcc cctataatct  20760
tcgtctatta caccacctcc tatatcaatg ccttttagtg acagaccaga cctaggagct  20820
attctaccat agcagaactt aggcatggac atactaatat ctgtcttaat taactgtctt  20880
tctcctggag ggatagtata atcgtaagcg ctatacaaat catatccggc agcacccggc  20940
gattgcctag taggagattt agctctgtta gtttccttaa caaatctaac tggtgagtta  21000
atattcatgt tgaacataaa actaatattt tatttcaaaa ttatttacca tcccatatat  21060
tccatgaata agtgtgatga ttgtacactt ctatagtatc tatatacgat ccacgataaa  21120
atcctcctat caatagcagt ttattatcca ctatgatcaa ttctggatta tccctcggat  21180
aaataggatc atctatcaga gtccatgtat tgctggattc acaataaaat tccgcatttc  21240
taccaaccaa gaataacctt ctaccgaaca ctaacgcgca tgatttataa tgaggataat  21300
aagtggatgg tccaaactgc cactgatcat gattgggtag caaatattct gtagttgtat  21360
cagtttcaga atgtcctccc attacgtata taacattgtt tatggatgcc actgctggat  21420
tacatctagg tttcagaaga ctcggcatat taacccaagc agcatccccg tggaaccaac  21480
gctcaacaga tgtgggattt ggtagacctc ctactacgta taatttattg ttagcgggta  21540
tcccgctagc atacagtctg ggctattca tcggaggaat tggaatccaa ttgtttgata  21600
```

```
tataatttac cgctatagca ttgttatgta tttcattgtt catccatcca ccgatgagat  21660
atactacttc tccaacatga gtacttgtac acatatggaa tatatctata atttgatcca  21720
tgttcatagg atactctatg aatggatact tgtatgattt gcgtggttgt ttatcacaat  21780
gaaatatttt ggtacagtct agtatccatt ttacattatt tatacctctg ggagaaagat  21840
aatttgacct gattacattt ttgataagga gtagcagatt tcctaattta tttcttcgct  21900
ttatatacca cttaatgaca aaatcaacta cataatcctc atctggaaca tttagttcat  21960
cgctttctag aataagtttc atagatagat aatcaaaatt gtctatgatg tcatcttcca  22020
gttccaaaaa gtgtttggca ataaagtttt tagtatgaca taagagattg gatagtccgt  22080
attctatacc catcatgtaa cactcgacac aatattcctt tctaaaatct cgtaagataa  22140
agtttataca agtgtagatg ataaattcta cagaggttaa tatagaagca cgtaataaat  22200
tgacgacgtt atgactatct atatatacct ttccagtata cgagtaaata actatagaag  22260
ttaaactgtg aatgtcaagg tctagacaaa ccctcgtaac tggatcttta tttttcgtgt  22320
atttttgacg taaatgtgtg cgaaagtaag gagataactt tttcaatatc gtagaattga  22380
ctattatatt gcctcctatg gcatcaataa ttgttttgaa tttcttagtc atagacaatg  22440
ctaatatatt cttacagtac acagtattga caaatatcgg catttatgtt tctttaaaag  22500
tcaacatcta gagaaaaatg attatctttt tgagacataa ctcccatttt ttggtattca  22560
cccacacgtt tttcgaaaaa attagttttt ccttccaatg atatattttc catgaaatca  22620
aacggattgg taacattata aattttttta aatcccaatt cagaaatcaa tctatccgcg  22680
acgaattcta tatatgtttt catcatttca caattcattc ctataagttt aactggaaga  22740
gccgcagtaa gaaattcttg ttcaatggat actgcatctg ttataataga tctaacggtt  22800
tcttcactcg gtggatgcaa taaatgttta aacatcaaac atgcgaaatc gcagtgcaga  22860
ccctcgtctc tactaattag ttcgttggaa aacgtgagtc cgggcattag gccacgcttt  22920
ttaagccaaa atatggaagc gaatgatccg gaaaagaaga ttccttctac tgcagcaaag  22980
gcaataagtc tctctccata accggcgctg tcatgtatcc acttttgagc ccaatcggcc  23040
ttcttttttta cacaaggcat cgtttctatg gcattaaaga gatagttttt ttcattacta  23100
tctttaacat aagtatcgat caaaagacta tacatttccg aatgaatgtt ttcaatggcc  23160
atctgaaatc cgtagaaaca tctagcctcg gtaatctgta cttctgtaca aaatcgttcc  23220
gccaaatttt cattcactat tccgtcactg gctgcaaaaa acgccaatac atgttttata  23280
aaatattttt cgtctggtgt tagtttattc caatcattga tatctttaga tatatctact  23340
tcttccactg tccaaaatga tgcctctgcc tttttataca tgttccagat gtcatgatat  23400
tggattggga aaataacaaa tctatttgga tttggtgcaa ggatgggttc cataactaaa  23460
ttaacaataa caataaattt tttttcagtt atctatatgc ctgtacttgg attttttgta  23520
catcgatatc gccgcaatca ctacaataat tacaagtatt attgatagca ttgttattag  23580
tactatcata attaaattat ctacattcat gggtgctgaa taatcgttat tatcatcatt  23640
atcattttgt aattgtgaca tcatactaga taaatcgttt gcgagattgt tgtgggaagc  23700
gggcatggag gatgcattat cattattatt taacgccttc catttggatt cacaaatgtt  23760
acgcacattc aacattttat ggaaactata attttgtgaa aacaaataac aagaaaactc  23820
gtcatcgttc aaatttttaa cgatagtaaa ccgattaaac gtcgagctaa tttctaacgc  23880
tagcgactct gttggatatg ggtttccaga tatatatctt ttcagttccc ctacgtatct  23940
ataatcatct gtaggaaatg gaagatattt ccatttatct actgttccta atatcatatg  24000
```

```
tggtggtgta gtagaaccat taagcgcgaa agatgttatt tcgcatcgta ttttaacttc  24060
gcaataattt ctggttagat aacgcactct accagtcaag tcaatgatat tagcctttac  24120
agatatattc atagtagtcg taacgatgac tccatctttt agatgcgata ctcctttgta  24180
tgtaccagaa tcttcgtacc tcaaactcga tatatttaaa caagttaatg agatattaac  24240
gcgttttatg aatgatgata tataaccaga agttttatcc tcggtggcta gcgctataac  24300
cttatcatta taataccaac tagtgtgatt aatatgtgac acgtcagtgt gggtacaaat  24360
atgtacatta tcgtctacgt cgtattcgat acatccgcat acagccaaca aatataaaat  24420
gacaaatact ctaacgccgt tcgtacccat cttgatgcgg tttaataaat gttttgattt  24480
caatttattg taaaaaaaga ttcggtttta tactgttcga tattctcatt gcttatattt  24540
tcatctatca tctccacaca gtcaaatccg tggttagcat gcacctcatc aaccggtaaa  24600
agactatcgg actcttctat cattataact ctagaatatt taatttggtc attattaatc  24660
aagtcaatta tcttattttt aacaaacgtg agtattttac tcattttta taaaaacttt  24720
tagaaatata cagactctat cgtgtgtcta tatcttcttt ttatatccaa tgtatttatg  24780
tctgattttt cttcatttat catatataat ggtccaaatt ctacacgtgc ttcggattca  24840
tccagatcat taaggttctt ataattgtaa catccttctc ttccctcttc tacatcttcc  24900
ttcttattct tattcttagc gtcacagaat ctaccacagc aggatcccat gacgagcgtc  24960
atattaaact aatccatttt caattataat atatgattag taatgaccat taaaataaaa  25020
aatattcttc ataaccggca agaaagtgaa aagttcacat tgaaactatg tcagtagtat  25080
acatcatgaa atgatgatat atatatactc tattttggtg gaggattata tgatataatt  25140
cgtggataat catttttaag acacatttct ttattcgtaa atcttttcac gttaaatgag  25200
tgtccatatt ttgcaatttc ttcatatgat ggcggtgtac gtggacgagg ctgctcctgt  25260
tcttgttgtg gtcgccgact gtcgtgtctg cgtttagatc cctccattat cgcgattgcg  25320
tagatggagt actattttat accttgtaat taaatttttt tattaattaa acgtataaaa  25380
acgttccgta tctgtattta agagccagat ttcgtctaat agaacaaata gctacagtaa  25440
aaataactag aataattgct acacccacta gaaaccacgg atcgtaatac ggcaatcggt  25500
tttcgataat aggtggaacg tatattttat ttaaggactt aacaattgtc tgtaaaccac  25560
aatttgcttc cgcggatcct gtattaacta tctgtaaaag catatgttga ccgggcggag  25620
ccgaacattc tccgatatct aatttctgta tatctataat attattaacc tccgcatacg  25680
cattacagtt cttttctagc ttggataccg cactaggtac atcgtctaga tctattccta  25740
tttcctcagc gatagctctt ctatcctttt ccggaagcaa tgaaatcact tcaataaatg  25800
attcaaccat gagtgtgaaa ctaagtcgag aattactcat gcatttgtta gttattcgga  25860
gcgcgcaatt tttaaactgt cctataacct ctcctatatg aatagcacaa gtgacattag  25920
tagggataga atgttgagct aatttttgta aataactatc tataaaaaga ttatacaaag  25980
ttttaaactc tttagtttcc gccatttatc cagtctgaga aaatgtctct cataataaat  26040
ttttccaaga aactaattgg gtgaagaatg gaaaccttta atctatattt atcacagtct  26100
gttttggtac acatgatgaa ttcttccaat gccgtactaa attcgatatc tttttcgatt  26160
tctggatatg tttttaataa agtatgaaca aagaaatgga aatcgtaata ccagttatgt  26220
ttaactttga aattgttttt tattttcttg ttaatgattc cagccacttg ggaaaagtca  26280
aagtcgttta atgccgattt aatacgttca ttaaaaacaa actttttatc ctttagatga  26340
```

```
attattattg gttcattgga atcaaaaagt aagatattat cgggtttaag atctgcgtgt  26400
aaaaagttgt cgcaacaggg tagttcgtag attttaatgt ataacagagc catctgtaaa  26460
aagataaact ttatgtattg taccaaagat ttaaatccta atttgatagc taactcggta  26520
tctactttat ctgccgaata cagtgctagg ggaaaaatta taatgtttcc tctttcatat  26580
tcgtagttag ttctcttttc atgttcgaaa aagtgaaaca tgcggttaaa atagtttata  26640
acattaatat tactgttaat aactgccgga taaaagtggg atagtaattt cacgaatttg  26700
atactgtcct ttctctcgtt aaacgccttt aaaaaaactt tagaagaata tctcaatgag  26760
agttcctgac catccatagt ttgtatcaat aatagcaaca tatgaagaac acgtttatac  26820
agagtatgta aaaatgttaa tttatagttt aatcccatgg cccacgcaca cacgattaat  26880
tttttttcat ctccctttag attgttgtat agaaatttgg gtactgtgaa ctccgccgta  26940
gtttccatgg gactatataa ttttgtggcc tcgaatacaa attttactac atagttatct  27000
atcttaaaga ctataccata tcctcctgta gatatgtgat aaaaatcgtc gtttatagga  27060
taaaatcgtt tatccttttg ttggaaaaag gatgaattaa tgtaatcatt ctcttctatc  27120
tttagtagtg tttccttatt aaaattctta aaataattta acaatctaac tgacggagcc  27180
caattttggt gtaaatctaa ttgggacatt atattgttaa aatacaaaca gtctcctaat  27240
ataacagtat ctgataatct atggggagac atccattgat attcagggga tgaatcattg  27300
gcaacaccca tttattgtac aaaaagcccc aatttacaaa cgaaagtcca ggtttgatag  27360
agacaaacaa ttaactattt tgtctctgtt tttaacacct ccacagtttt taatttcttt  27420
agtaatgaaa ttattcacaa tatcagtatc ttctttatct accagagatt ttactaactt  27480
gataaccttg gctgtctcat tcaatagggt agtaatattt gtatgtgtga tattgatatc  27540
tttttgaatt gtttctttta gaagtgattc tttgatggtg ccagcatacg aattacaata  27600
atgcagaaac tcggttaaca tgcaggaatt atagtaagcc aattccaatt gttgcctgtg  27660
ttgtattaga gtgtcaatat gagcaatggt gtccttgcgt ttctctgata gaatgcgagc  27720
agcgattttg gcgttatcat ttgacgatat ttctggaatg acgaatcctg tttctactaa  27780
ctttttggta ggacaaagtg aaacaatcaa gaagatagct tctcctccta tttgtggaag  27840
aaattgaact cctctagatg atctactgac gatagtatct ccttgacaga tattggaccg  27900
aattacagaa gtacctggaa tgtaaagccc tgaaaccccc tcattttta agcagattgt  27960
tgccgtaaat cctgcactat gcccaagata gagagctcct ttggtgaatc catctctatg  28020
tttcagttta accaagaaac agtcagctgg tctaaaattt ccatctctat ctaatacagc  28080
atctaacttg atgtcaggaa ctatgaccgg tttaatgtta tatgtaacat tgagtaaatc  28140
cttaagttca taatcatcac tgtcatcagt tatgtacgat ccaaacaatg tttctaccgg  28200
catagtggat acgaagatgc tatccatcag aatgtttccc tgattagtat tttctatata  28260
gctattcttc tttaaacgat tttccaaatc agtaactatg ttcatttttt taggagtagg  28320
acgcctagcc agtatggaag aggattttct agatcctctc ttcaacatct ttgatctcga  28380
tggaatgcaa aaccccatag tgaaacaacc aacgataaaa ataatattgt ttttcacttt  28440
ttataatttt accatctgac tcatggattc attaatatct ttataagagc tactaacgta  28500
taattcttta taactgaact gagatatata caccggatct atggtttcca taattgagta  28560
aatgaatgct cggcaataac taatggcaaa tgtatagaac aacgaaatta tactagagtt  28620
gttaaagtta atattttcta tgagctgttc caataaatta tttgttgtga ctgcgttcaa  28680
gtcataaatc atcttgatac tatccagtaa accgttttta agttctggaa tattatcatc  28740
```

```
ccattgtaaa gcccctaatt cgactatcga atatcctgct ctgatagcag tttcaatatc  28800
gacggacgtc aatactgtaa taaaggtggt agtattgtca tcatcgtgat aaactacggg  28860
aatatggtcg ttagtaggta cggtaacttt acacaacgcg atatataact ttccttttgt  28920
accattttta acgtagttgg gacgtcctgc agggtattgt tttgaagaaa tgatatcgag  28980
aacagatttg atacgatatt tgttggattc ctgattattc actataatat aatctagaca  29040
gatagatgat tcgataaata gagaaggtat atcgttggta ggataataca tccccattcc  29100
agtattctcg gatactctat tgatgacact agttaagaac atgtcttcta ttctagaaaa  29160
cgaaaacatc ctacatggac tcattaaaac ttctaacgct cctgattgtg tctcgaatgc  29220
ctcgtacaag gatttcaagg atgccataga ttctttgacc aacgatttag aattgcgttt  29280
agcatctgat tttttatta aatcgaatgg tcggctctct ggtttgctac cccaatgata  29340
acaatagtct tgtaaagata aaccgcaaga aaatttatac gcatccatcc aaataaccct  29400
agcaccatcg gatgatatta atgtattatt atagattttc catccacaat tattgggcca  29460
gtatactgtt agcaacggta tatcgaatag attactcatg taacctacta gaatgatagt  29520
tcgtgtacta gtcataatat ctttaatcca atctaaaaaa tttaaaatta gatttttttac  29580
actgttaaag ttaacaaaag tattacccgg gtacgtggat atcatatatg gcattggtcc  29640
attatcagta atagctccat aaactgatac ggcgatggtt tttatatgtg tttgatctaa  29700
cgaggaagaa attcgcgccc acaattcatc tctagatatg tatttaatat caaacggtaa  29760
cacatcaatt tcgggacgcg tatatgtttc taaattttta atccaaatat aatgatgacc  29820
tatatgccct attatcatac tgtcaactat agtacaccta gggaacttac gatacatctg  29880
tttcctataa tcgttaaatt ttacaaatct ataacatgct aaaccttttg acgacagcca  29940
ttcattaatt tctgatatgg aatctgtatt ctcgataccg tatcgttcta aagccagtgc  30000
tatatctccc tgttcgtggg aacgctttcg tataaatatcg atcaacggat aatctgaagt  30060
ttttggagaa taatatgact catgatctat ttcgtccata aacaatctag acataggaat  30120
tggaggcgat gatcttaatt ttgtgcaatg agtcgtcaat cctataactt ctaatcttgt  30180
aatattcatc atcgacataa tactatctat gttatcatcg tatattagta taccatgacc  30240
ttcttcattt cgtgccaaaa tgatatacag tcttaaatag ttacgcaata tctcaatagt  30300
ttcataattg ttagctgttt tcatcaaggt ttgtatcctg tttaacatga tggcgttcta  30360
taacgtctct attttctatt tttaattttt taaattttta acgatttact gtggctagat  30420
acccaatctc tctcaaatat ttttttagcc tcgcttacaa gctgtttatc tatactatta  30480
aaactgacga atccgtgatt ttggtaatgg gttccgtcga aatttgccga agtgatatga  30540
acatattcgt cgtcgactat caacaatttt gtattattct gaatagtgaa aaccttcaca  30600
gatagatcat tttgaacaca caacgcatct agacttttgg cggttgccat agaatatacg  30660
tcgttcttat cccaattacc aactagaagt ctgatcttaa ctcctctatt aatggctgct  30720
tctataatgg agttgtaaat gtcgggccaa tagtagctat taccgtcgac acgtgtagtg  30780
ggaactatgg ccaaatgttc aatatctata ctagtcttag ctgacctgag tttatcaata  30840
actacatcgg tatctagatc tctagaatat cccaataggt gttccggaga atcagtaaag  30900
aacactccac ctataggatt cttaatatga tacgcagtgc taactggcaa acaacaagcc  30960
gcagagcata aattcaacca tgaatttttt gcgctattaa aggctttaaa agtatcaaat  31020
cttctacgaa gatctgtggc cagcgggggga taatcagaat atacacctaa cgttttaatc  31080
```

```
gtatgtatag atcctccagt aaatgacgcg tttcctacat aacatctttc atcatctgac  31140
acccaaaaac aaccgagtag tagtcccaca ttattttttt tatctatatt aacggttata  31200
aaatttatat ccgggcagtg actttgtagc tctcccagat ttcttttccc tcgttcatct  31260
agcaaaacta ttattttaat cccttttttca gatgcctctt ttagtttatc aaaaataagc  31320
gctcccctag tcgtactcag aggattacaa caaaaagatg ctatgtatat atatttctta  31380
gctagagtga taatttcgtt aaaacattca aatgttgtta aatgatcgga tctaaaatcc  31440
atattttctg gtagtgtttc taccagccta cattttgctc ccgcaggtac cgatgcaaat  31500
ggccacattt agttaacata aaaacttata catcctgttc tatcaacgat tctagaatat  31560
catcggctat atcgctaaaa ttttcatcaa agtcgacatc acaacctaac tcagtcaata  31620
tattaagaag ttccatgatg tcatcttcgt ctatttctat atccgtatcc attgtagatt  31680
gttgaccgat tatcgagttt aaatcattac taatactcaa tccttcagaa tacaatctgt  31740
gtttcattgt aaatttatag gcggtgtatt taagttggta gattttcaat tatgtattaa  31800
tatagcaaca gtagttcttg ctcctccttg attctagcat cctcttcatt attttcttct  31860
acgtacataa acatgtccaa tacgttagac aacacaccga cgatggcggc cgctacagac  31920
acgaatatga ctaaaccgat gaccatttaa aaacccctct ctagctttca cttaaactgt  31980
atcgatcatt cttttagcac atgtataata taaaaacatt attctatttc gaatttaggc  32040
ttccaaaaat ttttcatccg taaaccgata ataatatata tagacttgtt aatagtcgga  32100
ataaatagat taatgcttaa actatcatca tctccacgat tagagataca atatttacat  32160
tctttttgct gtttcgaaac tttatcaata cacgttaata caaacccagg aaggagatat  32220
tgaaactgag gctgttgaaa atgaaacggt gaatacaata attcagataa tgtaaaatca  32280
tgattccgta ttctgatgat attagaactg ctaatggatg tcgatggtat gtatctagga  32340
gtatctattt taacaaagca tcgatttgct aatatacaat tatccttttg attaattgtt  32400
attttattca tattcttaaa aggtttcata tttatcaatt cttctacatt aaaaatttcc  32460
atttttaatt tatgtagccc cgcaatactc ctcattacgt ttcatttttt gtctataata  32520
tccattttgt tcatctcggt acatagatta tccaattgag aagcgcattt agtagttttg  32580
tacattttaa gtttattgac gaatcgtcga aaactagtta tagttaacat tttattattt  32640
gataccctga tattaatacc cctgccgtta ctattattta taactgatgt aatccacgta  32700
acattggaat taactatcga tagtaatgca tcgacgcttc caaaattgtc tattataaac  32760
tcaccgataa ttttttttatt gcatgttttc atattcatta ggattatcaa atctttaatc  32820
ttattacgat tgtatgcgtt gatattacaa gacgtcattc taaaagacgg aggatctcca  32880
tcaaatgcca gacaatcacg tacaaagtac atggaaatag gttttgttct attgcgcatc  32940
atagatttat atagaacacc cgtagaaata ctaatttgtt ttactctata aaatactaat  33000
gcatctattt catcgttttg tataacgtct ttccaagtgt caaattccaa attttttttca  33060
ttgatagtac caaattcttc tatctcttta actacttgca tagataggta attacagtga  33120
tgcctacatg ccgttttttg aaactgaata gatgcgtcta gaagcgatgc tacgctagtc  33180
acaatcacca ctttcatatt tagaatatat atatgtaaaa atatagtaga atttcatttt  33240
gtttttttct atgctataaa tgaattctca ttttgcatct gctcatactc cgttttatat  33300
taataccaaa gaaggaagat atctggttct aaaagccgtt aaagtatgcg atgttagaac  33360
tgtagaatgc gaaggaagta aagcttcctg cgtactcaaa gtagataaac cctcatcgcc  33420
cgcgtgtgag agaagacctt cgtccccgtc cagatgcgag agaatgaata accctggaaa  33480
```

```
acaagttccg tttatgagga cggacatgct acaaaatatg ttcgcggcta atcgcgataa  33540
tgtagcttct agacttttgt cctaaaatac tattatatcc ttttcgatat taataaatcc  33600
gtgtcgtcca ggttttttat ctctttcagt atgtgaatag ataggtattt tatctctatt  33660
catcatcgaa tttaagagat ccgataaaca ttgtttgtat tctccagatg tcagcatctg  33720
atacaacaat atatgtgcac ataaacctct ggcacttatt tcatgtacct tccccttatc  33780
actaaggaga atagtatttg agaaatatgt atacatgata ttatcatgaa ttagatatac  33840
agaatttgta acactctcga aatcacacga tgtgtcggcg ttaagatcta atatatcact  33900
cgataacaca ttttcatcta gatacactag acattttta aagctaaaat agtctttagt  33960
agtaacagta actatgcgat tattttcatc gatgatacat ttcatcggca tattattacg  34020
cttaccatca aagactatac catgtgtata tctaacgtat tctagcatgg ttgccatacg  34080
cgcattaaac ttttcaggat ctttggatag atcttccaat ctatctattt gagaaaacat  34140
ttttatcatg ttcaatagtt gaaacgtcgg atccactata tagatattat ctataaagat  34200
tttaggaact acgttcatgg tatcctggcg aatattaaaa ctatcaatga tatgattatc  34260
gttttcatct tttatcacca tatagtttct aagatatggg attttactta atataatatt  34320
atttcccgtg ataaatttta ttagaaaggc caaatctata agaaaagtcc tagaattagt  34380
ctgaagaata tctatatcgc cgtatagtat atttggatta attagatata gagaatatga  34440
tccgtaacat atacaacttt tattatggcg tctaagatat tcttccatca acttattaac  34500
atttttgact agggaagata cattatgacg tcccattact tttgccttgt ctattactgc  34560
gacgttcata gaatttagca tatctcttgc caattcttcc attgatgtta cattataaga  34620
aattttagat gaaattacat ttggagcttt aatagtaaga actcctaata tgtccgtgta  34680
tgtggtcact aatacagatt gtagttctat aatcgtaaat aatttaccta tattatatgt  34740
ttgagtctgt ttagaaaagt agctaagtat acgatctttt atttctgatg cagatgtatt  34800
aacatcggaa aaaaatcttt ttttattctt ttttactaaa gatacaaata tgtctttgtt  34860
aaaaacagtt attttctgaa tatttctagc ttgtaatttt aacatatgat attcgttcac  34920
actaggtact ctgcctaaat aggtttctat aatctttaat gtaatattag gaaaagtatt  34980
ctgatcagga ttcctattca ttttgaggat ttaaaactct gattattgtc taatatggtc  35040
tctacgcaaa ctttttcaca gagcgataga gtttttgata actcgttttt cttaagaaat  35100
ataaaactac tgtctccaga gctcgctcta tcttttattt tatctaattc gatacaaact  35160
cctgatactg gttcagaaag taattcatta attttcagtc ctttatagaa gatatttaat  35220
atagataata caaaatcttc agtttttgat atcgatctga ttgatcctag aactagatat  35280
attaataacg tgctcattag gcagtttatg gcagcttgat aattagatat agtatattcc  35340
agttcatatt tattagatac cgcattgccc agattttgat attctatgaa ttcctctgaa  35400
aataaatcca aaataactag acattctatt ttttgtggat tagtgtactc tcttccctct  35460
atcatgttca ctactggtgt ccacgatgat aaatatctag agggaatata atatagtcca  35520
taggatgcca atctagcaat gtcgaataac tgtaatttta ttcttcgctc ttcattatga  35580
attgattctt gaggtataaa cctaacacaa attatattat tagacttttc gtatgtaatg  35640
tctttcatgt tataagtttt taatcctgga atagaatcta ttttaatgag gcttttaaac  35700
gcagagttct ccaacgagtc aaagcataat actctgttgt ttttcttata tacgatgtta  35760
cgattttctt ctttgaatgg aataggtttt tgaattagtt tataattaca acataataga  35820
```

```
taaggaagtg tgcaaatagt acgcggaaaa aacataatag ctcccctgtt ttcatccatg  35880
gttttaagta aatgatcact ggcttcttta gtcaatggat attcgaacat taaccgtttc  35940
atcatcattg gacagaatcc atatttctta atgtaaagag tgatcaaatc attgtgttta  36000
ttgtaccatc ttgttgtaaa tgtgtattcg gttatcggat ctgctccttt ttctattaaa  36060
gtatcgatgt caatctcgtc taagaattca actatatcga catatttcat ttgtatacac  36120
ataaccatta ctaacgtaga atgtatagga agagatgtaa cgggaacagg gtttgttgat  36180
tcgcaaacta ttctaataca taattcttct gttaatacgt cttgcacgta atctattata  36240
gatgccaaga tatctatata attattttgt aagatgatgt taactatgtg atctatataa  36300
gtagtgtaat aattcatgta ttttgatata tgttccaact ctgtctttgt gatgtctagt  36360
ttcgtaatat ctatagcatc ctcaaaaaat atattcgcat atattcccaa gtcttcagtt  36420
ctatcttcta aaaaatcttc aacgtatgga atataataat ctattttacc tcttctgata  36480
tcattaatga tatagttttt gacactatct tctgtcaatt gattcttatt cactatatct  36540
aagaaacgga tagcgtccct aggacgaact actgccatta atatctctat tatagcttct  36600
ggacataatt catctattat accagaatta atgggaacta ttccgtatct atctaacata  36660
gttttaagaa agtcagaatc taagacttga tgttcatata ttggttcata catgaaatga  36720
tctctattga tgatagtgac tatttcattc tctgaaaatt ggtaactcat tctatatatg  36780
ctttccttgt tgatgaagga tagaatatac tcaatagaat ttgtaccaac aaactgttct  36840
cttatgaatc gtatatcatc atctgaaata atcatgtaag gcatacattt aacaattaga  36900
gacttgtctc ctgttatcaa tatactattc ttgtgataat ttatgtgtga ggcaaatttg  36960
tccacgttct ttaattttgt tatagtagat atcaaatcca atggagctac agttcttggc  37020
ttaaacagat atagtttttc tggaacaaat tctacaacat tattataaag gactttgggt  37080
aaataagtgg gatgaaatcc tattttaatt aatgcgatag ccttgtcctc gtgcagatat  37140
ccaaacgctt ttgtgatagt atggcattca ttgtctagaa acgctctacg aatatctgtg  37200
acagatatca tctttagaga atatactagt cgcgttaata gtactacaat ttgtattttt  37260
taatctatct caataaaaaa attaatatgt atgattcaat gtataactaa actactaact  37320
gttattgata actagaatca gaatctaatg atgacgtacc caagaagttt atctactgcc  37380
aatttagctg cattattttt agcatctcgt ttagattttc catctgcctt atcgaatact  37440
cttccgtcga tatctacaca ggcataaaat gtaggagagt tactaggccc aactgattca  37500
atacgaaaag accaatctct cttagttatt tggcagtact cattaataac ggtgacaggg  37560
ttagcatctt tccaatcaat aattttttta gccggaataa catcatcaaa agacttatga  37620
tcctctctca ttgatttttc gcgggataca tcatctatta tgacgtcagc cataacatca  37680
gcatccggct tatccgcctc cgttgtcata aaccaacgag gaggaatatc gtcggagctg  37740
tacaccatag cactacgttg aagatcgtac agagctttat taacttctcg cttctccata  37800
ttaagttgtc tagttagttg tgcagcagta gctccttcga ttccaatggt tttaatagcc  37860
tcacacacaa tctctgcgtt agaacgttcg tcgatataga ttttagacat ttttagagag  37920
aactaacaca accagcaata aaactgaacc tactttatca ttttttttatt catcatcctc  37980
tggtggttcg tcgttcctat caaatgtagc tctgattaac ccgtcatcta taggtgatgc  38040
tggttctgga gattctggag gagatggatt attatctgga agaatctctg ttatttcctt  38100
gttttcatgt atcgattgcg ttgtaacatt aagattgcga aatgctctaa atttgggagg  38160
cttaaagtgt tgtttgcaat ctctacacgc gtgtctaact agtggaggtt cgtcagctgc  38220
```

```
tctagtttga atcatcatcg gcgtagtatt cctactttta cagttaggac acggtgtatt  38280
gtatttctcg tcgagaacgt taaaataatc gttgtaactc acatccttta ttttatctat  38340
attgtattct actcctttct taatgcattt tataccgaat aagagatagc gaaggaattc  38400
tttttcggtg ccgctagtac ccttaatcat atcacatagt gttttatatt ccaaatttgt  38460
ggcaatagac ggtttatttc tatacgatag tttgtttctg gaatcctttg agtattctat  38520
accaatatta ttctttgatt cgaatttagt ttcttcgata ttagattttg tattacctat  38580
attcttgatg tagtactttg atgatttttc catggcccat tctattaagt cttccaagtt  38640
ggcatcatcc acatattgtg atagtaattc tcggatatca gtagcggcta ccgccattga  38700
tgtttgttca ttggatgagt aactactaat gtatacattt tccatttata acacttatgt  38760
attaactttg ttcatttata ttttttcatt attatgttga tattaacaaa agtgaatata  38820
tatatatgtt aataattgta ttgtggttat acggctacaa ttttataatg agtgaaagtc  38880
agtgtccgat gatcaatgac gatagcttta ctctgaaaag aaagtatcaa atcgatagtg  38940
cggagtcaac aataaaaatg gataagaaga ggataaagtt tcagaataga gccaaaatgg  39000
taaaagaaat aaatcagaca ataagagcag cacaaactca ttacgagaca ttgaaactag  39060
gatacataaa atttaagaga atgattagga ctactactct agaagatata gcaccatcta  39120
ttccaaataa tcagaaaact tataaactat tctcggacat ttcagccatc ggcaaagcat  39180
cacagaatcc gagtaagatg gtatatgctc tgctgcttta catgtttccc aatttgtttg  39240
gagatgatca tagattcatt cgttatagaa tgcatccaat gagtaaaatc aaacacaaga  39300
tcttctctcc tttcaaactt aatcttatta gaatattagt ggaagaaaga ttctataata  39360
atgaatgcag atctaataaa tggaaaataa ttggaacaca agttgataaa atgttgatag  39420
ctgaatctga taaatataca atagatgcaa ggtataacct aaaacccatg tatagaatca  39480
agggagaatc tgaagaagat accctcttca tcaaacagat ggtagaacaa tgtgtgacat  39540
cccaggaatt ggtggaaaaa gtgttgaaga tactgtttag agatttgttc aagagtggag  39600
aatacaaagc gtacagatac gatgatgatg tagaaaatgg atttattgga ttggatacac  39660
taaaattaaa cattgttcat gatatagttg aaccatgtat gcctgttcgt aggccagtgg  39720
ctaagatact gtgtaaagaa atggtaaata aatactttga gaatccgcta catattattg  39780
gtaagaatct tcaagagtgc attgactttg ttagtgaata ggcatttcat ctttctccaa  39840
tactaattca aattgttaaa ttaataatgg atagtataaa tagtaaaaat aattattaga  39900
ataagagtgt agtatcatag ataactctct tctataaaaa tggattttat tcgtagaaag  39960
tatcttatat acacagtaga aaataatata gattttttaa aggatgatac attaagtaaa  40020
gtaaacaatt ttaccctcaa tcatgtacta gctctcaagt atctagttag caattttcct  40080
caacacgtta ttactaagga tgtattagct aataccaatt tttttgtttt catacatatg  40140
gtacgatgtt gtaaagtgta cgaagcggtt ttacgacacg catttgatgc acccacgttg  40200
tacgttaaag cattgactaa gaattattta tcgtttagta acgcaataca atcgtacaag  40260
gaaaccgtgc ataaactaac acaagatgaa aaatttttag aggttgccga atacatggac  40320
gaattaggag aacttatagg cgtaaattat gacttagttc ttaatccatt atttcacgga  40380
ggggaaccca tcaaagatat ggaaatcatt tttttaaaac tgtttaagaa aacagacttc  40440
aaagttgtta aaaaattaag tgttataaga ttacttattt gggcatacct aagcaagaaa  40500
gatacaggca tagagtttgc ggataatgat agacaagata tatatactct atttcaacaa  40560
```

```
actggtagaa tcgtccatag caatctaaca gaaacgttta gagattatat ctttcccgga  40620
gataagacta gctattgggt gtggttaaac gaaagtatag ctaatgatgc ggatatcgtt  40680
cttaatagac ccgccattac catgtatgat aaaattctta gttatatata ctctgagata  40740
aaacaaggac gcgttaataa aaacatgctt aagttagttt atatctttga gcctgaaaaa  40800
gatatcagag aacttctgct agaaatcata tatgatattc ctggagatat cctatctatt  40860
attgatgcaa aaaacgacga ttggaaaaaa tattttatta gtttttataa agctaatttt  40920
attaacggta atacatttat tagtgataga acgtttaacg aggacttatt cagagttgtt  40980
gttcaaatag atcccgaata tttcgataat gaacgaatta tgtctttatt ctctacgagt  41040
gctgcggaca ttaaacgatt tgatgagtta gatattaata acagttatat atctaatata  41100
atttatgagg tgaacgatat cacattagat acaatggatg atatgaagaa gtgtcaaatc  41160
tttaacgagg atacgtcgta ttatgttaag gaatacaata catacctgtt tttgcacgag  41220
tcggatccca tggtcataga gaacggaata ctaaagaaac tgtcatctat aaaatccaag  41280
agtagacggc tgaacttgtt tagcaaaaac attttaaaat attatttaga cggacaattg  41340
gctcgtctag gtcttgtgtt agatgattat aaaggagact tgttagttaa aatgataaac  41400
catcttaagt ctgtggagga tgtatccgca ttcgttcgat tttctacaga taaaaaccct  41460
agtattcttc catcgctaat caaaactatt ttagctagtt ataatatttc catcatcgtc  41520
ttatttcaaa ggtttttgag agataatcta tatcatgtag aagaattctt ggataaaagc  41580
atccatctaa ccaagacgga taagaaatat atacttcaat tgataagaca cggtagatca  41640
tagaacagac caaatatatt attaataatt tgtatataca tagatataat tatcacacat  41700
ttttgataaa tgggaactgc tgcaacaatt cagactccca ccaaattaat gaataaagaa  41760
aatgcagaaa tgattttgga aaaaattgtt gatcatatag ttatgtatat tagtgacgaa  41820
tcaagtgatt cagaaaataa tcctgaatat attgattttc gtaacagata cgaagactat  41880
agatctctca ttataaaaag tgatcacgag tttgtaaagc tatgtaaaaa tcatgcggag  41940
aaaagttctc cagaaacgca acaaatgatt atcaaacaca tatacgaaca atatcttatt  42000
ccagtatctg aagtactatt aaaacctata atgtccatgg gtgacataat tacatataac  42060
ggatgtaaag acaatgaatg gatgctagaa caactctcta ccctaaactt taacaatctc  42120
cgcacatgga actcatgtag cataggcaat gtaacgcgtc tgttttatac attttttagt  42180
tatctgatga aagataaact aaatatataa gtataatccc attctaatac tttaacctga  42240
tgtattagca tcttattaga atattaacct aactaaaaga cataacataa aaactcatta  42300
catagttgat aaaaagcggt aggatataaa tattatggct gccaccgttc cgcgttttga  42360
cgacgtgtac aaaaatgcac aaagaagaat tctagatcaa gaaacatttt ttagtagagg  42420
tctaagtaga ccgttaatga aaaacacata tctatttgat aattacgcgt atggatggat  42480
accagaaact gcaatttgga gtagtagata cgcaaactta gatgcaagtg actattatcc  42540
catttcgttg ggattactta aaaagttcga gtttctcatg tctctatata aaggtcctat  42600
tccagtatac gaagaaaaag taaatactga attcattgct aatggatctt tctccggtag  42660
atacgtatca tatcttagaa agttttctgc tcttccaaca aacgagttta ttagtttttt  42720
gttactgact tccattccaa tctataatat cttgttctgg tttaaaaata ctcagtttga  42780
tattactaaa cacacattat tcagatacgt ctatacagat aatgccaaac acctggcgtt  42840
ggctaggtat atgtatcaaa caggagacta taagcctttg tttagtcgtc tcaaagagaa  42900
ttatatattt accggtcccg ttccaatatg tatcaaagat atagatcacc ctaatcttag  42960
```

```
tagagcaaga agtccatccg attatgagac attagctaat attagtacta tattgtactt  43020
taccaagtat gatccggtat taatgttttt attgttttac gtacctgggt attcaattac  43080
tacaaaaatt actccagccg tagaatatct aatggataaa ctgaatctaa caaagagcga  43140
cgtacaactg ttgtaaatta ttttatgctt cgtaaaatgt aggttttgaa ccaaacattc  43200
tttcaaagaa tgagatgcat aaaactttat tatccaatag attgactatt tcggacgtca  43260
atcgtttaaa gtaaacttcg taaaatattc tttgatcact gccgagttta aaacttctat  43320
cgataattgt ttcatatgtt ttaatattta caagtttttt ggtccatggt ccattaggac  43380
aaatatatgc aaaataatat cgttctccaa gttctatagt ctctggatta tttttattat  43440
attcagtaac caaatacata ttagggttat ctgcggattt ataatttgag tgatgcattc  43500
gactcaacat aaataattct agaggagacg atctactatc aaattcggat cgtaaatctg  43560
tttctaaaga acggagaata tctatacata cctgattaga attcatccgt ccttcagaca  43620
acatctcaga cagtctggtt ttgtacatct taatcatatt cttatgaaac ttggaaacat  43680
ctcttctagt ttcactagta cctttattaa ttctctcagg tacagatttt gaattcgacg  43740
atgctgagta tttcatcgtt gtatatttct tcttcgattg cataatcaga ttcttatata  43800
ccgcctcaaa ctctatttta aaattattaa acaatactct attattaatc agtcgttcta  43860
actctttcgc tatttctata gacttatcta catcttgact gtctatctct gtaaacacgg  43920
agtcggtatc tccatacacg ctacgaaaac gaaatctgta atctataggc aacgatgttt  43980
tcacaatcgg attaatatct ctatcgtcca tataaaatgg attacttaat ggattggcaa  44040
accgtaacat accgttagat aactctgctc catttagtac cgattctaga tacaagatca  44100
ttctacgtcc tatggatgtg caactcttag ccgaagcgta tgagtataga gcactatttc  44160
taaatcccat cagaccatat actgagttgg ctactatctt gtacgtatat tgcatggaat  44220
catagatggc cttttcagtt gaactggtag cctgttttag catcttttta tatctggctc  44280
tctctgccaa aaatgttctt aatagtctag gaatggttcc ttctatcgat ctatcgaaaa  44340
ttgctatttc agagatgagg ttcggtagtc taggttcaca atgaaccgta atatatctag  44400
gaggtggata tttctgaagc aatagctgat tatttatttc ttcttccaat ctattggtac  44460
taacaacgac accgactaat gtttccggag atagatttcc aaagatacac acattaggat  44520
acagactgtt ataatcaaag attaatacat tattactaaa catttttgt tttggagcaa  44580
ataccttacc gccttcataa ggaaactttt gttttgtttc tgatctaact aagatagttt  44640
tagtttccaa caatagcttt aacagtggac ccttgatgac tgtactcgct ctatattcga  44700
ataccatgga ttgaggaagc acatatgttg acgcacccgc gtctgttttt gtttctactc  44760
cataatactc ccacaaatac tgacacaaac aagcatcatg aatacagtat ctagccatat  44820
ctaaagctat gtttagatta taatccttat acatctgagc taaatcaacg tcatcctttc  44880
cgaaagataa tttatatgta tcattaggta aagtaggaca taatagtacg actttaaatc  44940
cattttccca aatatcttta cgaattactt tacatataat atcctcatca acagtcacat  45000
aattacctgt ggttaaaacc tttgcaaatg cagcggcttt gcctttcgcg tctgtagtat  45060
cgtcaccgat gaacgtcatt tctctaactc ctctatttaa tactttaccc atgcaactga  45120
acgcgttctt ggatatagaa tccaatttgt acgaatccaa tttttcaaat ttttgaatga  45180
atgaatatag atcgaaaaat atagttccat tattgttatt aacgtgaaac gtagtattgg  45240
ccatgccgcc tactccctta tgactagact gatttctctc ataaatacag agatgtacag  45300
```

```
cttccttttt gtccggagat ctaaagataa ttttctctcc tgttaataac tctagacgat  45360
tagtaatata tctcagatca aagttatgtc cgttaaaggt aacgacgtag tcgaacgtta  45420
gttccaacaa ttgtttagct attcgtaaca aaactatttc agaacataga actagttctc  45480
gttcgtaatc catttccatt agtgactgta tcctcaaaca tcctctatcg acggcttctt  45540
gtatttcctg ttccgttaac atctcttcat taatgagcgt aaacaataat cgtttaccac  45600
ttaaatcgat ataacagtaa cttgtatgcg agattgggtt aataaataca gaaggaaact  45660
tcttatcgaa gtgacactct atatctagaa ataagtacga tcttgggata tcgaatctag  45720
gtattttttt agcgaaacag ttacgtggat cgtcacaatg ataacatcca ttgttaatct  45780
ttgtcaaata ttgctcgtcc aacgagtaac atccgtctgg agatatcccg ttagaaatat  45840
aaaaccaact aatattgaga aattcatcca tggtggcatt ttgtatgctg cgtttctttg  45900
gctcttctat caaccacata tctgcgacgg agcattttct atctttaata tctagattat  45960
aacttattgt ctcgtcaatg tctatagttc tcatctttcc caacggcctc gcattaaatg  46020
gaggaggaga caatgactga tatatttcgt ccgtcactac gtaataaaag taatgaggaa  46080
atcgtataaa tacggtctca ccatttcgac atctggattt cagatataaa aatctgtttt  46140
caccgtgact ttcaaaccaa ttaatgcacc gaacatccat ttatagaatt tagaaatata  46200
ttttcattta aatgaatccc aaacattggg gaagagccgt atggaccatt atttttatag  46260
tactttcgca agcgggttta gacggcaaca tagaagcgtg taaacgaaaa ctatatacta  46320
tagttagcac tcttccatgt cctgcatgta gacggcacgc gactatcgct atagaggaca  46380
ataatgtcat gtctagcgat gatctgaatt atatttatta ttttttcatc agattattta  46440
acaatttggc atctgatccc aaatacgcga tcgatgtgac aaaggttaac cctttataaa  46500
cttaacccat tataaaactt atgattagtc acaactgaaa taaccgcgtg attatttttt  46560
ggtataattc tacacggcat ggtttctgtg actatgaatt caaccccccgt tacattagtg  46620
aaatctttaa caaacagcaa gggttcgtca aagacataaa actcattgtt tacaatcgaa  46680
atagaccccc tatcacactt aaaataaaaa atatccttat cctttaccac caaataaaat  46740
tctgattggt caatgtgaat gtattcactt aacagttcca caaatttatt tattaactcc  46800
gaggcacata catcgtcggt attttttatg gcaaacttta ctcttccagc atccgtttct  46860
aaaaaaatat taacgagttc catttatatc atccaatatt attgaaatga cgttgatgga  46920
cagatgatac aaataagaag gtacggtacc tttgtccacc atctcctcca attcatgctc  46980
tattttgtca ttaactttaa tgtatgaaaa cagtacgcca catgcttcca tgacagtgtg  47040
taacactttg gatacaaaat gtttgacatt agtataattg ttcaagactg tcaatctata  47100
atagatagta gctataatat attctatgat ggtattgaag aagatgacaa ccttggcata  47160
ttgatcattt aacacagaca tggtatcaac agatagcttg aatgaaagag aatcagtaat  47220
tggaataagc gtcttctcga tagagtgtcc gtataccaac atgtctgata ttttgatgta  47280
ttccattaaa ttatttagtt ttttcttttt attctcgtta aacagcattt ctgtcaacgg  47340
accccaacat cgttgaccga ttaagttttg attgattttt ccgtgtaagg cgtatctagt  47400
cagatcgtat agcctatcca ataatccatc atctgtgcgt agatcacatc gtacactttt  47460
taattctcta tagaagagcg acagacatct ggagcaatta cagacagcaa tttctttatt  47520
ctctacagat gtaagatact tgaagacatt cctatgatga tgcagaattt tggataacac  47580
ggtattgatg gtatctgtta ccataattcc tttgatggct gatagtgtca gagcacaaga  47640
tttccaatct ttgacaattt ttagcaccat tatctttgtt ttgatatcta tatcagacag  47700
```

```
catggtgcgt ctgacaacac agggattaag acggaaagat gaaatgattc tctcaacatc  47760
ttcaatagat accttgctat tttttctggc attatctata tgtgcgagaa tatcctctag  47820
agaatcagta tcctttttga tgatagtgga tctcaatgac atgggacgtt taaaccttct  47880
tattctatca ccagattgca tggtgatttg tcttctttct tttatcataa tgtaatctct  47940
aaattcatcg gcaaattgtc tatatctaaa atcataatat gagatgttta cctctacaaa  48000
tatctgttcg tccaatgtta gagtatttac atcagttttg tattccaaat taaacatggc  48060
aacggattta attttatatt cctctattaa gtcctcgtcg ataataacag aatgtagata  48120
atcatttaat ccatcgtaca tggttggaag atgcttgttg acaaaatctt taattgtctt  48180
gatgaaggtg ggactatatc taacatcttg attaataaaa tttataacat tgtccatagg  48240
atactttgta actagtttta tacacatctc ttcatcggta agtttagaca gaatatcgtg  48300
aacaggtggt atattatatt catcagatat acgaagaaca atgtccaaat ctatattgtt  48360
taatatatta tatagatgta gcgtagctcc tacaggaata tctttaacta agtcaatgat  48420
ttcatcaacc gttagatcta ttttaaagtt aatcatatag gcattgattt ttaaaaggta  48480
tgtagccttg actacattct cattaattaa ccattccaag tcactgtgtg taagaagatt  48540
atattctatc ataagcttga ctacatttgg tcccgatacc attaaagaat tcttatgata  48600
taaggaaaca gcttttaggt actcatctac tctacaagaa ttttggagag ccttaacgat  48660
atcagtgacg tttattattt caggaggaaa aaacctaaca ttgagaatat cggaattaat  48720
agcttccaga tacagtgatt ttggcaatag tccgtgtaat ccataatcca gtaacacgag  48780
ctggtgcttg ctagacacct tttcaatgtt taattttttt gaaataagct ttgataaagc  48840
cttcctcgca aattccggat acatgaacat gtcggcgaca tgattaagta ttgttttttc  48900
attattttct caataccccca atagatgata gaatatcacc caatgcgtcc atgttgtcta  48960
tttccaacag gtcgctatat ccaccaatag aagtttttcc aaaaaagatt ctaggaacag  49020
ttctaccacc agtaatttgt tcaaaatagt cacgcaattc attttcgggt ttaaattctt  49080
taatatcgac aatttcatac gctcctcttt tgaaactaaa cttatttaga atatccagtg  49140
catttctaca aaaaggacat gtatacttga caaaaattgt cactttgtta ttggccaacc  49200
tttgttgtac aaattcctcg gccattttaa tatttaagtg atataaaact atctcgactt  49260
atttaactct ttagtcgaga tatatggacg cagatagcta tatgatagcc aactacagaa  49320
ggcaaacgct ataaaaaaca taattacgac gagcatattt ataaatattt ttattcagca  49380
ttacttgata tagtaatatt aggcacagtc aaacattcaa ccactctcga tacattaact  49440
ctctcatttt ctttaacaaa ttctgcaata tcttcgtaaa aagattcttg aaacttttta  49500
gaatatctat cgactctaga tgaaatagcg ttcgtcaaca tactatgttt tgtatacata  49560
aaggcgccca ttttaacagt ttctagtgac aaaatgctag cgatcctagg atcctttaga  49620
atcacataga ttgacgattc gtctctctta gtaactctag taaaataatc atacaatcta  49680
gtacgcgaaa taatattatc cttgacttga ggagatctaa acaatctagt tttgagaaca  49740
tcgataagtt catcgggaat gacatacata ctatctttaa tagaactctt ttcatccagt  49800
tgaatggatt cgtccttaac caactgatta atgagatctt ctattttatc attttccaga  49860
tgatatgtat gtccattaaa gttaaattgt gtagcgcttc tttttagtct agcagccaat  49920
actttaacat cactaatatc gatatacaaa ggagatgatt tatctatggt attaagaatt  49980
cgtttttcga catccgtcaa aaccaattcc tttttgcctg tatcatccag ttttccatcc  50040
```

```
tttgtaaaga aattattttc tactagacta ttaataagac tgataaggat tcctccataa  50100
ttgcacaatc caaacttttt cacaaaacta gactttacaa gatctacagg aatgcgtact  50160
tcaggttttt tagcttgtga tttttttcttt tgcggacatt ttcttgtgac caactcatct  50220
accatttcat tgattttagc agtgaaataa gctttcaatg cacgggcact gatactattg  50280
aaaacgagtt gatcttcaaa ttccgccatt taagttcacc aaacaacttt taaatacaaa  50340
tatatcaata gtagtagaat aagaactata aaaaaaataa taattaacca ataccaaccc  50400
caacaaccgg tattattagt tgatgtgact gttttctcat cacttagaac agatttaaca  50460
atttctataa agtctgtcaa atcatcttcc ggagaccccca taaatacacc aaatatagcg  50520
gcgtacaact tatccattta tacattgaat attggctttt ctttatcgct atcttcatca  50580
tattcatcat caatatcaac aagtcccaga ttacgagcca gatcttcttc tacattttca  50640
gtcattgata cacgttcact atctccagag agtccgataa cgttagccac cacttctcta  50700
tcaatgatta gtttcttgag cgcgaaagta atttttgttt ccgttccgga tctatagaag  50760
acgataggtg tgataattgc cttggccaat tgtctttctc ttttactgag tgattctagt  50820
tcaccttcta tagatctgag aatggatgat tctccagtcg aaacatattc taccatggat  50880
ccgtttaatt tgttgatgaa gatggattca tccttaaatg ttttctctgt aatagtttcc  50940
accgaaagac tatgcaaaga atttggaatg cgttccttgt gcttaatgtt tccatagacg  51000
gcttctagaa gttgatacaa cataggacta gccgcggtaa cttttatttt tagaaagtat  51060
ccatcgcttc tatcttgttt agatttattt ttataaagtt tagtctctcc ttccaacata  51120
ataaaagtgg aagtcatttg actagataaa ctatcagtaa gttttataga gatagacgaa  51180
caattagcgt attgagaagc atttagtgta acgtattcga tacattttgc attagattta  51240
ctaatcgatt ttgcatactc tataacaccc gcacaagtct gtagagaatc gctagatgca  51300
gtaggtcttg gtgaagtttc aactctcttc ttgattacct tactcatgat taaacctaaa  51360
taattgtact ttgtaatata atgatatata ttttcacttt atctcatttg agaataaaaa  51420
tgtttttgtt taaccactgc atgatgtaca gatttcggaa tcgcaaacca ccagtggttt  51480
tattttatcc ttgtccaatg tgaattgaat gggagcggat gcgggtttcg tacgtagata  51540
gtacattccc gtttttagac cgagactcca tccgtaaaaa tgcatactcg ttagtttgga  51600
ataactcgga tctgctatat ggatattcat agattgactt tgatcgatga aggctcccct  51660
gtctgcagcc atttttatga tcgtcttttg tggaatttcc caaatagttt tataaactcg  51720
cttaatatct tctggaaggt ttgtattctg aatggatcca ccatctgcca taatcctatt  51780
cttgatctca tcattccata attttctctc ggttaaaact ctaaggagat gcggattaac  51840
tacttgaaat tctccagaca atactctccg agtgtaaata ttactggtat acggttccac  51900
cgactcatta tttcccaaaa tttgagcagt tgatgcagtc ggcataggtg ccaccaataa  51960
actatttcta agaccgtatg ttctgatttt atcttttaga ggttcccaat tccaaagatc  52020
cgacggtaca acattccaaa gatcatattg tagaataccg ttactggcgt acgatcctac  52080
atatgtatcg tatggtcctt ccttctcagc tagttcacaa ctcgcctcta atgcaccgta  52140
ataaatggtt tcgaagatct tcttatttag atcttgtgct tccaggctat caaatggata  52200
atttaagaga ataaacgcgt ccgctaatcc ttgaacacca ataccgatag gtctatgtct  52260
cttattagag atttcagctt ctggaatagg ataataatta atatctataa ttttattgag  52320
atttctgaca attactttga ccacatcctt cagtttgaga aaatcaaatc gcccatctat  52380
tacaaacatg ttcaaggcaa cagatgccag attacaaacg gctacctcat tagcatccgc  52440
```

atattgtatt atctcagtgc aaagattact acacttgata gttcctaaat tttgttgatt 52500
actctttttg ttacacgcat ccttataaag aatgaatgga gtaccagttt caatctgaga 52560
ttctataatc gctttccaga cgactcgagc ctttattata gatttgtatc tcctttctct 52620
ttcgtatagt gtatacaatc gttcgaactc gtctccccaa acattgtcca atccaggaca 52680
ttcatccgga cacatcaacg accactctcc gtcatccttc actcgtttca taaagagatc 52740
aggaatccaa agagctataa atagatctct ggttctatgt tcctcgtttc ctgtattctt 52800
tttaagatcg aggaacgcca taatatcaga atgccacggt tccaagtata tggccataac 52860
tccaggccgt ttgtttcctc cctgatctat gtatctagcg gtgttattat aaactctcaa 52920
cattggaata ataccgtttg atataccatt ggtaccggag atatagcttc cactggcacg 52980
aatattacta attgatagac ctattccccc tgccatttta gagattaatg cgcatcgttt 53040
taacgtgtca tagataccct ctatgctatc atcgatcatg ttaagtagaa aacagctaga 53100
catttggtga cgactagttc ccgcattaaa taaggtagga gaagcgtgcg taaaccattt 53160
ttcagaaagt agattgtacg tctcaatagc tgagtctata tcccattgat gaattcctac 53220
tgcgacacgc attaacatgt gctgaggtct ttcaacgatc ttgttgttta ttttcaacaa 53280
gtaggatttt tccaaagttt taaaaccaaa atagttgtat gaaaagtctc gttcgtaaat 53340
aataaccgag ttgagtttat ccttatattt gttaactata tccatggtga tacttgaaat 53400
aatcggagaa tgtttcccat ttttaggatt aacatagttg aataaatcct ccatcacttc 53460
actaaatagt ttttttgttt ccttgtgtag atttgatacg gctattctgg cggctagaat 53520
ggcataatcc ggatgttgtg tagtacaagt ggctgctatt tcggctgcca gagtgtccaa 53580
ttctaccgtt gttactccat tatatattcc ttgaataacc ttcatagcta ttttaatagg 53640
atctatatga tccgtgttta agccataaca taattttcta atacgagacg tgattttatc 53700
aaacatgaca ttttccttgt atccatttcg tttaatgaca aacatttttg ttggtgtaat 53760
aaaaaaatta tttaactttt cattaatagg gatttgacgt atgtagcgta caaaatgatc 53820
gttcctggta tatagataaa gagtcctata tatttgaaaa tcgttacggc tcgattaaac 53880
tttaatgatt gcatagtgaa tatatcatta ggatttaact ccttgactat catggcggcg 53940
ccagaaatta ccatcaaaag cattaataca gttatgccga tcgcagttaa aacggttata 54000
gcatccacca tttatatcta aaaattagat caaagaatat gtgacaaagt cctagttgta 54060
tactgagaat tgacgaaaca atgtttctta catatttttt tcttattagt aactgactta 54120
atagtaggaa ctggaaagct agacttgatt attctataag tatagatacc cttccagata 54180
atgttctctt tgataaaagt tccagaaaat gtagaatttt ttaaaaagtt atcttttgct 54240
attaccaaga ttgtgtttag acgcttatta ttaatatgag tgatgaaatc cacaccgcct 54300
ctagatatcg cctttatttc cacattagat ggtaaatcca atagtgaaac tatcttttta 54360
ggaatgtatg gactcgcgtt tagaggagtg aacgtcttgg gcgtcggaaa ggatgattcg 54420
tcaaacgaat aaacaatttc acaaatggat gttaatgtat tagtaggaaa ttttttgacg 54480
ctagtggaat tgaagattct aatggatgat gttctaccta tttcatccga taacatgtta 54540
atttccgaca ccaacggttt taatatttcg atgatatacg gtagtctctc tttcggactt 54600
atatagctta ttccacaata cgagtcatta tatactccaa aaaacaaaat aactagtata 54660
aaatctgtat cgaatgggaa aaacgaaatt atcgacatag gtatagaatc cggaacattg 54720
aacgtattaa tacttaattc tttttctgtg gtaagtaccg ataggttatt gacattgtat 54780

```
ggttttaaat attctataac ttgagacttg atagatatta gtgatgaatt gaaaattatt  54840
tttatcacca cgtgtgtttc aggatcatcg tcgacgcccg tcaaccaacc gaatggagta  54900
aaataaatat cattaatata tgctctagat attagtattt ttattaatcc tttgattatc  54960
atcttctcgt aggcgaatga ttccatgatc aagagtgatt tgagaacatc ctccggagta  55020
ttaatgggct tagtaaacag tccatcgttg caataataaa agttatccaa gttaaaggat  55080
attatgcatt cgtttaaaga tatcacctca tctgacggag acaatttttt ggtaggtttt  55140
agagactttg aagctacttg tttaacaaag ttattcatcg tcgtctacta ttctatttaa  55200
ttttgtagtt aatttatcac atatcacatt aattgacttt ttggtccatt tttccatacg  55260
tttatattct tttaatcctg cgttatccgt ttccgttata tccagggata gatcttgcaa  55320
gttaaataga atgctcttaa ataatgtcat tttcttatcc gctaaaaatt taaagaatgt  55380
ataaaccttt ttcagagatt tgaaactctt aggtggtgtc ctagtacaca atatcataaa  55440
caaactaata aacattccac attcagattc caacagctga ttaacttcca cattaataca  55500
gcctattttc gctccaaatg tacattcgaa aaatctgaat aaaacatcga tgtcacaatt  55560
tgtattatcc aatacagaat gtttgtgatt cgtgttaaaa ccatcggaga aggaatagaa  55620
ataaaaatta ttatagtggt ggaattcagt tggaatattg cctccggagt cataaaagga  55680
tactaaacat tgttttttat cataaattac acatttccaa tgagacaaat aacaaaatcc  55740
aaacattaca aatctagagg tagaactttt aattttgtct ttaagtatat acgataagat  55800
atgtttattc ataaacgcgt caaatttttc atgaatcgct aaggagttta agaatctcat  55860
gtcaaattgt cctatataat ccacttcgga tccataagca aactgagaga ctaagttctt  55920
aatacttcga ttgctcatcc aggctcctct ctcaggctct attttcatct tgacgacctt  55980
tggattttca ccagtatgta ttcctttacg tgataaatca tcgattttca aatccatttg  56040
tgagaagtct atcgccttag atactttttc ccgtagtcga ggtttaaaaa aatacgctaa  56100
cggtatacta gtaggtaact caaagacatc atatatagaa tggtaacgcg tctttaactc  56160
gtcggttaac tctttctttt gatcgagttc gtcgctacta ttgggtctgc tcaggtgccc  56220
cgactctact agttccaaca tcataccgat aggaatacaa gacactttgc cagcggttgt  56280
agatttatca tatttctcca ctacatatcc gttacaattt gttaaaaatt tagatacatc  56340
tatattgcta cataatccag ctagtgaata tatatgacat aataaattgg taaatcctag  56400
ttctggtatt ttactaatta ctaaatctgt atatctttcc atttatcatg gaaaagaatt  56460
taccagatat cttctttttt ccaaactgcg ttaatgtatt ctcttacaaa tattcacaag  56520
atgaattcag taatatgagt aaaacggaac gtgatagttt ctcattggcc gtgtttccag  56580
ttataaaaca tagatggcat aacgcacacg ttgtaaaaca taaaggaata tacaaagtta  56640
gtacagaagc acgtggaaaa aaagtatctc ctccatcact aggaaaaccc gcacacataa  56700
acctaaccgc gaagcaatat atatacagtg aacacacaat aagctttgaa tgttatagtt  56760
ttctaaaatg tataacaaat acagaaatca attcgttcga tgagtatata ttaagaggac  56820
tattagaagc tggtaatagt ttacagatat tttccaattc cgtaggtaaa cgaacagata  56880
ctataggtgt actagggaat aagtatccat ttagcaaaat tccattggcc tcattaactc  56940
ctaaagcaca acgagagata ttttcagcgt ggatttctca tagacctgta gttttaactg  57000
gaggaactgg agtgggtaag acgtcacagg tacccaagtt attgctttgg tttaattatt  57060
tatttggtgg attctctact ctagataaaa tcactgactt tcacgaaaga ccagtcattc  57120
tatctcttcc taggatagct ttagttagat tgcatagcaa taccatttta aaatcattgg  57180
```

gatttaaggt actagatgga tctcctattt ctttacggta cggatctata ccggaagaat 57240
taataaacaa acaaccaaaa aaatatggaa ttgtattttc tacccataag ttatctctaa 57300
caaaactatt tagttatggc actcttatta tagacgaagt tcatgagcat gatcaaatag 57360
gagatattat tatagcagta gcgagaaagc atcatacgaa aatagattct atgtttttaa 57420
tgactgccac gttagaggat gacagggaac ggctaaaagt atttttacct aatcccgcat 57480
ttatacatat tcctggagat acactgttta aaattagcga ggtatttatt cataataaga 57540
taaatccatc ttccagaatg gcatacatag aagaagaaaa gagaaattta gttactgcta 57600
tacagatgta tactcctcct gatggatcat ccggtatagt ctttgtggca tccgttgcac 57660
agtgtcacga atataaatca tatttagaaa aaagattacc gtatgatatg tatattattc 57720
atggtaaggt cttagatata gacgaaatat tagaaaaagt gtattcatca cctaatgtat 57780
cgataattat ttctactcct tatttggaat ccagcgttac tatacgcaat gttacacaca 57840
tttatgatat gggtagagtt tttgtccccg ctccttttgg aggatcgcaa caatttattt 57900
ctaaatctat gagagatcaa cgaaaaggaa gagtaggaag agttaatcct ggtacatacg 57960
tctatttcta tgatctgtct tatatgaagt ctatacagcg aatagattca gaatttctac 58020
ataattatat attgtacgct aataagttta atctaacact ccccgaagat ttgtttataa 58080
tccctacaaa tttggatatt ctatggcgta caaaggaata tatagactcg ttcgatatta 58140
gtacagaaac atggaataaa ttattatcca attattatat gaagatgata gagtatgcta 58200
aactttatgt actaagtcct attctcgctg aggagttgga taactttgag aggacgggag 58260
aattaactag tattgtacga gaagccattt tatctctaaa tttacaaatt aagattttaa 58320
attttaaaca taaagatgat gatacgtata tacacttttg taaaatatta ttcggtgtct 58380
ataacggaac aaacgctact atatattatc atagacctct aacgggatat atgaatatga 58440
tttcagatac tatatttgtt cctgtagata ataactaaaa atcaaactct aatgaccaca 58500 tctttttta gagatgaaaa attttccaca tctccttttg tagacacgac taaacatttt 58560
gcagaaaaaa gtttattagt gtttagataa tcgtatactt catcagtgta gatagtaaat 58620
gtgaacagat aaaaggtatt cttgctcaat agattggtaa attccataga atatattaat 58680
cctttcttct tgagatccca catcatttca accagagacg ttttatccaa tgatttacct 58740
cgtactatac cacatacaaa actagatttt gcagtgacgt cgtacctggt attcctacca 58800
aacaaaattt tacttttagt tcttttagaa aattctaagg tagaatctct atttgccaat 58860
atgtcatcta tggaattacc actagcaaaa aatgatagaa atatatattg atacatcgca 58920
gctggttttg atctactata ctttaaaaac gaatcagatt ccataattgc ctgtatatca 58980
tcagctgaaa aactatgttt tacacgtatt ccttcggcat ttctttttaa tgatatatct 59040
tgtttagaca atgataaagt tatcatgtcc atgagagacg cgtctccgta tcgtataaat 59100
atttcattag atgttagacg cttcattagg ggtatacttc tataaggttt cttaatcagt 59160
ccatcattgg ttgcgtcaag aactactatc ggatgttgtt gggtatctct agtgttacac 59220
atggccttac taaagtttgg gtaaataact atgatatctc tattaattat agatgcatat 59280
atttcattcg tcaaggatat tagtatcgac ttgctatcgt cattaatacg tgtaatgtaa 59340
tcatataaat catgcgatag ccaaggaaaa tttaaataga tgttcatcat ataatcgtcg 59400
ctataattca tattaatacg ttgacattga ctaatttgta atatagcctc gccacgaaga 59460
aagctctcgt attcagtttc atcgataaag gataccgtta aatataactg gttgccgata 59520

```
gtctcatagt ctattaagtg gtaagtttcg tacaaataca gaatccctaa aatattatct  59580
aatgttggat taatctttac cataactgta taaaatggag acggagtcat aactatttta  59640
ccgtttgtac ttactggaat agatgaagga ataatctccg gacatgctgg taaagaccca  59700
aatgtctgtt tgaagaaatc caatgttcca ggtcctaatc tcttaacaaa aattacgata  59760
ttcgatcccg atatcctttg cattctattt accagcatat cacgaactat attaagatta  59820
tctatcatgt ctattctccc accgttatat aaatcgcctc cgctaagaaa cgttagtata  59880
tccatacaat ggaatacttc atttctaaaa tagtattcgt tttctaattc tttaatgtga  59940
aatcgtatac tagaaaggga aaaattatct ttgagttttc cgttagaaaa gaaccacgaa  60000
actaatgttc tgattgcgtc cgattccgtt gctgaattaa tggatttaca ccaaaaactc  60060
atataacttc tagatgtaga agcattcgct aaaaaattag tagaatcaaa ggatataagt  60120
agatgttcca acaagtgagc aattcccaag atttcatcta tatcattctc gaatccgaaa  60180
ttagaaattc ccaagtagat atccttttc atccgatcgt tgatgaaaat acgaacttta  60240
ttcggtaaga caatcattta ctaaggagta aaataggaag taatgttcgt atgtcgttat  60300
catcgtataa attaaaggtg tgttttttac cattaagtga cattataatt ttaccaatat  60360
tggaattata atataggtgt atttgcgcac tcgcgacggt tgatgcatcg gtaaatatag  60420
ctgtatctaa tgttctagtc ggtatttcat catttcgctg tctaataata gcgttttctc  60480
tatctgtttc cattacagct gcctgaagtt tattggtcgg ataatatgta aaataataag  60540
aaatacatac gaataacaaa aataaaataa gatataataa agatgccatt tagagatcta  60600
attttgttta acttgtccaa attcctactt acagaagatg aggaatcgtt ggagatagtg  60660
tcttccttat gtagaggatt tgaaatatct tataatgact tgataactta ctttccagat  60720
aggaaatacc ataaatatat ttataaagta tttgaacatg tagatttatc ggaggaatta  60780
agtatggaat tccatgatac aactctgaga gatttagtct atcttagatt gtacaagtat  60840
tccaagtgta tacggccgtg ttataaatta ggagataatc taaaaggcat agttgttata  60900
aaggacagga atatttatat tagggaagca aatgatgact tgatagaata tctcctcaag  60960
gaatacactc ctcagattta tacatattct aatgagcgcg tccccataac tggttcaaaa  61020
ttaattcttt gtggattttc tcaagttaca tttatggcgt atacaacgtc gcatataaca  61080
acaaataaaa aggtagatgt tctcgtttcc aaaaaaatgta tagatgaact agtcgatcca  61140
ataaattatc aaatacttca aaatttattt gataaaggaa gcggaacaat aaacaaaata  61200
ctcaggaaga tattttattc ggtaacaggt ggccaaactc cataggtagc tttttctatt  61260
tcggatttta gaatttccaa attcaccagc gatttatcgg ttttggtgaa atccaaggat  61320
ttattaatgt ccacaaatgc catttgtttt gtctgtggat tgtatttgaa aatggaaacg  61380
atgtagttag atagatgcgc tgcgaagttt cctattaggg ttccgcgctt cacgtcaccc  61440
agcatacttg aatcaccatc ctttaaaaaa aatgataaga tatcaacatg gagtatatca  61500
tactcggatt ttaattcttc tactgcatca ctgacatttt cacaaatact acaatacggt  61560
ttaccgaaaa taatcagtac gttcttcatt tatgggtatc aaaaacttaa aatcgttact  61620
gctggaaaat aaatcactga cgatattaga tgataattta tacaaagtat acaatggaat  61680
atttgtggat acaatgagta tttatatagc cgtcgccaat tgtgtcagaa acttagaaga  61740
gttaactacg gtattcataa aatacgtaaa cggatgggta aaaaagggag ggcatgtaac  61800
cctttttatc gatagaggaa gtataaaaat taaacaagac gttagagaca agagacgtaa  61860
atattctaaa ttaaccaagg acagaaaaat gttagaatta gaaaagtgta catccgaaat  61920
```

```
acaaaatgtt accggattta tggaagaaga aataaaggca gaaatgcaat taaaaatcga  61980
taaactcaca tttcaaatat atttatctga ttctgataac ataaaaatat cattgaatga  62040
gatactaaca catttcaaca ataatgagaa tgttacatta ttttattgtg atgaacgaga  62100
cgcagaattc gttatgtgtc tcgaggctaa aacacatttc tctaccacag gagaatggcc  62160
gttgataata agtaccgatc aggatactat gctatttgca tctgctgata atcatcctaa  62220
gatgataaaa aacttaactc aactgtttaa atttgttccc tcggcagagg ataactattt  62280
agcaaaatta acggcgttag tgaatggatg tgatttcttt cctggactct atggggcatc  62340
tataacaccc accaacttaa acaaaataca attgtttagt gattttacaa tcgataatat  62400
agtcactagt ttggcaatta aaaattatta tagaaagact aactctaccg tagacgtgcg  62460
taatattgtt acgtttataa acgattacgc taatttagac gatgtctact cgtatattcc  62520
tccttgtcaa tgcactgttc aagaatttat attttccgca ttagatgaaa aatggaatga  62580
atttaaatca tcttatttag aaagcgtgcc gttaccctgc caattaatgt acgcgttaga  62640
accacgcaag gagattgatg tttcagaagt taaaacttta tcatcttata tagatttcga  62700
aaatactaaa tcagatatcg atgttataaa atctatatcc tcgatcttcg gatattctaa  62760
cgaaaactgt aacacgatag tattcggcat ctataaggat aatttactac tgagtataaa  62820
taattcattt tactttaacg atagtctgtt aataaccaat actaaaagtg ataatataat  62880
aaatataggt tactagatta aaaatggtgt tccaactcgt gtgctctaca tgcggtaaag  62940
atatttctca cgaacgatat aaattgatta tacgaaaaaa atcattaaag gatgtactcg  63000
tcagtgtaaa gaacgaatgt tgtaggttaa aattatctac acaaatagaa cctcaacgta  63060
acttaacagt gcaacctcta ttggatataa actaatatgg atccggttaa ttttatcaag  63120
acatatgcgc ctagaggttc tattattttt attaattata ccatgtcatt aacaagtcat  63180
ttgaatccat cgatagaaaa acatgtgggt atttattatg gtacgttatt atcggaacac  63240
ttggtagttg aatctaccta tagaaaagga gttcgaatag tcccattgga tagttttttt  63300
gaaggatatc ttagtgcaaa agtatacatg ttagagaata ttcaagttat gaaaatagca  63360
gctgatacgt cattaacttt attgggtatt ccgtatggat ttggtcataa tagaatgtat  63420
tgttttaaat tggtagctga ctgttataaa aatgccggta ttgatacatc gtctaaacga  63480
atattgggca aagatatttt tctgagccaa aacttcacag acgataatag atggataaag  63540
atatatgatt ctaataattt aacattttgg caaattgatt accttaaagg gtgagttaat  63600
atgcataact actcctccgt tgttttttcc ctcgttcttt ttcttaacgt tgtttgccat  63660
cactctcata atgtaaagat attctaaaat ggtaaacttt tgcatatcgg acgcagaaat  63720
tggtataaat gttgtaattg tattatttcc cgtcaatgga ctagtcacag ctccatcagt  63780
tttatatcct ttagagtatt tctcactcgt gtctaacatt ctagagcatt ccatgatctg  63840
tttatcgttg atattggccg gaaagataga ttttttattt tttattatat tactattggc  63900
aattgtagat ataacttctg gtaaatattt ttctaccttt tcaatctctt ctattttcaa  63960
gccggctata tattctgcta tattgttgct agtatcaata ccttttctgg ctaagaagtc  64020
atatgtggta ttcactatat cagttttaac tggtagttcc attagccttt ccacttctgc  64080
agaataatca gaaattggtt ctttaccaga aaatccagct actataatag gctcaccgat  64140
gatcattggc aaaatcctat attgtaccag attaatgaga gcatatttca tttccaataa  64200
ttctgctagt tcttgagaca ttgatttatt tgatgaatct agttggttct ctagatactc  64260
```

```
taccatttct gccgcataca ataacttgtt agataaaatc agggttatca aagtgtttag  64320
cgtggctaga atagtgggct tgcatgtatt aaagaatgcg gtagtatgag taaaccgttt  64380
taacgaatta tatagtctcc agaaatctgt ggcgttacat acatgagccg aatgacatcg  64440
aagattgtcc aatattttta atagctgctc tttgtccatt atttctatat ttgactcgca  64500
acaattgtag ataccattaa tcaccgattc ctttttcgat gccggacaat agcacaattg  64560
tttagctttg gactctatgt attcagaatt aatagatata tctctcaata cagattgcac  64620
tatacatttt gaaactatgt caaaaattgt agaacgacgc tgttctgcag ccatttaact  64680
ttaaataatt tacaaaaatt taaaatgagc atccgtataa aaatcgataa actgcgccaa  64740
attgtggcat atttttcaga gttcagtgaa gaagtatcta taaatgtaga ctcgacggat  64800
gagttaatgt atatttttgc cgccttgggc ggatctgtaa acatttgggc cattatacct  64860
ctcagtgcat cagtgtttta ccgaggagcc gaaaatattg tgtttaatct tcctgtgtcc  64920
aaggtaaaat cgtgtttgtg tagttttcac aatgatgcca tcatagatat agaacctgat  64980
ctggaaaata atctagtaaa actttctagt tatcatgtag taagtgtcga ttgtaacaag  65040
gaactgatgc ctattaggac agatactact atttgtctaa gtatagatca aaagaaatct  65100
tacgtgttta attttcacaa gtatgaagaa aaatgttgtg gtagaaccgt cattcattaa  65160
gtgacattat aattttacca atattggaat tataatatag gtgtatttgc gcacttgcga  65220
cggttgatgc atcggtaaat atagctgtat ctaatgttct agtcggtatt tcatcatttc  65280
gctgtctaat aatagcgttt tctctatctg tttccattac agctgcctga agtttattgg  65340
tcggataata tgtaaaataa taagaaatac atacgaataa caaaaaataaa ataagatata  65400
ataaagatgc catttagaga tctaattttg tttaacttgt ccaaattcct acttacagaa  65460
gatgaggaat cgttggagat agtgtcttcc ttatgtagag gatttgaaat atcttataat  65520
gacttgataa cttactttcc agataggaaa taccataaat atatttataa agtatttgaa  65580
catgtagatt tatcggagga attaagtatg gaattccatg atacaactct gagagattta  65640
gtctatctta gattgtacaa gtattccaag tgtatacggc cgtgttataa attaggagat  65700
aatctaaaag gcatagttgt tataaaggac aggaatattt atattaggga agcaaatgat  65760
gacttgatag aatatctcct caaggaatac actcctcaga tttatacata ttctaatgag  65820
cgcgtcccca taactggttc aaaattaatt ctttgtggat tttctcaagt tacatttatg  65880
gcgtatacaa cgtcgcatat aacaacaaat aaaaaggtag atgttctcgt ttccaaaaaa  65940
tgtatagatg aactagtcga tccaataaat tatcaaatac ttcaaaattt atttgataaa  66000
ggaagcggaa caataaacaa aatactcagg aagatatttt attcggtaac aggtggccaa  66060
actccatagg tagctttttc tatttcggat tttagaattt ccaaattcac cagcgattta  66120
tcggttttgg tgaaatccaa ggatttatta atgtccacaa atgccatttg ttttgtctgt  66180
ggattgtatt tgaaaatgga aacgatgtag ttagatagat gcgctgcgaa gtttcctatt  66240
agggttccgc gcttcacgtc acccagcata cttgaatcac catcctttaa aaaaaatgat  66300
aagatatcaa catggagtat atcatactcg gattttaatt cttctactgc atcactgaca  66360
ttttcacaaa tactacaata cggtttaccg aaaataatca gtacgttctt catttatggg  66420
tatcaaaaac ttaaaatcgt tactgctgga aaataaatca ctgacgatat tagatgataa  66480
tttatacaaa gtatacaatg gaatatttgt ggatacaatg agtatttata tagccgtcgc  66540
caattgtgtc agaaacttag aagagttaac tacggtattc ataaaatacg taaacggatg  66600
ggtaaaaaag ggagggcatg taacccttt tatcgataga ggaagtataa aaattaaaca  66660
```

```
agacgttaga gacaagagac gtaaatattc taaattaacc aaggacagaa aaatgctaga  66720
attagaaaag tgtacatccg aaatacaaaa tgttaccgga tttatggaag aagaaataaa  66780
ggcagaaatg caattaaaaa tcgataaact cacatttcaa atatatttat ctgattctga  66840
taacataaaa atatcattga atgagatact aacacatttc aacaataatg agaatgttac  66900
attattttat tgtgatgaac gagacgcaga attcgttatg tgtctcgagg ctaaaacaca  66960
tttctctacc acaggagaat ggccgttgat aataagtacc gatcaggata ctatgctatt  67020
tgcatctgct gataatcatc ctaagatgat aaaaaactta actcaactgt ttaaatatgt  67080
tccatctgca gaggataact atttagcaaa attaacggcg ttagtgaatg gatgtgattt  67140
ctttcctgga ctctatgggg catctataac acccaccaac ttaaacaaaa tacaattgtt  67200
tagtgatttt acaatcgata atatagtcac tagtttggca attaaaaatt attatagaaa  67260
gactaactct accgtagacg tgcgtaatat tgttacgttt ataaacgatt acgctaattt  67320
agacgatgtc tactcgtatg ttcctccttg tcaatgcact gttcaagaat ttatattttc  67380
cgcattagat gaaaaatgga atgaatttaa atcatcttat ttagagaccg tgccgttacc  67440
ctgtcaatta atgtacgcgt tagaaccacg taaggagatt gatgtttcag aagttaaaac  67500
tttatcatct tatatagatt tcgaaaatac taaatcagat atcgatgtta taaaatctat  67560
atcctcgatc ttcggatatt ctaacgaaaa ctgtaacacg atagtattcg gcatctataa  67620
ggataattta ctactgagta taaataattc attttacttt aacgatagtc tgttaataac  67680
caatactaaa agtgataata taataaatat aggttactag attaaaaatg gtgttccaac  67740
tcgtgtgctc tacatgcggt aaagatattt ctcacgaacg atataaattg attatacgaa  67800
aaaaatcatt aaaggatgta ctcgtcagtg taaagaacga atgttgtagg ttaaaattat  67860
ctacacaaat agaacctcaa cgtaacttaa cagtgcaacc tctattggat ataaactaat  67920
atggatccgg ttaattttat caagacatat gcgcctagag gttctattat ttttattaat  67980
tataccatgt cattaacaag tcatttgaat ccatcgatag aaaaacatgt gggtatttat  68040
tatggtacgt tattatcgga acacttggta gttgaatcta cctatagaaa aggagttcga  68100
atagtcccat tggatagttt ttttgaagga tatcttagtg caaaagtata catgttagag  68160
aatattcaag ttatgaaaat agcagctgat acgtcattaa ctttattggg tattccgtat  68220
ggatttggtc ataatagaat gtattgtttt aaattggtag ctgactgtta taaaaatgcc  68280
ggtattgata catcgtctaa acgaatattg ggcaaagata tttttctgag ccaaaacttc  68340
acagacgata atagatggat aaagatatat gattctaata atttaacatt ttggcaaatt  68400
gattacctta aagggtgagt taatatgcat aactactcct ccgttgtttt ttccctcgtt  68460
ctttttctta acgttgtttg ccatcactct cataatgtaa agatattcta aaatggtaaa  68520
cttttgcata tcggacgcag aaattggtat aaatgttgta attgtattat ttccatatta  68580
ttatgaagac tcctggtaat actgatggcg ttttccaggg aatattctat gactgaatgt  68640
tctcaagaac tacaaaagtt ttctttcaaa atagctatct cgtctctcaa caaactacga  68700
ggattcaaaa agagagtcaa tgtttttgaa actagaatcg taatggataa tgacgataac  68760
attttaggaa tgttgttttc ggatagagtt caatccttta agatcaacat ctttatggcg  68820
tttttagatt aatactttca atgagataaa tatgggtggc ggagtaagtg ttgagctccc  68880
taaacgggat ccgcacccgg gagtacccac tgatgagatg ttattaaacg tggataaaat  68940
gcatgacgtg atagctcccg ctaagctttt agaatatgtg catataggac cactagcaaa  69000
```

```
agataaagag gataaagtaa agaaaagata tccagagttt agattagtca acacaggacc  69060
cggtggtctt tcggcattgt taagacaatc gtataatgga accgcaccca attgctgtcg  69120
cacttttaat cgtactcatt attggaagaa ggatggaaag atatcagata agtatgaaga  69180
gggtgcagta ttagaatcgt gttggccaga cgttcacgac actggaaaat gcgatgttga  69240
tttattcgac tggtgtcagg gggatacgtt cgatagaaac atatgccatc agtggatcgg  69300
ttcagccttt aataggagta atagaactgt agagggtcaa caatcgttaa taaatctgta  69360
taataagatg caaacattat gtagtaaaga tgctagtgta ccaatatgcg aatcattttt  69420
gcattattta cgcgcacaca atacagaaga tagcaaagag atgatcgatt atattctaag  69480
acaacagtct gcggacttta aacagaaata tatgagatgt agttatccca ctagagataa  69540
gttagaagag tcattaaaat atgcggaacc tcgagaatgt tgggatccag agtgttcgaa  69600
tgccaatgtt aatttcttac taacacgtaa ttataataat ttaggacttt gcaatattgt  69660
acgatgtaat accagcgtga acaacttaca gatggataaa acttcctcat taagattgtc  69720
atgtggatta agcaatagtg atagattttc tactgttccc gtcaatagag caaaagtagt  69780
tcaacataat attaaacact cgttcgacct aaaattgcat ttgatcagtt tattatctct  69840
cttggtaata tggatactaa ttgtagctat ttaaatgggt gccgcggcaa gcatacagac  69900
gacggtgaat acactcagcg aacgtatctc gtctaaatta gaacaagaag cgaacgctag  69960
tgctcaaaca aaatgtgata tagaaatcgg aaatttttat atccgacaaa accatggatg  70020
taacctcact gttaaaaata tgtgctctgc ggacgcggat gctcagttgg atgctgtgtt  70080
atcagccgct acagaaacat atagtggatt aacaccggaa caaaaagcat acgtgccagc  70140
tatgtttact gctgcgttaa acattcagac gagtgtaaac actgttgtta gagattttga  70200
aaattatgtg aaacagactt gtaattctag cgcggtcgtc gataacaaat taaagataca  70260
aaacgtaatc atagatgaat gttacggagc cccaggatct ccaacaaatt tggaatttat  70320
taatacagga tctagcaaag gaaattgtgc cattaaagcg ttgatgcaat tgacgactaa  70380
ggccactact caaatagcac ctagacaagt tgctggtaca ggagttcagt tttatatgat  70440
tgttatcggt gttataatat tggcagcgtt gtttatgtac tatgccaagc gtatgttgtt  70500
cacatccacc aatgataaaa tcaaacttat tttagccaat aaggaaaacg tccattggac  70560
tacttacatg gacacattct ttagaacttc tccgatggtt attgctacca cggatatgca  70620
aaactgaaaa tatattgata atattttaat agattaacat ggaagttatc gctgatcgtc  70680
tagacgatat agtgaaacaa aatatagcgg atgaaaaatt tgtagatttt gttatacacg  70740
gtctagagca tcaatgtcct gctatacttc gaccattaat taggttgttt attgatatac  70800
tattatttgt tatagtaatt tatattttta cggtacgtct agtaagtaga aattatcaaa  70860
tgttgttggt ggtgctagtc atcacattaa ctattttttta ttactttata ctataatagt  70920
actagactga cttctaacaa acatctcacc tgccataaat aaatgcttga tattaaagtc  70980
ttctatttct aacactattc catctgtgga aaataatact ctgacattat cgctaattga  71040
cacatcggtg agtgatatgc ctataaagta ataatcttct ttgggcacat ataccagtgt  71100
accaggttct aacaacctat ttactggtgc tcctgtagca tactttttct ttaccttgag  71160
aatatccatc gtttgcttgg tcaatagcga tatgtgattt tttatcaacc actcaaaaaa  71220
gtaattggag tgttcatatc ctctacgggc tattgtctca tggccgtgta tgaaatttaa  71280
gtaacacgac tgtggtagat ttgttctata gagccgattg ccgcaaatag atagaactac  71340
caatatgtct gtacaaatgt taaacattaa ttgattaaca gaaaaaacaa tgttcgttct  71400
```

```
gggaatagaa accagatcaa aacaaaattc gttagaatat atgccacgtt tatacatgga  71460
atataaaata actacagttt gaaaaataac agtatcattt aaacatttaa cttgcggggt  71520
taatctcaca actttactgt ttttgaactg ttcaaaatat agcatcgatc cgtgagaaat  71580
acgtttagcc gcctttaata gaggaaatcc caccgccttt ctggatctca ccaacgacga  71640
tagttctgac cagcaactca tttcttcatc atccacctgt tttaacatat aataggcagg  71700
agatagatat ccgtcattgc aatattcctt ctcgtaggca cacaatctaa tattgataaa  71760
atctccattc tcttctctgc atttattatc ttgtctcggt ggctgattag gctgtggtct  71820
tggtttaggc cttggtctat cgttgttgaa tctattttgg tcattaaatc tttcatttct  71880
tcctggtata tttctatcac ctcgtttggt tggatttttg tctatattat cgtttgtaac  71940
atcggtacgg gtattcattt atcacaaaaa aaacttctct aaatgagtct actgctagaa  72000
aacctcatcg aagaagatac catatttttt gcaggaagta tatctgagta tgatgattta  72060
caaatggtta ttgccggcgc aaaatccaaa tttccaagat ctatgctttc tatttttaat  72120
atagtaccta gaacgatgtc aaaatatgag ttggagttga ttcataacga aaatatcaca  72180
ggagcaatgt ttaccacaat gtataatata agaaacaatt tgggtctagg agatgataaa  72240
ctaactattg aagccattga aaactatttc ttggatccta acaatgaagt tatgcctctt  72300
attattaata atacggatat gactgccgtc attcctaaaa aaagtggtag gagaaagaat  72360
aagaacatgg ttatcttccg tcaaggatca tcacctatct tgtgcatttt cgaaactcgt  72420
aaaaagatta atatttataa agaaaatatg gaatccgcgt cgactgagta tacacctatc  72480
ggagacaaca aggctttgat atctaaatat gcgggaatta atgtcctgaa tgtgtattct  72540
ccttccacat ccataagatt gaatgccatt tacggattca ccaataaaaa taaactagag  72600
aaacttagta ctaataagga actagaatcg tatagttcta gccctcttca agaacccatt  72660
aggttaaatg attttctggg actattggaa tgtgttaaaa agaatattcc tctaacagat  72720
attccgacaa aggattgatt actataaatg gagaatgttc ctaatgtata ctttaatcct  72780
gtgtttatag agcccacgtt taaacattct ttattaagtg tttataaaca cagattaata  72840
gttttatttg aagtattcgt tgtattcatt ctaatatatg tattttttag atctgaatta  72900
aatatgttct tcatgcctaa acgaaaaata cccgatccta ttgatagatt acgacgtgct  72960
aatctagcgt gtgaagacga taaattaatg atctatggat taccatggat gacaactcaa  73020
acatctgcgt tatcaataaa tagtaaaccg atagtgtata aagattgtgc aaagcttttg  73080
cgatcaataa atggatcaca accagtatct cttaacgatg ttcttcgcag atgatgattc  73140
atttttaag tatttggcta gtcaagatga tgaatcttca ttatctgata tattgcaaat  73200
cactcaatat ctagactttc tgttattatt attgatccaa tcaaaaaata aattagaagc  73260
tgtgggtcat tgttatgaat ctctttcaga ggaatacaga caattgacaa aattcacaga  73320
ctttcaagat tttaaaaaac tgtttaacaa ggtccctatt gttacagatg gaagggtcaa  73380
acttaataaa ggatatttgt tcgactttgt gattagtttg atgcgattca aaaaagaatc  73440
ctctctagct accaccgcaa tagatcctgt tagatacata gatcctcgtc gtgatatcgc  73500
attttctaac gtgatggata tattaaagtc gaataaagtg aacaataatt aattctttat  73560
tgtcatcatg aacggcggac atattcagtt gataatcggc cccatgtttt caggtaaaag  73620
tacagaatta attagacgag ttagacgtta tcaaatagct caatataaat gcgtgactat  73680
aaaatattct aacgataata gatacggaac gggactatgg acgcatgata agaataattt  73740
```

```
tgaagcattg gaagcaacta aactatgtga tgtcttggaa tcaattacag atttctccgt  73800
gataggtatc gatgaaggac agttctttcc agacattgtt taattctgtg agcgtatggc  73860
aaacgaagga aaaatagtta tagtagccgc actcgatggg acatttcaac gtaaaccgtt  73920
taataatatt ttgaatctta ttccattatc tgaaatggtg gtaaaactaa ctgctgtgtg  73980
tatgaaatgc tttaaggagg cttccttttc taaacgattg ggtgaggaaa ccgagataga  74040
gataatagga ggtaatgata tgtatcaatc ggtgtgtaga aagtgttacg tcggctcata  74100
atattatatt ttttatctaa aaaactaaaa ataaacattg attaaatttt aatataatac  74160
ttaaaaatgg atgttgtgtc gttagataaa ccgtttatgt attttgagga aattgataat  74220
gagttagatt acgaaccaga aagtgcaaat gaggtcgcaa aaaaactgcc gtatcaagga  74280
cagttaaaac tattactagg agaattattt tttcttagta agttacagcg acacggtata  74340
ttagatggtg ccaccgtagt gtatatagga tcggctcctg gtacacatat acgttatttg  74400
agagatcatt tctataattt aggagtgatc atcaaatgga tgctaattga cggccgccat  74460
catgatccta ttttaaatgg attgcgtgat gtaactctag tgactcggtt cgttgatgag  74520
gaatatctac gatccatcaa aaaacaactg catccttcta agattatttt aatttctgat  74580
gtaagatcca aacgaggagg aaatgaacct agtacggcgg atttactaag taattacgct  74640
ctacaaaatg tcatgattag tattttaaac cccgtggcat ctagtcttaa atggagatgc  74700
ccgtttccag atcaatggat caaggacttt tatatcccac acggtaataa aatgttacaa  74760
ccttttgctc cttcatattc agctgaaatg agattattaa gtatttatac cggtgagaac  74820
atgagactga ctcgagttac caaattagac gctgtaaatt atgaaaaaaa gatgtactac  74880
cttaataaga tcgtccgtaa caaagtagtt gttaactttg attatcctaa tcaggaatat  74940
gactattttc acatgtactt tatgctgagg accgtgtact gcaataaaac atttcctact  75000
actaaagcaa aggtactatt tctacaacaa tctatatttc gtttcttaaa tattccaaca  75060
acatcaactg aaaaagttag tcatgaacca atacaacgta aaatatctag caaaaattct  75120
atgtctaaaa acagaaatag caagagatcc gtacgcggta ataaatagaa acgtactact  75180
gagatatact accgatatag agtataatga tttagttact ttaataaccg ttagacataa  75240
aattgattct atgaaaactg tgtttcaggt atttaacgaa tcatccataa attatactcc  75300
ggttgatgat gattatggag aaccaatcat tataacatcg tatcttcaaa aaggtcataa  75360
caagtttcct gtaaattttc tatacataga tgtggtaata tctgacttat ttcctagctt  75420
tgttagacta gatactacag aaactaatat agttaatagt gtactacaaa caggcgatgg  75480
taaaaagact cttcgtcttc ccaaaatgtt agagacggaa atagttgtca agattctcta  75540
tcgccctaat ataccattaa aaattgttag atttttccgc aataacatgg taactggagt  75600
agagatagcc gatagatctg ttatttcagt cgctgattaa tcaattagta gagatgagat  75660
aagaacatta taataatcaa taatatatct tatatcttat atcttatatc ttatatcttg  75720
tttagaaaaa tgctaatatt aaaatagcta acgctagtaa tccaatcgga agccatttga  75780
tatctataat agggtatcta atttcctgat ttaaatagcg gacagctata ttctcggtag  75840
ctactcgttt ggaatcacaa acattattta catctaattt actatctgta atggaaacgt  75900
ttcccaatga aatggtacaa tccgatacat tgcattttgt tatatttttt tttaaagagg  75960
ctggtaacaa cgcatcgctt cgtttacatg gctcgtacca acaataatag ggtaatcttg  76020
tatctattcc tatccgtact atgcttttat caggataaat acatttacat cgtatatcgt  76080
ctttgttagc atcacagaat gcataaattt gttcgtccgt catgataaaa atttaaagtg  76140
```

```
taaatataac tattattttt atagttgtaa taaaaaggga aatttgattg tatactttcg  76200
gttctttaaa agaaactgac ttgataaaaa tggctgtaat ctctaaggtt acgtatagtc  76260
tatatgatca aaaagagatt aatgctacag atattatcat tagtcatgtt aaaaatgacg  76320
acgatatcgg taccgttaaa gatggtagac taggtgctat ggatggggca ttatgtaaga  76380
cttgtgggaa aacggaattg gaatgtttcg gtcactgggg taaagtaagt atttataaaa  76440
ctcatatagt taagcctgaa tttatttcag aaattattcg tttactgaat catatatgta  76500
ttcactgcgg attattgcgt tcacgagaac cgtattccga cgatattaac ctaaaagagt  76560
tatcgggaca cgctcttagg agattaaagg ataaaatatt atccaagaaa aagtcatgtt  76620
ggaacagtga atgtatgcaa ccgtatcaaa aaattacttt ttcaaagaaa aaggtttgtt  76680
tcgtcaacaa gttggatgat attaacgttc ctaattctct catctatcaa aagttaattt  76740
ctattcatga aaagttttgg ccattattag aaattcatca atatccagct aacttatttt  76800
atacagacta ctttcccatc cctccgttga ttattagacc ggctattagt ttttggatag  76860
atagtatacc caaagagacc aatgaattaa cttacttatt aggtatgatc gttaagaatt  76920
gtaacttgaa tgctgatgaa caggttatcc agaaggcggt aatagaatac gatgatatta  76980
aaattatttc taataacact accagtatca atttatcata tattacatcc ggcaaaaata  77040
atatgattag aagttatatc gtcgcccgac gaaaagatca gaccgctaga tctgtaattg  77100
gtcccagtac atctatcacc gttaatgagg taggaatgcc cgcatatatt agaaatacac  77160
ttacagaaaa gatatttgtt aatgccttta cagtggataa agttaaacaa ctattagcgt  77220
caaaccaagt taaattttac tttaataaac gattaaacca attaacaaga atacgccaag  77280
gaaagtttat taaaaataaa atacatttat tgcctggtga ttgggtagaa gtagctgttc  77340
aagaatatac aagtattatt tttggaagac agccgtctct acatagatac aacgtcatcg  77400
cttcatctat cagagctacc gaaggagata ctatcaaaat atctcccgga attgccaact  77460
ctcaaaatgc tgatttcgac ggggatgagg aatggatgat attagaacaa aatcctaaag  77520
ctgtaattga acaaagtatt cttatgtatc cgacgacgtt actcaaacac gatattcatg  77580
gagcccccgt ttatggatct attcaagatg aaatcgtagc agcgtattca ttgtttagga  77640
tacaagatct ttgtttagat gaagtattga acatcttggg gaaatatgga agagagttcg  77700
atcctaaagg taaatgtaaa ttcagcggta aagatatcta tacttacttg ataggtgaaa  77760
agattaatta tccgggtctc ttaaaggatg gtgaaattat tgcaaacgac gtagatagta  77820
attttgttgt ggctatgagg catctgtcat tggctggact cttatccgat cataagtcga  77880
acgtggaagg tatcaacttt attatcaagt catcttatgt ttttaagaga tatctatcta  77940
tttacggttt tggggtgaca ttcaaagatc tgagaccaaa ttcgacgttc actaataaat  78000
tggaggccat caacgtagaa aaaatagaac ttatcaaaga agcatacgcc aaatatctca  78060
acgatgtaag agacgggaaa atagttccat tatctaaagc tttagaggcg gactatgtgg  78120
aatccatgtt atccaacttg acaaatctta atatccgaga gatagaagaa catatgagac  78180
aaacgctgat agatgatcca gataataacc tcctgaaaat ggccaaagcg ggttataaag  78240
taaatcccac agaactaatg tatattctag gtacgtatgg acaacaaagg attgatggtg  78300
aaccagcaga gactcgagta ttgggtagag ttttacctta ctatcttcca gactctaagg  78360
atccagaagg aagaggttat attcttaatt ctttaacaaa aggattaacg ggttctcaat  78420
attacttttc gatgctggtt gcaagatctc aatctactga tatcgtctgt gaaacatcac  78480
```

```
gtaccggaac actggctaga aaaatcatta aaaagatgga ggatatggtg gtcgacggat  78540
acggacaagt agttataggt aatacgctca tcaagtacgc cgccaattat accaaaattc  78600
taggctcagt atgtaaacct gtagatctta tctatccaga tgagtccatg acttggtatt  78660
tggaaattag tgctctgtgg aataaaaataa aacagggatt cgtttactct cagaaacaga  78720
aacttgcaaa gaagacattg gcgccgttta atttcctagt attcgtcaaa cccaccactg  78780
aggataatgc tattaaggtt aaggatctgt acgatatgat tcataacgtc attgatgatg  78840
tgagagagaa atacttcttt acggtatcta atatagattt tatggagtat atattcttga  78900
cgcatcttaa tccttctaga attagaatta caaaagaaac ggctatcact atctttgaaa  78960
agttctatga aaaactcaat tatactctag gtggtggaac tcctattgga attatttctg  79020
cacaggtatt gtctgagaag tttacacaac aagccctgtc cagttttcac actactgaaa  79080
aaagtggtgc cgtcaaacaa aaacttggtt tcaacgagtt taataacttg actaatttga  79140
gtaagaataa gaccgaaatt atcactctgg tatccgatga tatctctaaa cttcaatctg  79200
ttaagattaa tttcgaattt gtatgtttgg gagaattaaa tccaaacatc actcttcgaa  79260
aagaaacaga taggtatgta gtagatataa tagtcaatag attatacatc aagagagcag  79320
aaataaccga attagtcgtc gaatatatga ttgaacgatt catctccttt agcgtcattg  79380
taaaggaatg gggtatggag acattcattg aggacgagga taatattaga tttactgtct  79440
acctaaattt cgttgaaccg gaagaattga atcttagtaa gtttatgatg gttcttccgg  79500
gggcagccaa caagggaaag attagtaaat tcaagattcc tatctctgac tatacgggat  79560
atgacgactt caatcaaaca aaaaagctca ataagatgac tgtagaactc atgaatctaa  79620
aagaattggg ttctttcgat ttggaaaacg tcaacgtgta tcctggagta tggaatacat  79680
acgatatctt cggtatcgag gccgctcgtg aatacttgtg cgaagccatg ttaaacacct  79740
atggagaagg gttcgattat ctgtatcagc cttgtgatct tctcgctagt ttactatgtg  79800
ctagttacga accagaatca gtgaataaat tcaagttcgg cgcagctagt actcttaaga  79860
gagctacgtt cggagacaat aaagcattgt taaacgcggc tcttcataaa aagtcagaac  79920
ctattaacga taatagtagc tgccactttt ttagcaaggt ccctaatata ggaactggat  79980
attacaaata ctttatcgac ttgggtcttc tcatgagaat ggaaaggaaa ctatctgata  80040
agatatcttc tcaaaagatc aaggaaatgg aagaaacaga agacttttaa ttcttatcaa  80100
taacatattt ttctatgatc tgtcttttaa acgatggatt ttccacaaat gcgcctctca  80160
agtccctcat agaatgatac acgtataaaa aatatagcat aggcaatgac tccttatttt  80220
tagacattag atatgccaaa atcatagccc cgcttctatt tactcccgca gcacaatgaa  80280
ccaacacggg ctcgtttcgt tgatcacatt tagataaaaa ggcggttacg tcgtcaaaat  80340
atttactaat atcggtagtt gtatcatcta ccaacggtat atgaataata ttaatattag  80400
agttaggtaa tgtatattta tccatcgtca aatttaaaac atatttgaac ttaacttcag  80460
atgatggtgc atccatagca tttttataat ttcccaaata cacattattg gttacccttg  80520
tcattatagt gggagatttg gctctgtgca tatctccagt tgaacgtagt agtaagtatt  80580
tatacaaact tttcttatcc atttataacg tacaaatgga taaaactact ttatcggtaa  80640
acgcgtgtaa tttagaatac gttagagaaa aggctatagt aggcgtacaa gcagccaaaa  80700
catcaacact tatattcttt gttattatat tggcaattag tgcgctatta ctctggtttc  80760
agacgtctga taatccagtc tttaatgaat taacgagata tatgcgaatt aaaaatacgg  80820
ttaacgattg gaaatcatta acggatagca aaacaaaatt agaaagtgat agaggtagac  80880
```

ttctagccgc tggtaaggat gatatattcg acttcaaatg tgtggatttc ggcgcctatt 80940
ttatagctat gcgattggat aagaaaacat atctgccgca agctattagg cgaggtactg 81000
gagacgcgtg gatggttaaa aaggcggcaa aggtcgatcc atctgctcaa caattttgtc 81060
agtatttgat aaaacacaag tctaataatg ttattacttg tggtaatgag atgttaaatg 81120
aattaggtta tagcggttat tttatgtcac cgcattggtg ttccgatttt agtaatatgg 81180
aatagtgtta gataaatgcg gtaacgaatg ttcctgtaag gaaccataac agcttagatt 81240
taacgttaaa gatgagcata aacataataa acaaaattac aatcaaactt ataacattaa 81300
tatcaaacaa tccaaaaaat gaaatcagtg gagtagtaaa cgcgtacata actcctggat 81360
aacgtttagc agctgccgtt cctattctag accaaaaatt cggtttcatg ttttcgaaac 81420
ggtattctgc aacaagtcga ggatcgtgtt ctacatattt ggcggcatta tccagtatct 81480
gcctattgat cttcatttcg ttttcaattc tggctatttc aaaataaaat cccgatgata 81540
gacctccaga ctttataatt tcatctacga tgttcagcgc cgtagtaact ctaataatat 81600
aggctgataa gctaacatca taccctcctg tatatgtgaa tatggcatga tttttgtcca 81660
ttacaagctc ggttttaact ttattgcctg taataatttc tctcatctgt aggatatcta 81720
ttttttgtc atgcattgcc ttcaagacgg gacgaagaaa cgtaatatcc tcaataacgt 81780
tatcgttttc tacaataact acatattcta ccttttttatt ttctaactcg gtaaaaaaat 81840
tagaatccca tagggctaaa tgtctagcga tatttctttt cgtttcctct gtacacatag 81900
tgttacaaaa ccctgaaaag aagtgagtat acttgtcatc atttctaatg tttcctccag 81960
tccactgtat aaacgcataa tccttgtaat gatctggatc atccttgact accacaacat 82020
ttctttttc tggcataact tcgttgtcct ttacatcatc gaacttctga tcattaatat 82080
gctcatgaac attaggaaat gtttctgatg gaggtctatc aataactggc acaacaataa 82140
caggagtttt caccgccgcc atttagttat tgaaattaat catatacaac tctttaatac 82200
gagttatatt ttcgtctatc cattgtttca cattgacata tttcgacaaa aagatataaa 82260
atgcgtattc caatgcttct ctgtttaatg aattactaaa atatacaaac acgtcactgt 82320
ctggcaataa atgatatctt agaatattgt aacaatgtaa ggaaccataa cagtttagat 82380
ttaacgttaa agatgagcat aaacataata aacaaaatta caatcaaacc tataacatta 82440
atatcaaaca atccaaaaaa tgaaatcagt ggagtagtaa acgcgtacat aactcctgga 82500
taacgtttag cagctgccgt tcctattcta gaccaaaaat ttggtttcat gttttcgaaa 82560
cggtattctg caacaagtcg gggatcgtgt tctacatatt tggcggcatt atccagtatc 82620
tgcctattga tcttcatttc gttttcgatt ctggctattt caaaataaaa tcccgatgat 82680
agacctccag actttataat ttcatctacg atgttcagcg ccgtagtaac tctaataata 82740
taggctgata agctaacatc ataccctcct gtatatgtga atatggcatg atttttgtcc 82800
attacaagct cggttttaac tttattgcct gtaataattt ctctcatctg taggatatct 82860
attttttgt catgcattgc cttcaagacg ggacgaagaa acgtaatatc ctcaataacg 82920
ttatcgtttt ctacaataac tacatattct accttttttat tttctaactc ggtaaaaaaa 82980
ttagaatccc atagggctaa atgtctagcg atatttcttt tcgtttcctc tgtacacata 83040
gtgttacaaa accctgaaaa gaagtgagta tacttgtcat catttctaat gtttcctcca 83100
gtccactgta taaacgcata atccttgtaa tgatctggat catccttgac taccacaaca 83160
tttcttttt ctggcataac ttcgttgtcc tttacatcat cgaacttctg atcattaata 83220

```
tgctcatgaa cattaggaaa tgtttctgat ggaggtctat caataactgg cacaacaata  83280
acaggagttt tcaccgccgc catttagtta ttgaaattaa tcatatacaa ctctttaata  83340
cgagttatat tttcgtctat ccattgtttc acatttacat atttcgacaa aaagatataa  83400
aatgcgtatt ccaatgcttc tctgtttaat gaattactaa aatatacaaa cacgtcactg  83460
tctggcaata aatgatatct tagaatattg taacaattta ttttgtattg cacatgttcg  83520
tgatctatga gttcttcttc gaatggcata ggatctccga atctgaaaac gtataaatag  83580
gagttagaat aataatattt gagagtattg gtaatatata aactctttag cggtataatt  83640
agttttttc tctcaatttc tatttttaga tgtgatggaa aaatgactaa ttttgtagca  83700
ttagtatcat gaactctaat caaaatctta atatcttcgt cacacgttag ctctttgaag  83760
tttttaagag atgcatcagt tggttctaca gatggagtag gtgcaacaat tttttgttct  83820
acacatgtat gtactggagc cattgtttta actataatgg tgcttgtatc gaaaaacttt  83880
aatgcagata gcggaagctc ttcgccgcga ctttctacgt cgtaattggg ttctaacgcc  83940
gatctctgaa tggatactag ttttctaagt tctaatgtga ttctctgaaa atgtaaatcc  84000
aattcctccg gcattataga tgtgtataca tcggtaaata aaactatagt atccaacgat  84060
cccttctcgc aaattctagt cttaaccaaa aaatcgtata taaccacgga gatggcgtat  84120
ttaagagtgg attcttctac cgttttgttc ttggatgtca tataggaaac tataaagtcc  84180
gcactactgt taagaatgat tactaacgca actatatagt ttaaattaag cattttggaa  84240
acataaaata actctgtaga cgatacttga ctttcgaata agtttgcaga caaacgaaga  84300
aagaacagac ctctcttaat ttcagaagaa aacttttttt cgtattcctg acgtctagag  84360
tttatatcaa taagaaagtt aagaattagt cggttaatgt tgtatttcat tacccaagtt  84420
tgagatttca taatattatc aaaagacatg ataatattaa agataaagcg ctgactatga  84480
acgaaatagc tatatggttc gctcaagaat atagtcttgt taaacgtgga aacgataact  84540
gtatttttaa tcacgtcagc ggcatctaaa ttaaatatag gtatatttat tccacacact  84600
ctacaatatg ccacaccatc ttcataataa ataaattcgt tagcaaaatt attaatttta  84660
gtgaaatagt tagcgtcaac tttcatagct tccttcaatc taatttgatg ctcacacggt  84720
gcgaattcca ctctaacatc ccttttccat gcctcaggtt catcgatctc tataatatct  84780
agtttttgc gtttcacaaa cacaggctcg tctctcgcga tgagatctgt atagtaacta  84840
tgtaaatgat aactagatag aaagatgtag ctatatagat gacgatcctt taagagaggt  84900
ataataactt taccccaatc agatagactg ttgttatggt cttcggaaaa agaattttta  84960
taaattttc cagtattttc caaatatacg tacttaacat ctaaaaaatc cttaatgata  85020
ataggaatgg ataatccgtc tattttataa agaaatacat atcgcacatt atactttttt  85080
ttggaaatgg gaataccgat gtgtctacat aaatatgcaa agtctaaata ttttttagag  85140
aatcttagtt ggtccaaatt cttttccaag tacggtaata gatttttcat attgaacggt  85200
atcttcttaa tctctggttc tagttccgca ttaaatgatg aaactaagtc actattttta  85260
taactaacga ttacatcacc tctaacatca tcatttacca gaatactgat cttcttttgt  85320
cgtaaataca tgtctaatgt gttaaaaaaa agatcataca agttatacgt catttcatct  85380
gtggtattct tgtcattgaa ggataaactc gtactaatct cttctttaac agcctgttca  85440
aatttatatc ctatatacga aaaaatagca accagtgttt gatcatccgc gtcaatattc  85500
tgttctatcg tagtgtataa caatcgtata tcttcttctg tgatagtcga tacgttataa  85560
aggttgataa cgaaaatatt tttatttcgt gaaataaagt catcgtagga ttttggactt  85620
```

```
atattcgcgt ctagtagata tgcttttatt tttggaatga tctcaattag aatagtctct  85680
ttagagtcca tttaaagtta caaacaacta ggaaattggt ttatgatgta taattttttt  85740
agtttttata gattctttat tctatactta aaaaatgaaa ataaatacaa aggttcttga  85800
gggttgtgtt aaattgaaag cgagaaataa tcataaatta tttcattatc gcgatatccg  85860
ttaagtttgt atcgtaatgg cgtggtcaat tacgaataaa gcggatacta gtagcttcac  85920
aaagatggct gaaatcagag ctcatctaaa aaatagcgct gaaaataaag ataaaaacga  85980
ggatattttc ccggaagatg taataattcc atctactaag cccaaaacca aacgagccac  86040
tactcctcgt aaaccagcgg ctactaaaag atcaaccaaa aaggaggaag tggaagaaga  86100
agtagttata gaggaatatc atcaaacaac tgaaaaaaat tctccatctc ctggagtcag  86160
cgacattgta gaaagcgtgg ccgctgtaga gctcgatgat agcgacgggg atgatgaacc  86220
tatggtacaa gttgaagctg gtaaagtaaa tcatagtgct agaagcgatc tctctgacct  86280
aaaggtggct accgacaata tcgttaaaga tcttaagaaa attattacta gaatctctgc  86340
agtatcgacg gttctagagg atgttcaagc agctggtatc tctagacaat ttacttctat  86400
gactaaagct attacaacac tatctgatct agtcaccgag ggaaaatcta aagttgttcg  86460
taaaaaagtt aaaacttgta agaagtaaat gcgtgcactt ttttataaag atggtaaact  86520
ctttaccgat aataattttt taaatcctgt atcagacgat aatccagcgt atgaggtttt  86580
gcaacatgtt aaaattccta ctcatttaac agatgtagta gtatatgaac aaacgtggga  86640
ggaggcgtta actagattaa tttttgtggg aagcgattca aaaggacgta gacaatactt  86700
ttacggaaaa atgcatgtac agaatcgcaa cgctaaaaga gatcgtattt ttgttagagt  86760
atataacgtt atgaaacgaa ttaattgttt tataaacaaa aatataaaga aatcgtccac  86820
agattccaat tatcagttgg cggtttttat gttaatggaa actatgtttt ttattagatt  86880
tggtaaaatg aaatatctta aggagaatga aacagtaggg ttattaacac taaaaaaataa  86940
acacatagaa ataagtcccg atgaaatagt tatcaagttt gtaggaaagg acaaagtttc  87000
acatgaattt gttgttcata agtctaatag actatataaa ccgctattga aactgacgga  87060
tgattctagt cccgaagaat ttctgttcaa caaactaagt gaacgaaagg tatacgaatg  87120
tatcaaacag tttggtatta gaatcaagga tctccgaacg tatggagtca attatacgtt  87180
tttatataat ttttggacaa atgtaaagtc catatctcct cttccgtcac caaaaaagtt  87240
aatagcgtta actatcaaac aaactgctga agtggtaggt catactccat caatttcaaa  87300
aagagcttat atggcaacga ctattttaga aatggtaaag gataaaaatt ttttagatgt  87360
agtatctaaa actacgttcg atgaattcct atctatagtc gtagatcacg ttaaatcatc  87420
tacggatgga tgatatagat ctttacacaa ataattacaa gaccgataaa tggaaatgga  87480
taagcgtatg aaatctctcg caatgacagc tttcttcgga gagctaagca cattagatat  87540
tatggcattg ataatgtcta tatttaaacg ccatccaaac aataccattt tttcagtgga  87600
taaggatggt cagtttatga ttgatttcga atacgataat tataaggctt ctcaatattt  87660
ggatctgacc ctcactccga tatctggaga tgaatgcaag actcacgcat cgagtatagc  87720
cgaacaattg gcgtgtgtgg atattattaa agaggatatt agcgaatata tcaaaactac  87780
tccccgtctt aaacgattta taaaaaaata ccgcaataga tcagatactc gcatcagtcg  87840
agatacagaa aagcttaaaa tagctctagc taaaggcata gattacgaat atataaaaga  87900
cgcttgttaa taagtaaatg aaaaaaaact agtcgtttat aataaaacac gatatggatg  87960
```

```
ccaacgtagt atcatcttct actattgcga cgtatataga cgctttagcg aagaatgctt  88020
cagaattaga acagaggtct accgcatacg aaataaataa tgaattggaa ctagtattta  88080
ttaagccgcc attgattact ttgacaaatg tagtgaatat ctctacgatt caggaatcgt  88140
ttattcgatt taccgttact aataaggaag gtgttaaaat tagaactaag attccattat  88200
ctaaggtaca tggtctagat gtaaaaaatg tacagttagt agatgctata gataacatag  88260
tttgggaaaa gaaatcatta gtgacggaaa atcgtcttca caaagaatgc ttgttgagac  88320
tatcgacaga ggaacgtcat atatttttgg attacaagaa atatggatcc tctatccgac  88380
tagaattagt caatcttatt caagcaaaaa caaaaaactt tacgatagac tttaagctaa  88440
aatattttct aggatccggt gcccaatcta aaagttcttt gttgcacgct attaatcatc  88500
caaagtcaag gcctaataca tctctggaaa tagaattcac acctagagac aatgaaacag  88560
ttccatatga tgaactaata aaggaattga cgactctctc gcgtcatata tttatggctt  88620
ctccagagaa tgtaattctt tctccgccta ttaacgcgcc tataaaaacc tttatgttgc  88680
ctaaacaaga tatagtaggt ttggatctgg aaaatctata tgccgtaact aagactgacg  88740
gcattcctat aactatcaga gttacatcaa acgggttgta ttgttatttt acacatcttg  88800
gttatattat tagatatcct gttaagagaa taatagattc cgaagtagta gtctttggtg  88860
aggcagttaa ggataagaac tggaccgtat atctcattaa gctaatagag cccgtgaatg  88920
ctatcagtga tagactagaa gaaagtaagt atgttgaatc taaactagtg gatatttgtg  88980
atcggatagt attcaagtca aagaaatacg aaggtccgtt tactacaact agtgaagtcg  89040
tcgatatgtt atctacatat ttaccaaagc aaccagaagg tgttattctg ttctattcaa  89100
agggacctaa atctaacatt gattttaaaa ttaaaaagga aaatactata gaccaaactg  89160
caaatgtagt atttaggtac atgtccagtg aaccaattat ctttggagaa tcgtctatct  89220
ttgtagagta taagaaattt agcaacgata aaggctttcc taaagaatat ggttctggta  89280
agattgtgtt atataacggc gttaattatc taaataatat ctattgtttg gaatatatta  89340
atacacataa tgaagtgggt attaagtccg tggttgtacc tattaagttt atagcagaat  89400
tcttagttaa tggagaaata cttaaaccta gaattgataa aaccatgaaa tatattaact  89460
cagaagatta ttatggaaat caacataata tcatagtcga acatttaaga gatcaaagca  89520
tcaaaatagg agatatcttt aacgaggata aactatcgga tgtgggacat caatacgcca  89580
ataatgataa atttagatta aatccagaag ttagttattt tacgaataaa cgaactagag  89640
gaccgttggg aattttatca aactacgtca agactcttct tatttctatg tattgttcca  89700
aaacattttt agacgattcc aacaaacgaa aggtattggc gattgatttt ggaaacggtg  89760
ctgacctgga aaaatacttt tatggagaga ttgcgttatt ggtagcgacg gatccggatg  89820
ctgatgctat agctagagga aatgaaagat acaacaaatt aaactctgga attaaaacca  89880
agtactacaa atttgactac attcaggaaa ctattcgatc cgatacattt gtctctagtg  89940
tcagagaagt attctatttt ggaaagttta atatcatcga ctggcagttt gctatccatt  90000
attcttttca tccgagacat tatgctaccg tcatgaataa cttatccgaa ctaactgctt  90060
ctggaggcaa ggtattaatc actaccatgg acggagacaa attatcaaaa ttaacagata  90120
aaaagacttt tataattcat aagaatttac ctagtagcga aaactatatg tctgtagaaa  90180
aaatagctga tgatagaata gtggtatata atccatcaac aatgtctact ccaatgactg  90240
aatacattat caaaaagaac gatatagtca gagtgtttaa cgaatacgga tttgttcttg  90300
tagataacgt tgatttcgct acaattatag aacgaagtaa aaagtttatt aatggcgcat  90360
```

ctacaatgga agatagaccg tctacaaaaa actttttcga actaaataga ggagccatta 90420
aatgtgaagg tttagatgtc gaagacttac ttagttacta tgttgtttat gtcttttcta 90480
agcggtaaat aataatatgg tatgggttct gatatccccg ttctaaatgc attaaataat 90540
tccaatagag cgatttttgt tcctatagga ccttccaact gtggatactc tgtattgtta 90600
atagatatat taatactttt gtcgggtaac agaggttcta cgtcttctaa aaataaaagt 90660
tttataacat ctggcctgtt cataaataaa aacttggcga ttctatatat actcttatta 90720
tcaaatctag ccattgtctt atagatgtga gctactgtag gtgtaccatt tgattttctt 90780
tctaatacta tatatttctc tcgaagaagt tcttgcacat catctgggaa taaaatacta 90840
ctgttgagta aatcagttat tttttttata tcgatattga tggacatttt tatagttaag 90900
gataataagt atcccaaagt cgataacgac gataacgaag tatttatact tttaggaaat 90960
cacaatgact ttatcagatt aaaattaaca aaattaaagg agcatgtatt tttttctgaa 91020
tatattgtga ctccagatac atatggatct ttatgcgtcg aattaaatgg gtctagtttt 91080
cagcacggtg gtagatatat agaggtggag gaatttatag atgctggaag acaagttaga 91140
tggtgttcta catccaatca tatatctaaa gatatacccg aagatatgca cactgataaa 91200
tttgtcattt atgatatata cacttttgac gctttcaaga ataaacgatt ggtattcgta 91260
caggtacctc cgtcgttagg agatgatagt catttgacta atccgttatt gtctccgtat 91320
tatcgtaatt cagtagccag acaaatggtc aataatatga tttttaatca agattcattt 91380
ttaaaatatt tattagaaca tctgattaga agccactata gagtttctaa acatataaca 91440
atagttagat acaaggatac cgaagaatta aatctaacga gaatatgtta taatagagat 91500
aagtttaagg cgtttgtatt cgcttggttt aacggcgttt cggaaaatga aaaggtacta 91560
gatacgtata aaaaggtatc taatttgata taatgaattc agtgactgta tcacacgcgc 91620
catatactat tacttatcac gatgattggg aaccagtaat gagtcaattg gtagagtttt 91680
ataacgaagt agccagttgg ctgctacgag acgagacgtc gcctattcct gataagttct 91740
ttatacagtt gaaacaaccg cttagaaata aacgagtatg tgtgtgcggt atagatccgt 91800
atccgaaaga tggaactggt gtaccgttcg aatcaccaaa ttttacaaaa aaatcaatta 91860
aggagatagc ttcatctata tctagattaa ccggagtaat tgattataaa ggttataacc 91920
ttaatataat agacggggtt ataccctgga attattactt aagttgtaaa ttaggagaaa 91980
caaaaagtca cgcgatctac tggggataaga tttccaagtt actgctgcag catataacta 92040
aacacgttag tgttctttat tgtttgggta aaacagattt ctcgaatata cgggcaaagt 92100
tagaatcccc ggtaactacc atagtcggat atcatccagc ggctagagac cgccaattcg 92160
agaaagatag atcatttgaa attatcaacg ttttactgga attagacaac aaggcaccta 92220
taaattgggc tcaagggttt atttattaat gctttagtga aattttaact tgtgttctaa 92280
atggatgcgg ctattagagg taatgatgtt atctttgttc ttaagactat aggtgtcccg 92340
tcagcgtgca gacaaaatga agatccaaga tttgtagaag catttaaatg cgacgagtta 92400
gaaagatata ttgagaataa tccagaatgt acactattcg aaagtcttag ggatgaggaa 92460
gcatactcta tagtcagaat tttcatggat gtagatttag acgcgtgtct agacgaaata 92520
gattatttaa cggctattca agattttatt atcgaggtgt caaactgtgt agctagattc 92580
gcgtttacag aatgcggtgc cattcatgaa aatgtaataa aatccatgag atctaatttt 92640
tcattgacta agtctacaaa tagagataaa acaagttttc atattatctt tttagacacg 92700

```
tataccacta tggatacatt gatagctatg aaacgaacac tattagaatt aagtagatca  92760
tctgaaaatc cactaacaag atcgatagac actgccgtat ataggagaaa aacaactctt  92820
cgggttgtag gtactaggaa aaatccaaat tgcgacacta ttcatgtaat gcaaccaccg  92880
catgataata tagaagatta cctattcact tacgtggata tgaacaacaa tagttattac  92940
ttttctctac aacaacgatt ggaggattta gttcctgata agttatggga accagggttt  93000
atttcattcg aagacgctat aaaaagagtt tcaaaaatat tcattaattc tataataaac  93060
tttaatgatc tcgatgaaaa taattttaca acggtaccac tggtcataga ttacgtaaca  93120
ccttgtgcat tatgtaaaaa acgatcgcat aaacatccgc atcaactatc gttggaaaat  93180
ggtgctatta gaatttacaa aactggtaat ccacatagtt gtaaagttaa aattgttccg  93240
ttggatggta ataaactgtt taatattgca caaagaattt tagacactaa ctctgtttta  93300
ttaaccgaac gaggagacca tatagtttgg attaataatt catggaaatt taacagcgaa  93360
gaacccttga taacaaaact aattttgtca ataagacatc aactacctaa ggaatattca  93420
agcgaattac tctgtccgag gaaacgaaag actgtagaag ctaacatacg agacatgtta  93480
gtagattcag tggagaccga tacctatccg gataaacttc cgtttaaaaa tggtgtattg  93540
gacctggtag acggaatgtt ttactctgga gatgatgcta aaaaatatac gtgtactgta  93600
tcaaccggat ttaaatttga cgatacaaag ttcgtcgaag acagtccaga aatggaagag  93660
ttaatgaata tcattaacga tatccaacca ttaacggatg aaaataagaa aaatagagag  93720
ctatatgaaa aaacattatc tagttgttta tgcggtgcta ccaaaggatg tttaacattc  93780
ttttttggag aaactgcaac tggaaagtcg acaaccaaac gtttgttaaa gtctgctatc  93840
ggtgacctgt ttgttgagac gggtcaaaca attttaacag atgtattgga taaaggacct  93900
aatccattta tcgctaacat gcatttgaaa agatctgtat tctgtagcga actacctgat  93960
tttgcatgta gtgggtcaaa gaaaatcaga tctgataata ttaaaaagtt gacagaacct  94020
tgtgtcattg gaagaccgtg tttctccaat aaaattaata atagaaacca tgcgacaatc  94080
attatcgata ctaattacaa acctgttttt gataggatag ataacgcatt aatgagaaga  94140
attgccgtcg tgcgattcag aacacacttt tctcaacctt ctggtagaga ggctgctgaa  94200
aataatgacg cgtacgataa agtcaaacta ttagacgagg ggttagatgg taaaatacaa  94260
aataatagat atagattcgc atttctatac ttgttggtga aatggtacag aaaatatcat  94320
gttcctatta tgaaactata tcctacaccc gaagagattc ctgactttgc attctatctc  94380
aaaataggta ctctgttggt atctagctct gtaaagcata ttccattaat gacggacctc  94440
tccaaaaagg gatatatatt gtacgataat gtggtcactc ttccgttgac tactttccaa  94500
cagaaaatat ccaagtattt taattctaga ctatttggac acgatataga gagcttcatc  94560
aatagacata agaaatttgc caatgttagt gatgaatatc tgcaatatat attcatagag  94620
gatatttcat ctccgtaaat atatgctcat atatttatag aagatatcac atatctaaat  94680
gaataccgga atcatagatt tatttgataa tcatgttgat agtataccaa ctatattacc  94740
tcatcagtta gctactctag attatctagt tagaactatc atagatgaga acagaagcgt  94800
gttattgttc catattatgg gatcaggtaa aacaataatc gctttgttgt tcgccttggt  94860
agcttccaga tttaaaaagg tttacattct agtgccgaac atcaacatct taaaaatttt  94920
caattataat atgggtgtag ctatgaactt gtttaatgac gaattcatag ctgagaatat  94980
ctttattcat tccacaacaa gtttttattc tcttaattat aacgataacg tcattaatta  95040
taacggatta tctcgctaca ataactctat ttttatcgtt gatgaggcac ataatatctt  95100
```

```
tgggaataat actggagaac ttatgaccgt gataaaaaat aaaaacaaga ttcctttttt  95160
actattgtct ggatctccca ttactaacac acctaatact ctgggtcata ttatagattt  95220
aatgtccgaa gagacgatag attttggtga aattattagt cgtggtaaga aagtaattca  95280
gacacttctt aacgaacgcg gtgtgaatgt acttaaggat ttgcttaaag gaagaatatc  95340
atattacgaa atgcctgata aagatctacc aacgataaga tatcacggac gtaagtttct  95400
agatactaga gtagtatatt gtcacatgtc taaacttcaa gagagagatt atatgattac  95460
tagacgacag ctatgttatc atgaaatgtt tgataaaaat atgtataacg tgtcaatggc  95520
agtattggga caacttaatc tgatgaataa tttagatact ttatttcagg aacaggataa  95580
ggaattgtac ccaaatctga aaataaataa tggcgtgtta tacggagaag aattggtaac  95640
gttaaacatt agttccaaat ttaaatactt tattaatcgg atacagacac tcaacggaaa  95700
acattttata tacttttcta attctacata tggcggattg gtaattaaat atatcatgct  95760
cagtaatgga tattctgaat ataatggttc tcagggaact aatccacata tgataaacgg  95820
caaaccaaaa acatttgcta tcgttactag taaaatgaaa tcgtctttag aggatctatt  95880
agatgtgtat aattctcctg aaaacgatga tggtagtcaa ttgatgtttt tgttttcatc  95940
aaacattatg tccgaatcct atactctaaa agaggtaagg catatttggt ttatgactat  96000
cccagatact ttttctcaat acaaccaaat tcttggacga tctattagaa aattctctta  96060
cgccgatatt tctgaaccag ttaatgtata tcttttagcc gccgtatatt ccgatttcaa  96120
tgacgaagtg acgtcattaa acgattacac acaggatgaa ttaattaatg ttttaccatt  96180
tgacatcaaa aagctgttgt atctaaaatt taagacgaaa gaaacgaata gaatatactc  96240
tattcttcaa gagatgtctg aaacgtattc tcttccacca catccatcaa ttgtaaaagt  96300
tttattggga gaattggtca gacaattttt ttataataat tctcgtatta agtataacga  96360
taccaagtta cttaaaatgg ttacatcagt tataaaaaat aaagaagacg ctaggaatta  96420
catagatgat attgtaaacg gtcacttctt tgtatcgaat aaagtatttg ataaatctct  96480
tttatacaaa tacgaaaacg atattattac agtaccgttt agactttcct acgaaccatt  96540
tgtttgggga gttaactttc gtaaagaata taacgtggta tcttctccat aaaactgatg  96600
agatatataa agaaataaat gtcgagcttt gttaccaatg gataccttc cgttacattg  96660
gaacctcatg agctgacgtt agacataaaa actaatatta ggaatgccgt atataagacg  96720
tatctccata gagaaattag tggtaaaatg gccaagaaaa tagaaattcg tgaagacgtg  96780
gaattacctc tcggcgaaat agttaataat tctgtagtta taaacgttcc gtgtgtaata  96840
acctacgcgt attatcacgt tggggatata gtcagaggaa cattaaacat cgaagatgaa  96900
tcaaatgtaa ctattcaatg tggagattta atctgtaaac taagtagaga ttcgggtact  96960
gtatcattta gcgattcaaa gtactgcttt tttcgaaatg gtaatgcgta tgacaatggc  97020
agcgaagtca ctgccgttct aatggaggct caacaaggta tcgaatctag ttttgttttt  97080
ctcgcgaata tcgtcgactc ataaaaaaga gaatagcggt aagtataaac acgaatacta  97140
tggcaataat tgcgaatgtt ttattctctt cgatatattt ttgataatat gaaaaacatg  97200
tctctctcaa atcggacaac catctcataa aatagttctc gcgcgctgga gaggtagttg  97260
ccgctcgtat aatctctcca gaataatata cttgcgtgtc gtcgttcaat ttatacggat  97320
ttctatagtt ctctgttata taatgcggtt tgccctcatg attagacgac gacaatagtg  97380
ttctaaattt agatagttga tcagaatgaa tgtttattgg cgttggaaaa attatccata  97440
```

```
cagcgtctgc agagtggttg atagttgttc ctagatatgt aaaataatcc aacttactag  97500
gcagcaaatt gtctagataa aatactgaat caaacggtgc agacgtattg gcggatctaa  97560
tggaatccaa ttgattaact atcttttgaa aatatacatt tttatgatcc aatacttgta  97620
agaatataga aataatgata agtccatcat cgtgtttttt tgcctcttca taagaactat  97680
atttttcttt attccaatga acaagattaa tctctccaga gtatttgtac acatctatca  97740
agtgattgga tccataatcg tcttcctttc cccaatatat atgtagtgat gataacacat  97800
attcattggg gagaaaccct ccacttatat atcctccttt aaaattaatc cttactagtt  97860
ttccagtgtt ctggatagtg gttggtttcg actcattata atgtatgtct aacggcttca  97920
atcgcgcgtt agaaattgct tttttagttt ctatattaat aggagatagt tgttgcggca  97980
tagtaaaaat gaaatgataa ctgtttaaaa atagctctta gtatgggaat tacaatggat  98040
gaggaagtga tatttgaaac tcctagagaa ttaatatcta ttaaacgaat aaaagatatt  98100
ccaagatcaa aagacacgca tgtgtttgct gcgtgtataa caagtgacgg atatccgtta  98160
ataggagcta gaagaacttc attcgcgttc caggcgatat tatctcaaca aaattcagat  98220
tctatcttta gagtatccac taaactatta cggtttatgt actacaatga actaagagaa  98280
atctttagac ggttgagaaa aggttctatc aacaatatcg atcctcactt tgaagagtta  98340
atattattgg gtggtaaact agataaaaag gaatctatta aagattgttt aagaagagaa  98400
ttaaaagagg aaagtgatga acgtataaca gtaaaagaat ttggaaatgt aattctaaaa  98460
cttacaacac gggataaatt atttaataaa gtatatataa gttattgcat ggcgtgtttt  98520
attaatcaat cgttggagga tttatcgcat actagtattt acaatgtaga aattagaaag  98580
attaaatcat taaatgattg tattaacgac gataaatacg aatatctgtc ttatatttat  98640
aatatgctag ttaatagtaa atgaactttt acagatctag tataattagt cagattatta  98700
agtataatag acgactagct aagtctatta tttgcgagga tgactctcaa attattacac  98760
tcacggcatt cgttaaccaa tgcctatggt gtcataaacg agtatccgtg tccgctattt  98820
tattaactac tgataacaaa atattagtat gtaacagacg agatagtttt ctctattctg  98880
aaataattag aactagaaac atgtttagaa agaaacgatt atttctgaat tattccaatt  98940
atttgaacaa acaggaaaga agtatactat cgtcattttt ttctctagat ccagctacta  99000
ctgataatga tagaatagac gctatttatc cgggtggcat acccaaaagg ggtgagaatg  99060
ttccagagtg tttatccagg gaaattaaag aagaagttaa tatagacaat tcttttgtat  99120
tcatagacac tcggtttttt attcatggca tcatagaaga taccattatt aataaatttt  99180
ttgaggtaat cttctttgtc ggaagaatat ctctaacgag tgatcaaatc attgatacat  99240
ttaaaagtaa tcatgaaatc aaggatctaa tatttttaga tccgaattca ggtaatggac  99300
tccaatacga aattgcaaaa tatgctctag atactgcaaa acttaaatgt tacggccata  99360
gaggatgtta ttatgaatca ttaaaaaaat taactgagga tgattgatta aaaaatataa  99420
attaatttac catcgtgtat ttttataacg ggattgtccg gcatatcatg tagatagtta  99480
ccgtctacat cgtatactcg accatctacg cctttaaatc ctctatttat tgacattaat  99540
ctattagaat tggaatacca aatattagta ccctcaatta gtttattggt aatatttttt  99600
ttagacgata gatcgatggc tcttgaaacc aaggttttcc aaccggactc attgtcgatc  99660
ggtgagaagt ctttttcatt agcatgaatc cattctaatg atgtatgttt aaacactcta  99720
aacaattgga caaattcttt tgatttgctt tgaatgattt caaataggtc ttcgtctaca  99780
gtaggcatac cattagataa tctagccatt ataaagtgca cgtttacata tctacgttct  99840
```

```
ggaggagtaa gaacgtgact attgagacga atggctcttc ctactatctg acgaagagac  99900
gcctcgttcc atgtcatatc taaaatgaag atatcattaa ttgagaaaaa actaataccc  99960
tcgcctccac tagaagagaa tacgcatgtt ttaatgcatt ctccgttagt gtttgattct 100020
tggttaaact cagccaccgc cttgattcta gtatcttttg ttctagatga gaactctata 100080
ttagagatac caaagacttt gaaatatagt aataagattt ctattcctga ctgattaaca 100140
aatggttcaa agactagaca tttaccatgg gatgctaata ttcccaaaca tacatctata 100200
aatttgacgc ttttctcttt taattcagta aatagagaga tatcagccgc actagcatcc 100260
cctttcaata gttctccctt tttaaaggta tctaatgcgg atttagaaaa ctctctatct 100320
cttaatgaat ttttaaaatc attatatagt gttgctatct cttgcgcgta ttcgcccgga 100380
tcacgatttt gtctttcagg aaagctatcg aacgtaaacg tagtagccat acgtctcaga 100440
attctaaatg atgatatacc tgtttttatt tcagcgagtt tagccttttg ataaatttct 100500
tcttgctttt tcgacatatt aacgtatcgc attaatactg ttttcttagc gaatgatgca 100560
gacccttcta cgtcatcaaa aatagaaaac tcgttattaa ctatatacga acatagtcct 100620
cctagtttgg agactaattc tttttcatcg actagacgtt tattctcaaa tagtgattgg 100680
tgttgtaagg atcctggtcg tagtaagtta accaacatgg tgaattcttg cacactattg 100740
acgataggtg tagccgataa acaaatcatc ttatggtttt ttaacgcaat ggtcttagat 100800
aaaaaattat atactgaacg agtaggacgg atcttaccat cttctttgat taatgattta 100860
gaaatgaagt tatgacattc atcaatgatg acgcatattc tactcttgga attaatagtt 100920
ttgatattag taaaaaattt atttctaaaa ttttgatcat cgtaattaat aaaaatacaa 100980
tccttcgtta tctctggagc gtatctgagt atagtgttca tccaaggatc ttctatcaaa 101040
gcctttttca ccaataagat aatagcccaa ttcgtataaa tatccttaag atgtttgaga 101100
atatatacag tagtcattgt tttaccgaca cccgtttcat ggaacaataa aagagaatgc 101160
atactgtcta atcctaagaa aactcttgct acaaaatgtt gataatcctt gaggcgtact 101220
acgtccgacc ccatcatttc aacgggcata ttagtagttc tgcgtaaggc ataatcgata 101280
taggccgcgt gtgatttact catttatgag tgataagtaa taactatgtt ttaaaaatca 101340
cagcagtagt ttaactagtc ttctctgatg tttgttttcg atactttttg aatcagaagt 101400
catactagaa taaagcaacg agtgaacgta atagagagct tcgtatactc tattcgaaaa 101460
ctctaagaac ttattaatga attccgtatc cactggattg tttaaaatac taaattgaac 101520
actgttcaca tccttccaag aagaagactt agtgacggac ttaacatgag acataaataa 101580
atccaaattt tttttacaaa catcactagc caccataatg gcgctatctt tcaaccagct 101640
atcgcttacg cattttagca gtctaacatt tttaaagaga ctacaatata ttctcatagt 101700
atcgattaca cctctaccga ataaagttgg aagtttaata atacaatatt tttcgtttac 101760
aaaatcaaat aatggtcgaa acacgtcgaa ggttaacatc ttataatcgc taatgtatag 101820
attgttttca gtgagatgat tattagattt aatagcatct cgttcacgtt tgaacagttt 101880
attgcgtgcg ctgaggtcgg caactacggc gtccgcttta gtactcctcc cataatactt 101940
tacgctatta atctttaaaa tttcatagac tttatctaga tcgctttctg gtaacatgat 102000
atcatgtgta aaaagtttta acatgtcggt cggcattcta tttagatcat taactctaga 102060
aatctgaaga aagtaattag ctccgtattc cagactaggt aatgggcttt tacctagaga 102120
cagattaagt tctggcaatg tttcataaaa tggaagaagg acatgcgttc cctcccggat 102180
```

atttttttaca atttcatcca tttacaactc tatagtttgt tttcattatt attagttatt 102240
atctcccata atcttggtaa tacttacccc ttgatcgtaa gataccttat acaggtcatt 102300
acatacaact accaattgtt tttgtacata atagattgga tggttgacat ccatggtgga 102360
ataaactact cgaacagata gtttatcttt cccccctagat acattagccg taatagttgt 102420
cggcctaaag aatatctttg gtgtaaagtt aaaagttagg gttcttgttc cattattgct 102480
ttttgtcagt agttcattat aaattctcga gatgggtccg ttctctgaat atagaacatc 102540
atttccaaat ctaacttcta gtctagaaat aatatcggtc ttattcttaa aatctattcc 102600
cttgatgaag ggatcgttaa tgaacaaatc cttggccttt gattcggctg atctattatc 102660
tccgttatag acgttacgtt gactagtcca aagacttaca ggaatagatg tatcgatgat 102720
gttgatacta tgtgatatgt gagcaaagat tgttctctta gtggcatcac tatatgttcc 102780
agtaatggcg gaaaactttt tagaaatgtt atatataaaa gaattttttc gtgttccaaa 102840
cattagcaga ttagtatgaa gataaacact catattatca ggaacattat caatttttac 102900
atacacatca gcatcttgaa tagaaacgat accatcttct ggaacctcta cgatctcggc 102960
agactccgga taaccagtcg gtgggccatc gctaacaata actagatcat ccaacaatct 103020
actcacatat gcatctatat aatctttttc atcttgtgag taccctggat acgaaataaa 103080
tttattatcc gtatttccat aataaggttt agtataaaca gagagagatg ttgccgcatg 103140
aacttcagtt acagtcgccg ttggttggtt tatttgacct attactctcc taggtttctc 103200
tataaacgat ggtttaattt gtacattctt aaccatatat ccaataaagc tcaattcagg 103260
aacataaaca aattctttgt tgaacgtttc aaagtcgaac gaagagtcac gaataacgat 103320
atcggatact ggattgaagg ttaccgttac ggtaattttt gaatcggata gtttaagact 103380
gctgaatgta tcttccacat caaacggagt tttaatataa acgtatactg tagatggttc 103440
tttaatagtg tcattaggag ttaggccaat agaaaatatca ttaagttcac tagaatatcc 103500
agagtgtttc aaagcaattg tattattgat acaattatta tataattctt cgccctcaat 103560
ttcccaaata acaccgttac acgaagagat agatacgtga ttaatacatt tatatccaac 103620
atatggtacg taactgaatc ttcccatacc tttaacttct ggaagttcca aactcagaac 103680
caaatgatta agcgcagtaa tatactgatc cctaatttcg aagctagcga tagcctgatt 103740
gtctggacca tcgtttgtca taactccgga tagagaaata tattgcggca tatataaagt 103800
tggaatttga ctatcgactg cgaagacatt agaccgttta atagagtcat ccccaccgat 103860
caaagaatta atgatagtat tattcatttt ctatttaaaa tggaaaaagc ttacaataaa 103920
ctccgtagag aaatatctat aatttgtgag ttttccttaa agtaacagct tccgtaaacg 103980
ccgtctttat ctcttagtag gtttattgta tttatgacct tttccttatc ttcatagaat 104040
actaaaggca acaaagaaat ttttggttct tctctaagag ctacgtgaga cttaaccata 104100
gaagccaacg aatccctaca tattttagaa cagaaatacc ctacttcacc acccttgtat 104160
gtctcaatac taataggtct aaaaaccaaa tcttgattac aaaaccaaca cttatcaatt 104220
acactatttg tcttaataga cacatctgcc atagatttat aatactttgg tagtatacaa 104280
gcgagtgctt cttctttagc gggcttaaag actgctttag gtgctgaaat aaccacatct 104340
ggaaggctta ctcgcttagc catttaatta cggaactatt tttttatact tctaatgagc 104400
aagtagaaaa cctctcatct acaaaaaacgt actcgtgtcc ataatcctct accatagtta 104460
cacgtttttt agatctcata tgtgctaaaa agttttccca tactaattgg ttactattat 104520
ttttcgtata atttttaaca gtttgaggtt ttagattttt agttacagaa gtgatatcga 104580

```
atattttatc caaaaagaat gaataattaa ttgtcttaga aggagtgttt tcttggcaaa 104640
agaataccaa gtgcttaaat atttctacta cttcattaat cttttctgta ctcagattca 104700
gtttctcatc ttttacttga ttgattattt caaagactaa cttataatcc tttttattta 104760
ttctctcgtt agccttaaga aaactagata caaaatttgc atctacatca tccgtggata 104820
tttgattttt ttccatgata tccaagagtt ccgagataat ttctccagaa cattgatgag 104880
acaataatct ccgcaataca tttctcaaat gaataagttt attagacacg tggaagtttg 104940
actttttttg tacctttgta catttttgaa ataccgactc gcaaaaaata caatattcat 105000
atccttgttc agatactata ccgttatgtc tacaaccgct acataatcgt agattcatgt 105060
taacactcta cgtatctcgt cgtccaatat tttatataaa aacattttat ttctagacgt 105120
tgccagaaaa tcctgtaata tttttagttt tttgggctgt gaataaagta tcgccctaat 105180
attgttaccg tcttccgcca atatagtagt taaattatcc gcacatgcag aagaacaccg 105240
cttaggcgga ttcagtacaa tgttatattt ttcgtaccaa ctcatttaaa tatcataatc 105300
taaaatagtt ctgtaatatg tctagcgcta atatattgat cataatcctg tgcataaatt 105360
aagatacaac aatgtctcga aatcatcgac atggcttctt ccatagttag aagatcgtcg 105420
tcaaagttag caacgtgatt catcaacatt tgctgttttg aggcagcaaa tactgaaccg 105480
tcgccattca accattcata aaaaccatcg tctgaatcca ttgataattt cttgtactgg 105540
tttttgagag ctcgcatcaa tctagcattt ctagctcccg gattgaaaac agaaagagga 105600
tcgtacatcc agggtccatt ttctgtaaat agaatcgtat aatgtccctt caagaagata 105660
tcagacgatc cacaatcaaa gaattggtct ccgagtttgt aacaaactgc ggactttaac 105720
ctatacatga taccgtttag cataatttct ggtgatacgt caatcggagt atcatctatt 105780
agagatctaa agccggtgta acattctcca ccaaacatat tcttattctg acgtcgttct 105840
acataaaaca tcattgctcc attaacgata acaggggaat gaacagcact acccatcaca 105900
ttagttccca atggatcaat gtgtgtaact ccagaacatc ttccatagcc tatgttagga 105960
ggagcgaaca ccactcttcc actattgcca tcgaatgcca tagaataaat atccttggaa 106020
ttgatagaaa tcggactgtc ggatgttgtg atcatcttca taggattaac aactatgtat 106080
ggtgccgcct gaagtttcat atcgtaactg atgccgttta taggtctagc cacagaaacc 106140
aacgtaggtc taaatccaac tatagacaaa atagaagcca atatctgttc ctcatctgtc 106200
ataacttgag agcatccagt atgaataatc ttcattagat ggggatctac cgcatcatca 106260
tcgttacaat aaaaaattcc cattctaatg ttcataattg cttttctaat catggtatgc 106320
atgtttgctc tctgaatctc tgtggaaatt agatctgata cacctgtaat cactatcgga 106380
ttatcctccg taagacgatt aaccaacaac atataattat aagactttac ttttctaaat 106440
tcataaagtt gctggattag gctataggtg tctccatgta catacgcgtt ctcgagcgca 106500
ggaagtttaa taccgaatag tgccatcaga ataggatgaa tatagtaatt agtttctggt 106560
tttctataaa taaaagacaa atcttgtgaa ctagacatat cggtaaaatg catggattgg 106620
aatcgtgtag tcgacagaag aatatgatga ttagatggag agtatatttt atctaactct 106680
ttgagttggt caccgattct aggactagct cgagaatgaa taagtactaa aggatgagta 106740
catttcacag aaacactagc attgttcaat gtgctcttta catgggtaag gagttgaaat 106800
agctcgtttc tatttgttct gacaatattt agtttattca taatgttaag catatcctga 106860
atagtaaagt tagatgtgtc atacttgtta gtagttagat atttagcaat tgcattccca 106920
```

```
tcatttctca atctcgtact ccaatcatgt gtagatgcta cttcgtcgat ggaaaccata 106980
caatcctttt tgataggctg ttgagattga tcatttcctg cacgtttagg tttggtacgt 107040
tgatttctag cccctgcgga tataaagtca tcgtctacaa tttgggacaa tgaattgcat 107100
acactacaag acaaagattt atcagaagtg tgaatatgat cttcatctac caaagaaaga 107160
gtttgattag tataactaga ttttagtcct gcgttagatg ttaaaaaaac atcgctattg 107220
accacggctt ccattattta tattcgtagt ttttactcga aagcgtgatt ttaatatcca 107280
atcttattac ttttggaatc gttcaaaacc tttgactagt tgtagaattt gatctattgc 107340
cctacgcgta tactcccttg catcatatac gttcgtcacc agatcgtttg tttcggcctg 107400
aagttggtgc atatctcttt caacattcga catgagatcc ttaagggcca tatcgtctag 107460
attttgttga gatgctgctc ctggatttgg attttgttgt gctgttgtac atactgtacc 107520
accagtaggt gtaggagtac atacagtggc cacaatagga ggttgagaaa gtgtaaccgt 107580
tggagtagta caagaaatac ttccatccga ttgttgtgta catgtagttg ttggtaacgt 107640
ctgagaaggt tgggtagatg gcggcgtcgt cgttttttga tctttattaa atttagagat 107700
aatatcctga acagcattgc tcggcgtcaa cgctggaagg agtgaactcg ccggcgcatc 107760
agtatcttca gacagccaat caaaaagatt agacatatca gatgatgtat tagtttgttg 107820
tcgtggtttt ggtgtaggag cagtactact aggtagaaga ataggagccg atgtagctgt 107880
tggaaccggc tgtggagtta tatgaatagt tggttgtagc ggttggatag gctgtctgct 107940
ggcggccatc atattatctc tagctagttg ttctcgcaac tgtctttgat aatacgactc 108000
ttgagacttt agtcctattt caatcgcttc atcctttttc gtatccggat ccttttcttc 108060
agaataatag attgacgact ttggtgtaga ggattctgcc agcctctgtg agaacttgtt 108120
aaagaagtcc atttaaggct ttaaaattga attgcgatta taagattaaa tggcagacac 108180
agacgatatt atcgactatg aatccgatga tctcaccgaa tacgaggatg atgaagaaga 108240
ggaagaagat ggagagtcac tagaaactag tgatatagat cccaaatctt cttataagat 108300
tgtagaatca gcatccactc atatagaaga tgcgcattcc aatcttaaac atatagggaa 108360
tcatatatct gctcttaaac gacgctatac tagacgtata agtctatttg aaatagcggg 108420
tataatagca gaaagctata acttgcttca acgaggaaga ttacctctag tttcagaatt 108480
ttctgacgaa acgatgaagc aaaatatgct acatgtaatt atacaagaga tagaggaggg 108540
ttcttgtcct atagtcatcg aaaagaacgg agaattgttg tcggtaaacg attttgacaa 108600
agatggtcta aaattccatc tagactatat tatcaaaatt tggaaacttc aaaaacgata 108660
ttagaattta tacgaatatc gttctctaaa tgtcacaatc aagtctcgca tgttcagcaa 108720
tttattgtcg tactttatat cgtgttcatt aacgatatct tgcaaaatag taatgattct 108780
atcttccttc gatagatatt cttcagagat tattgtctta tattctttct tgttatcaga 108840
tatgaatttg ataagacttt gaacattatt gatacccgtc tgtttaattt tttctacaga 108900
tattttagtt ttggcagatt ctatcgtatc tgtcaataga catccaacat cgacattcga 108960
cgtcaattgt ctataaatca acgtataaat tttagaaata acattagcga attgttgtgc 109020
gttgatgtcg ttattctgaa acagtatgat tttaggtagc attttcttaa caaagagaac 109080
gtatttattg ttactcagtt gaacagatga tatatccaga ttactaacgc atctgattcc 109140
gtataccaaa ctttcagaag aaatggtata caattgtttg tattcattca atgtctcttt 109200
ttcagaaatt agtttagagt cgaatactgc aataattttc aagagatagt tttcatcaga 109260
taagatttta tttagtgtag atatgataaa actattgttt tgttggagaa cttgatacgc 109320
```

```
cgcgttctct gtagtcgacg ctctcaaatg ggaaacaatc tccattattt ttttggaatc 109380
ggatactata tcttcggtat cttgacgcag tctagtatac atagagttaa gagagattag 109440
agtttgtaca ttaagcaaca tgtctctaaa tgtggctaca aacttttcct ttttcacatc 109500
atctagttta ttatataccg atttcacaac ggcaccagat ttaaggaacc agaatgaaaa 109560
actctgataa ctacaatatt tcatcatagt tacgatttta tcatcttcta tagttggtgt 109620
aatagcgcat accttttttct ccaagactgg aaccaacgtc ataaaaatgt ttaaatcaaa 109680
atccatatca acatctgatg cgctaagacc agtctcgcgt tcaagattat ctttactaat 109740
ggtgacgaac tcatcgtata aaactctaag tttgtccatt atttatttac agatttagtt 109800
gtttaattta tttgtgctct tccagagttg ggatagtatt tttctaacgt cggtattata 109860
ttattaggat ctacgttcat atgtatcata atattaatca tccacgtttt gataaatcta 109920
tctttagctt ctgaaataac gtatttaaac aaaggagaaa aatatttagc tacggcatca 109980
gacgcaataa catttttttgt aaatgtaacg tatttagacg acagatcttc gttaaaaagt 110040
tttccatcta tgtagaatcc atcggttgtt aacaccattc ccgcgtcaga ttgaatagga 110100
gtttgaatag tttgttttgg aaatagatcc ttcaataact tatagttggg tgggaaaaaa 110160
tcgattttat cactagactc tttctttttt actatcatta cctcatgaac tatttcttga 110220
atgagtatat gtattttctt tcctatatcg gacgcgttca ttggaaaata taccatgtcg 110280
ttaactataa gaatattttt atcctcgttt acaaactgaa taatatcaga tgtagttcgt 110340
aaacgaacta tatcatcacc agcacaacat ctaactatat gatatccact agtttccttt 110400
agccgtttat tatcttgttc catattagca gtcattccat catttaagaa ggcgtcaaag 110460
ataataggga gaaatgacat tttggattct gttacgactt taccaaaatt aaggatatac 110520
ggacttacta tctttttctc aacgtcaatt tgatgaacac acgatgaaaa tgtgcttcta 110580
tgagattgat catgtagaaa acaacaaggg atacaatatt tccgcatatc atgaaatata 110640
ttaagaaatc ccaccttatt atatttcccc aaaggatcca tgcacgtaaa cattatgccg 110700
ttatcattaa taaagacttc tttctcatcg gatctgtaaa agttgttact gatttttttc 110760
attccaggat ctagataatt aataatgatg ggttttctat tcttattctt tgtattttgg 110820
catatcctag accagtaaac agtttccact ttggtaaaat cagcagactt ttgaacgcta 110880
ttaaacatgg cattaatggc aataactaaa aatgtaaaat atttttctat gttaggaata 110940
tggtttttca ctttaataga tatatggttt ttggccaaaa tgatagatat tttttttatcc 111000
gaggatagta aaatattatt agtcgccgtc tctataaaaa tgaagctagt ctcgatatcc 111060
aattttattc tagaattgat aggagtcgcc aaatgtacct tatacgttat atctcccttg 111120
atgcgttcca tttgtgtatc tatatcggac acaagatctg taaatagttt tacgttatta 111180
atcatcacgg tatcgccgtc gctagataac gctaatgtac catccaagtc ccaaatggag 111240
agatttaact gttcatcgtt tagaataaaa tgattaccgg tcatattaat aaagtgttca 111300
tcgtatctag ataacaacga cttataatta atgtccaagt cttgaactcg ctgaatgatc 111360
ttttttaacc cagttagttt tagattggta cgaaatatat tgttaaactt tgattctaca 111420
gtaatgtcca aatctagttg tggaaatact tccatcaaca ttgtttcaaa cttgataata 111480
ttattatcta catcttcgta cgatccaaat tccggaatag atgtatcgca cgctctggcc 111540
acccagataa ccaaaaagtc acacgctcca ggatatacat tgtataaaaa gctatcgttt 111600
tttagtaggg ttttttttctg cgtgtatacg aagggattaa aaatagtatt atcaacgtaa 111660
```

-continued

```
ctatattcca aattattctt atgagaatag ataataatat cgtccttaat atctaacaaa 111720
tttcctaaat atccctttaa ttgagtcatt cgaagcgtca atagaatatg tctcttaact 111780
atttccggct gttgtatatt taaatgactt cgtaaaaaat aatatatggg cgacttctca 111840
tctatgtaat catatggagt gagatatagg gctcgttcta cctcctgccc cttacccacc 111900
tgtaatacca attgcggact tactatatat cgcatattta tatcgtgggg taaagtgaaa 111960
atctactacc gatgatgtaa gtcttacaat gttcgaacca gtaccagatc ttaatttgga 112020
ggcctccgta gaactagggg aggtaaatat agatcaaaca acacctatga taaaggagaa 112080
tagcggtttt atatcccgca gtagacgtct attcgcccat agatctaagg atgatgagag 112140
aaaactagca ctacgattct ttttacaaag actttatttt ttagatcata gagagattca 112200
ttatttgttc agatgcgttg acgctgtaaa agacgtcact attaccaaaa aaaataacat 112260
tatcgtggcg ccttatatag cacttttaac tatcgcatca aaaggatgca aacttacaga 112320
aacaatgatt gaagcattct ttccagaact atataatgaa catagtaaga aatttaaatt 112380
caactctcaa gtatccatca tccaagaaaa actcggatac cagtttggaa actatcacgt 112440
ttatgatttt gaaccgtatt actctacagt agctctggct attcgagatg aacattcatc 112500
tggcattttt aatatccgtc aagagagtta tctggtaagt tcattatctg aaataacata 112560
tagattttat ctaattaatc taaaatctga tcttgttcaa tggagtgcta gtacgggcgc 112620
tgtaattaat caaatggtaa atactgtatt gattacagtg tatgaaaagt tacaactggt 112680
catagaaaat gattcacaat ttacatgttc attggctgtg gaatcaaaac ttccaataaa 112740
attacttaaa gatagaaatg aattatttac aaaattcatt aacgagttaa aaaagaccag 112800
ttcattcaag ataagcaaac gcgataagga tacgctacta aaatatttta cttaggactg 112860
gagttagaat ttatagacga ctcatttcgt ttatcattgt tactattatt actattacta 112920
tcattattag tgttggcatt attagtattc ttcttgtcat cttgttcaga aatatacagc 112980
aatgctatac ctaatactaa atacattatc atgctcgcaa tggctctaac aacaacgaac 113040
caaaatgaat ttggtcgtag cttttgttca caaaaataca taaagaaatg tctacataaa 113100
tctatggcgc cattggctac ttgaaatagc gccagtcctc ctacagattt taatatagct 113160
gtataacatg acatttattc atcatcaaaa gagacagagt caccatctgt catatttaga 113220
tttttttca tgtgttcaaa gtatcctcta ctcatttcat tataatagtt tatcatactt 113280
agaattttag gacggatcaa tgagtaagac ttgactagat cgtcagtagt aatttgtgca 113340
tcgtctattc tgcatccgct tcgtcgaata atgtatagca tcgctttgag attctccata 113400
gctatcaagt ctttatacaa tgacatggaa atatctgtga atactttata cttctccaac 113460
atcgatgcct taacatcatc gcctacttta gcattgaaaa tacgttctat tgtgtagatg 113520
gatgtagcaa gatttttaaa caacaatgcc atcttacacg atgattgcct caagtctcca 113580
atcgtttgtt tagaacgatt agctacagag tccaatgctt ggctgactag catattatta 113640
tctttagaaa ttgtattctt caatgaggcg tttatcatat ctgtgatttc gttagtcata 113700
ttacagtctg actgggttgt aatgttatcc aacatatcac ctatggatac ggtacacgta 113760
ccagcatttg taataatcct atctaagatg ttgtatggca ttgcgcagaa aatatcttct 113820
cctgtaatat ctccactctc gataaatcta ctcagattat tcttaaatgc cttattctct 113880
ggagaaaaga tatcagtgtc catcatttca ttaatagtat acgcagaaaa gataccacga 113940
gtatcaattc tatccaagat acttatcggt tccgagtcac agataatggt ttcctctcct 114000
tcgggagatc ctgcatagaa atatctagga caatagtttc tatactgtct gtaactctga 114060
```

```
taatctctaa agtcactaac tgataccatg aaattgagaa gatcaaacgc tgaagtaatt 114120
aatttttctg cctcgttttt actacaacta gttttcatca atgtagtgac gatgtattgt 114180
ttagttactt ttggtctaat actgatgata gagatattat tgcttcccat aatggatctt 114240
ctagtagtca ccttaaagcc cattgatgcg aatagcagat agataaagtc ttggtatgac 114300
tcctttctaa tatagtacgg actacctttg tcacccaact ttatacccac ataagccata 114360
acaacctctt taatagccgt ttcatgaggt ttatcagcca tgagcctgag tagttggaag 114420
aatctcatga atcccgtctc agaaagtcct atatgcatga tagatttatc tttcctggga 114480
aactctcgta tagtcataga tgaaatactc tttaaagttt ctgaaataag attagtaaca 114540
gtcttacctc cgactactct aggtaacaaa caaactctaa taggtgtttt ctctgcggag 114600
ataaatatcag aaaggataga gcaataagta gtattattgt gattataaag accgaataca 114660
taacaggtag aatttataaa catcatgtcc tgaaggtttt tagacttgta ttcctcgtaa 114720
tccataccgt cccaaaacat ggatttggta actttgatag ccgtagatct ttgttccttc 114780
gccaacaggt taaagaaatt aataaagaat ttgttgtttc tatttatgtc cacaaattgc 114840
acgtttggaa gcgccacggt tacattcact gcagcatttt gaggatcgcg agtatgaagt 114900
acgatgttat tgtttactgg tatatctgga aagaaatcta ccagtctagg aataagagat 114960
tgatatcgca tagaaatagt aaagtttata atctcatcat cgaagagcat tttgttacca 115020
ttgtaataaa tatccactct gtcatatgta taaatgaagt actgttcaaa catgatgaga 115080
tgtttatatg ttggcatagt agtgagatcg acgtttggta atggcaatgt attaagatta 115140
actccataat gtctagcagc atctgcgatg ttataagcgt cgtcaaagcg gggtcgatct 115200
tgtattgtta tatattgtct aacacctata agattatcaa aatcttgtct gcttaataca 115260
ccgttaacaa tttttgcctt gaattctttt attggtgcat taataacatc cttatagagg 115320
atgttaaaca aataagtgtt atcaaagtta agatctggat atttcttttc tgctagaaca 115380
tccattgagt cggagccatc tggtttaata taaccaccga taaatctagc tctgtattct 115440
gtatccgtca atctaatatt aagaaggtgt tgagtgaaag gtggaagatc gtaaaagctg 115500
tgagtattaa tgataggatt agtttccgaa ctaatgttaa ttggggtatt aataatatct 115560
atatttccag cgttaagtgt aacattaaac agttttaatt cacgtgacgt ggtatcaatt 115620
aaataattaa tgcccaattt ggatatagca gcctgaagct catcttgttt agttacggat 115680
cctaatgagt tattaagcaa tatatcgaac ggatgaacga aggttgtttt aagttggtca 115740
catactttgt aatctagaca tagatgcgga agaacggtag aaactatacg aaataaatat 115800
tcagagtcct ctaattgatc aagagtaact attgacttaa taggcatcat ttatttagta 115860
ttaaatgacg accgtaccag tgacggatat acaaaacgat ttaattacag agttttcaga 115920
agataattat ccatctaaca aaaattatga aataactctt cgtcaaatgt ctattctaac 115980
tcacgttaac aacgtggtag atagagaaca taatgccgcc gtagtgtcat ctccagagga 116040
aatatcctca caacttaatg aagatctatt tccagatgat gattcaccgg ccactattat 116100
cgaacgagta caacctcata ctactattat tgacgatact ccacctccta cgtttcgtag 116160
agagttatta atatcggaac aacgtcaaca acgagaaaaa agatttaata ttacagtatc 116220
gaaaaatgct gaagcaataa tggaatctag atctatgata acttctatgc caacacaaac 116280
accatccttg ggagtagttt atgataaaga taaaagaatt cagatgttag aggatgaagt 116340
ggttaatctt agaaatcaac gatctaatac aaaatcatct gataatttag ataattttac 116400
```

caaaatacta tttggtaaga ctccgtacaa atcaacagaa gttaataagc gtatagccat 116460
cgttaattat gcaaatttga acgggtcccc cttatcagtc gaggacttgg atgtttgttc 116520
ggaggatgaa atagatagaa tctataaaac gattaaacaa tatcacgaaa gtagaaaacg 116580
aaaaattatc gtcactaacg tgattattat tgtcataaac attatcgagc aggcattgct 116640
aaaactcgga tttgaagaaa tcaaaggact gagtaccgat atcacttcag aaattatcga 116700
tgtggagatc ggagatgact gcgatgctgt agcatctaaa ctaggaatcg gtaacagtcc 116760
ggttcttaat attgtattgt ttatactcaa gatattcgtt aaacgaatta aaattattta 116820
atttaataca ttcccatatc cagacaacaa tcgtctggat taatctgttc ctgtcgtctc 116880
ataccggacg acatattaat ctttttatta gtgggcatct ttttagatgg tttctttttc 116940
ccagcattaa ctgagtcgat acctagaaga tcgtgattga tctctccgac cattccacga 117000
acttctaatt ggccgtctct gacggtacca taaactattt taccagcatt agtaacagct 117060
tggacaatct gaccatccat cgcattgtac gatgtagtag taactgttgt tctacgtcta 117120
ggagcaccag aagtattttt ggagcccttg gatgttgatg tagaagaaga cgaggatttt 117180
gattttggtt tacatgtaat acattttgaa ctctttgatt ttgtatcaca tgcgccggca 117240
gtcacatctg tttgagaatt aagattattg ttgcctcctt tgacggctgc atctccaccg 117300
atttgcgcta gtagattttt aagctgtggt gtaatcttat taactgtttc gatataatca 117360
tcgtaactgc ttctaacggc taaatttttt ttatccgcca tttagaagct aaaaatattt 117420
ttatttatgc agaagattta actagattat acaatgaact aatatgatcc ttttccagat 117480
tatttacaaa cttggtattt tttggttctg gaggaggcga atttaaattc ggacttggat 117540
tcggattttg taagttcttg atcttattat acatcgagta taggatggcg acagtaactg 117600
ctacacaaat accgatcaaa agaagaatac caatcattta ttgacaataa cttcactatt 117660
gatcaagtat gcaatatatc atcttttcac taaataagta gtaataatga ttcaacaatg 117720
tcgagatata tggacgataa taatttagtt catggaaata tcgctatgat tggtgtgaat 117780
gactccgcta actctgtggg gtgcgcagtg ctttccccac atagaataaa ttagcattcc 117840
gactgtgata ataataccaa gtataaacgc cataatactc aatactttcc atgtacgagt 117900
gggactggta gacttactaa agtcaataaa ggcgaagata cacgaaagaa tcaaaagaat 117960
gattccagcg attagcacgc cggaaaaata atttccaatc ataagcatca tgtccattta 118020
actaataaaa attttaaatc gccgaatgaa caaagtggaa tataaaccat ataaaaacaa 118080
tagtttgtac tgcaaaaata atatctattt ttgttttcga agatatggta aaattaaata 118140
gtagtacaca gcatgttata actaacagca gcaacggctc gtaattactt atcatttact 118200
agacgaaaag gtggtgggat attttcttgc tcaaataata cgaatatatc acccatccat 118260
tttatgcgat gtttatatac tctaatcttt aatagatcta tagacgacgg gtttaccaac 118320
aatatagatt ttatcgattc atctaattta aacccttcct taaacgtgaa tgatctatta 118380
tctggcataa cgatgaccct acctgatgaa tcggacaatg tactgggcca tgtagaataa 118440
attatcaacg aattatcgtc tacgaacatt tatatcattt gttttaattt taggacgcga 118500
ataaatggat ataaaataga aaataacaga tattacaacc agtgttatgg ccgcgcccaa 118560
ccaggtaggc agttttattt tatcttttac tacaggttct cctggatgta cgtcaccaac 118620
ggcggacgta gttctagtac aattagacgt aagttccgct tgggaatttt ttaacgctaa 118680
agagttaacg ttaatcgtgc acccaacgta tttacatcta gttcgttgaa catcttgatt 118740
ataatataac cattttctat ctctagattc gtcagtgcac tcatgtaacc aacataccct 118800
aggtcctaaa tatttatctc cggaattaga ttttggataa ttcgcgcacc aacaatttct 118860
atttccttta tgatcgttac aaaagacgta taatgccgta tccccaaaag taaaataatc 118920
aggacgaata attctaataa actcagaaca atatctcgca tccatatgtt tggagcaaat 118980
atcggaataa gtagacatag ccggtttccg ttttgcacgt aaccattcta aacaattggg 119040
gtttccagga tcgtttctac aaaatccagt catgaaatcg tcacaatgtt ctgtcttgta 119100
attattatta aatatttttg gacagtgttt ggtatttgtc ttagaacaac attttgccac 119160
gctatcacta tcgcccagga gataatcctt ttttataaaa tgacatcgtt gcccggatgc 119220
tatataatca gtagcgtgtt ttaaatcctt aatatattca ggagttacct cgttctgata 119280
atagattaat gatccaggac gaaatttgaa agaactacat ggttctccat gaattaatac 119340
atattgttta gcaaattcag gaactataaa actactacaa tgatctatcg acataccatc 119400
tatcaaacaa aacttgggtt taatttctcc cggagatgtt tcataatagt acgtataact 119460
ttcttctgca aacttaacag ctctattata ttcaggataa ttaaaaccta attccatata 119520
tttgtctcgt atatctgcta ttcctggtgc tattttgatt ctattaagag taacagctgc 119580
ccccattctt aataatcgtc agtatttaaa ctgttaaatg ttggtatatc aacatctacc 119640
ttatttcccg cagtataagg tttgttgcag gtatactgtt caggaatggt tacatttata 119700
cttcttctat agtcctgtct ttcgatgttc atcacatatg caaagaacag aataaacaaa 119760
ataatgtaag aaataatatt aaatatctgt gaattcgtaa atacattgat tgccataata 119820
attacagcag ctacaataca cacaatagac attcccacag tgttgccatt acctccacga 119880
tacatttgag ttactaagca ataggtaata actaagctag taagaggcaa tagaaaagat 119940
gagataaata tcatcaatat agagattaga ggagggctat atagagccaa gacgaacaaa 120000
atcaaaccga gtaacgttct aacatcatta tttttgaaga ttcccaaata atcattcatt 120060
cctccataat cgttttgcat catacctcca tctttaggca taaacgattg ctgctgttcc 120120
tctgtaaata aatctttatc aagcactcca gcacccgcag agaagtcgtc aagcatattg 120180
taatatctta aataactcat ttatatatta aaaaatgtca ctattaaaga tggagtataa 120240
tctttatgcc gaactaaaaa aaatgacttg tggtcaaccc ctaagtcttt ttaacgaaga 120300
cggggatttc gtagaagttg aaccgggatc atcctttaag tttctgatac ctaagggatt 120360
ttacgcctct ccttccgtaa agacgagtct agtattcgag acattaacaa cgaccgataa 120420
taaaatcact agtatcaatc caacaaatgc gccaaagtta tatcctcttc aacgcaaagt 120480
cgtatctgaa gtagtttcta atatgaggaa aatgatcgaa tcaaaacgtc ctctatacat 120540
tactcttcac ttggcgtgtg gatttggtaa gactattacc acgtgttatc ttatggctac 120600
acacggtaga aaaaccgtca tttgcgtacc caataaaatg ttaatacatc aatggaagac 120660
acaggtagag gcagtcggat tggaacataa gatatccata gatggagtaa gtagtctatt 120720
aaaggaacta aagactcaaa gtccggatgt attaatagta gtcagtagac atctgacaaa 120780
cgatgccttt tgtaaatata tcaataagca ttatgatttg ttcatcttgg atgaatcaca 120840
tacgtataat ctgatgaaca atacagcagt tacaagattt ttagcgtatt atcctccgat 120900
gatgtgttat tttttaactg ctacacctag accatctaac cgaatttatt gtaacagtat 120960
tattaatatt gccaagttat ccaatctaaa aaaaactatc tatgcagtag atagtttttt 121020
tgagccatat tccacagata atattagaca tatggtaaaa cgactagatg gaccatctaa 121080
taaatatcat atatataccg agaagttatt atctgtagac gagcctagaa atcaacttat 121140

```
tcttgatacc ctggtagaag aattcaagtc aggaactatt aatcgcattt tagttattac 121200
taaactacgt gaacatatgg tattattcta caaacgatta ttagattttt tcggaccaga 121260
ggttgtattt ataggagacg cccaaaatag acgtactcca gatatggtca aatcaatcaa 121320
ggaactaaat agatttatat tcgtatccac cttattttat tccggtactg gtttagatat 121380
tcctagtttg gattcgttgt tcatttgctc ggcagtaatc aacaatatgc aaatagagca 121440
attactaggg agggtatgtc gagaaacaga actattagat aggacggtat atgtatttcc 121500
taacacatcc atcaaagaaa taaagtacat gataggaaat ttcatgcaac gaattattag 121560
tctgtctgta gataaactag gatttaaaca aaaaagttat cggaaacatc aagaatccga 121620
tcccacttct gcatgtacaa catcatccag agaagaacgt gtattaaata gaatatttaa 121680
ctcgcaaaat cgttaagaag tttaagcgac gatccgcatg ctgcgcaggc cagtgtatta 121740
cccctcatag tattaatata atccaatgat acttttgtga tgtcggaaat cttaaccaat 121800
ttagactgac aggcagaaca cgtcatgcaa tcatcatcgt catcgataac tgtagtcttg 121860
ggcttctttt tgcgactctt cattccggaa cgcacattgg tgctatccat ttaggtagta 121920
aaaaataagt cagaatatgc cctataacac gatcgtgcaa aacctggtat atcgtctcta 121980
tctttatcac aatatagtgt atcgacattt ttattattat tgacctcgtt tatcttggaa 122040
catggaatgg gaacattttt gttatcaacg gccatctttg ccttaattcc agatgttgta 122100
aaattataac taaacagtct atcatcgaca caaatgaaat tcttgtttag acgtttgtag 122160
tttacgtatg cggctcgttc gcgtctcatt ttttcagata ttgcaggtac tataatatta 122220
aaaataagaa tgaaataaca taggattaaa aataaagtta tcatgacttc tagcgctgat 122280
ttaactaact taaaagaatt acttagtctg tacaaaagtt tgagattttc agattctgcg 122340
gctatagaaa agtataattc tttggtagaa tggggaacat ctacttactg gaaaataggc 122400
gtgcaaaagg tagctaatgt cgagacgtca atatctgatt attatgatga ggtaaaaaat 122460
aaaccgttta atattgatcc gggctattac attttcttac cggtatattt tgggagcgtc 122520
tttatttatt cgaagggtaa aaatatggta gaacttggat ctggaaactc ttttcaaata 122580
ccagatgata tgcgaagtgc gtgtaacaaa gtattagaca gcgataacgg aatagacttt 122640
ctgagatttg ttttgttaaa caatagatgg ataatggaag atgctatatc aaaatatcag 122700
tctccagtta atatatttaa actagctagt gagtacggat taaacatacc caaatattta 122760
gaaattgaaa tagaggaaga cacattattt gacgacgagt tatactctat tatagaacgc 122820
tctttcgatg ataaatttcc aaaaatatcc atatcgtata ttaagttggg agaacttaga 122880
cggcaagttg tagacttttt caaattctca ttcatgtata ttgagtccat caaggtagat 122940
cgtataggag ataatatttt tattcctagc gttataacaa aatcaggaaa aaagatatta 123000
gtaaaagatg tagaccattt aatacgatcc aaggttagag aacatacatt tgtaaaagta 123060
aaaaagaaaa acacattttc cattttatac gactatgatg gaaacggaac agaaactaga 123120
ggagaagtaa taaaacgaat tatagacact ataggacgag actattatgt taacggaaag 123180
tatttctcta aggttggtag tgcaggctta aagcaattga ctaataaatt agatattaat 123240
gagtgcgcaa ctgtcgatga gttagttgat gagattaata aatccggaac tgtaaaacga 123300
aaaataaaaa accaatcagc atttgattta agcagagaat gtttgggata tccagaagcg 123360
gattttataa cgttagttaa taacatgcgg ttcaaaatag aaaattgtaa ggttgtaaat 123420
ttcaatattg aaaatactaa ttgtttaaat aacccgagta ttgaaactat atatggaaac 123480
tttaaccagt tcgtctcaat ctttaatgtc gtcaccgatg tcaaaaaaag attattcgag 123540
```

tgaaataata tgcgcctttg atataggtgc aaaaaatcct gccagaactg ttttagaagt 123600
caaggataac tccgttaggg tattggatat atcaaaatta gactggagtt ctgattggga 123660
aaggcgcata gctaaagatt tgtcacaata tgaatacact acagttcttc tagaacgtca 123720
gcctagaagg tcgccgtatg ttaaatttat ctattttatt aaaggctttt tatatcatac 123780
atcggctgcc aaagttattt gcgtctcgcc tgtcatgtct ggtaattcat atagagatcg 123840
aaaaaagaga tcggtcgaag catttcttga ttggatggac acattcggat tgcgagactc 123900
cgttccggat agacgcaaat tagacgatgt agcggatagt ttcaatttgg ctatgagata 123960
cgtattagat aaatggaata ctaattatac accttataat aggtgtaaat ctagaaatta 124020
cataaaaaaa atgtaataac gttagtaacg ccattatgga taatctattt acctttctac 124080
atgaaataga agatagatat gccagaacta tttttaactt tcatctaata agttgcgatg 124140
aaataggaga tatatatggt cttatgaaag aacgcatttc ctcagaggat atgtttgata 124200
atatagtgta taataaagat atacatcctg ccattaagaa actagtgtat tgcgacatcc 124260
aacttactaa acacattatt aatcagaata cgtatccggt atttaacgat tcttcacaag 124320
tgaaatgttg tcattatttc gacataaact cagataatag caatattagc tctcgtacag 124380
tagagatatt tgagagggaa aagtcatctc ttgtatcata tattaaaact accaataaga 124440
agagaaaggt caattacggc gaaataaaga aaactgttca tggaggcact aatgcaaatt 124500
acttttccgg taaaaagtct gacgagtatc tgagtactac agttagatcc aacattaatc 124560
aaccttggat caaaaccatc tctaagagga tgagagttga tatcattaat cactctatag 124620
taacgcgtgg aaaaagctct atattacaaa ctatagaaat tatttttact aatagaacat 124680
gtgtgaaaat attcaaggat tctactatgc acattattct atccaaggac aaggatgaaa 124740
aggggtgtat acacatgatt gacaaattat tctatgtcta ttataattta tttctgttgt 124800
tcgaagatat catccaaaac gagtacttta aagaagtagc taatgttgta aaccacgtac 124860
tcacggctac ggcattagat gagaaattat tcctaattaa gaaaatggct gaacacgatg 124920
tttatggagt tagcaatttc aaaataggga tgtttaacct gacatttatt aagtcgttgg 124980
atcataccgt tttcccctct ctgttagatg aggatagcaa aataaagttt tttaagggga 125040
aaaagctcaa tattgtagca ttacgatctc tggaggattg tataaattac gtgactaaat 125100
ccgagaatat gatagaaatg atgaaggaaa gatcgactat tttaaatagc atagatatag 125160
aaacggaatc ggtagatcgt ctaaaagaat tgcttctaaa atgaaaaaaa acactaattc 125220
agaaatggat caacgactag ggtataagtt tttggtgcct gatcctaaag ccggagtttt 125280
ttatagaccg ttacatttcc aatatgtatc gtattctaat tttatattgc atcgattgca 125340
tgaaatcttg accgtcaagc ggccactctt atcgtttaag aataatacag aacgaattat 125400
gatagaaatt agcaatgtta aagtgactcc tccagattac tcacctataa tcgcgagtat 125460
taaaggtaag agttatgacg cattagccac gttcactgta aatatcttta aagaggtaat 125520
gaccaaagag ggtatatcca tcactaaaat aagtagttat gagggaaaag attctcattt 125580
gataaaaatt ccgctactaa taggatacgg gaataaaaat ccacttgata cagccaagta 125640
tcttgttcct aatgtcatag gtggagtctt tatcaataaa caatctgtcg aaaaagtagg 125700
aattaatcta gtagaaaaga ttacaacatg gccaaaattt agggttgtta agccaaactc 125760
attcactttc tcgttttcct ccgtatcccc tcctaatgta ttaccgacaa gatatcgcca 125820
ttacaagata tctctggata tatcacaatt ggaagcgttg aatatatcat cgacaaagac 125880
atttataacg gtcaatattg ttttgctgtc tcaatattta tctagagtga gtctagaatt 125940
cattagacgt agtttatcat acgatatgcc tccagaagtt gtctatctag taaacgcgat 126000
aatagatagt gctaaacgaa ttactgaatc tattactgac tttaatattg atacatacat 126060
taatgacctg gtggaagctg aacacattaa acaaaaatct cagttaacga ttaacgagtt 126120
caaatatgaa atgctgcata actttttacc tcatatgaac tatacacccg atcaactaaa 126180
gggattttat atgatatctt tactaagaaa gtttctctac tgtatcttcc acacttctag 126240
atatccagat agagattcga tggtttgtca tcgcatccta acgtacggca aatattttga 126300
gacgttggca catgatgaat tagagaatta cataggcaac atccgaaacg atatcatgaa 126360
caatcacaag aacagaggca cttacgcggt aaacattcat gtactaacaa ctcccggact 126420
taatcacgcg ttttctagct tattgagtgg aaagttcaaa aagtcagacg gtagttatcg 126480
aacacatcct cactattcat ggatgcagaa tatttctatt cctaggagtg ttggatttta 126540
tccggatcaa gtaaagattt caaagatgtt ttctgtcaga aaataccatc caagtcaata 126600
tctttacttt tgttcatcag acgttccgga aagaggtcct caggtaggtt tagtatctca 126660
attgtctgtc ttgagttcca ttacaaatat actaacgtct gagtatttgg atttggaaaa 126720
gaaaatttgt gagtatatca gatcatatta taaagatgat ataagttact ttgaaacagg 126780
atttccaatc actatagaaa atgctctagt cgcatctctt aatccaaata tgatatgtga 126840
ttttgtaact gactttagac gtagaaaacg gatgggattc ttcggtaact tggaggtagg 126900
tattacttta gttagggatc acatgaatga aattcgcatt aatattggag cgggaagatt 126960
agtcagacca ttcttggttg tggataacgg agagctcatg atggatgtgt gtccggagtt 127020
agaaagcaga ttagacgaca tgacattctc tgacattcag aaagagtttc cgcatgtcat 127080
cgaaatggta gatatagaac aatttacttt tagtaacgta tgtgaatcgg ttcaaaaatt 127140
tagaatgatg tcaaaggatg aaagaaagca atacgattta tgtgactttc ctgccgaatt 127200
tagagatgga tatgtagcat cttcactagt gggaatcaat cacaattctg gacccagagc 127260
tattcttgga tgtgctcaag ctaaacaagc tatctcttgt ctgagttcgg atatacgaaa 127320
taaaatagac aatggaattc atttgatgta tccagagagg ccaatcgtga ttagtaaggc 127380
tttagaaact tcaaagattg cggctaattg cttcggccaa catgttacta tagcattaat 127440
gtcgtacaaa ggtatcaatc aagaggatgg aattatcatc aaaaaacaat ttattcagag 127500
aggcggtctc gatattgtta cagccaagaa acatcaagta gaaattccat tggaaaactt 127560
taataacaaa gaaagagata ggtctaacgc ctattcaaaa ttagaaagta atggattagt 127620
tagactgaat gctttcttgg aatccggaga cgctatggca cgaaatatct catcaagaac 127680
tcttgaagat gattttgcta gagataatca gattagcttc gatgtttccg agaaatatac 127740
cgatatgtac aaatctcgcg ttgaacgagt acaagtagaa cttactgaca aagttaaggt 127800
acgagtatta accatgaaag aaagaagacc cattctagga gacaaattta ccactagaac 127860
gagtcaaaag ggaacagtcg cgtatgtcgc ggatgaaacg gaacttccat acgacgaaaa 127920
tggtatcaca ccagatgtca ttattaattc tacatccatc ttctctagaa aaactatatc 127980
tatgttgata gaagttattt taacagccgc atattctgct aagccgtaca acaataaggg 128040
agaaaaccga cctgtctgtt ttcctagtag taacgaaaca tccatcgata catatatgca 128100
attcgctaaa caatgttatg agcattcaaa tccgaaattg tccgatgaag aattatcgga 128160
taaaatcttt tgtgaaaaga ttctctatga tcctgaaacg gataagcctt atgcatccaa 128220
agtatttttt ggaccaattt attacttgcg tctgaggcat ttaactcagg acaaggcaac 128280
cgttagatgt agaggtaaaa agacgaagct cattagacag gcgaatgagg gacgaaaacg 128340
tggaggaggt atcaagttcg gagaaatgga gagagactgt ttaatagcgc atggtgcagc 128400
caatactatt acagaagttt tgaaagattc ggaagaagat tatcaagatg tgtatgtttg 128460
tgaaaattgt ggagacatag cagcacaaat caagggtatt aatacatgtc ttagatgttc 128520
aaaacttaat ctctctcctc tcttaacaaa aattgatacc acgcacgtat ctaaagtatt 128580
tcttactcaa atgaacgcca gaggcgtaaa agtcaaatta gatttcgaac gaaggcctcc 128640
ttcgttttat aaaccattag ataaagttga tctcaagccg tcttttctgg tgtaatattc 128700
tagtttggta gtagatacat atcaatatca tcaaattcga gatccgaatt ataaaatggg 128760
cgtggattgt taactataga atcggacgtc tgatattcga aaatctgtgg agtttcaggt 128820
tttggtggag gtgtaactgc tacttgggat actgaagtct gatattcaga aagctgtgga 128880
tgttctggtt cggcatccac cgatggtgtc acatcactaa tcggttcggt aacgtctgtg 128940
gatggaggtg ctacttctac agaacctgta gcctcagttg tcaacggaga tacattttta 129000
atgcgagaaa atgtataatt tggtaatggt ttcttatgtg gatctgaaga agaggtaaga 129060
tatctactag aaagataccg atcacgttct agttctcttt tgtagaactt aacttttttct 129120 ttctccgcat ctagttgata ttccaacctc ttcacgttac tacgttcaga ttccaattca 129180
cgttcgcatg ggttacctcc gcagttttta cgagcgattt cacgttcagc cttcatgcgt 129240
ctctccctct ctctatcgag tttatcagag cagtctttct gaaggcgatc gaactccata 129300
aatttctcca acgctttgat tgtttccata gatttccgaa gttcagcttt taggactgtg 129360
attctttttc tttcgaattc acagctggat gtacaaccgt ttccattacc gccatctcta 129420
agtttctttt ctagatcggc aacatttcat ccccatgcct tttacattcc tcgagtctac 129480
tgtcgtcgaa atatcgttcc agctcctttt cgacatcaat aactttagca cgttgtctct 129540
caagctctct tttgtagtta tctgattccc tggcacgttt aagatcttca tgcaattgag 129600
tcagctctta acttcctctc ttgcttcttc gtcatagtac gcgcaatcac tgtgagatcc 129660
attgttacca cgtctacact cggcgagctc gcgtttaaga gattcaattt cccgtttgta 129720
ttggtccatg tttccattgc taccaccatt agatttacag gctgctagtt gtcgttcgag 129780
atcagaaata cgggttttct tggaattgat ttcgtcgatg tacttggcat cgaaacactt 129840
attaagttct tttccaatt ctacgatttt atttctttcg cgagtcaatt ccctcctgta 129900
gtaactatct gttttgtcag attcacgctc tctacgtaga ctttcttgca agttactaat 129960
ttgttcccta gcacgtccga gtttagtttt atatgctgaa tagagttctg attcatcctt 130020
tgagcagatc tctagcgatc gtttaagatt cctaattcta gtctttagcc tatttacctc 130080
ctcagaagat gttccgttac cgttgcgttt acactcgtta agctgtctat caagatccat 130140
gattctatct ctaagacgtt gcatctctct ttccatatca gcattgcttt cattattacg 130200
tctgcagtca ctcaactgtc tttcaatatc tgagattcta tctctaagac gtcgcatctc 130260
tctctgtttc ggcattggtt tcattattac gtctacagtc gttcaactgt ctttcaagat 130320
ctgatattct agattggagt ctgctaatct ctgtagcatt ttcacggcat tcactcagtt 130380
gtctttcaag atctgaaatt ttagattgga gtctgctaat ctctgtaaga tttcctcctc 130440
cgctctcgat gcagtcggtc aacttattct ctagttctct aatacgcgaa cgcagtgcat 130500
caacttcttg cgtgtcttcc tggttgcgtg tacattcatc gagtctagat tcgagatctc 130560
taacgcgtcg tcgttcttcc tcaagttctc tgcgtactac agaaagcgtg tccttatctt 130620

```
gttgatattt agcaatttct gattctagag tactgatttt gcttacgtag ttactaatat 130680
ttgtcttggc cttatcaaga tcctccttgt atttgtcgca ttccttgata tccctacgaa 130740
gtctggacag ttcccattcg acattacgac gtttatcgat ttcagctcgg agatcgtcat 130800
cgcgttgttt tagccacata cgactgagtt caagttctcg ttgacaagat ccatctactt 130860
ttccattcct aatagtatcc agttcctttt ctagttctga acgcatttct cgttccctat 130920
caagcgattc tctcaattct cggatagtct tcttatcaat ttctaataaa tctgaaccat 130980
catctgtccc attttgaata tccctgtgtt ctttgatctc ttttgtaagt cggtcgattc 131040
tttcggtttt ataaacagaa tccctttcca aagtcctaat cttactgagt ttatcactaa 131100
gttctgcatt caattcggtg agttttctct tggcttcttc caactctgtt ttaaactctc 131160
cactatttcc gcattcttcc tcgcatttat ctaaccattc aattagttta ttaataacta 131220
gttggtaatc agcgattcct atagccgttc ttgtaattgt gggaacataa ttaggatctt 131280
ctaatggatt gtatggcttg atagcatcat ctttatcatt attaggggga tggacaacct 131340
taattggttg gtcctcatct cctccagtag cgtgtggttc ttcaatacca gtgttagtaa 131400
taggcttagg caaatgcttg tcgtacgcgg gcacttcctc atccatcaag tatttataat 131460
cgggttctac ttcagaatat tcttttctaa gagacgcgac ttcgggagtt agtagaagaa 131520
ctctgtttct gtatctatca acgctggaat caatactcaa gttaaggata gcgaatacct 131580
catcgtcatc atccgtatct tctgaaacac catcatatga catttcatga agtctaacgt 131640
attgataaat agaatcagat ttagtattaa acagatcctt aaccttttta gtaaacgcat 131700
atgtatattt tagatctcca gatttcataa tatgatcaca tgccttaaat gtcagtgctt 131760
ccatgatata atctggaaca ctaatgggtg acgaaaaaga tacagcacca tatgctacgt 131820
tgataaataa atctgaacca ctaagtagat aatgattaat gttaagaaag aggaaatatt 131880
cagtgtatag gtatgtcttg gcgtcatatc ttgtactaaa cacgctaaac agtttgttaa 131940
tgtgatcaat ttccaataga ttaattagag cagcgggaat accaacaaac atattaccac 132000
atccgtattt tctatgaata tcacatatca tgttaaaaaa tcttgataga agagcgaata 132060
tctcgtctga cttaatgagt cgtagttcag cagcaacata agtcataact gtaaatagaa 132120
catactttcc tgtagtgttg attctagact ccacatcaac accattatta aaaatagttt 132180
tatatacatc tttaatctgc tctccgttaa tcgtcgaacg ttctagtata cggaaacact 132240
ttgatttctt atctgtagtt aatgacttag tgatatcacg aagaatatta cgaattacat 132300
ttcttgtttt tcttgagaga cctgattcag aactcaactc atcgttccat agtttttcta 132360
cctcagtggc gaaatctttg gagtgcttgg tacatttttc aataaggttc gtgacctcca 132420
tttattataa aaaatttatt caaaacttaa ctacaatcgg gtaattataa aatcgtagat 132480
ctcccatgtg gcggaatact accatctatc gcatgtggat ggacagtagg taatggccat 132540
gggaacagta atgtttgcat atttatcttt cttgccagta ttactgcata ttgtcccaat 132600
gtttcgatgt gatgttctaa cctatcaact gccgctgtat cacaacaata gtgtccgatg 132660
aaattaagat tatgatccaa tgtgtttaat atatgattat caagtcttat acgatccgcg 132720
tctttttga caggatcagg ttcttctaca ggaagaagtt tcggcctctt atgatattca 132780
tgtctgggaa acggtggtct agggtgaggc tccggtatcg gagtgggttt tggattataa 132840
tcatcatcgt ctatgacatc atcttcgact tcgatattta ttttgctatc ttgatgatgt 132900
cctgtatcag ttgcattttc agcactcgac tgaatattag cgcattcatt gtctattatt 132960
accatatttc taaacccaaa atgtatgtgt tgaacatcag tactatcgtt gatgagtctt 133020
```

atagcatgaa ttcgcttatc gttatcgggt ttatcttctg tcaccttagc aattcctttt 133080
ttattaaact ctacataatc atatccattt ctattgtttg ttctaatata aacgagtata 133140
gcatcattgc taaatttttc aatagtatca aaaacagaat atcctaaacc atataatata 133200
tattcaggaa cactcaaact aaatgtccag gattctccta aatacgtaaa ctttaatagt 133260
gcgaaatcat tcaaaaatct accacttata gatagatagt acataaatgc gtatagtagt 133320
ctacctatct ctttattatg aaaaccggca ttacgatcat atatgtcgtg atatacctgt 133380
gatccgttta cgttaaacca taaatacatg ggtgatccta taaacatgaa tttatttcta 133440
attctcagag ctatagttaa ttgaccgtgt aatatttgct tacatgcata cttgatacgc 133500
ttattaataa gatttttatc attgctcgtt atttcagaat cgtatatata aggagtacca 133560
tcgtgattct taccagatat tatacaaaat actatatata aaatatattg acccacgtta 133620
gtaatcatat aaatgtttaa cgttttaaat tttgtattca atgatccatt atcatacgct 133680
atcatggtct tgtaatattc attctttaaa atataatatt gtgttagcca ttgcattgga 133740
gctcctaatg gagattttct attctcatcc attttaggat aggctttcat aaagtcccta 133800
ataacttcgt gaataatgtt tctatgtttt ctactgatgc atgtatttgc ttcgattttt 133860
ttatcccatg tttcatctat catagattta aacgcagtaa tgctcgcaac attaacatct 133920
tgaaccgttg gtacaattcc gttccataaa tttataatgt tcgccattta tataactcat 133980
tttttgaata tacttttaat taacaaaaga gttaagttac tcatatggac gccgtccagt 134040
ctgaacatca atctttttag ccagagatat catagccgct cttagagttt cagcgtgatt 134100
ttccaaccta aatagaactt catcgttgcg tttacaacac ttttctattt gttcaaactt 134160
tgttgttaca ttagtaatct ttttttccaa attagttagc cgttgtttga gagtttcctc 134220
attgtcgtct tcatcggctt taacaattgc ttcgcgttta gcctctggct ttttagcagc 134280
ctttgtagaa aaaaattcag ttgctggaat tgcaagatcg tcatctccgg ggaaaagagt 134340
tccgtccatt taaagtacag attttagaaa ctgacactct gcgttattta tatttggtac 134400
aacacatgga ttataaatat tgatgttaat aacatcagaa aatgtaaagt ctatacattg 134460
ttgcatcgtg ttaaatttttc taatggatct agtattattg ggtccaactt ctgcctgaaa 134520
tccaaatatg gaagcggata caaaaccgtt tcctggataa accacacatc tccacttttg 134580
ctttacatca gaaattgtgt cgttgacatc ttgaactctc ctatctaatg ccggtgttcc 134640
acctatagat tttgaatatt cgaatgctgc atgagtagca ttaaattcct taatattgcc 134700
ataattttca tatattgagt aaccctggat aaaaagtaaa cacaccgcag ccgtcgctac 134760
cacaataaaa aaaattgata gagagttcat ttataatcta ttagaagctg acaaaatttt 134820
tttacacgca tcagacaatg ctttaataaa tagttcaaca tctacttttg tcatatcgaa 134880
ccgatggtat gattctaacc tagaattaca tccgaaaaag ttgactatgt tcatagtcat 134940
taagtcatta acaaacaaca ttccagactc tggattataa gacgatactg tttcgtcaca 135000
attacctacc ttaatcatgt gattatgaat attggctatt agagcacctt ctaagaaatc 135060
tataatatct ttgaaacacg atttaaaatc aaaccacgaa tatacttcta cgaagaaagt 135120
tagtttaccc ataggagaaa taactataaa tggagatcta aatacaaaat ccggatctat 135180
gatagtttta acattattat attctctatt aaatacctcc acatctaaaa atgttaattt 135240
tgaaactatg tcttcgttta ttaccgtacc tgaactaaac gctataagct ctattgtttg 135300
agaactcttt aaacgatatt cttgaaatac atgtaacaaa gtttccttta actcggtcgg 135360

```
tttatctacc atagttacag aatttgtatc cttatctata atataataat caaaatcgta 135420
taaagttata taattatcgc gttcagattg ggatcttttc aaatagacta aaaaccccat 135480
ttctctagta agtatcttat gtatatgttt gtaaaatatc ttcatggtgg gaatatgctc 135540
taccgcagtt agccattcct cattgacagc ggtagatgta ttagacaaaa ctattccaat 135600
gtttaacaag ggccatttta cgagattatt aaatccttgt ttgataaatg tagccaatga 135660
gggttcgagt tcaacgacga ttgaattctc ttcccgcgga tgctgcatga tgaacgacgg 135720
gatgttgttc gattgatttg gaattctttt tcgacttttt gtttatatta aatattttaa 135780
aatttatagc ggatagcaat tcatgtacca cggataatgt agacgcgtat tgcgcatcga 135840
tatctttatt attagataaa tttatcaata aatgtgagaa gtttgcctcg ttaaggtctt 135900
ccatttaaat attatataaa catttgtgtt tgtaacttat tcgtctttta tggaatagtt 135960
ttttactagt aaagctgcaa ttacacactt tgtccgtaaa acataaatat aaacaccagc 136020
ttttatcaat cgttccaaaa agtcgacggc ggacattttt aacatggcat ctattttaaa 136080
tacacttagg tttttggaaa aaacatcatt ttataattgt aacgattcaa taactaaaga 136140
aaagattaag attaaacata agggaatgtc atttgtattt tataagccaa agcattctac 136200
cgttgttaaa tacttgtctg gaggaggtat atatcatgat gatttggttg tattggggaa 136260
ggtaacaatt aataatctaa agatgatgct attttacatg gatttatcat atcatggagt 136320
gacaagtagt ggagcaattt acaaattggg atcgtctatc gatagacttt ctctaaatag 136380
gactattgtt acaaaagtta ataattatga tgatacattt tttgacgacg atgattgatc 136440
gctattgcac aattttgttt ttgtactttc taatatagtg tttaggttct ttttcatatg 136500
agaatattga tttactaaaa tatctatgtt taacttttgt tctatgacgt ccttatcggc 136560
ggtatcggta catatacgta attcaccttc acaaaatacg gagtcttcga taataatagc 136620
caatcgatta ttggatctag ctgtctgtat catattcaac atgtttaata tatcctttcg 136680
tttccccttt acaggcatcg atcgtagcat attttccgcg tctgatatgg aaatgttaaa 136740
actacaaaaa tgcgtaatgt tagcccgtcc taatattggt acgtgtctat aagtttggca 136800
tagtagaata atagacgtgt ttaaatgcct tccaaagttt aagaattcta ttagagtatt 136860
gcattttgat agtttatcgc ctacatcatc aaaaataagt aaaaagtgtg ctgatttttt 136920
atgattttgt gcgacagcaa tacatttttc tatgttactt ttagttcgta tcagattata 136980
ttctagagat tcctgactac taacgaaatt aatatgattt ggccaaatgt atccatcata 137040
atctgggtta taaacgggtg taaacaagaa tatatgttta tattttttaa ctagtgtaga 137100
aaacagagat agtaaataga tagtttttcc agatccagat cctcctgtta aaaccattct 137160
aaacggcatt tttaataaat tttctcttga aaattgtttt tcttggaaac aattcataat 137220
tatatttaca gttactaaat taatttgata ataaatcaaa atatggaaaa ctaaggttgt 137280
tagtagggag gagaacaaag aaggcacatc gtgatataaa taacatttat tatcatgatg 137340
acaccagaaa acgacgaaga gcagacatct gtgttctccg ctactgttta cggagacaaa 137400
attcagggaa agaataaacg caaacgcgtg attggtctat gtattagaat atctatggtt 137460
atttcactac tatctatgat taccatgtcc gcgtttctca tagtgcgcct aaatcaatgc 137520
atgtctgcta acgaggctgc tattactgac gccgctgttg ccgttgctgc tgcatcatct 137580
actcatagaa aggttgcgtc tagcactaca caatatgatc acaaagaaag ctgtaatggt 137640
ttatattacc agggttcttg ttatatatta cattcagact accagttatt ctcggatgct 137700
aaagcaaatt gcactgcgga atcatcaaca ctacccaata aatccgatgt cttgactacc 137760
```

tggctcattg attatgttga ggatacatgg ggatctgatg gtaatccaat tacaaaaact 137820
acatccgatt atcaagattc tgatgtatca caagaagtta gaaagtattt ttgtgttaaa 137880
acaatgaact aatatttatt tttgtacatt aataaatgaa atcgcttaat agacaaactg 137940
taagtaggtt taagaagttg tcggtgccgg ccgctataat gatgatactc tcaaccatta 138000
ttagtggcat aggaacattt ctgcattaca aagaagaact gatgcctagt gcttgcgcca 138060
atggatggat acaatacgat aaacattgtt atttagatac taacattaaa atgtctacag 138120
ataatgcggt ttatcagtgt cgtaaattac gagctagatt gcctagacct gatactagac 138180
atctgagagt attgtttagt attttttata aagattattg ggtaagttta aaaaagacca 138240
atgataaatg gttagatatt aataatgata aagatataga tattagtaaa ttaacaaatt 138300
ttaaacaact aaacagtacg acggatgctg aagcgtgtta tatatacaag tctggaaaac 138360
tggttaaaac agtatgtaaa agtactcaat ctgtactatg tgttaaaaaa ttctacaagt 138420
gacaacaaaa aatgaattaa taataagtcg ttaacgtacg ccgccatgga cgccgcgttt 138480
gttattactc caatgggtgt gttgactata acagatacat tgtatgatga tctcgatatc 138540
tcaatcatgg actttatagg accatacatt ataggtaaca taaaaactgt ccaaatagat 138600
gtacgggata taaaatattc cgacatgcaa aaatgctact ttagctataa gggtaaaata 138660
gttcctcagg attctaatga tttggctaga ttcaacattt atagcatttg tgccgcatac 138720
agatcaaaaa ataccatcat catagcatgc gactatgata tcatgttaga tatagaagat 138780
aaacatcagc cattttatct attcccatct attgatgttt ttaacgctac aatcatagaa 138840
gcgtataacc tgtatacagc tggagattat catctaatca tcaatccttc agataatctg 138900
aaaatgaaat tgtcgtttaa ttcttcattc tgcatatcag acggcaatgg atggatcata 138960
attgatggga aatgcaatag taattttta tcataaaagt tgtaaagtaa ataataaaac 139020
aataaatatt gaactagtag tacgtatatt gagcaatcag aaatgatgct ggtacctctt 139080
atcacggtga ccgtagttgc gggaacaata ttagtatgtt atatattata tatttgtagg 139140
aaaaagatac gtactgtcta taatgacaat aaaattatca tgacaaaatt aaaaaagata 139200
aagagttcta attccagcaa atctagtaaa tcaactgata gcgaatcaga ctgggaggat 139260
cactgtagtg ctatggaaca aaacaatgac gtagataata tttctaggaa tgagatattg 139320
gacgatgata gcttcgctgg tagtttaata tgggataacg aatccaatgt tatggcgcct 139380
agcacagaac acatttacga tagtgttgct ggaagcacgc tgctaataaa taatgatcgt 139440
aatgaacaga ctatttatca gaacactaca gtagtaatta atgaaacgga gactgttgaa 139500
gtacttaatg aagataccaa acagaatcct aactattcat ccaatccttt cgtaaattat 139560
aataaaacca gtatttgtag caagtcaaat ccgtttatta cagaacttaa caataaattt 139620
agtgagaata atccgtttag acgagcacat agcgatgatt atcttaataa gcaagaacaa 139680
gatcatgaac acgatgatat agaatcatcg gtcgtatcat tggtgtgatt agtttccttt 139740
ttataaaatt gaagtaatat ttagtattat tgctgccgtc acgttgtaca aatggagata 139800
ttccctgtat tcggcatttc taaaattagc aattttattg ctaataatga ctgtagatat 139860
tatatagata cagaacatca aaaaattata tctgatgaga tcaatagaca gatggatgaa 139920
acggtacttc ttaccaacat cttaagcgta gaagttgtaa atgacaatga gatgtaccat 139980
cttattcctc atagattatc gacgattata ctctgtatta gttctgtcgg aggatgtgtt 140040
atctctatag ataatgacat caatggcaaa aatattctaa cctttcccat tgatcatgct 140100
gtaatcatat ccccactgag taaatgtgtc gtagttagca agggtcctac aaccatattg 140160
gttgttaaag cggatatacc tagcaaacga ttggtaacat cgtttacaaa cgacatacta 140220
tatgtaaaca atctgtcact gattaattat ttgccgttgt ctgtattcat tattagacga 140280
gtcaccgact atttggatag acacatatgc gatcagatat ttgctaataa taagtggtat 140340
tcccttataa ccatcgacga taagcaatat cctattccat caaactgtat aggtatgtcc 140400
tctgccaagt acataaattc tagcatcgag caagatactt taatccatgt ttgtaacctc 140460
gagcatccgt tcgactcagt atacaaaaaa atgcagtcgt acaattctct acctatcaag 140520
gaacaaatat tgtacggtag aattgataat ataaatatga gcattagtat ttctgtggat 140580
taatagattt ctagtatggg gatcattaat catctctaat ctctaaatac ctcataaaac 140640
gaaaaaaaag ctattatcaa atactgtacg gaatggattc attctcttct ctttttatga 140700
aactctgttg tatatctact gataaaactg gaagcaaaaa atctgataga aagaataaga 140760
ataagatcaa ggattatatg gaacacgatt attataaaat aacaatagtt cctggttcct 140820
cttccacgtc tactagctcg tggtattata cacatgccta gtaatagtct ctttgcgttg 140880
acggaaagca gactagaaat aacaggctaa aatgttcaga caccataata gttcccaacc 140940
cagataataa cagagttcca tcaacacatt cctttaaact caatcccaaa cccaaaaccg 141000
ttaaaatgta tccggccaat tgatagtaga taatgaggtg tacagcgcat gataatttac 141060
acagtaacca aaatgaaaat actttagtaa ttataagaaa tatagacggt aatgtcatca 141120
tcaacaatcc gataatatgc ctgagagtaa acattgacgg ataaaacaaa aatgctccgc 141180
ataactctat catggcaata acacaaccaa atacttgtaa gattcctaaa ttagtagaaa 141240
atacaacgaa tatcgatgta taagtgatct cgagaaataa taagaataaa gtaatgcccg 141300
taaagataaa catcaacatt gtttggtaat cattaaacca attagtatga agttgaacta 141360
atttcacagt agattttatt ccagtgttat cctcgcatgt ataagtacct ggtaagatat 141420
ctttatattc cataatcaat gagacatcac tatctgataa cgaatgaagt ctagcactag 141480
tatgccattt acttaatatt gtcgtcttgg aagttttatt ataagttaaa atatcatggt 141540
tatccaattt ccatctaata tactttgtcg gattatctat agtacacgga ataatgatgg 141600
tatcattaca tgctgtatac tctatggtct ttgtagttgt tataacaacc aacgtataga 141660
ggtatatcaa cgatattcta actcttgaca ttttttattt atttaaaatg ataccttttgt 141720 tatttatttt attctatttt gctaacggta ttgaatggca taagtttgaa acgagtgaag 141780
aaataatttc tacttactta ttagacgacg tattatacac gggtgttaat ggggcggtat 141840
acacattttc aaataataaa ctaaacaaaa ctggtttaac taataataat tatataacaa 141900
catctataaa agtagaggat gcggataagg atacattagt atgcggaacc aataacggaa 141960
atcccaaatg ttggaaaata gacggttcag acgacccaaa acatagaggt agaggatacg 142020
ctccttatca aaatagcaaa gtaacgataa tcagtcacaa cggatgtgta ctatctgaca 142080
taaacatatc aaaagaagga attaaacgat ggagaagatt tgacggacca tgtggttatg 142140
atttattcac ggcggataac gtaattccaa aagatggttt acgaggagca ttcgtcgata 142200
aagacggtac ttatgacaaa gtttacattc ttttcactga tactatcggc tcaaagagaa 142260
ttgtcaaaat tccgtatata gcacaaatgt gcctaaacga cgaaggtggt ccatcatcat 142320
tgtctagtca tagatggtcg acgtttctca aagtcgaatt agaatgtgat atcgacggaa 142380
gaagttatag acaaattatt cattctagaa ctataaaaac agataatgat acgatactat 142440
atgtattctt cgatagtcct tattccaagt ccgcattatg tacctattct atgaatacca 142500

```
ttaaacaatc tttttctacg tcaaaattgg aaggatatac aaagcaattg ccgtctccag 142560
ctcctggtat atgtttacca gctggaaaag ttgttccaca taccacgttt gaagtcatag 142620
aacaatataa tgtactagat gatattataa agcctttatc taaccaacct atcttcgaag 142680
gaccgtctgg tgttaaatgg ttcgatataa aggagaagga aaatgaacat cgggaatata 142740
gaatatactt cataaaagaa aattctatat attcgttcga tacaaaatct aaacaaactc 142800
gtagctcgca agtcgatgcg cgactatttt cagtaatggt aactgcgaaa ccgttattta 142860
tagcagatat agggatagga gtaggaatgc cacaaatgaa aaaaatactt aaaatgtaat 142920
cttaatcgag tacaccacac gacaatgaac aaacataaga cagattatgc tggttatgct 142980
tgctgcgtaa tatgcggtct aattgtcgga attattttta cagcgacact attaaaagtt 143040
gtagaacgta aattagttca tacaccatta atagataaaa cgataaaaga tgcatatatt 143100
agagaagatt gtcctactga ctggataagc tataataata aatgtatcca tttatctact 143160
gatcgaaaaa cctgggagga aggacgtaat gcatgcaaag ctctaaattc aaattcggat 143220
ctaattaaga tagagactcc aaacgagtta agttttttaa gaagccttag acgaggctat 143280
tgggtaggag aatccgaaat attaaaccag acaaccccat ataattttat agctaagaat 143340
gccacgaaga atggaactaa aaaacggaaa tatatttgta gcacaacgaa tactcccaaa 143400
ctgcattcgt gttacactat ataacaatta cactacattt ttatcatacc actacttcgg 143460
ttagatgttt tagaaaaaaa taaatatcgc cgtaccgttc ttgtttttat aaaaataaca 143520
attaacaatt atcaaatttt ttctttaata ttttacgtgg ttgaccattc ttggtggtaa 143580
aataatctct tagtgttgga atggaatgct gtttaatgtt tccacactca tcgtatattt 143640
tgacgtatgt agtcacatcg tttacgcaat agtcagactg tagttctatc atgcttccta 143700
catcagaagg aggaacagtt ttaaagtctc ttggttttaa tctattaccg ttagttttca 143760
tgaaatcctt tgttttatcc acttcacatt ttaaataaat gtccactata cattcttttg 143820
ttaattttac tagatcgtca tgggtcatag aatttatagg ttccgtagtc catggatcca 143880
aactagcaaa cttcgcgtat acggtatcgc gattagtgta tacaccaact gtatgaaaat 143940
taagaaaaca gtttaataaa tcaacagaaa tatttaatcc tccgtttgat acagatgcgc 144000
catatttatg gatttcggat tcacacgttg tttgtctgag gtgttcgtct agtgttgctt 144060
ctacgtaaac ttcgattccc atatattctt tattgtcaga atcgcatacc gatttatcat 144120
catacactgt ttgaaaacta aatggtatac acatcaaaat aataaataat aacgagtaca 144180
ttctgcaata ttgttatcgt aattggaaaa atagtgttcg agtgagttgg attatgtgag 144240
tattggattg tatattttat tttatatttt gtaataagaa taaaatgcta atgtcaagtt 144300
tattccaata gatgtcttat taaaaacata tataataaat aacaatggct gaatggcata 144360
aaattatcga ggatatctca aaaaataata agttcgagga tgccgccatc gttgattaca 144420
agactacaaa gaatgttcta gctgctattc ctaacagaac atttgccaag attaatccgg 144480
gtgaaattat tcctctcatc actaatcgta atattctaaa acctcttatt ggtcagaaat 144540
attgtattgt atatactaac tctctaatgg atgagaacac gtatgctatg gagttgctta 144600
ctgggtacgc ccctgtatct ccgatcgtta tagcgagaac tcataccgca cttatatttt 144660
tgatgggtaa gccaacaaca tccagacgtg acgtgtatag aacgtgtaga gatcacgcta 144720
cccgtgtacg tgcaactggt aattaaaata aaaagtaata ttcatatgta gtgtcaattt 144780
taaatgatga tgatgaaatg gataatatcc atattgacga tgtcaataat gccggtattg 144840
```

gcatacagtt catcgatttt tagatttcat tcagaggatg tggaattatg ttatgggcat 144900
ttgtattttg ataggatcta taatgtagta aatataaaat ataatccgca tattccatat 144960
agatataatt ttattaatcg cacgttaacc gtagatgaac tagacgataa tgtctttttt 145020
acacatggtt atttttaaa acacaaatat ggttcactta atcctagttt gattgtctca 145080
ttatcaggaa acttaaaata taatgatata caatgctcag taaatgtatc gtgtctcatt 145140
aaaaatttgg caacgagtac atctactata ttaacatcta aacataagac ttattctcta 145200
catcggtcca cgtgtattac tataatagga tacgattcta ttatatggta taaagatata 145260
aatgacaagt ataatgacat ctatgatttt actgcaatat gtatgctaat agcgtctaca 145320
ttgatagtga ccatatacgt gtttaaaaaa ataaaaatga actcttaatt atgctatgct 145380
attagaaatg gataaaatca aaattacggt tgattcaaaa attggtaatg ttgttaccat 145440
atcgtataac ttggaaaaga taactattga tgtcacacct aaaaagaaaa aagaaaagga 145500
tgtattatta gcgcaatcag ttgctgtcga agaggcaaaa gatgtcaagg tagaagaaaa 145560
aaatattatc gatattgaag atgacgatga tatggatgta gaaagcgcat aatacgatct 145620
ataaaaataa gtatataaat actttttatt tactgtactc ttactgtgta gtggtgatac 145680
cctactcgat tattttttta aaaaaaaaat acttattctg attcttctaa ccatttccgt 145740
gttcgttcga atgccacatc gacgtcaaag ataggggagt agttaaaatc tagttctgca 145800
ttgttggtac acaccttaaa tgtagtgttg gatatcttca acgtatagtt gttgagtagt 145860
gatggttttc taaatagaat tctcttcata tcattcttgc acgcgtacat ttttagcatc 145920
catcttggaa accttaactt tcgaggttat tggttgtgga tcttctacaa tatctatgac 145980
tctgatttct tgaacatcat ctgcactaat taacagtttt actatatacc tgcctagaaa 146040
tccggcacca ccagtaaccg cgtacacggc cattgctgcc actcataata tcagactact 146100
tattctattt tactaaataa tggctgtttg tataatagac cacgataata tcagaggagt 146160
tatttacttt gaaccagtcc atggaaaaga taaagtttta ggatcagtta ttggattaaa 146220
atccggaacg tatagtttga taattcatcg ttacggagat attagtcaag gatgtgattc 146280
cataggcagt ccagaaatat ttatcggtaa catctttgta aacagatatg gtgtagcata 146340
tgtttattta gatacagatg taaatatatc tacaattatt ggaaaggcgt tatctatttc 146400
aaaaaatgat cagagattag cgtgtggagt tattggtatt tcttacataa atgaaaagat 146460
aatacatttt cttacaatta acgagaatgg cgtttgatat atcagttaat gcgtctaaaa 146520
caataaatgc attagtttac ttttctactc agcaaaataa attagtcata cgtaatgaag 146580
ttaatgatac acactacact gtcgaatttg atagggacaa agtagttgac acgtttattt 146640
catataatag acataatgac accatagaga taagaggggt gcttccagag gaaactaata 146700
ttggttgcgc ggttaatacg ccggttagta tgacttactt gtataataag tatagtttta 146760
aactgatttt agcagaatat ataagacaca gaaatactat atccggcaat atttattcgg 146820
cattgatgac actagatgat ttggctatta aacagtatgg agacattgat ctattattta 146880
atgagaaact taaagtagac tccgattcgg gactatttga ctttgtcaac tttgtaaagg 146940
atatgatatg ttgtgattct agaatagtag tagctctatc tagtctagta tctaaacatt 147000
gggaattgac aaataaaaag tataggtgta tggcattagc cgaacatata tctgatagta 147060
ttccaatatc tgagctatct agactacgat acaatctatg taagtatcta cgcggacaca 147120
ctgagagcat agaggataaa tttgattatt ttgaagacga tgattcgtct acatgttctg 147180
ccgtaaccga cagggaaacg gatgtataat ttttttata gcgtgaagga tatgataaaa 147240

```
aatataattg ttgtatttat cccattccaa tcaccttata tgattctgta acacaataaa 147300
ggagtcttat agatgtatag aggtcagata ctggtttgat aaactgttta ttccacataa 147360
gtatgtttga ctttatggtt agacccgcat actttaacaa atcactgaaa attggagtta 147420
ggtattgacc tctcagaatc agttgccgtt ctggaacatt aaatgtattt tttatgatat 147480
actccaacgc atttatgtgg gcatacaaca agtcattact aatggaatat tccaagagtt 147540
ttagttgtct agtatttaac aagagaagag atttcaacag actgtttatg aactcgaatg 147600
ccgcctcatt gtcgcttata ttgatgatgt cgaattctcc caatatcatc accgatgagt 147660
agctcatctt gttatcggga tccaagtttt ctaaagatgt cattaaaccc tcgatcatga 147720
atggatttat catcatcgtt tttatgttgg acatgagctt agtccgtttg tccacatcta 147780
tagaagatga tttctgaatt atttcatata tctctctctt taactccagg aacttgtcag 147840
gatggtctac tttaatatgt tctcgtctaa gagatgaaaa tctttggatg gttgcacgcg 147900
acttttctct aaaggatgac gttgcccaag atcctctctt aaatgaatcc atcttatcct 147960
tggacaagat ggacagtcta ttttccttag atggtttaat atttttgtta cccatgatct 148020
ataaaggtag acctaatcgt ctcggatgac catatattta ttttcagttt tattatacgc 148080
ataaattgta aaaaatatgt taggtttaca aaaatgtctc gtggggcatt aatcgttttt 148140
gaaggattgg acaaatctgg aaaaacaaca caatgtatga acatcatgga atctataccg 148200
gcaaacacga taaaatatct taactttcct cagagatcca ctgtcactgg aaaaatgata 148260
gatgactatc taactcgtaa aaaaacctat aatgatcata tagttaatct attattttgt 148320
gcaaatagat gggagtttgc atcttttata caagaacaac tagaacaggg aattacttta 148380
atagttgata gatacgcatt ttctggagta gcgtatgccg ccgctaaagg cgcgtcaatg 148440
actctcagta agagttatga atctggattg cctaaacccg acttagttat attcttggaa 148500
tctggtagca aagaaattaa tagaaacgtc ggcgaggaaa tttatgaaga tgttacattc 148560
caacaaaagg tattacaaga atataaaaaa atgattgaag aaggagatat tcattggcaa 148620
attatttctt ctgaattcga ggaagatgta aagaaggagt tgattaagaa tatagttata 148680
gaggctatac acacggttac tggaccagtg gggcaactgt ggatgtaata gtgaaattac 148740
attttttata aatagatgtt agtacagtgt tataaatgga tgaagcatat tactctggca 148800
acttggaatc agtactcgga tacgtgtccg atatgcatac cgaactcgca tcaatatctc 148860
aattagttat tgccaagata gaaactatag ataatgatat attaaacaag gacattgtaa 148920
attttatcat gtgtagatca aacttggata atccatttat ctctttccta gatactgtat 148980
atactattaa aaataactag ttataagttt gaatccgtca attttgattc caaaattgaa 149040
tggactgggg atggtctata caatatatcc cttaaaaatt atggcatcaa gacgtggcaa 149100
acaatgtata caaatgtacc agaaggaaca tacgacatat ccgcatttcc aaagaatgat 149160
ttcgtatctt tctgggttaa atttgaacaa ggcgattata aagtggaaga gtattgtacg 149220
ggactatgcg tcgaagtaaa aattggacca ccgactgtaa cattaactga atacgacgac 149280
catatcaatt tgtacatcga gcatccgtat gctactagag gtagcaaaaa gattcctatt 149340
tacaaacgcg gtgacatgtg tgatatctac ttgttgtata cggctaactt cacattcgga 149400
gattctaaag aaccagtacc atatgatatc gatgactacg attgcacgtc tacaggttgc 149460
agcatagact ttgtcacaac agaaaaagtg tgcgtgacag cacagggagc cacagaaggg 149520
tttctcgaaa aaattactcc atggagttcg aaagtatgtc tgacacctaa aaagagtgta 149580
```

tatacatgcg caattagatc caaagaagat gttcccaatt tcaaggacaa aatggccaga 149640
gttatcaaga gaaaatttaa tacacagtct caatcttatt taactaaatt tctcggtagc 149700
acatcaaatg atgttaccac ttttcttagc atgcttaact tgactaaata ttcataatta 149760
ttttttatta atgatacaaa aacgaaataa aactgcatat tatacactgg ttaacgccct 149820
tataggctct aaccattttc aagatgaggt ccctgattat agtccttctg ttcccctcta 149880
tcatctactc catgtctatt agacgatgtg agaagactga agaggaaaca tggggattga 149940
aaatagggtt gtgtataatt gccaaagatt tctatcccga aagaactgat tgcagtgttc 150000
atctcccaac tgcaagtgaa ggattgataa ctgaaggcaa tggattcagg gatatacgaa 150060
acaccgataa attataaaaa aagcaatgtg tccgctgttt ccgttaataa tactattttc 150120
gtaactggcg gattattcat aaataactct aatagcacga tcgtggacat ttataaagac 150180
aaacaatggt cgattataga aatggctagg gtatatcacg gcatcgactc gacatttgga 150240
atgttatatt ttgccggagg tctatccgtt accgaacaat atggtaattt agagaaaaac 150300
aacgagatat cttgttacaa tcctagaacg aataagtggt ttgatatttc atatactatt 150360
tataagatat ccatatcatc attgtgtaaa ctaaataacg tcttctatgt atttagtaag 150420
gacattggat atgtggaaaa gtatgatggt gcatggaagt tagtacatga tcgtctcccc 150480
gctataaagg cattatcaac ttctccttat tgattgaaaa tgaaaatata aatagttttt 150540
atgtatagca gtattaccct atagttttat tgcttactac taacatggat acagatgtta 150600
caaatgtaga agatatcata aatgaaatag atagagagaa agaagaaata ctaaaaaatg 150660
tagaaattga aaataataaa aacattaaca agaatcatcc caatgaatat attagagaag 150720
cactcgttat taataccagt agtaatagtg attccattga taaagaagtt atagaatgta 150780
tcagtcacga tgtaggaata tagatcatat ctactaattt ttataatcga tacaaaacat 150840
aaaaaacaac tcgttattac atagcaggca tggaatcctt caagtattgt tttgataacg 150900
atggcaagaa atggattatc ggaaatactt tatattctgg taattcaata ctctataagg 150960
tcagaaaaaa tttcactagt tcgttctaca attacgtaat gaagatagat cacaaatcac 151020
acaagccatt gttgtctgaa atacgattct atatatctgt attggatcct ttgactatcg 151080
acaactggac acgggaacgt ggtataaagt atttggctat tccagatctg tatggaattg 151140
gagaaaccga tgattatatg ttcttcgtta taaagaattc gggaagagta ttcgccccaa 151200
aggatactga atcagtcttc gaagcatgcg tcactatgat aaacacgtta gagtttatac 151260
actctcgagg atttacccat ggaaaaatag aaccgaggaa tatactgatt agaaataaac 151320
gtctttcact aattgactat tctagaacta acaaactata caagagtgga aactcacata 151380
tagattacaa cgaggacatg ataacttcag gaaatatcaa ttatatgtgt gtagacaatc 151440
atcttggagc aacagtttca agacgaggag atttagaaat gttgggatat tgcatgatag 151500
aatggttcgg tggcaaactt ccatggaaaa acgaaagtag tataaaagta ataaaacaaa 151560
aaaaagaata taaaaaattt atagctactt tctttgagga ctgttttcct gaaggaaatg 151620
aacctctgga attagttaga tatatagaat tagtatacac gttagattat tctcaaactc 151680
ctaattatga cagactacgt aaactgttta tacaagattg aaattatatt ctttttttta 151740
tagagtgtgg tagtgttacg gatatctaat attaatatta gactatctct atcgcgctac 151800
acgaccaata tcgattacta tggatatctt ctatgaaagg agagaatgta tttatttctc 151860
cagcgtcaat ctcgtcagta ttgacaatac tgtattatgg agctaatgga tccactgctg 151920
aacagctatc aaaatatgta gaaacggagg agaacacgga taaggttagc gctcagaata 151980
tctcattcaa atccatgaat aaagtatatg ggcgatattc tgccgtgttt aaagattcct 152040
ttttgagaaa aattggcgat aagtttcaaa ctgttgactt cactgattgt cgcactatag 152100
atgcaatcaa caagtgtgta gatatcttta ctgaggggaa aatcaatcca ctattggatg 152160
aaccattgtc tcctagcaat tagtgccgta tactttaaag caaaatggtt gacgccattc 152220
gaaaaggaat ttaccagtga ttatcccttt tacgtatctc cgacggaaat ggtagacgta 152280
agtatgatgt ctatgtacgg caaggcattt aatcacgcat ctgtaaaaga atcattcggc 152340
aacttttcaa tcatagaact gccatatgtt ggagatacta gtatgatggt cattcttcca 152400
gacaagattg atggattaga atccatagaa caaaatctaa cagatacaaa ttttaagaaa 152460
tggtgtgact ttatggatgc tatgtttata gatgttcaca ttcccaagtt taaggtaaca 152520
ggctcgtata atctggtgga tactctagta aagtcaggac tgacagaggt gttcggttca 152580
actggagatt atagcaatat gtgtaattta gatgtgagtg tcgacgctat gatccacaaa 152640
acgtatatag atgtcaatga agagtataca gaagcagctg cagcaacttc tgtactagtg 152700
gcagactgtg catcaacaat tacaaatgag ttctgtgcag atcatccgtt catctatgtg 152760
attaggcatg ttgatggaaa aattcttttc gttggtagat attgctctcc gacaactaat 152820
tgttaaccat ttttttaaa aaaaacaatg ggtgatggat acacttgatg gtataatgat 152880
gaatgaacgc gatgtttctg taagcgttgg caccggaata ctattcatgg aaatgttttt 152940
ccgttacaat aaaaatagta tcaacaatca actaatgtat gatataatta atagcgtatc 153000
tataagtgta gctaattata gatatagaag ctgcttttaa cgacgatggt atatacatcc 153060
gtagaaatat gattaacaag ttgtacggat acgcatctct aactactatt ggcacgatcg 153120
ctggaggtgt ttgttattat ctgttgatgc atctagttag tttgtataaa taattatttc 153180
aatatactag ttaaaatttt aagattttaa atgtataaaa aactaataac gtttttattt 153240
gtaataggtg cattagcatc ctattcgaat aatgagtaca ctccgtttaa taaactgagt 153300
gtaaaactct atatagatgg agtagataat atagaaaatt catatactga tgataataat 153360
gaattggtgt taaattttaa agagtacaca atttctatta ttacagagtc atgcgacgtc 153420
ggatttgatt ccatagatat agatgttata aacgactata aaattattga tatgtatacc 153480
attgactcgt ctactattca acgcagaggt cacacgtgta gaatatctac caaattatca 153540
tgccattatg ataagtaccc ttatattcac aaatatgatg gtgatgagcg acaatattct 153600
attactgcag agggaaaatg ctataaagga ataaaatatg aaataagtat gatcaacgat 153660
gatactctat tgagaaaaca tactcttaaa attggatcta cttatatatt tgatcgtcat 153720
ggacatagta atacatatta ttcaaaatat gatttttaaa aatttaaaat atattatcac 153780
ttcagtgaca gtagtcaaat aacaaacaac accatgagat atattataat tctcgcagtt 153840
ttgttcatta atagtataca cgctaaaata actagttata agtttgaatc cgtcaatttt 153900
gattccaaaa ttgaatggac tggggatggt ctatacaata tatcccttaa aaattatggc 153960
atcaagacgt ggcaaacaat gtatacaaat gtaccagaag gaacatacga catatccgca 154020
tttccaaaga atgatttcgt atctttctgg gttaaatttg aacaaggcga ttataaagtg 154080
gaagagtatt gtacgggact atgcgtcgaa gtaaaaattg gaccaccgac tgtaacattg 154140
actgaatacg acgaccatat caatttgtac atcgagcatc cgtatgctac tagaggtagc 154200
aaaaagattc ctatttacaa acgcggtgac atgtgtgata tctacttgtt gtatacggct 154260
aacttcacat tcggagattc taaagaacca gtaccatatg atatcgatga ctacgattgc 154320
acgtctacag gttgcagcat agactttgtc acaacagaaa aagtgtgcgt gacagcacag 154380
ggagccacag aagggtttct cgaaaaaatt actccatgga gttcgaaagt atgtctgaca 154440
cctaaaaaga gtgtatatac atgcgcaatt agatccaaag aagatgttcc caatttcaag 154500
gacaaaatgg ccagagttat caagagaaaa tttaatacac agtctcaatc ttatttaact 154560
aaatttctcg gtagcacatc aaatgatgtt accacttttc ttagcatgct taacttgact 154620
aaatattcat aactaatttt tattaatgat acaaaaacga aataaaactg catattatac 154680
actggttaac gcccttatag gctctaacca ttttcaagat gaggtccctg attatagtcc 154740
ttctgttccc ctccatgtct attagacgat gtgagaagac tgaagaggaa acatggggat 154800
tgaaaatagg gttgtgtata attgccaaag atttttatcc cgaaagaact gattgcagtg 154860
ttcatctccc aactgcaagt gaaggattga taactgaagg caatggattc agggatatac 154920
gaaacaccga taaattataa aaaaagcaat gtgtccgctg tttccgttaa taatactatt 154980
ttcgtaactg gcggattatt cataaataac tctaatagca cgatcgtgga catttataaa 155040
gacaaacaat ggtcgattat agaaatggct agggtatatc acggcatcga ctcgacattt 155100
ggaatgttat attttgccgg aggtctatcc gttaccgaac aatatggtaa tttatagaaa 155160
aacaacgaga tatcttgtta caatcctaga acgaataagt ggtttgatat ttcatatact 155220
atttataaga tatccatatc atcattgtgt aaactaaata acgtcttcta tgtatttagt 155280
aaggacattg gatatgtgga aaagtatgat ggtgcatgga agttagtaca tgatcgtctc 155340
cccgctataa aggcattatc aacttctcct tattgattga aaatgaaaat ataaatagtt 155400
tttatgtata gcagtattac cctatagttt tattgcttac tactaacatg gatacagatg 155460
ttacaaatgt agaagatatc ataaatgaaa tagatagaga gaaagaagaa atactaaaaa 155520
atgtagaaat tgaaaataat aaaaacatta acaagaatca tcccaatgaa tatattagag 155580
aagcactcgt tattaatacc agtagtaata gtgattccat tgataaagaa gttatagaat 155640
gtatcagtca cgatgtagga atatagatca tatctactaa tttttataat cgatacaaaa 155700
cataaaaaac aactcgttat tacatagcag gcatggaatc cttcaagtat tgttttgata 155760
acgatggcaa gaaatggatt atcggaaata ctttatattc tggtaattca atactctata 155820
aggtcagaaa aaatttcact agttcgttct acaattacgt aatgaagata gatcacaaat 155880
cacacaagcc attgttgtct gaaatacgat tctatatatc tgtattggat cctttgacta 155940
tcgacaactg gacacgggaa cgtggtataa agtatttggc tattccagat ctgtatggaa 156000
ttggagaaac cgatggatta tatgttcttc gttataaaga attcgggaag agtattcgcc 156060
ccaaaggata ctgaatcagt cttcgaagca tgcgtcacta tgataaacac gttagagttt 156120
atacactctc gaggatttac ccatggaaaa atagaaccga ggaatataat attaaaactt 156180
accacgtaaa acttaaaatt taaaatgata tttcattgac agatagatca cacattatga 156240
actttcaagg acttgtgtta actgacaatt gcaaaaatca atgggtcgtt ggaccattaa 156300
taggaaaagg tggatttggt agtatttata ctactaatga caataattat gtagtaaaaa 156360
tagagcccaa agctaacgga tcattattta ccgaacaggc attttatact agagtactta 156420
aaccatccgt tatcgaagaa tggaaaaaat ctcacaatat aaagcacgta ggtcttatca 156480
cgtgcaaggc atttggtcta tacaaatcca ttaatgtgga atatcgattc ttggtaatta 156540
atagattagg tgcagatcta gatgcggtga tcagagccaa taataataga ctaccaaaaa 156600
ggtcggtgat gttgatcgga atcgaaatct taaataccat acaatttatg cacgagcaag 156660
gatattctca cggagatatt aaagcgagta atatagtctt agatcaaata gataagaata 156720

```
aattatatct agtggattac ggattggttt ctaaattcat gtctaatggc gaacatgttc 156780
catttataag aaatccaaat aaaatggata acggtactct agaatttaca cctatagatt 156840
cgcataaagg atacgttgta tctagacgtg gagatctaga aacacttgga tattgtatga 156900
ttagatggtt gggaggtatc ttaccatgga ctaagatatc tgaaacaaag aattgtgcat 156960
tagtaagtgc cacaaaacag aaatatgtta acaatactgc gactttgtta atgaccagtt 157020
tgcaatatgc acctagagaa ttgctgcaat atattaccat ggtaaactct ttgacatatt 157080
ttgaggaacc caattacgac aagtttcggc acatattaat gcagggtgta tattattaag 157140
tgtggtgttt ggtcgataaa aattaaaaaa taacttaatt tattattgat ctcgtgtgta 157200
caaccgaaat catggcgatg ttttacgcac acgctctcgg tgggtacgac gagaatcttc 157260
atgcctttcc tggaatatca tcgactgttg ccaatgatgt caggaaatat tctgttgtgt 157320
cagtttataa taacaagtat gacattgtaa aagacaaata tatgtggtgt tacagtcagg 157380
tgaacaagag atatattgga gcactgctgc ctatgtttga gtgcaatgaa tatctacaaa 157440
ttggaaatcc gatccatgat caagaaggaa atcaaatctc tatcatcaca tatcgccaca 157500
aaaactacta tgctctaagc ggaatcgggt acgagagtct agacttgtgt ttggaaggag 157560
tagggattca tcatcacgta cttgaaacag gaaacgctgt atatggaaaa gttcaacatg 157620
attattctac tatcaaagag aaggccaaag aaatgagtgc acttagtcca ggacctatca 157680
tcgattacca cgtctggata ggagattgta tctgtcaagt tactgctgtg gacgtacatg 157740
gaaaggaaat tatgaaaatg agattcaaaa agggtgcggt gcttccgatc ccaaatctgg 157800
taaaagttaa acttggggag aatgatacag aaaatctttc ttctactata tcggcgacac 157860
catcgaggta accacctctc tggaagacag cgtgaataat gtactcatga aacgtttgga 157920
aactatacgc catatgtggt ctgttgtata tgatcatttt gatattgtga atggtaaaga 157980
atgctgttat gtgcatacgc atttgtctaa tcaaaatctt ataccgagta ctgtaaaaac 158040
aaatttgtac atgaagacta tgggatcatg cattcaaatg gattccatgg aagctctaga 158100
gtatcttagc gaactgaagg aatcaggtgg atggagtccc agaccagaaa tgcaggaatt 158160
tgaatatcca gatggagtgg aagacactga atcaattgag agattggtag aggagttctt 158220
caatagatca gaacttcagg ctggtgaatc agtcaaattt ggtaattcta ttaatgttaa 158280
acatacatct gtttcagcta agcaactaag aacacgtata cggcagcagc ttccttctat 158340
actctcatct tttaccaaca caaagggtgg atatttgttc attggagttg ataataatac 158400
acacaaagta tttggattca cggtgggtta cgactacctc agactgatag agaatgatat 158460
agaaaagcat atcaaaagac tttgtgttgt gtatttctgt gagaagaaag aggacatcaa 158520
gtacgcgtgt cgattcatca aggtatataa acctggggat gaggctacct cgacatacgt 158580
gtgcgctatc aaagtggaaa gatgctgttg tgctgtgttt gcagattggc cagaatcatg 158640
gtatatggat actaatggta tcaagaagta ttctccagat gaatgggtgt cacatataaa 158700
attttaatta atgtaactat agagaacaaa taataaggtt gtaatatcat atagacaata 158760
actaacaatt aattagtaac tgttatctct tttttaatta accaactaac tatataccta 158820
ttaatacatc gtaattatag ttcttaacat ctattaatca ttaattcgct tctttaattt 158880
tttataaact aacattgtta attgaaaagg gataacatgt tacagaatat aaattatata 158940
tggatttttt taaaaaggaa atacttgact ggagtatata tttatctctt cattatatag 159000
cacgcgtgtt ttccaatttt tccacatccc atataataca ggattataat ctcgttcgaa 159060
```

catacgagaa agtggataaa acaatagttg attttttatc taggttgcca aatttattcc 159120
atattttaga atatggggaa aatattctac atatttattc tatggatgat gctaatacga 159180
atattataat ttttttcta gatagagtat taaatattaa taagaacggg tcatttatac 159240
acaatctcgg gttatcatca tccattaata taaaagaata tgtatatcaa ttagttaata 159300
atgatcatcc agataatagg ataagactaa tgcttgaaaa tggacgtaga acaagacatt 159360
ttttgtccta tatatcagat acagttaata tctatatatg tattttaata aatcatggat 159420
tttatataga tgccgaagac agttacggtt gtacattatt acatagatgt atatatcact 159480
ataagaaatc agaatcagaa tcatacaatg aattaattaa gatattgtta aataatggat 159540
cagatgtaga taaaaaagat acgtacggaa acacaccttt tatcctatta tgtaaacacg 159600
atatcaacaa cgtggaattg tttgagatat gtttagagaa tgctaatata gactctgtag 159660
actttaatag atatacacct cttcattatg tctcatgtcg taataaatat gattttgtaa 159720
agttattaat ttctaaagga gcaaatgtta atgcgcgtaa taaattcgga actactccat 159780
tttattgtgg aattatacac ggtatctcgc ttataaaact atatttggaa tcagacacag 159840
agttagaaat agataatgaa catatagttc gtcatttaat aatttttgat gctgttgaat 159900
ctttagatta tctattatcc agaggagtta ttgatattaa ctatcgtact atatacaacg 159960
aaacatctat ttacgacgct gtcagttata atgcgtataa tacgttggtc tatctattaa 160020
acaaaaatgg tgattttgag acgattacta ctagtggatg tacatgtatt tcggaagcag 160080
tcgcaaacaa caacaaaata ataatggaag tactattgtc taaacgacca tctttgaaaa 160140
ttatgataca gtctatgata gcaattacta aacataaaca gcataatgca gatttattga 160200
aaatgtgtat aaaatatact gcgtgtatga ccgattatga tactcttata gatgtacagt 160260
cgctacagca atataaatgg tatattttaa gatgtttcga tgaaatagat atcatgaaga 160320
gatgttatat aaaaaataaa actgtattcc aattagtttt ttgtatcaaa gacattaata 160380
ctttaatgag atacggtaaa catccttctt tcgtgaaatg cactagtctc gacgtatacg 160440
gaagtcgtgt acgtaatatc atagcatcta ttagatatcg tcagagatta attagtctat 160500
tatccaagaa gctggatcct ggagataaat ggtcgtgttt tcctaacgaa ataaaatata 160560
aaatattgga aaactttaac gataacgaac tatccacata tctaaaaatc ttataaacat 160620
tattaaaata taaaatctaa gtaggataaa atcacactac atcattgttt ccttttagtg 160680
ctcgacagtg tatactattt ttaacgctca taaataaaaa tgaaaacgat ttccgttgtt 160740
acgttgttat gcgtactacc tgctgttgtt tattcaacat gtactgtacc cactatgaat 160800
aacgctaaat taacgtctac cgaaacatcg tttaatgata accagaaagt tacgtttaca 160860
tgtgatcagg gatatcattc tttggatcca aatgctgtct gtgaaacaga taaatggaaa 160920
tacgaaaatc catgcaaaaa aatgtgcaca gtttctgatt atgtctctga actatataat 160980
aaaccgctat acgaagtgaa ttccaccatg acactaagtt gcaacggcga aacaaaatat 161040
tttcgttgcg aagaaaaaaa tggaaatact tcttggaatg atactgttac gtgtcctaat 161100
gcggaatgtc aacctcttca attagaacac ggatcgtgtc aaccagttaa agaaaaatac 161160
tcatttgggg aatatatgac tatcaactgt gatgttggat atgaggttat tggtgcttcg 161220
tacataagtt gtacagctaa ttcttggaat gttattccat catgtcaaca aaaatgtgat 161280
atgccgtctc tatctaacgg attaatttcc ggatctacat tttctatcgg tggcgttata 161340
catcttagtt gtaaaagtgg ttttacacta acggggtctc catcatccac atgtatcgac 161400
ggtaaatgga atcccatact cccaatatgt gtacgaacta acgaaaaatt tgatccagtg 161460
gatgatggtc ccgacgatga gacagatttg agcaaactct cgaaagacgt tgtacaatat 161520
gaacaagaaa tagaatcgtt agaagcaact tatcatataa tcatagtggc gttgacaatt 161580
atgggcgtca tatttttaat ctccgttata gtattagttt gttcctgtga caaaaataat 161640
gaccaatata agttccataa attgctaccg taaatataaa tccgttaaaa taattaataa 161700
tttaataaca aacaagtatc aaaagattaa agacttatag ctagaatcaa ttgagatgtc 161760
ttcttcagtg gatgttgata tctacgatgc cgttagagca tttttactca ggcactatta 161820
taacaagaga tttattgtgt atggaagaag taacgccata ttacataata tatacaggct 161880
atttacaaga tgcgccgtta taccgttcga tgatatagta cgtactatgc caaatgaatc 161940
acgtgttaaa caatgggtga tggatacact taatggtata atgatgaatg aacgcgatgt 162000
ttctgtaagc gttggcaccg gaatactatt catggaaatg tttttcgatt acaataaaaa 162060
tagtatcaac aatcaactaa tgtatgatat aattaatagc gtatctataa ttctagctaa 162120
tgagagatat agaagcgctt ttaacgacga tggtatatac atccgtagaa atatgattaa 162180
caagttgtac ggatacgcat ctctaactac tattggcacg atcgctggag gtgtttgtta 162240
ttatctgttg atgcatctag ttagtttgta taaataatta tttcaatata ctagttaaaa 162300
ttttaagatt ttaaatgtat aaaaaactaa taacgttttt atttgtaata ggtgcattag 162360
catcctattc gaataatgag tacactccgt ttaataaact gagtgtaaaa ctctatatag 162420
atggagtaga taatatagaa aattcatata ctgatgataa taatgaattg gtgttaaatt 162480
ttaaagagta cacaatttct attattacag agtcatgcga cgtcggattt gattccatag 162540
atatagatgt tataaacgac tataaaatta ttgatatgta taccattgac tcgtctacta 162600
ttcaacgcag aggtcacacg tgtagaatat ctaccaaatt atcatgccat tatgataagt 162660
acccttatat tcacaaatat gatggtgatg agcgacaata ttctattact gcagagggaa 162720
aatgctataa aggaataaaa tatgaaataa gtatgatcaa cgatgatact ctattgagaa 162780
aacatactct taaaattgga tctacttata tatttgatcg tcatggacat agtaatacat 162840
attattcaaa atatgatttt taaaaattta aaatatatta tcacttcagt gacagtagtc 162900
aaataacaaa caacaccatg agatatatta taattctcgc agttttgttc attaatagta 162960
tacatgctaa aataactagt tataagtttg aatccgtcaa ttttgattcc aaaattgaat 163020
ggactgggga tggtctatac aatatatccc ttaaaaatta tggcatcaag acgtggcaaa 163080
caatgtatac aaatgtacca gaaggaacat acgacatatc cgcatttcca aagaatgatt 163140
tcgtatcttt ctgggttaaa tttgaacaag gcgattataa agtggaagag tattgtacgg 163200
gactatgcgt cgaagtaaaa attggaccac cgactgtaac attgactgaa tacgacgacc 163260
ataaacagaa aaagtgtgcg tgacagcaca gggagccaca gaagggtttc tcgaaaaaat 163320
tactccatgg agttcgaaag tatgtctgac acctaaaaag agtgtatata catgcgcaat 163380
tagatccaaa gaagatgttc ccaatttcaa ggacaaaatg gccagagtta tcaagagaaa 163440
atttaataca cagtctcaat cttatttaac taaatttctc ggtagcacat caaatgatgt 163500
taccactttt cttagcatgc ttaacttgac taaatattca taactaattt ttattaatga 163560
tacaaaaacg aaataaaact gcatattata cactggttaa cgcccttata ggctctaacc 163620
attttcaaga tgaggtccct gattatagtc cttctgttcc cctctatcat ctactccatg 163680
tctattagac gatgtgagaa gactgaagag gaaacatggg gattgaaaat agggttgtgt 163740
ataattgcca aagatttcta tcccgaaaga actgattgca gtgttcatct cccaactgca 163800
agtgaaggat tgataactga aggcaatgga ttcagggata tacgaaacac cgataaatta 163860
taaaaaaagc aatgtgtccg ctgtttccgt taataatact attttcgtaa ctggcggatt 163920
attcataaat aactctaata gcacgatcgt ggttaacaat atggaaaaac ttgacattta 163980
taaagacaaa caatggtcga ttatagaaat gcctatggct agggtatatc acggcattga 164040
ctcgacattt ggaatgttat attttgccgg aggtctatcc gttaccgaac aatatggtaa 164100
tttagagaaa aacaacgaga tatcttgtta caatcctaga acgaataagt ggtttgatat 164160
ttcatatact atttataaga tatccatatc atcattgtgt aaactaaata acgtcttcta 164220
tgtatttagt aaggacattg gatatgtgga aaagtatgat ggtgcatgga agttagtaca 164280
tgatcgtctc cccgctataa aggcattatc aacttctcct tattgattga aaatataaat 164340
agtttttatg tatagcagta ttaccctata gttttattgc ttactactaa catggataca 164400
gatgttacaa atgtagaaga tatcataaat gaaatagata gagagaaaga agaaatacta 164460
aaaaatgtag aaattgaaaa taataaaaac attaacaaga atcatcccaa tgaatatatt 164520
agagaagcac tcgttattaa taccagtagt aatagtgatt ccattgataa agaagttata 164580
gaatgtatca gtcacgatgt aggaatatag atcatatcta ctaattttta taatcgatac 164640
aaaacataaa aaacaactcg ttattacata gcaggcatgg aatccttcaa gtattgtttt 164700
gataacgatg gcaagaaatg gattatcgga aatactttat attctggtaa ttcaatactc 164760
tataaggtca gaaaaaattt cactagttcg ttctacaatt acgtaatgaa gatagatcac 164820
aaatcacaca agccattgtt gtctgaaata cgattctata tatctgtatt ggatcctttg 164880
actatcgaca actggacacg ggaacgtggt ataaagtatt tggctattcc agatctgtat 164940
ggaattggag aaaccgatga ttatatgttc ttcgttataa agaattcggg aagagtattc 165000
gccccaaagg atactgaatc agtcttcgaa gcatgcgtca ctatgataaa cacgttagag 165060
tttatacact ctcgaggatt tacccatgga aaaatagaac cgaggaatat actgattaga 165120
aataaacgtc tttcactaat tgactattct agaactaaca aactatacaa gagtggaaac 165180
tcacatatag attacaacga ggacatgata acttcaggaa atatcaatta tatgtgtgta 165240
gacaatcatc ttggagcaac agtttcaaga cgaggagatt tagaaatgtt gggatattgc 165300
atgatagaat ggttcggtgg caaacttcca tggaaaaacg aaagtagtat aaaagtaata 165360
aaacaaaaaa aagaatataa aaaatttata gctactttct ttgaggactg ttttcctgaa 165420
ggaaatgaac ctctggaatt agttagatat atagaattag tatacacgtt agattattct 165480
caaactccta attatgacag actacgtaaa ctgtttatac aagattgaaa ttatattctt 165540
ttttttatag agtgtggtag tgttacggat atctaatatt aatattagac tatctctatc 165600
gcgctacacg accaatatcg attactatgg atatcttcta tgaaaggaga gaatgtattt 165660
atttctccag cgtcaatctc gtcagtattg acaatactgt attatggagc taatggatcc 165720
actgctgaac agctatcaaa atatgtagaa acggaggaga acacggataa ggttagcgct 165780
cagaatatct cattcaaatc catgaataaa gtatatgggc gatattctgc cgtgtttaaa 165840
gattcctttt tgagaaaaat tggcgataag tttcaaactg ttgacttcac tgattgtcgc 165900
actatagatg caatcaacaa gtgtgtagat atctttactg aggggaaaat caatccacta 165960
ttggatgaac cattgtctcc tagcaattag tgccgtatac tttaaagcaa aatggttgac 166020
gccattcgaa aaggaattta ccagtgatta tcccttttac gtatctccga cggaaatggt 166080
agacgtaagt atgatgtcta tgtacggcaa ggcatttaat cacgcatctg taaaagaatc 166140
attcggcaac ttttcaatca tagaactgcc atatgttgga gatactagta tgatggtcat 166200

-continued tcttccagac aagattgatg gattagaatc catagaacaa aatctaacag atacaaattt 166260
taagaaatgg tgtgacttta tggatgctat gtttatagat gttcacattc ccaagtttaa 166320
ggtaacaggc tcgtataatc tggtggatac tctagtaaag tcaggactga cagaggtgtt 166380
cggttcaact ggagattata gcaatatgtg taatttagat gtgagtgtcg acgctatgat 166440
ccacaaaacg tatatagatg tcaatgaaga gtatacagaa gcagctgcag caacttctgt 166500
actagtggca gactgtgcat caacaattac aaatgagttc tgtgcagatc atccgttcat 166560
ctatgtgatt aggcatgttg atggaaaaat tcttttcgtt ggtagatatt gctctccgac 166620
aactaattgt taaccatttt ttttaaaaaa aatagaaaaa acatgtggta ttagtgcagg 166680
tcgttgttct tccaattgca attggtaaga tgacggccaa ctttagtacc cacgtctttt 166740
caccacagca ctgtggatgt gacagactga ccagtattga tgacgtcaaa caatgtttga 166800
ctgaatatat ttattggtcg tcctatgcat accgcaacag gcaatgcgct ggacaattgt 166860
attccacact cctctctttt agagatgatg cggaattagt gttcatcgac attcgcgagc 166920
tggtaaaaaa tatgccgtgg gatgatgtca aagattgtac agaaatcatc cgttgttata 166980
taccggatga gcaaaaaacc atcagagaga tttcggccat catcggactt tgtgcatatg 167040
ctgctactta ctggggaggt gaagaccatc ccactagtaa cagtctgaac gcattgtttg 167100
tgatgcttga gatgctaaat tacgtggatt ataacatcat attccggcgt atgaattgat 167160
gagttgtaca tcttgacatt ttctttcttc tcttctccct ttcttctctt ctcccttcct 167220
ccctcttctc cctttcccag aaacaaactt ttttacccac tataaaataa aatgagtata 167280
ctacctgtta tatttctttc tatatttttt tattcttcat tcgttcagac ttttaacgcg 167340
tctgaatgta tcgacaaagg gcaatatttt gcatcattca tggagttaga aaacgagcca 167400
gtaatcttac catgtcctca aataaatacg ctatcatccg gatataatat attagatatt 167460
ttatgggaaa aacgaggagc ggataatgat agaattatac cgatagataa tggtagcaat 167520
atgctaattc tgaacccgac acaatcagac tctggtattt atatatgcat taccacgaac 167580
gaaacctact gtgacatgat gtcgttaaat ttgacaatcg tgtctgtctc agaatcaaat 167640
atagatttta tctcgtatcc acaaatagta aatgagagat ctactggcga aatggtatgt 167700
cccaatatta atgcatttat tgctagtaac gtaaacgcag atattatatg gagcggacat 167760
cgacgcctta gaaataagag acttaaacaa cggacacctg gaattattac catagaagat 167820
gttagaaaaa atgatgctgg ttattataca tgtgttttag aatatatata cggtggcaaa 167880
acatataacg taaccagaat tgtaaaatta gaggtacggg ataaaataat accttctact 167940
atgcaattac cagatggcat tgtaacttca ataggtagta atttgactat tgcatcgttg 168000
agacctccca caacggatgc agacgtcttt tggataagta atggtatgta ttacgaagaa 168060
gatgatgggg acggaaacgg tagaataagt gtagcaaata aaatctatat gaccgataag 168120
agacgtgtta ttacatcccg gttaaacatt aatcctgtca aggaagaaga tgctacaacg 168180
tttacgtgta tggcgtttac tattcctagc atcagcaaaa cagttactgt tagtataacg 168240
tgaatgtatg ttgttacatt tccatgtcaa ttgagtttat aagaattttt atacattatc 168300
ttccaacaaa caattgacga acgtattgct atgattaact cccacgatac tatgcatatt 168360
attaatcatt aacttgcaga ctatacctag tgctattttg acatactcat gttcttgtgt 168420
aattgcggta tctatattat taaagtacgt aaatctagct atagttttat tatttaattt 168480
tagataatat accgtctcct tatttttaaa aattgccaca tcctttatta aatcatgaat 168540

```
gggaatttct atgtcatcgt tagtatattg tgaacaacaa gagcagatat ctataggaaa 168600
gggtggaatg cgatacattg atctatgtag ttttaaaaca cacgcgaact ttgaagaatt 168660
tatataaatc attccatcga tacatccttc tatgttgaga tgtatatatc caggaattcg 168720
tttattaata tcgggaaatg tataaactaa aacattgccc gaaagcggtg cctctatctg 168780
cgttatatcc gttcttaact tacaaaatgt aaccaatacc tttgcatgac ttgttttgtt 168840
cggcaacgtt agtttaaact tgacgaatgg attaattaca atagcatgat ccgcgcatct 168900
attaagtttt tttactttaa cgcccttgta tgtttttaca gagactttat ctaaatttct 168960
agtgcttgta tgtgttataa atataacggg atatagaacc gaatcaccta ccttagatac 169020
ccaattacat tttatcagat ccagataata aacaaatttt gtcgccctaa ctaattctat 169080
attgttatat attttacaat tggttatgat atcatgtaat aacttggagt ctaacgcgca 169140
tcgtcgtacg tttatacaat tgtgatttag tgtagtatat ctacacatgt atttttccgc 169200
actatagtat tctggactag tgataaaact atcgttatat ctatcttcaa tgaactcatc 169260
gagatattgc tctctgtcat attcatacac ctgcataaac tttctagaca tcttacaatc 169320
cgtgttattt taggatcata tttacatatt tacgggtata tcaaagatgt tagattagtt 169380
aatgggaatc gtctataata atgaatatta aacaattata tgaggacttt taccacaaag 169440
catcataaaa atgagtcgtc gtctgattta tgttttaaat atcaaccgca aatcaactca 169500
taaaatacaa gagaatgaaa tatatacata ttttagtcat tgcaatatag accatacttc 169560
tacagaactt gattttgtag ttaaaaacta tgatctaaac agacgacaac ctgtaactgg 169620
gtatactgca ctacactgct atttgtataa taattacttt acaaacgatg tactgaagat 169680
attattaaat catggagtgg atgtaacgat gaaaaccagt agcggacgta tgcctgttta 169740
tatattgctt actagatgtt gtaatatttc acatgatgta gtgatagata tgatagacaa 169800
agataaaaac cacttattac atagagacta ttccaaccta ttactagagt atataaaatc 169860
tcgttacatg ttattaaagg aagaggatat cgatgagaac atagtatcca ctttattaga 169920
taagggaatc gatcctaact ttaaacaaga cggatataca gcgttacatt attattattt 169980
gtgtctcgca cacgtttata aaccaggtga gtgtagaaaa ccgataacga taaaaaaggc 170040
caagcgaatt atttctttgt ttatacaaca tggagctaat ctaaacgcgt tagataattg 170100
tggtaataca ccattccatt tgtatcttag tattgaaatg tgtaataata ttcatatgac 170160
taaaatgctg ttgactttta atccgaattt cgaaatatgt aataatcatg gattaacgcc 170220
tatactatgt tatataactt ccgactacat acaacacgat attcttgtta tgttaataca 170280
tcactatgaa acaaatgttg gagaaatgcc gatagatgag cgtcgtatga tcgtattcga 170340
gtttatcaaa acatattcta cacgtccggc agattcgata acttatttga tgaataggtt 170400
taaaaatata aatatttata cccgctatga aggaaagaca ttattacacg tagcatgtga 170460
atataataat acacacgtaa tagattatct tatacgtatc aacggagata taaatgcgtt 170520
aaccgacaat aacaaacacg ctacacaact cattatagat aacaaagaaa attccccata 170580
taccattaat tgtttactgt atatacttag atatattgta gataagaatg tgataagatc 170640
gttggtggat caacttccat ctctacctat cttcgatata aaatcatttg agaaattcat 170700
atcctactgt atacttttag atgacacatt ttacgatagg cacgttaaga atcgcgattc 170760
taaaacgtat cgatacgcat tttcaaaata catgtcgttt gataaatacg atggtataat 170820
aactaaatgt cacgacgaaa caatgttact caaactgtcc actgttctag acactacact 170880
atatgcagtt ttaagatgtc ataattcgag aaagttaaga agatacctca acgagttaaa 170940
```

aaaatataat aacgataagt cctttaaaat atattctaat attatgaatg agagatacct 171000
taatgtatat tataaagata tgtacgtgtc aaaggtatat gataaactat ttcctgtttt 171060
cacagataaa aattgtctac taacattact accttcagaa attatatacg aaatattata 171120
catgctgaca attaacgatc tttataatat atcgtatcca cctaccaaag tatagttgta 171180
tttttctcat gcgatgtgtg taaaaaaact gatattatat aaatatttta gtgccgtata 171240
ataaagatga cgatgaaaat gatggtacat atatatttcg tatcattatt gttattgcta 171300
ttccacagtt acgccataga catcgaaaat gaaatcacag aattcttcaa taaaatgaga 171360
gatactctac cagctaaaga ctctaaatgg ttgaatccag catgtatgtt cggaggcaca 171420
atgaatgata tagccgctct aggagagcca ttcagcgcaa agtgtcctcc tattgaagac 171480
agtcttttat cgcacagata taaagactat gtggttaaat gggagaggct agaaaagaat 171540
agacggcgac aggtttctaa taaacgtgtt aaacatggtg atttatggat agccaactat 171600
acatctaaat tcagtaaccg taggtatttg tgcaccgtaa ctacaaagaa tggtgactgt 171660
gttcagggta tagttagatc tcatattaaa aaacctcctt catgcattcc aaaaacatat 171720
gaactaggta ctcatgataa gtatggcata gacttatact gtggaattct ttacgcaaaa 171780
cattataata atataacttg gtataaagat aataaggaaa ttaatatcga cgacattaag 171840
tattcacaaa cgggaaagga attaattatt cataatccag agttagaaga tagcggaaga 171900
tacgactgtt acgttcatta cgacgacgtt agaatcaaga atgatatcgt agtatcaaga 171960
tgtaaaatac ttacggttat accgtcacaa gaccacaggt ttaaactaat actagatccg 172020
aaaatcaacg taacgatagg agaacctgcc aatataacat gcactgctgt gtcaacgtca 172080
ttattgatcg acgatgtact gattgaatgg gaaaatccat ccggatggct tataggattc 172140
gattttgatg tatactctgt tttaactagt agaggcggta tcaccgaggc gaccttgtac 172200
tttgaaaatg ttactgaaga atatataggt aatacatata aatgtcgtgg acacaactat 172260
tattttgaaa aaacccttac aactacagta gtattggagt aaatatacaa tgcattttta 172320
tatacattac tgaattatta ttactgaatt attattactg aattattatt aattatatcg 172380
tatttgtgct atagaatgga tgaagatacg cgactatcta ggtatttgta tctcaccgat 172440
agagaacata taaatgtaga ctctattaaa cagttgtgta aaatatcaga tcctaatgca 172500
tgttatagat gtggatgtac ggctttacat gagtactttt ataattatag atcagtcaac 172560
ggaaaataca agtatagata caacggttac tatcaatatt attcatctag cgattatgaa 172620
aattataatg aatattatta tgatagaact ggtatgaaca gtgagagtga taatatatca 172680
atcaaaacag aatatgaatt ctatgatgaa acacaagatc aaagtacaca actagtaggt 172740
tacgacatta aactcaaaac caatgaggat gattttatgg ctatgataga tcagtgggtg 172800
tccatgatta tatagatgaa tcaattaata aagtagtata tggaagagag tctcacgtaa 172860
gatggcggga tatatggcaa gaacataatg atggcgtata cagtatagga aaggagtgca 172920
tagataatat atacgaagac aaccataccg tagacgaatt ctacaagata gacagcgtat 172980
cagatgtaga tgacgcggaa cacatatctc cgataactaa aaaaccatag aatcagttga 173040
tgataatacc tacatttcta atcttccgta taccatcaaa tacaaaatat tcgagcaaca 173100
ataagtattt tttatacctt taaaactgat aaataaattt tttctagtga tattttggca 173160
agatgagaat cctatttctc atcgctttca tgtatgggtg tgttcactca tatgttaacg 173220
cggttgaaac caaatgtcca aatctagaca ttgtaacatc ttctggagaa tttcattgtt 173280

```
caggatgtgt ggaacatatg cctgagttta gctatatgta ttggttggca aaggatatga 173340
aatcggacga ggataccaag tttatagaac atctgggtga tggcatcaaa gaagatgaaa 173400
ccgttcgtac cacagatagt ggaatcgtca ctctacgtaa agtccttcat gtaaccgata 173460
ctaataaatt tgataattat aggttcactt gtgtcctcac tacgatagat ggcgtttcaa 173520
aaaagaatat ttggctgaag tagtgcgtgc tactattttt atttatgata taatctaatg 173580
gaattaattt gaattgatat ttatccaata ctaaagatta tattagaatc aaattaatct 173640
tttatacgag aaaaaataac gacatacgtc gtcaacaaat taaacttttt atttattagt 173700
taactagctt atagaacttg ctcattgtta tgtttctaaa acgggtacgg catataggac 173760
aattatccga cgcaccggtt tctcttcgtg ttctatgcca tatattgatg catgttatgc 173820
aaaatatatg agtacacgaa tccaataaac caaagtatct atcgttttga gtaaacaact 173880
tcatagcaaa ttccacattc tttttcttta cttactctat acacgtcctc gtatttattt 173940
agtattttga tgatatccaa ctcagaaatg gttgttgtat tattgggtgt ataggtatta 174000
ttagctatgt accaatttac caaccctctt aatattgatt gataatcaca tcggttatcc 174060
aatcaataac cacattaata actaaattgt agtgtatata tagaccatat atgtttctat 174120
ttttttgaca gttacgtata gtttcagtaa gttttgattg ttgtattcct gtatctctag 174180
ataagttagt catatagtcc cttccggcga tacgtttttt ccaagcccga aattgattag 174240
ccaaatgtgt atttattttt gtgatattga tataatattt cggataatgc atactgttag 174300
tcttatatca tttggttcat ctatgtattg taatattgtt acatgatcta tagatgatgt 174360
attgattttg gcaggatcga attccatatc cgcgactaaa cagtgaaaaa aatgtaaata 174420
ctttttaaat tttaaattag taaaactttt ttttattttt tatgattcca aaaatactga 174480
atacaaagtc ctaaattata aatatggaga tcatactacc acaacttatt attatgtata 174540
caaggccggt gtaatagata gatatatata attctattac accggcagac aattaccgac 174600
cggtatttgt cgttaccaac ataccgtata atatgtaata tacaattcca taacccattg 174660
acagttgtta tacatcaaaa ttgcaattct tttgattacg atgttataag aatgtagtta 174720
attgatgtat gatgttaatg tgtcctcttt cctcttataa catcgtaatc aaaaactttt 174780
ttataatata tacctaataa tgtgtcttaa tagttctcgt gattcgtcaa acaatcattc 174840
ttataaaata taataaagca acgtaaaaac acataaaaat aagcgtaact aataagacaa 174900
tggatattta cgacgataaa ggtctacaga ctattaaact gtttaataat gaatttgatt 174960
gtataaggaa tgacatcaga gaattattta aacatgtaac tgattccgat agtatacaac 175020
ttccgatgga agacaattct gatattatag aaaatatcag aaaaatacta tatagacgat 175080
taaaaaatgt agaatgtgtt gacatcgata acacaataac ttttatgaaa tacgatccaa 175140
atgatgataa taagcgtacg tgttctaatt gggtaccctt aactaataac tatatggaat 175200
attgtctagt aatatatttg gaaacaccga tatgtggagg caaaataaaa ttataccacc 175260
ctacaggaaa tataaagtcg gataaggata ttatgtttgc aaagactcta gactaagata 175320
gacagcgtat cagatgtaga tgacgcggaa cacatatctc ctataactaa tgatgtatct 175380
acacaaacat gggaaaagaa atcagagtta gatagataca tggaatcgta tcctcgtcat 175440
agatatagta aacattctgt atttaaggga ttttctgata aagttagaaa aaatgattta 175500
gacatgaatg tggtaaaaga attactttct aacggtgcat ctctaacaat caaggatagc 175560
agtaataagg atccaattgc tgtttatttt agaagaacga taatgaattt agaaatgatt 175620
gatattatta acaaacatac aactattgat gaacgaaagt atatagtaca ctcctatcta 175680
```

aaaaattata gaaatttcga ttatccattt ttcaggaagt tagttttgac taataaacat 175740
tgtctcaaca attattataa tataagcgac agcaaatatg gaacaccgct acatatattg 175800
gcgtctaata aaaaattaat aactcctaat tacatgaagt tattagtgta taacggaaat 175860
gatataaacg cacgaggtga agatacacaa atgcgaacca actcagaaat ggttgttgta 175920
ttattgggtg tataggtatt attagctatg taccaattta ccaaccctct taatattgat 175980
tgataatcac atcggttatc caattaataa ctaaattgta gtgtatatat agaccatata 176040
tgtttctatt tttttgacag ttacgtatag tttcagtaag ttttgattgt tgtattcctg 176100
tatctctaga taagttagtc atatagtccc ttccggcgat acgttttttc caagcccgaa 176160
attgattagc caaatgtgta tttatttttg tgatattgat ataatatttc ggataatgca 176220
tactgttagt cttatatcat ttggttcatc tatgtattgt aatattgtta catgatctat 176280
agatgatgta ttgattttgg caggatcgaa ttccatatcc gcgactaaac agtgaaaaaa 176340
atgtaaatac tttttaaatt ttaaattagt aaaacttttt tttatttttt atgattccaa 176400
aaatactgaa tacaaagtcc taaattataa atatggagat catactacca caacttatta 176460
ttatgtatac aaggccggtg taatagatag atatatataa ttctattaca ccggcagaca 176520
attaccgacc ggtatttgtc gttaccaaca taccgtataa tatgtaatat acaattccat 176580
aacccattga cagttgttat acatcaaaat tgcaattctt ttgattacga tgttataaga 176640
atgtagttaa ttgatgtatg atgttaatgt gtcctctttc ctcttataac atcgtaatca 176700
aaaacttttt tataatatat acctaataat gtgtcttaat agttctcgtg attcgtcaaa 176760
caatcattct tataaaatat aataaagcaa cgtaaaaaca cataaaaata agcgtaacta 176820
ataagacaat ggatatttac gacgataaag gtctacagac tattaaactg tttaataatg 176880
aatttgattg tataaggaat gacatcagag aattatttaa acatgtaact gattccgata 176940
gtatacaact tccgatggaa gacaattctg atattataga aaatatcaga aaaatactat 177000
atagacgatt aaaaaatgta gaatgtgttg acatcgataa cacaataact tttatgaaat 177060
acgatccaaa tgatgataat aagcgtacgt gttctaattg ggtaccctta actaataact 177120
atatggaata ttgtctagta atatatttgg aaacaccgat atgtggaggc aaaataaaat 177180
tataccaccc tacaggaaat ataaagtcgg ataaggatat tatgtttgca aagactctag 177240
actttaaatc aacgaaagtg ttaactggac gtaaaacaat tgccgttcta gacatatccg 177300
tttcatataa tagatcaatg actactattc actacaacga cgacgttgat atagatatac 177360
atactgataa aaatggaaaa gagttatgtt attgttatat aacaatagat gatcattact 177420
tggttgatgt ggaaactata ggagttatag tcaatagatc tggaaaatgt ctgttagtaa 177480
ataaccatct aggtataggt atcgttaaag ataaacgtat aagcgatagt tttggagatg 177540
tatgtatgga tacaatattt gacttttctg aagcacgaga gttattttca ttaactaatg 177600
atgataacag gaatatagca tgggacactg ataaactaga cgatgataca gatatatgga 177660
ctcccgtcac agaagatgat tacaaatttc tttctagact agtattgtat gcaaaatctc 177720
aatcggatac tgtatttgac tattatgttc ttactggtga tacggaacca cccactgtat 177780
tcattttcaa ggtaactaga ttttacttta atatgccgaa ataaaaaatt tttgtataat 177840
atctagaggt agaggtattg tttagataaa tacaaataac atagatacat cgcatactta 177900
gcatttttat aaatatacat aagacataca ctttatacat ttttgtaaaa atactcataa 177960
aaaaatttat aaaaattatg gcacaaccat atcttgtata ggtagtttag ttcgtcgagt 178020
gaacctataa acagataata gacaacacat aataatgcct actaatacaa gcataatacc 178080
gggagatggg atatatgacg ttgtagtgtt tgggttttct gaacgttgat agtctactaa 178140
tactacatgc tgacatctaa tgcctgtata accatgagag catctacaat acataccgtc 178200
aatatctcta gcgtggatac agtcaccgtg taaacaatat ccatctccct ctggaccgca 178260
taatctgata gctggaatat ctgttgtagc gtttgtaatt tctggcaatg tcgtttcgat 178320
agcgttacca ctatcggcga atgatctgat tatcatagca gcgaacaaca acatcagata 178380
atttatcaac atttttgatg gattctgtgt ttatgctgtt tctcagtgtg tgtttatgac 178440
aagattggga attttatatt attaattcag taatataaac taataatata ttgttaattg 178500
tgtaaataat ataaaaataa caatacaata ttgaatgtgt tgctgttaaa aatgtatgtg 178560
ttaatataat agaataaaat aaatgagtat gatcatttta gataacgatt gattttatca 178620
ttaccgcttc attcttatat tctttgctta cggaacctat atttagaaac atctactaac 178680 aatttttat gcttgcatta ttaatggtat gtaatatgat tgattgtgta cgcaatacca 178740
atttgttaag tatgaatacg gggtacaaac ataaattgaa atttaacatt atttatttat 178800
gatatatatc gttatcgtta ggtctatacc atggatatct ttaaagaact aatcttaaaa 178860
caccctgatg aaaatgtttt gatttctcca gtttccattt tatctacttt atctattcta 178920
aatcatggag cagctggttc tacagctgaa caactatcaa aatatataga gaatatgaat 178980
gagaatacac ccgatgacaa taatgatgac atggaggtag atattccgta ttgtgcgaca 179040
ctagctaccg caaataaaat atacggtagc gatagtatcg agttccacgc ctccttccta 179100
caaaaaataa aagacgattt tcaaactgta aactttaata atgctaacca aacaaaggaa 179160
ctaatcaacg aatgggttaa gacaatgaca aatggtaaaa ttaattcctt attgactagt 179220
ccgctatcca ttaatactcg tatgacagtt gttagcgccg tccattttaa agcaatgtgg 179280
aaatatccat tttctaaaca tcttacatat acagacaagt tttatatttc taagaatata 179340
gttaccagcg ttgatatgat ggtgggtacc gagaataact tgcaatatgt acatattaat 179400
gaattattcg gaggattctc tattatcgat attccatacg agggaaactc tagtatggta 179460
attatactac cggacgacat agaaggtata tataacatag aaaaaaatat aacagatgaa 179520
aaatttaaaa aatggtgtgg tatgttatct actaaaagta tagacttgta tatgccaaag 179580
tttaaagtgg aaatgacaga accgtataat ctggtaccga ttttagaaaa tttaggactt 179640
actaatatat tcggatatta tgcagatttt agcaagatgt gtaatgaaac tatcactgta 179700
gaaaaatttc tacatacgac gtttatagat gttaatgagg agtatacaga agcatcggcc 179760
gttacaggag tatttacgat taacttttcg atggtatatc gtacgaaggt ctacataaac 179820
catccattca tgtacatgat taaagacacc acaggacgta tactttttat agggaaatac 179880
tgctatccgc aataaatata aacaaataga cttttataaa gagtcttcaa cgataagtat 179940
atcgacatac tacttatgct gcgaaagatt ctgaacgaga acgactatct caccctcttg 180000
gatcatatcc gcactgctaa atactaaatc tccactacac tttttatcat cttatgagga 180060
atgattgcct tcgtgaaata ggaataatta gcaccagaat agctatggat tattgtggta 180120
gagagtgcac tattctatgt cgtctactgg atgaagatgt gacgtacaaa aaaataaaac 180180
tagaaattga aacgtgtcac aacttatcaa aacatataga tagacgagga aacaatgcgc 180240
tacattgtta cgtctccaat aaatgcgata cagacattaa gattgttctc tcgcggagtc 180300
gagagacttt gtagaaacaa cgaaggatta actccgctag gagtatacag taagcataga 180360
tacgtaaaat ctcagattgt gcatctactg atatccagct attcaaattc ctctaacgaa 180420

```
ctcaagtcga atataaatga tttcgatctg tattcggata atatcgactt acgtctgcta 180480
aaatacctaa ttgtggataa acggatacgt ccgtccaaga atacgaatta tgcaatcaat 180540
ggtctcggat tggtggatat atacgtaacg acgcctaatc cgagaccaga agtattgcta 180600
tggcttctta aatcagaatg ttacagcacc ggttacgtat ttcgtacctg tatgtacgac 180660
agtgatatgt gtaagaactc tcttcattac tatatatcgt ctcatagaga atctcaatct 180720
ctatccaagg atgtaattaa atgtttgatc gataacaatg tttccatcca tggcagagac 180780
gaaggaggat ctttacccat ccaatactac tggtctttct caaccataga tatagagatt 180840
gttaaattat tattaataaa ggatgtggac acgtgtagag tatacgacgt cagccctata 180900
ttagaggcgt attatctaaa caagcgattt agagtaaccc catataatgt agacatggaa 180960
atcgttaatc ttcttattga gagacgtcat actcttgtcg acgtaatgcg tagtattact 181020
tcgtacgatt ccagagaata taaccactac atcatcgata acattctaaa gagatttaga 181080
caacaggatg tacaagccat gttgataaac tacttacatt acggcgatat ggtcgttcga 181140
tgcatgttag ataacggaca acaactatcc tctgcacgac tactttgtta ataataatct 181200
cgtcgatgta aacgtcgtaa ggtttatcgt ggaaaatatg gacacgcggc tgtaaatcac 181260
gtatcgaaca atggccgtct atgtatgtac ggtctgatat tatcgagatt taataattgc 181320
gggtatcact gttatgaaac catactgata gatgtatttg atatactaag caagtacatg 181380
gatgatatag atatgatcga taactctact atattacgcg gtcgatgtca ataatataca 181440
atttgcaaag cggttattgg aatatggagc gagtgtcacg ctcgataatc aatacggcca 181500
tccagaaaag cagttaccaa agagaaaaca aaacgaagct agttgattta ttactgagtt 181560
accatcccac tctagagact atgattgacg catttaatag agatatacgc tatctatatc 181620
ctgaaccatt attcgcctgt atcagatacg ccttaatcct agatgatgat tttccttcta 181680
aagtaaagta tgatatcgcc ggtcgtcata aggaactaaa gcgctataga gtagacatta 181740
atagaatgaa gaatgtctac atatcaggcg tctccatgtt tgatatatta tttaaacgaa 181800
gcaaacgcca caaattgaga tacgcaaaga atccgacatc aaatggtaca aaaaagaact 181860
aacgtccatc attacagaaa ctgtaaagaa caatgagagg atcgactcca tagtggacaa 181920
cattaataca gacgataact tgatttcgaa attacccatg gagatacttt attactccat 181980
taaataattt atcatggagc gataatgtcc tgtttcattt gtttccatga catattacaa 182040
aatcgattcc gtccaagatg ataaaaacat ttaccggcat cataaacacg gagtttattt 182100
tatatgtctc gcataaacat tactaaaaaa atatattgtc gataacttga tttcgaaatt 182160
acccatggag atactttatt actccattaa ataatttatc atggagcgat aatgtcctgt 182220
ttcatttgtt tccatgacat attacaaaat cgattccgtc caagatgata aaaacattta 182280
ccggcatcat aaacacggag tttattttat atgtctcgca taaacattac taaaaaaata 182340
tattgttctg tttttctttc acatctttaa ttatgaaaaa gtaaatcatt atgagatgga 182400
cgagattgta cgcatcgttc gcgacagtat gtggtacata cctaacgtat ttatggacga 182460
cggtaagaat gaaggtcacg tttctgtcaa caatgtctgt catatgtatt ttacgttctt 182520
tgatgtggat acatcgtctc atctgtttaa gctagttatt aaacactgcg atctgaataa 182580
acgaggtaac tctccattac attgctatac gatgaataca cgatttaatc catctgtatt 182640
aaagatattg ttacaccacg gcatgcgtaa ctttgatagc aaggatgacc actatcaatc 182700
gataacaaga tctttgatat actaacggac accattgatg actttagtaa atcatccgat 182760
```

```
ctattgctgt gttatcttag atataaattc aatgggagct taaactatta cgttctgtac 182820
aaaggatccg accctaattg cgccgacgag gatgaactca cttctcttca ttactactgt 182880
aaacacatat ccacgttcta cgaaagcaat tattacaagt taagtcacac taagatgcga 182940
gccgagaagc gattcatcta cgcgataata gattatggag caaacattaa cgcggttaca 183000
cacttacctt caacagtata ccaaacatag tcctcgtgtg gtgtatgctc ttttatctcg 183060
aggagccgat acgaggatac gtaataatct tgattgtaca cccatcatgg aacgattgtg 183120
caacaggtca tattctcata atgttactca attggcacga acaaaaggaa gaaggacaac 183180
atctacttta tctattcata aaacataatc aaggatacac tctcaatata ctacggtatc 183240
tattagatag gttcgacatt cagaaagacg aatactataa taccgccttt caaaattgta 183300
acaacaatgt tgcctcatac atcggatacg acatcaacct tccgactaaa gacggtattc 183360
gacttggtgt ttgaaaacag aaacatcata tacaaggcgg atgttgtgaa tgacatcatc 183420
caccacagac tgaaagtatc tctacctatg attaaatcgt tgttctacaa gatgtctctc 183480
cctacgacga ttactacgta aaaaagatac tagcctactg cctattaagg gacgagtcat 183540
tcgcggaact acatagtaaa ttctgtttaa acgaggacta taaaagtgta tttatgaaaa 183600
atatatcatt cgataagata gattccatca tcgtgacata agtcgcctca aagagattcg 183660
aatctccgac accgacctgt atacggtatc acagctatct taaagccata cattcagaca 183720
gtcacatttc atttcccatg tacgacgatc tcatagaaca gtgccatcta tcgatggagc 183780
gtaaaagtaa actcgtcgac aaagcactca ataaattaga gtctaccatc ggtcaatcta 183840
gactatcgta tttgcctccg gaaattatgc gcaatatcat ctaaacagta tgttgtacgg 183900
aaagaaccat tacaaatatt atccatgata gaaagaaaat atctatatga ttggagaagt 183960
aggaaacagg aacaagacaa cgattactac attattaaat catgaagtcc gtattatact 184020
cgtatatatt gtttctctca tgtataataa taaacggaag agatatagca ccgcatgcac 184080
catccgatgg aaagtgtaaa gacaacgaat acaaacgcca taatttgtgt ccgggaacat 184140
acgcttccag attatgcgat agcaagacta acacacgatg tacgccgtgt ggttcgggta 184200
ccttcacatc tcgcaataat catttacccg cttgtctaag ttgtaacgga agacgcgatc 184260
gtgtaacacg actcacaata gaatctgtga atgctctccc ggatattatt gtcttctcaa 184320
aggatcatcc ggatgcaagg catgtgtttc ccaaacaaaa tgtggaatag gatacggagt 184380
atccggagac gtcatctgtt ctccgtgtgg tctcggaaca tattctcaca ccgtctcttc 184440
cgcagataaa tgcgaacccg tacccagaaa tacgtttaac tatatcgatg tggaaattaa 184500
cctgtatcca gttaacgaca cgtcgtgtac tcggacgacc actaccggtc tcagcgaatc 184560
catctcaacg tcggaactaa ctattactat gaatcataaa gactgtaatc ccgtatttcg 184620
tgatggatac ttctccgttc ttaataaggt agcgacttca ggtttcttta caggagaaag 184680
gtgtgcactc tgaatttcga gattaaatgc aataacaaag attcttcctc caaacagtta 184740
acgaaagcaa agaatgatac tatcatgccg cattcggaga cagtaactct agtgggcgac 184800
atctatatac tatatagtaa taccaatact caagactacg aaactgatac aatctcttat 184860
catgtgggta atgttctcga tgtcgatagc catatgcccg gtagttgcga tatacataaa 184920
ctgatcacta attccaaacc cacccacttt ttatagtaag tttttcaccc ataaataata 184980
aatacaataa ttaatttctc gtaaaagtag aaaatatatt ctaatttatt gcacggtaag 185040
gaagtagaat cataaagaac agtactcaat caatagcaat tatgaaacaa tatatcgtcc 185100
tggcatgcat gtgcctggcg gcagctgcta tgcctgccag tcttcagcaa tcatcctcat 185160
```

```
cctcctcctc gtgtacggaa gaagaaaaca aacatcatat gggaatcgat gttattatca 185220

aagtcacaaa gcaagaccaa acaccgacca atgataagat ttgccaatcc gtaacggaaa 185280

ttacagagtc cgagtcagat ccagatcccg aggtggaatc agaagatgat tccacatcag 185340

tcgaggatgt agatcctcct accacttatt actccatcat cggtggaggt ctgagaatga 185400

actttggatt caccaaatgt cctcagatta aatccatctc agaatccgct gatggaaaca 185460

cagtgaatgc tagattgtcc agcgtgtccc caggacaagg taaggactct cccgcgatca 185520

ctcatgaaga agctcttgct atgatcaaag actgtgaagt gtctatcgac atcagatgta 185580

gcgaagaaga gaaagacagc gacatcaaga cccatccagt actcgggtct aacatctctc 185640

ataagaaagt gagttacgaa gatatcatcg gttcaacgat cgtcgataca aaatgcgtca 185700

agaatctaga gtttagcgtt cgtatcggag acatgtgcaa ggaatcatct gaacttgagg 185760

tcaaggatgg attcaagtat gtcgacggat cggcatctga aggtgcaacc gatgatactt 185820

cactcatcga ttcaacaaaa ctcaaagcgt gtgtctgaat cgataactct attcatctga 185880

aattggatga gtagggttaa tcgaacgatt caggcacacc acgaattaaa aaagtgtacc 185940

ggacactata ttccggtttg caaaacaaaa atgttcttaa ctacattcac aaaaagttac 186000

ctctcgcgac ttcttctttt tctgtctcaa tagtgtgata cgattatgac actattccta 186060

ttcctattcc tatttccttt cagagtatca caaaaatatt aaacctcttt ctgatggtct 186120

cataaaaaaa gttttacaaa aatattttta ttctctttct ctctttgatg gtctcataaa 186180

aaaagtttta caaaaatatt tttattctct ttctctcttt gatggtctca taaaaaaagt 186240

tttacaaaaa tatttttatt ctctttctct ctttgatggt ctcataaaaa aagttttaca 186300

aaaatatttt tattctcttt ctctctttga tggtctcata aaaaaagttt tacaaaaata 186360

tttttattct ctttctctct ttgatggtct cataaaaaaa gttttacaaa aatattttta 186420

ttctctttct ctctttgatg gtctcataaa aaaagtttta caaaaatatt tttattctct 186480

ttctctcttt gatggtctca taaaaaaagt tttacaaaaa tatttttatt ctctttctct 186540

ctttgatggt ctcataaaaa aagttttaca aaaatatttt tattctcttt ctctctttga 186600

tggtctcata aaaaaagttt tacaaaaata tttttattct ctttctctct ttgatggtct 186660

cataaaaaaa gttttacaaa aatattttta ttctctttct ctctttgatg gtctcataaa 186720

aaaagtttta caaaaatatt tttattctct ttctctcttt gatggtctca taaaaaaagt 186780

tttacaaaaa tatttttatt ctctttctct ctttgatggt ctcataaaaa aagttttaca 186840

aaaatatttt tatt                                                   186854
```

<210> SEQ ID NO 35
<211> LENGTH: 1131
<212> TYPE: DNA
<213> ORGANISM: Human Herpesvirus-1
<300> PUBLICATION INFORMATION:
<308> DATABASE ACCESSION NUMBER: GenBank No. NC_00180
<309> DATABASE ENTRY DATE: 2004-01-13

<400> SEQUENCE: 35

```
atggcttcgt acccctgcca tcaacacgcg tctgcgttcg accaggctgc gcgttctcgc     60

ggccataaca accgacgtac ggcgttgcgc cctcgccggc aacaaaaagc cacggaagtc    120

cgcctggagc agaaaatgcc cacgctactg cgggtttata tagacggtcc ccacgggatg    180

gggaaaacca ccaccacgca actgctggtg gccctgggtt cgcgcgacga tatcgtctac    240

gtacccgagc cgatgactta ctggcgggtg ttgggggctt ccgagacaat cgcgaacatc    300
```

```
tacaccacac aacaccgcct cgaccagggt gagatatcgg ccggggacgc ggcggtggta    360

atgacaagcg cccagataac aatgggcatg ccttatgccg tgaccgacgc cgttctggct    420

cctcatatcg ggggggaggc tgggagctca catgccccgc ccccggccct caccctcatc    480

ttcgaccgcc atcccatcgc cgccctcctg tgctacccgg ccgcgcgata ccttatgggc    540

agcatgaccc cccaggccgt gctggcgttc gtggccctca tcccgccgac cttgcccggc    600

acaaacatcg tgttgggggc ccttccggag gacagacaca tcgaccgcct ggccaaacgc    660

cagcgccccg gcgagcggct tgacctggct atgctggccg cgattcgccg cgtttatggg    720

ctgcttgcca atacggtgcg gtatctgcag ggcggcgggt cgtggcggga ggattgggga    780

cagctttcgg gggcggccgt gccgccccag ggtgccgagc cccagagcaa cgcgggccca    840

cgaccccata tcggggacac gttatttacc ctgtttcggg cccccgagtt gctggccccc    900

aacggcgacc tgtataacgt gtttgcctgg gctttggacg tcttggccaa acgcctccgt    960

cccatgcatg tctttatcct ggattacgac caatcgcccg ccggctgccg ggacgccctg   1020

ctgcaactta cctccgggat ggtccagacc cacgtcacca ccccaggctc cataccgacg   1080

atctgcgacc tggcgcgcac gtttgcccgg gagatggggg aggctaactg a            1131
```

```
<210> SEQ ID NO 36
<211> LENGTH: 376
<212> TYPE: PRT
<213> ORGANISM: Human Herpesvirus-1
<300> PUBLICATION INFORMATION:
<308> DATABASE ACCESSION NUMBER: GenBank No. NP_04462
<309> DATABASE ENTRY DATE: 2004-01-13

<400> SEQUENCE: 36

Met Ala Ser Tyr Pro Cys His Gln His Ala Ser Ala Phe Asp Gln Ala
 1               5                  10                  15

Ala Arg Ser Arg Gly His Asn Asn Arg Arg Thr Ala Leu Arg Pro Arg
            20                  25                  30

Arg Gln Gln Lys Ala Thr Glu Val Arg Leu Glu Gln Lys Met Pro Thr
        35                  40                  45

Leu Leu Arg Val Tyr Ile Asp Gly Pro His Gly Met Gly Lys Thr Thr
    50                  55                  60

Thr Thr Gln Leu Leu Val Ala Leu Gly Ser Arg Asp Asp Ile Val Tyr
65                  70                  75                  80

Val Pro Glu Pro Met Thr Tyr Trp Arg Val Leu Gly Ala Ser Glu Thr
                85                  90                  95

Ile Ala Asn Ile Tyr Thr Thr Gln His Arg Leu Asp Gln Gly Glu Ile
            100                 105                 110

Ser Ala Gly Asp Ala Ala Val Val Met Thr Ser Ala Gln Ile Thr Met
        115                 120                 125

Gly Met Pro Tyr Ala Val Thr Asp Ala Val Leu Ala Pro His Ile Gly
    130                 135                 140

Gly Glu Ala Gly Ser Ser His Ala Pro Pro Pro Ala Leu Thr Leu Ile
145                 150                 155                 160

Phe Asp Arg His Pro Ile Ala Ala Leu Leu Cys Tyr Pro Ala Ala Arg
                165                 170                 175

Tyr Leu Met Gly Ser Met Thr Pro Gln Ala Val Leu Ala Phe Val Ala
            180                 185                 190

Leu Ile Pro Pro Thr Leu Pro Gly Thr Asn Ile Val Leu Gly Ala Leu
        195                 200                 205
```

```
Pro Glu Asp Arg His Ile Asp Arg Leu Ala Lys Arg Gln Arg Pro Gly
    210                 215                 220

Glu Arg Leu Asp Leu Ala Met Leu Ala Ala Ile Arg Arg Val Tyr Gly
225                 230                 235                 240

Leu Leu Ala Asn Thr Val Arg Tyr Leu Gln Gly Gly Gly Ser Trp Arg
                245                 250                 255

Glu Asp Trp Gly Gln Leu Ser Gly Ala Ala Val Pro Pro Gln Gly Ala
            260                 265                 270

Glu Pro Gln Ser Asn Ala Gly Pro Arg Pro His Ile Gly Asp Thr Leu
        275                 280                 285

Phe Thr Leu Phe Arg Ala Pro Glu Leu Leu Ala Pro Asn Gly Asp Leu
    290                 295                 300

Tyr Asn Val Phe Ala Trp Ala Leu Asp Val Leu Ala Lys Arg Leu Arg
305                 310                 315                 320

Pro Met His Val Phe Ile Leu Asp Tyr Asp Gln Ser Pro Ala Gly Cys
                325                 330                 335

Arg Asp Ala Leu Leu Gln Leu Thr Ser Gly Met Val Gln Thr His Val
            340                 345                 350

Thr Thr Pro Gly Ser Ile Pro Thr Ile Cys Asp Leu Ala Arg Thr Phe
        355                 360                 365

Ala Arg Glu Met Gly Glu Ala Asn
    370                 375
```